(12) United States Patent
Miller et al.

(10) Patent No.: US 12,049,474 B2
(45) Date of Patent: Jul. 30, 2024

(54) NUCLEOSIDE PRODRUGS AND USES RELATED THERETO

(71) Applicant: Emory University, Atlanta, GA (US)

(72) Inventors: Eric Miller, Atlanta, GA (US); Nicole Pribut, Atlanta, GA (US); Michael D'Erasmo, Atlanta, GA (US); Madhuri Dasari, Atlanta, GA (US); Kyle Giesler, Berkeley, CA (US); Sabrina Iskandar, Carrboro, NC (US); Dennis C. Liotta, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 17/637,365

(22) PCT Filed: Aug. 24, 2020

(86) PCT No.: PCT/US2020/047631
§ 371 (c)(1),
(2) Date: Feb. 22, 2022

(87) PCT Pub. No.: WO2021/035214
PCT Pub. Date: Feb. 25, 2021

(65) Prior Publication Data
US 2022/0298185 A1    Sep. 22, 2022

Related U.S. Application Data

(60) Provisional application No. 62/890,452, filed on Aug. 22, 2019, provisional application No. 62/890,684, filed on Aug. 23, 2019.

(51) Int. Cl.
*C07F 9/6512* (2006.01)
*C07F 9/6561* (2006.01)

(52) U.S. Cl.
CPC ........ *C07F 9/65128* (2013.01); *C07F 9/6512* (2013.01); *C07F 9/65616* (2013.01)

(58) Field of Classification Search
CPC ............................ C07F 9/6512; C07F 9/65616
See application file for complete search history.

(56) References Cited

U.S. PATENT DOCUMENTS

| | | | |
|---|---|---|---|
| 4,797,479 A | 1/1989 | Shuto | |
| 5,770,725 A | 6/1998 | Gosselin | |
| 5,849,905 A | 12/1998 | Gosselin | |
| 6,020,482 A | 2/2000 | Gosselin | |
| 6,555,676 B2 | 4/2003 | Gosselin | |
| 7,749,983 B2 | 7/2010 | Hostetler | |
| 7,902,202 B2 | 3/2011 | Sommadossi | |
| 8,871,785 B2 | 10/2014 | Boojamra | |
| 9,694,024 B2 | 7/2017 | Lanier | |
| 10,688,112 B2 | 6/2020 | Liotta | |
| 11,090,316 B2 | 8/2021 | Liotta | |
| 2008/0009462 A1* | 1/2008 | Hostetler | A61P 33/00 514/86 |
| 2010/0298256 A1 | 11/2010 | Dong | |
| 2012/0164230 A1 | 6/2012 | Feazell | |
| 2015/0291639 A1 | 10/2015 | Phull | |

FOREIGN PATENT DOCUMENTS

| | | |
|---|---|---|
| EP | 3730503 | 10/2020 |
| WO | 1996015132 | 5/1996 |
| WO | 1996039831 | 12/1996 |
| WO | 1998038202 | 9/1998 |
| WO | 2001039724 | 6/2001 |
| WO | 2002008241 | 1/2002 |
| WO | 2005087788 | 9/2005 |
| WO | 2006110656 | 10/2006 |
| WO | 2006130217 | 12/2006 |
| WO | 2006137953 | 12/2006 |
| WO | 2007130783 | 11/2007 |
| WO | 2010135520 | 11/2010 |
| WO | 2011011519 | 1/2011 |
| WO | 2011017253 | 2/2011 |
| WO | 2011130557 | 10/2011 |
| WO | 2014124430 | 8/2014 |
| WO | 2014143643 | 9/2014 |
| WO | 2015038596 | 3/2015 |

(Continued)

OTHER PUBLICATIONS

Basson et al. Novel lipid prodrugs of tenofovir with improved metabolic properties have promising potential as safer, long-acting antivirals for the treatment of HIV-1, Abst, ACS Fall 2020 Virtual Meeting.

De Clercq, Clinical Potential of the Acyclic Nucleoside Phosphonates Cidofovir, Adefovir, and Tenofovir in Treatment of DNA Virus and Retrovirus Infections, Clinical Microbiology Reviews, 2003, 569-596.

Gendelman et al. The Promise of Long-Acting Antiretroviral Therapies: From Need to Manufacture, Trends in Microbiology, Jul. 2019, vol. 27, No. 7 , 593-606.

Giesler et al., Reduction Sensitive Lipid Conjugates of Tenofovir: Synthesis, Stability, and Antiviral Activity, J. Med. Chem., 2016, 59(15), 7097-7110.

Giesler et al., Next-Generation Reduction Sensitive Lipid Conjugates of Tenofovir: Antiviral Activity and Mechanism of Release, J. Med. Chem., 2016, 59(22), 10244-10252.

Kim et al. Adherence to antiretroviral therapy and factors affecting low medication adherence among incident HIV-Infected individuals during 2009-2016: A nationwide study, Scientific Reports (2018) 8:3133.

(Continued)

*Primary Examiner* — Laura L Stockton
(74) *Attorney, Agent, or Firm* — Emory Patent Group

(57) ABSTRACT

Disclosed are acyclic nucleoside prodrugs with improved metabolic stability and oral bioavailability. In general, the prodrugs are derivatives of acyclic nucleoside phosphonates containing a lipid-like moiety that can increase oral absorption and subsequent stability in the liver and plasma. Preferably, the lipid-like moiety can resist enzyme-mediated ω-oxidation, such as ω-oxidation catalyzed by cytochrome P450 enzymes. Also disclosed are pharmaceutical formulations of the acyclic nucleoside prodrugs. The acyclic nucleoside prodrugs and pharmaceutical formulations thereof can be used to treat viral infections, such as HIV infections, and/or viral-associated cancer, such as HPV-associated cancers.

23 Claims, 13 Drawing Sheets

(56) References Cited

FOREIGN PATENT DOCUMENTS

| | | |
|---|---|---|
| WO | 2015085256 | 6/2015 |
| WO | 2016044281 | 3/2016 |
| WO | 2016069630 | 5/2016 |
| WO | 2017024310 | 2/2017 |
| WO | 2017048956 | 3/2017 |
| WO | 2018113652 | 6/2018 |
| WO | 2018144991 | 8/2018 |
| WO | 2019120084 | 6/2019 |

OTHER PUBLICATIONS

Painter et al. Evaluation of Hexadecyloxypropyl-9-R-[2-(Phosphonomethoxy)Propyl]- Adenine, CMX157, as a Potential Treatment for Human Immunodeficiency Virus Type 1 and Hepatitis B Virus Infections, Antimicrobial Agents and Chemotherapy, 2007, 505-3509.

Pradere et al., Synthesis of Nucleoside Phosphate and Phosphonate Prodrugs, Chemical Reviews, 2014, 114, 9154-9218.

Pribut et al. ω-Functionalized Lipid Prodrugs of HIV NiRTI Tenofovir with Enhanced Pharmacokinetic Properties, J. Med. Chem. 2021, 64, 12917-12937.

Pubchem, compound CID 135484963, available at https://pubchem.ncbi.nlm.nih.gov/compound/135484963, create date Jan. 15, 2019.

Rautio et al., Prodrugs: design and clinical Applications, Nature Reviews Drug Discovery, 2008, 7, 255-270.

Alexander et al. The Novel Phospholipid Mimetic KPC34 is Highly Active Against Acute Myeloid Leukemia with Activated Protein Kinase C, Translational Oncology, 2020, 13, 100780.

Beadle et al. Alkoxyalkyl Esters of Cidofovir and Cyclic Cidofovir Exhibit Multiple-Log Enhancement of Antiviral Activity against Cytomegalovirus and Herpesvirus Replication In Vitro, Antimicrobial Agents and Chemotherapy, 2002, 46, 2381-2386.

Beadle et al. Synthesis and Antiviral Evaluation of Alkoxyalkyl Derivatives of 9-(S)-(3-Hydroxy-2-phosphonomethoxypropyl)adenine against Cytomegalovirus and Orthopoxviruses, 2006, J. Med. Chem., 49, 2010-2015.

Giesler, The Design, Synthesis, and Biological Evaluation of Novel Prodrugs and Antiviral Agents for HIV and Other Chronic Viral Infections, Doctoral Dissertation, 2017.

Hong et al. Nucleoside-ether lipid conjugates as biotransformed prodrugs of antitumor and antiviral nucleosides, J. Lipid Mediators Cell Signalling, 1994, 10, 159-161.

Miller et al. Structure-stability relationships of tetrahydroisoquinoline-containing CXCR4 antagonists and lipid prodrugs of tenofovir in liver microsomes, Abstract for the 256th ACS National Meeting (2018).

Naguib et al. Synthesis, Characterization, and In Vitro and In Vivo Evaluations of 4-(N)-Docosahexaenoyl 2', 2'- Difluorodeoxycytidine with Potent and Broad-Spectrum Antitumor Activity, Neoplasia, 2016, 18, 33-48.

Ruiz et al. Synthesis, metabolic stability and antiviral evaluation of various alkoxyalkyl esters of cidofovir and 9-(S)-[3- hydroxy-2-(phosphonomethoxy) propyl]adenine, Bioorganic & Medicinal Chemistry, 2011, 19, 2950-2958.

Shen et al. Synthesis of nucleoside phosphonate analogs having phosphonodifluoromethylene moieties and their biological activities, Journal of Fluorine Chemistry, 2019, 224, 1-34.

Stepan et al. Metabolism-guided drug design, Med. Chem. Commun., 2013, 4, 631-652.

Third Party Observation submitted for PCT/US2020/047631, 2021.

* cited by examiner

NUCLEOSIDE PRODRUGS AND USES RELATED THERETO

CROSS-REFERENCE TO RELATED APPLICATIONS

This application claims the benefit of U.S. Provisional Application No. 62/890,452 filed Aug. 22, 2019 and U.S. Provisional Application No. 62/890,684 filed Aug. 23, 2019. The entirety of each of these applications is hereby incorporated by reference for all purposes.

TECHNICAL FIELD

The present disclosure relates to prodrugs of nucleosides and acyclic nucleoside phosphonates and derivatives thereof, pharmaceutical formulations and uses related thereto.

BACKGROUND

Numerous synthetic nucleoside analogs have been approved by regulatory agencies, such as the FDA, for therapeutic utility against various human diseases. These agents have found profound clinical application with human immunodeficiency virus/acquired immune-deficiency syndrome (HIV/AIDS) as inhibitors of HIV reverse transcriptase (HIV-RT), the viral protein responsible for reverse transcription of viral RNA to DNA.

One example of this is tenofovir (TFV, shown below), which is an acyclic nucleoside phosphonate that exhibits a broad range of activity against several viruses, including HIV, hepatitis B virus (HBV) and herpes simplex virus type 2 (HSV-2). Mechanistically, TFV undergoes 2 kinase-mediated phosphorylation events to generate the active TFV diphosphate, which inhibits viral DNA polymerase activity and arrests viral replication. A key feature of nucleoside phosphonates, such as TFV, is a metabolically stable phosphonate linkage (—P—CH$_2$) that prevents undesirable enzymatic and chemical hydrolysis. Furthermore, these nucleoside phosphonates mimic nucleoside monophosphates, thereby bypassing the relatively sluggish initial phosphorylation event that is required by most nucleoside analogs. Although circumventing this first phosphorylation event enables facile conversion to their active metabolites, this phosphonate moiety gives TFV and other acyclic analogs significant dianionic character at physiological pH. This restricts their ability to diffuse across cell membranes and results in rapid renal clearance, decreased bioavailability, reduced antiviral activity and nephrotoxicity, which is a consequence of renal tubular efflux-mediated accumulation of TFV in the kidneys.

To improve these properties, prodrugs of TFV, namely TFV disoproxil fumarate (TDF) and TFV alafenamide fumarate (TAF) (shown below), have been designed to mask the dual negative charges. The clinically approved TDF features two isopropyloxymethyl carbonate functionalities that depend on an esterase-activated cleavage mechanism to release TFV. Though the two isopropyl carbonates increase the oral bioavailability of TFV, the ubiquitous distribution of esterases, particularly in the liver and plasma, causes TDF to undergo significant hydrolysis. This results in systemic exposure of TFV, which accumulates in kidney and bone, leading to nephrotoxicity, bone mineral density depletion (BMD) and other negative side-effects after long-term exposure. In contrast, TAF features a phosphoramidate linkage that is selectively cleaved intracellularly by cathepsin A, a serine protease predominantly localized in endosomes and lysosomes. This selective intracellular cleavage mechanism overcomes the poor plasma stability of TDF that gives rise to circulating TFV, which causes nephrotoxicity and BMD. Unfortunately, both TFV prodrugs tend to concentrate in the hepatic system, thereby limiting availability to HIV-infected cells in other tissues. In dogs for instance, 65% of a single oral dose of TAF was extracted by the liver, concentrating in hepatocytes as TFV diphosphate due to undesired cleavage by carboxylesterase 1, thereby encouraging hepatotoxicity. Furthermore, 17% was converted to plasma TFV, which is primed for bone and kidney sequestration and related toxicities. Because of this undesired metabolism, only 18% achieved access to plasma unscathed, thereby conferring availability for HIV-infected cell entry, while 82% was sequestered for toxic side effects that compromise patient adherence to antiretroviral therapy.

A more recent strategy has focused on disguising acyclic nucleoside phosphonates as lysophospholipids in order to increase oral absorption and subsequent stability in the liver and plasma. In principle, this should increase systemic exposure, thereby elevating the fraction of orally administered prodrug that reaches plasma unscathed. One example of these lipid prodrugs is hexadecyloxypropyl-9-R-[2-(phosphonomethoxy) propyl]-adenine, CMX157 (also shown below), a prodrug of TFV containing a hexadecyloxypropyl lipid tail (Painter et al. Antimicrob. Agents Chemother. 51, 3505-3509, 2007). However, CMX157 suffers from undesired ω-oxidation at the terminal methyl group on the lipid chain by cytochrome P450 (CYP) enzymes located in the small intestine and liver. This catabolic event is initiated by introducing a hydroxyl group at the terminus of the lipid chain, which then undergoes sequential oxidations by alcohol and aldehyde dehydrogenases to produce the corresponding carboxylic acid. The resulting carboxylic acid can subsequently undergo β-oxidations, degrading the lipid chain two carbons at a time, releasing TFV and several undesired metabolites pre-systemically, thereby substantially limiting the fraction of orally administered prodrug that is available for HIV-infected cells.

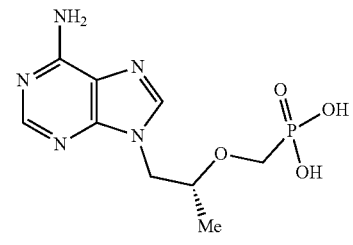

Tenofovir (TFV)

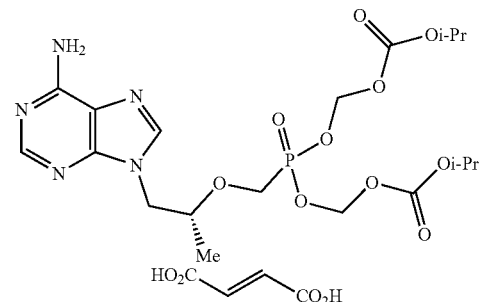

Tenofovir disoproxil fumarate (TDF)

-continued

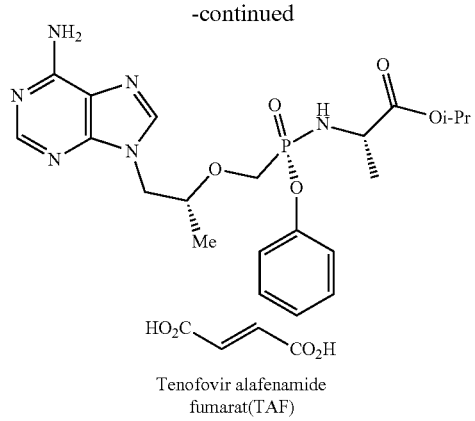

Tenofovir alafenamide fumarat(TAF)

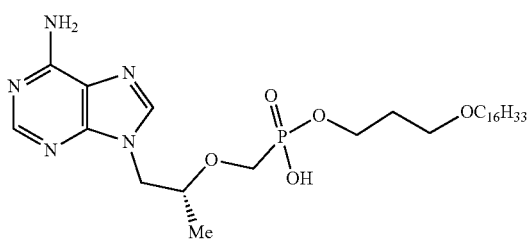

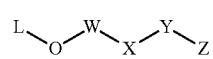

CMX157

As reported by a 2010 meta-analysis of 84 clinical studies, only 62% of HIV patients reported an average adherence rate of ≥90%, which confers optimal viral suppression. When patients miss scheduled doses, resistant, transmissible viruses can emerge, often requiring second- or third-line therapy options that demand stricter compliance for sustained efficacy. In addition to toxic side effects, patient adherence to chronic antiretroviral therapy is significantly encumbered by high dosing frequency. As the absence of a cure requires indefinite compliance to ensure prolonged viral suppression across a patient's lifetime, antiretroviral success is defined by life-long adherence. This is supported by the inverse correlation of patient adherence with HIV viral load, the emergence of drug resistance, as well as with progression to AIDS. Accordingly, the currently required frequency of antiretroviral dosing remains a significant obstacle. Ultimately, while many of the 20.9 million HIV/AIDS patients with access to TDF- and TAF-containing antiretrovirals suffer from organ-specific toxicities and frequent dosing schedules that threaten adherence, the 15.8 million patients without affordable access to therapy lack access partially because of cost, which is markedly driven by the quantity of drug needed to treat target patient populations. There is thus a need for improved therapies.

SUMMARY

Disclosed are acyclic nucleoside prodrugs with improved metabolic stability and oral bioavailability. In general, the prodrugs are derivatives of acyclic nucleoside phosphonates containing a lipid-like moiety that can increase oral absorption and subsequent stability in the liver and plasma. Preferably, the lipid-like moiety can resist enzyme-mediated ω-oxidation, such as ω-oxidation catalyzed by cytochrome P450 enzymes.

In some embodiments, the disclosed compounds have a structure of Formula I or a pharmaceutically acceptable salt thereof:

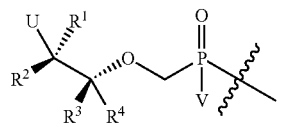

(I)

wherein:

L is an acyclic nucleoside phosphonate;

W is absent or a saturated $C_1$-$C_9$ alkyl chain (i.e., bridging $C_1$-$C_9$ alkylene);

X is absent or is selected from substituted methylene or ethylene, —O—, —S—, —S(=O)—, and —S(O)$_2$—;

Y is a saturated $C_2$-$C_{20}$ alkyl chain (i.e., bridging $C_2$-$C_{20}$ alkylene); and Z is selected from hydrogen, optionally substituted methyl or ethyl, optionally substituted unsaturated $C_2$-$C_3$ alkyl, optionally substituted carbocyclyl, optionally substituted heterocyclyl, optionally substituted aryl, optionally substituted heteroaryl, Si-substituted silyl, S-substituted thiol, O-substituted hydroxyl, ester, and —SF$_5$, wherein when X is —O—, Z is not hydrogen, methyl, or ethyl, wherein when both W and X are absent, Z is not hydrogen, methyl, or ethyl, and wherein when W is absent, X is also absent.

In some embodiments, both W and X are present.

In some embodiments, L has a structure of Formula V:

Formula V wherein:

U is a nucleobase;

V is —O—R$^Y$ or —S—R$^Z$;

R$^1$, R$^2$, R$^3$, and R$^4$ are independently selected from hydrogen, deuterium, halogen, azido, cyano, isocyano, nitrate, nitrosooxy, nitroso, nitro, formyl, carboxyl, optionally substituted alkyl, optionally substituted heteroalkyl, optionally substituted carbocyclyl, optionally substituted heterocyclyl, optionally substituted aryl, optionally substituted heteroaryl, azo, acyl, optionally O-substituted hydroxyl, optionally S-substituted mercapto, sulfinyl, sulfonyl, sulfonate, optionally N-substituted amino, optionally N-substituted amide, optionally N-substituted sulfamoyl, optionally Si-substituted silyl, ester, carbonate ester, optionally substituted carbamate, optionally N-substituted aminooxy, and optionally N- and/or O-substituted hydroxyamino; and R$^Y$ and R$^Z$ are independently selected from hydrogen, optionally substituted alkyl, optionally substituted heteroalkyl, optionally substituted carbocyclyl, optionally substituted heterocarbocyclyl, optionally substituted aryl, and optionally substituted heteroaryl.

In some embodiments, L has a structure of Formula V':

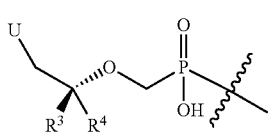

wherein U, $R^3$, and $R^4$ are the same as defined above.

In some embodiments, L is selected from the following:

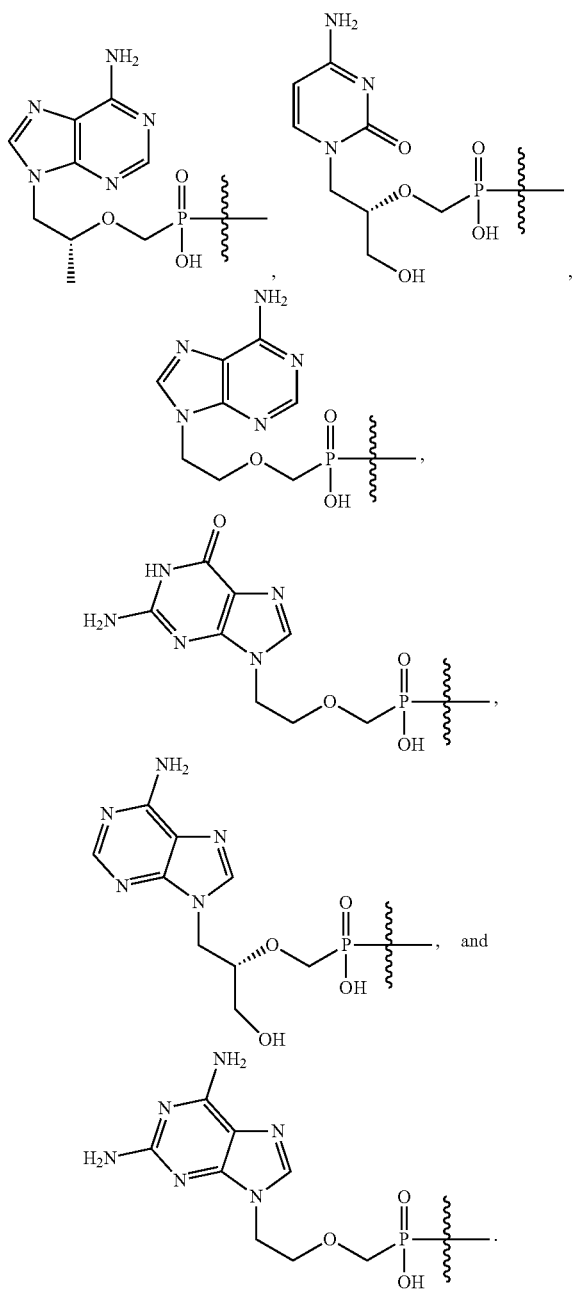

In some embodiments, W is a $C_1$-$C_9$ alkylene. In some embodiments, W is a linear $C_1$-$C_9$ alkylene, such as ethylene (—$CH_2CH_2$—) or propylene (—$CH_2CH_2CH_2$—).

In some embodiments, X is selected from substituted methylene or ethylene, —O—, —S—, —S(=O)—, and —S(O)$_2$—. In some embodiments, X is —CF$_2$—, —O—, or —S—.

In some embodiments, Y is a linear $C_2$-$C_{20}$ alkylene. In some embodiments, Y is a linear $C_8$-$C_{20}$ alkylene.

In some embodiments, Z is selected from substituted methyl or ethyl, optionally substituted unsaturated $C_2$-$C_3$ alkyl, optionally substituted carbocyclyl, optionally substituted heterocyclyl, optionally substituted aryl, optionally substituted heteroaryl, Si-substituted silyl, S-substituted thiol, O-substituted hydroxyl, ester, and —SF$_5$.

In some embodiments, Z is selected from the following: —CD$_3$, —CF$_3$, —CD$_2$CD$_3$, —CF$_2$CF$_3$, —S-Ph, —O-Ph, —C≡CH, —C≡CCD$_3$, —CH$_2$FC≡C, —CHF$_2$C≡C, —C≡CSi(CH$_3$)$_3$, —C≡CC(CH$_3$)$_3$, —C≡CCF$_3$, —C≡CSF$_5$, —Si(CH$_3$)$_3$, —C(CH$_3$)$_3$, —C(O)OCH$_3$, —SF$_5$,

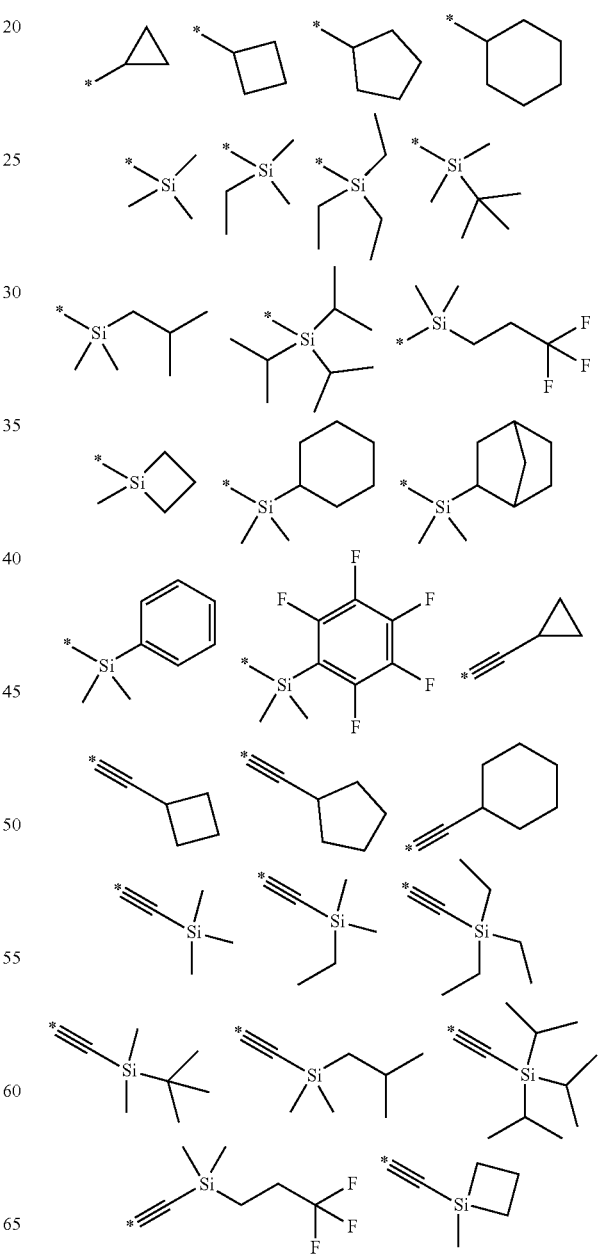

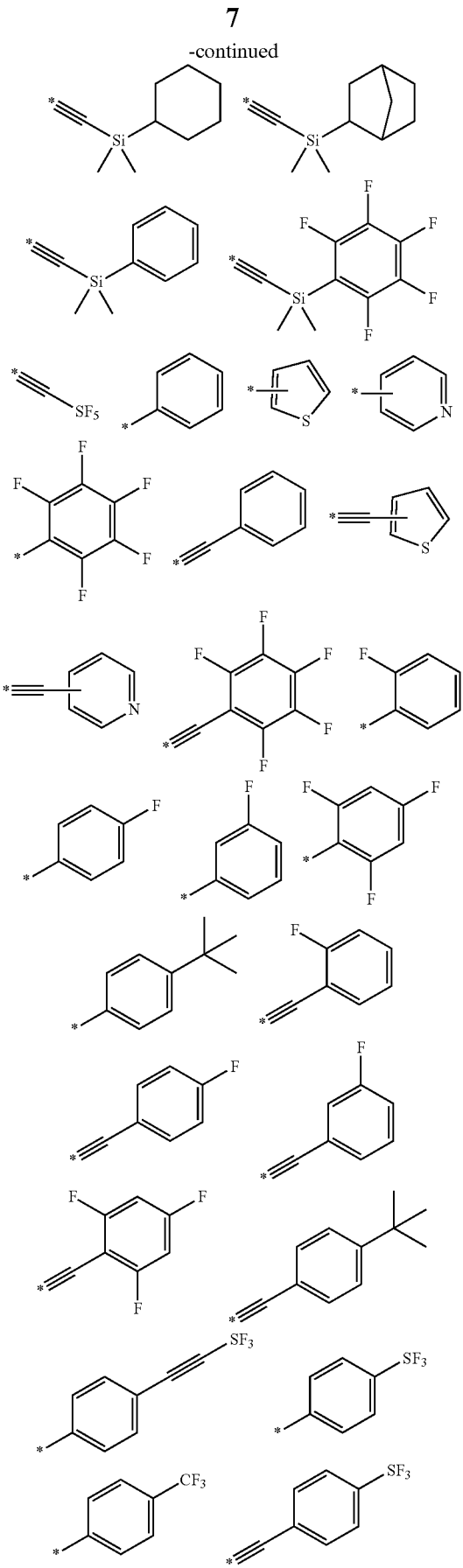

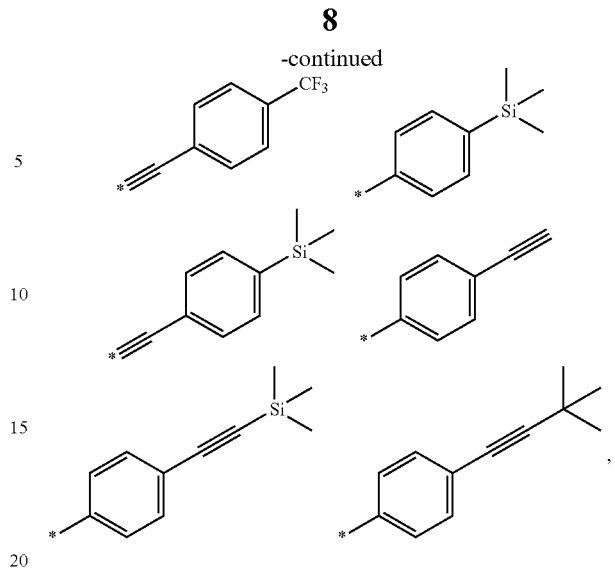

wherein * indicates the point of attachment to Y In some embodiments, Z is —CF$_3$ or —C≡CSi(CH$_3$)$_3$.

In some embodiments, the compounds have the following features:

W is —CH$_2$CH$_2$— or —CH$_2$CH$_2$CH$_2$—;
X is —CF$_2$—, —O—, or —S—;
Y is a linear C$_8$-C$_{20}$ alkylene; and
Z is selected from the group consisting of substituted methyl or ethyl, optionally substituted unsaturated C$_2$-C$_3$ alkyl, optionally substituted carbocyclyl, optionally substituted heterocyclyl, optionally substituted aryl, optionally substituted heteroaryl, Si-substituted silyl, S-substituted thiol, O-substituted hydroxyl, ester, and —SF$_5$.

Exemplary compounds are described in the detailed description shown below.

In some embodiments, the compounds have a higher human liver microsome (HLM) stability (t$_{1/2}$) than that of CMX157. For example, the compounds may have an HLM t$_{1/2}$ longer than 45 min, 60 min, 90 min, or 120 min.

Also disclosed are pharmaceutical formulations of the disclosed compounds. In general, the pharmaceutical formulations also contain a pharmaceutically acceptable carrier. In some embodiments, the pharmaceutical formulations are in the form of tablet, capsule, pill, gel, cream, granule, solution, suspension, emulsion, or nanoparticulate formulation. In some embodiments, the pharmaceutical formulations are oral formulations.

Also disclosed are methods for treating viral infections or viral-associated cancers in a subject in need thereof. Generally, the methods include administering an effective amount of a compound disclosed herein or a pharmaceutical formulation thereof to the subject. In some embodiments, the compound or pharmaceutical formulation is administered orally.

In some embodiments, the disclosed compounds and pharmaceutical formulations thereof are used to treat viral infections such as those caused by human immunodeficiency virus (HIV), hepatitis viruses, herpes viruses, flaviviruses, pox viruses, paramyxoviruses, influenzas, corona viruses, smallpox viruses, human papillomavirus (HPV), or filoviruses.

In some embodiments, the disclosure also relates to methods of preparing compounds disclosed herein including mixing one or more starting materials with reagents under conditions such that the products are formed.

It is an object of the disclosure to provide therapeutic agents with improved drug properties.

It is another object of the disclosure to provide pharmaceutically acceptable formulations of the therapeutic agents disclosed herein.

It is yet another object of the disclosure to provide improved antiviral and/or anticancer therapies involving the therapeutic agents disclosed herein and their pharmaceutically acceptable formulations thereof.

DETAILED DESCRIPTION

Figure 1A:
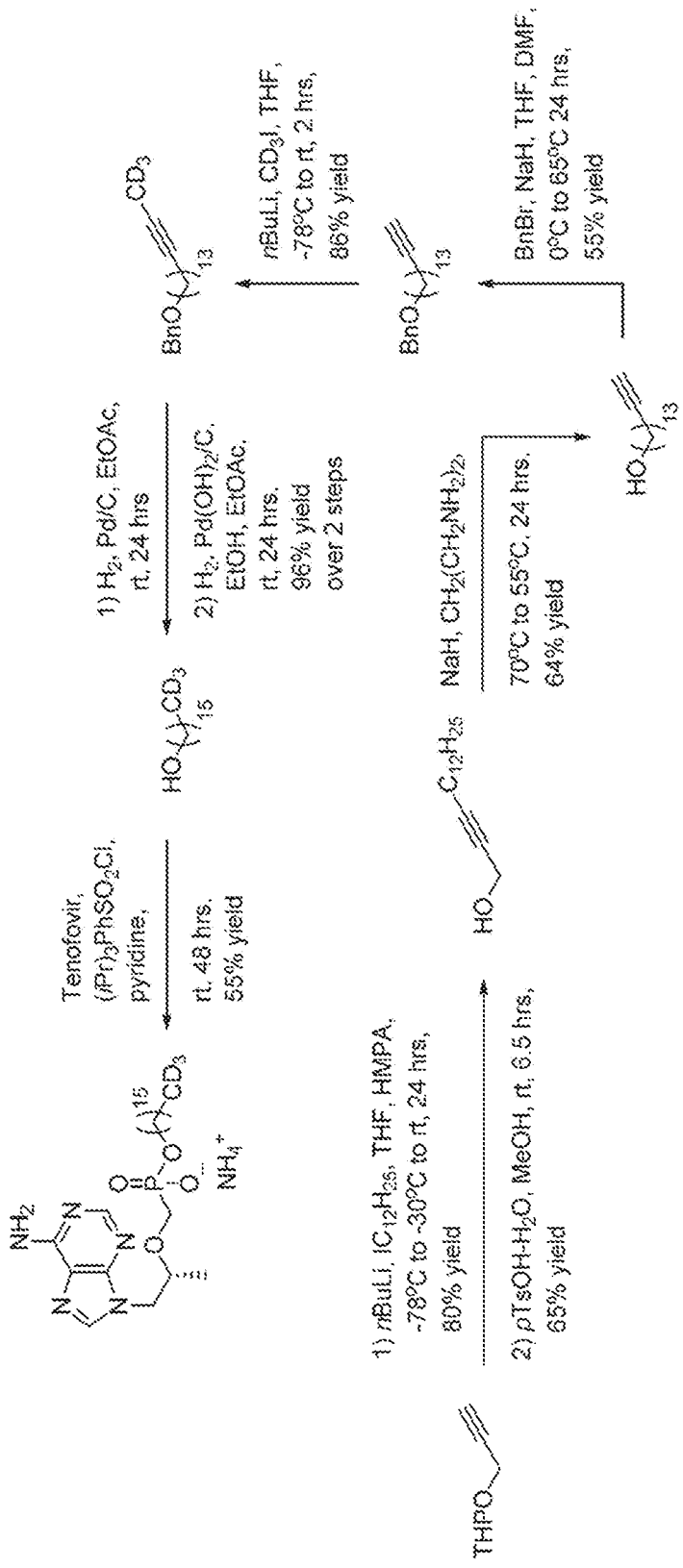
FIG. 1A illustrates the synthetic procedures involved in Example 3.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

To the extent that chemical formulas reported herein contain one or more unspecified chiral centers, the formulas are intended to encompass all stable stereoisomers, enantiomers, and diastereomers. It is also understood that formula encompass all tautomeric forms.

It will be appreciated that exemplary compounds of the present disclosure include ammonium salts of tenofovir-based prodrugs and 9-[2-(phosphonomethoxy)ethyl] guanine (PMEG)-based prodrugs. Other salts, nucleosides, and acyclic nucleosides not exemplified are equally applicable and included within the scope of this disclosure.

I. Definitions

It must be noted that, as used in the specification, the singular forms "a," "an," and "the" include plural referents unless the context clearly dictates otherwise.

"Subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments of the present disclosure also contemplate treatment that merely reduces symptoms and/or delays disease progression.

As used herein, the term "combination with" when used to describe administration with an additional treatment means that the agent may be administered prior to, together with, or after the additional treatment, or a combination thereof.

A "linking group" refers to any variety of molecular arrangements that can be used to bridge two molecular moieties together. An example formula may be —$R_m$— wherein R is selected individually and independently at each occurrence as: —$CR_mR_m$—, —$CHR_m$—, —CH—, —C—, —$CH_2$—, —$C(OH)R_m$, —C(OH)(OH)—, —C(OH)H, —C(Hal)$R_m$—, —C(Hal)(Hal)-, —C(Hal)H—, —C($N_3$)$R_m$—, —C(CN)$R_m$—, —C(CN)(CN)—, —C(CN)H—, —C($N_3$)($N_3$)—, —C($N_3$)H—, —O—, —S—, —N—, —NH—, —$NR_m$—, —(C=O)—, —(C=NH)—, —(C=S)—, —(C=$CH_2$)—, which may contain single, double, or triple bonds individually and independently between the R groups. If an R is branched with an $R_m$ it may be terminated with a group such as —$CH_3$, —H, —CH=CH₂, —CCH, —OH, —SH, —NH₂, —N₃, —CN, or -Hal, or two branched Rs may form a cyclic structure. It is contemplated that in certain instances, the total Rs or "m" may be less than 100 or 50 or 25 or 10. Examples of linking groups in include bridging alkyl groups and alkoxyalkyl groups. It is contemplated the linking group can be an acyclic linking group such as substituted or unsubstituted alkoxy phosphonates, including substituted or unsubstituted (phosphonomethoxy)ethyl.

As used herein, "alkyl" means a noncyclic, straight chain or branched chain, unsaturated or saturated hydrocarbon such as those containing from 1 to 25 carbon atoms. For example, a "$C_8$-$C_{18}$" refers to an alkyl containing 8 to 18 carbon atoms. Likewise, a "$C_6$-$C_{22}$" refers to an alkyl containing 6 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

As used herein, "heteroalkyl" refers to alkyl groups where one or more carbon atoms are replaced with a heteroatom, such as, O, N, or S. Similar to alkyl groups, heteroalkyl groups can be straight or branched, saturated or saturated. Optionally, the nitrogen and/or sulphur heteroatom(s) can be oxidized, and the nitrogen heteroatom(s) can be quaternized. Suitable heteroalkyl groups may contain 1 to 25 carbon atoms and 1 to 4 heteroatoms.

Non-aromatic, mono or polycyclic alkyls are referred to herein as "carbocycles" or "carbocyclyl" groups. Representative saturated carbocycles include cyclopropyl, cyclobutyl, cyclopentyl, cyclohexyl, and the like; while representative unsaturated carbocycles include cyclopentenyl, cyclohexenyl, and the like. In polycyclic carbocyclyl groups, the rings can be attached together in a pendant manner (i.e., two rings are connected by a single bond), in a spiro manner (i.e., two rings are connected through a defining single common atom), in a fused manner (i.e., two rings share two adjacent atoms; in other words, two rings share one covalent bond), in a bridged manner (i.e., two rings share three or more atoms, separating the two bridgehead atoms by a bridge containing at least one atom), or a combination thereof. The number of "members" of a carbocyclyl group refers to the total number of carbon atoms in the ring(s) of the carbocyclyl group.

"Heterocarbocycles" or "heterocarbocyclyl" groups are carbocycles which contain from 1 to 4 heteroatoms independently selected from nitrogen, oxygen and sulphur, wherein the nitrogen and/or sulphur heteroatom(s) may be optionally oxidized, and the nitrogen heteroatom(s) may be optionally quaternized. Heterocarbocycles may be saturated or unsaturated (but not aromatic), monocyclic or polycyclic. Exemplary heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, and the like. The number of "members" of a heterocarbocyclyl group refers to the total number of carbon atoms and heteroatoms in the ring(s) of the heterocarbocyclyl group.

The term "aryl" refers to aromatic homocyclic (i.e., hydrocarbon) mono-, bi- or tricyclic ring-containing groups, preferably having 6 to 12 members, such as phenyl, naphthyl and biphenyl. Optionally, the aryl group is phenyl. In polycyclic aryl groups, the rings can be attached together in a pendant manner or can be fused. The number of "members" of an alkyl group refers to the total number of carbon atoms in the ring(s) of the alkyl group.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent. The number of "members" of a heteroaryl group refers to the total number of carbon atoms and heteroatoms in the ring(s) of the heteroaryl group.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like. In polycyclic heterocyclyl groups, the rings can be attached together in a pendant manner (i.e., two rings are connected by a single bond), in a spiro manner (i.e., two rings are connected through a defining single common atom), in a fused manner (i.e., two rings share two adjacent atoms; in other words, two rings share one covalent bond), in a bridged manner (i.e., two rings share three or more atoms, separating the two bridgehead atoms by a bridge containing at least one atom), or a combination thereof. The number of "members" of a heterocyclyl group refers to the total number of carbon atoms and heteroatoms in the ring(s) of the heterocyclyl group.

"Alkoxy" or "alkyloxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkoxyalkyl" refers an alkoxy group as defined above with the indicated number of carbon atoms attached through an alkyl bridge (i.e., —CH₂—O—CH₂CH₃).

"Alkylamino" refers an alkyl group as defined above with the indicated number of carbon atoms attached through an amino bridge. An example of an alkylamino is methylamino (i.e., —NH—CH₃).

"Alkylthio" refers to an alkyl group as defined above with the indicated number of carbon atoms attached through a sulfur bridge. An example of an alkylthio is methylthio (i.e., —S—CH₃).

"Alkanoyl" refers to an alkyl as defined above with the indicated number of carbon atoms attached through a carbonyl bridge (i.e., —(C=O)alkyl).

The terms "cycloalkyl" and "cycloalkenyl" refer to mono-, bi-, or tri homocyclic ring groups of 3 to 15 carbon atoms which are, respectively, fully saturated and partially unsaturated (but not aromatic).

The terms "halogen" or "Hal" refer to fluorine, chlorine, bromine, and iodine.

The term "substituted" refers to a molecule wherein at least one hydrogen atom is replaced with a substituent. The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NR$^a$R$^b$, —NR$^a$C(=O)R$^b$, —NR$^a$C(=O)NR$^a$R$^b$, —NR$_a$C(=O)OR$_b$, —NR$_a$SO$_2$R$_b$, —C(=O)R$^a$, —C(=O)OR$^a$, —C(=O)NR$^a$R$^b$, —OC(=O)NR$_a$R$_b$, —OR$_a$, —SR$_a$, —SOR$_a$, —S(=O)$_2$R$_a$, —OS(=O)$_2$R$_a$, and —S(=O)$_2$OR$_a$. R$_a$ and R$_b$ in this context may be the same or different, and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, or heteroarylalkyl.

The term "optionally substituted," as used herein, means that substitution is optional and therefore it is possible for the designated atom to be unsubstituted.

It is understood that any substitution is in accordance with permitted valence of the substituted atom and the substituent, and that the substitution results in a stable compound, i.e., a compound that does not spontaneously undergo transformation such as by rearrangement, cyclization, elimination, etc., at room temperature.

The term "nucleoside" refers to a non-aromatic five membered ring substituted, e.g., tetrahydrofuran-2-yl substituted in the 5 position, with a nucleobase or heterocyclic derivative thereof. The five membered ring and/or nucleobase may be further substituted or derivatized. Examples of nucleosides with modified adenosine or guanosine include, but are not limited to, hypoxanthine, xanthine, and 7-methylguanine. Examples of nucleosides with modified cytidine, thymidine, or uridine include 5,6-dihydrouracil, 5-methylcytosine, and 5-hydroxymethylcytosine.

The term "acyclic nucleoside phosphonate" refers to a nucleobase or heterocyclic derivative thereof substituted with an acyclic linking group such as substituted or unsubstituted alkoxy phosphonates, including substituted or unsubstituted (phosphonomethoxy)ethyl. Examples include tenofovir, cidofovir, adefovir, (9-[2-(phosphonomethoxy) ethyl] guanine), 9-(3-hydroxy-2-phosphonylmethoxypropyl)adenine and 9-(2-phosphonylmethoxyethyl)-2,6-diaminopurine.

A "nucleobase" refers to any variety of nitrogen containing monocyclic or bicyclic heterocycles. Nucleobases typically have at least one optionally substituted amino group connected to the ring(s), or a carbonyl/hydroxyl group within the ring(s), or an optionally substituted amide connected to the ring(s). Typically having two to four nitrogen atoms in the ring(s). Examples of a nucleobase include adenine, guanine, cytosine, uracil, thymine, inosine, and heterocycles of the following structures:

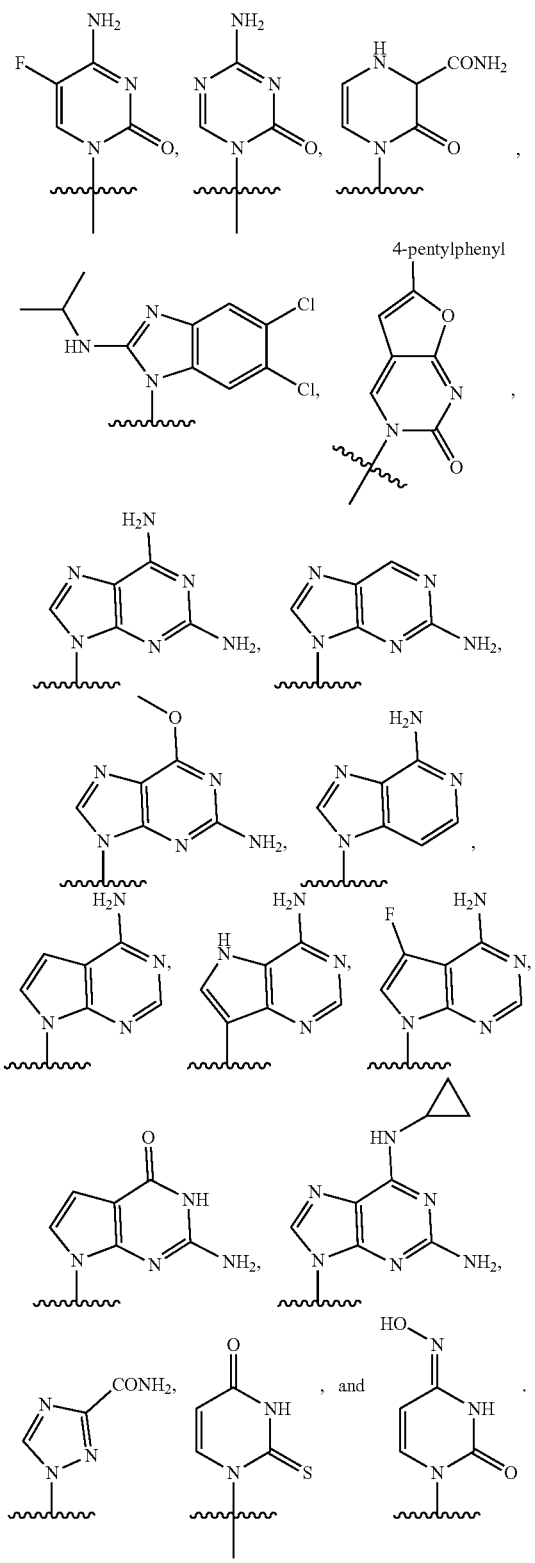

With regard to the nucleobases, it is contemplated that the term encompasses isobases. Contemplated isobases include 2'-deoxy-5-methylisocytidine (iC) and 2'-deoxy-isoguanosine (iG).

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, adding a hydroxyl group, replacing an oxygen atom with a sulfur atom, or replacing an amino group with a hydroxyl group, oxidizing a hydroxyl group to a carbonyl group, reducing a carbonyl group to a hydroxyl group, and reducing a carbon-to-carbon double bond to an alkyl group or oxidizing a carbon-to-carbon single bond to a double bond. A derivative optional has one or more, the same or different, substitutions. Derivatives may be prepared by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

II. Compounds

Disclosed are nucleoside prodrugs having a structure of Formula I or a pharmaceutically acceptable salt thereof:

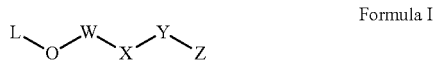

Formula I wherein:
L is an acyclic nucleoside phosphonate;
W is absent or a saturated $C_1$-$C_9$ alkyl chain (i.e., bridging $C_1$-$C_9$ alkylene);
X is absent or is selected from substituted methylene or ethylene, —O—, —S—, —S(=O)—, and —S(O)$_2$—;
Y is a saturated $C_2$-$C_{20}$ alkyl chain (i.e., bridging $C_2$-$C_{20}$ alkylene); and
Z is selected from hydrogen, optionally substituted methyl or ethyl, optionally substituted unsaturated $C_2$-$C_3$ alkyl, optionally substituted carbocyclyl, optionally substituted heterocyclyl, optionally substituted aryl, optionally substituted heteroaryl, Si-substituted silyl, S-substituted thiol, O-substituted hydroxyl, ester, and —SF$_5$.

Preferably, when X is —O—, Z is not hydrogen, methyl, or ethyl.

Preferably, when both W and X are absent, Z is not hydrogen, methyl, or ethyl.

Preferably, when W is absent, X is also absent.

In some embodiments, both W and X are present, i.e., L-O—W—X—Y—Z.

In some embodiments, both W and X are absent, i.e., L-O—Y—Z.

In some embodiments, W is present, and X is absent, i.e., L-O—W—Y—Z.

The substituted groups or optionally substituted groups described in Formula I can have one or more substituents independently selected from deuterium, halogen, azido, cyano, isocyano, nitrate, nitrosooxy, nitroso, nitro, formyl, carboxyl, alkyl, heteroalkyl, carbocyclyl, heterocyclyl, aryl, heteroaryl, azo, acyl, hydroxyl, mercapto, sulfinyl, sulfonyl, sulfonate, sulfamoyl, amino, acylamino, amide, silyl, ester, carbonate ester, carbamate, aminooxy, hydroxyamino, and —SF$_5$, wherein each substituent may be further substituted by one or more $R^A$ groups. In some embodiments, two substituents on the same atom can join together with that atom to form a cyclic moiety, such as a carbocycle or a heterocycle.

For example, the Si-substituted silyl in Formula I can have one, two, or three substituents independently selected from those described above. When there are multiple substituents, two of the substituents can join together with the Si atom to form a cyclic moiety, such as a heterocycle. In some embodiments, the substituent(s) is independently selected from alkyl, heteroalkyl, carbocyclyl, heterocyclyl, aryl, and heteroaryl, wherein each substituent may be further substituted by one or more $R^A$ groups. In some embodiments, the Si-substituted silyl has three substituents, independently selected from alkyl, heteroalkyl, carbocyclyl, heterocyclyl, aryl, and heteroaryl, wherein each substituent may be further substituted by one or more $R^A$ groups. Exemplary Si-substituted silyl groups include, but are not limited to, the following:

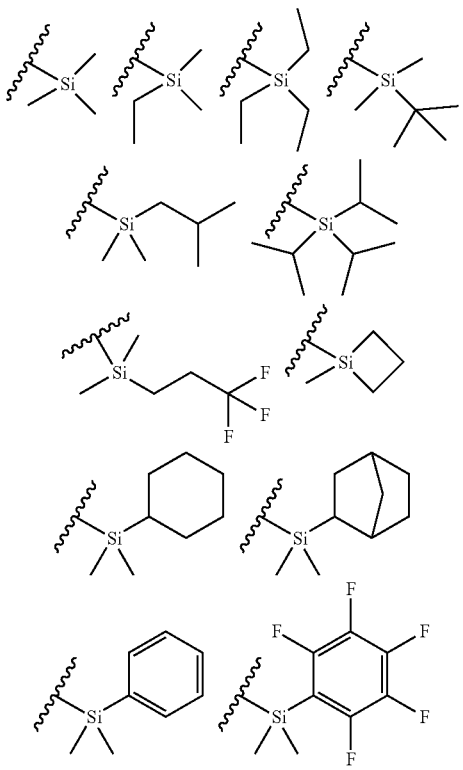

$R^A$, in each occurrence, can be independently selected from halogen, alkyl optionally substituted by one or more halogen, heteroalkyl optionally substituted by one or more halogen, carbocyclyl optionally substituted by one or more halogen, heterocyclyl optionally substituted by one or more halogen, aryl optionally substituted by one or more halogen, heteroaryl optionally substituted by one or more halogen, —OH, —SH, —NH$_2$, —N$_3$, —OCN, —NCO, —ONO$_2$, —CN, —NC, —ONO, —CONH$_2$, —NO, —NO$_2$, —ONH$_2$, —SCN, —SNCS, —SF$_5$, —CF$_3$, —CH$_2$CF$_3$, —CH$_2$Cl, —CHCl$_2$, —CH$_2$NH$_2$, —NHCOH, —CHO, —COOH, —SO$_3$H, —CH$_2$SO$_2$CH$_3$, —PO$_3$H$_2$, —OPO$_3$H$_2$, —P(=O)(OR$^{G1}$)(OR$^{G2}$), —OP(=O)(OR$^{G1}$)(OR$^{G2}$), —BR$^{G1}$(OR$^{G2}$), —B(OR$^{G1}$)(OR$^{G2}$), —Si(R$^{G1}$)(R$^{G2}$)(R$^{G3}$), or -GR$^{G1}$ in which -G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G3}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, —NR$^{G2}$C(=S)—, —SC(=S)NR$^{G2}$—, —NR$^{G2}$C(=S)S—, —NR$^{G2}$C(=S)NR$^{G3}$—, —SC(=NR$^{G2}$)—, —C(=S)NR$^{G2}$—, —OC(=S)NR$^{G2}$—, —NR$^{G2}$C(=S)O—, —SC(=O)NR$^{G2}$—, —NR$^{G2}$C(=O)S—, —C(=O)S—, —SC(=O)—, —SC(=O)S—, —C(=S)O—, —OC(=S)—, —OC(=S)O—, —SO$_2$NR$^{G2}$—, —BR$^{G2}$—, or —PR$^{G2}$—, wherein each occurrence of R$^{G1}$, R$^{G2}$, and R$^{G3}$ is, independently, a hydrogen atom, a halogen atom, an alkyl group optionally substituted by one or more halogen, a heteroalkyl group optionally substituted by one or more halogen, a carbocyclyl group optionally substituted by one or more halogen, a heterocyclyl group optionally substituted by one or more halogen, an aryl group optionally substituted by one or more halogen, or a heteroaryl group optionally substituted by one or more halogen. When R$^A$ is —Si(R$^{G1}$)(R$^{G2}$)(R$^{G3}$) two groups from R$^{G1}$, R$^{G2}$, and R$^{G3}$ can join together with the Si atom to form a cyclic moiety, such as a heterocycle.

In some embodiments, two R$^A$ on the same atom can join together with that atom to form a cyclic moiety, such as a carbocycle or a heterocycle.

In some embodiments, the substituted groups or optionally substituted groups described in Formula I can have one or more substituents independently selected from deuterium, halogen, nitro, cyano, hydroxyl, trifluoromethoxy, trifluoromethyl, alkylsilyl (such as trimethylsilyl, methyl(methyl)(ethyl)silyl, triethylsilyl, triisopropylsilyl, methyl(methyl)(tert-butyl)silyl, methyl(methyl)(isobutyl)silyl), formyl, carboxyl, mercapto, sulfamoyl, alkyl (such as methyl, ethyl, isopropyl, tert-butyl), alkyloxy (such as methoxy, ethoxy), acyl (such as acetyl), acyloxy (such as acetoxy), amino, alkylamino (such as methylamino, ethylamino, dimethylamino, diethylamino, N-methyl-N-ethylamino), acylamino (acetylamino), carbamoyl, N-alkylcarbamoyl (such as N-methylcarbamoyl, N-ethylcarbamoyl, N,N-dimethylcarbamoyl, N,N-diethylcarbamoyl, N-methyl-N-ethylcarbamoyl), alkylthio (such as methylthio, ethylthio), alkylsulfinyl (such as methylsulfinyl, ethylsulfinyl), alkylsulfonyl (such as mesyl, ethylsulfonyl), alkyloxycarbonyl (such as methoxycarbonyl, ethoxycarbonyl), N-alkylsulfamoyl (such as N-methylsulfamoyl, N-ethylsulfamoyl, N,N-dimethylsulfamoyl, N,N-diethylsulfamoyl, N-methyl-N-ethylsulfamoyl), arylalkyl (such as benzyl), arylcarbonyl (such as benzoyl), heteroalkyl, carbocyclyl, heterocyclyl, aryl, heteroaryl, and —SF$_5$.

In some embodiments, the substituted groups or optionally substituted groups described in Formula I can have one or more substituents independently selected from deuterium, halogen, nitro, cyano, hydroxyl, trifluoromethoxy, trifluoromethyl, trimethylsilyl, amino, formyl, carboxyl, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, benzyl, benzoyl, alkyl, carbocyclyl, aryl, and heterocyclyl.

As used herein, "alkylene" refers to divalent functional groups derived from an alkane (i.e., acyclic saturated hydrocarbon) by removal of two hydrogen atoms from two different carbon atoms.

As used herein, "silyl" refers to the univalent radical derived from silane by removal of a hydrogen atom, i.e., —SiH$_3$.

As used herein, "thiol" refers to the univalent radical —SH.

As used herein, "acyl" refers —C(=O)R$^B$, wherein R$^B$ is an alkyl group, a heteroalkyl group, a carbocyclyl group, a heterocyclyl group, an aryl group, or a heteroaryl group. As described above, the acyl group can be optionally substituted by one or more R$^A$ groups.

As used herein, "sulfonate" refers to —SO$_3^-$.

As used herein, "amide" refers to —C(=O)NR$^C$R$^D$, wherein R$^C$ and R$^D$ are independently selected from hydrogen, alkyl, heteroalkyl, carbocyclyl, heterocyclyl, aryl, and heteroaryl. When both R$^C$ and R$^D$ are hydrogen, the amide group is carbamoyl. As described above, the amide group can be optionally substituted by one or more R$^A$ groups.

As used herein, "sulfamoyl" refers to —S(=O)$_2$NH$_2$. As described above, the sulfamoyl group can be optionally substituted by one or more R$^A$ groups.

As used herein, "ester" refers to —C(=O)OR$^E$ or —OC(=O)R$^F$, wherein R$^E$ and R$^F$ are independently selected from alkyl, heteroalkyl, carbocyclyl, heterocyclyl, aryl, and heteroaryl. As described above, the ester group can be optionally substituted by one or more R$^A$ groups.

As used herein, "carbonate ester" refers to —OC(=O)OR$^H$, wherein R$^H$ is an alkyl group, a heteroalkyl group, a carbocyclyl group, a heterocyclyl group, an aryl group, or a heteroaryl group. As described above, the carbonate ester group can be optionally substituted by one or more R$^A$ groups.

As used herein, "carbamate" refers to —OC(=O)NR$^I$R$^J$ or —NR$^K$[(C=O)OR$^L$], wherein R$^I$, R$^J$, R$^K$, and R$^L$ are independently selected from hydrogen, alkyl, heteroalkyl, carbocyclyl, heterocyclyl, aryl, and heteroaryl. As described above, the carbamate group can be optionally substituted by one or more R$^A$ groups.

As used herein, "aminooxy" refers to —O—NH$_2$. As described above, the aminooxy group can be optionally substituted by one or more R$^A$ groups.

As used herein, "hydroxyamino" refers to —NH(OH). As described above, the hydroxyamino group can be optionally substituted by one or more R$^A$ groups.

As used herein, "sulfinyl" refers to —S(=O)R$^M$, wherein R$^M$ is an alkyl group, a heteroalkyl group, a carbocyclyl group, a heterocyclyl group, an aryl group, or a heteroaryl group. As described above, the sulfinyl group can be optionally substituted by one or more R$^A$ groups.

As used herein, "sulfonyl" refers to —S(=O)$_2$R$^N$, wherein R$^N$ is an alkyl group, a heteroalkyl group, a carbocyclyl group, a heterocyclyl group, an aryl group, or a heteroaryl group. As described above, the sulfonyl group can be optionally substituted by one or more R$^A$ groups.

As used herein, "acylamino" refers to —NR$^O$[C(=O)R$^P$], wherein R$^O$ is hydrogen, an alkyl group, a heteroalkyl group, a carbocyclyl group, a heterocyclyl group, an aryl group, or a heteroaryl group, and R$^P$ is an alkyl group, a heteroalkyl group, a carbocyclyl group, a heterocyclyl group, an aryl group, or a heteroaryl group. As described above, the acylamino group can be optionally substituted by one or more $R^A$ groups.

"Pharmaceutically acceptable salt" refers to the modification of the original compound by making the acid or base salts thereof. Examples of pharmaceutically acceptable salts include, but are not limited to, mineral or organic acid salts of basic residues such as amines, as well as alkali or organic salts of acidic residues such as carboxylic acids or phosphorus acids. For original compounds containing a basic residue, the pharmaceutically acceptable salts can be prepared by treating the compounds with an appropriate amount of a non-toxic inorganic or organic acid; alternatively, the pharmaceutically acceptable salts can be formed in situ during the preparation of the original compounds. Exemplary salts of the basic residue include salts with an acid selected from hydrochloric, hydrobromic, sulfuric, sulfamic, phosphoric, and nitric acids; suitable organic acids include acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, naphthalenesulfonic, methanesulfonic, ethane disulfonic, oxalic, and isethionic acids. For original compounds containing an acidic residue, the pharmaceutically acceptable salts can be prepared by treating the compounds with an appropriate amount of a non-toxic base; alternatively, the pharmaceutically acceptable salts can be formed in situ during the preparation of the original compounds. Exemplary salts of the acidic residue include salts with a base selected from ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, and histidine. Optionally, the pharmaceutically acceptable salts can be prepared by reacting the free acid or base form of the original compounds with a stoichiometric amount or more of the appropriate base or acid, respectively, in water, in an organic solvent, or in a mixture thereof. L ists of suitable pharmaceutically acceptable salts can be found in Remington's Pharmaceutical Sciences, 20th Ed., Lippincott Williams & Wilkins, Baltimore, MD, 2000, p. 704; and Handbook of Pharmaceutical Salts: Properties, Selection, and Use, Stahl and Wermuth, Eds., Wiley-VCH, Weinheim, 2002.

In some embodiments, the pharmaceutical acceptable salts of the compounds disclosed herein are salts with ammonium hydroxide, i.e., ammonium salts.

The disclosed compounds may be present in a mixture of stereoisomers. In some embodiments, the compounds in the mixture of stereoisomers may be in greater than 60%, 70%, 80%, 90%, 95%, 98% diastereomeric or enantiomeric excess. In some embodiments, the compounds in the mixture of stereoisomers may be in greater than 90% diastereomeric or enantiomeric excess.

Methods of making exemplary compounds are disclosed. The methods are compatible with a wide variety of functional groups and compounds, and thus a wide variety of derivatives can be obtainable from the disclosed methods. For example, a general method for phosphonate monoesterification on tenofovir and PMEG is exemplified in the examples. Depending on the properties of the lipid-like moiety (i.e., —W—X—Y—Z) to be incorporated in the compounds, the synthetic method involves the use of DCC or EDC as the coupling agent in the presence of triethylamine (TEA) and DMAP. The reaction can be conducted under high heat (e.g., 90-105° C.) for 18-24 hours, and the product can be purified immediately after a quench with water. The purification of the compounds can be performed using a sequential normal (DCM:MeOH:NH$_4$Cl) and reverse (H$_2$O:MeOH) phase column chromatography approach. In some embodiments, a deprotection step either in NH$_3$/MeOH or AcOH/MeOH can be performed to produce the unprotected product.

A. Structural Features

1. The "L" Moiety

L is an acyclic nucleoside phosphonate.

In some embodiments, L is a nucleobase or heterocyclic derivative thereof substituted with an acyclic linking group, wherein the acyclic linking group is a substituted or unsubstituted alkoxy phosphonate. In some embodiments, the alkoxy phosphonate is a substituted or unsubstituted (phosphonomethoxy)ethyl group.

In some embodiments, L has a structure of Formula V:

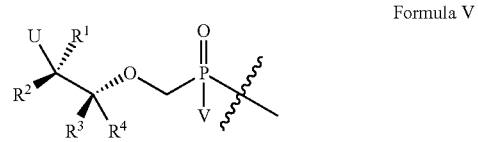

Formula V wherein:

U is a nucleobase;

V is —O—$R^Y$ or —S—$R^Z$;

$R^1$, $R^2$, $R^3$, and $R^4$ are independently selected from hydrogen, deuterium, halogen, azido, cyano, isocyano, nitrate, nitrosooxy, nitroso, nitro, formyl, carboxyl, optionally substituted alkyl, optionally substituted heteroalkyl, optionally substituted carbocyclyl, optionally substituted heterocyclyl, optionally substituted aryl, optionally substituted heteroaryl, azo, acyl, optionally O-substituted hydroxyl, optionally S-substituted mercapto, sulfinyl, sulfonyl, sulfonate, optionally N-substituted amino, optionally N-substituted amide, optionally N-substituted sulfamoyl, optionally Si-substituted silyl, ester, carbonate ester, optionally substituted carbamate, optionally N-substituted aminooxy, and optionally N- and/or O-substituted hydroxyamino; and $R^Y$ and $R^Z$ are independently selected from hydrogen, optionally substituted alkyl, optionally substituted heteroalkyl, optionally substituted carbocyclyl, optionally substituted heterocarbocyclyl, optionally substituted aryl, and optionally substituted heteroaryl.

The optionally substituted groups described in Formula V can have one or more substituents independently selected from deuterium, halogen, azido, cyano, isocyano, nitrate, nitrosooxy, nitroso, nitro, formyl, carboxyl, alkyl, heteroalkyl, carbocyclyl, heterocyclyl, aryl, heteroaryl, azo, acyl, hydroxyl, mercapto, sulfinyl, sulfonyl, sulfonate, sulfamoyl, amino, acylamino, amide, silyl, ester, carbonate ester, carbamate, aminooxy, hydroxyamino, and —SF$_5$, wherein each substituent may be further substituted by one or more $R^A$ groups as described in Formula I above. In some embodiments, two substituents on the same atom can join together with that atom to form a cyclic moiety, such as a carbocycle or a heterocycle.

In some embodiments, U is selected from adenine, guanine, cytosine, uracil, thymine, inosine, and heterocycles of the following structures:

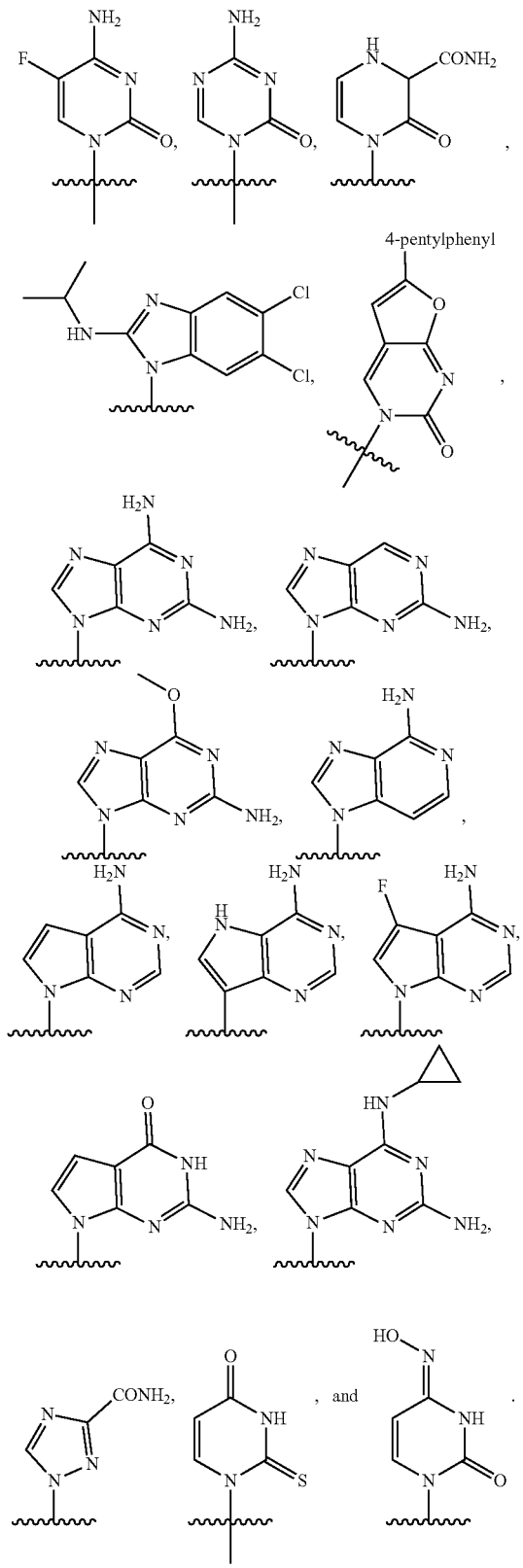

In some embodiments, U is adenine. In some embodiments, U is guanine. In some embodiments, U is cytosine. In some embodiments, U is

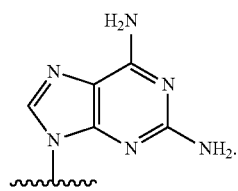 [SMILES: *n1cnc2c(N)nc(N)nc21]

In some embodiments, V is —O—$R^Y$. In some embodiments, $R^Y$ is hydrogen. In some embodiments, $R^Y$ is optionally substituted alkyl, such as benzyl. In some embodiments, $R^Y$ is optionally substituted aryl, such as phenyl or naphthyl.

In some embodiments, V is —S—$R^Z$. In some embodiments, $R^Z$ is hydrogen. In some embodiments, $R^Z$ is optionally substituted alkyl, such as benzyl. In some embodiments, $R^Z$ is optionally substituted aryl, such as phenyl or naphthyl.

In some embodiments, $R^1$, $R^2$, $R^3$, and $R^4$ are independently selected from hydrogen, optionally substituted alkyl, optionally substituted heteroalkyl, optionally substituted carbocyclyl, optionally substituted heterocyclyl, optionally substituted aryl, and optionally substituted heteroaryl.

In some embodiments, $R^1$ is hydrogen.
In some embodiments, $R^2$ is hydrogen.
In some embodiments, $R^3$ is hydrogen. In some embodiments, $R^3$ is optionally substituted alkyl. In some embodiments, $R^3$ is methyl or hydroxyl methyl.
In some embodiments, $R^4$ is hydrogen. In some embodiments, $R^4$ is optionally substituted alkyl. In some embodiments, $R^4$ is methyl or hydroxyl methyl.
In some embodiments, $R^1$, $R^2$, $R^3$, and $R^4$ are hydrogen.
In some embodiments, $R^1$ and $R^2$ are hydrogen, one of $R^3$ and $R^4$ is hydrogen, and the other one of $R^3$ and $R^4$ is optionally substituted alkyl. In some embodiments, $R^1$, $R^2$, and $R^3$ are hydrogen, and $R^4$ is methyl or hydroxyl methyl.
In some embodiments, $R^1$, $R^2$, and $R^4$ are hydrogen, and $R^3$ is methyl or hydroxyl methyl.
In some embodiments, L has a structure of Formula V':

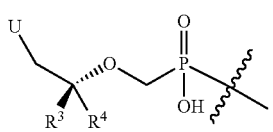

Formula V' wherein U, $R^3$, and $R^4$ are the same as defined above. In some embodiments, $R^3$ is hydrogen. In some embodiments, $R^3$ is optionally substituted alkyl. In some embodiments, $R^3$ is methyl or hydroxyl methyl. In some embodiments, $R^4$ is hydrogen. In some embodiments, $R^4$ is optionally substituted alkyl. In some embodiments, $R^4$ is methyl or hydroxyl methyl. In some embodiments, both $R^3$ and $R^4$ are hydrogen. In some embodiments, one of $R^3$ and $R^4$ is hydrogen, and the other one of $R^3$ and $R^4$ is optionally substituted alkyl. In some embodiments, $R^3$ is hydrogen, and $R^4$ is methyl or hydroxyl methyl. In some embodiments, $R^4$ is hydrogen, and $R^3$ is methyl or hydroxyl methyl.

In some embodiments, L is selected from a tenofovir moiety, a cidofovir moiety, an adefovir moiety, a 9-[2-(phosphonomethoxy)ethyl] guanine moiety, a 9-(3-hydroxy- 2-phosphonylmethoxypropyl)adenine moiety (preferably the (S)-HPMPA stereoisomer), and a 9-(2-phosphonyl-methoxyethyl)-2,6-diaminopurine moiety, as shown below:

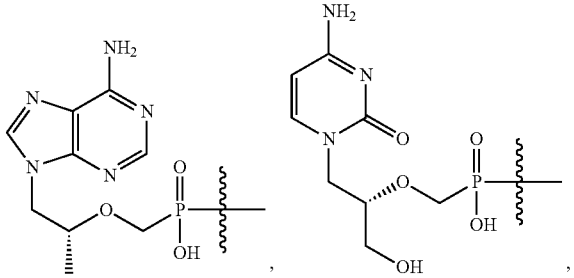

,

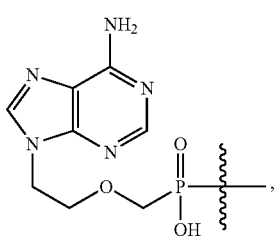

,

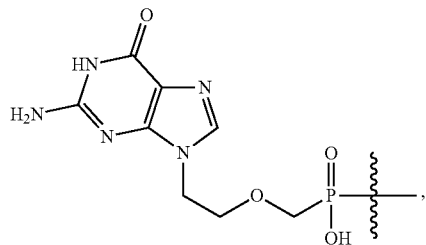

,

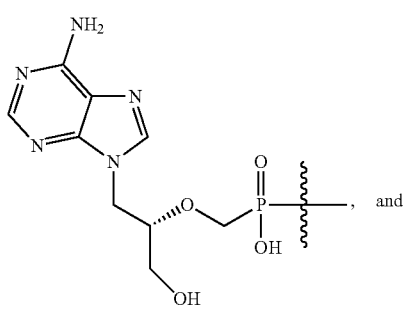

, and

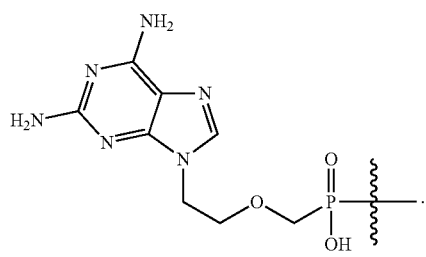

In some embodiments, L is

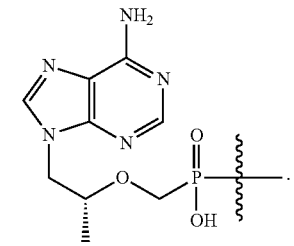 [SMILES: *P(=O)(O)CO[C@H](C)Cn1cnc2c(N)ncnc21]

.

In some embodiments, L is

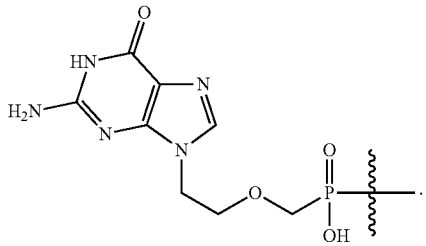 [SMILES: *P(=O)(O)COCCn1cnc2c(=O)[nH]c(N)nc21]

.

In some embodiments, L is

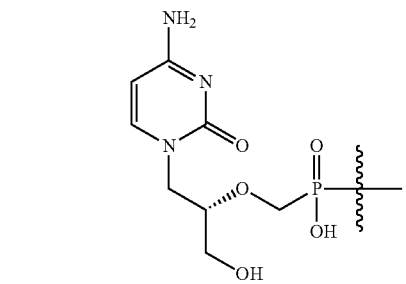

.

Other exemplary acyclic nucleoside phosphonates can be found in Clercq, *Biochemical Pharmacology*, 2007, 73, 911-922.

2. The "W" Moiety

W is absent or a saturated $C_1$-$C_9$ alkyl chain (i.e., $C_1$-$C_9$ alkylene). In some embodiments, W is absent. In some embodiments, W is a saturated $C_1$-$C_9$ alkyl chain (i.e., $C_1$-$C_9$ alkylene). In some embodiments, W is a saturated, linear $C_1$-$C_9$ alkyl chain (i.e., linear $C_1$-$C_9$ alkylene), such as methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), heptylene (—$CH_2CH_2CH_2CH_2CH_2CH_2CH_2$—), octylene (—$CH_2CH_2CH_2CH_2CH_2CH_2CH_2CH_2$—), and nonylene (—$CH_2CH_2CH_2CH_2CH_2CH_2CH_2CH_2CH_2$—).

In some embodiments, W is ethylene (—$CH_2CH_2$—), propylene (—$CH_2CH_2CH_2$—), or nonylene (—$CH_2CH_2CH_2CH_2CH_2CH_2CH_2CH_2CH_2$—). In some embodiments, W is ethylene (—$CH_2CH_2$—) or propylene (—$CH_2CH_2CH_2$—).

3. The "X" Moiety

X is absent or is selected from substituted methylene or ethylene, —O—, —S—, —S(=O)—, and —S(O)$_2$—.

In some embodiments, X is absent. In some embodiments, X is selected from substituted methylene or ethylene, —O—, —S—, —S(=O)—, and —S(O)$_2$—. In some embodiments, the substituted methylene or ethylene contains one or more halogen substituents. In some embodiments, the one or more halogen substituents are fluorine.

In some embodiments, X is substituted methylene, such as —CF$_2$—. In some embodiments, X is —O—. In some embodiments, X is —S—.

4. The "Y" Moiety

Y is a saturated C$_2$-C$_{20}$ alkyl chain (i.e., C$_2$-C$_{20}$ alkylene). In some embodiments, Y is a saturated, linear C$_2$-C$_{20}$ alkyl chain (i.e., linear C$_2$-C$_{20}$ alkylene), such as ethylene (—CH$_2$CH$_2$—), propylene (—CH$_2$CH$_2$CH$_2$—), butylene (—CH$_2$CH$_2$CH$_2$CH$_2$—), pentylene (—CH$_2$CH$_2$CH$_2$CH$_2$CH$_2$—), hexylene (—CH$_2$CH$_2$CH$_2$CH$_2$CH$_2$CH$_2$—), heptylene (—CH$_2$CH$_2$CH$_2$CH$_2$CH$_2$CH$_2$CH$_2$—), octylene (—CH$_2$CH$_2$CH$_2$CH$_2$CH$_2$CH$_2$CH$_2$CH$_2$—), nonylene [—(CH$_2$)$_9$—], decylene [—(CH$_2$)$_{10}$—], undecylene [—(CH$_2$)$_{11}$—], dodecylene [—(CH$_2$)$_{12}$—], tridecylene [—(CH$_2$)$_{13}$—], tetradecylene [—(CH$_2$)$_{14}$—], pentadecylene [—(CH$_2$)$_{15}$—], hexadecylene [—(CH$_2$)$_{16}$—], heptadecylene [—(CH$_2$)$_{17}$—], octadecylene [—(CH$_2$)$_{18}$—], nonadecylene [—(CH$_2$)$_{19}$—], and icosylene [—(CH$_2$)$_{20}$—].

In some embodiments, Y is a saturated, linear C$_2$-C$_7$ alkyl chain (i.e., linear C$_2$-C$_7$ alkylene). In some embodiments, Y is a saturated, linear C$_8$-C$_{20}$ alkyl chain (i.e., linear C$_8$-C$_{20}$ alkylene).

5. The "Z" Moiety

Z is selected from hydrogen, optionally substituted methyl or ethyl, optionally substituted unsaturated C$_2$-C$_3$ alkyl, optionally substituted carbocyclyl, optionally substituted heterocyclyl, optionally substituted aryl, optionally substituted heteroaryl, Si-substituted silyl, S-substituted thiol, O-substituted hydroxyl, ester, and —SF$_5$.

Examples of Z include, but are not limited to, —CD$_3$, —CF$_3$, —CD$_2$CD$_3$, —CF$_2$CF$_3$, —S-Ph, —O-Ph, —C≡CH, —C≡CCD$_3$, —CH$_2$FC≡C, —CHF$_2$C≡C, —C≡CSi(CH$_3$)$_3$, —C≡CC(CH$_3$)$_3$, —C≡CCF$_3$, —C≡CSF$_5$, —Si(CH$_3$)$_3$, —C(CH$_3$)$_3$, —C(O)OCH$_3$, —SF$_5$, as well as the following:

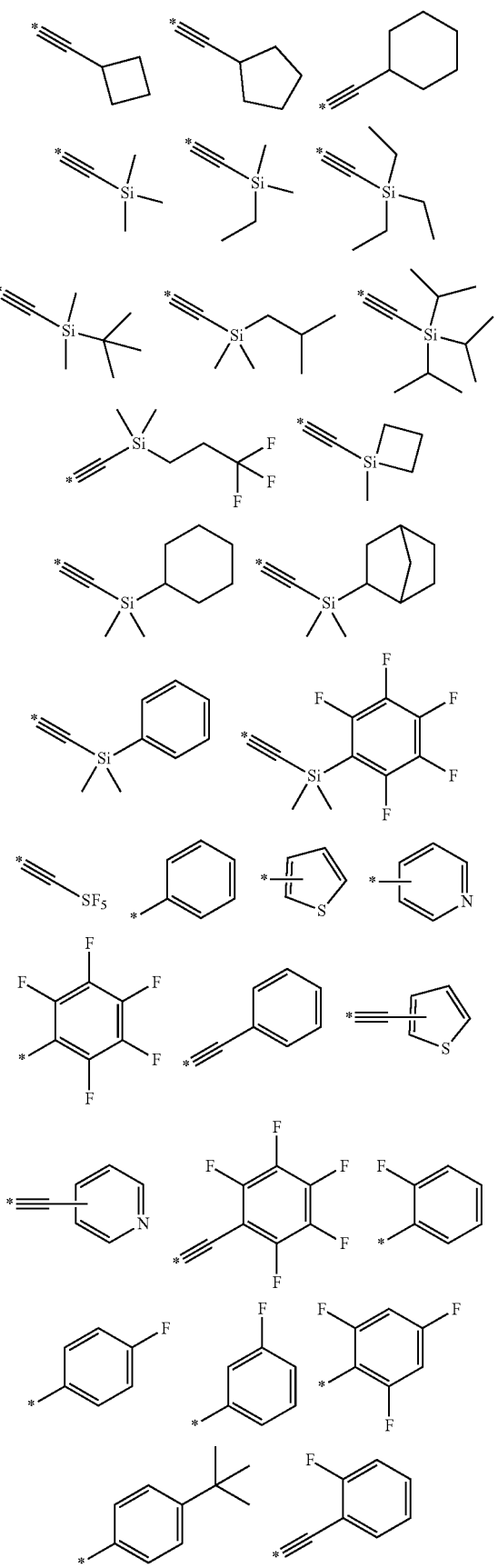

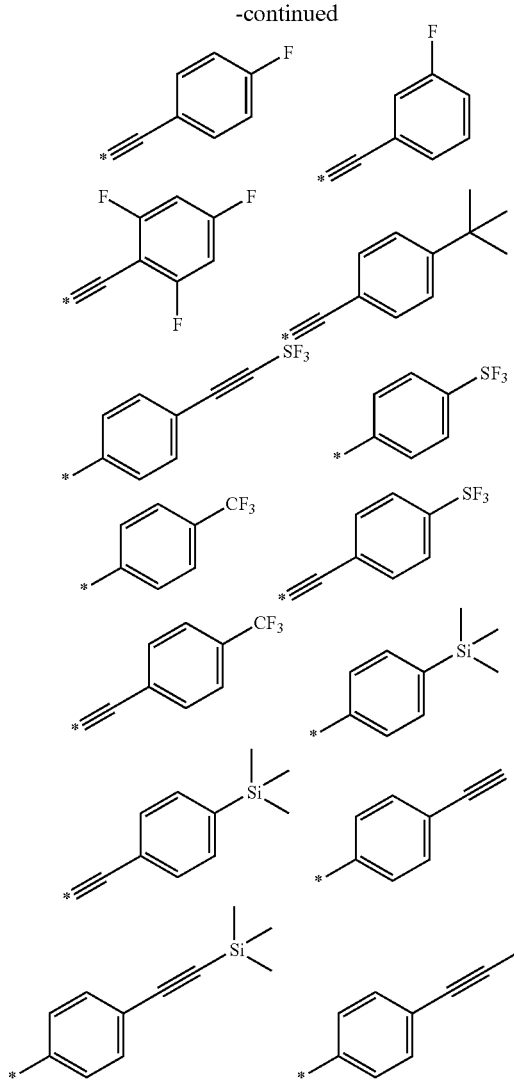

wherein * indicates the point of attachment to Y

In some embodiments, Z is hydrogen, methyl or ethyl. In some embodiments, Z is hydrogen.

In some embodiments, Z is selected from substituted methyl or ethyl, optionally substituted unsaturated $C_2$-$C_3$ alkyl, optionally substituted carbocyclyl, optionally substituted heterocyclyl, optionally substituted aryl, optionally substituted heteroaryl, Si-substituted silyl, S-substituted thiol, O-substituted hydroxyl, ester, and —$SF_5$.

In some embodiments, Z is substituted methyl or ethyl, having one or more substituents.

In some embodiments, the one or more substituents are independently selected from deuterium, halogen, and alkyl. In some embodiments, Z is selected from —$CD_3$, —$CF_3$, —$C(CH_3)_3$, —$CD_2CD_3$, and —$CF_2CF_3$. In some embodiments, Z is —$CF_3$.

In some embodiments, Z is optionally substituted unsaturated $C_2$-$C_3$ alkyl, which may have one or more substituents. For example, Z can be optionally substituted $C_2$-$C_3$ alkynyl, such as optionally substituted ethynyl and optionally substituted propynyl (including optionally substituted 1-propynyl and optionally substituted 2-propynyl). In some embodiments, the one or more substitutions are independently selected from deuterium, halogen (such as fluorine), alkyl, heteroalkyl, carbocyclyl (such as cyclopropyl, cyclobutyl, cyclopentyl, and cyclohexyl), heterocyclyl, aryl (such as phenyl), heteroaryl (such as pyridinyl and thiophenyl), silyl, and —$SF_5$, wherein each substituent may be further substituted by one or more $R^A$ groups as described in Formula I above. In some embodiments, Z is selected from —C≡CH, —C≡CCD$_3$, —C≡CCH$_2$F, —C≡CCHF$_2$, —C≡CCF$_3$, —C≡CSi(CH$_3$)$_3$, —C≡CC(CH$_3$)$_3$, —C≡CSF$_5$, as well as the following:

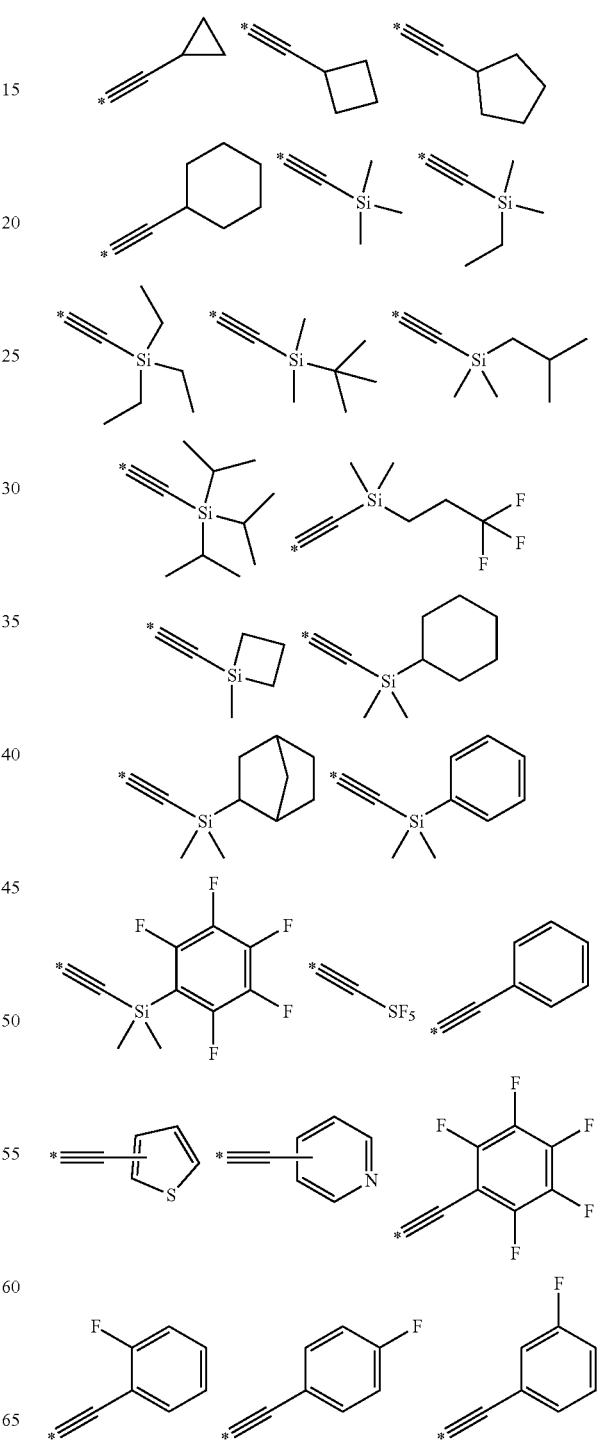

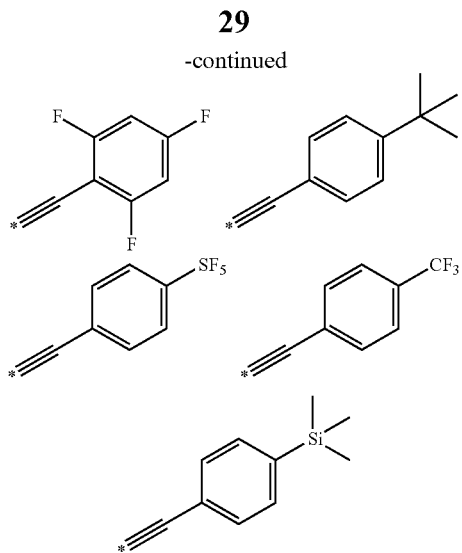

wherein * indicates the point of attachment to Y In some embodiments, Z is —C≡CSi(CH₃)₃.

In some embodiments, Z is optionally substituted carbocyclyl, optionally substituted heterocyclyl, optionally substituted aryl, or optionally substituted heteroaryl. In some embodiments, the substituent(s) is independently selected from halogen, alkyl, heteroalkyl, silyl, and —SF₅, wherein each substituent may be further substituted by one or more $R^A$ groups as described in Formula I above. Exemplary substituents of Z include fluorine, trifluoromethyl, ethynyl, 2-pentafluorosulfanylethynyl, 2-trimethylsilylethynyl, 2-(tert-butyl)ethynyl, tert-butyl, trimethylsilyl, and —SF₅. In some embodiments, Z is optionally substituted carbocyclyl, such as optionally substituted cyclopropyl, optionally substituted cyclobutyl, optionally substituted cyclopentyl, and optionally substituted cyclohexyl. In some embodiments, Z is optionally substituted heterocyclyl. In some embodiments, Z is optionally substituted aryl, such as optionally substituted phenyl (e.g., phenyl, 2-fluorophenyl, 3-fluorophenyl, 4-fluorophenyl, 2,4,6-trifluorophenyl, 2,3,4,5,6-pentafluorophenyl, 4-(tert-butyl)phenyl, 4-(pentafluorosulfanyl)phenyl, 4-(trifluoromethyl)phenyl, 4-ethynylphenyl, 4-(2-pentafluorosulfanylethynyl)phenyl, 4-(2-trimethylsilylethynyl)phenyl, 4-(2-(tert-butyl)ethynyl)phenyl. In some embodiments, Z is optionally substituted heteroaryl, such as optionally substituted pyridinyl and optionally substituted thiophenyl. In some embodiments, Z is selected from the following:

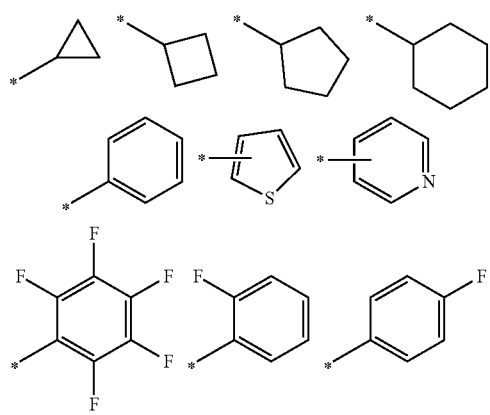

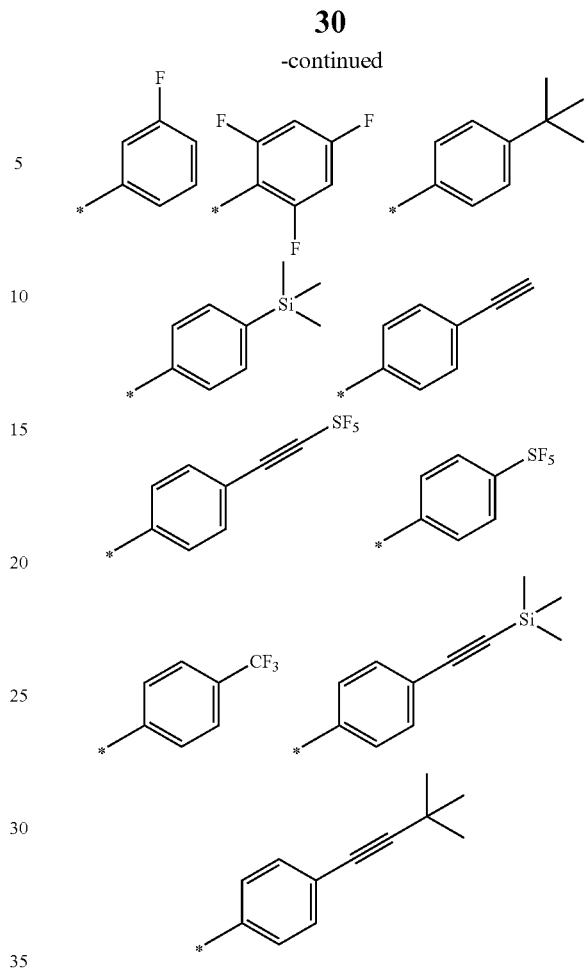

wherein * indicates the point of attachment to Y.

In some embodiments, Z is Si-substituted silyl, having one or more substituents. When there are multiple substituents, two of the substituents can join together with the Si atom to form a cyclic moiety, such as a heterocycle. In some embodiments, the one or more substituents are independently selected from alkyl (such as methyl, ethyl, propyl, isopropyl, tert-butyl, and isobutyl), heteroalkyl, carbocyclyl (such as cyclohexyl and bicyclo[2.2.1]heptyl), heterocyclyl, aryl (such as phenyl), and heteroaryl, wherein each substituent may be further substituted by one or more $R^A$ groups as described in Formula I above. In some embodiments, the Si-substituted silyl has three substituents, independently selected from alkyl, heteroalkyl, carbocyclyl, heterocyclyl, aryl, and heteroaryl, wherein each substituent may be further substituted by one or more $R^A$ groups. In some embodiments, Z is selected from the following:

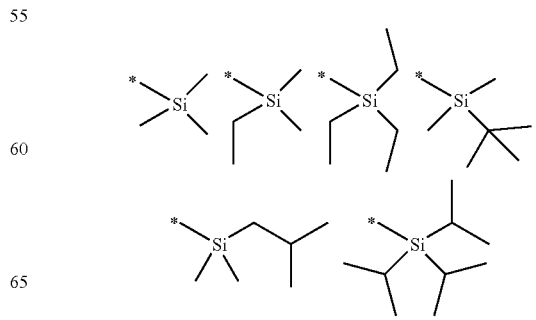

wherein * indicates the point of attachment to Y. In some embodiments, Z is trimethylsilyl.

In some embodiments, Z is S-substituted thiol, having one substituent. In some embodiments, the substituent is selected from alkyl, heteroalkyl, carbocyclyl, heterocyclyl, aryl (such as phenyl), and heteroaryl, which may be further substituted by one or more $R^A$ groups as described in Formula I above. In some embodiments, the substituent is aryl, which may be further substituted by one or more $R^A$ groups. In some embodiments, Z is —S-Ph.

In some embodiments, Z is O-substituted hydroxyl, having one substituent. In some embodiments, the substituent is selected from alkyl, heteroalkyl, carbocyclyl, heterocyclyl, aryl (such as phenyl), and heteroaryl, which may be further substituted by one or more $R^A$ groups as described in Formula I above. In some embodiments, the substituent is aryl, which may be further substituted by one or more $R^A$ groups. In some embodiments, Z is —O-Ph.

In some embodiments, Z is an ester. In some embodiments, Z is —C(O)OCH$_3$.

In some embodiments, Z is —SF$_5$.

B. Metabolic Stability and Pharmaceutical Properties

In some embodiments, the compounds have better metabolic stability than CMX157. In some embodiments, the compounds can resist enzyme-mediated ω-oxidation, such as ω-oxidation catalyzed by cytochrome P450 enzymes (e.g., isoforms 3A4 and 2D36). The compounds can have higher resistance against ω-oxidation by cytochrome P450 enzymes, compared to CMX157.

In some embodiments, the compounds have a higher human liver microsome (HLM) stability ($t_{1/2}$) than that of CMX157 ($t_{1/2}$=42 min). In some embodiments, the compounds have an HLM $t_{1/2}$ longer than 45 min, preferably longer than 60 min, more preferably longer than 90 min, most preferably longer than 120 min. The HLM $t_{1/2}$ values can be determined using methods described in Example 38.

The lipid-derived prodrugs descried herein, such as lipid-derived prodrugs of TFV, can avoid first-pass degradation to the active drug (e.g., TFV) in the liver by targeting lymphatic uptake. Upon achieving access to enterocytes, these prodrugs can be transported to the endoplasmic reticulum (ER) by lipid binding proteins. Once deposited into the ER membrane, association with triglyceride- and phospholipid-rich lipoproteins called chylomicrons occurs. Drug-associated chylomicrons are then secreted into the interstitium via vesicular transport. Chylomicrons are size-excluded from the portal vein capillaries due to tight intercellular junctions, resulting in preferential uptake by lymphatic vessels with larger intercellular gaps. Drug-associated chylomicrons are then trafficked to the thoracic duct, which feeds into systemic circulation just upstream of the heart and lung. Accordingly, by associating with chylomicrons in intestinal enterocytes, the lipophilic prodrugs have the potential to hijack physiological lipid trafficking mechanisms to efficiently access the lymphatic vasculature. This mechanism imparts the lipid-derived prodrugs of TFV disclosed herein with distinct advantages over TDF and TAF. Firstly, bypassing first-pass liver metabolism would lower TFV levels in liver and plasma, not only reducing bone mineral density depletion, renal toxicity, and hepatotoxicity, but also extending duration of action. Additionally, because the gut-associated and intestinal lymphatics system hosts 50-70% of the body's lymphoid cells, lymphatically-delivered TFV prodrugs would directly target an HIV reservoir.

In some embodiments, the lipid-derived prodrugs disclosed herein can resist specific mechanisms of first-pass liver metabolism because they contain functional groups that can deactivate key metabolic sites. For example, the lipid-derived prodrugs of TFV disclosed herein that target lymphatic uptake and chemically resist hepatic metabolism can diminish TDF- and TAF-induced organ-specific toxicities and extend duration of drug action, both of which are anticipated to improve patient adherence to chronic antiretroviral dosing schedules. By virtue of efficient access to HIV-infected cells and extended duration of action, these TFV prodrugs have the potential to dramatically reduce the quantity of drugs required to treat all HIV/AIDS patients globally, especially those without affordable access to therapy in the developing world.

In some embodiments, the lipid-derived prodrugs can resist CYP-mediated ω-oxidation. In some embodiments, the lipid-derived prodrugs contain functional groups at the terminus that are resistant or can slow this enzymatic process. For example, the lipid-derived prodrugs may contain metabolically less reactive terminal alkynes as exemplified in this disclosure. The lipid-derived prodrugs containing terminal alkynes can benefit from a larger C—H bond dissociation energy (acetylene C—H=133.3 kcal/mol) that may confer slow enzymatic oxidation relative to their saturated counterparts (ethane C—H=101.1 kcal/mol). By introducing trifluoromethyl or pentafluoroethyl groups onto the terminal acetylene may attenuate ω-oxidation. Bioisosteric replacement of hydrogen with fluorine may overcome issues pertaining to poor pharmacokinetic performance as a result of oxidative metabolism. Pentadeuteroethyl and trideuteromethyl analogs may resist ω-oxidation via kinetic isotope effect. Terminally silylated lipid-derived prodrugs may resist CYP-mediated ω-oxidation because the termini of these compound may be sterically congested and electronically deactivated relative to unsubstituted alkane counterparts. Terminally CF$_3$-substituted lipid-derived prodrugs may resist CYP-mediated ω-oxidation because the termini of these compound may be electronically deactivated relative to unsubstituted alkane counterparts. Terminally carbocyclyl-, heterocyclyl-, aryl- or heteroaryl-substituted lipid-derived prodrugs may resist CYP-mediated ω-oxidation because the termini of these compound may be sterically congested and electronically deactivated relative to unsubstituted alkane counterparts.

Generally, the "L" moiety of the lipid-derived prodrugs determines the therapeutic effect. In some embodiments, the L moiety can be separated from the rest of the structure after administration and become the active drug. The "W—X—Y—Z" fraction of the lipid-derived prodrugs can modulate the bioavailability (especially oral bioavailability) and pharmacokinetics of the lipid-derived prodrugs.

C. Exemplary Structures

1. L-O—W—X—Y—Z

In some embodiments, both W and X are present, i.e., L-O—W—X—Y—Z.

In some embodiments, the compounds have the following features:

L is

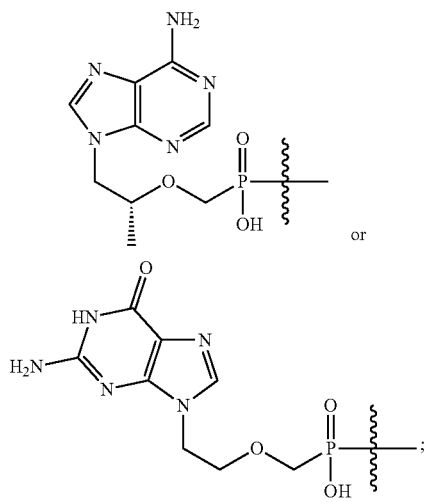

W is —CH₂CH₂— or —CH₂CH₂CH₂—;
X is —CF₂—, —O—, or —S—;
Y is a saturated, linear C₈-C₂₀ alkyl chain (i.e., linear C₈-C₂₀ alkylene); and
Z is selected from substituted methyl or ethyl, optionally substituted unsaturated C₂-C₃ alkyl, optionally substituted carbocyclyl, optionally substituted heterocyclyl, optionally substituted aryl, optionally substituted heteroaryl, Si-substituted silyl, S-substituted thiol, O-substituted hydroxyl, ester, and —SF₅.

In some embodiments, the compounds have the following features:

L is

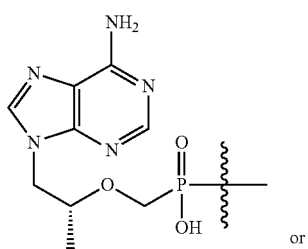

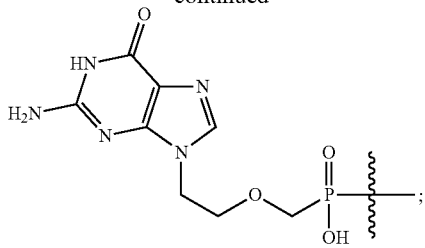

W is —CH₂CH₂— or —CH₂CH₂CH₂—;
X is —CF₂—, —O—, or —S—;
Y is a saturated, linear C₈-C₂₀ alkyl chain (i.e., linear C₈-C₂₀ alkylene); and
Z is selected from —CD₃, —CF₃, —CD₂CD₃, —CF₂CF₃, —S-Ph, —O-Ph, —C≡CH, —C≡CCD₃, —CH₂FC≡C, —CHF₂C≡C, —C≡CSi(CH₃)₃, —C≡CC(CH₃)₃, —C≡CCF₃, —C≡CSF₅, —Si(CH₃)₃, —C(CH₃)₃, —C(O)OCH₃, —SF₅, as well as the following:

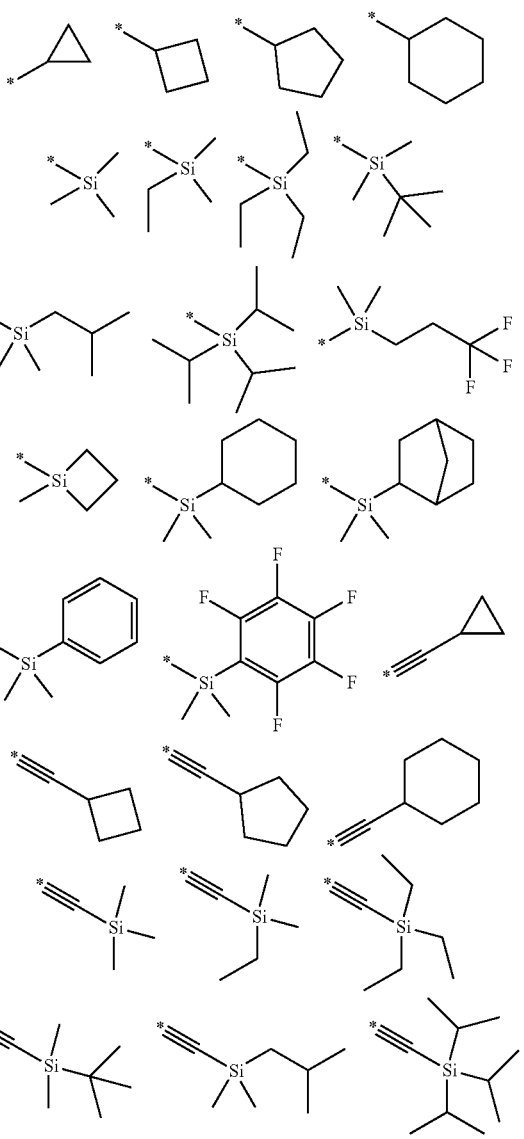

-continued
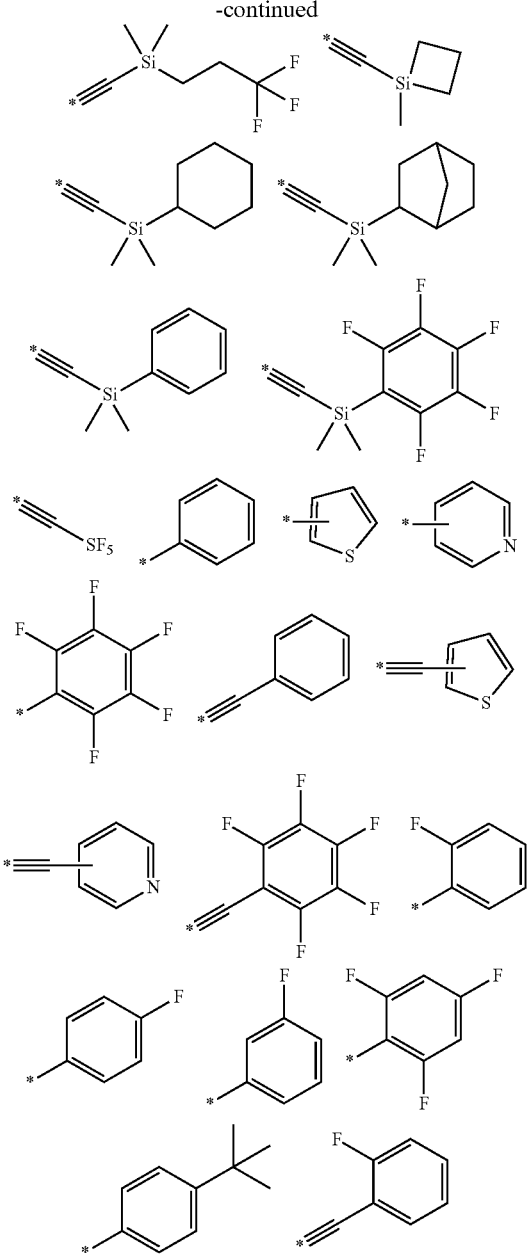
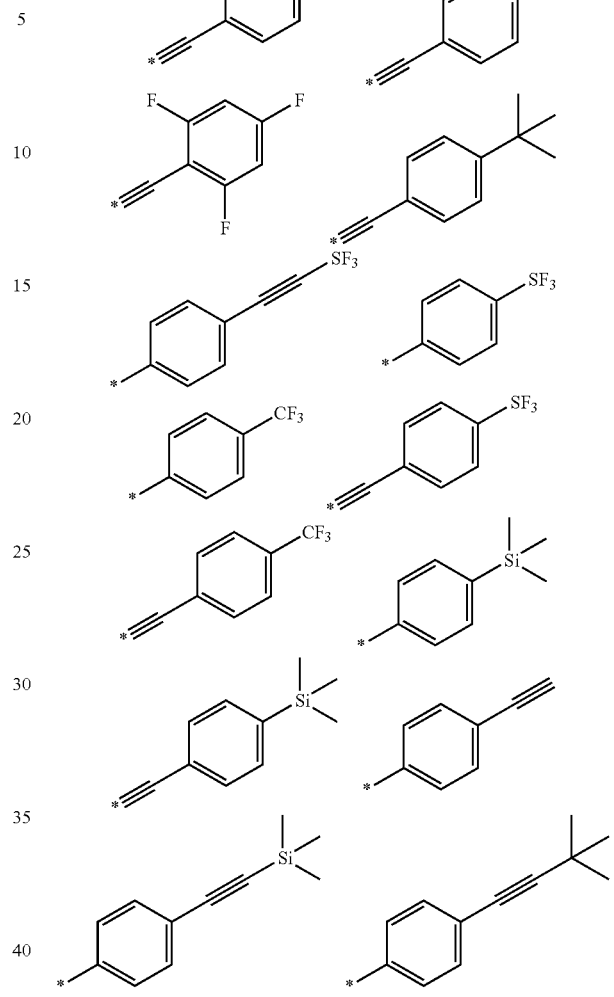
wherein * indicates the point of attachment to Y.
Exemplary compounds include, but are not limited to, the following compounds and pharmaceutically acceptable salts (such as ammonium salts) thereof:
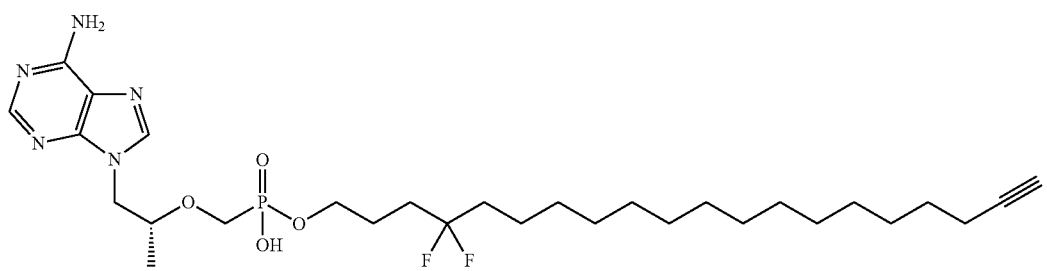
4,4-difluoroicos-19-yn-1-yl hydrogen ((((R)-1-(6-amino-9H-purin-9-yl)propan-2-yl)oxy)methyl)phosphonate

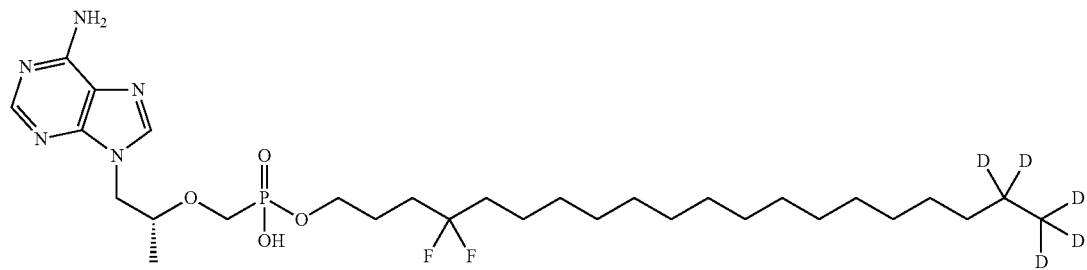

4,4-difluoroicosyl-19,19,20,20,20-d5 hydrogen ((((R)-1-(6-amino-9H-purin-9-yl)propan-2-yl)oxy)methyl)phosphonate

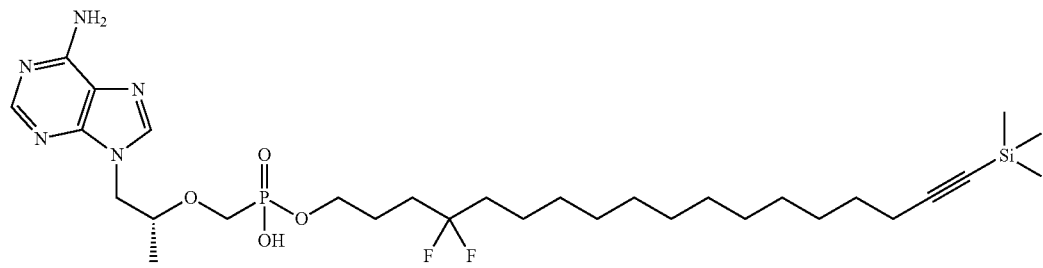

4,4-difluoro-18-(trimethylsilyl)octadec-17-yn-1-yl hydrogen ((((R)-1-(6-amino-9H-purin-9-yl)propan-2-yl)oxy)methyl)phosphonate

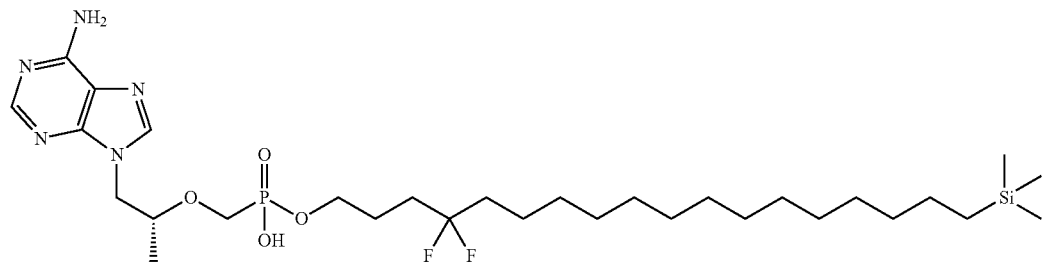 [SMILES: CCCCCCCCCCCCCCCCC(F)(F)CCCOP(=O)(O)CO[C@H](C)Cn1cnc2c(N)ncnc21]

4,4-difluoro-18-(trimethylsilyl)octadecyl hydrogen ((((R)-1-(6-amino-9H-purin-9-yl)propan-2-yl)oxy)methyl)phosphonate

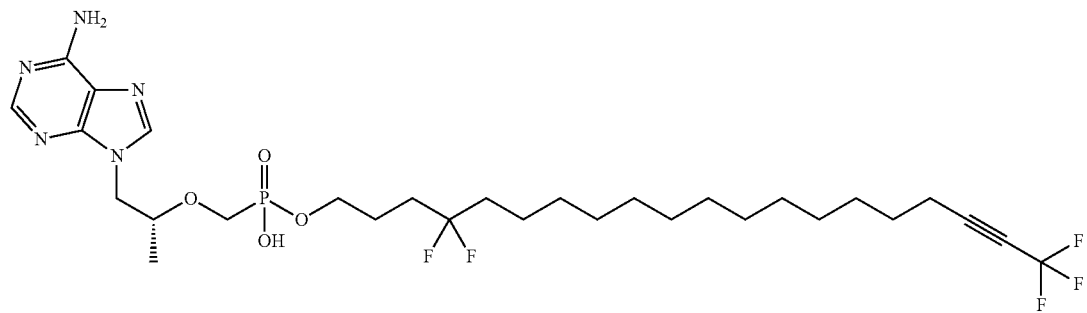

4,4,20,20,20-pentafluoroicos-18-yn-1-yl hydrogen ((((R)-1-(6-amino-9H-purin-9-yl)propan-2-yl)oxy)methyl)phosphonate

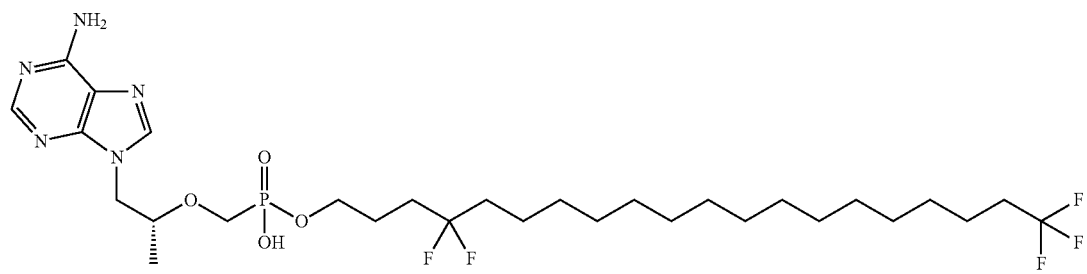

4,4,20,20,20-pentafluoroicosyl hydrogen ((((R)-1-(6-amino-9H-purin-9yl)propan-2-yl)oxy)methyl)phosphonate

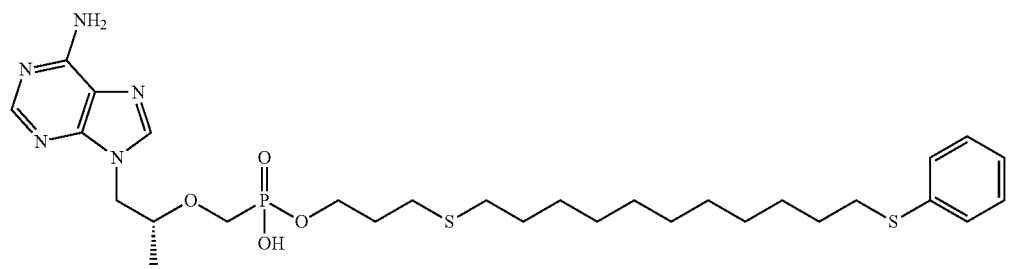

3-((11-(phenylthio)undecyl)thio)propyl hydrogen ((((R)-1-(6-amino-9H-purin-9-yl)propan-2-yl)oxy)methyl)phosphonate

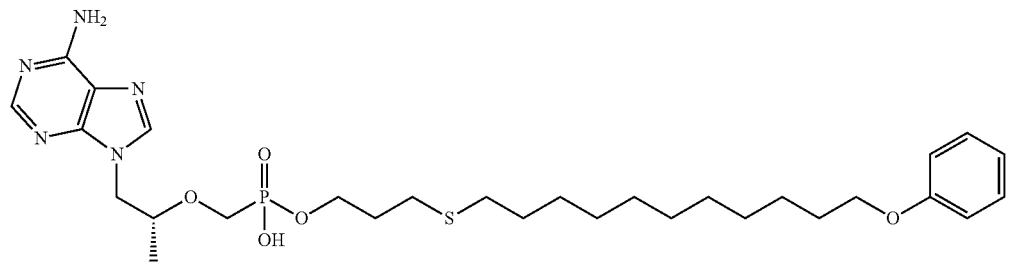

3-((11-phenoxyundecyl)thio)propyl hydrogen ((((R)-1-(6-amino-9H-purin-9-yl)propan-2-yl)oxy)methyl)phosphonate

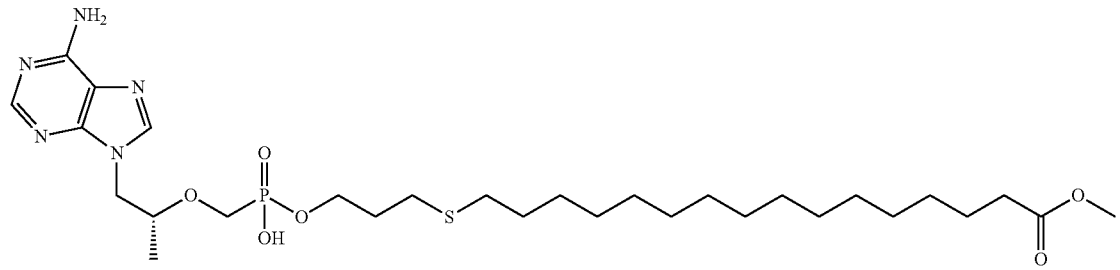

methyl 16-((3-((((((R)-1-(6-amino-9H-purin-9-yl)propan-2-yl)oxy)methyl)(hydroxy)phosphoryl)oxy)propyl)thio)hexadecanoate

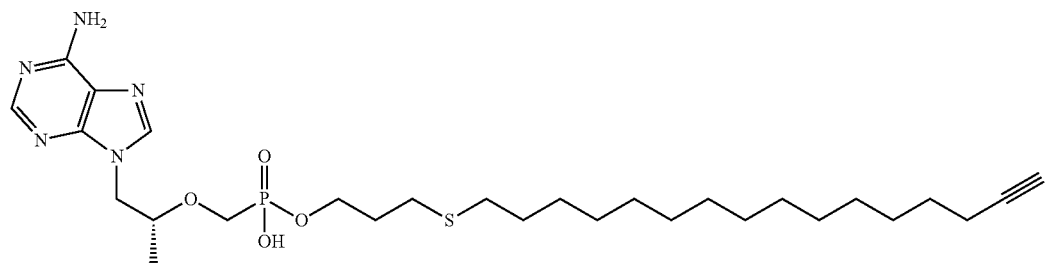

3-(hexadec-15-yn-1-ylthio)propyl hydrogen ((((R)-1-(6-amino-9H-purin-9-yl)propan-2-yl)oxy)methyl)phosphonate

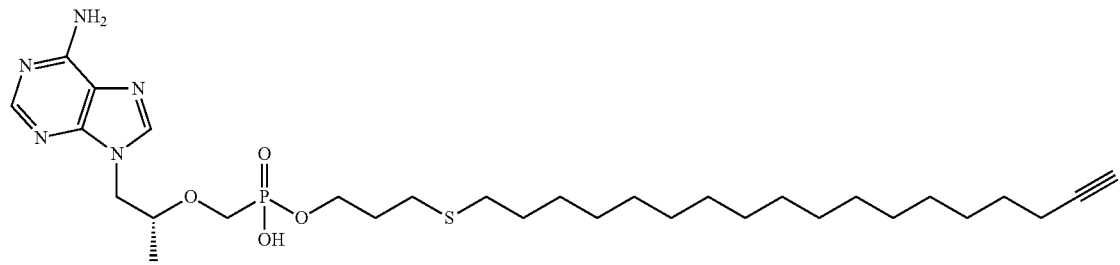

3-(octadec-17-yn-1-ylthio)propyl hydrogen ((((R)-1-(6-amino-9H-purin-9-yl)propan-2-yl)oxy)methyl)phosphonate -continued

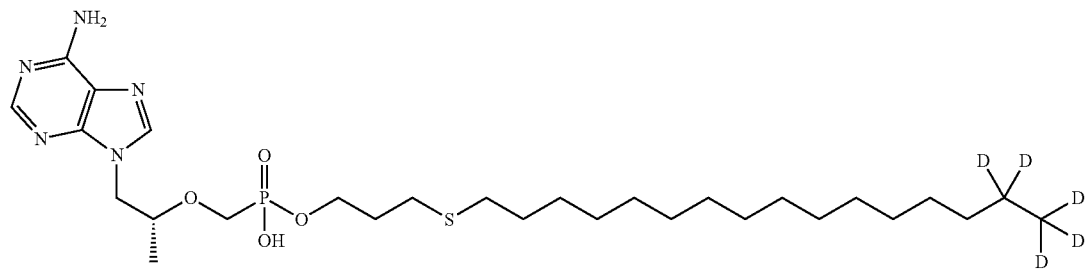

3-((hexadecyl-15, 15, 16, 16, 16-d$_5$)thio)propyl hydrogen ((((R)-1-(6-amino-9H-purin-9-yl)propan-2-yl)oxy)methyl)phosphonate

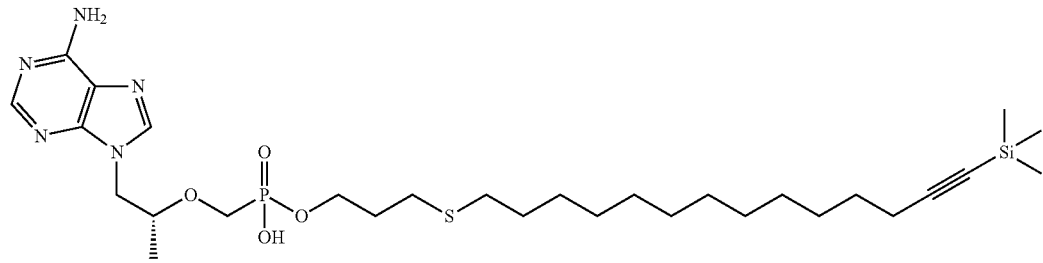

3-((14-(trimethylsilyl)tetradec-13-yn-1-yl)thio)propyl hydrogen ((((R)-1-(6-amino-9H-purin-9-yl)propan-2-yl)oxy)methyl)phosphonate

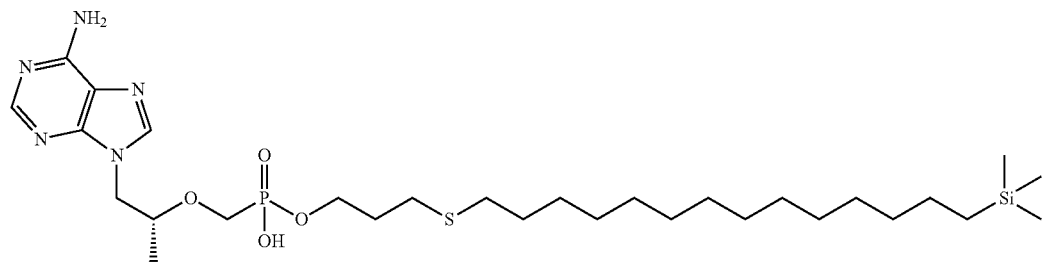

3-((14-(trimethylsilyl)tetradecyl)thio)propyl hydrogen ((((R)-1-(6-amino-9H-purin-9-yl)propan-2-yl)oxy)methyl)phosphonate

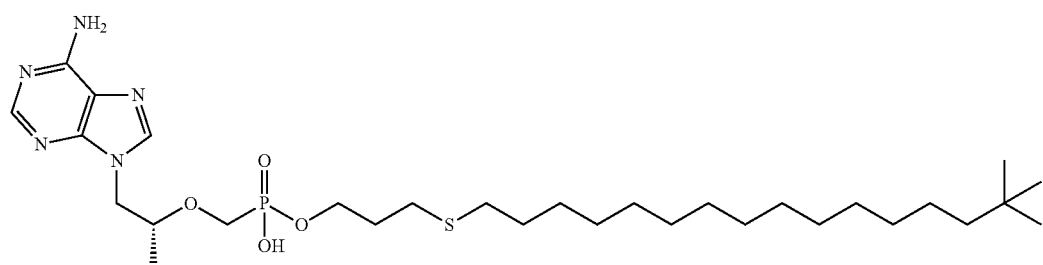

3-((15, 15-dimethylhexadecyl)thio)propyl hydrogen ((((R)-1-(6-amino-9H-purin-9-yl)propan-2-yl)oxy)methyl)phosphonate

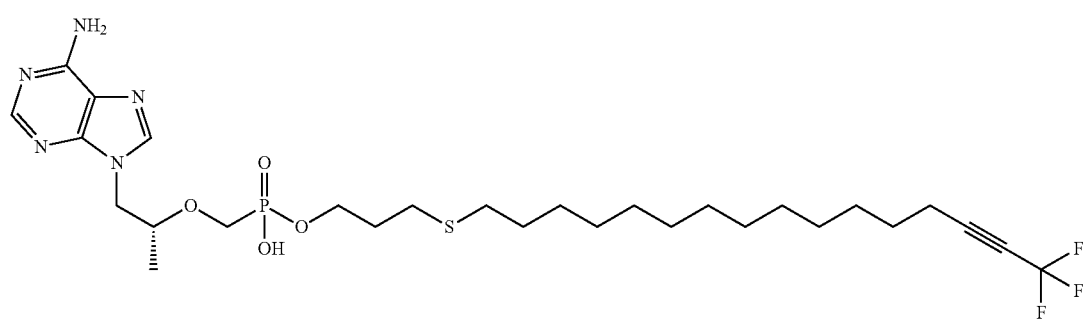

3-((16, 16, 16-trifluorohexadec-14-yn-1-yl)thio)propyl hydrogen ((((R)-1-(6-amino-9H-purin-9-yl)propan-2-yl)oxy)methyl)phosphonate

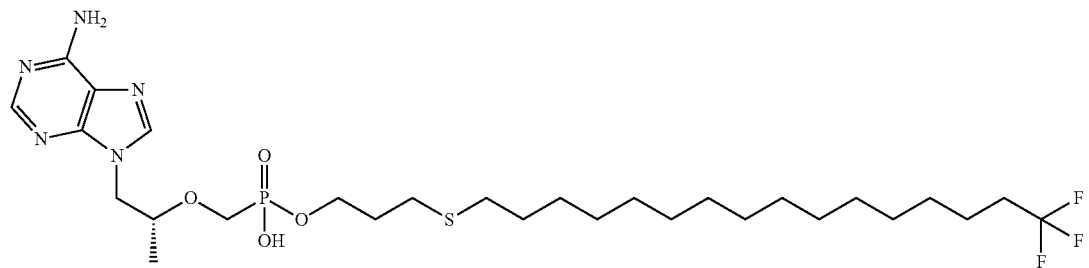

3-((16,16,16-trifluorohexadecyl)thio)propyl hydrogen ((((R)-1-(6-amino-9H-purin-9-yl)propan-2-yl)oxy)methyl)phosphonate

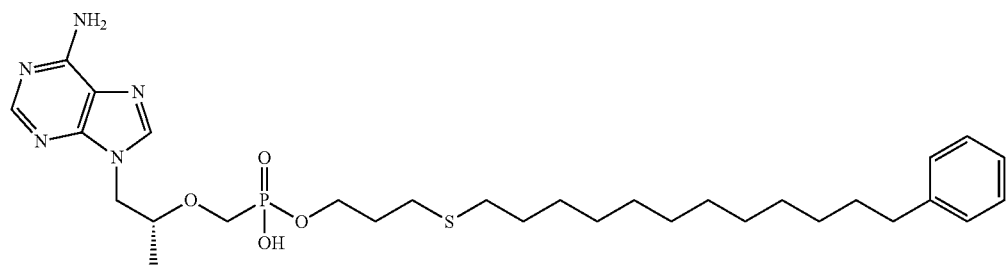

3-((12-phenyldodecyl)thio)propyl hydrogen ((((R)-1-(6-amino-9H-purin-9-yl)propan-2-yl)oxy)methyl)phosphonate

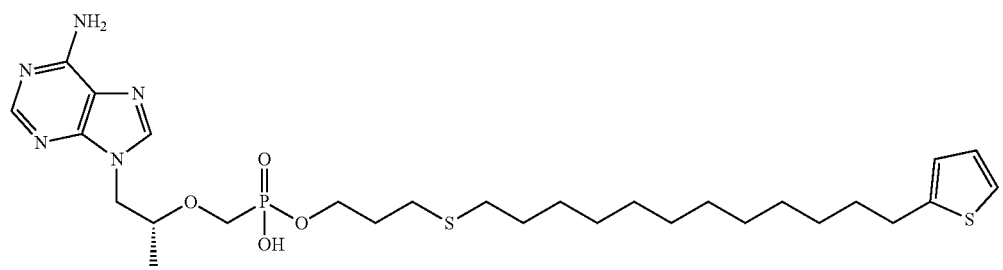

3-((12-thiophen-2-yl)dodecyl)thio)propyl hydrogen ((((R)-1-(6-amino-9H-purin-9-yl)propan-2-yl)oxy)methyl)phosphonate

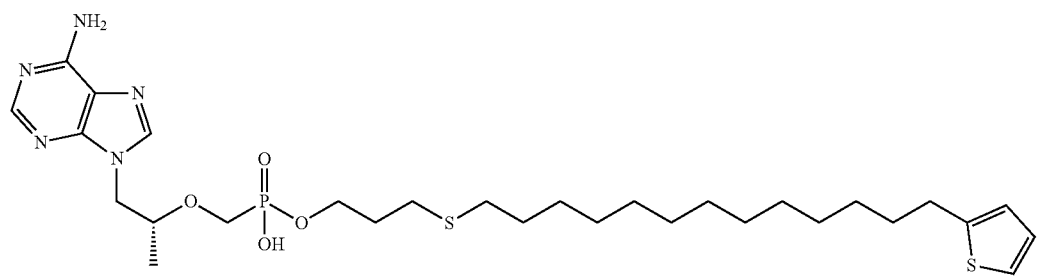

3-((13-(thiophen-2-yl)tridecyl)thio)propyl hydrogen ((((R)-1-(6-amino-9H-purin-9-yl)propan-2-yl)oxy)methyl)phosphonate

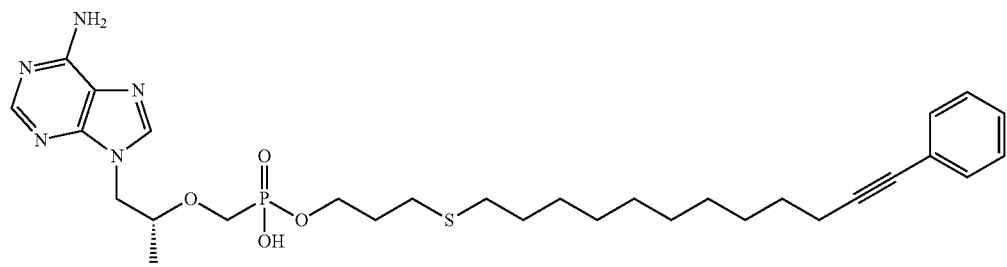

3-((12-phenyldodec-11-yn-1-yl)thio)propyl hydrogen ((((R)-1-(6-amino-9H-purin-9-yl)propan-2-yl)oxy)methyl)phosphonate

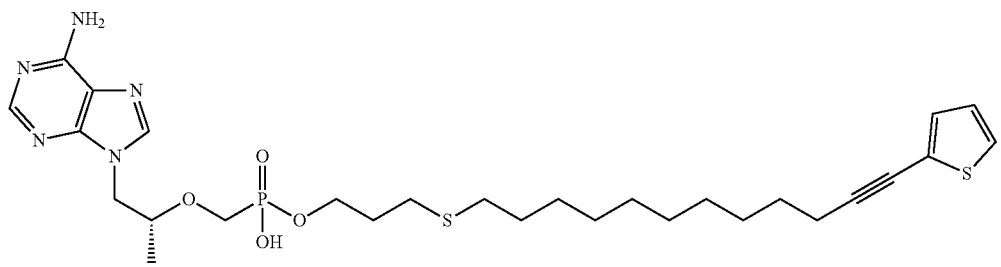

3-((12-thiophen-2-yl)dodec-1--yn-1-yl)thio)propyl hydrogen ((((R)-1-(6-amino-9H-purin-9-yl)propan-2-yl)oxy)methyl)phosphonate

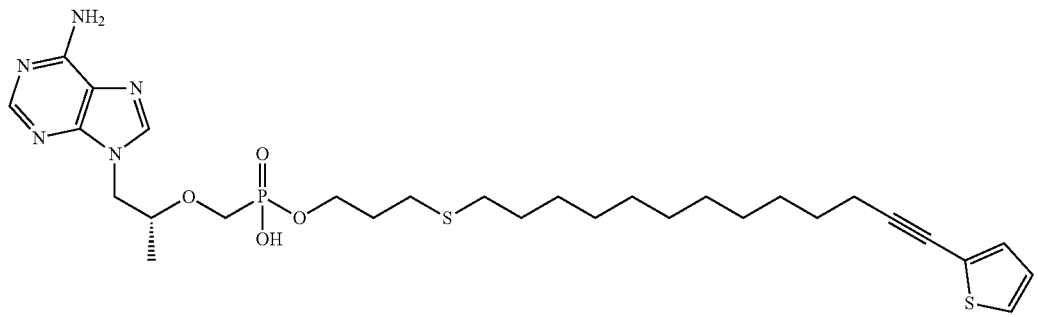

3-((13-(thiophen-2-yl)tridec-12-yn-1-yl)thio)propyl hydrogen ((((R)-1-(6-amino-9H-purin-9-yl)propan-2-yl)oxy)methyl)phosphonate

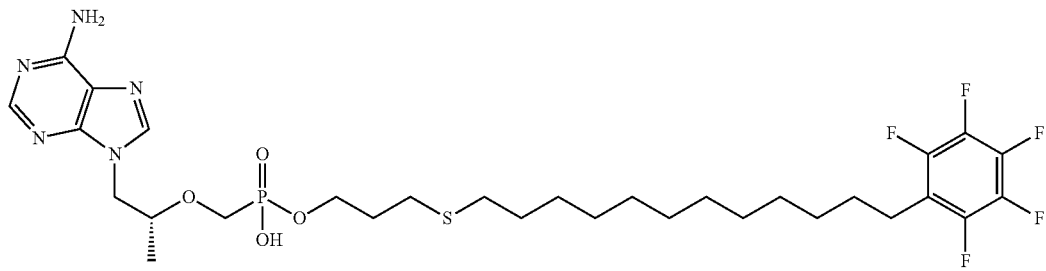

3-((12-(perfluorophenyl)dodecyl)thio)propyl hydrogen ((((R)-1-(6-amino-9H-purin-9-yl)propan-2-yl)oxy)methyl)phosphonate

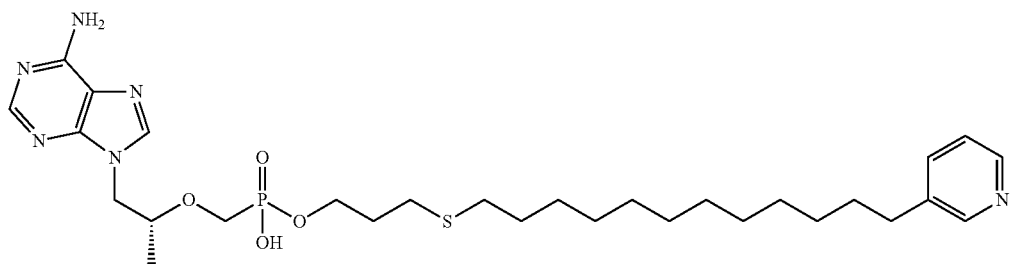

3-((12-(pyridin-3-yl)dodecyl)thio)propyl hydrogen ((((R)-1-(6-amino-9H-purin-9-yl)propan-2-yl)oxy)methyl)phosphonate

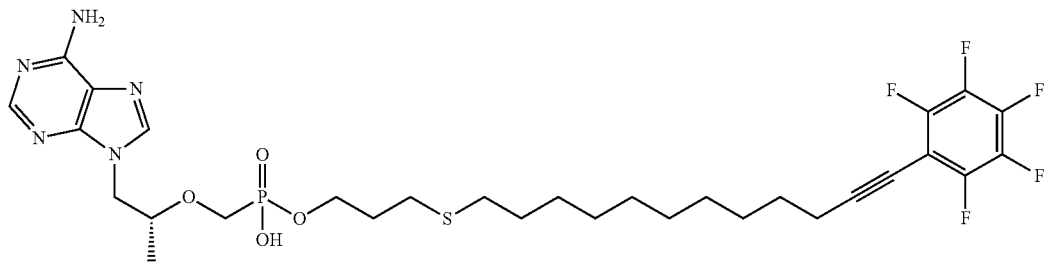

3-((12-(perfluorophenyl)dodec-11-yn-1-yl)thio)propyl hydrogen ((((R)-1-(6-amino-9H-purin-9-yl)propan-2-yl)oxy)methyl)phosphonate

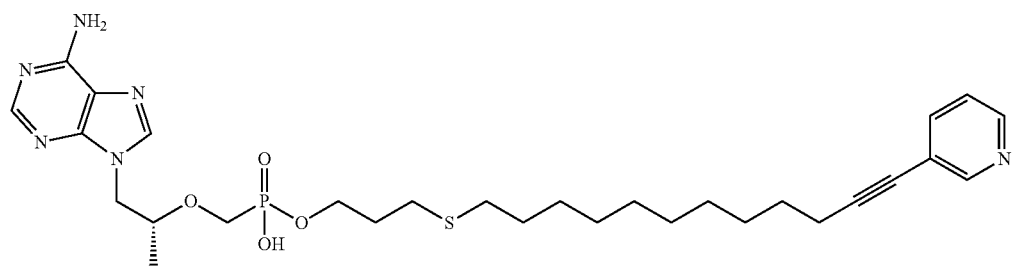

3-((12-(pyridin-3-yl)dodec-11-yn-1-yl)thio)propyl hydrogen ((((R)-1-(6-amino-9H-purin-9-yl)propan-2-yl)oxy)methyl)phosphonate

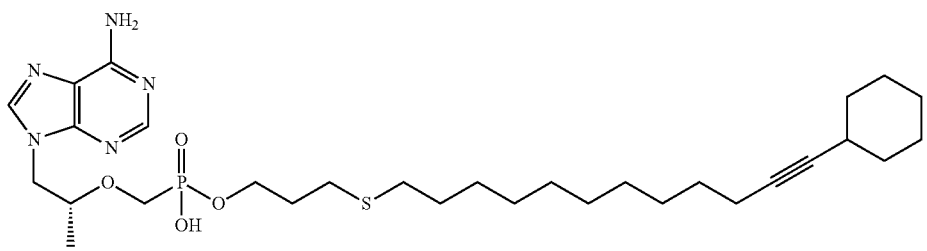

3-((12-cyclohexyldodec-11-yn-1-yl)thio)propyl hydrogen ((((R)-1-(6-amino-9H-purin-9-yl)propan-2-yl)oxy)methy)phosphonate

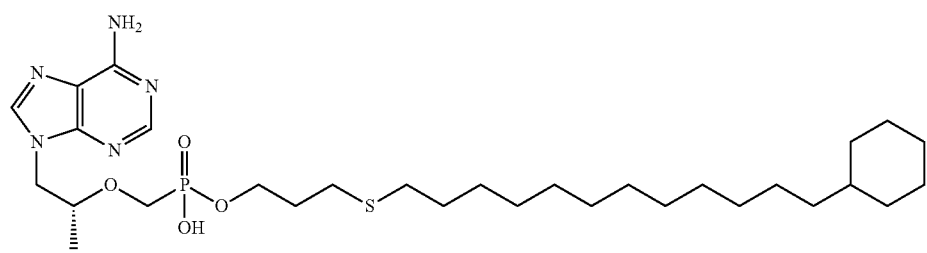

3-((12-cyclohexyldodecyl)thio)propyl hydrogen ((((R)-1-(6-amino-9H-purin-9-yl)propan-2-yl)oxy)methyl)phosphonate

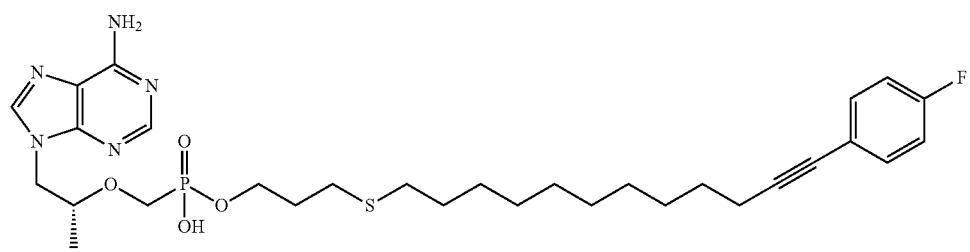

3-((12-(4-fluorophenyl)dodec-11-yn-1-yl)thio)propyl hydrogen ((((R)-1-(6-amino-9H-purin-9-yl)propan-2-yl)oxy)methyl) phosphonate

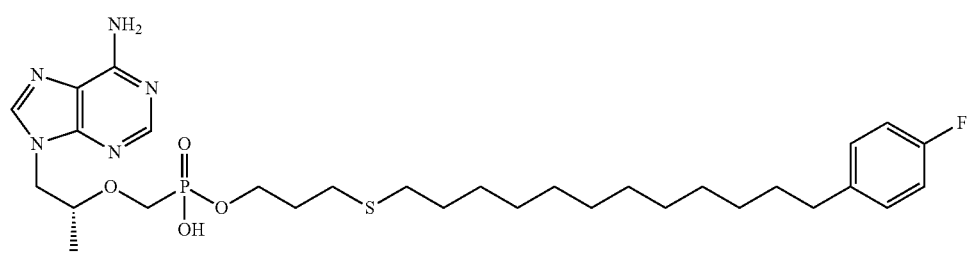

3-((12-(4-fluorophenyl)dodecyl)thio)propyl hydrogen ((((R)-1-(6-amino-9H-purin-9-yl)propan-2-yl)oxy)methyl)phosphonate

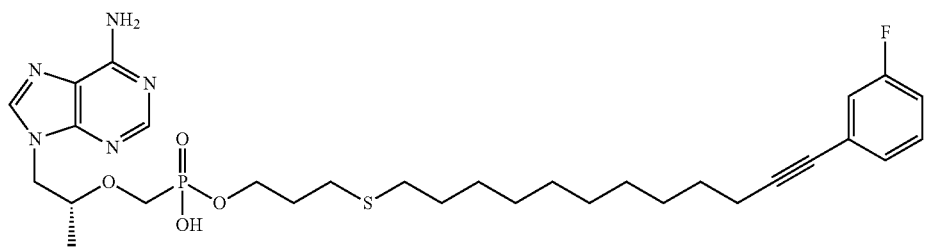

3-((12-(3-fluorophenyl)dodec-11-yn-1-yl)thio)propyl hydrogen ((((R)-1-(6-amino-9H-purin-9-yl)propan-2-yl)oxy)
methyl)phosphonate

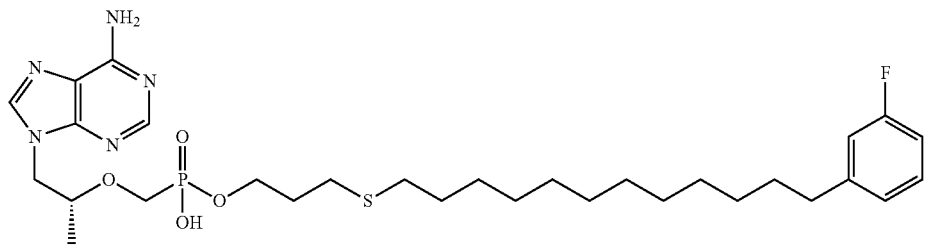

3-((12-(3-fluorophenyl)dodecyl)thio)propyl hydrogen ((((R)-1-(6-amino-9H-purin-9-yl)propan-2-yl)oxy)methyl)
phosphonate

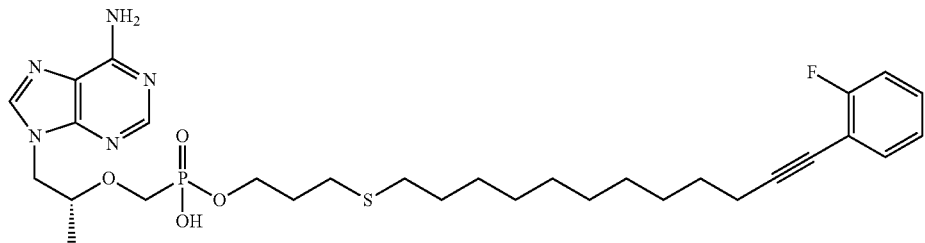

3-((12-(2-fluorophenyl)dodec-11-yn-1-yl)thio)propyl hydrogen ((((R)-1-(6-amino-9H-purin-9-yl)propan-2-yl)oxy)
methyl)phosphonate

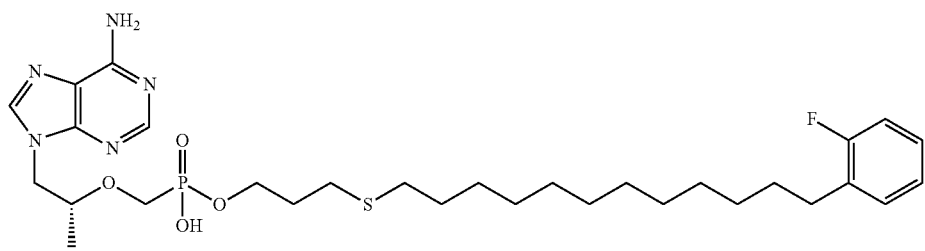

3-((12-(2-fluorophenyl)dodecyl)thio)propyl hydrogen ((((R)-1-(6-amino-9H-purin-9-yl)propan-2-yl)oxy)methyl)
phosphonate

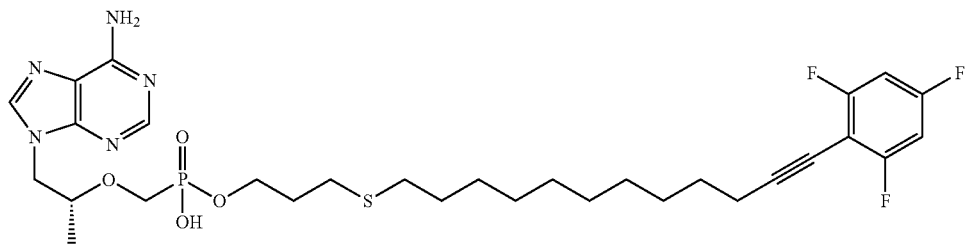

3-((12-(2,4,6-trifluorophenyl)dodec-11-yn-1-yl)thio)propyl hydrogen ((((R)-1-(6-amino-9H-purin-9-yl)propan-2-yl)oxy)
methyl)phosphonate

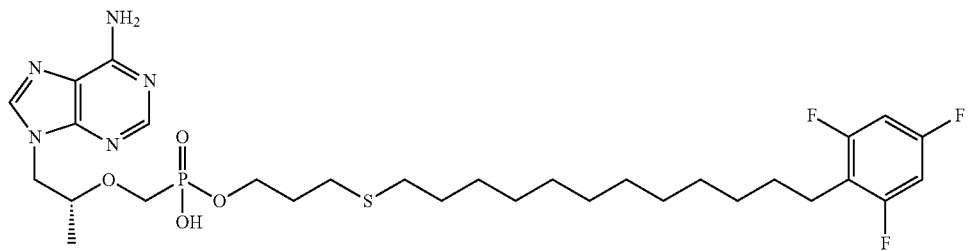

3-((12-(2,4,6-trifluorophenyl)dodecyl)thio)propyl hydrogen ((((R)-1-(6-amino-9H-purin-9-yl)propan-2-yl)oxy)methyl) phosphonate

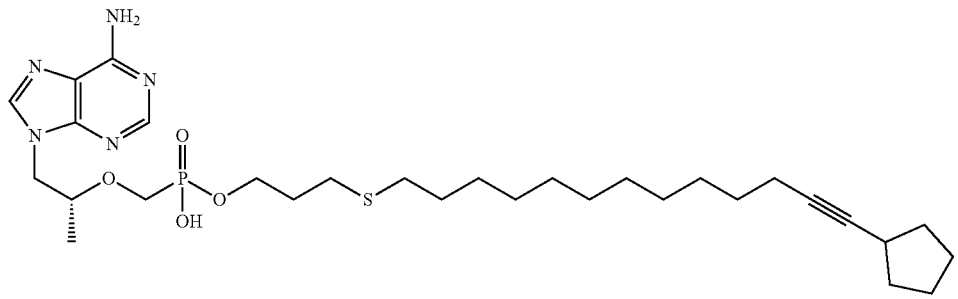

3-((13-cyclopentyltridec-12-yn-1-yl)thio)propyl hydrogen ((((R)-1-(6-amino-9H-purin-9-yl)propan-2-yl)oxy)methyl) phosphonate

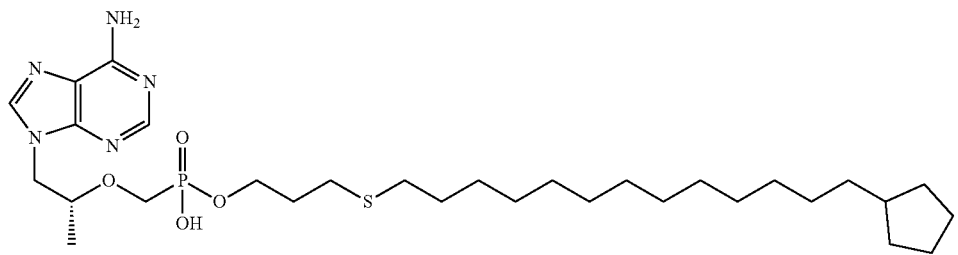

3-((13-cyclopentyltridecyl)thio)propyl hydrogen ((((R)-1-(6-amino-9H-purin-9-yl)propan-2-yl)oxy)methyl)phosphonate

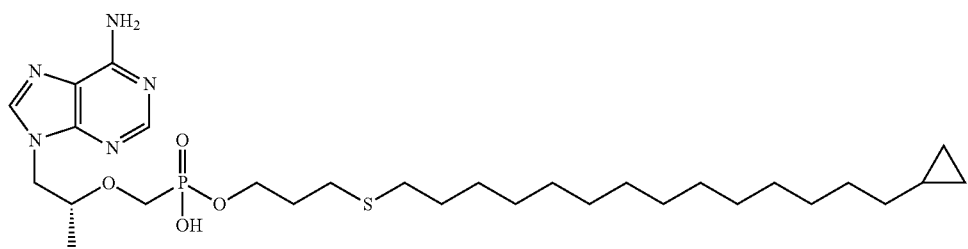

3-((14-cyclopropyltetradecyl)thio)propyl hydrogen ((((R)-1-(6-amino-9H-purin-9-yl)propan-2-yl)oxy)methyl)phosphonate

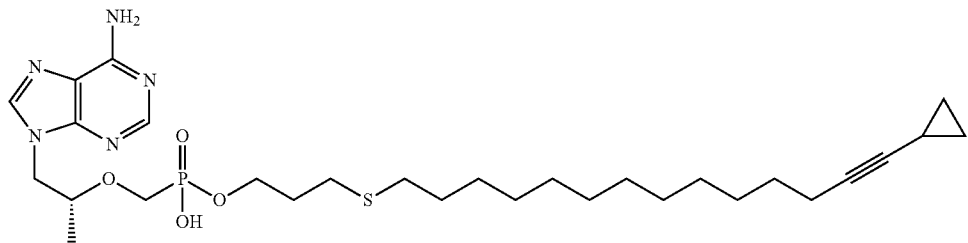

3-((14-cyclopropyltetradec-13-yn-1-yl)thio)propyl hydrogen ((((R)-1-(6-amino-9H-purin-9-yl)propan-2-yl)oxy)methyl) phosphonate

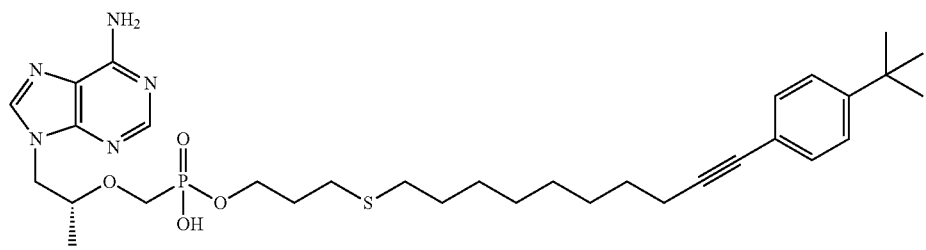

3-((10-(4-(tert-butyl)phenyl)dec-9-yn-1-yl)thio)propyl hydrogen ((((R)-1-(6-amino-9H-purin-9-yl)propan-2-yl)oxy)methyl) phosphonate

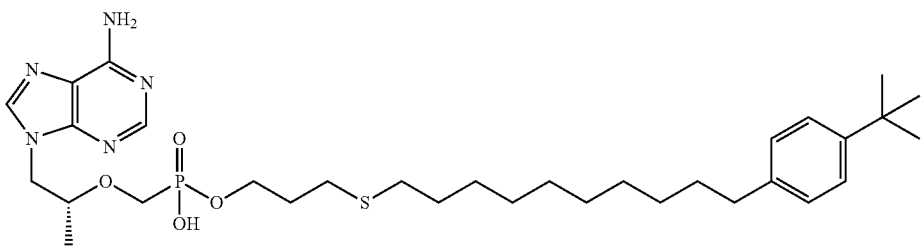

3-((10-(4-(tert-butyl)phenyl)decyl)thio)propyl hydrogen ((((R)-1-(6-amino-9H-purin-9-yl)propan-2-yl)oxy)methyl) phosphonate

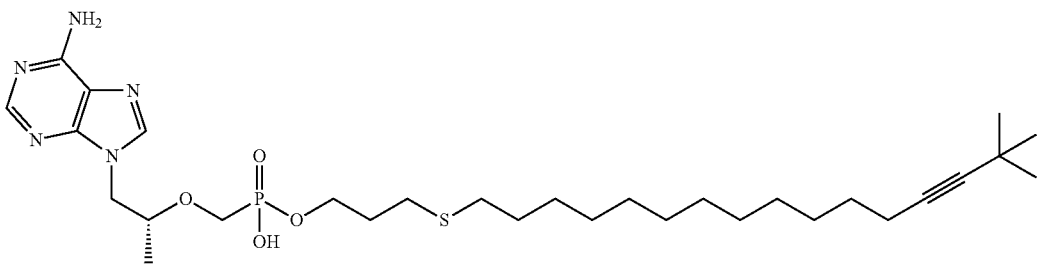

3-((15, 15-dimethylhexadec-13-yn-1-yl)thio)propyl hydrgoen ((((R)-1-(6-amino-9H-purin-9-yl)propan-2-yl)oxy)methyl)phosphonate

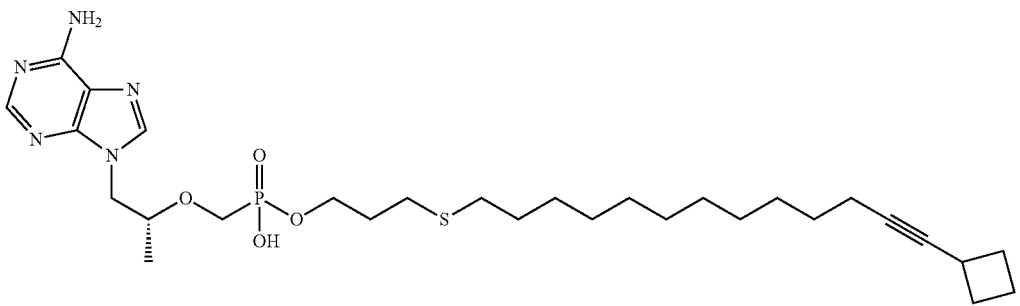

3-((13-cyclobutyltridec-12-yn-1-yl)thio)propyl hydrogen ((((R)-1-(6-amino-9H-purin-9-yl)propan-2-yl)oxy)methyl)phosphonate

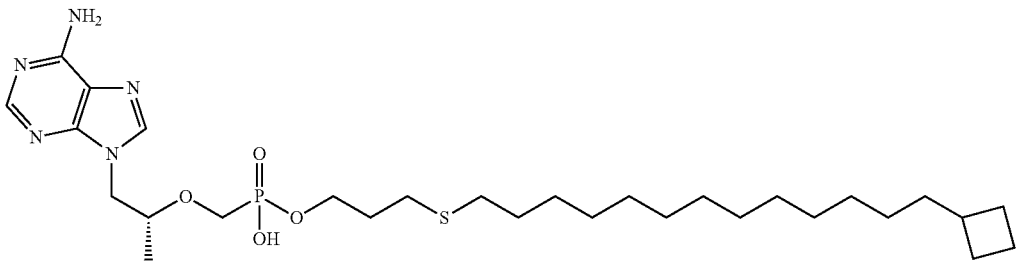

3-((13-cyclobutyltridecyl)thio)propyl hydrogen ((((R)-1-(6-amino-9H-purin-9-yl)propan-2-yl)oxy)methyl)phosphonate

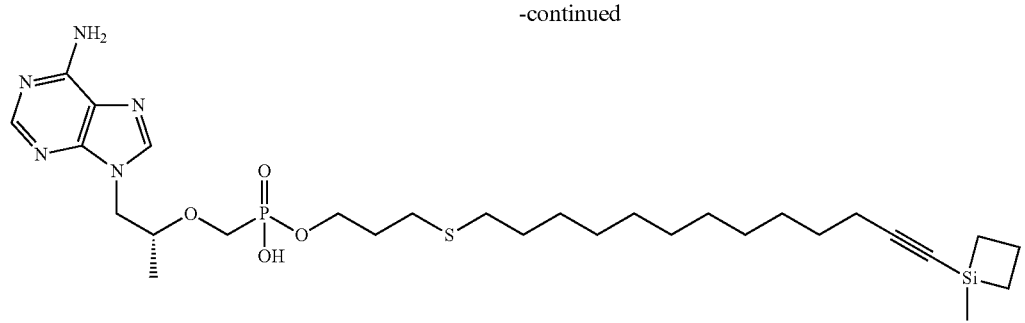

3-((13-(1-methylsiletan-1-yl)tridec-12-yn-1-yl)thio)propyl hydrogen ((((R)-1-(6-amino-9H-purin-9-yl)propan-2-yl)oxy)methyl) phosphonate

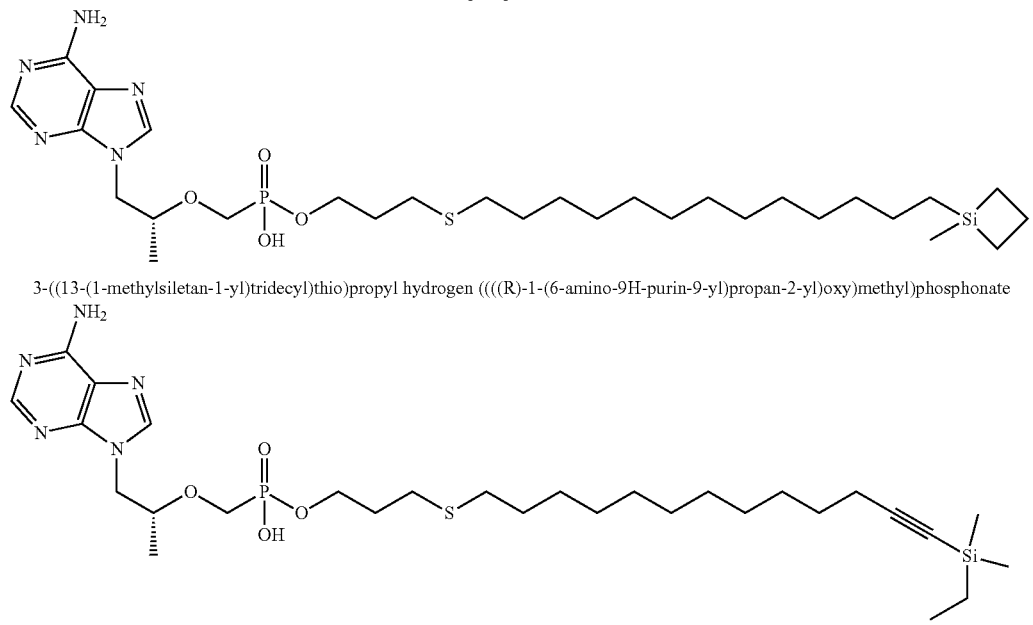

3-((13-(1-methylsiletan-1-yl)tridecyl)thio)propyl hydrogen ((((R)-1-(6-amino-9H-purin-9-yl)propan-2-yl)oxy)methyl)phosphonate 3-((13-(ethyldimethylsilyl)tridec-12-yn-1-yl)thio)propyl hydrogen ((((R)-1-(6-amino-9H-purin-9-yl)propan-2-yl)oxy)methyl) phosphonate

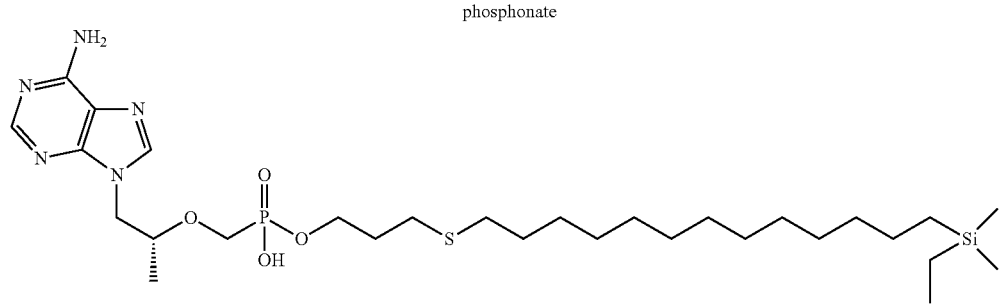

3-((13-(ethyldimethylsilyl)tridecyl)thio)propyl hydrogen ((((R)-1-(6-amino-9H-purin-9-yl)propan-2-yl)oxy)methyl)phosphonate

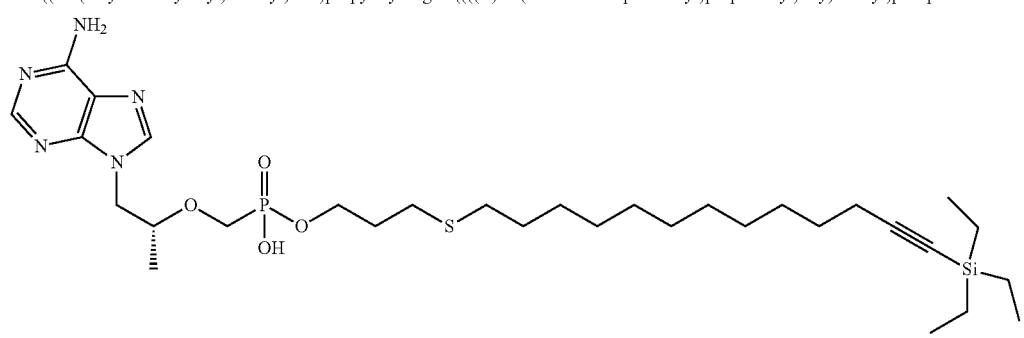

3-((13-(triethylsilyl)tridec-12-yn-1-yl)thio)propyl hydrogen ((((R)-1-(6-amino-9H-purin-9-yl)propan-2-yl)oxy)methyl)phosphonate

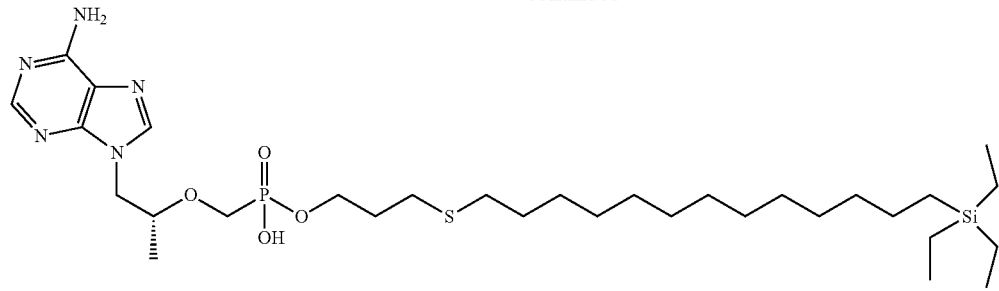

3-((13-(triethylsilyl)tridecyl)thio)propyl hydrogen ((((R)-1-(6-amino-9H-purin-9-yl)propan-2-yl)oxy)methyl)phosphonate

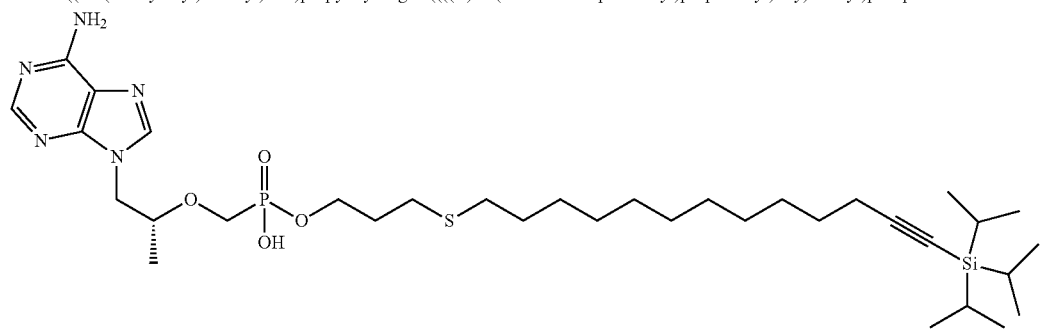

3-((13-(triisopropylsilyl)tridec-12-yn-1-yl)thio)propyl hydrogen ((((R)-1-(6-amino-9H-purin-9-yl)propan-2-yl)oxy)methyl)phosphonate

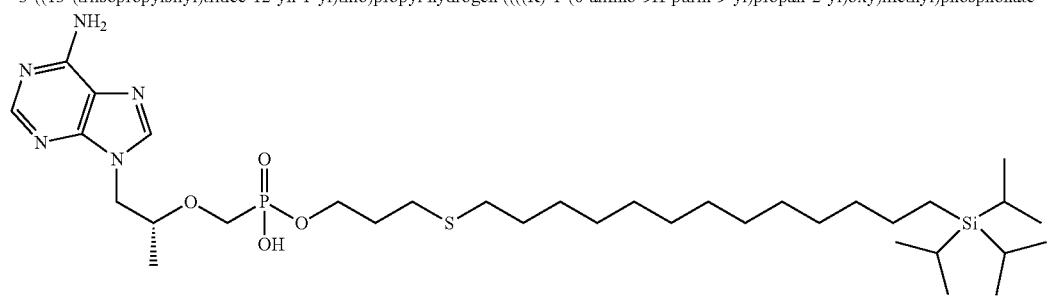

3-((13-(triisopropylsilyl)tridecyl)thio)propyl hydrogen ((((R)-1-(6-amino-9H-purin-9-yl)propan-2-yl)oxy)methyl)phosphonate

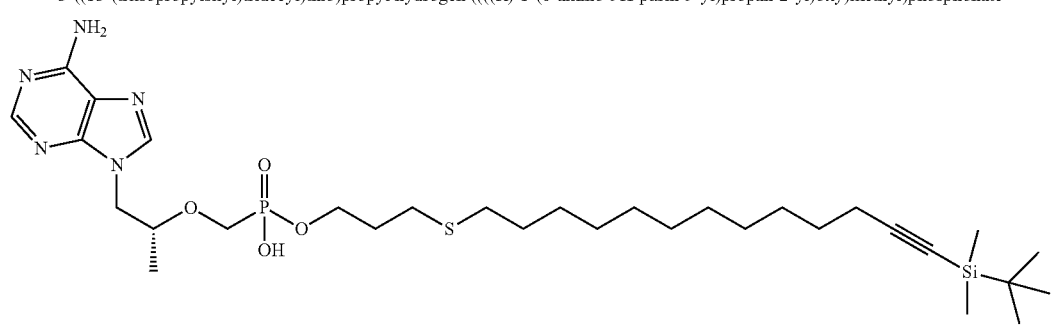

3-((13-(tert-butyldimethylsilyl)tridec-12-yn-1-yl)thio)propyl hydrogen ((((R)-1-(6-amino-9H-purin-9-yl)propan-2-yl)oxy)methyl) phosphonate

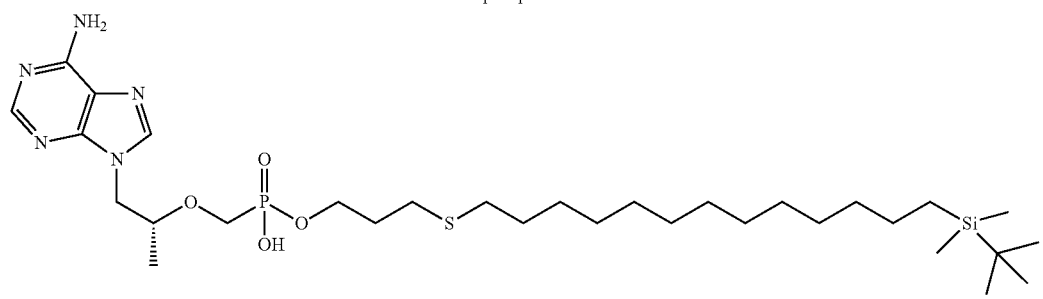

3-((13-(tert-butyldimethylsilyl)tridecyl)thio)propyl hydrogen ((((R)-1-(6-amino-9H-purin-9-yl)propan-2-yl)oxy)methyl)phosphonate

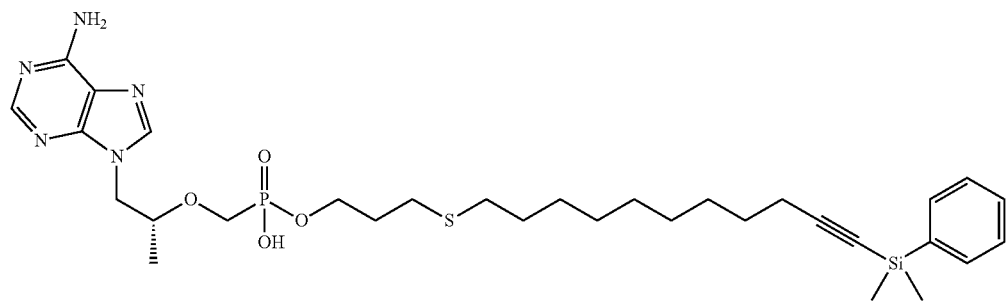

3-((11-(dimethyl(phenyl)silyl)undec-10-yn-1-yl)thio)propyl hydrogen ((((R)-1-(6-amino-9H-purin-9-yl)propan-2-yl)oxy)methyl) phosphonate

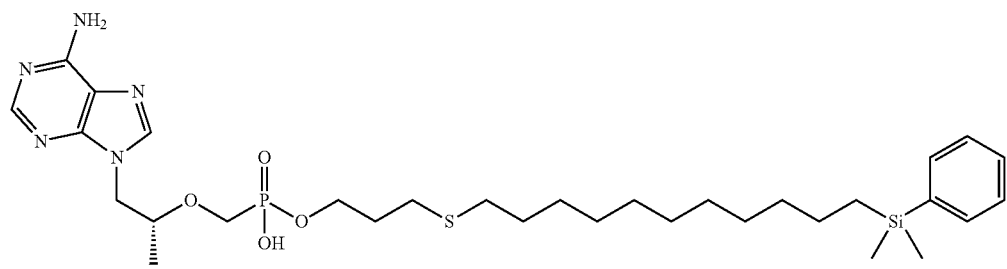

3-(11-(dimethyl(phenyl)silyl)undecyl)thio)propyl hydrogen ((((R)-1-(6-amino-9H-purin-9-yl)propan-2-yl)oxy)methyl)phosphonate

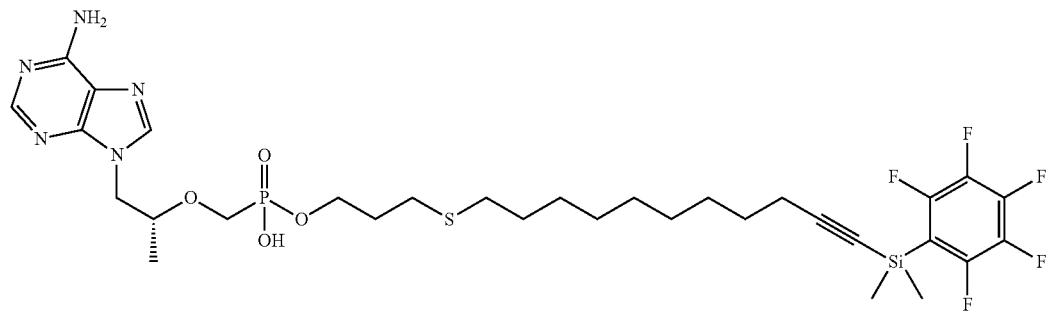

3-((11-(dimethyl(perfluorophenyl)silyl)undec-10-yn-1-yl)propyl hydrogen ((((R)-1-(6-amino-9H-purin-9-yl)propan-2-yl)oxy)methyl) phosphonate

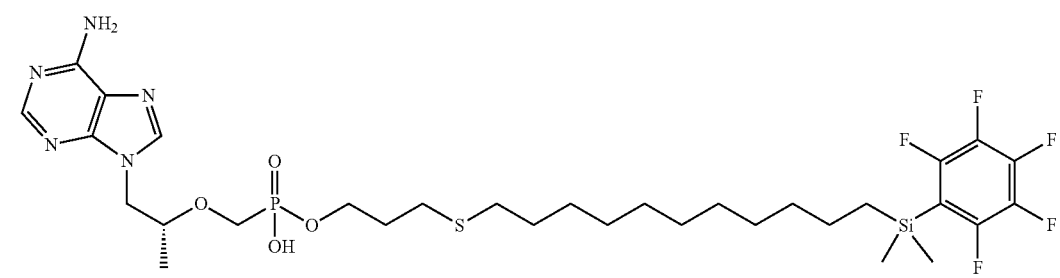

3-((11-(dimethyl(perfluorophenyl)silyl)undecyl)thio)propyl hydrogen ((((R)-1-(6-amino-9H-purin-9-yl)propan-2-yl)oxy)methyl)phosphonate

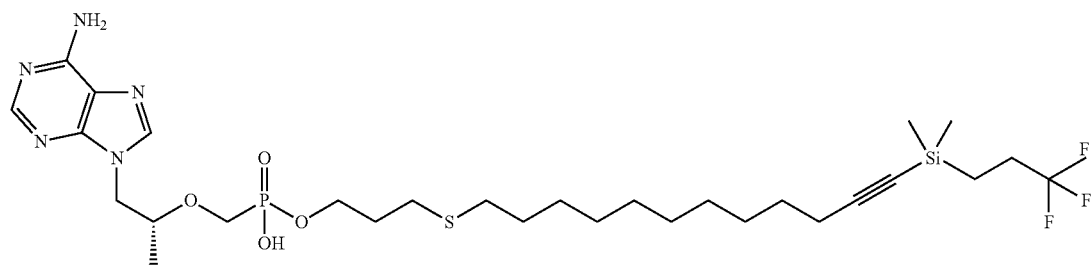

3-((12-(dimethyl(3,3,3-trifluoropropyl)silyl)dodec-11-yn-1-yl)thio)propyl hydrogen ((((R)-1-(6-amino-9H-purin-9-yl)propan-2-yl(oxy)methyl) phosphonate

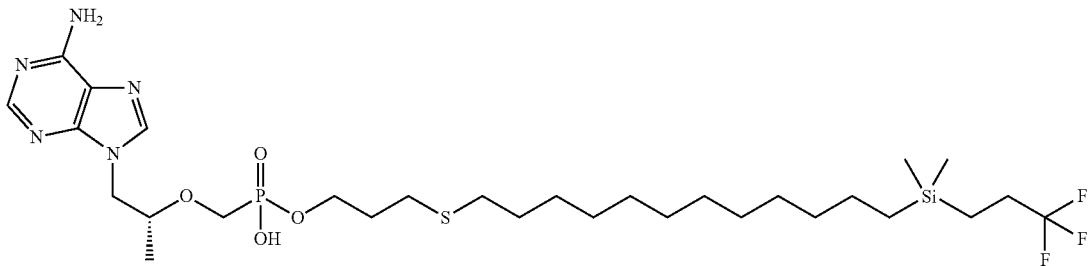

3-((12-(dimethyl(3,3,3-trifluoropropyl)silyl)dodecyl)thio)propyl hydrogen ((((R)-1-(6-amino-9H-purin-9-yl)propan-2-yl)oxy)methyl)phosphonate

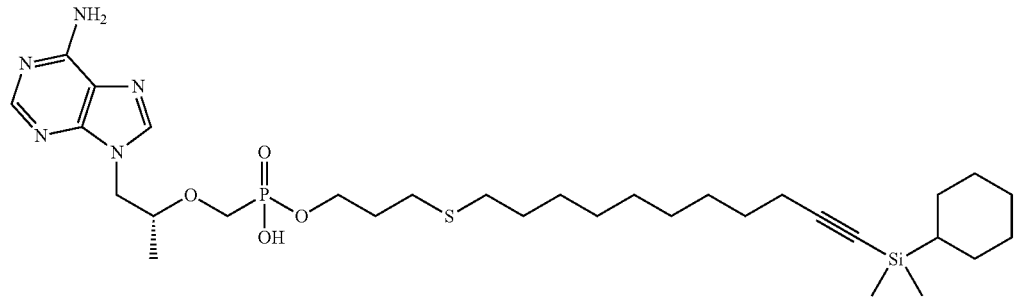

3-((11-(cyclohexyldimethylsilyl)undec-10-yn-1-yl)thio)propyl hydrogen ((((R)-1-(6-amino-9H-purin-9-yl)propan-2-yl)oxy)methyl)phosphonate

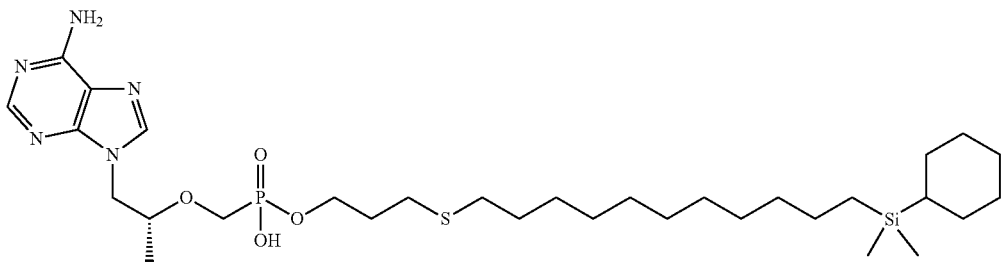

3-((11-(cyclohexyldimethylsilyl)undecyl)thio)propyl hydrogen ((((R)-1-(6-amino-9H-purin-9-yl)propan-2-yl)oxy)methyl)phosphonate

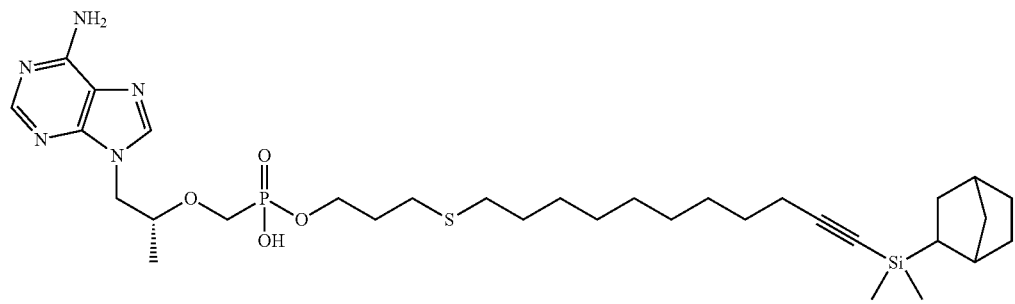

3-((11-(bicyclo[2.2.1]heptan-2-yldimethylsilyl)undec-10-yn-1-yl)thio)propyl hydrogen ((((R)-1-(6-amino-9H-purin-9-yl)propan-2-yl)oxy)methyl)phosphonate

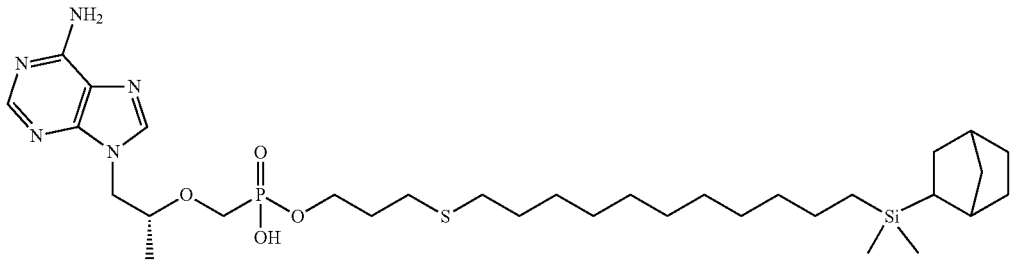

3-((11-(bicyclo[2.2.1]heptan-2-yldimethylsilyl)undecyl)thio)propyl hydrogen ((((R)-1-(6-amino-9H-purin-9-yl)propan-2yl)oxy)methyl)phosphonate -continued

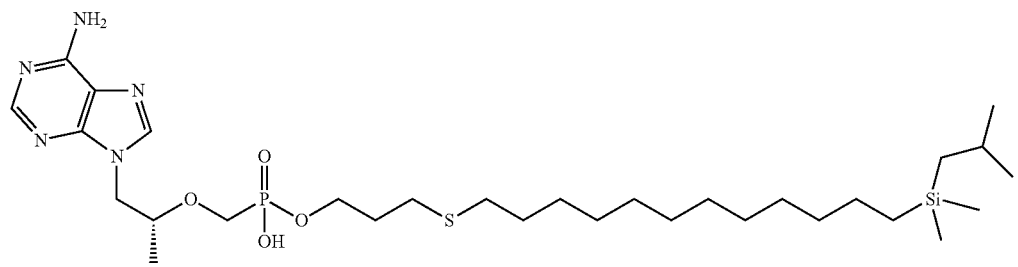

3-((12-(isobutyldimethylsilyl)dodecyl)thio)propyl hydrogen ((((R)-1-(6-amino-9H-purin-9-yl)propan-2-yl)oxy)methyl)phosphonate

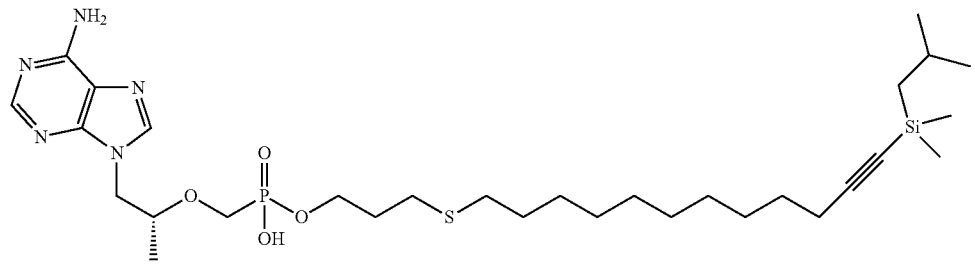

3-((12-(isobutyldimethylsilyl)dodec-11-yn-1-yl)thio)propyl hydrogen ((((R)-1-(6-amino-9H-purin-9-yl)propan-2-yl)oxy)methyl)phosphonate

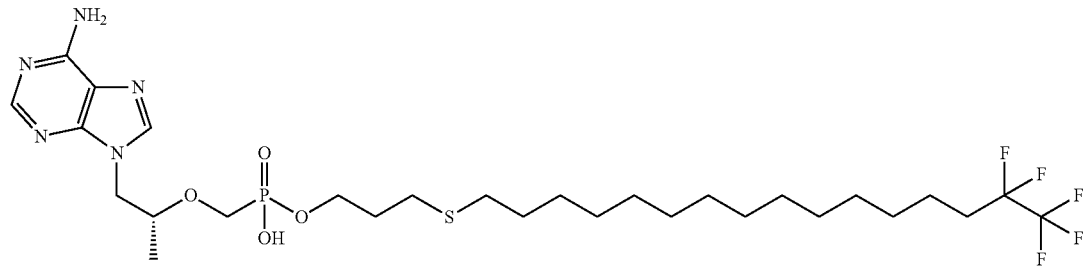

3-((15,15,16,16,16-pentafluorohexadecyl)thio)propyl hydrogen ((((R)-1-(6-amino-9H-purin-9-yl)propan-2-yl)oxy)methyl)phosphonate

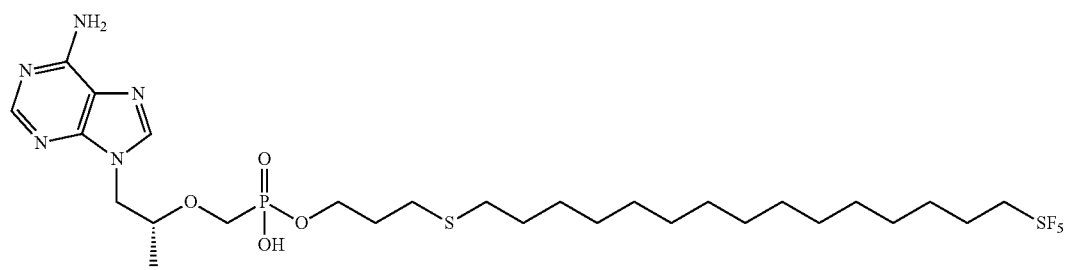

3-((15-(pentafluoro-λ⁶-sufanyl)pentadecyl)thio)propyl hydrogen ((((R)-1-(6-amino-9H-purin-9-yl)propan-2-yl)oxy)methyl)phosphonate

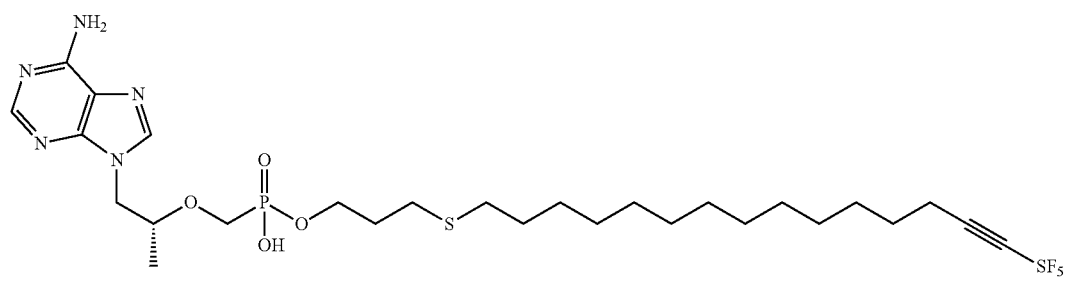

3-((15-(pentafluoro-λ⁶-sufanyl)pentadec-14-yn-1-yl)thio)propyl hydrogen ((((R)-1-(6-amino-9H-purin-9-yl)propan-2-yl)oxy)methyl)phosphonate

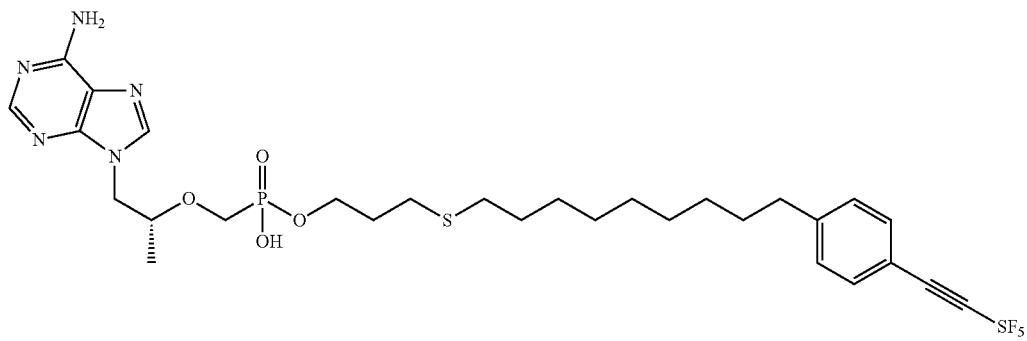

3-((9-(4-((pentafluoro-λ⁶-sufanyl)ethynyl)phenyl)nonyl)thio)propyl hydrogen ((((R)-1-(6-amino-9H-purin-9-yl)propan-2-yl)oxy)methyl)phosphonate

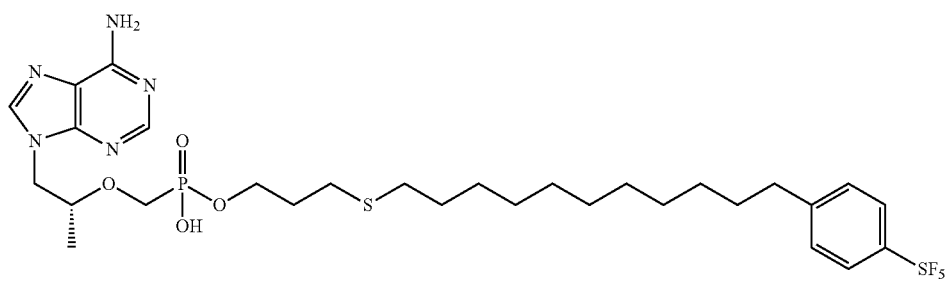

3-((11-(pentafluoro-λ⁶-sufanyl)phenyl)undecyl)thio)propyl hydrogen ((((R)-1-(6-amino-9H-purin-9-yl)propan-2-yl)oxy)methyl)phosphonate

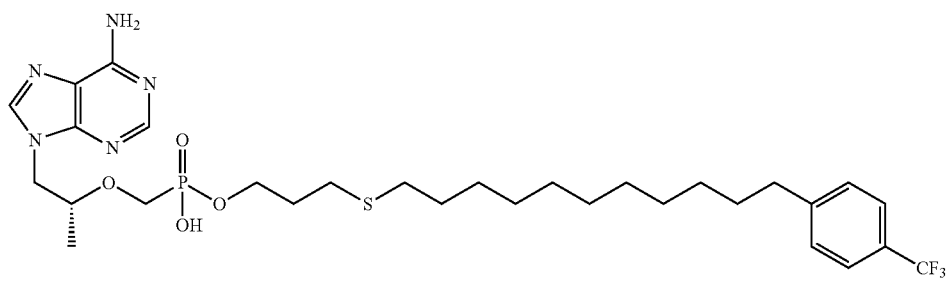

3-((11-(4-(trifluoromethyl)phenyl)undecyl)thio)propyl hydrogen ((((R)-1-(6-amino-9H-purin-9-yl)propan-2-yl)oxy)methyl)phosphonate

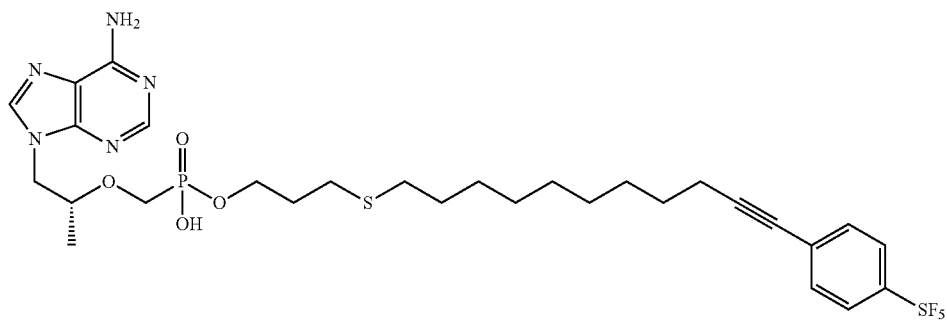

3-((11-(pentafluoro-λ⁶-sufanyl)phenyl)undec-10-yn-1-yl)thio)propyl hydrogen ((((R)-1-(6-amino-9H-purin-9-yl)propan-2-yl)oxy)methyl)phosphonate -continued

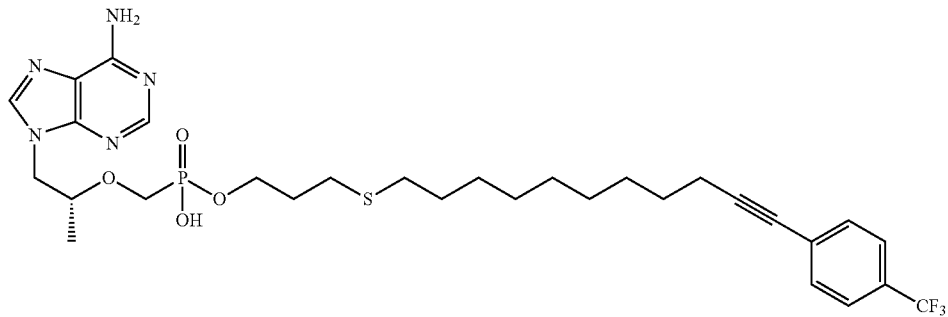

3-((11-(trifluoromethyl)phenyl)undec-10-yn-1-yl)thio)propyl hydrogen ((((R)-1-(6-amino-9H-purin-9-yl)propan-2-yl)oxy)methyl)phosphonate

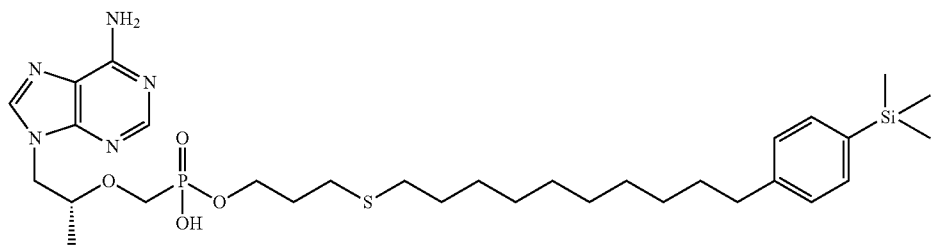

3-((10-(4-(trimethylsilyl)phenyl)decyl)thio)propyl hydrogen ((((R)-1-(6-amino-9H-purin-9-yl)propan-2-yl)oxy)methyl)phosphonate

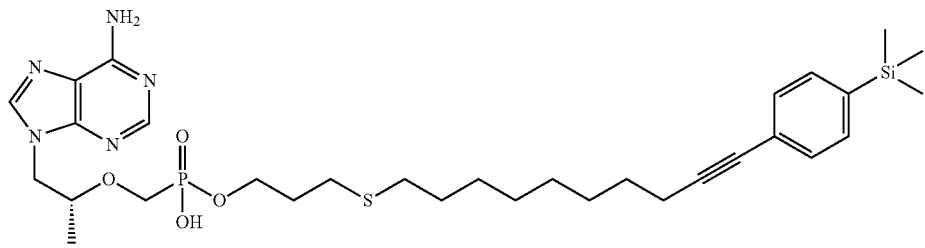

3-((10-(4-(trimethylsilyl)phenyl)dec-9-yn-1-yl)thio)propyl hydrogen ((((R)-1-(6-amino-9H-purin-9-yl)propan-2-yl)oxy)methyl)phosphonate

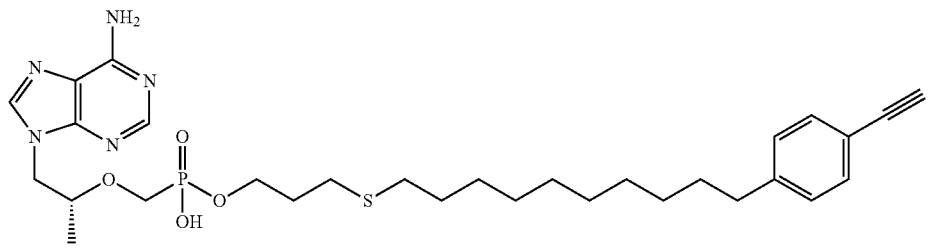

3-((10-(4-ethynylphenyl)decyl)thio)propyl hydrogen ((((R)-1-(6-amino-9H-purin-9-yl)propan-2-yl)oxy)methyl)phosphonate

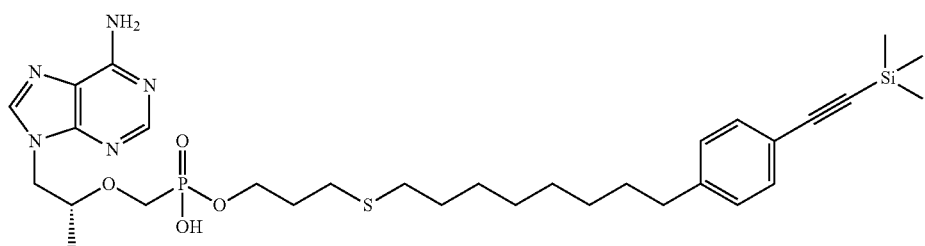

3-((8-(4-((trimethylsilyl)ethynyl)phenyl)octyl)thio)propyl hydrogen ((((R)-1-(6-amino-9H-purin-9-yl)propan-2-yl)oxy)methyl)phosphonate

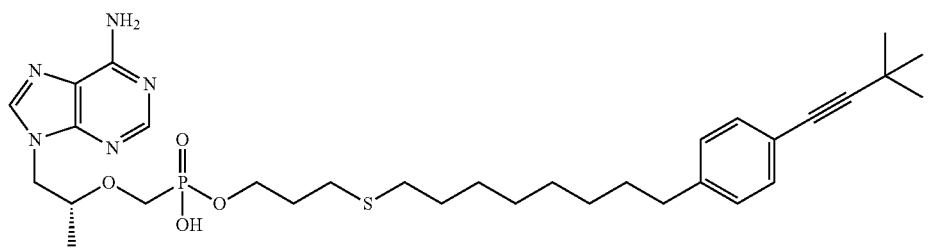

3-((8-(4-(3,3-dimethylbut-1-yn-1yl)phenyl)octyl)thio)propyl hydrogen ((((R)-1-(6-amino-9H-purin-9-yl)propan-2-yl)oxy)methyl)phosphonate

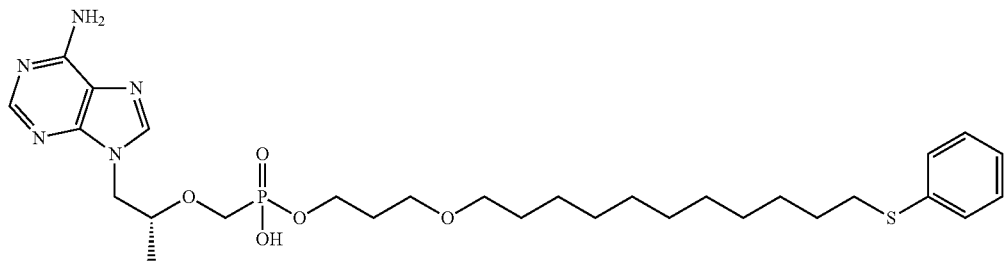

3-((11-(phenylthio)undecyl)oxy)propyl hydrogen ((((R)-1-(6-amino-9H-purin-9-yl)propan-2-yl)oxy)methyl)phosphonate

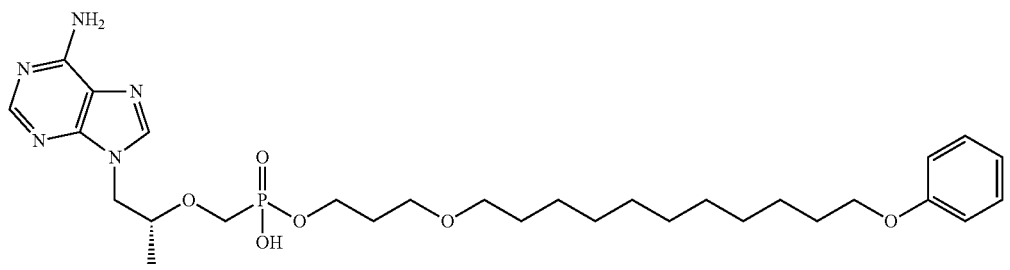

3-((11-(phenoxyundecyl)oxy)propyl hydrogen ((((R)-1-(6-amino-9H-purin-9-yl)propan-2-yl)oxy)methyl)phosphonate

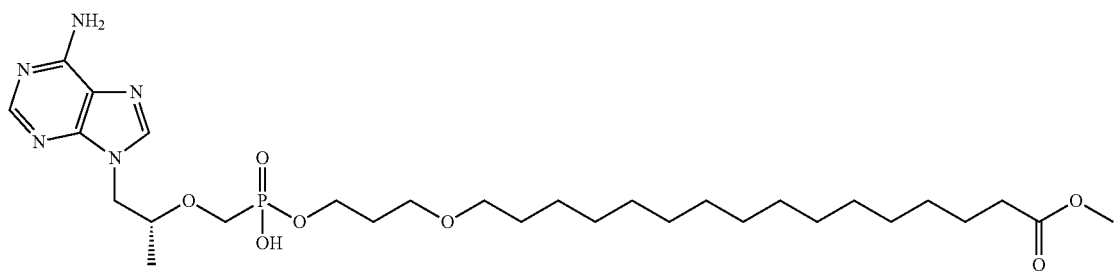

methyl 16-(3-((((((R)-1-(6-amino-9H-purin-9-yl)propan-2-yl)oxy)methyl)(hydroxy)phosphoryl)oxy)propoxy)hexadecanoate

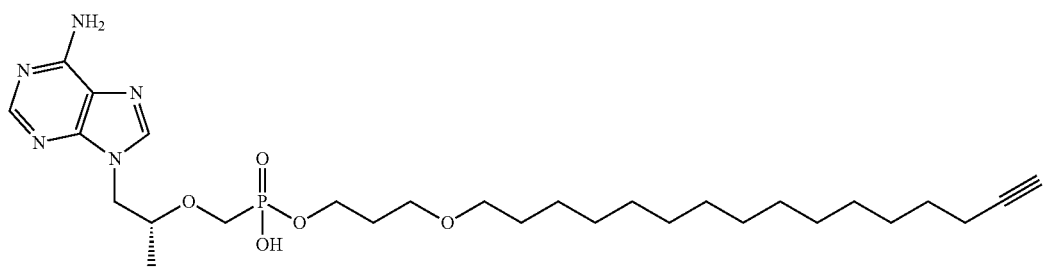

3-(hexadec-15-yn-1-yloxy)propyl hydrogen ((((R)-1-(6-amino-9H-purin-9-yl)propan-2-yl)oxy)methyl)phosphonate

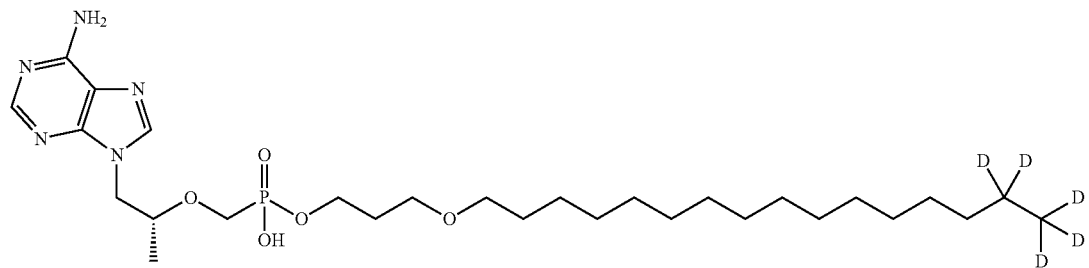

3-((hexadecyl-15, 15, 16, 16-d5)oxy)propyl hydrogen ((((R)-1-(6-amino-9H-purin-9-yl)propan-2-yl)oxy)methyl)phosphonate

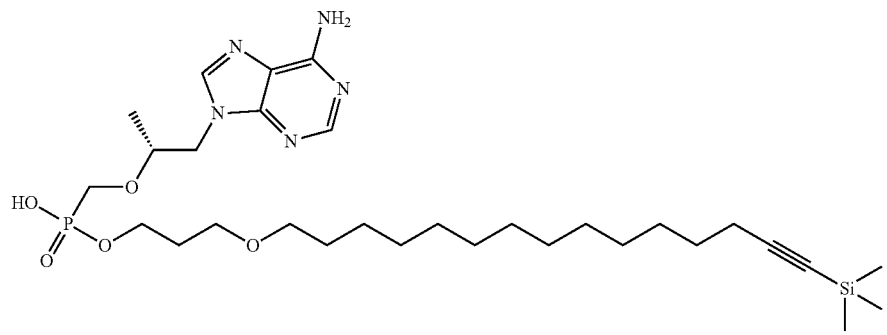

3-((15-(trimethylsilyl)pentadec-14-yn-1-yl)oxy)propyl hydrogen ((((R)-1-(6-amino-9H-purin-9-yl)propan-2-yl)oxy)methyl)phosphonate

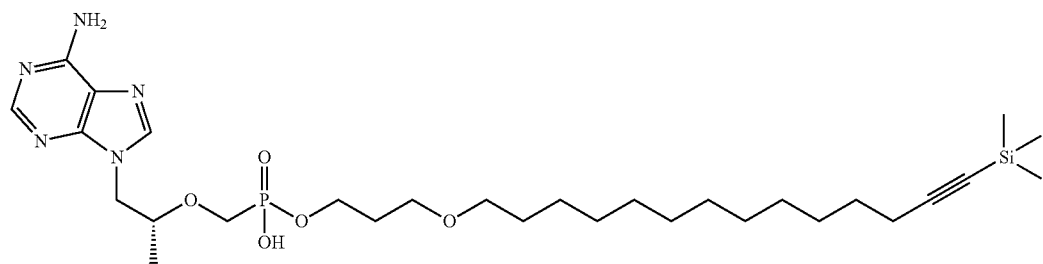

3-((14-(trimethylsilyl)tetradec-13-yn-1-yl)oxy)propyl hydrogen ((((R)-1-(6-amino-9H-purin-9-yl)propan-2-yl)oxy)methyl)phosphonate

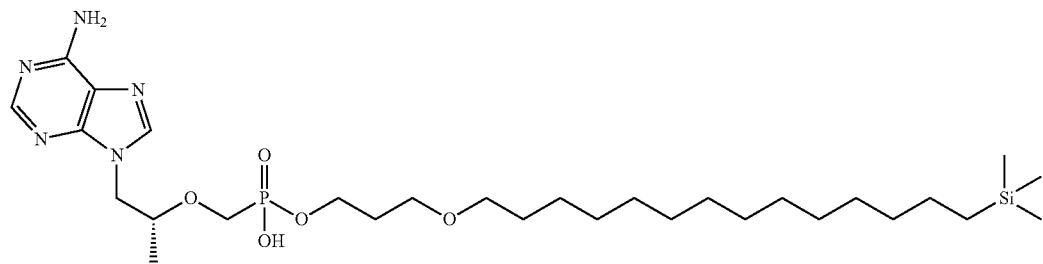

3-((14-(trimethylsilyl)tetradecyl)oxy)propyl hydrogen ((((R)-1-(6-amino-9H-purin-9-yl)propan-2-yl)oxy)methyl)phosphonate

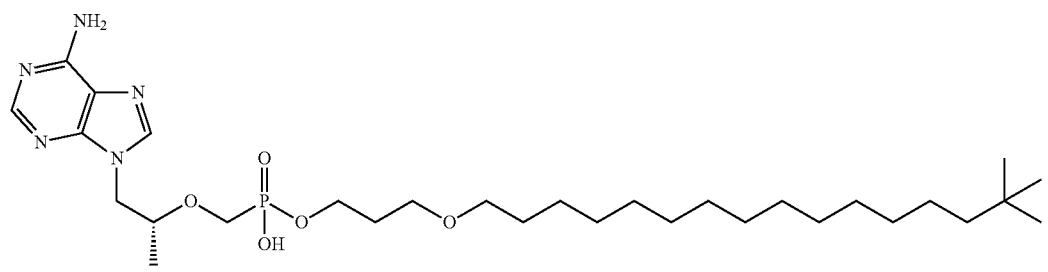

3-((15, 15-dimethylhexadecyl)oxy)propl hydrogen ((((R)-1-(6-amino-9H-purin-9-yl)propan-2-yl)oxy)methyl)phosphonate

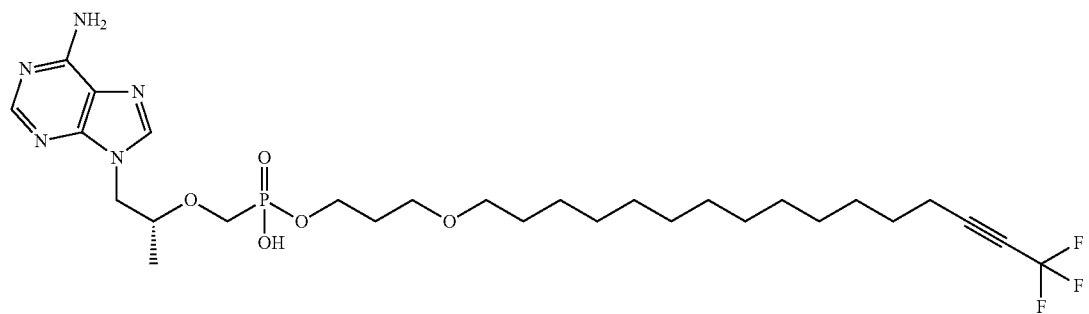

3-((16, 16, 16-trifluorohexadec-14-yn-1-yl)oxy)propyl hydrogen ((((R)-1-(6-amino-9H-purin-9-yl)propan-2-yl)oxy)methyl)phosphonate

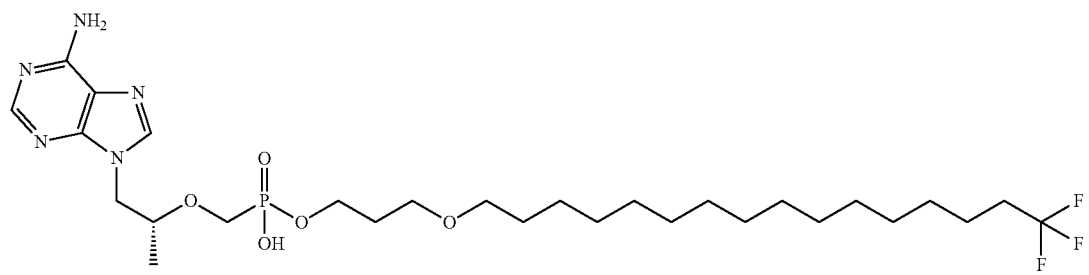

3-((16, 16, 16-trifluorohexadecyl)oxy)propyl hydrogen ((((R)-1-(6-amino-9H-purin-9-yl)propan-2-yl)oxy)methyl)phosphonate

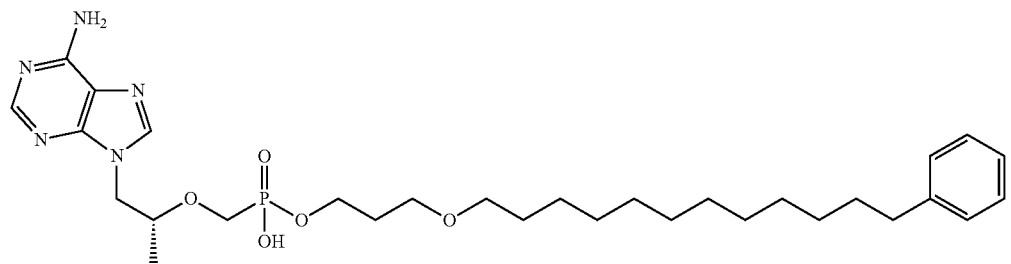

3-((12-phenyldodecyl)oxy)propyl hydrogen ((((R)-1-(6-amino-9H-purin-9-yl)propan-2-yl)oxy)methyl)phosphonate

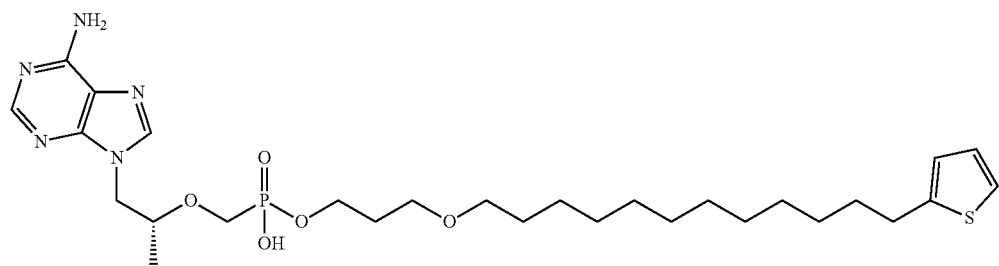

3-((12-(thiophen-2-yl)dodecyl)oxy)propyl hydrogen ((((R)-1-(6-amino-9H-purin-9-yl)propan-2-yl)oxy)methyl)phosphonate

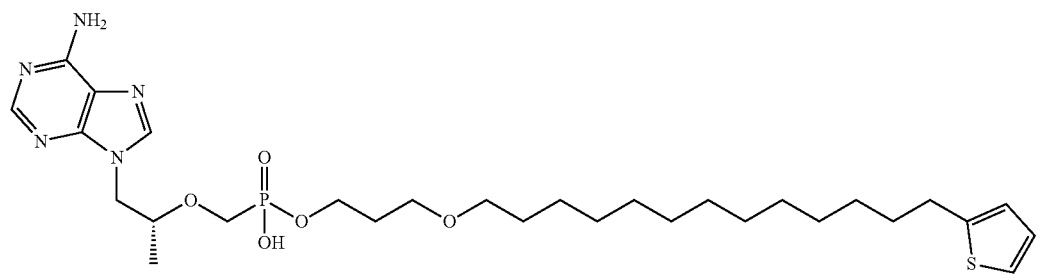

3-((13-(thiophen-2-yl)tridecyl)oxy)propyl hydrogen ((((R)-1-(6-amino-9H-purin-9-yl)propan-2-yl)oxy(methyl)phosphonate

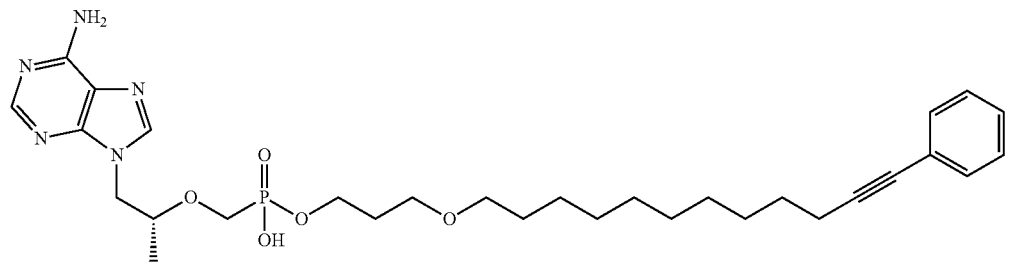

3-((12-phenyldodec-11-yn-1-yl)oxy)propyl hydrogen ((((R)-1-(6-amino-9H-purin-9-yl)propan-2-yl)oxy)methyl)phosphonate

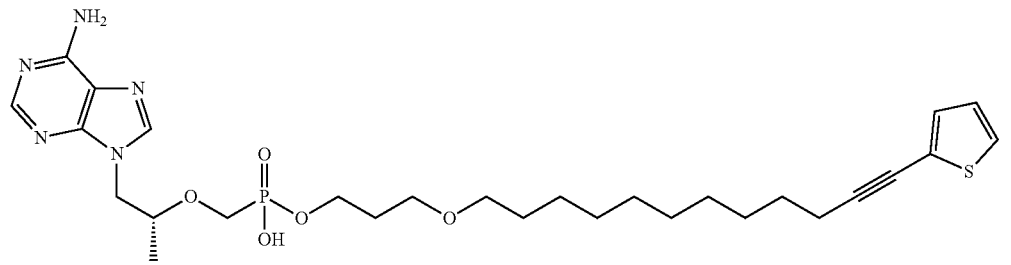

3-((12-thiophen-2-yl)dodec-11-yn-1-yl)oxy)propyl hydrogen ((((R)-1-(6-amino-9H-purin-9-yl)propan-2-yl)oxy)methyl) phosphonate

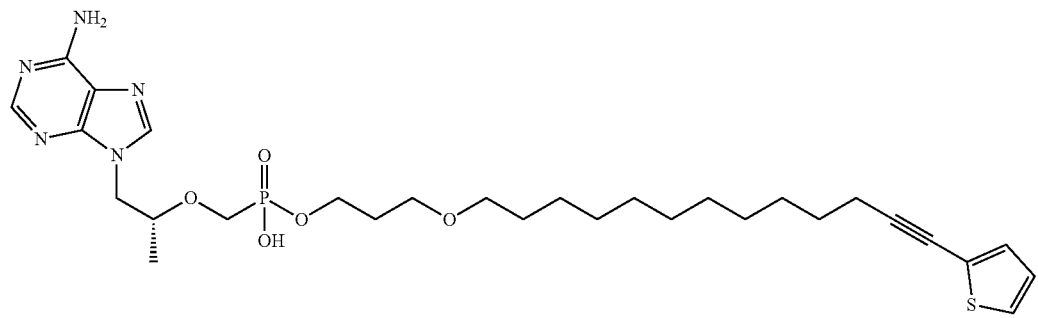

3-((13-(thiophen-2-yl)tridec-12-yn-1-yl)oxy)propyl hydrogen ((((R)-1-(6-amino-9H-purin-9-yl)propan-2-yl)oxy)methyl)phosphonate

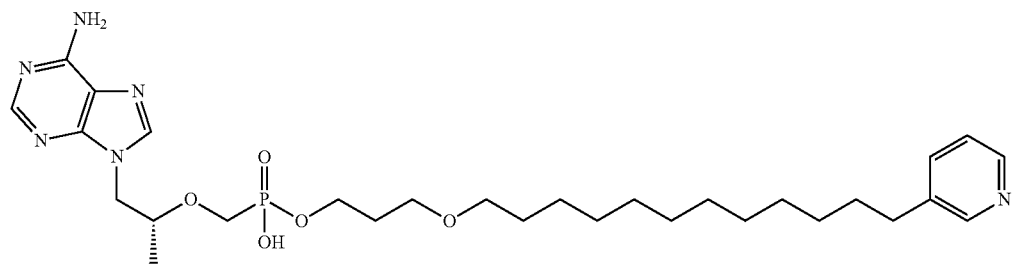

3-((12-(pyridin-3-yl)dodecyl)oxy)propyl hydrogen ((((R)-1-(6-amino-9H-purin-9yl)propan-2-yl)oxy)methyl)phosphonate

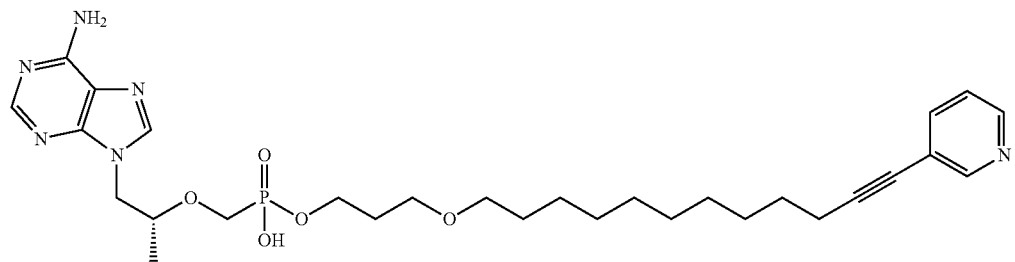

3-((12-pyridin-3-yl)dodec-11-yn-1-yl)oxy)propyl hydrogen ((((R)-1-(6-amino-9H-purin-9-yl)propan-2-yl)oxy)methyl)phosphonate

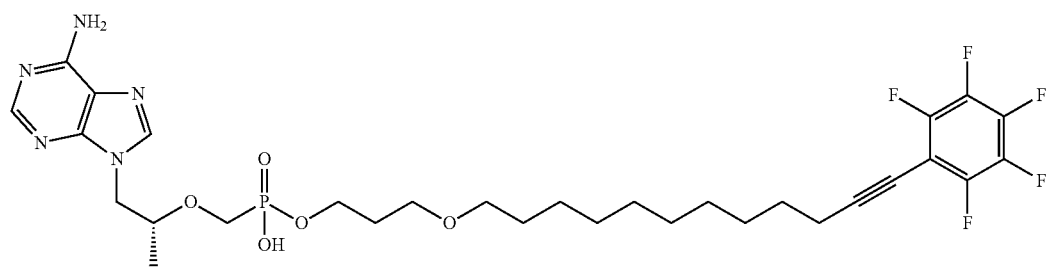

3-((12-(perfluorophenyl)dodec-11-yn-1-yl)oxy)propyl hydrogen ((((R)-1-(6-amino-9H-purin-9-yl)propan-2-yl)oxy)methyl)phosphonate

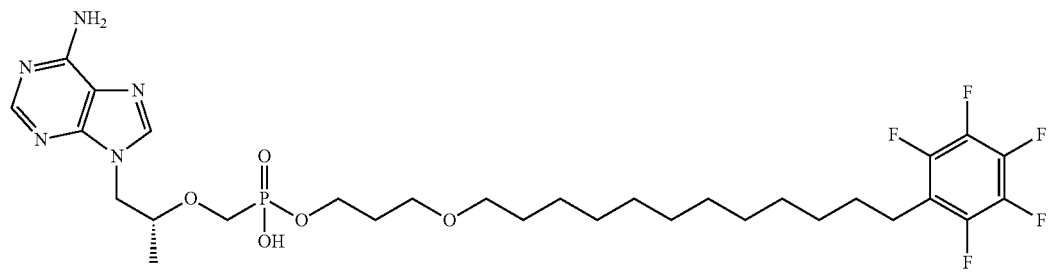

3-((12-(perfluorophenyl)dodecyl)oxy)propyl hydrogen ((((R)-1-(6-amino-9H-purin-9-yl)propan-2-yl)oxy)methyl)phosphonate

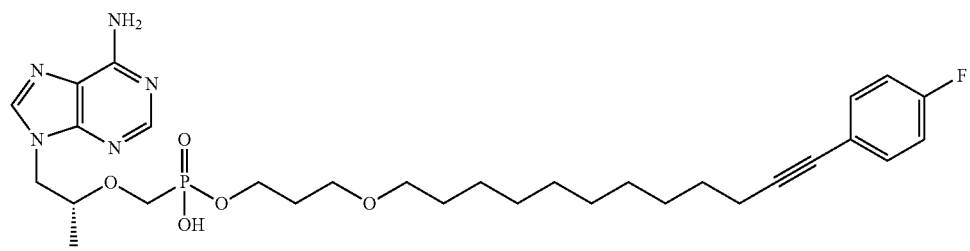

3-((12-(4-fluorophenyl)dodec-11-yn-1-yl)oxy)propy hydrogen ((((R)-1-(6-amino-9H-purin-9-yl)propan-2-yl)oxy)methyl)phosphonate

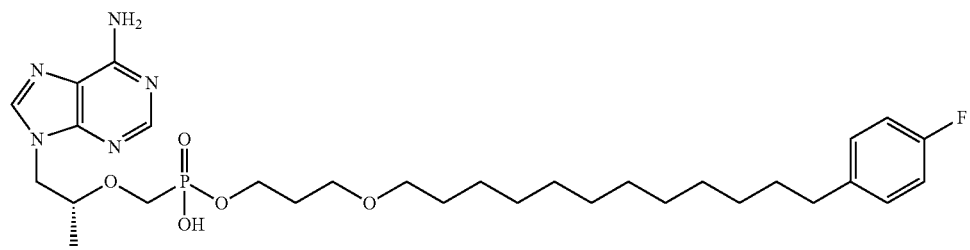

3-((12-(4-fluorophenyl)dodecyl)oxy)propyl hydrogen ((((R)-1-(6-amino-9H-purin-9-yl)propan-2-yl)oxy)methyl)phosphonate

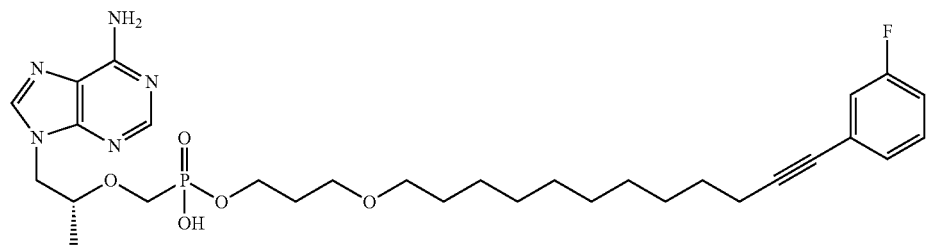

3-((12-(3-fluorophenyl)dodec-11-yn-1-yl)oxy)propyl hydrogen ((((R)-1-(6-amino-9H-purin-9-yl)propan-2-yl)oxy)methyl)phosphonate

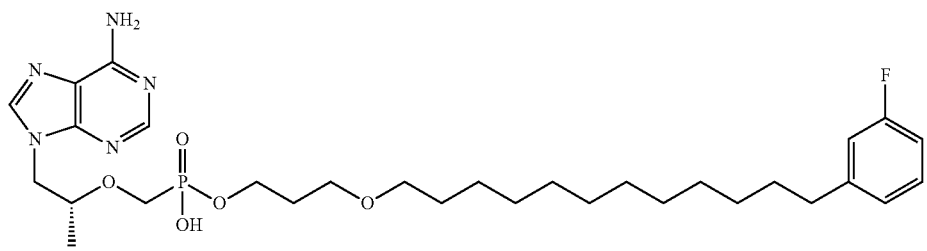

3-((12-(3-fluorophenyl)dodecycl)oxy)propyl hydrogen ((((R)-1-(6-amino-9H-purin-9-yl)propan-2-yl)oxy)methyl) phosphonate

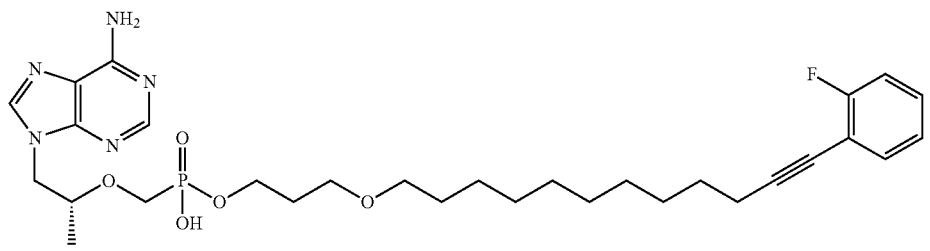

3-((12-(2-fluorophenyl)dodec-11-yn-1-yl)oxy)propyl hydrogen ((((R)-1-(6-amino-9H-purin-9-yl)propan-2-yl)oxy)methyl) phosphonate

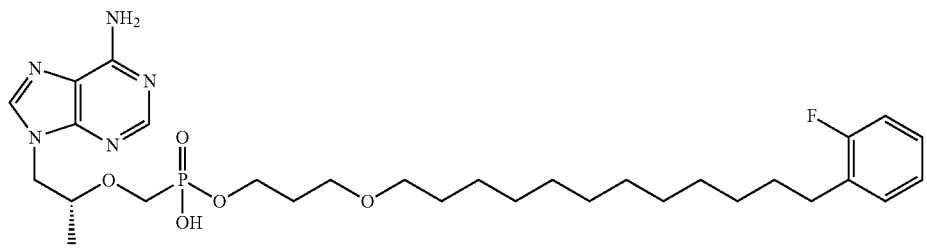

3-((12-(2-fluorophenyl)dodecycl)oxy)propyl hydrogen ((((R)-1-(6-amino-9H-purin-9-yl)propan-2-yl)oxy)methyl) phosphonate

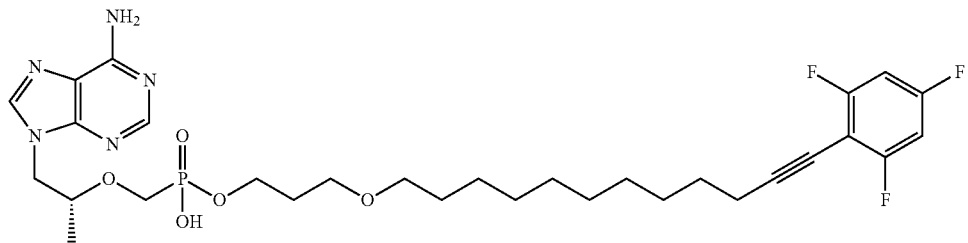

3-((12-(2,4,6-trifluorophenyl)dodec-11-yn-1-yl)oxy)propyl hydrogen ((((R)-1-(6-amino-9H-purin-9-yl)propan-2-yl)oxy) methyl)phosphonate

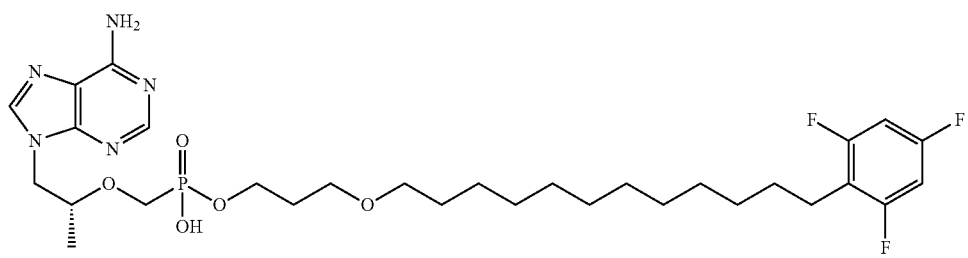

3-((12-(2,4,6-trifluorophenyl)dodecyl)oxy)propyl hydrogen ((((R)-1-(6-amino-9H-purin-9-yl)propan-2-yl)oxy)methyl) phosphonate -continued

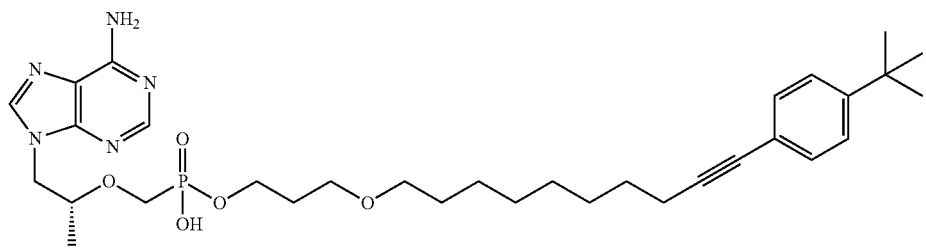

3-((10-(4-(tert-butyl)phenyl)dec-9-yn-1-yl)oxy)propyl hydrogen ((((R)-1-(6-amino-9H-purin-9-yl)propan-2-yl)oxy)methyl) phosphonate

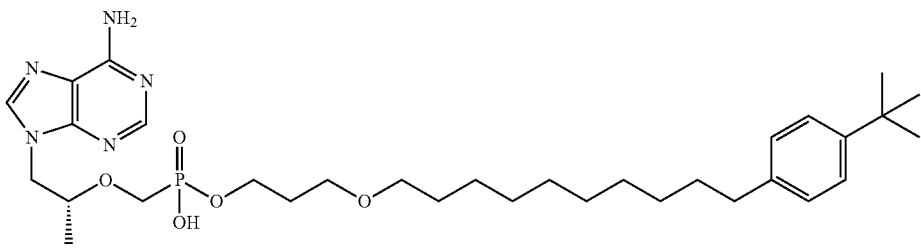

3-((10-(4-(tert-butyl)phenyl)decyl)oxy)propyl hydrogen ((((R)-1-(6-amino-9H-purin-9-yl)propan-2-yl)oxy)methyl) phosphonate

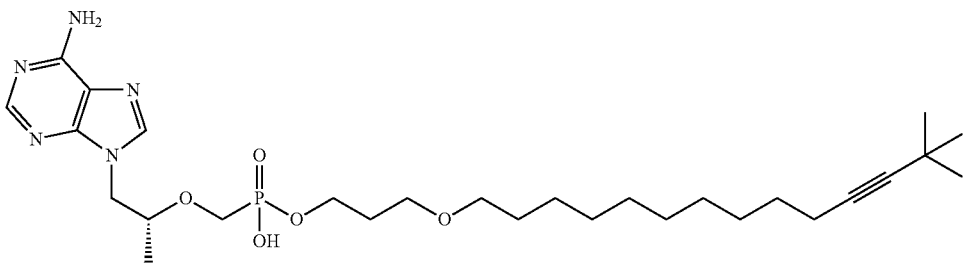

3-((15, 15-dimethylhexadec-13-yn-1-yl)oxy)propyl hydrogen ((((R)-1-(6-amino-9H-purin-9-yl)propan-2-yl)oxy)methyl) phosphonate

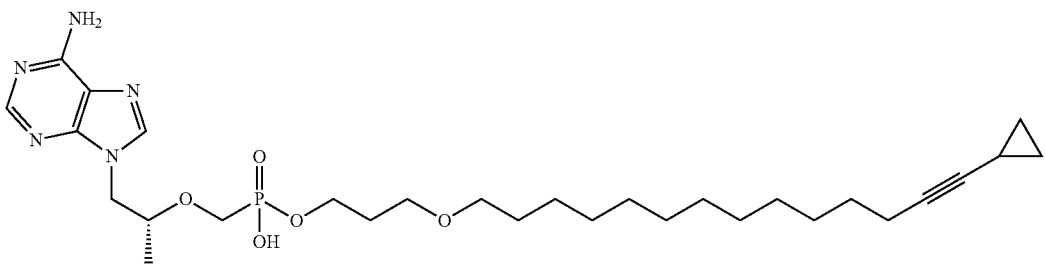

3-(((14-cyclopropyltetradec-13-yn-1-yl)oxy)propyl hydrogen ((((R)-1-(6-amino-9H-purin-9-yl)propan-2-(yl(oxy)methyl)phosphonate

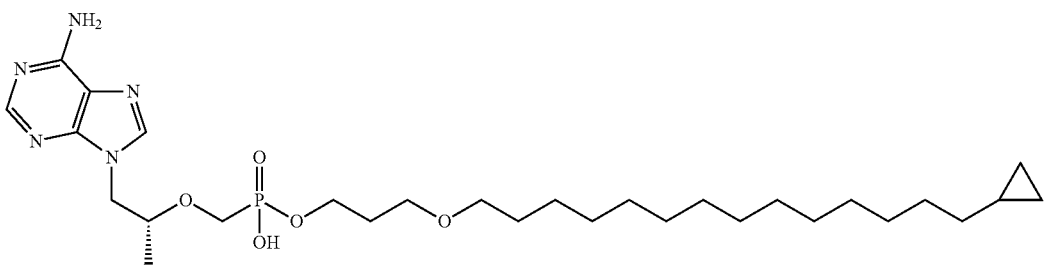

3-((14-cyclopropyltetradecyl)oxy)propyl hydrogen ((((R)-1-(6-amino-9H-purin-9-yl)propan-2-yl)oxy)methyl)phosphonate

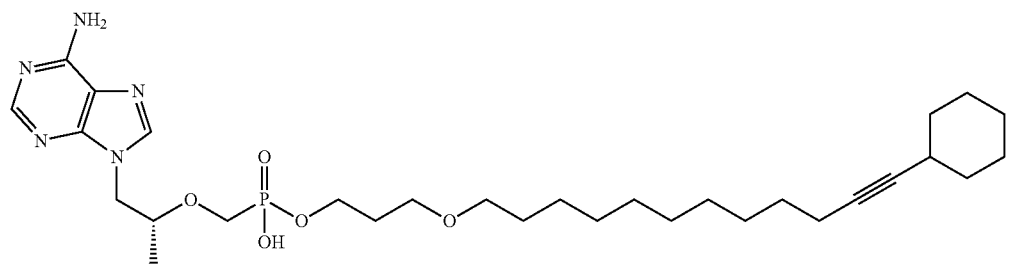

3-((12-cyclohexyldodec-11-yn-1-yl)oxy)propyl hydrogen ((((R)-1-(6-amino-9H-purin-9-yl)propan-2-yl)oxy)methyl)phosphonate

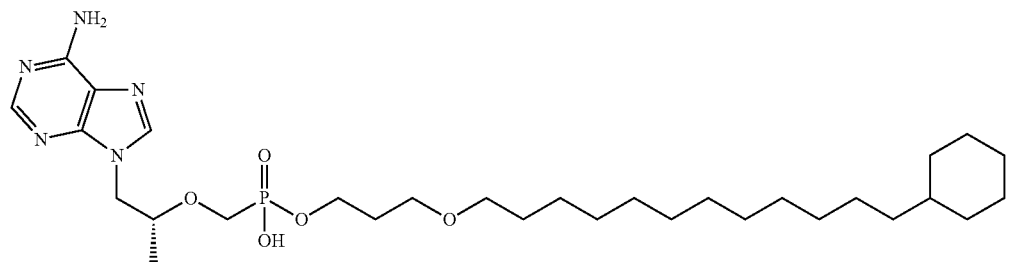

3-((12-cyclohexyldodecyl)oxy)propyl hydrogen ((((R)-1-(6-amino-9H-purin-9-yl)propan-2-yl)oxy)methyl)phosphonate

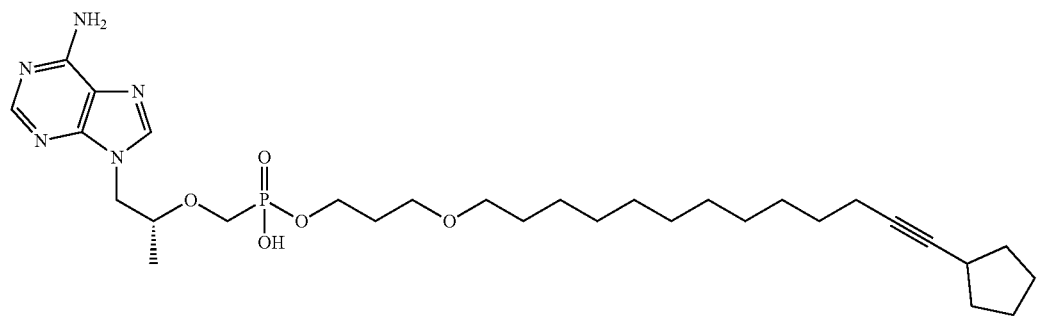

3-((13-cyclopentyltridec-12-yn-1-yl)oxy)propyl hydrogen ((((R)-1-(6-amino-9H-purin-9-yl)propan-2-yl)oxy)methyl)phosphonate

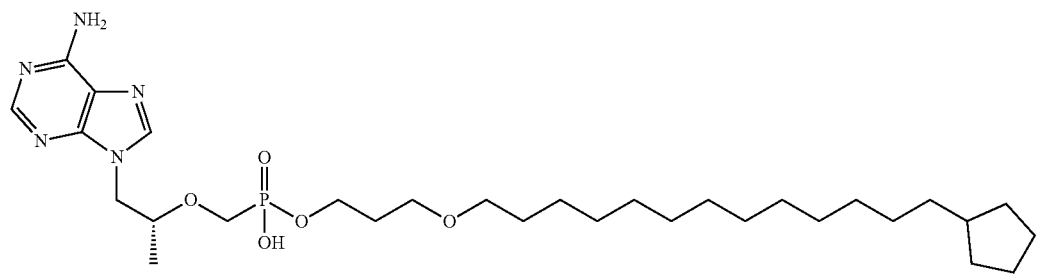

3-((13-cyclopentyltridecyl)oxy)propyl hydrogen ((((R)-1-(6-amino-9H-purin-9-yl)propan-2-yl)oxy)methyl)phosphonate

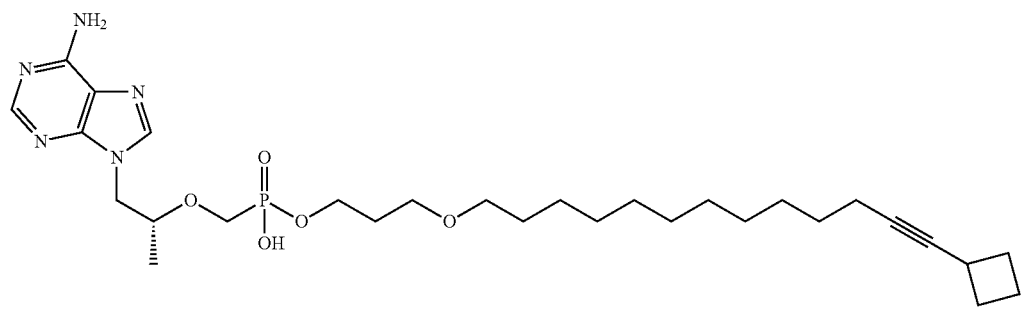

3-((13-cyclobutyltridec-12-yn-1-yl)oxy)propyl hydrogen ((((R)-1-(6-amino-9H-purin-9-yl)propan-2-yl)oxy)methyl)phosphonate

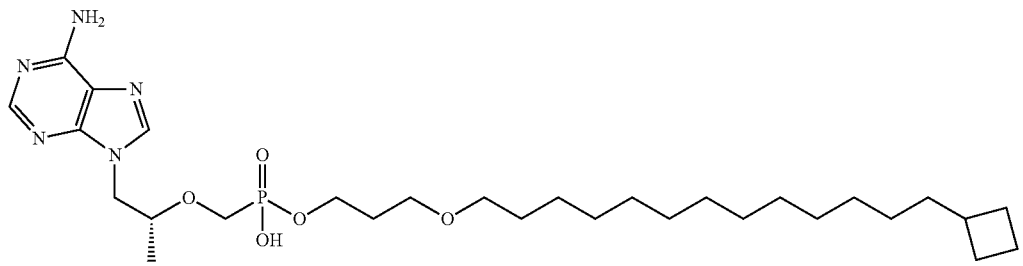

3-((13-cyclobutyltridecyl)oxy)propyl hydrogen ((((R)-1-(6-amino-9H-purin-9-yl)propan-2-yl)oxy)methyl)phosphonate

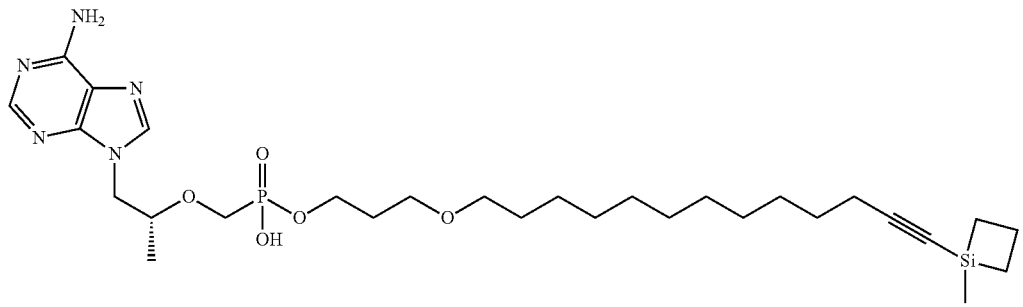

3-((13-(1-methylsiletan-1-yl)tridec-12-yn-1-yl)oxy)propyl hydrogen ((((R)-1-(6-amino-9H-purin-9-yl)propan-2-yl)oxy)methyl) phoshonate

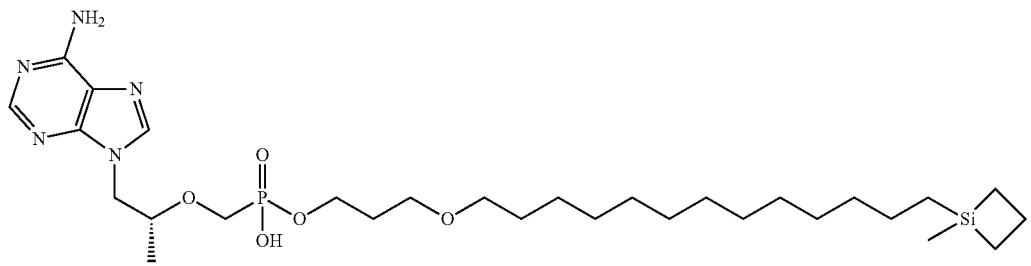

3-((13-(1-methylsiletan-1-yl)tridecyl)oxy)propyl hydrogen ((((R)-1-(6-amino-9H-purin-9-yl)propan-2-yl)oxy)methyl)phosphonate

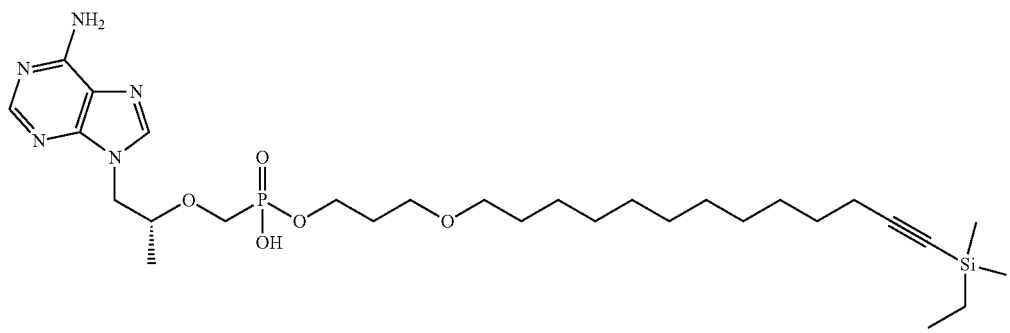

3-((13-(ethyldimethylsilyl)tridec-12-yn-1-yl)oxy)propyl hydrogen ((((R)-1-(6-amino-9H-purin-9-yl)propan-2-yl)oxy)methyl) phosphonate

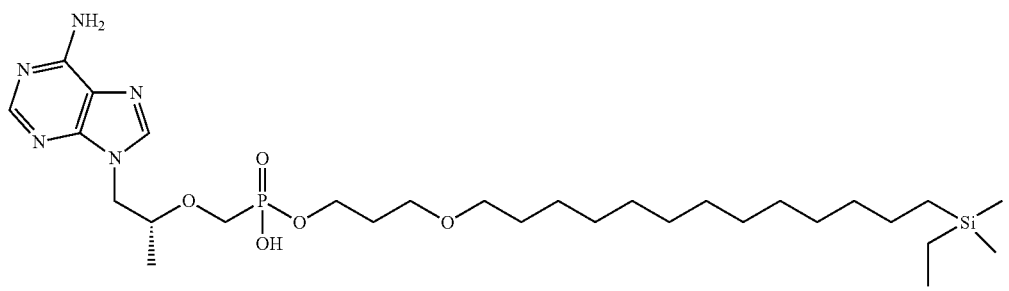

3-((13-ethyldimethylsilyl)tridecyl)oxy)propyl hydrogen ((((R)-1-(6-amino-9H-purin-9-yl)propan-2-yl)oxy)methyl)phosphonate

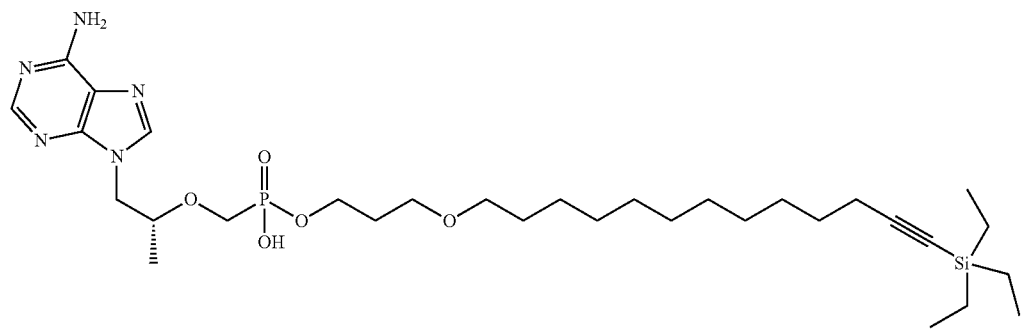

3-(((13-(triethylsilyl)tridec-12-yn-1-yl)oxy)propyl hydrogen ((((R)-1-(6-amino-9H-purin-9-yl)propan-2-yl)oxy)methyl)phosphonate

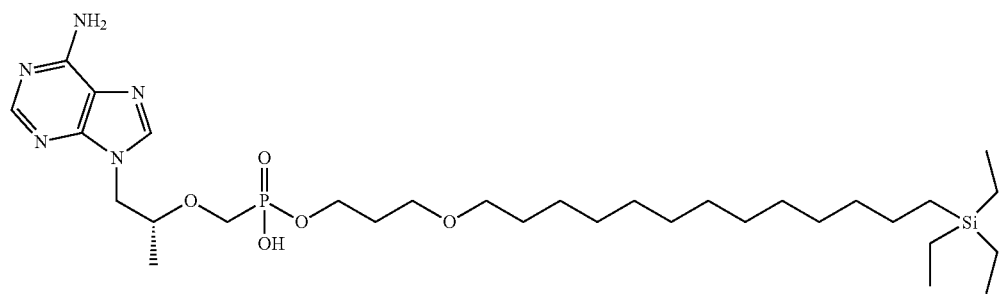

3-((13-(triethylsily)tridecyl)oxy)propyl hydrogen ((((R)-1-(6-amino-9H-purin-9-yl)propan-2-yl)oxy)methyl)phosphonate

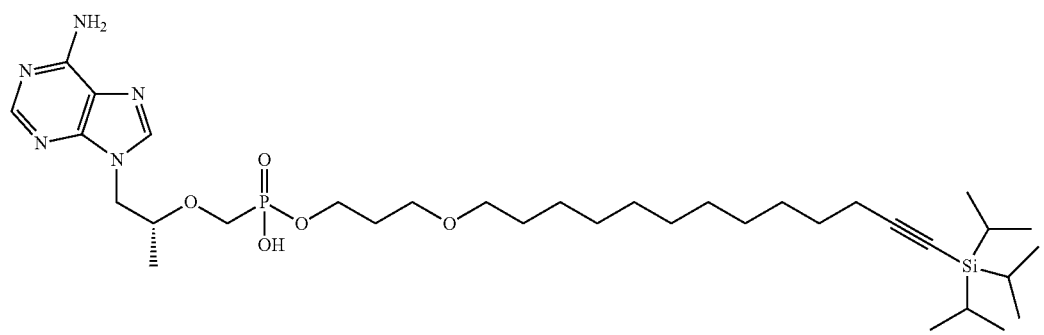

3-((13-(triisopropylsilyl)tridec-12-yn-1-yl)oxy)propyl hydrogen ((((R)-1-(6-amino-9H-purin-9-yl)propan-2-yl)oxy)methyl)phosphonate

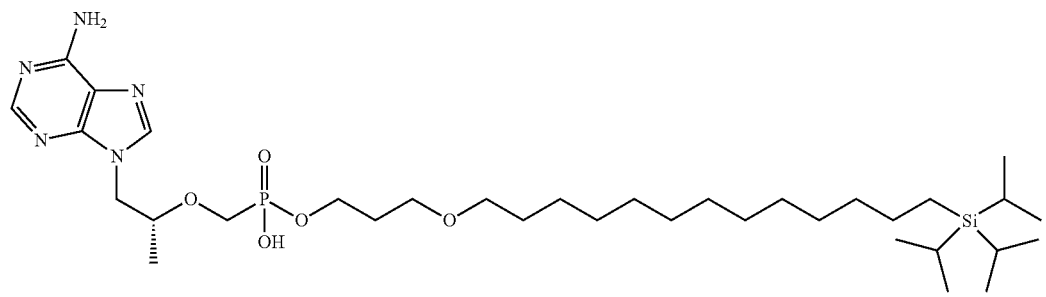

3-((13-(triisopropylsilyl)tridecyl)oxy)propyl hydrogen ((((R)-1-(6-amino-9H-purin-9-yl)propan-2-yl)oxy)methyl)phosphonate

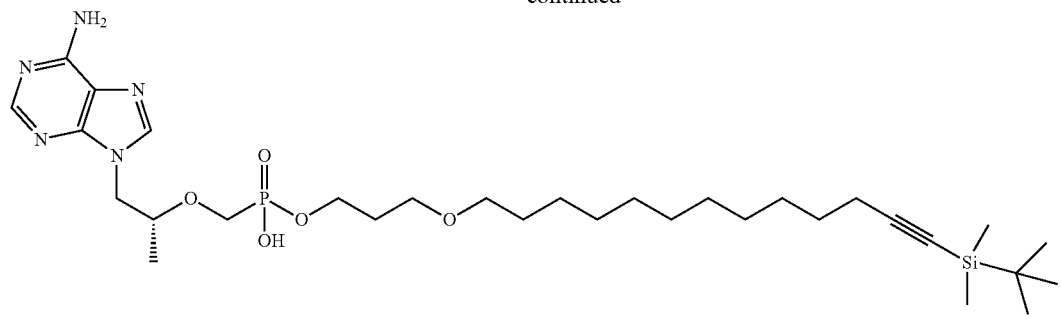

3-((13-(tert-butyldimethylsilyl)tridec-12-yn-1-yl)oxy)propyl hydrogen ((((R)-1-(6-amino-9H-purin-9-yl)propan-2-yl)oxy)methyl)phosphonate

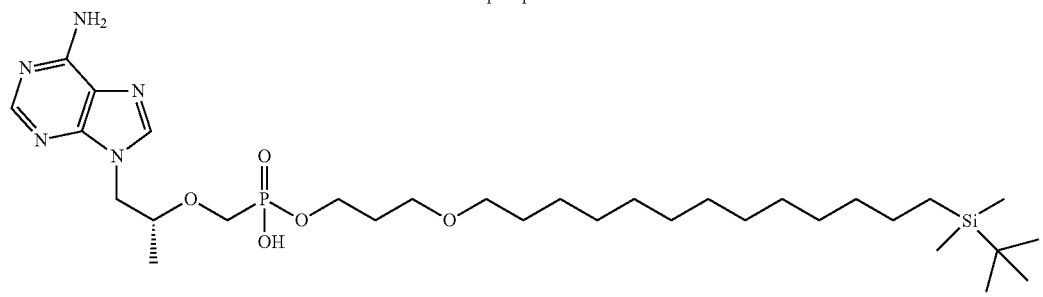

3-((13-(tert-butyldimethylsilyl)tridecyl)oxy)propyl hydrogen ((((R)-1-(6-amino-9H-purin-9-yl)propan-2-yl)oxy)methyl)phosphonate

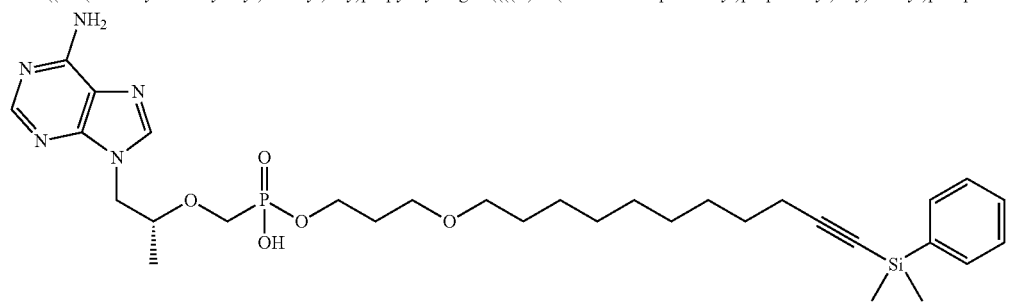

3-((11-(dimethyl(phenyl)silyl)undec-10-yn-1-yl)oxy)propy hydrogen ((((R)-1-(6-amino-9H-purin-9-yl)propan-2-yl)oxy)methyl)phosphonate

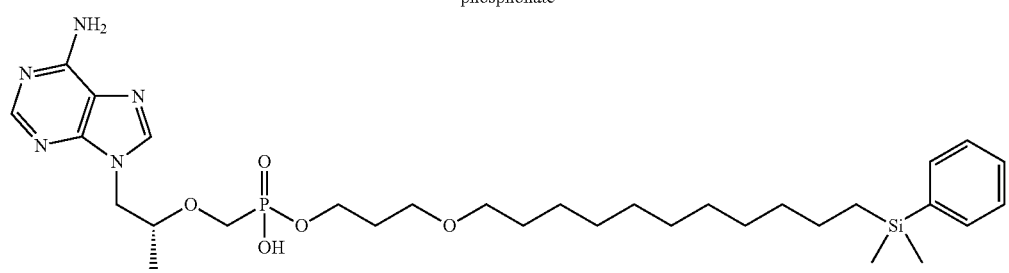

3-((11-(dimethyl(phenyl)silyl)undecyl)oxy)propyl hydrogen ((((R)-1-(6-amino-9H-purin-9-yl)propan-2-yl)oxy)methyl)phosphonate

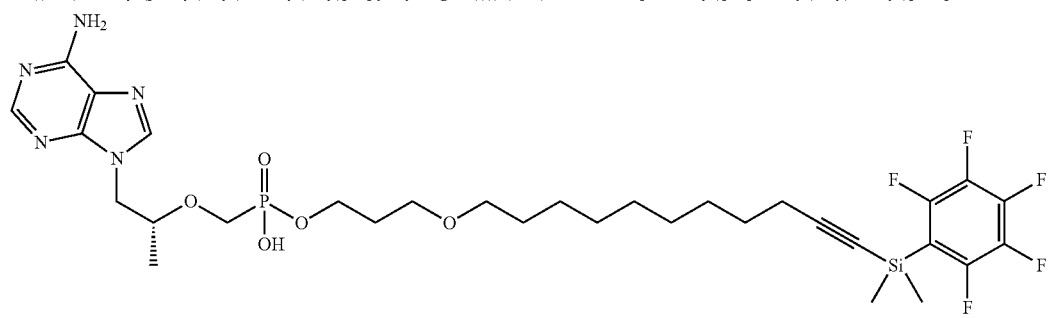

3-((11-(dimethyl(perfluorophenyl)silyl)undec-10-yn-1-yl)oxy)propyl hydrogen ((((R)-1-(6-amino-9H-purin-9-yl)propan-2-yl)oxy)methyl)phosphonate

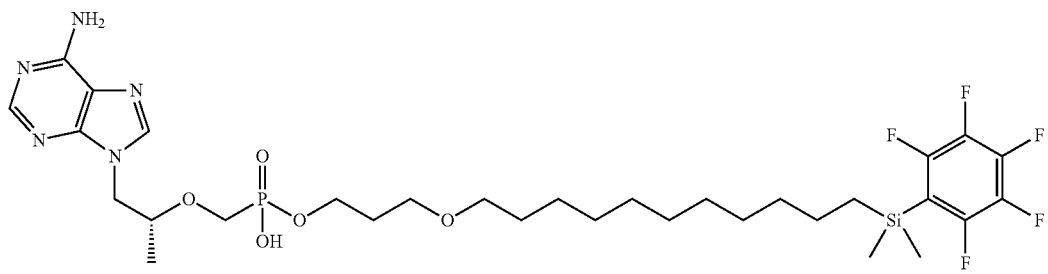

3-((11-(dimethyl(erfluorophenyl)silyl)undecyl)oxy)propyl hydrogen ((((R)-1-(6-amino-9H-purin-9-yl)propan-2-yl)oxy)methyl)
phosphonate

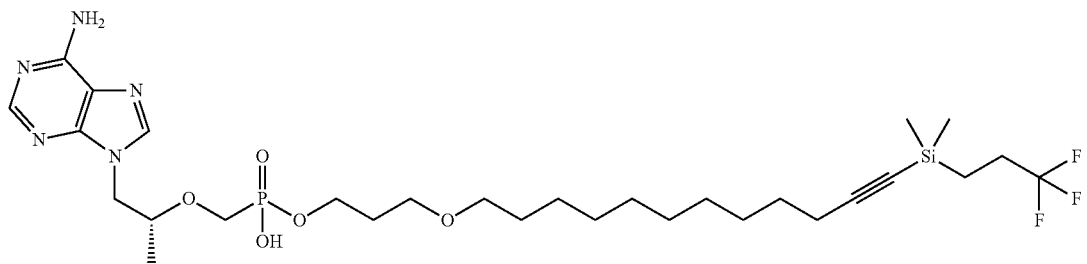

3-((12-(dimethyl(3,3,3-trifluoropropyl)silyl)dodec-11-yn-1-yl)oxy)propyl hydrogen ((((R)-1-(6-amino-9H-purin-9-yl)propan-2-yl)oxy)
methyl)phosphonate

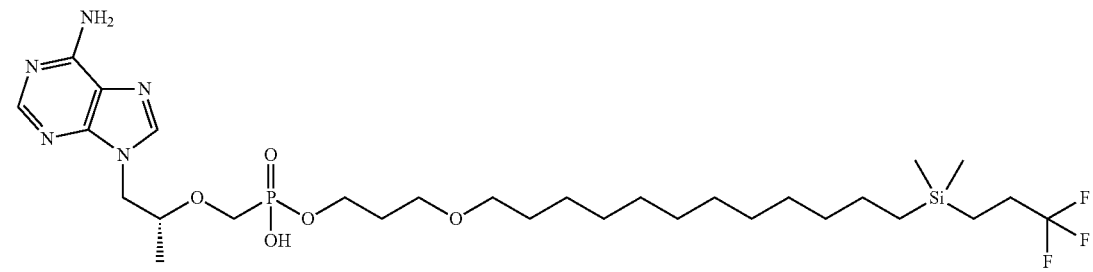

3-((12-(dimethyl(3,3,3-trifluoropropyl)silyl)dodecyl)oxy)propyl hydrogen ((((R)-1-(6-amino-9H-purin-9-yl)propan-2-yl)oxy)methyl)phosphonate

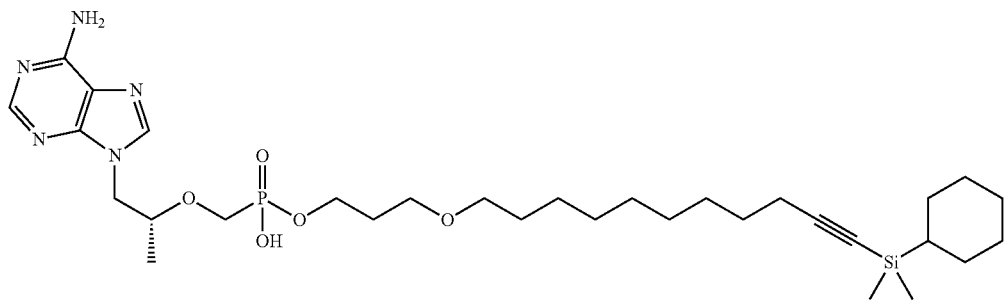

3-((11-(cyclohexyldimethylsilyl)undec-10-yn-1-yl)oxy)propyl hydrogen ((((R)-1-(6-amino-9H-purin-9-yl)propan-2-yl)oxy)
methyl)phosphonate

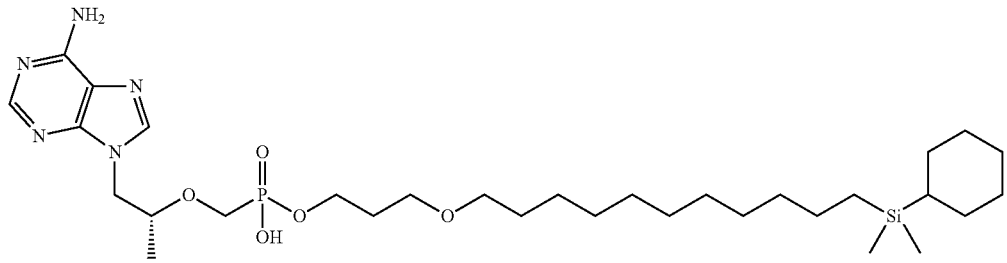

3-((11-(cyclohexyldimethylsilyl)undecyl)oxy)propyl hydrogen ((((R)-1-(6-amino-9H-purin-9-yl)propan-2-yl)oxy)methyl)
phosphonate

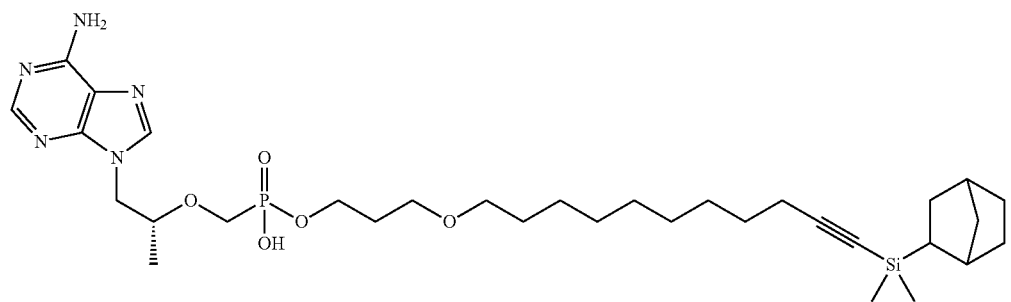

3-((11-(bicyclo[2.2.1]heptan-2-yldimethylsilyl)undec-10-yn-1-yl)oxy)propyl hydrogen ((((R)-1-(6-amino-9H-purin-9-yl)propan-2-yl)oxy)methyl)phosphonate

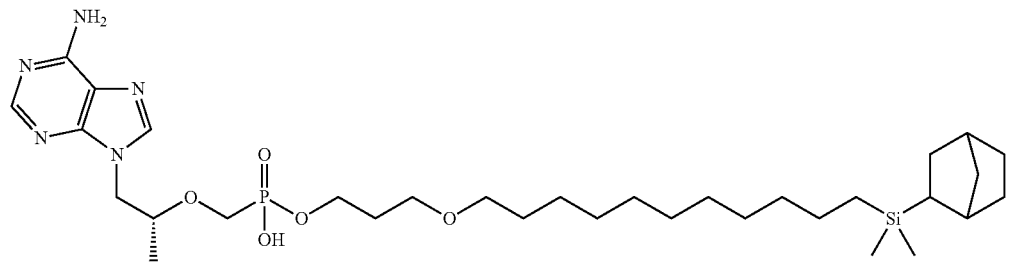

3-((11-(bicyclo[2.2.1]heptan-2-yldimethylsilyl)undecyl)oxy)propyl hydrogen ((((R)-1-(6-amino-9H-purin-9-yl)propan-2-yl)oxy)methyl)phosphonate

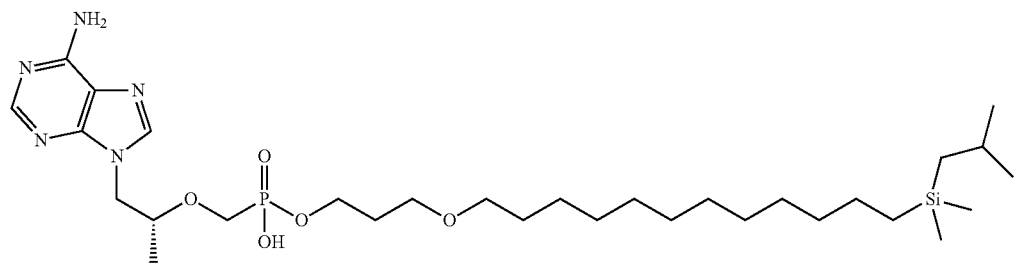

3-((12-(isobutyldimethylsilyl)dodecyl)oxy)propyl hydrogen ((((R)-1-(6-amino-9H-purin-9-yl)propan-2-yl)oxy)methyl)phosphonate

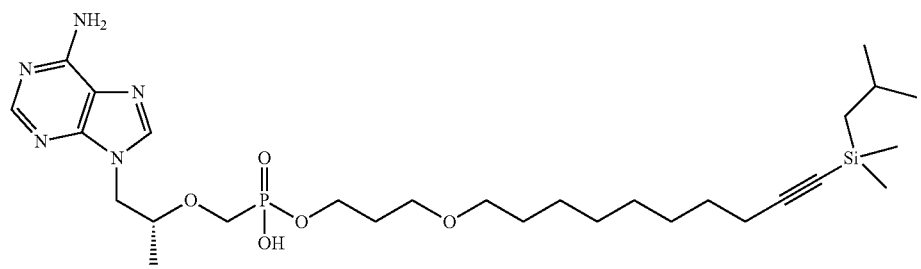

3-((12-(isobutyldimethylsilyl)dodec-11-yn-1-yl)oxy)propyl hydrogen ((((R)-1-(6-amino-9H-purin-9-yl)propan-2-yl)oxy)methyl)phosphonate

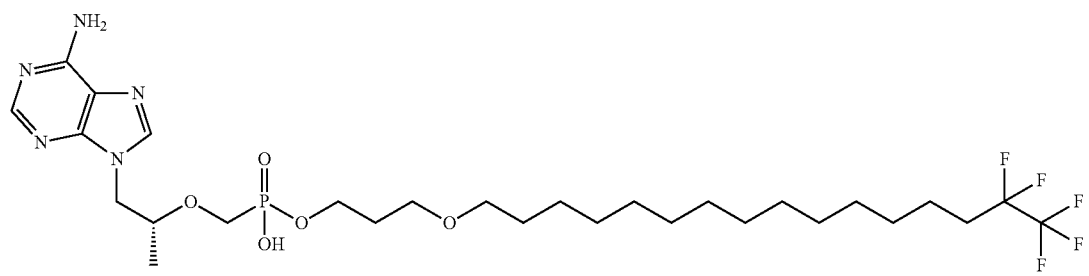

3-((15,15,16,16,16-pentafluorohexadecyl)oxy)propy hydrogen ((((R)-1-(6-amino-9H-purin-9-yl)propan-2-yl)oxy)methyl)phosphonate

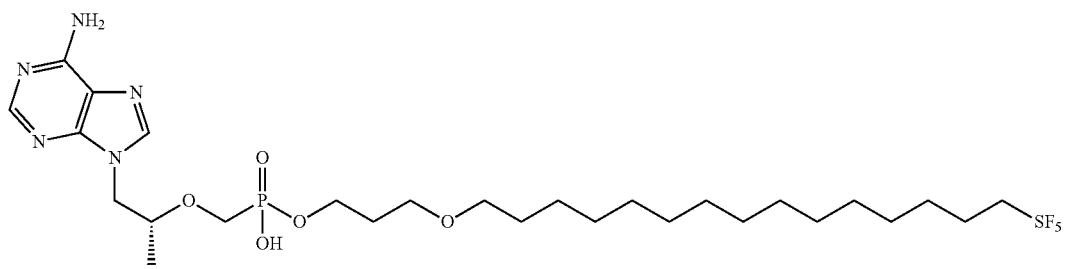

3-((15-(pentafluoro-λ⁶-sulfanyl)pentadecyl)oxy)propyl hydrogen ((((R)-1-(6-amino-9H-purin-9-yl)propan-2-yl)oxy)methyl) phosphonate

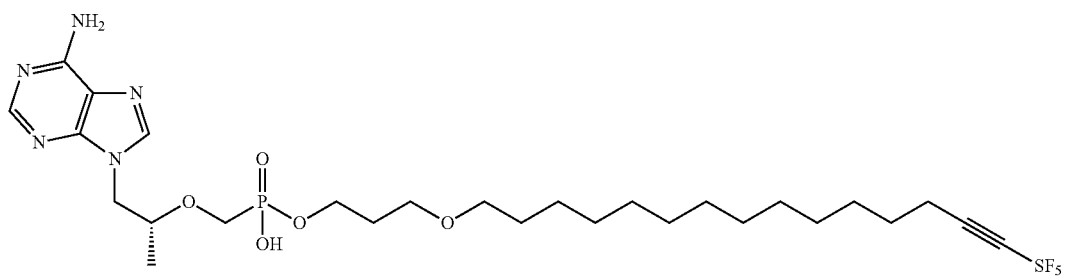

3-((15-(pentafluoro-λ⁶-sulfanyl)pentadec-14-yn-1-yl)oxy)propyl hydrogen ((((R)-1-(6-amino-9H-purin-9-yl)propan-2-yl)oxy) methyl)phosphonate

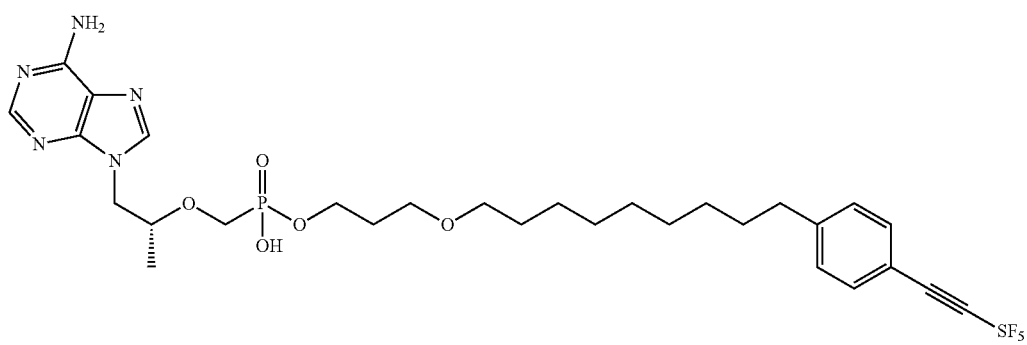

3-((9-(4-(pentafluoro-λ⁶-sulfanyl)ethynyl)phenyl)nonyl)oxy)propyl hydrogen ((((R)-1-(6-amino-9H-purin-9-yl)propan-2-yl)oxy)methyl)phosphonate

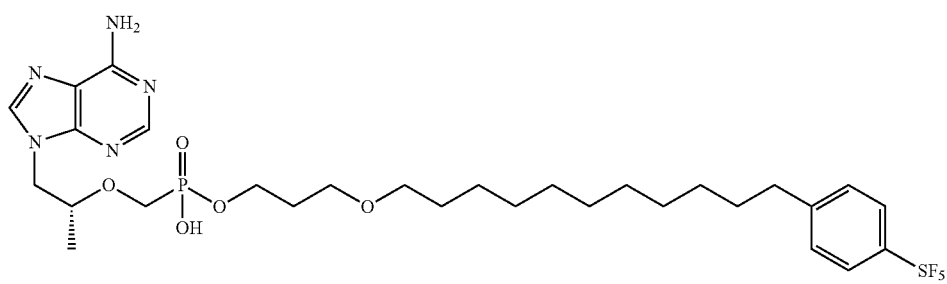

3-((11-(4-(pentafluoro-λ⁶-sulfanyl)phenyl)undecyl)oxy)propyl hydrogen ((((R)-1-(6-amino-9H-purin-9-yl)propan-2-yl)oxy) methyl)phosphonate

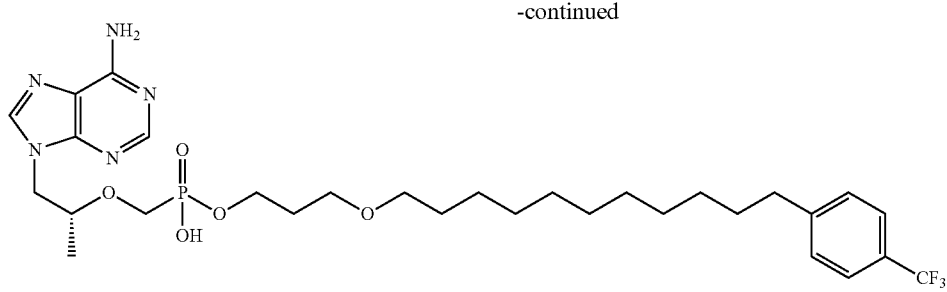

3-((11-(4-(triflouromethyl)phenyl)undecyl)oxy)propyl hydrogen ((((R)-1-(6-amino-9H-purin-9-yl)propan-2-yl)oxy)methyl)phosphonate

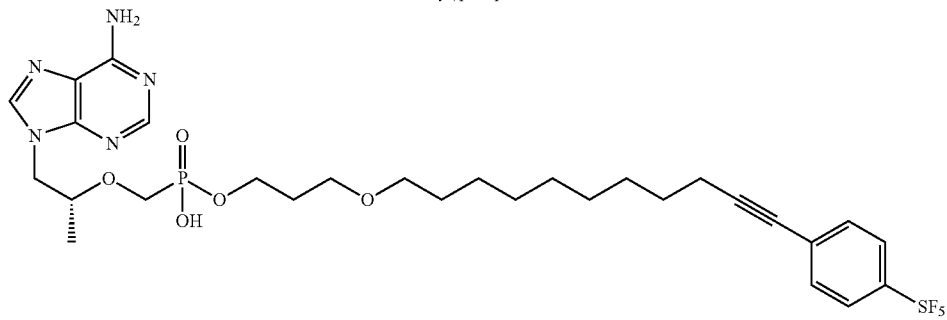

3-((11-(4-(pentafluoro-$\lambda^6$-sulfanyl)phenyl)undec-10-yn-1-yl)oxy)propyl hydrogen ((((R)-1-(6-amino-9H-purin-9-yl)propan-2-yl)oxy)methyl)phosphonate

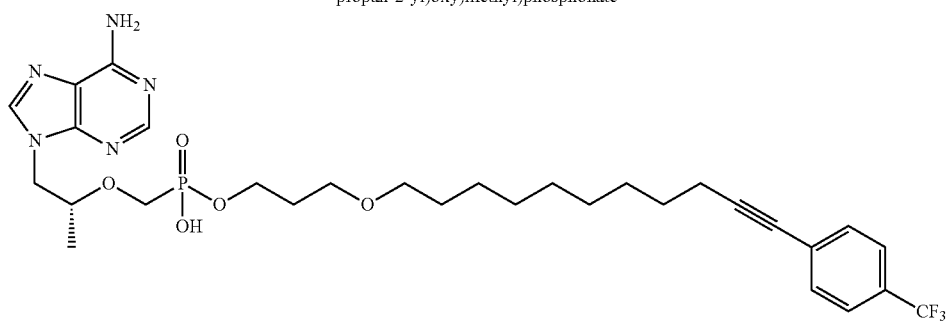

3-((11-(4-(trifluoromethyl)phenyl)undec-10-yn-1-yl)oxy)propyl hydrogen ((((R)-1-(6-amino-9H-purin-9-yl)propan-2-yl)oxy)methyl)phosphonate

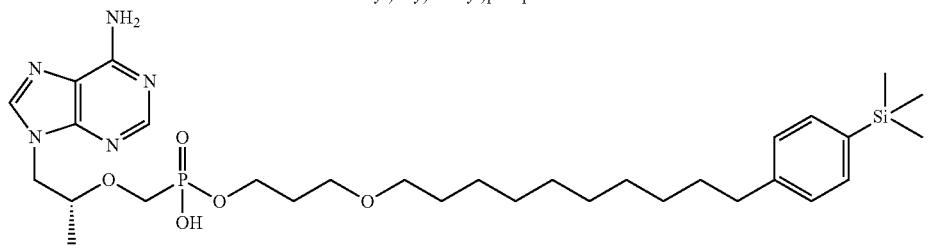

3-((10-(4-(trimethylsilyl)phenyl)decycl)oxy)propyl hydrogen ((((R)-1-(6-amino-9H-9-yl)propan-2-yl)oxy)methyl)phosphonate

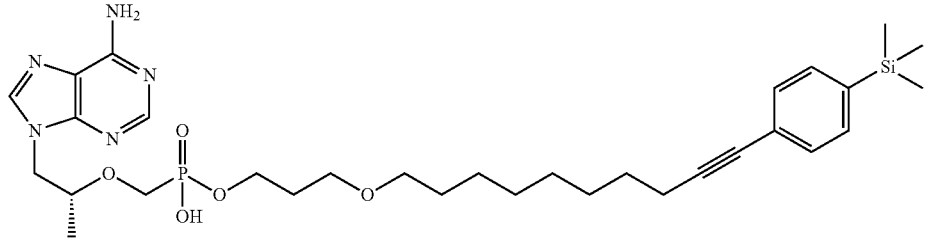

3-((10-(4-(trimethylsily)phenyl)dec-9-yn-1-yl)oxy)propyl hydrogen (((((R)-1-(6-amino-9H-purin-9 yl)propan-2-yl)oxy)methyl)phosphonate

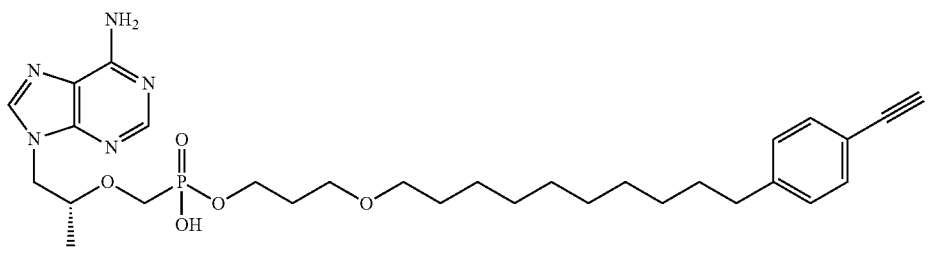

3-((10-(4-ethynylphenyl)decyl)oxy)propyl hydrogen ((((R)-1-(6-amino-9H-purin-9-yl)propan-2-yl)oxy)methyl)phosphonate

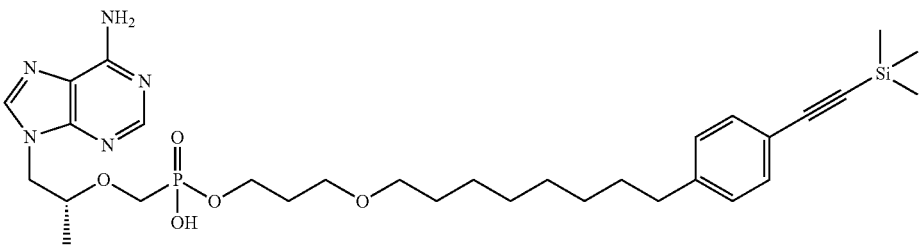

3-((8-(4-(trimethylsilyl)ethynyl)phenyl)octyl)oxy)propyl hydrogen ((((R)-1-(6-amino-9H-purin-9-yl)propan-2-yl)oxy)methyl)phosphonate

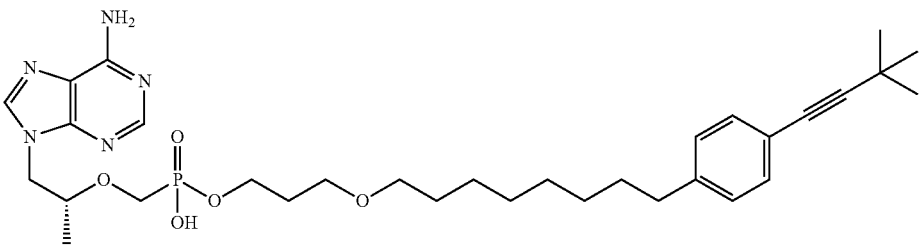

3-((8-(4-((3,3-dimethylbut-1-yn-1-yl)phenyl)octyl)oxy)propyl hydrogen ((((R)-1-(6-amino-9H-purin-9-yl)propan-2-yl)oxy)methyl)phosphonate

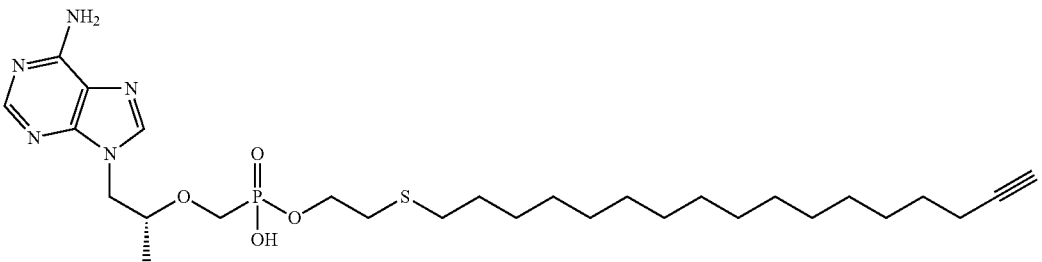

2-(heptadec-16-yn-1-ylthio)ethyl hydrogen ((((R)-1-(6-amino-9H-purin-9-yl)propan-2-yl)oxy)methyl)phosphonate

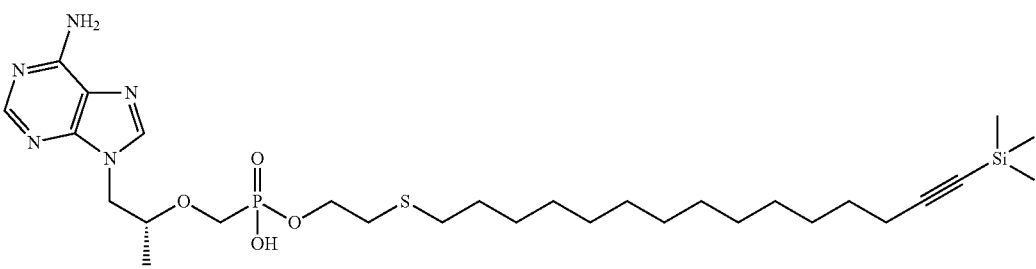

2-((15-(trimethylsilyl)pentadec-14-yn-1-yl)thio)ethyl hydrogen ((((R)-1-(6-amino-9H-purin-9-yl)propan-2-yl)oxy)methyl)phosphonate

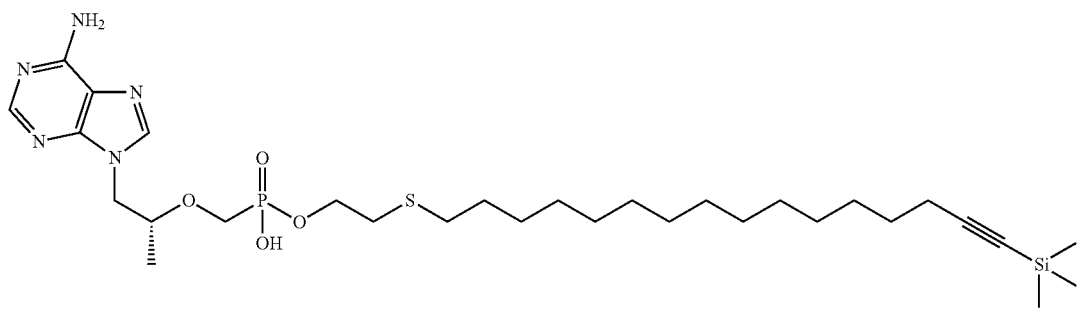

2-((16-(trimethylsilyl)hexadec-15-yn-1-yl)thio)ethyl hydrogen ((((R)-1-(6-amino-9H-purin-9-yl)propan-2-yl)oxy)methyl)phosphonate

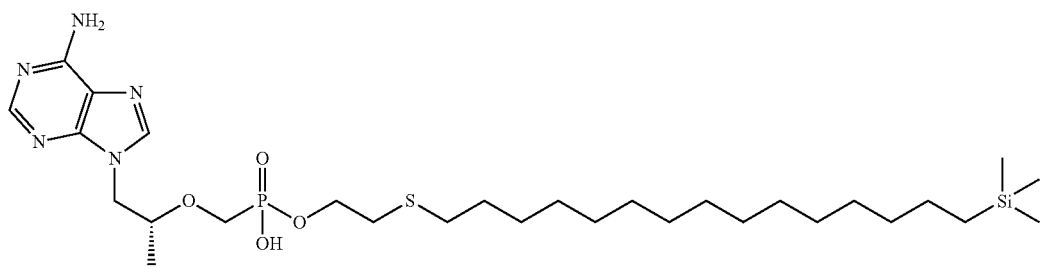

2-((15-(trimethylsilyl)pentadecyl)thio)ethyl hydrogen ((((R)-1-(6-amino-9H-purin-9-yl)propan-2-yl)oxy)methyl)phosphonate

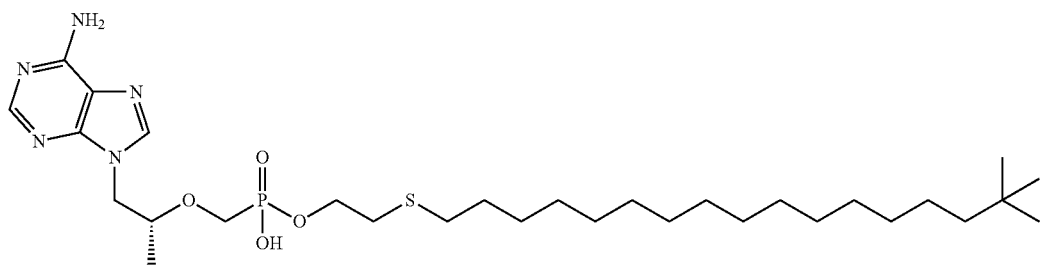

2-((16,16-dimethylheptadecyl)thio)ethyl hydrogen ((((R)-1-(6-amino-9H-purin-9-yl)propan-2-yl)oxy)methyl)phosphonate

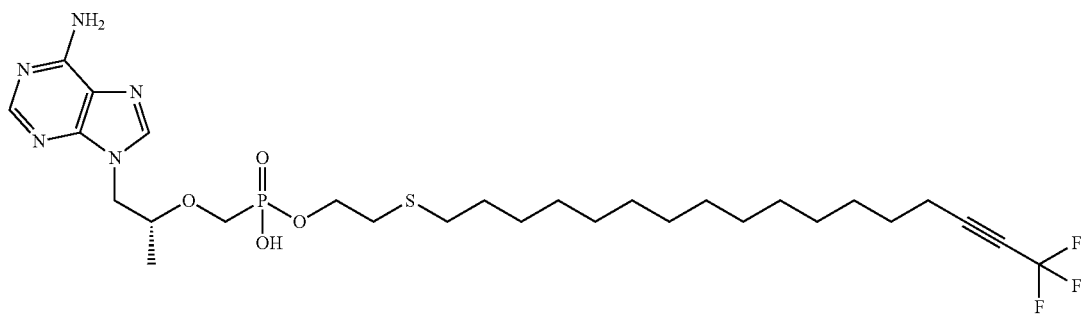

2-((17,17,17-trifluoroheptadec-15-yn-1-yl)thio)ethyl hydrogen ((((R)-1-(6-amino-9H-purin-9-yl)propan-2-yl)oxy)methyl)phosphonate

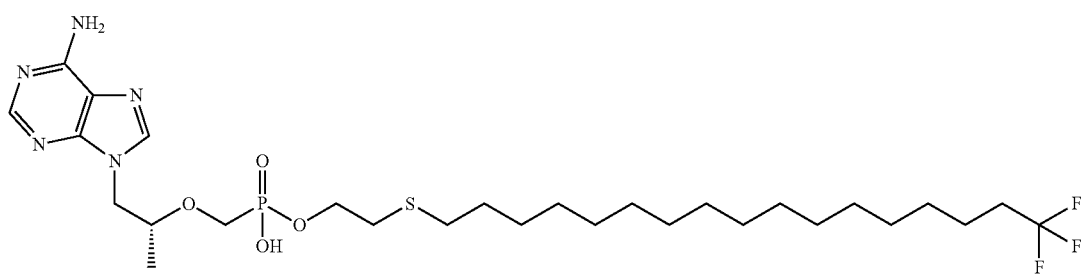

2-((17,17,17-trifluoroheptadecyl)thio)ethyl hydrogen ((((R)-1-(6-amino-9H-purin-9-yl)propan-2-yl)oxy)methyl)phosphonate -continued

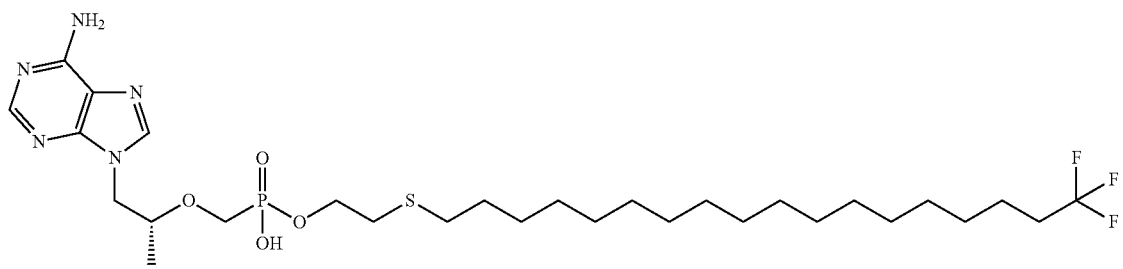

2-((18,18,18-trifluorooctadecyl)thio)ethyl hydrogen ((((R)-1-(6-amino-9H-purin-9-yl)propan-2-yl)oxy)methyl)phosphonate

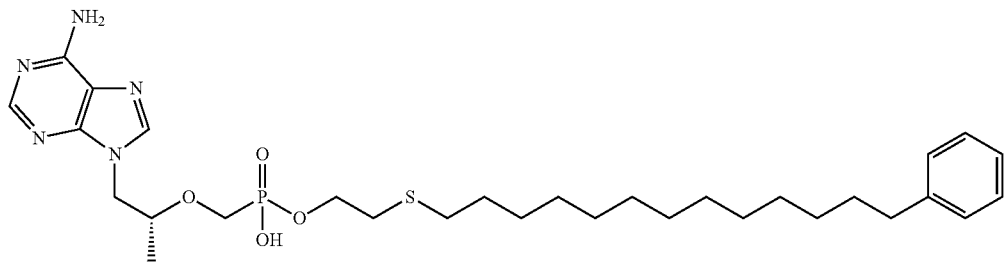

2-((13-phenyltridecyl)thio)ethyl hydrogen ((((R)-1-(6-amino-9H-purin-9-yl)propan-2-yl)oxy)methyl)phosphonate

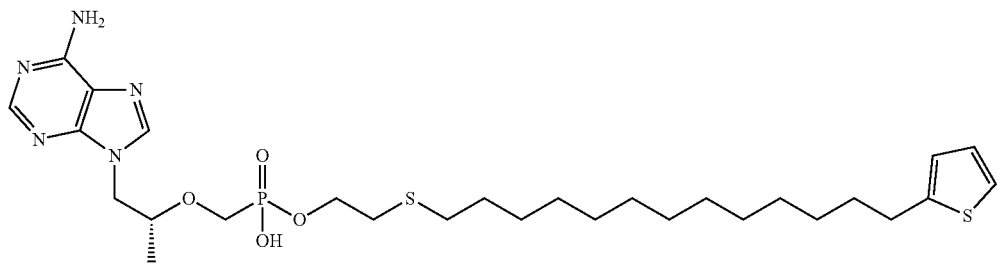

2-((13-(thiophen-2-yl)tridecyl)thio)ethyl hydrogen ((((R)-1-(6-amino-9H-purin-9-yl)propan-2-yl)oxy)methyl)phosphonate

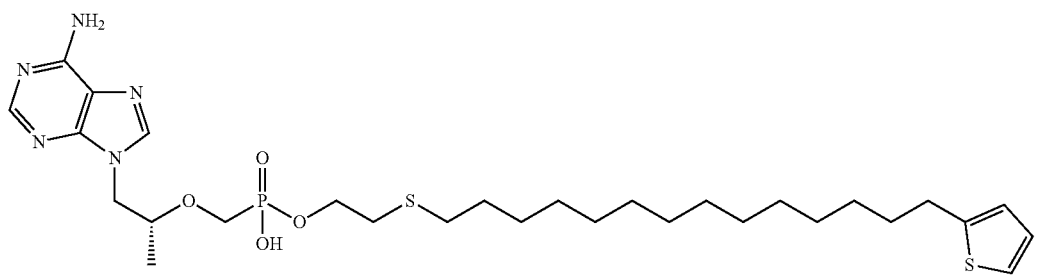

2-((14-(thiophen-2-yl)tetradecyl)thio)ethyl hydrogen ((((R)-1-(6-amino-9H-purin-9-yl)propan-2-yl)oxy)methyl)phosphonate

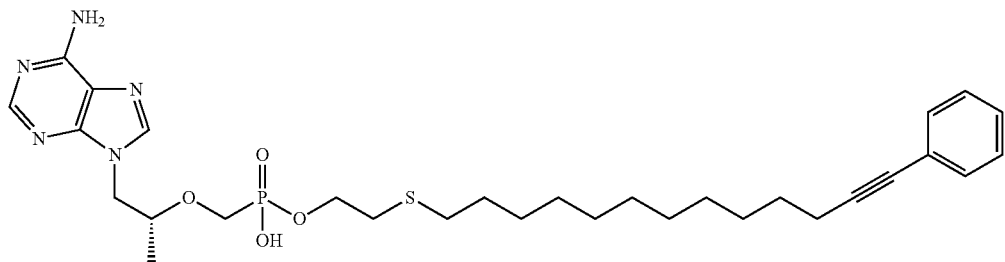

2-((13-phenyltridec-12-yn-1-yl)thio)ethyl hydrogen ((((R)-1-(6-amino-9H-purin-9-yl)propan-2-yl)oxy)methyl)phosphonate

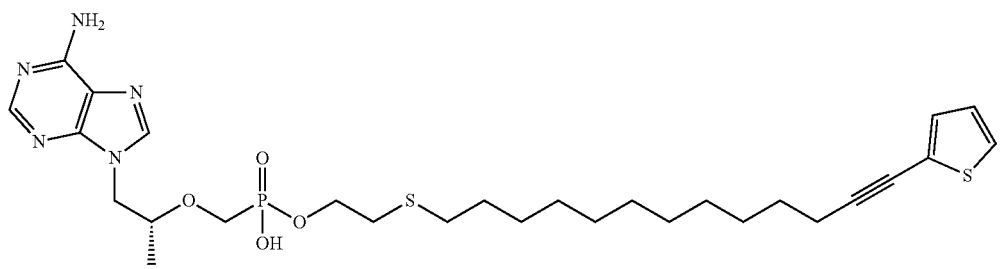

2-(((13-thiophen-2-yl)tridec-12-yn-1-yl)thio)ethyl hydrogen ((((R)-1-(6-amino-9H-purin-9-yl)propan-2-yl)oxy)methyl)phosphonate

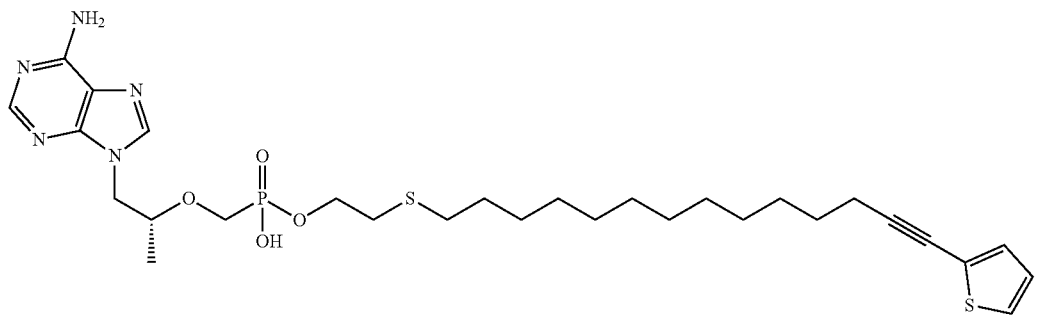

2-((14-thiophen-2-yl)tetradec-13-yn-1-yl)thio)ethyl hydrogen ((((R)-1-(6-amino-9H-purin-9-yl)propan-2-yl)oxy)methyl)phosphonate

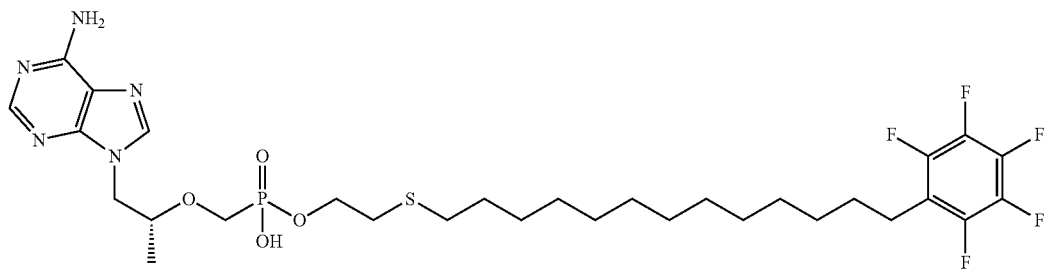

2-((13-(perfluorophenyl)tridecyl)thio)ethyl hydrogen ((((R)-1-(6-amino-9H-purin-9-yl)propan-2-yl)oxy)methyl)phosphonate

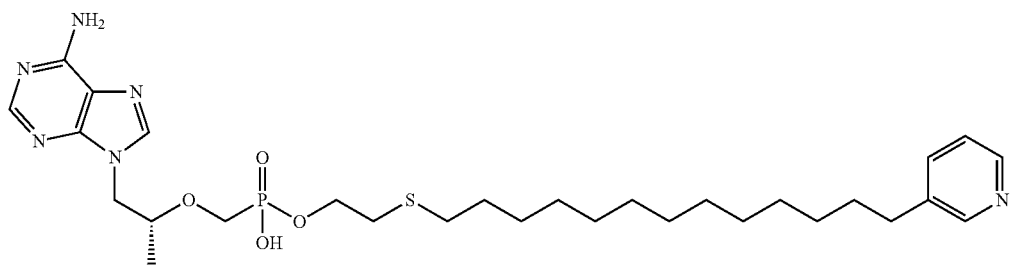

2-((13-(pyridin-3-yl)tridecyl)thio)ethyl hydrogen ((((R)-1-(6-amino-9H-purin-9-yl)propan-2-yl)oxy)methyl)phosphonate

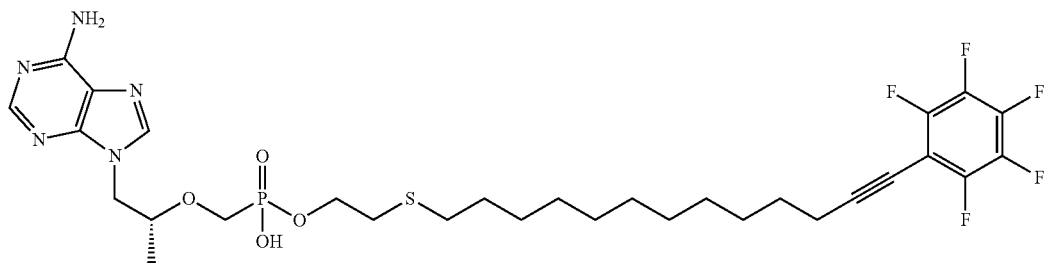

2-((13-(perfluorophenyl)tridec-12-yn-1-yl)thio)ethyl hydrogen (((((R)-1-(6-amino-9H-purin-9-yl)propan-2-yl)oxy)methyl)phosphonate

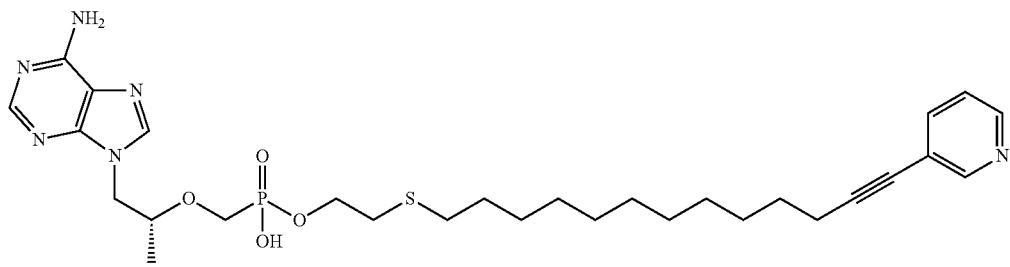

2-((13-(pyridin-3-yl)tridec-12-yn-1-yl)thio)ethyl hydrogen ((((R)-1-(6-amino-9H-purin-9-yl)propan-2-yl)oxy)methyl)phosphonate

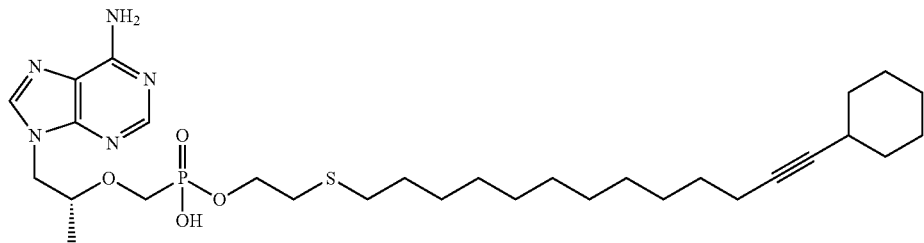

2-((13-cyclohexyltridec-12-yn-1-yl)thio)ethyl hydrogen ((((R)-1-(6-amino-9H-purin-9-yl)propan-2-yl)oxy)methyl)phosphonate

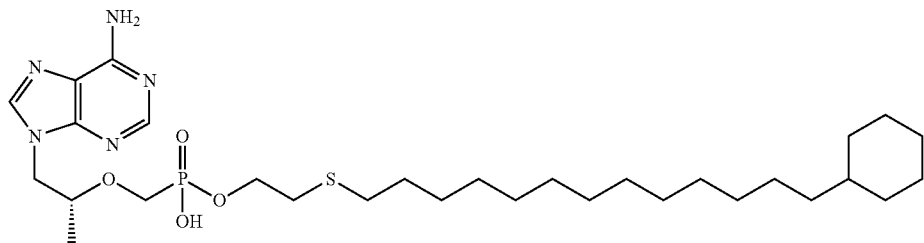

2-((13-cyclohexyltridecyl)thio)ethyl hydrogen ((((R)-1-(6-amino-9H-purin-9-yl)propan-2-yl)oxy)methyl)phosphonate

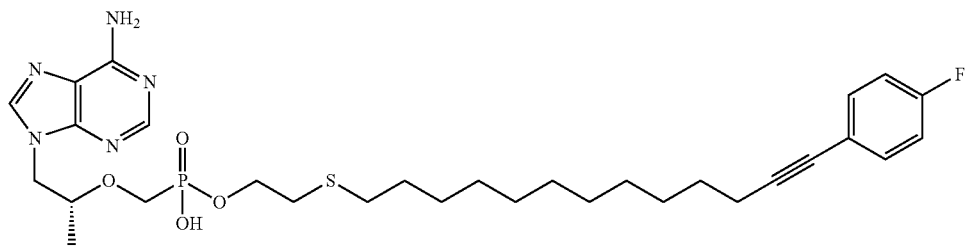

2-((13-(4-fluorophenyl)tridec-12-yn-1-yl)thio)ethyl hydrogen ((((R)-1-(6-amino-9H-purin-9-yl)propan-2-yl)oxy)methyl)phosphonate

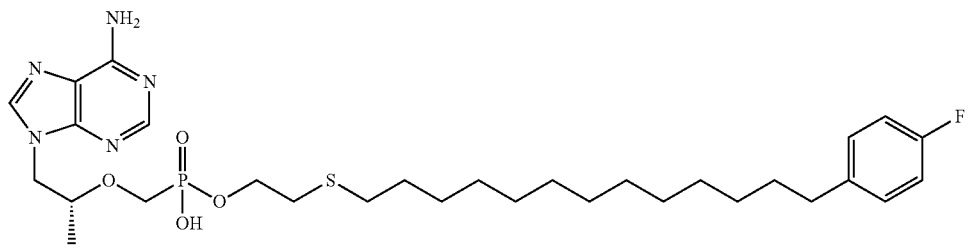

2-((13-(4-fluorophenyl)tridecyl)thio)ethyl hydrogen ((((R)-1-(6-amino-9H-purin-9-yl)propan-2-yl)oxy)methyl)phosphonate

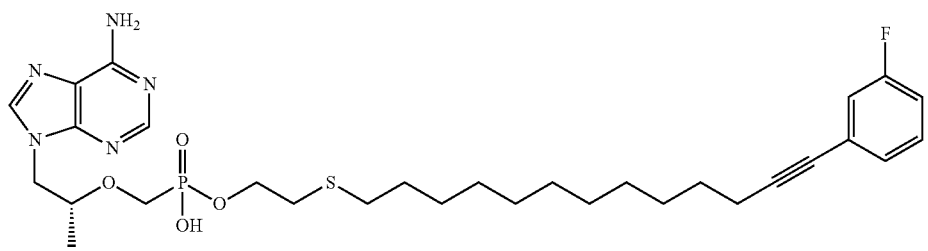

2-((13-(3-fluorophenyl)tridec-12-yn-1-yl)thio)ethyl hydrogen ((((R)-1-(6-amino-9H-purin-9-yl)propan-2-yl)oxy)methyl)phosphonate

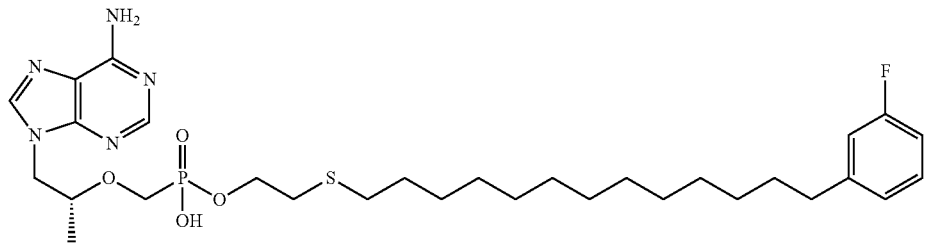

2-((13-(3-fluorophenyl)tridecyl)thio)ethyl hydrogen ((((R)-1-(6-amino-9H-purin-9-yl)propan-2-yl)oxy)methyl)phosphonate

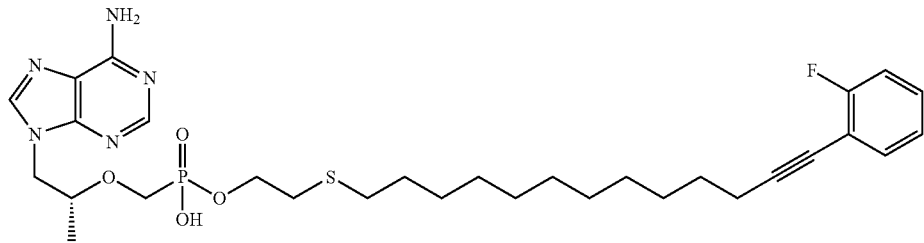

2-((13-(2-fluorophenyl)tridec-12-yn-1-yl)thio)ethyl hydrogen ((((R)-1-(6-amino-9H-purin-9-yl)propan-2-yl)oxy)methyl)phosphonate

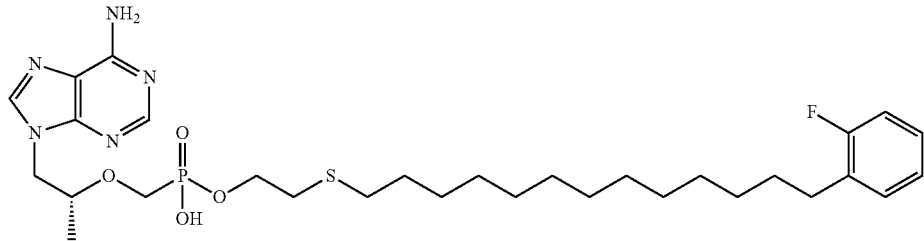

2-((13-(2-fluorophenyl)tridecyl)thio)ethyl hydrogen ((((R)-1-(6-amino-9H-purin-9-yl)propan-2-yl)oxy)methyl)phosphonate

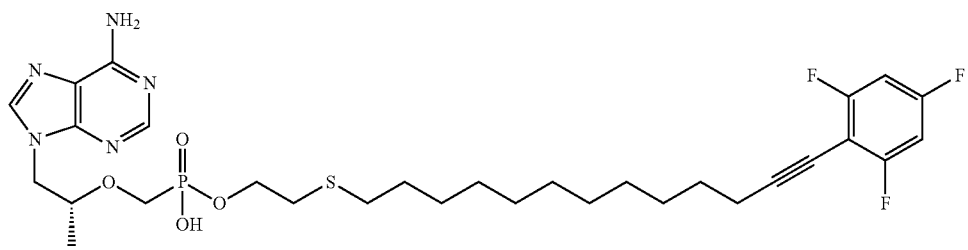

2-((13-(2,4,6-trifluorophenyl)tridec-12-yn-1-yl)thio)ethyl hydrogen ((((R)-1-(6-amino-9H-purin-9-yl)propan-2-yl)oxy)methyl)phosphonate

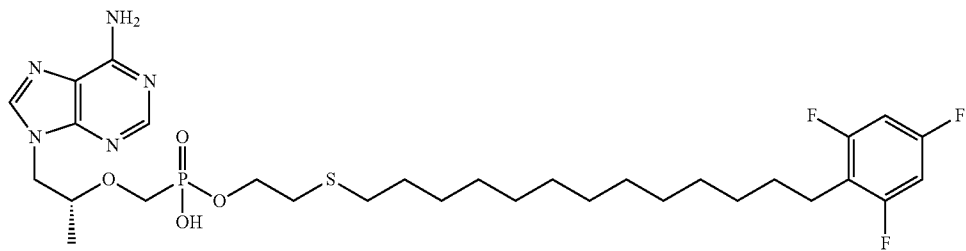

2-((13-(2,4,6-trifluorophenyl)tridecyl)thio)ethyl hydrogen ((((R)-1-(6-amino-9H-purin-9-yl)propan-2-yl)oxy)methyl)phosphonate

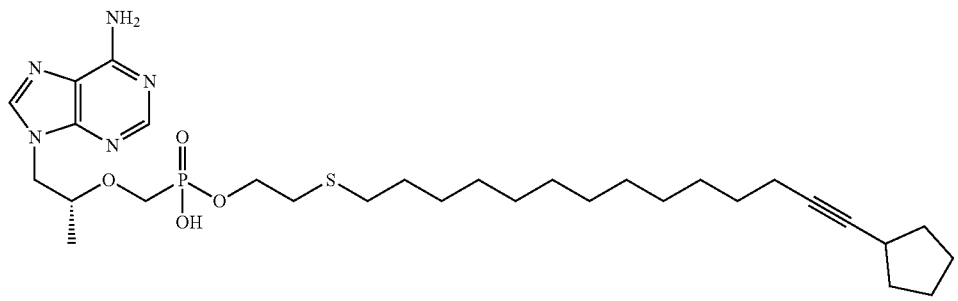

2-((14-cyclopentyltetradec-13-yn-1-yl)thio)ethyl hydrogen ((((R)-1-(6-amino-9H-purin-9-yl)propan-2-yl)oxy)methyl)phosphonate

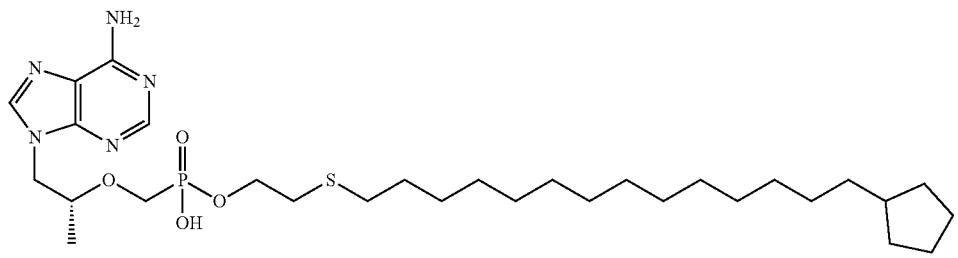

2-((14-cyclopentyltetradecyl)thio)ethyl hydrogen ((((R)-1-(6-amino-9H-purin-9-yl)propan-2-yl)oxy)methyl)phosphonate

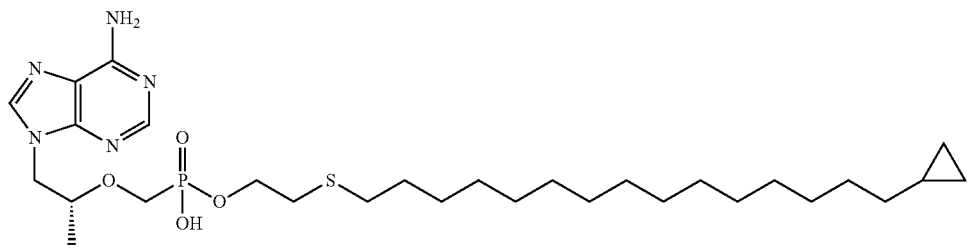

2-((15-cyclopropylpentadecyl)thio)ethyl hydrogen ((((R)-1-(6-amino-9H-purin-9-yl)propan-2-yl)oxy)methyl)phosphonate

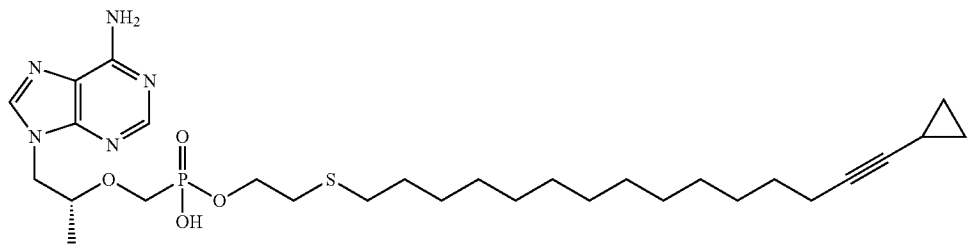

2-((15-cyclopropylpentadec-14-yn-1-yl)thio)ethyl hydrogen ((((R)-1-(6-amino-9H-purin-9-yl)propan-2-yl)oxy)methyl)phosphonate

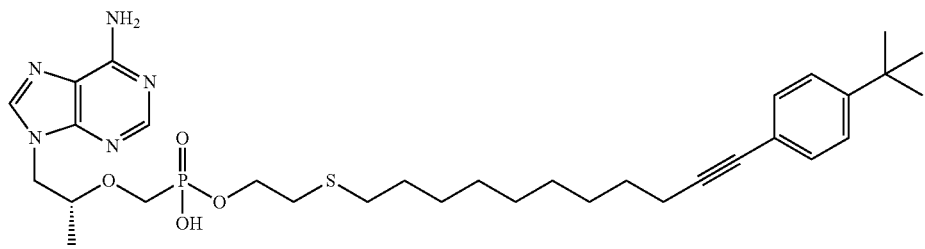

2-((11-(4-(tert-butyl)phenyl)undec-10-yn-1-yl)thio)ethyl hydrogen ((((R)-1-(6-amino-9H-purin-9-yl)propan-2-yl)oxy)methyl)phosphonate

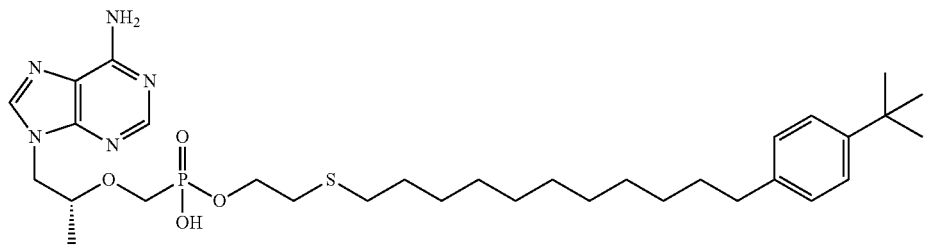

2-((11-(4-(tert-butyl)phenyl)undecyl)thio)ethyl hydrogen ((((R)-1-(6-amino-9H-purin-9-yl)propan-2-yl)oxy)methyl)phosphonate

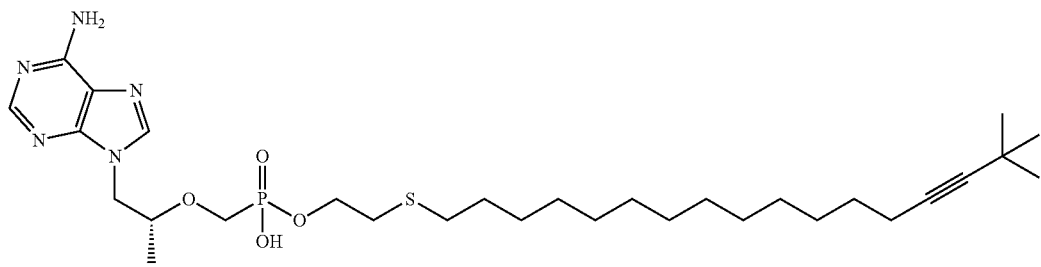

2-(((16,16-dimethylheptadec-14-yn-1-yl)thio)ethyl hydrogen ((((R)-1-(6-amino-9H-purin-9-yl)propan-2-yl)oxy)methyl)phosphonate

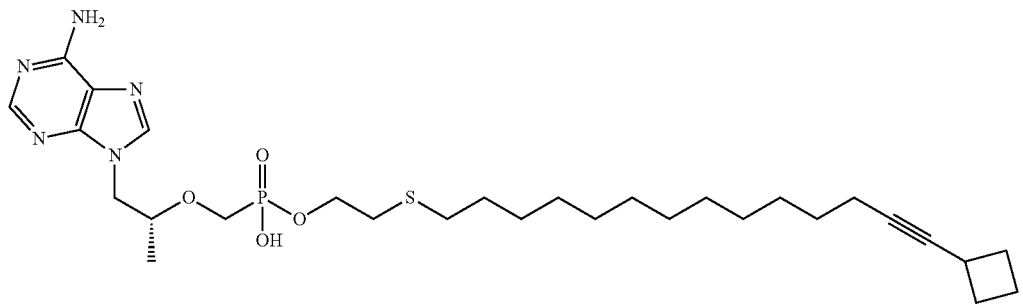

2-((14-cyclobutyltetradec-13-yn-1-yl)thio)ethyl hydrogen ((((R)-1-(6-amino-9H-purin-9-yl)propan-2-yl)oxy)methyl)phosphonate

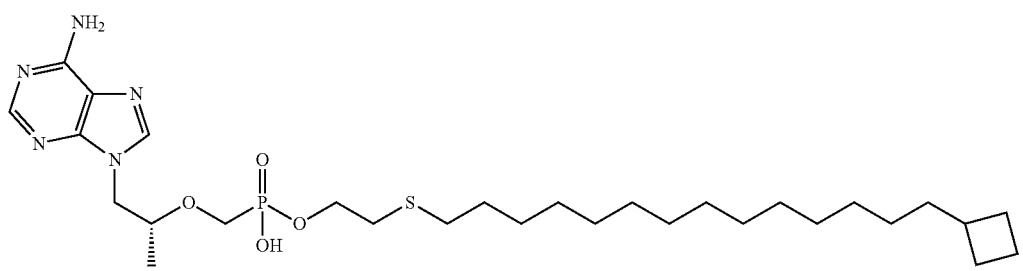

2-((14-cyclobutyltetradecyl)thio)ethyl hydrogen ((((R)-1-(6-amino-9H-purin-9-yl)propan-2-yl)oxy)methyl)phosphonate

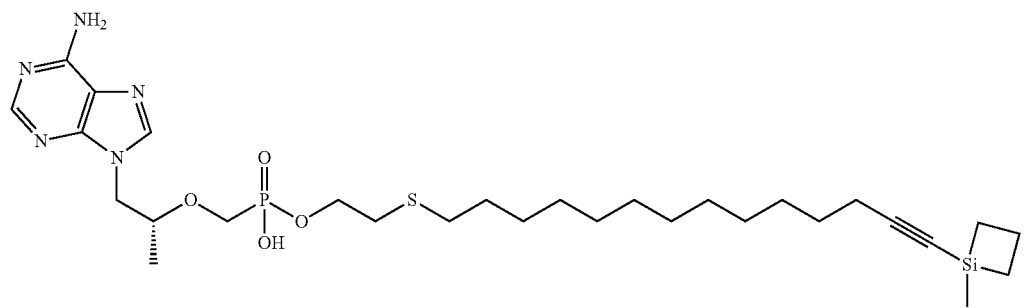

2-((14-(1-methylsiletan-1-yl)tetradec-13-yn-1-yl)thio)ethyl hydrogen ((((R)-1-(6-amino-9H-purin-9-yl)propan-2-yl)oxy)methyl)phosphonate

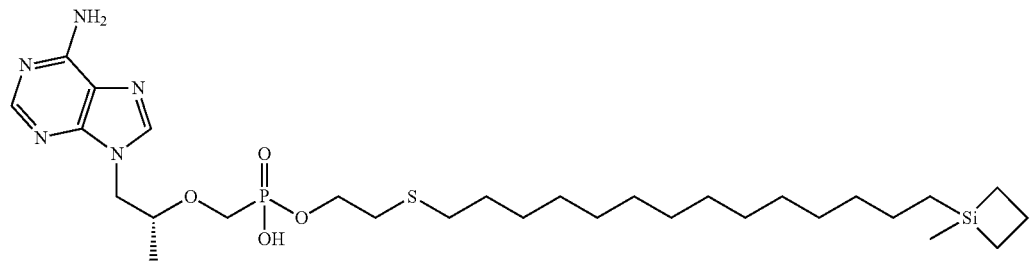

2-((14-(1-methylsiletan-1-yl)tetradecyl)thio)ethyl hydrogen ((((R)-1-(6-amino-9H-purin-9-yl)propan-2-yl)oxy)methyl)phosphonate

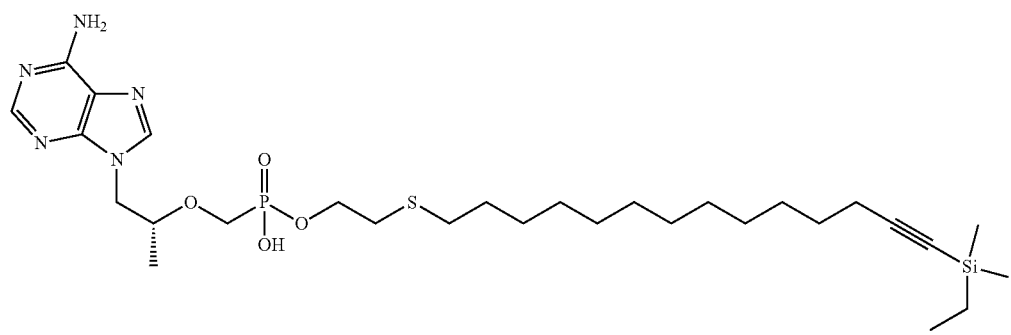

2-((14-(ethyldimethylsilyl)tetradec-13-yn-1-yl)thio)ethyl hydrogen ((((R)-1-(6-amino-9H-purin-9-yl)propan-2-yl)oxy)methyl)phosphonate

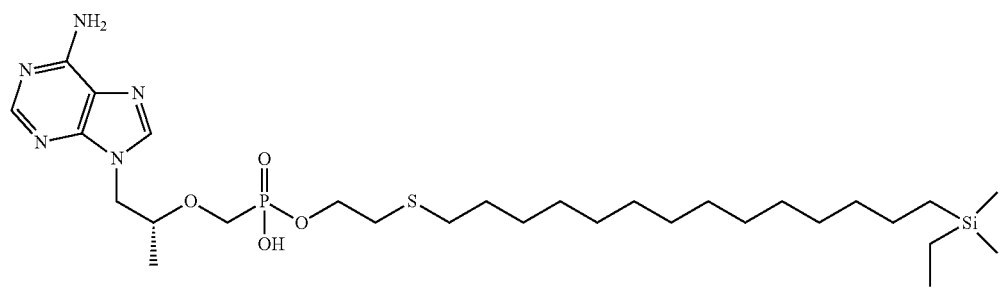

2-((14-(ethyldimethylsilyl)tetradecyl)thio)ethyl hydrogen ((((R)-1-(6-amino-9H-purin-9-yl)propan-2-yl)oxy)methyl)phosphonate -continued

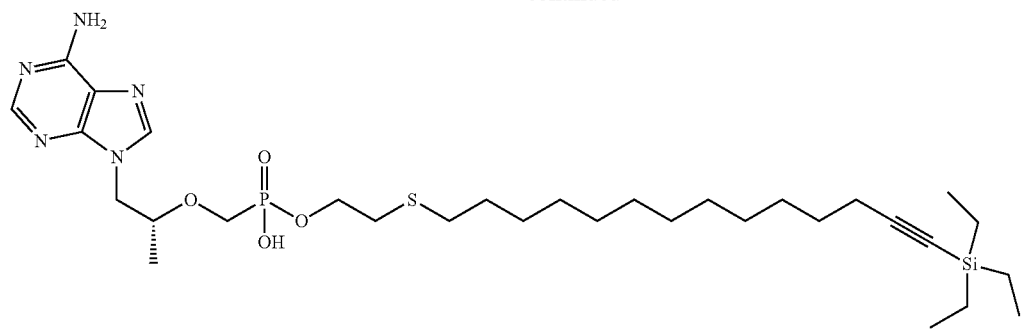

2-((14-(triethylsilyl)tetradec-13-yn-1-yl)thio)ethyl hydrogen ((((R)-1-(6-amino-9H-purin-9-yl)propan-2-yl)oxy)methyl)phosphonate

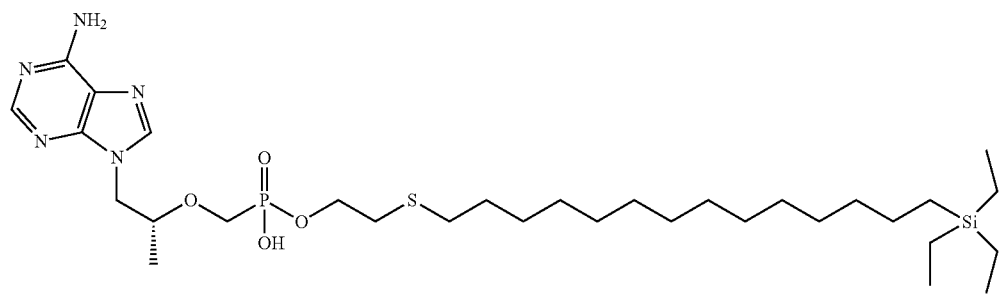

2-((14-(triethylsilyl)tetradecyl)thio)ethyl hydrogen ((((R)-1-(6-amino-9H-purin-9-yl)propan-2-yl)oxy)methyl)phosphonate

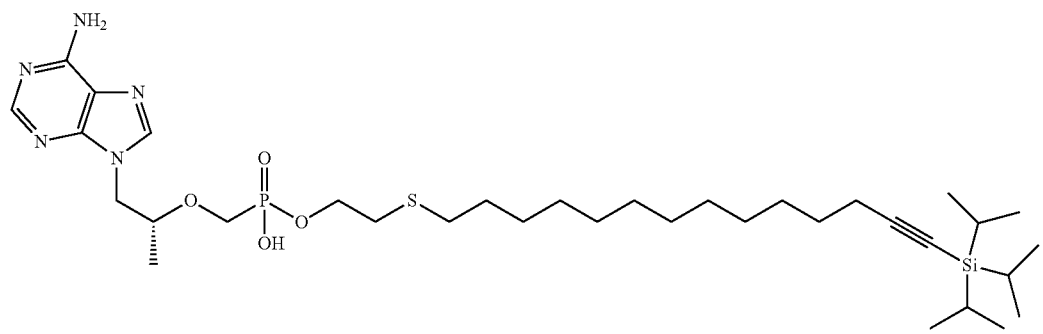

2-((14-(triisopropylsilyl)tetradec-13-yn-1-yl)thio)ethyl hydrogen ((((R)-1-(6-amino-9H-purin-9-yl)propan-2-yl)oxy)methyl)phosphonate

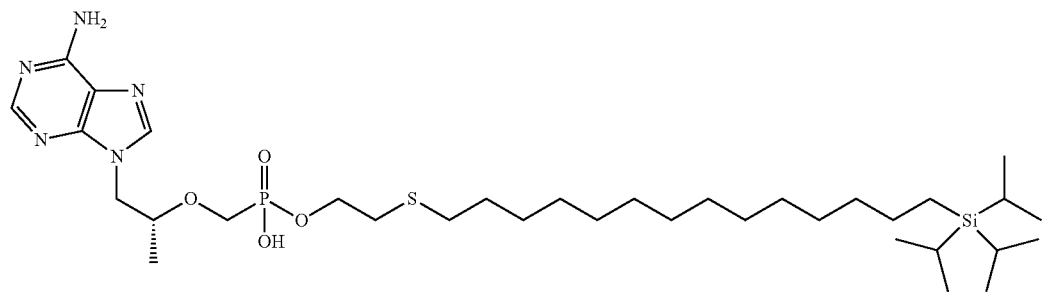

2-((14-(triisopropylsilyl)tetradecyl)thio)ethyl hydrogen ((((R)-1-(6-amino-9H-purin-9-yl)propan-2-yl)oxy)methyl)phosphonate

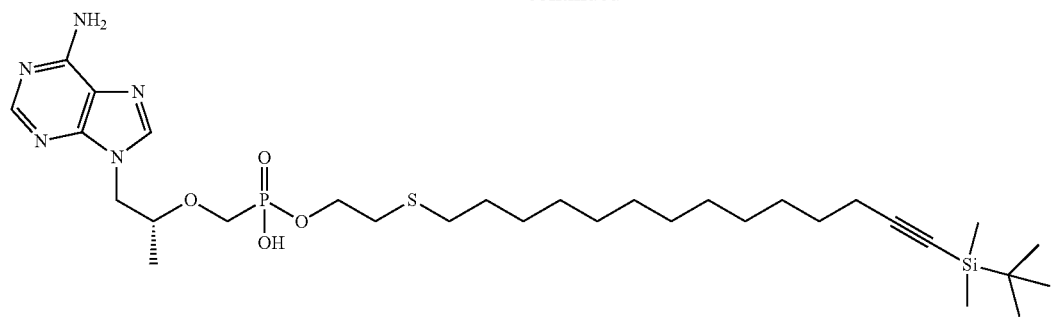

2-((14-(tert-butyldimethylsilyl)tetradec-13-yn-1-yl)thio)ethyl hydrogen ((((R)-1-(6-amino-9H-purin-9-yl)propan-2-yl)oxy)methyl)phosphonate

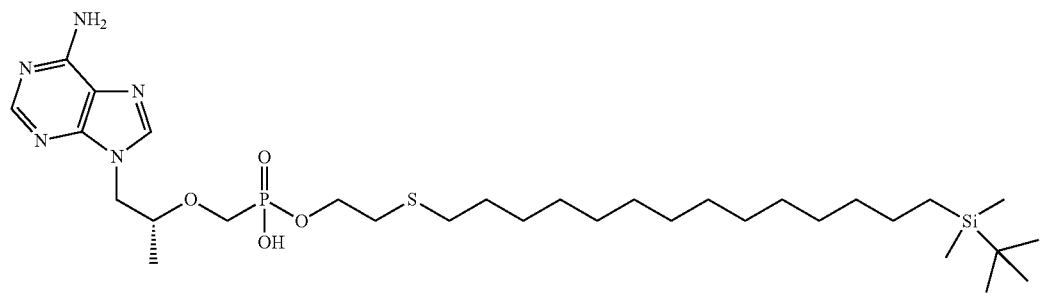

2-((14-(tert-butyldimethylsilyl)tetradecyl)thio)ethyl hydrogen ((((R)-1-(6-amino-9H-purin-9-yl)propan-2-yl)oxy)methyl)phosphonate

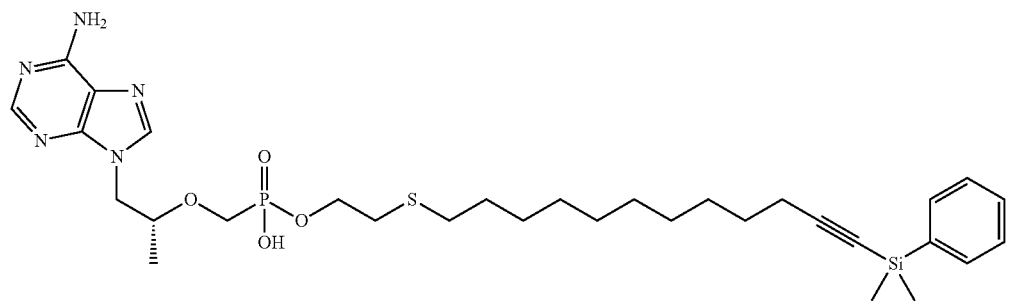

2-((12-(dimethyl(phenyl)silyl)dodec-11-yn-1-yl)thio)ethyl hydrogen ((((R)-1-(6-amino-9H-purin-9-yl)propan-2-yl)oxy)methyl)phosphonate

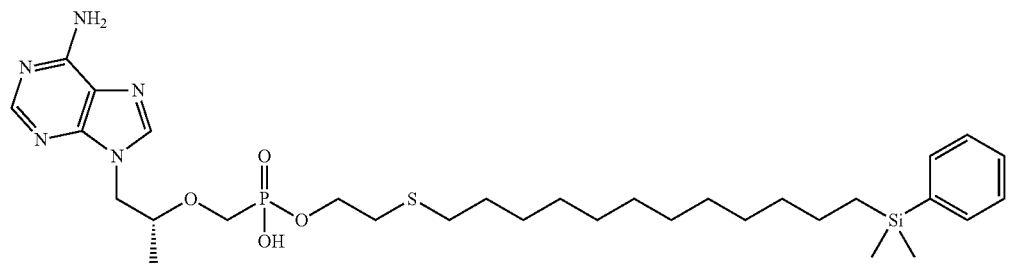

2-((12-(dimethyl(phenyl)silyl)dodecyl)thio)ethyl hydrogen ((((R)-1-(6-amino-9H-purin-9-yl)propan-2-yl)oxy)methyl)phosphonate

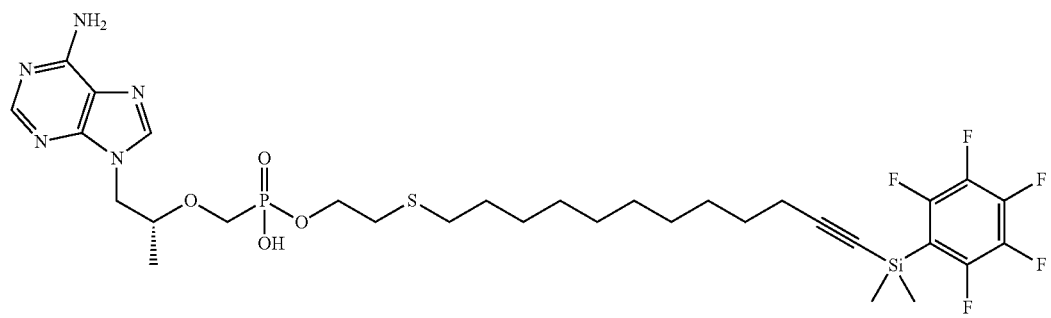

2-((12-(dimethyl(perfluorophenyl)silyl)dodec-11-yn-1-yl)thio)ethyl hydrogen ((((R)-1-(6-amino-9H-purin-9-yl)propan-2-yl)oxy)methyl)phosphonate

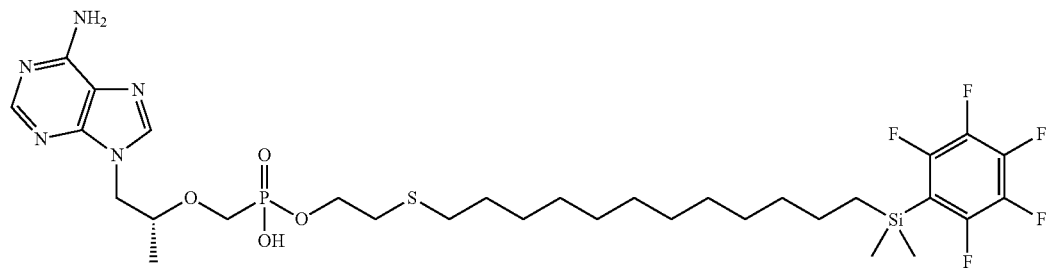

2-((12-(dimethyl(perfluorophenyl)silyl)dodecyl)thio)ethyl hydrogen ((((R)-1-(6-amino-9H-purin-9-yl)propan-2-yl)oxy)methyl)phosphonate

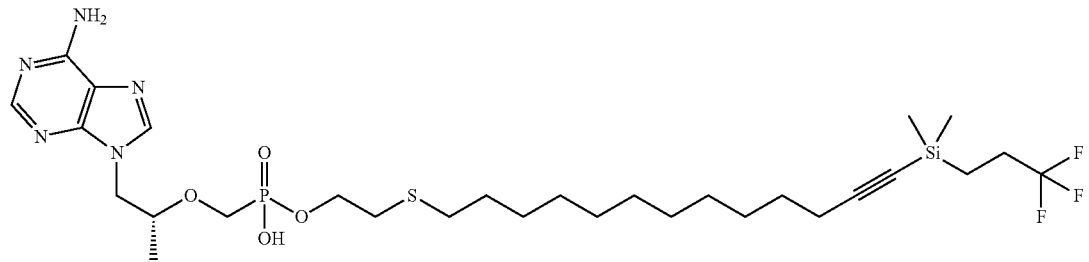

2-((13-(dimethyl((3,3,3,-trifluoropropyl)silyl)tridec-12-yn-1-yl)thio)ethyl hydrogen(6-amino-9H-purin-9-yl)propan-2-yl)oxy)methyl)phosphonate

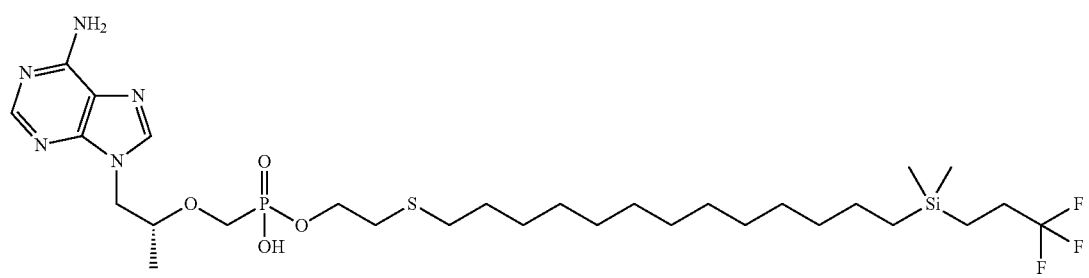

2-((13-(dimethyl(3,3,3-trifluoropropyl)silyl)tridecyl)thio)ethyl hydrogen ((((R)-1-(6-amino-9H-purin-9-yl)propan-2-yl)oxy)methyl)phosphonate

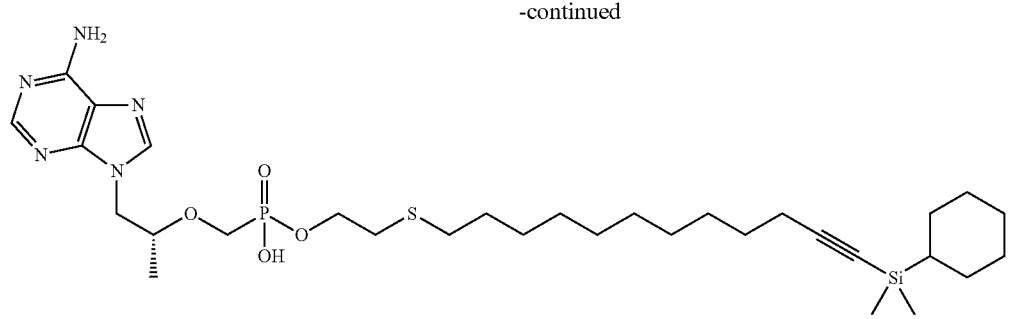

2-((12-(cyclohexyldimethylsilyl)dodec-11-yn-1-yl)thio)ethyl hydrogen ((((R)-1-(6-amino-9H-purin-9-yl)propan-2-yl)oxy)methyl)phosphonate

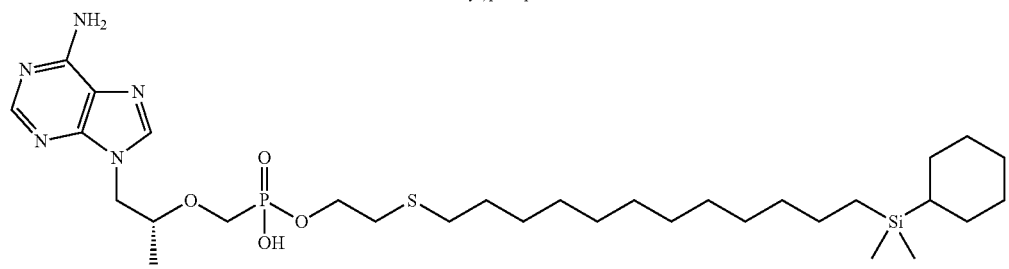

2-((12-(cyclohexyldimethylsilyl)dodecyl)thio)ethyl hydrogen ((((R)-1-(6-amino-9H-purin-9-yl)propan-2-yl)oxy)methyl)phosphonate

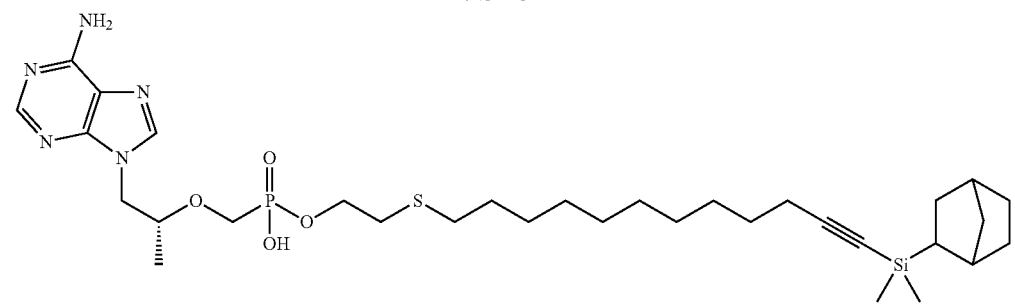

2-((12-(bicyclo[2.2.1]heptan-2-yldimethylsilyl)dodec-11-yn-1-yl)thio)ethyl hydrogen ((((R)-1-(6-amino-9H-purin-9-yl)propan-2-yl)oxy)methyl)phosphonate

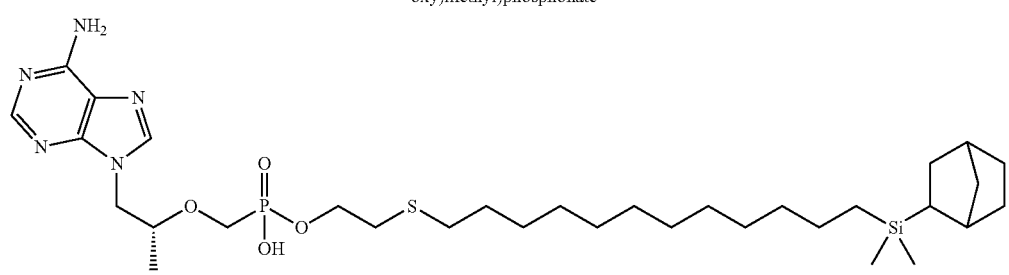

2-((12-(bicyclo[2.2.1]heptan-2-yldimethylsilyl)dodecyl)thio)ethyl hydrogen ((((R)-1-(6-amino-9H-purin-9-yl)propan-2-yl)oxy)methyl)phosphonate

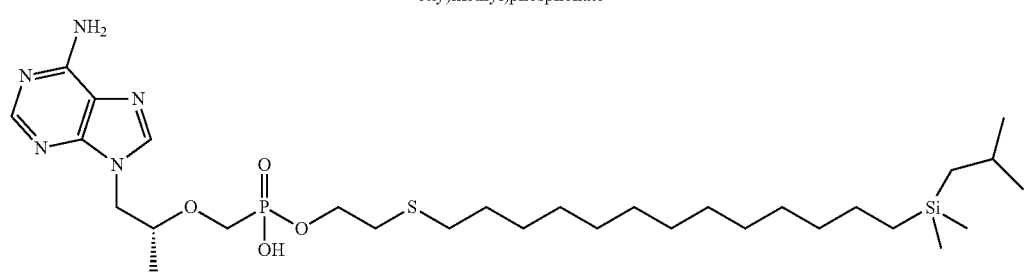

2-((13-(isobutyldimethylsilyl)tridecyl)thio)ethyl hydrogen ((((R)-1-(6-amino-9H-purin-9-yl)propan-2-yl)oxy)methyl)phosphonate

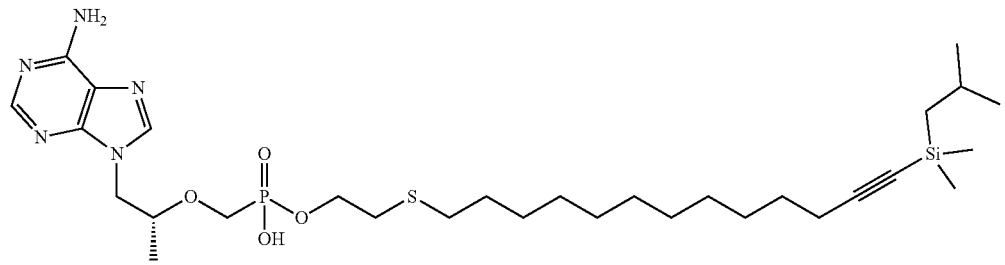

2-((13-(isobutyldimethylsilyl)tridec-12-yn-1-yl)thio)ethyl hydrogen ((((R)-1-(6-amino-9H-purin-9-yl)propan-2-yl)oxy)methyl)phosphonate

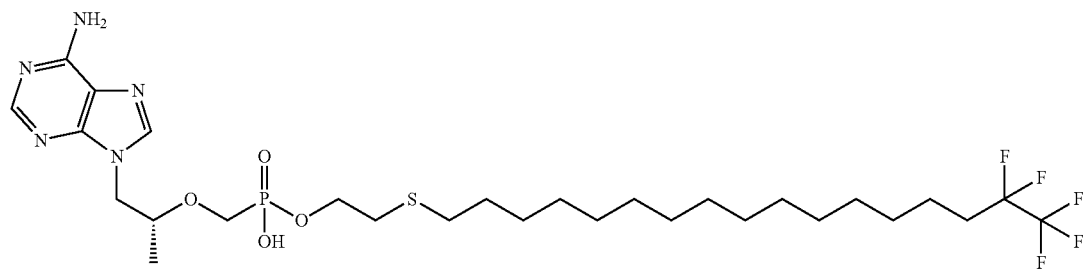

2-((16,16,17,17,17-pentafluoroheptadecyl)thio)ethyl hydrogen ((((R)-1-(6-amino-9H-purin-9-yl)propan-2-yl)oxy)methyl)phosphonate

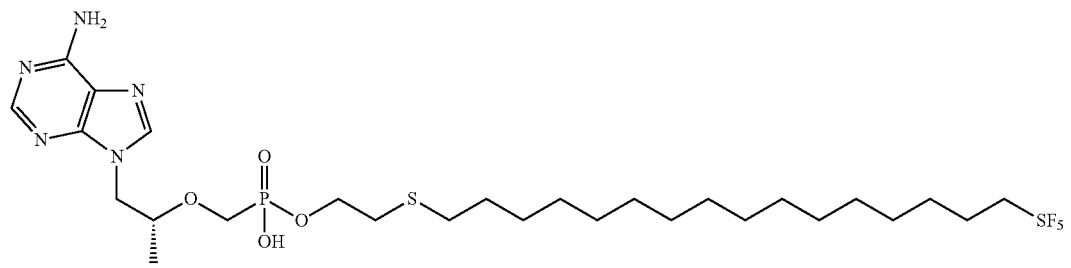

2-((16-(pentafluoro-$\lambda^6$-sulfanyl)hexadecyl)thio)ethyl hydrogen ((((R)-1-(6-amino-9H-purin-9-yl)propan-2-yl)oxy)methyl)phosphonate

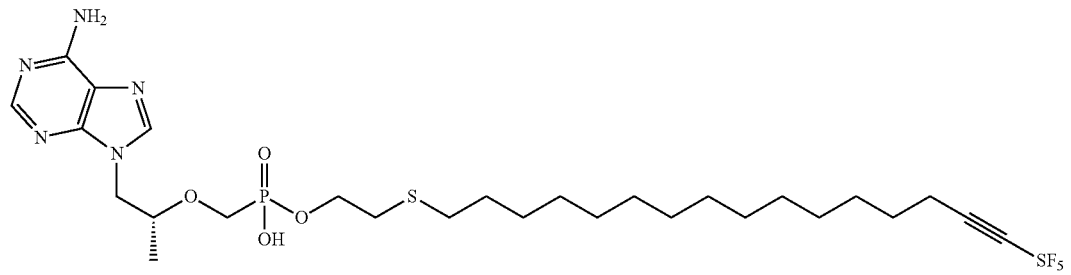

2-((16-(pentafluoro-$\lambda^6$-sulfanyl)hexadec-15-yn-1-yl)thio)ethyl hydrogen ((((R)-1-(6-amino-9H-purin-9-yl)propan-2-yl)oxy)methyl)phosphonate

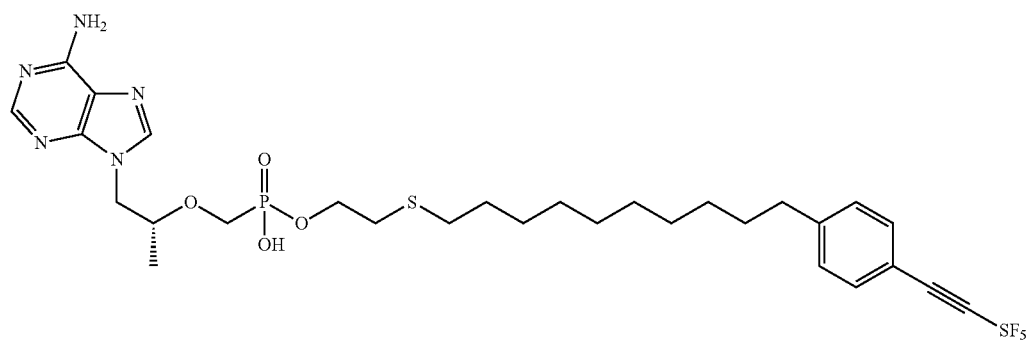

2-((10-(4-((pentafluoro-$\lambda^6$-sulfanyl)ethynyl)phenyl)decyl)thio)ethyl hydrogen ((((R)-1-(6-amino-9H-purin-9-yl)propan-2-yl)oxy)methyl)phosphonate

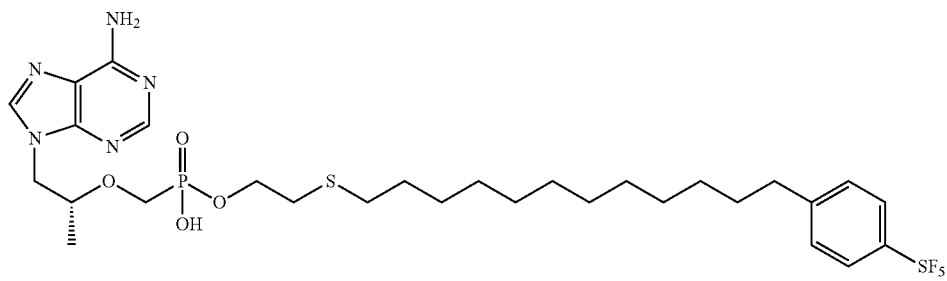

2-((12-(4-(pentafluoro-λ$^6$-sulfanyl)phenyl)dodecyl)thio)ethyl hydrogen ((((R)-1-(6-amino-9H-purin-9-yl)propan-2-yl)oxy)methyl)phosphonate

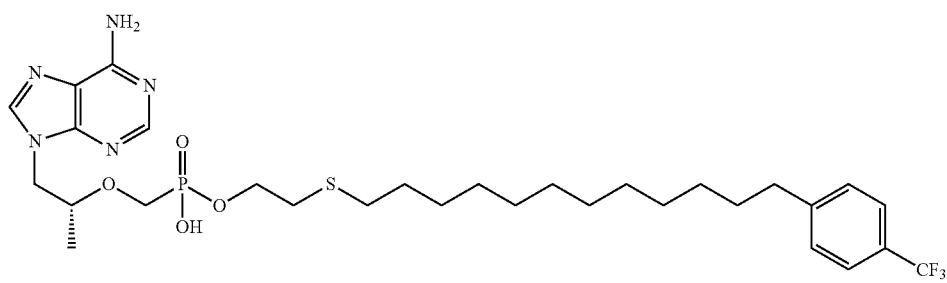

2-((12-(4-(trifluoromethyl)phenyl)dodecyl)thio)ethyl hydrogen ((((R)-1-(6-amino-9H-purin-9-yl)propan-2-yl)oxy)methyl)phosphonate

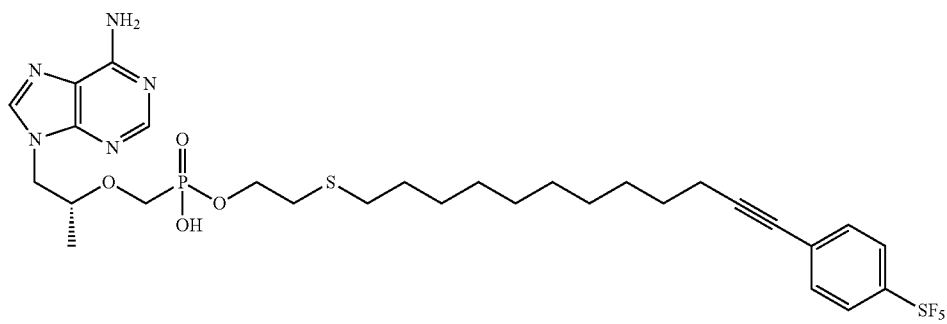

2-((12-(4-(pentafluoro-λ$^6$-sulfanyl)phenyl)dodec-11-yn-1-yl)thio)ethyl hydrogen ((((R)-1-(6-amino-9H-purin-9-yl)propan-2-yl)oxy)methyl)phosphonate

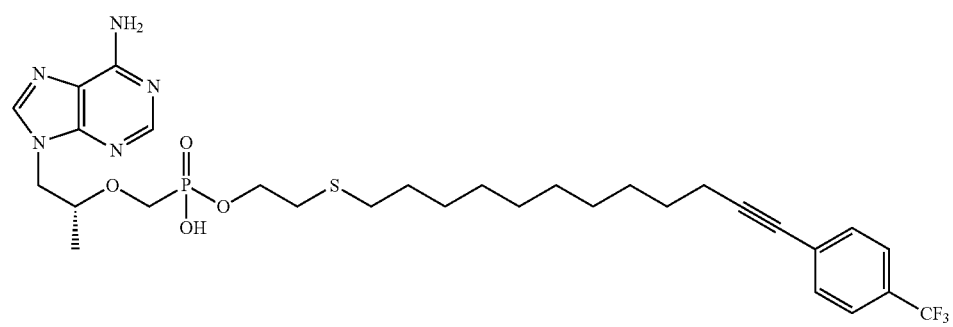

2-((12-(4-((trifluoromethyl)phenyl)dodec-11-yn-1-yl)thio)ethyl hydrogen ((((R)-1-(6-amino-9H-purin-9-yl)propan-2-yl)oxy)methyl)phosphonate

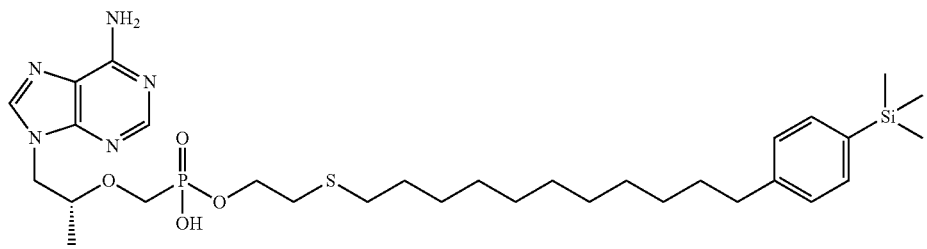

2-((11-(4-(trimethylsilyl)phenyl)undecyl)thio)ethyl hydrogen ((((R)-1-(6-amino-9H-purin-9-yl)propan-2-yl)oxy)methyl)phosphonate

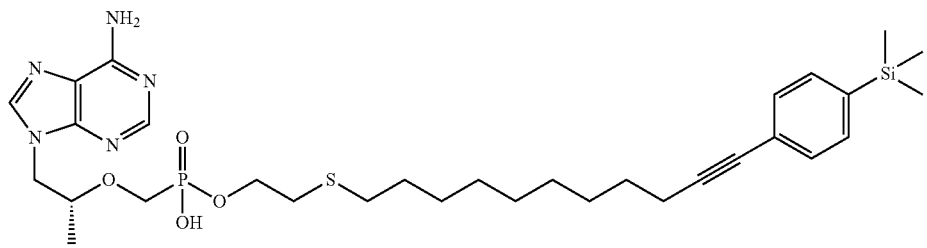

2-((11-(4-(trimethylsilyl)phenyl)undec-10-yn-1-yl)thio)ethyl hydrogen ((((R)-1-(6-amino-9H-purin-9-yl)propan-2-yl)oxy)methyl)phosphonate

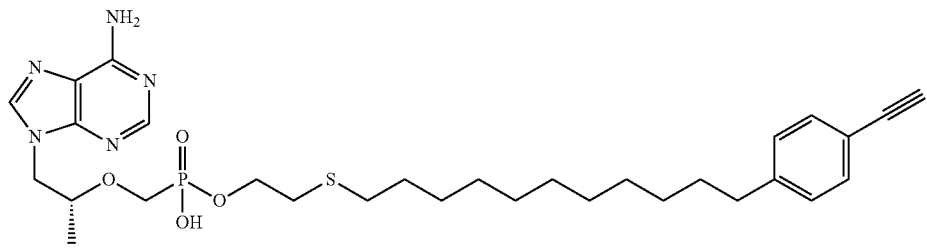

2-((11-(4-ethynylphenyl)undecyl)thio)ethyl hydrogen ((((R)-1-(6-amino-9H-purin-9-yl)propan-2-yl)oxy)methyl)phosphonate

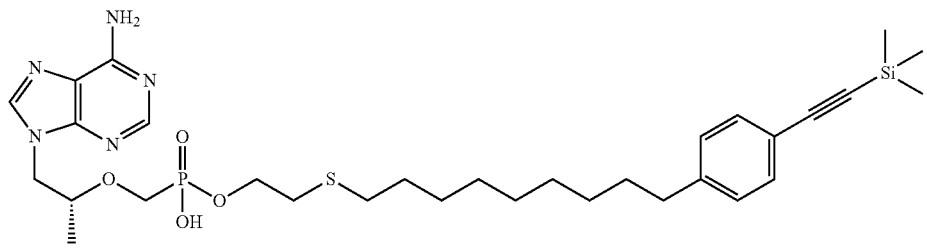

2-((9-(4-(trimethylsilyl)ethynyl)phenyl)nonyl)thio)ethyl hydrogen ((((R)-1-(6-amino-9H-purin-9-yl)propan-2-yl)oxy)methyl)phosphonate

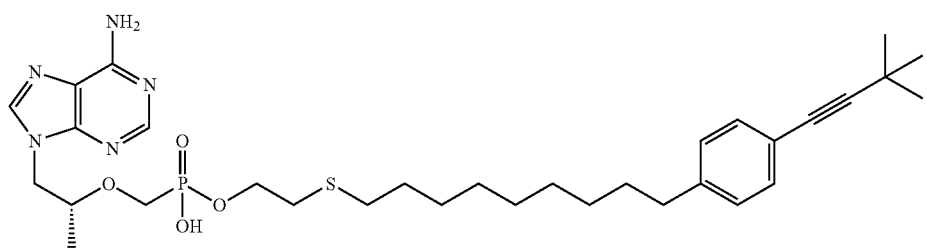

2-((9-(4-(3,3-dimethylbut-1-yn-1-yl)phenyl)nonyl)thio)ethyl hydrogen ((((R)-1-(6-amino-9H-purin-9-yl)propan-2-yl)oxy)methyl)phosphonate

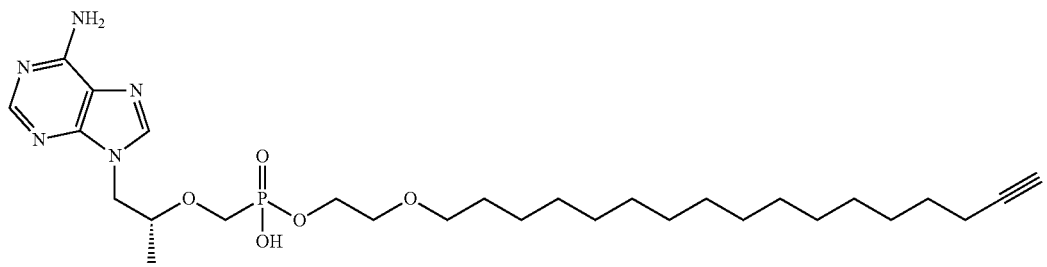

2-(heptadec-16-yn-1-yloxy)ethyl hydrogen ((((R)-1-(6-amino-9H-purin-9-yl)propan-2-yl)oxy)methyl)phosphonate

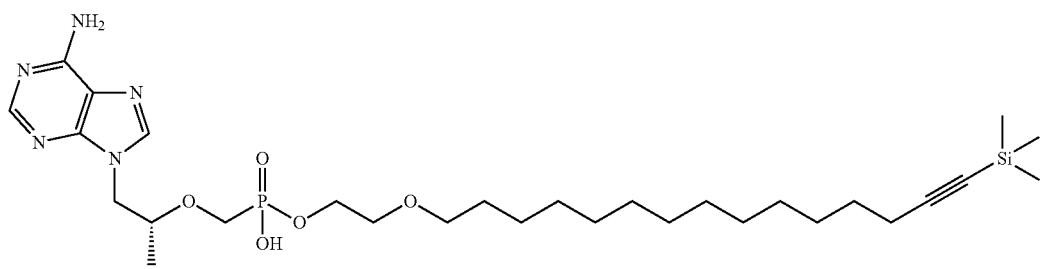

2-((15-(trimethylsilyl)pentadec-14-yn-1-yl)oxy)ethyl hydrogen ((((R)-1-(6-amino-9H-purin-9-yl)propan-2-yl)oxy)methyl)phosphonate

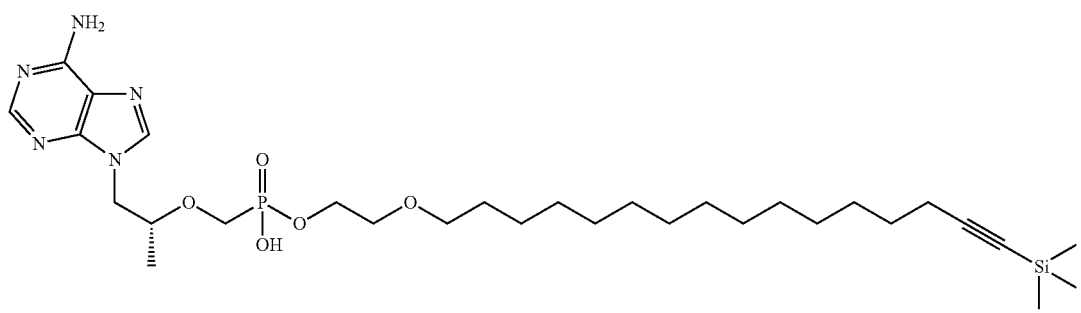

2-((16-(trimethylsilyl)hexadec-15-yn-1-yl)oxy)ethyl hydrogen ((((R)-1-(6-amino-9H-purin-9-yl)propan-2-yl)oxy)methyl)phosphonate

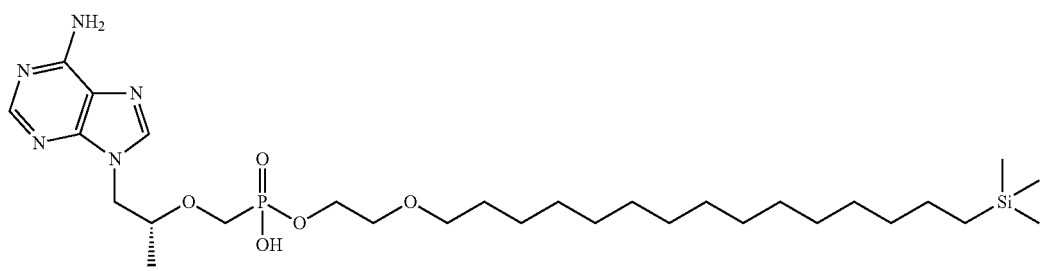

2-((15-(trimethylsilyl)pentadecyl)oxy)ethyl hydrogen ((((R)-1-(6-amino-9H-purin-9-yl)propan-2-yl)oxy)methyl)phosphonate

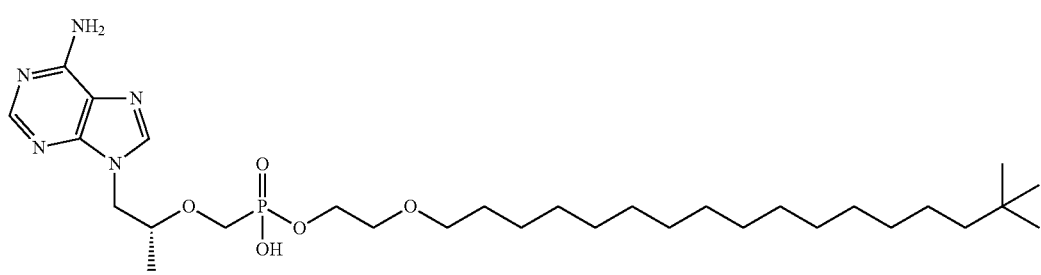

2-((16,16-dimethylheptadecyl)oxy)ethyl hydrogen ((((R)-1-(6-amino-9H-purin-9-yl)propan-2-yl)oxy)methyl)phosphonate

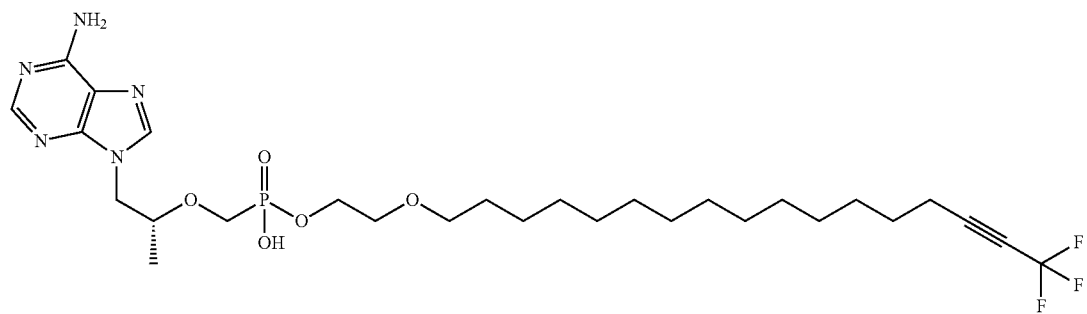

2-((17,17,17-trifluoroheptadec-15-yn-1-yl)oxy)ethyl hydrogen ((((R)-1-(6-amino-9H-purin-9-yl)propan-2-yl)oxy)methyl)phosphonate

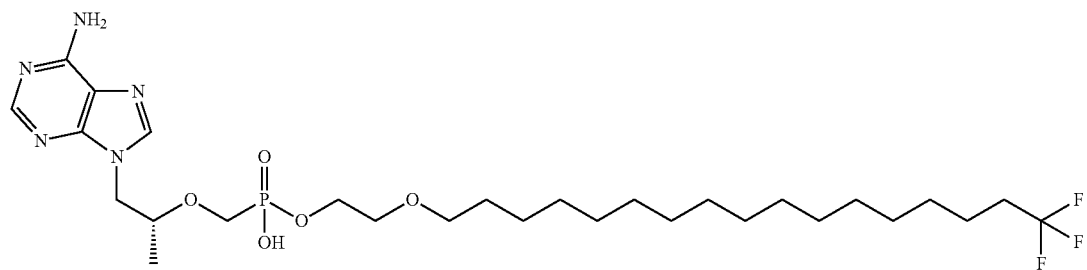

2-((17,17,17-trifluoroheptadecyl)oxy)ethyl hydrogen ((((R)-1-(6-amino-9H-purin-9-yl)propan-2-yl)oxy)methyl)phosphonate

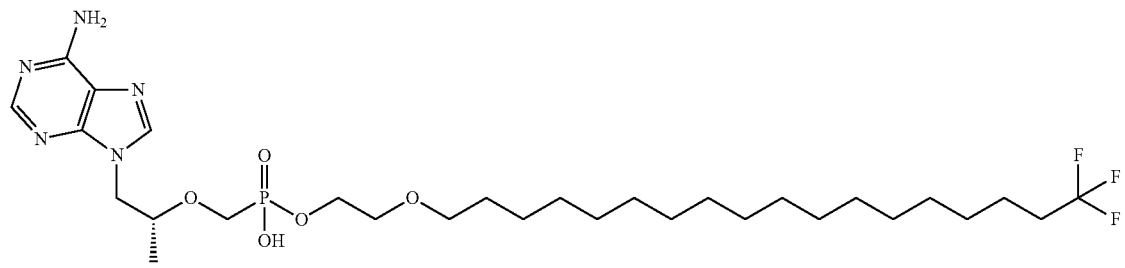

2-((18,18,18-trifluorooctadecyl)oxy)ethyl hydrogen ((((R)-1-(6-amino-9H-purin-9-yl)propan-2-yl)oxy)methyl)phosphonate

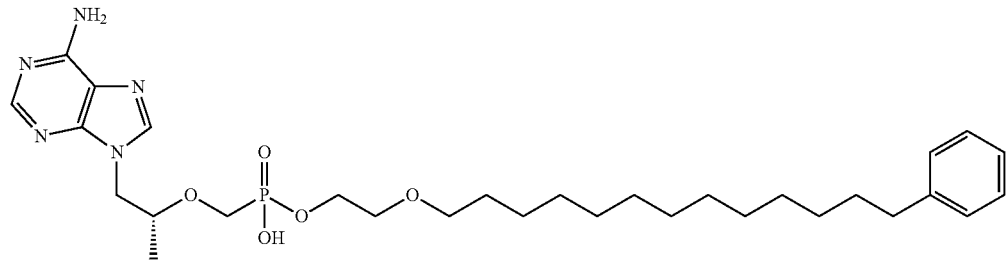

2-((13-phenyltridecyl)oxy)ethyl hydrogen ((((R)-1-(6-amino-9H-purin-9-yl)propan-2-yl)oxy)methyl)phosphonate

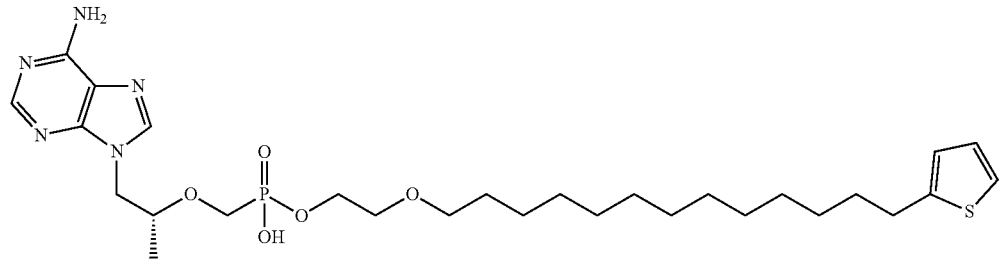

2-((13-(thiophen-2-yl)tridecyl)oxy)ethyl hydrogen ((((R)-1-(6-amino-9H-purin-9-yl)propan-2-yl)oxy)methyl)phosphonate

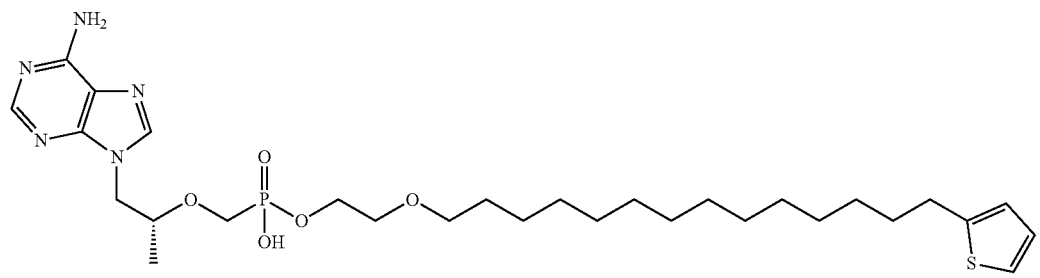

2-((14-(thiophen-2-yl)tetradecyl)oxy)ethyl hydrogen ((((R)-1-(6-amino-9H-purin-9-yl)propan-2-yl)oxy)methyl)phosphonate

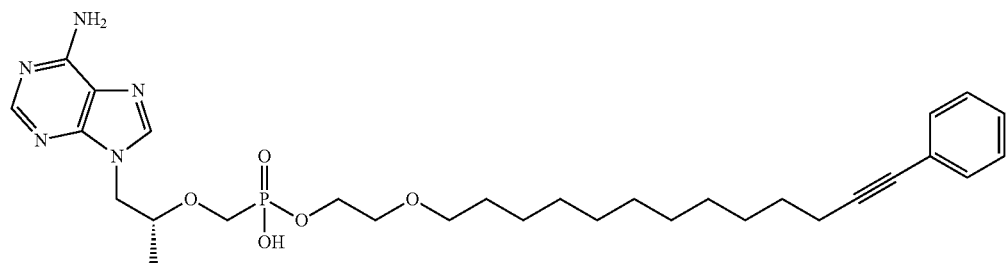

2-((13-phenyltridec-12-yn-1-yl)oxy)ethyl hydrogen ((((R)-1-(6-amino-9H-purin-9-yl)propan-2-yl)oxy)methyl)phosphonate

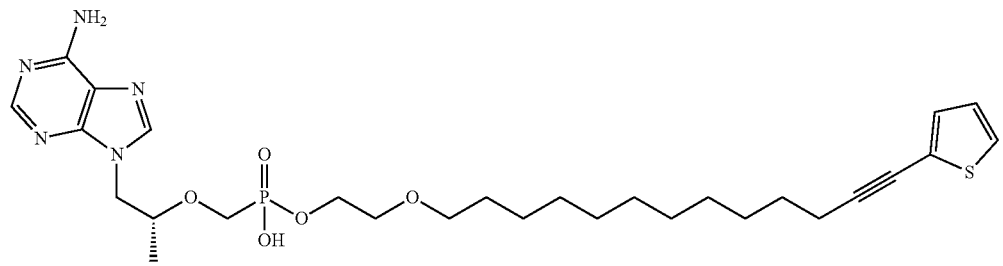

2-((13-thiophen-2-yl)tridec-12-yn-1-yl)oxy)ethyl hydrogen ((((R)-1-(6-amino-9H-purin-9-yl)propan-2-yl)oxy)methyl)phosphonate

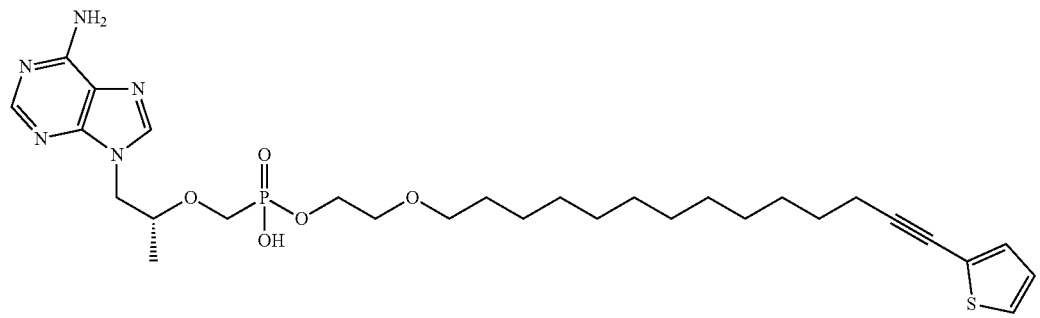

2-((14-thiophen-2-yl)tetradec-13-yn-1-yl)oxy)ethyl hydrogen ((((R)-1-(6-amino-9H-purin-9-yl)propan-2-yl)oxy)methyl)phosphonate

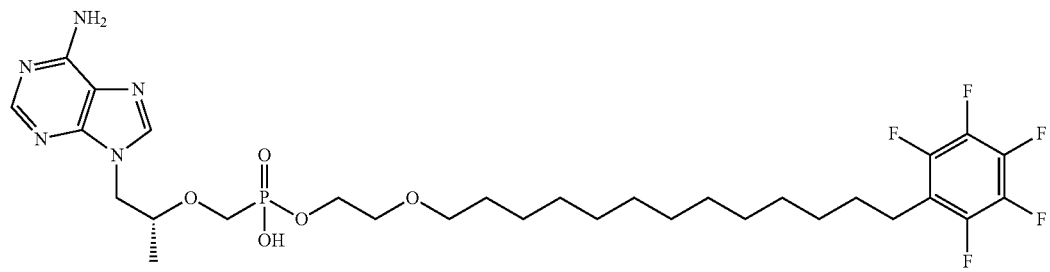

2-((13-(perfluorophenyl)tridecyl)oxy)ethyl hydrogen ((((R)-1-(6-amino-9H-purin-9-yl)propan-2-yl)oxy)methyl)phosphonate

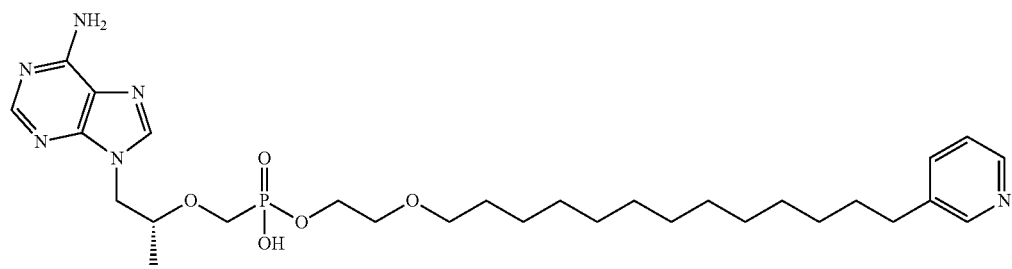

2-((13-(pyridin-3-yl)tridecyl)oxy)ethyl hydrogen ((((R)-1-(6-amino-9H-purin-9-yl)propan-2-yl)oxy)methyl)phosphonate

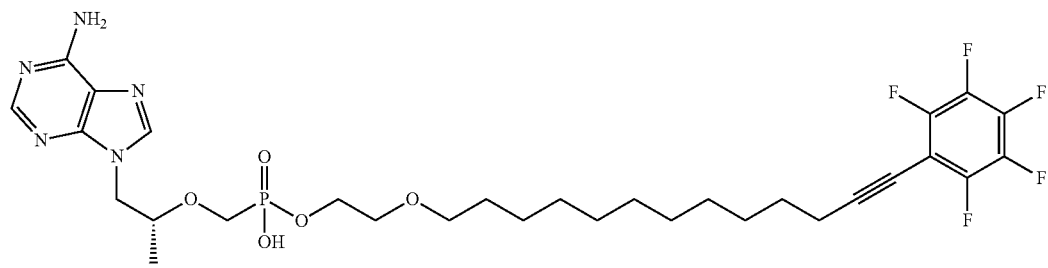

2-((13-(perfluorophenyl)tridec-12-yn-1-yl)oxy)ethyl hydrogen ((((R)-1-(6-amino-9H-purin-9-yl)propan-2-yl)oxy)methyl)phosphonate

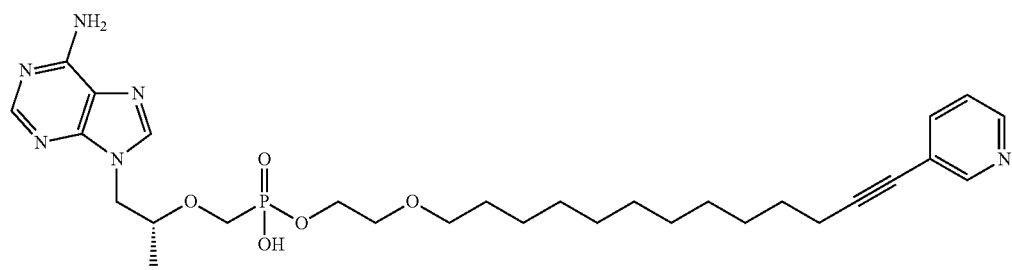

2-((13-(pyridin-3-yl)tridec-12-yn-1-yl)oxy)ethyl hydrogen ((((R)-1-(6-amino-9H-purin-9-yl)propan-2-yl)oxy)methyl)phosphonate

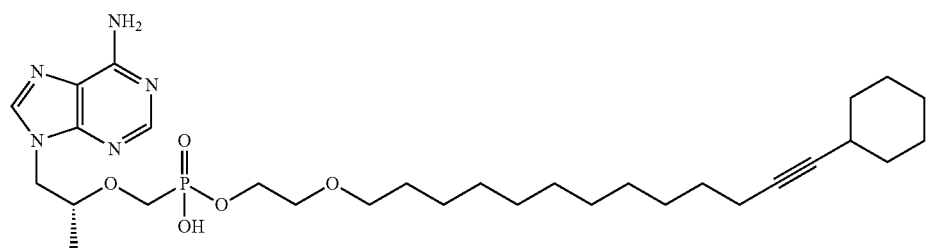

2-((13-cyclohexyltridec-12-yn-1-yl)oxy)ethyl hydrogen ((((R)-1-(6-amino-9H-purin-9-yl)propan-2-yl)oxy)methyl)phosphonate

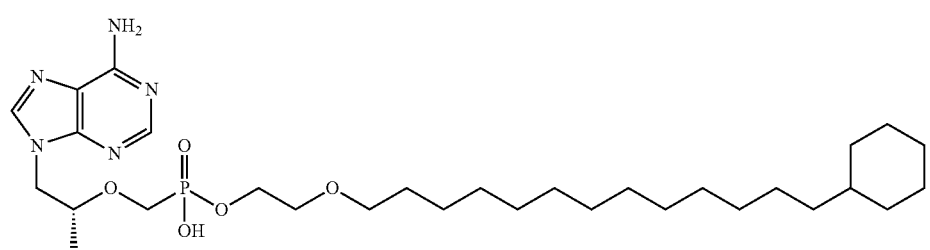

2-((13-cyclohexyltridecyl)oxy)ethyl hydrogen ((((R)-1-(6-amino-9H-purin-9-yl)propan-2-yl)oxy)methyl)phosphonate

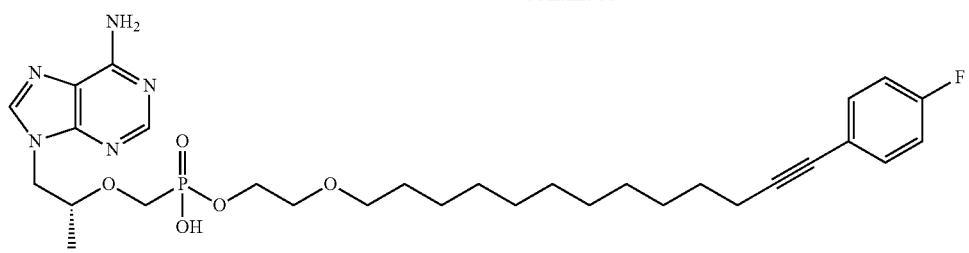

2-((13-(4-fluorophenyl)tridec-12-yn-1-yl)oxy)ethyl hydrogen ((((R)-1-(6-amino-9H-purin-9-yl)propan-2-yl)oxy)methyl)phosphonate

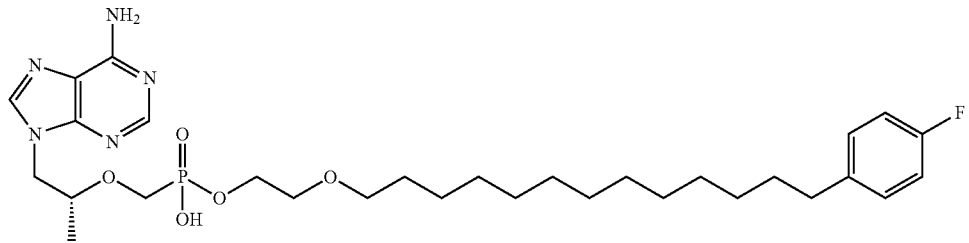

2-((13-(4-fluorophenyl)tridecyl)oxy)ethyl hydrogen ((((R)-1-(6-amino-9H-purin-9-yl)propan-2-yl)oxy)methyl)phosphonate

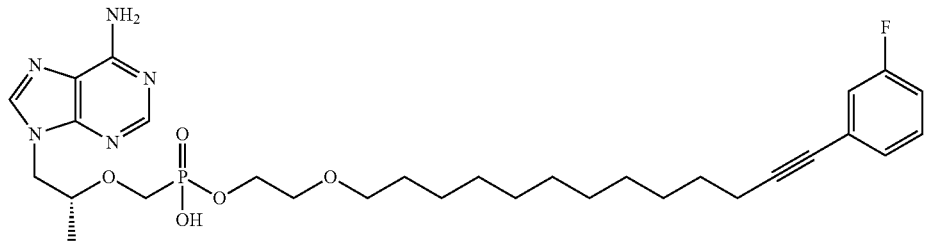

2-((13-(3-fluorophenyl)tridec-12-yn-1-yl)oxy)ethyl hydrogen ((((R)-1-(6-amino-9H-purin-9-yl)propan-2-yl)oxy)methyl)phosphonate

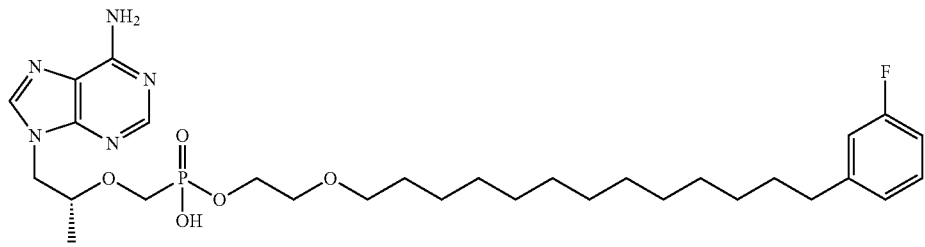

2-((13-(3-fluorophenyl)tridecyl)oxy)ethyl hydrogen ((((R)-1-(6-amino-9H-purin-9-yl)propan-2-yl)oxy)methyl)phosphonate

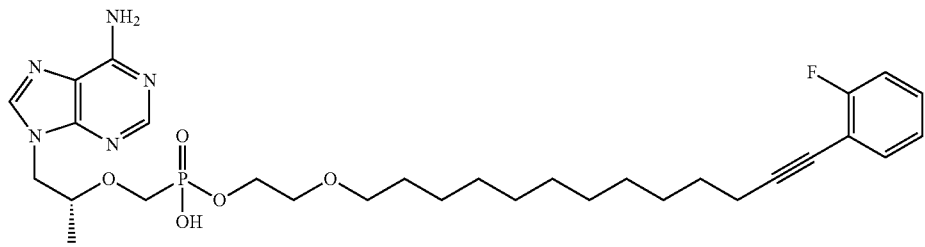

2-((13-(2-fluorophenyl)tridec-12-yn-1-yl)oxy)ethyl hydrogen ((((R)-1-(6-amino-9H-purin-9-yl)propan-2-yl)oxy)methyl)phosphonate

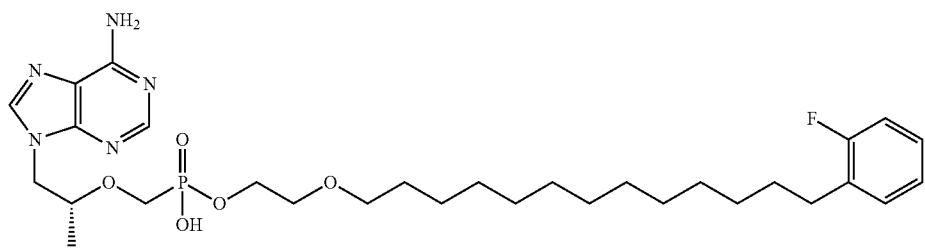

2-((13-(2-fluorophenyl)tridecyl)oxy)ethyl hydrogen ((((R)-1-(6-amino-9H-purin-9-yl)propan-2-yl)oxy)methyl)phosphonate

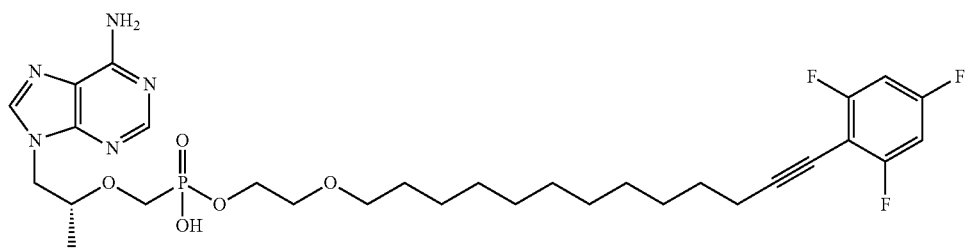

2-((13-(2,4,6-trifluorophenyl)tridec-12-yn-1-yl)oxy)ethyl hydrogen ((((R)-1-(6-amino-9H-purin-9-yl)propan-2-yl)oxy)methyl)phosphonate

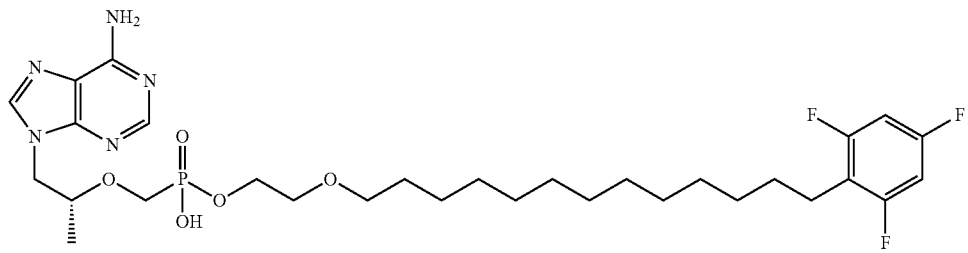

2-((13-(2,4,6-trifluorophenyl)tridecyl)oxy)ethyl hydrogen ((((R)-1-(6-amino-9H-purin-9-yl)propan-2-yl)oxy)methyl)phosphonate

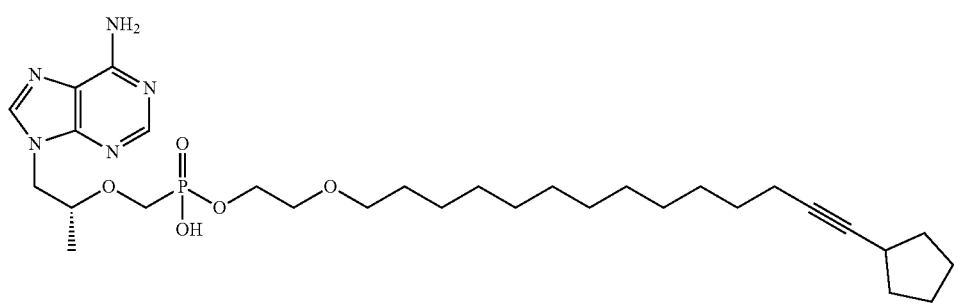

2-((14-cyclopentyltetradec-13-yn-1-yl)oxy)ethyl hydrogen ((((R)-1-(6-amino-9H-purin-9-yl)propan-2-yl)oxy)methyl)phosphonate

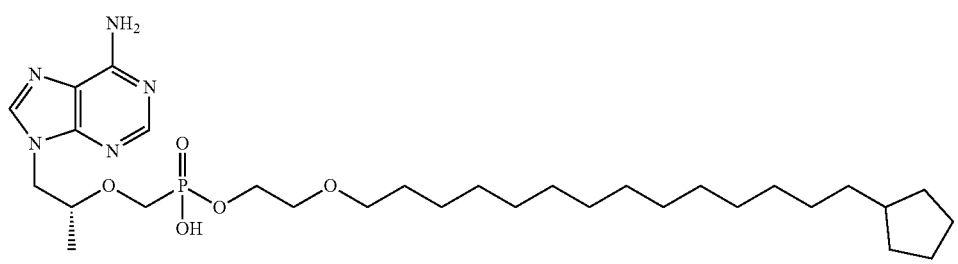

2-((14-cyclopentyltetradecyl)oxy)ethyl hydrogen ((((R)-1-(6-amino-9H-purin-9-yl)propan-2-yl)oxy)methyl)phosphonate

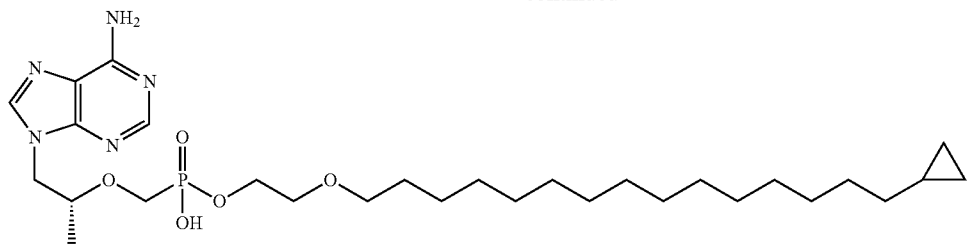

2-((15-cyclopropylpentadecyl)oxy)ethyl hydrogen ((((R)-1-(6-amino-9H-purin-9-yl)propan-2-yl)oxy)methyl)phosphonate

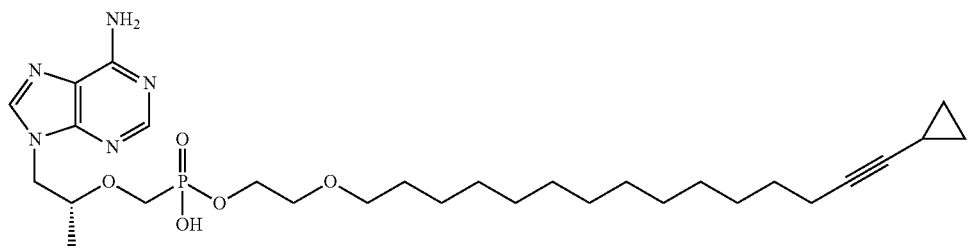

2-((15-cyclopropylpentadec-14-yn-1-yl)oxy)ethyl hydrogen ((((R)-1-(6-amino-9H-purin-9-yl)propan-2-yl)oxy)methyl)phosphonate

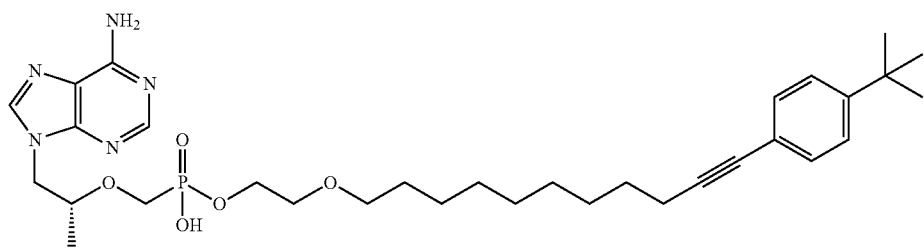

2-((11-(4-(tert-butyl)phenyl)undec-10-yn-1-yl)oxy)ethyl hydrogen ((((R)-1-(6-amino-9H-purin-9-yl)propan-2-yl)oxy)methyl)phosphonate

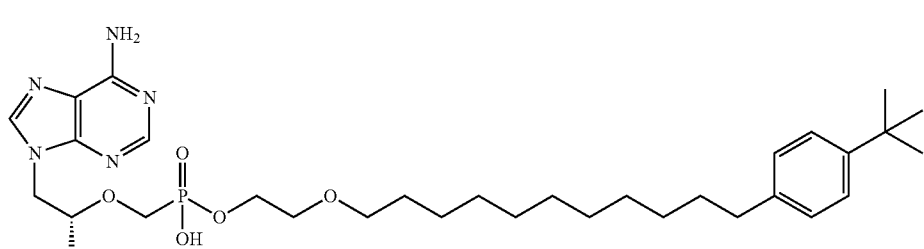

2-(((11-(4-(tert-butyl)phenyl)undecyl)oxy)ethyl hydrogen ((((R)-1-(6-amino-9H-purin-9-yl)propan-2-yl)oxy)methyl)phosphonate

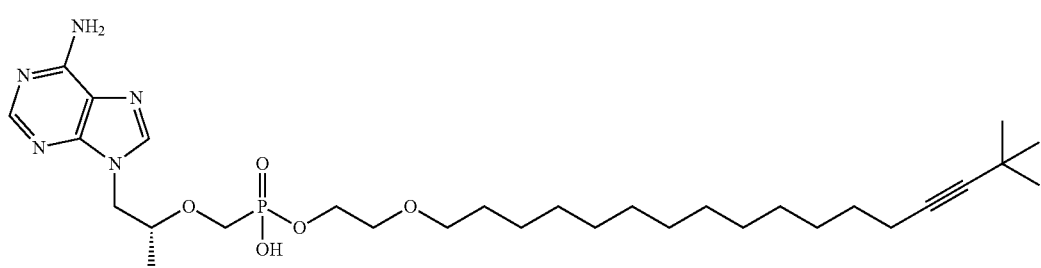

2-((16,16-dimethylheptadec-14-yn-1-yl)oxy)ethyl hydrogen ((((R)-1-(6-amino-9H-purin-9-yl)propan-2-yl)oxy)methyl)phosphonate

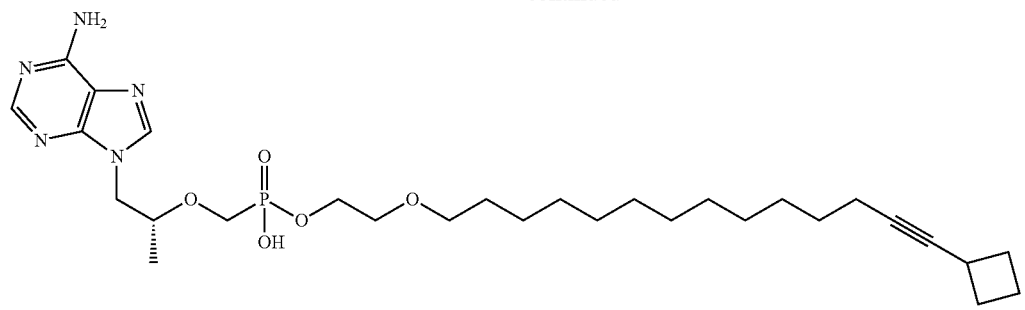

2-((14-cyclobutyltetradec-13-yn-1-yl)oxy)ethyl hydrogen ((((R)-1-(6-amino-9H-purin-9-yl)propan-2-yl)oxy)methyl)phosphonate

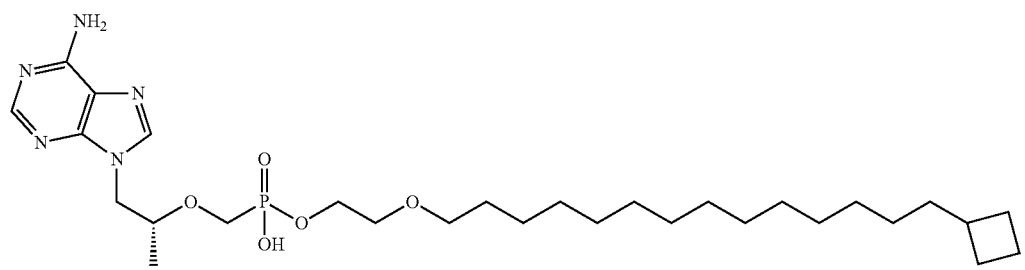

2-((14-cyclobutyltetradecyl)oxy)ethyl hydrogen ((((R)-1-(6-amino-9H-purin-9-yl)propan-2-yl)oxy)methyl)phosphonate

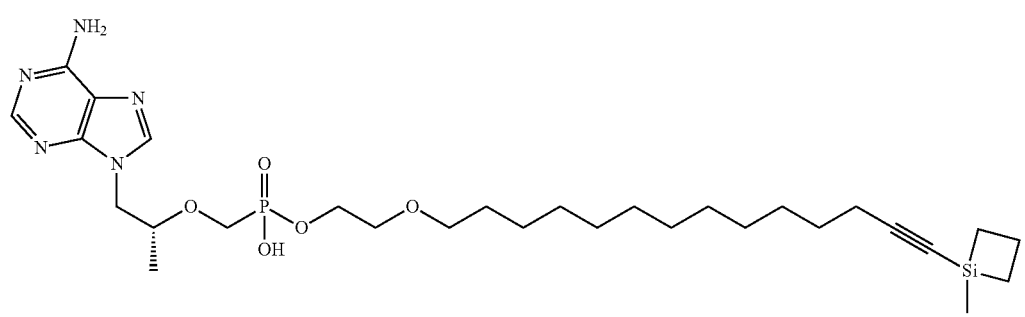

2-((14-(1-methylsiletan-1-yl)tetradec-13-yn-1-yl)oxy)ethyl hydrogen ((((R)-1-(6-amino-9H-purin-9-yl)propan-2-yl)oxy)methyl)phosphonate

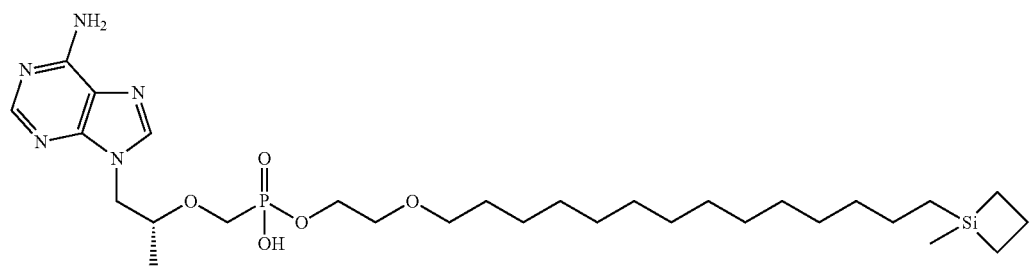

2-(((14-(1-methylsiletan-1-yl)tetradecyl)oxy)ethyl hydrogen ((((R)-1-(6-amino-9H-purin-9-yl)propan-2-yl)oxy)methyl)phosphonate -continued

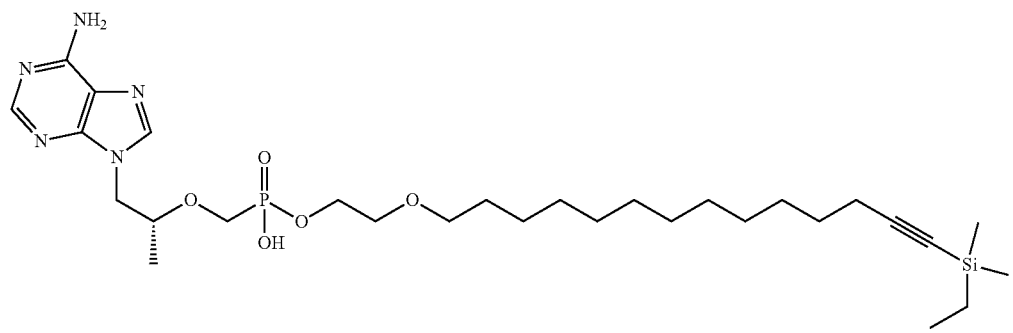

2-((14-(ethyldimethylsilyl)tetradec-13-yn-1-yl)oxy)ethyl hydrogen ((((R)-1-(6-amino-9H-purin-9-yl)propan-2-yl)oxy)methyl)phosphonate

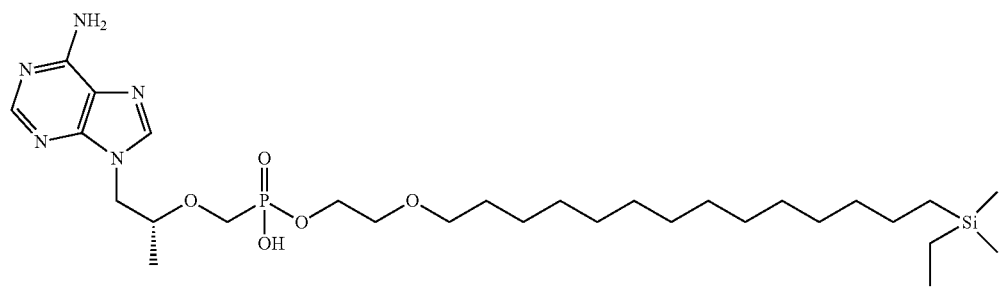

2-((14-(ethyldimethylsilyl)tetradecyl)oxy)ethyl hydrogen ((((R)-1-(6-amino-9H-purin-9-yl)propan-2-yl)oxy)methyl)phosphonate

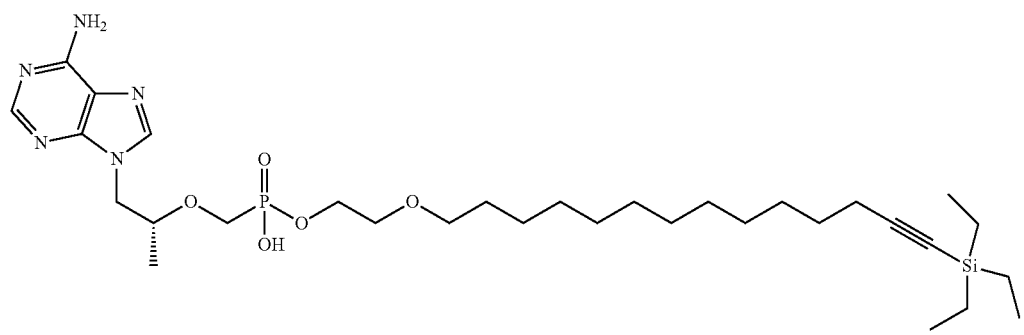

2-(((14-(triethylsilyl)tetradec-13-yn-1-yl)oxy)ethyl hydrogen ((((R)-1-(6-amino-9H-purin-9-yl)propan-2-yl)oxy)methyl)phosphonate

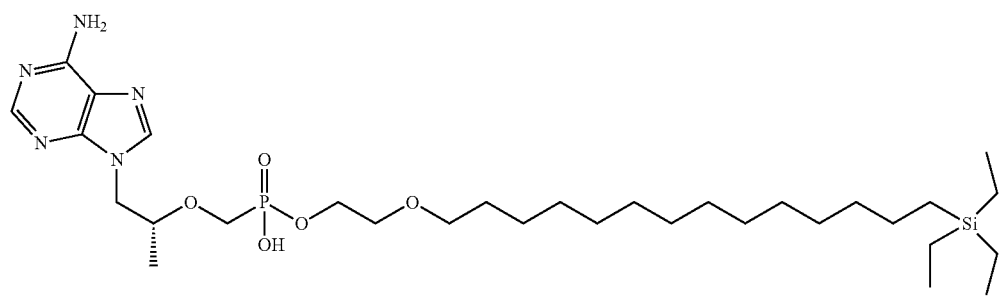

2-((14-(triethylsilyl)tetradecyl)oxy)ethyl hydrogen ((((R)-1-(6-amino-9H-purin-9-yl)propan-2-yl)oxy)methyl)phosphonate

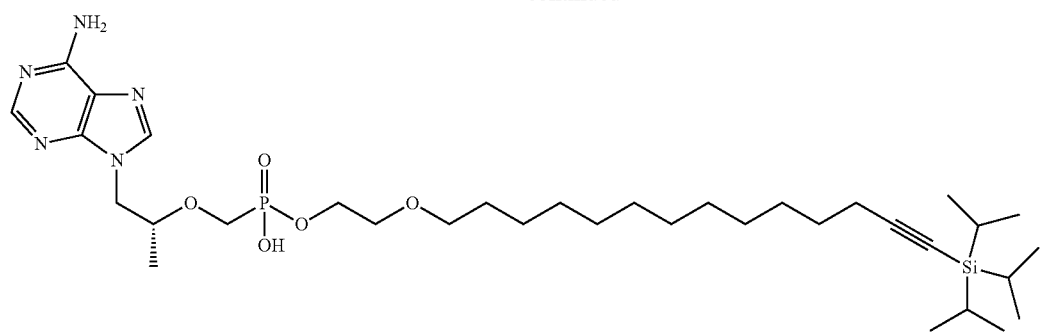

2-((14-(triisopropylsilyl)tetradec-13-yn-1-yl)oxy)ethyl hydrogen ((((R)-1-(6-amino-9H-purin-9-yl)propan-2-yl)oxy)methyl)phosphonate

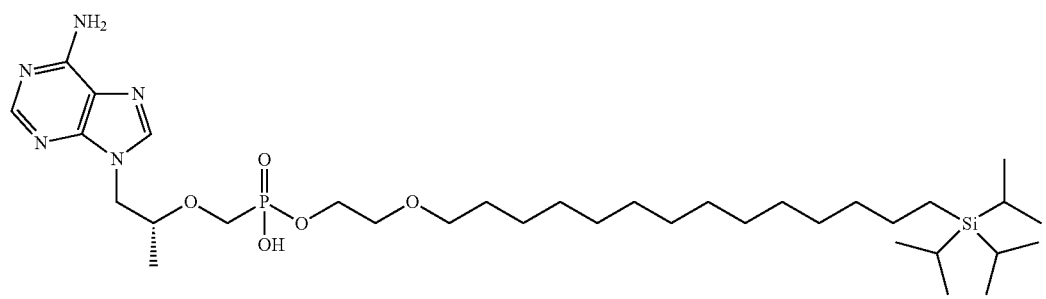

2-((14-(triisopropylsilyl)tetradecyl)oxy)ethyl hydrogen ((((R)-1-(6-amino-9H-purin-9-yl)propan-2-yl)oxy)methyl)phosphonate

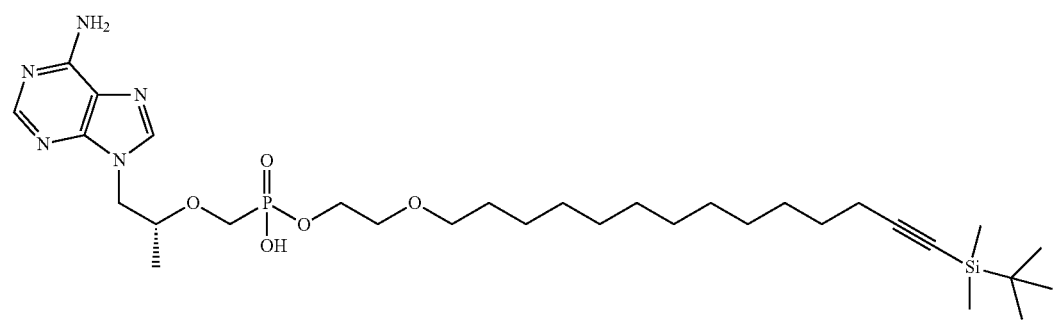

2-((14-(tert-butyldimethylsilyl)tetradec-13-yn-1-yl)oxy)ethyl hydrogen ((((R)-1-(6-amino-9H-purin-9-yl)propan-2-yl)oxy)methyl)phosphonate

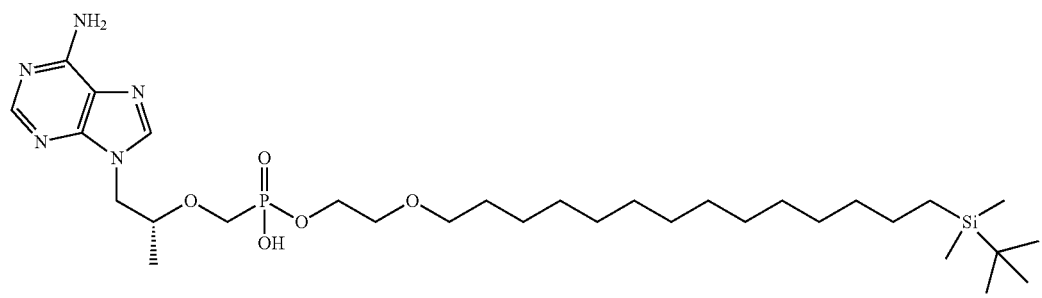

2-((14-(tert-butyldimethylsilyl)tetradecyl)oxy)ethyl hydrogen ((((R)-1-(6-amino-9H-purin-9-yl)propan-2-yl)oxy)methyl)phosphonate

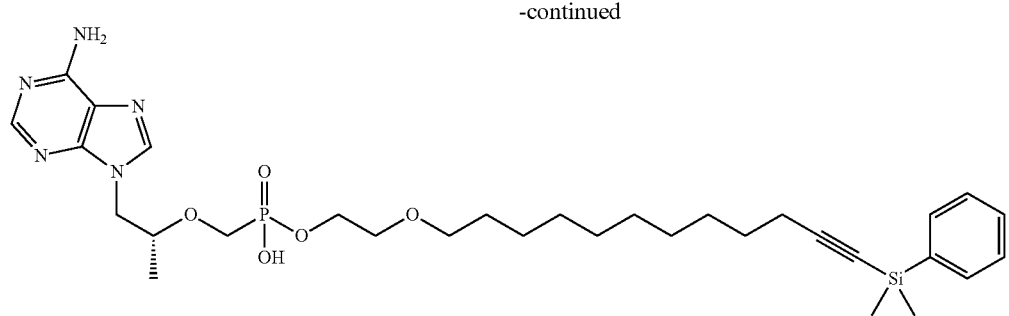

2-((12-(dimethyl(phenyl)silyl)dodec-11-yn-1-yl)oxy)ethyl hydrogen ((((R)-1-(6-amino-9H-purin-9-yl)propan-2-yl)oxy)methyl)phosphonate

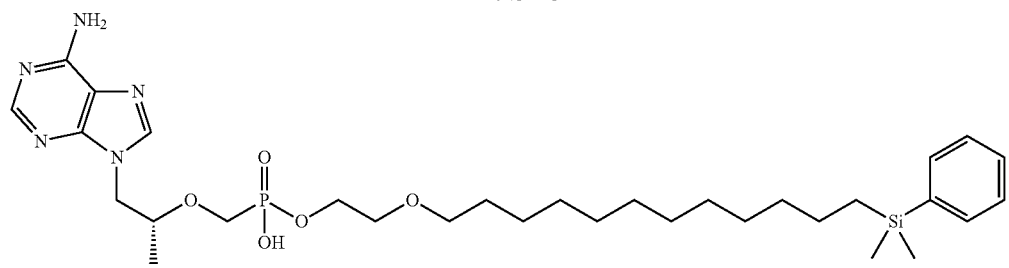

2-((12-(dimethyl(phenyl)silyl)dodecyl)oxy)ethyl hydrogen ((((R)-1-(6-amino-9H-purin-9-yl)propan-2-yl)oxy)methyl)phosphonate

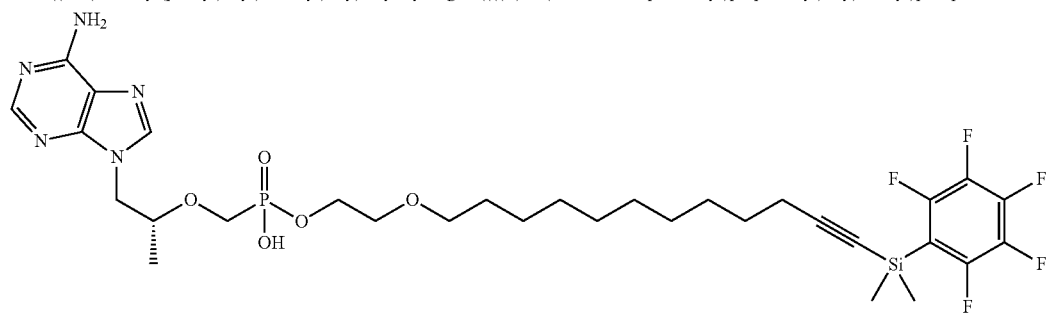

2-((12-(dimethyl(perfluorophenyl)silyl)dodec-11-yn-1-yl)oxy)ethyl hydrogen ((((R)-1-(6-amino-9H-purin-9-yl)oxy)methyl)phosphonate

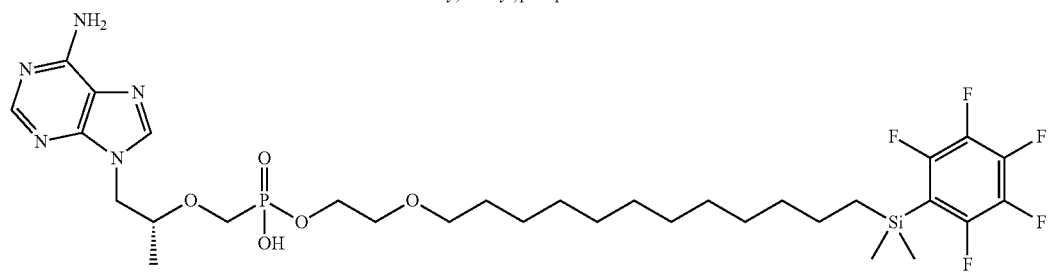

2-((12-(dimethyl(perfluorophenyl)silyl)dodecyl)oxy)ethyl hydrogen ((((R)-1-(6-amino-9H-purin-9-yl)propan-2-yl)oxy)methyl)phosphonate

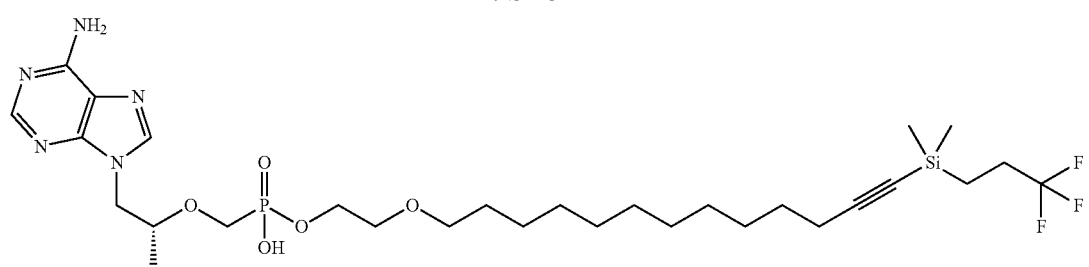

2-((13-(dimethyl((3,3,3,-trifluoropropyl)silyl)tridec-12-yn-1-yl)oxy)ethyl hydrogen(6-amino-9H-purin-9-yl)propan-2-yl)oxy)methyl)phosphonate

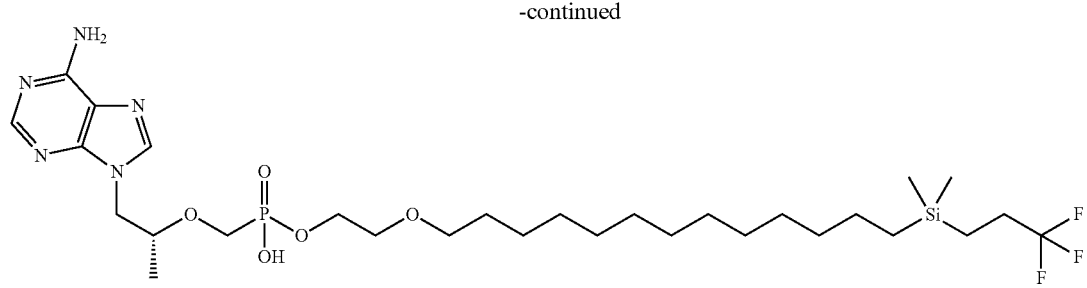

2-((13-(dimethyl(3,3,3-trifluoropropyl)silyl)tridecyl)oxy)ethyl hydrogen ((((R)-1-(6-amino-9H-purin-9-yl)propan-2-yl)oxy)methyl)phosphonate

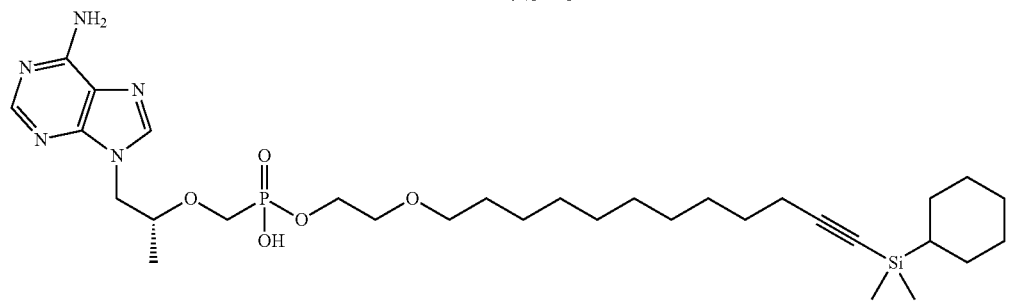

2-((12-(cyclohexyldimethylsilyl)dodec-11-yn-1-yl)oxy)ethyl hydrogen ((((R)-1-(6-amino-9H-purin-9-yl)propan-2-yl)oxy)methyl)phosphonate

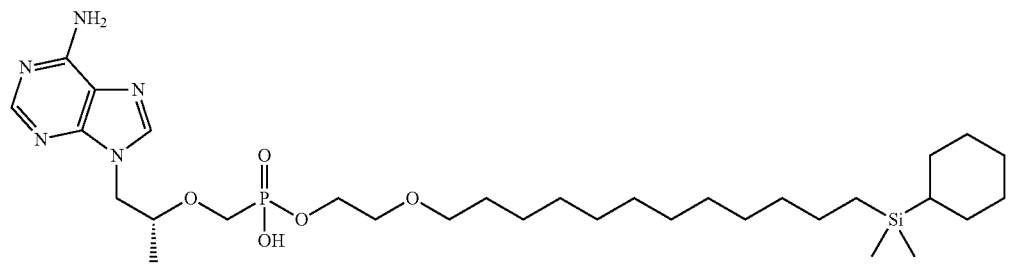

2-((12-(cyclohexyldimethylsilyl)dodecyl)oxy)ethyl hydrogen ((((R)-1-(6-amino-9H-purin-9-yl)propan-2-yl)oxy)methyl)phosphonate

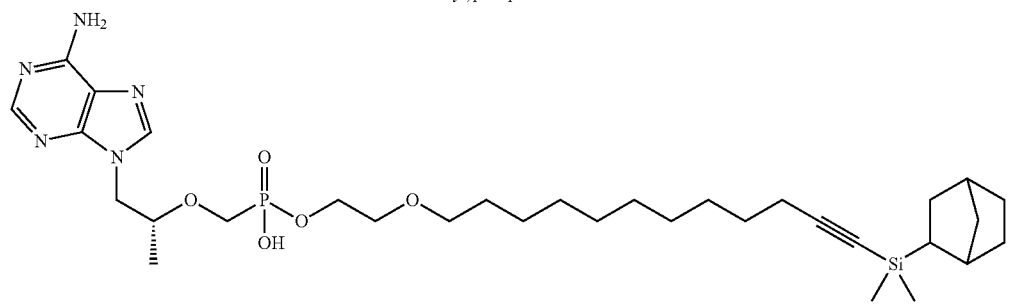

2-((12-(bicyclo[2.2.1]heptan-2-yldimethylsilyl)dodec-11-yn-1-yl)oxy)ethyl hydrogen ((((R)-1-(6-amino-9H-purin-9-yl)propan-2-yl)oxy)methyl)phosphonate

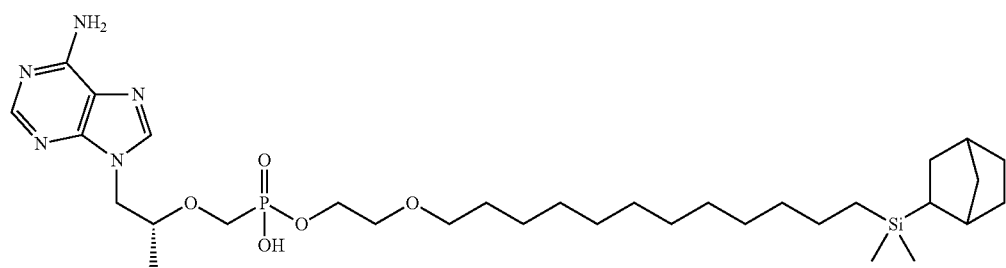

2-((12-(bicyclo[2.2.1]heptan-2-yldimethylsilyl)dodecyl)oxy)ethyl hydrogen ((((R)-1-(6-amino-9H-purin-9-yl)propan-2-yl)oxy)methyl)phosphonate

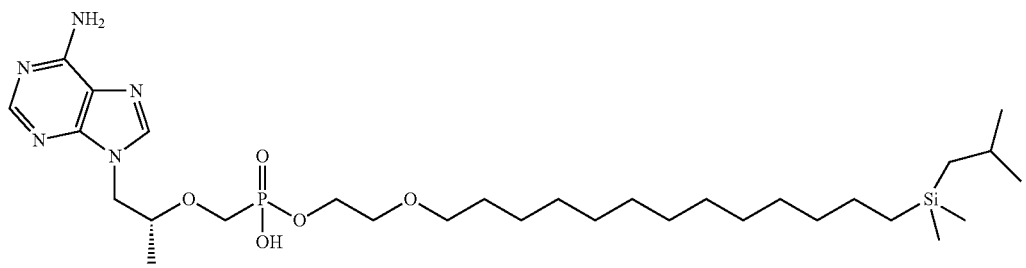

2-(((13-(isobutyldimethylsilyl)tridecyl)oxy)ethyl hydrogen ((((R)-1-(6-amino-9H-purin-9-yl)propan-2-yl)oxy)methyl)phosphonate

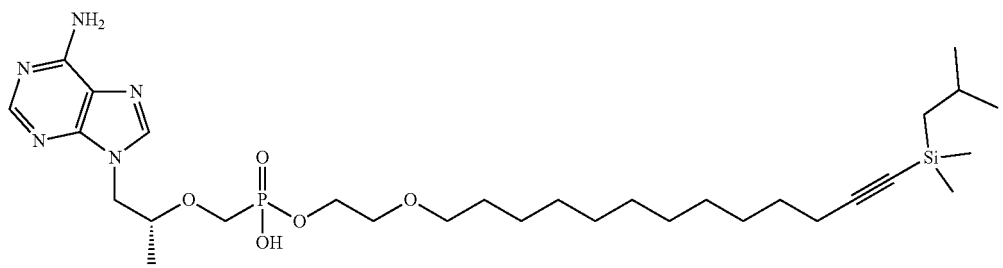

2-((13-(isobutyldimethylsilyl)tridec-12-yn-1-yl)oxy)ethyl hydrogen ((((R)-1-(6-amino-9H-purin-9-yl)propan-2-yl)oxy)methyl)phosphonate

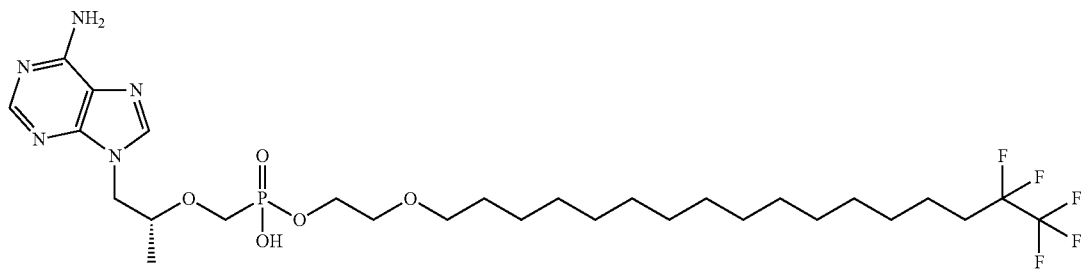

2-((16,16,17,17,17-pentafluoroheptadecyl)oxy)ethyl hydrogen (((((R)-1-(6-amino-9H-purin-9-yl)propan-2-yl)oxy)methyl)phosphonate

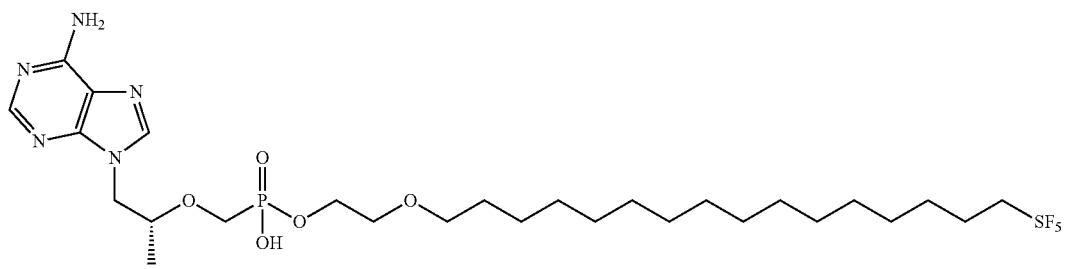

2-((16-(pentafluoro-$\lambda^6$-sulfanyl)hexadecyl)oxy)ethyl hydrogen (((((R)-1-(6-amino-9H-purin-9-yl)propan-2-yl)oxy)methyl)phosphonate

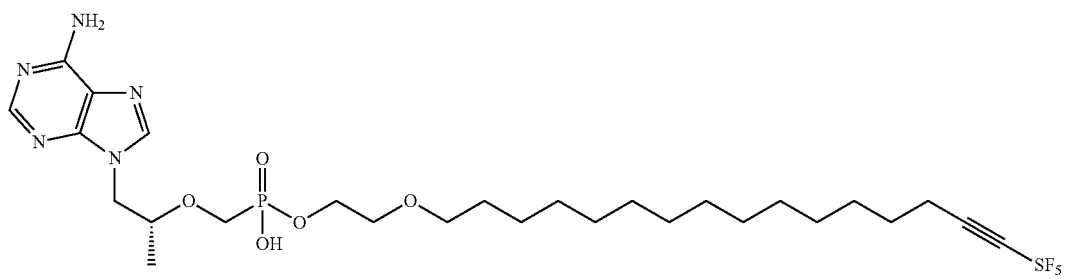

2-((16-(pentafluoro-$\lambda^6$-sulfanyl)hexadec-15-yn-1-yl)oxy)ethyl hydrogen ((((R)-1-(6-amino-9H-purin-9-yl)propan-2-yl)oxy)methyl)phosphonate

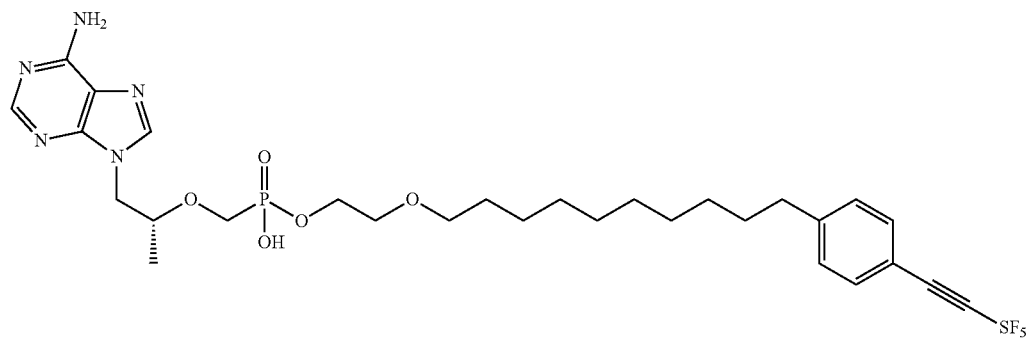

2-((10-(4-((pentafluoro-λ⁶-sulfanyl)ethynyl)phenyl)decyl)oxy)ethyl hydrogen ((((R)-1-(6-amino-9H-purin-9-yl)propan-2-yl)oxy)methyl)phosphonate

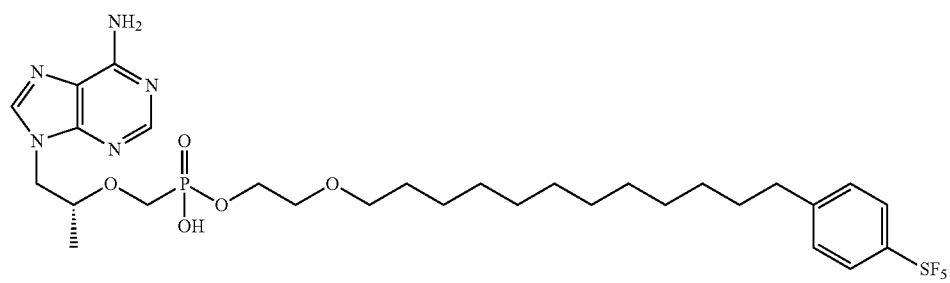

2-((12-(4-(pentafluoro-λ⁶-sulfanyl)phenyl)dodecyl)oxy)ethyl hydrogen ((((R)-1-(6-amino-9H-purin-9-yl)propan-2-yl)oxy)methyl)phosphonate

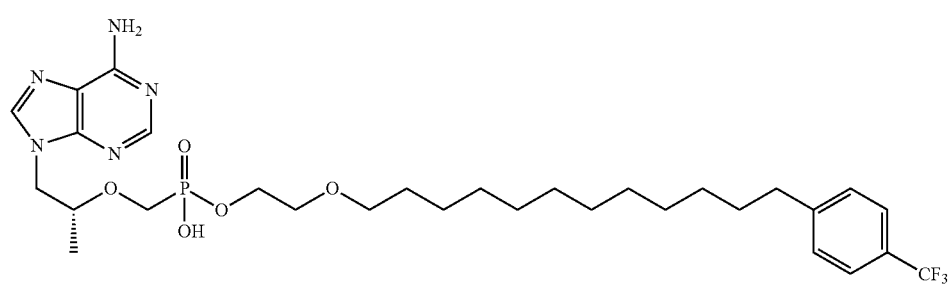

2-((12-(4-(trifluoromethyl)phenyl)dodecyl)oxy)ethyl hydrogen ((((R)-1-(6-amino-9H-purin-9-yl)propan-2-yl)oxy)methyl)phosphonate

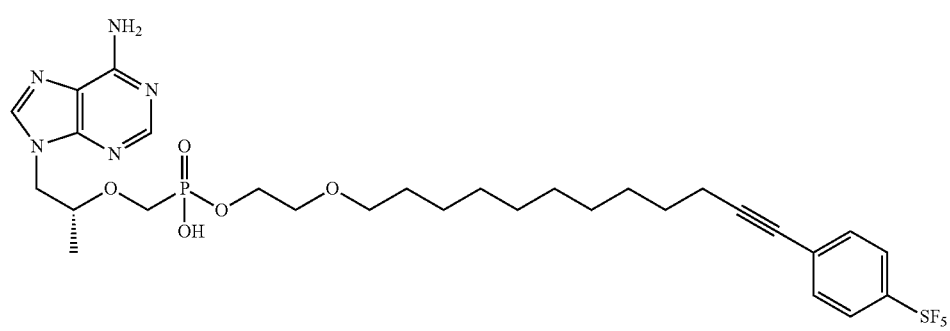

2-((12-(4-(pentafluoro-λ⁶-sulfanyl)phenyl)dodec-11-yn-1-yl)oxy)ethyl hydrogen ((((R)-1-(6-amino-9H-purin-9-yl)propan-2-yl)oxy)methyl)phosphonate

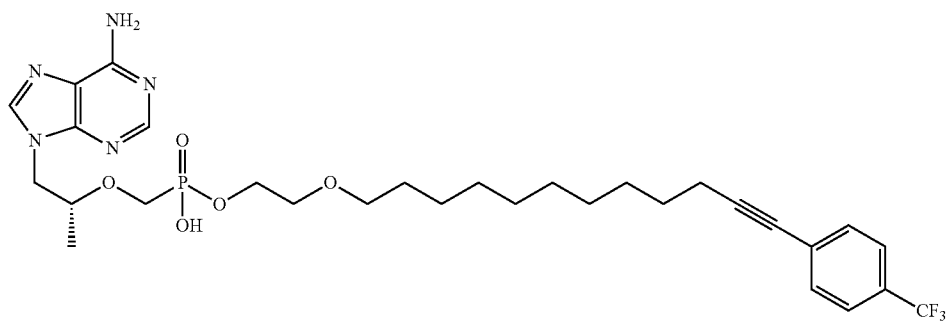

2-((12-(4-((trifluoromethyl)phenyl)dodec-11-yn-1-yl)oxy)ethyl hydrogen ((((R)-1-(6-amino-9H-purin-9-yl)propan-2-yl)oxy)methyl)phosphonate

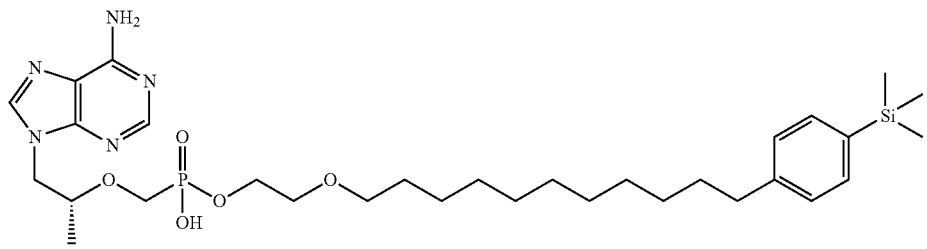

2-((11-(4-(trimethylsilyl)phenyl)undecyl)oxy)ethyl hydrogen ((((R)-1-(6-amino-9H-purin-9-yl)propan-2-yl)oxy)methyl)phosphonate

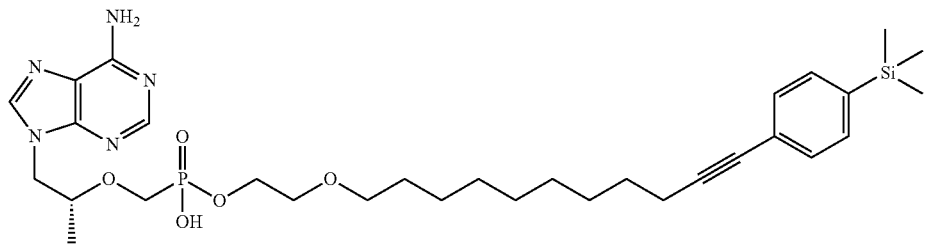

2-((11-(4-(trimethylsilyl)phenyl)undec-10-yn-1-yl)oxy)ethyl hydrogen ((((R)-1-(6-amino-9H-purin-9-yl)propan-2-yl)oxy)methyl)phosphonate

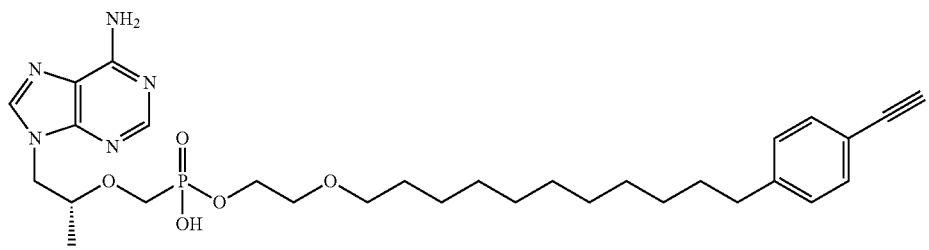

2-((11-(4-ethynylphenyl)undecyl)oxy)ethyl hydrogen ((((R)-1-(6-amino-9H-purin-9-yl)propan-2-yl)oxy)methyl)phosphonate

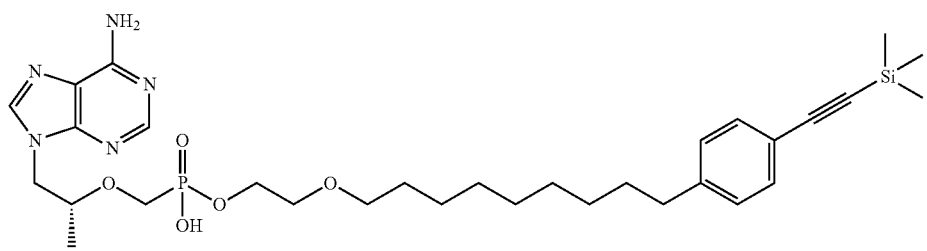

2-((9-(4-(trimethylsilyl)ethynyl)phenyl)nonyl)oxy)ethyl hydrogen ((((R)-1-(6-amino-9H-purin-9-yl)propan-2-yl)oxy)methyl)phosphonate

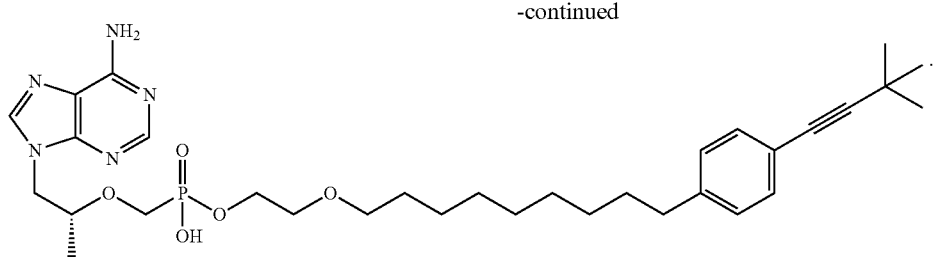

2-((9-(4-(3,3-dimethylbut-1-yn-1-yl)phenyl)nonyl)oxy)ethyl hydrogen ((((R)-1-(6-amino-9H-purin-9-yl)propan-2-yl)oxy)methyl)phosphonate Other exemplary compounds include, but are not limited to, the following compounds and pharmaceutically acceptable salts (such as ammonium salts) thereof:

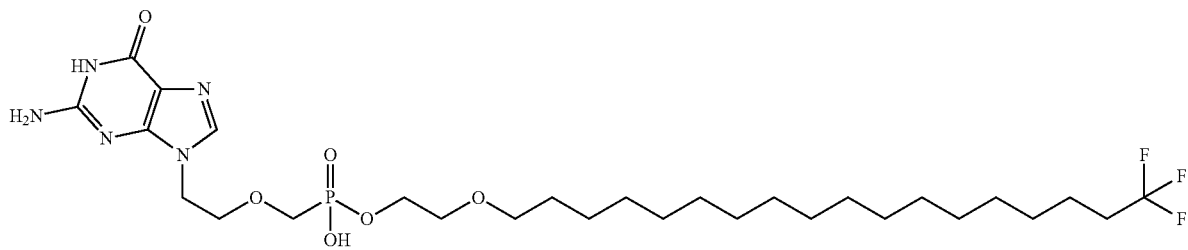

2-((18,18,18-trifluorooctadecyl)oxy)ethyl hydrogen ((2-(2-amino-6-oxo-1,6-dihydro-9H-purin-9-yl)ethoxy)methyl)phosphonate

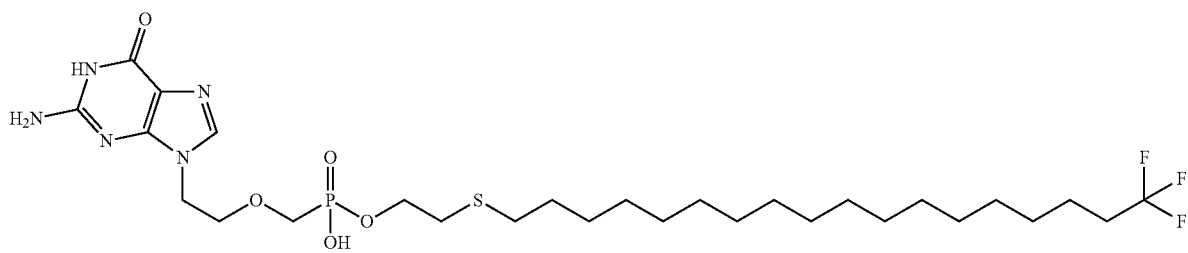

2-((18,18,18-trifluorooctadecyl)thio)ethyl hydrogen ((2-(2-amino-6-oxo-1,6-dihydro-9H-purin-9-yl)ethoxy)methyl)phosphonate

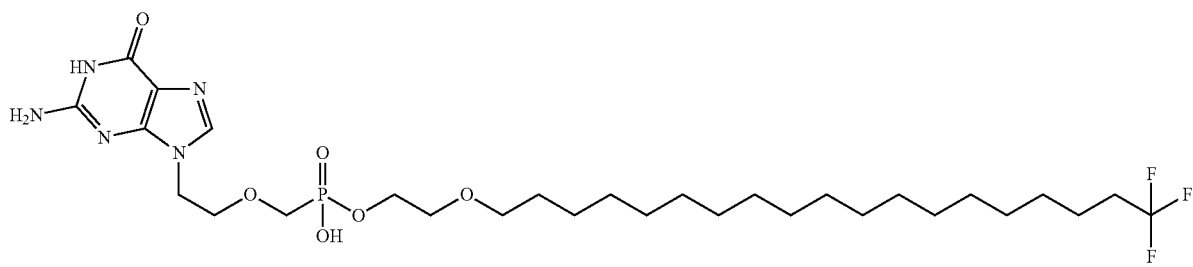

2-((19,19,19-trifluorononadecyl)oxy)ethyl hydrogen ((2-(2-amino-6-oxo-1,6-dihydro-9H-purin-9-yl)ethoxy)methyl)phosphonate

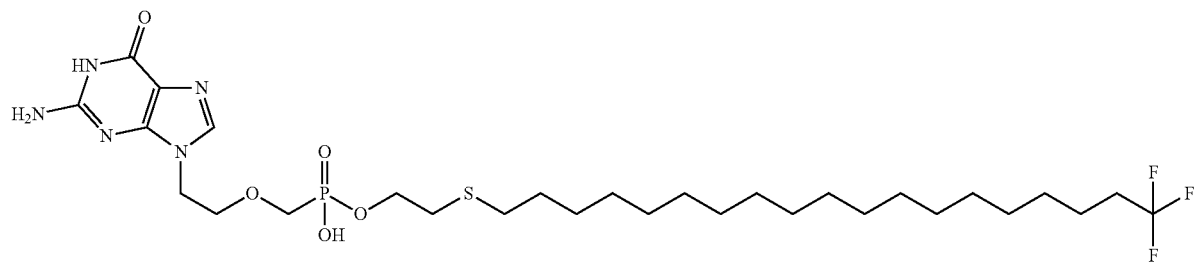

2-((19,19,19-trifluorononadecyl)thio)ethyl hydrogen ((2-(2-amino-6-oxo-1,6-dihydro-9H-purin-9-yl)ethoxy)methyl)phosphonate

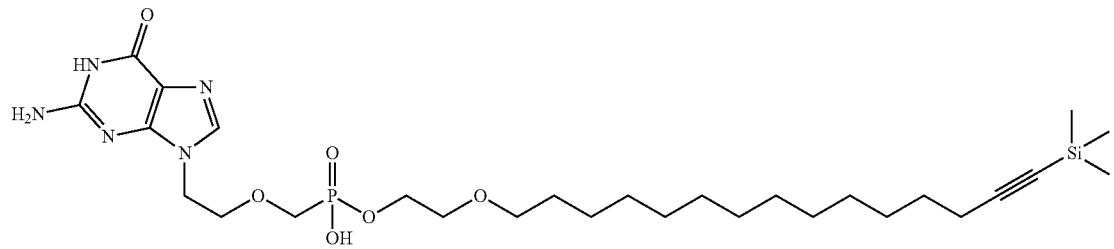

2-((15-(trimethylsilyl)pentadec-14-yn-1-yl)oxy)ethyl hydrogen ((2-(2-amino-6-oxo-1,6-dihydro-9H-purin-9-yl)ethoxy)methyl)phosphonate

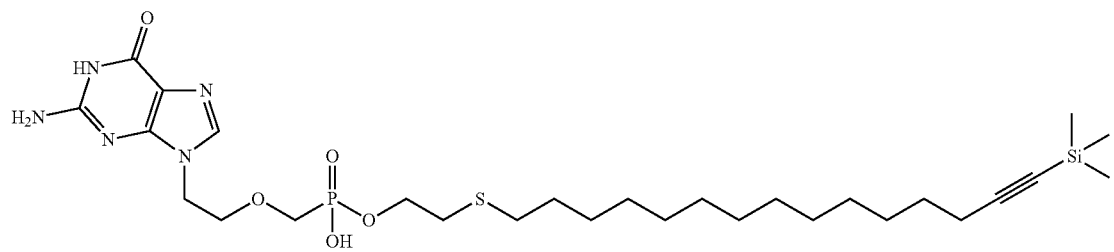

2-((15-(trimethylsilyl)pentadec-14-yn-1-yl)thio)ethyl hydrogen ((2-(2-amino-6-oxo-1,6-dihydro-9H-purin-9-yl)ethoxy)methyl)phosphonate

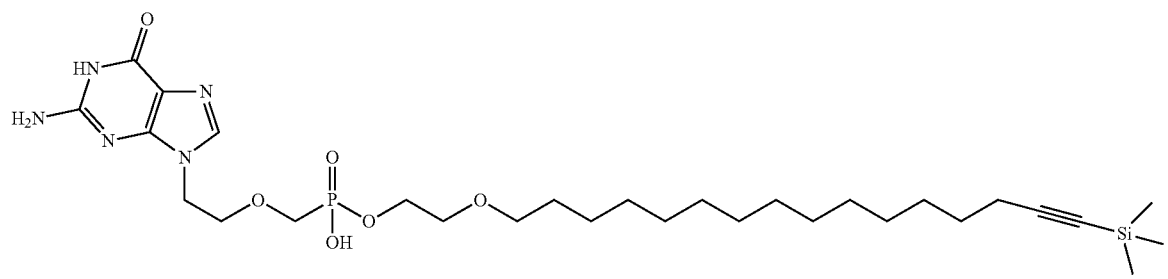

2-((16-(trimethylsilyl)hexadec-15-yn-1-yl)oxy)ethyl hydrogen ((2-(2-amino-6-oxo-1,6-dihydro-9H-purin-9-yl)ethoxy)methyl)phosphonate

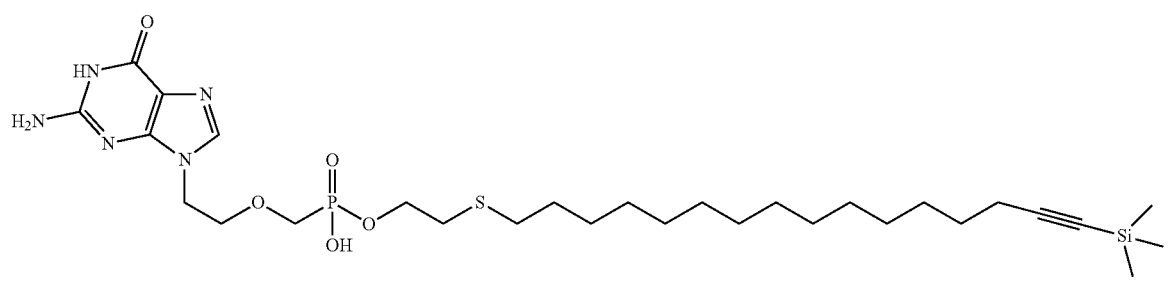

2-((16-(trimethylsilyl)hexadec-15-yn-1-yl)thio)ethyl hydrogen ((2-(2-amino-6-oxo-1,6-dihydro-9H-purin-9-yl)ethoxy)methyl)phosphonate -continued

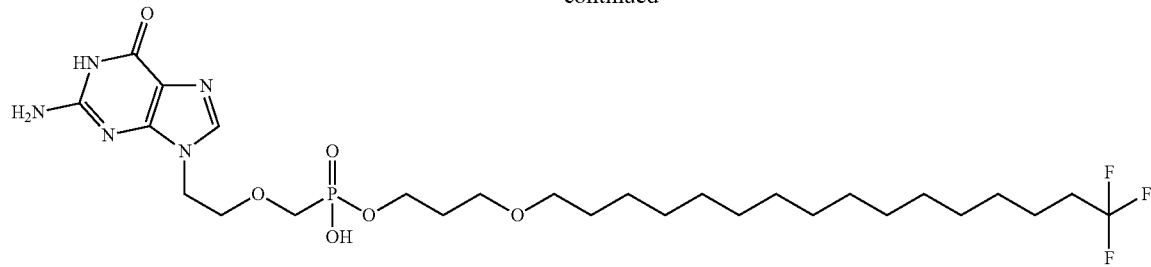

3-((16,16,16-trifluorohexadecyl)oxy)propyl hydrogen ((2-(2-amino-6-oxo-1,6-dihydro-9H-purin-9-yl)ethoxy)methyl)phosphonate

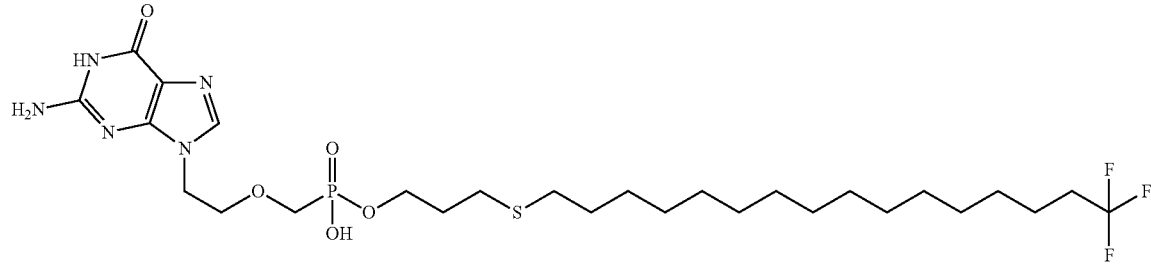

3-((16,16,16-trifluorohexadecyl)thio)propyl hydrogen ((2-(2-amino-6-oxo-1,6-dihydro-9H-purin-9-yl)ethoxy)methyl)phosphonate

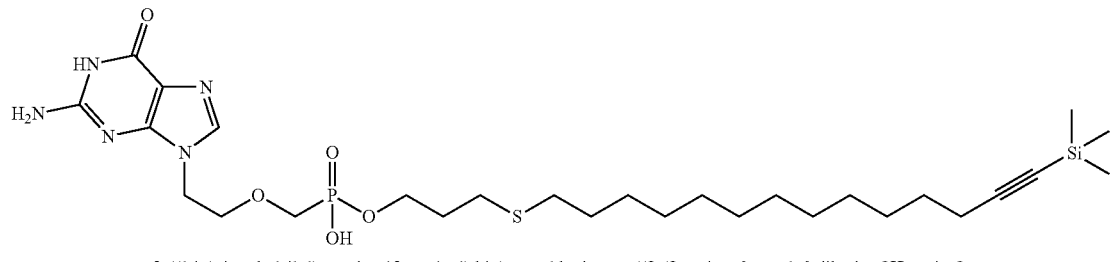

3-((14-(trimethylsilyl)tetradec-13-yn-1-yl)thio)propyl hydrogen ((2-(2-amino-6-oxo-1,6-dihydro-9H-purin-9-yl)ethoxy)methyl)phosphonate

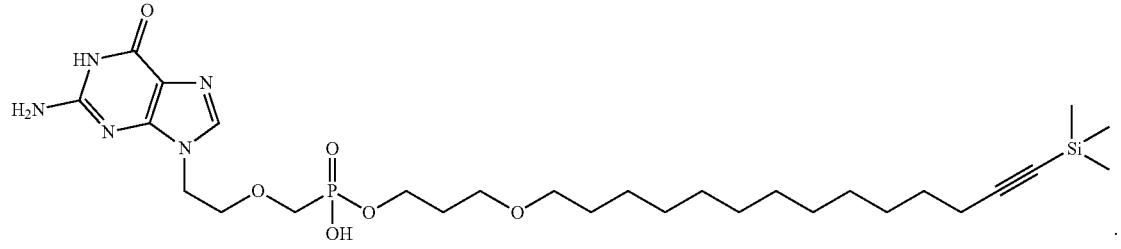

3-((14-(trimethylsilyl)tetradec-13-yn-1-yl)oxy)propyl hydrogen ((2-(2-amino-6-oxo-1,6-dihydro-9H-purin-9-yl)ethoxy)methyl)phosphonate In some embodiments, the compounds have the following features:

L is

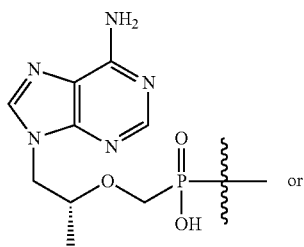 or

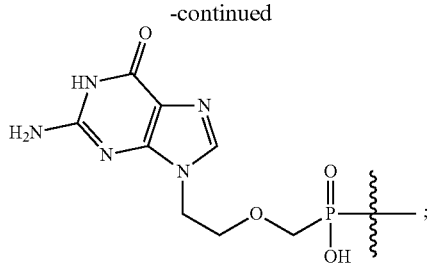;

W is a saturated, linear $C_1$-$C_9$ alkyl chain (i.e., linear $C_1$-$C_9$ alkylene);

X is —CF$_2$—, —O—, or —S—;
Y is a saturated, linear C$_2$-C$_{20}$ alkyl chain (i.e., linear C$_2$-C$_{20}$ alkylene); and
Z is hydrogen, methyl, or ethyl.

In some embodiments, the compounds have the following features:

L is

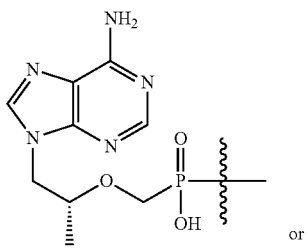

or

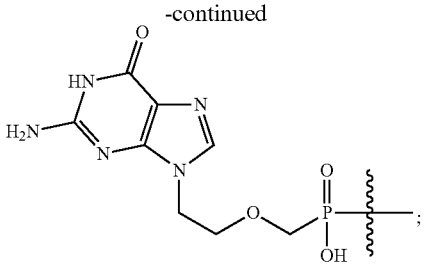

;

W is a saturated, linear C$_1$-C$_9$ alkyl chain (i.e., linear C$_1$-C$_9$ alkylene);
X is —CF$_2$— or —S—;
Y is a saturated, linear C$_2$-C$_{20}$ alkyl chain (i.e., linear C$_2$-C$_{20}$ alkylene); and
Z is hydrogen, methyl, or ethyl.

Exemplary compounds include, but are not limited to, the following compounds and pharmaceutically acceptable salts (such as ammonium salts) thereof:

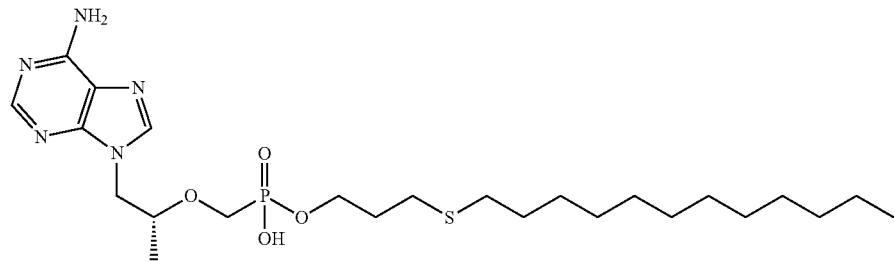

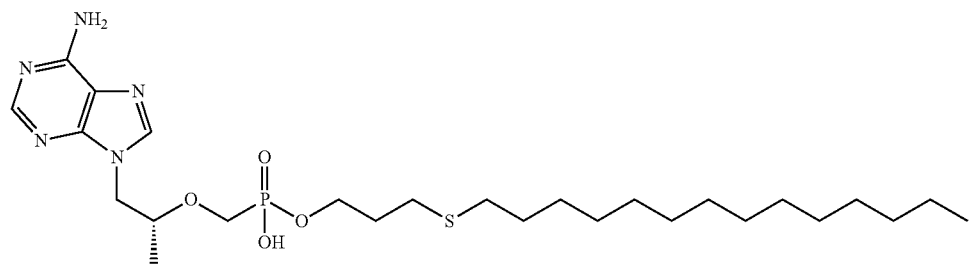

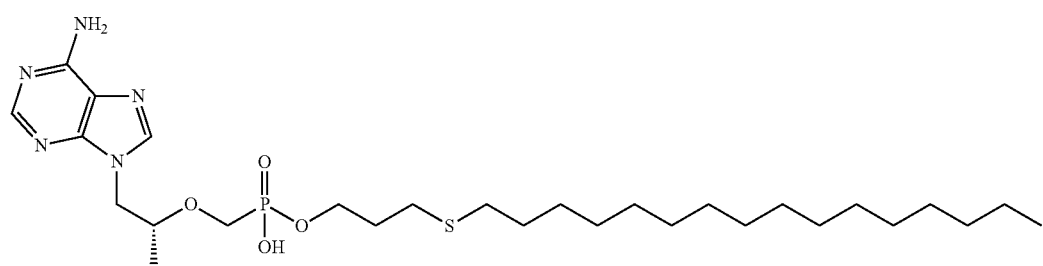

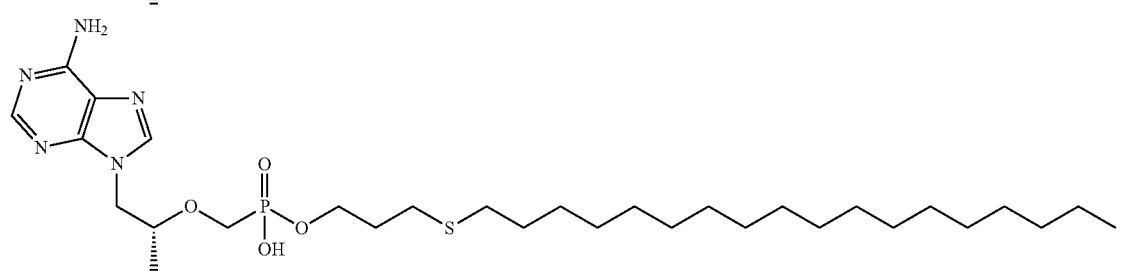

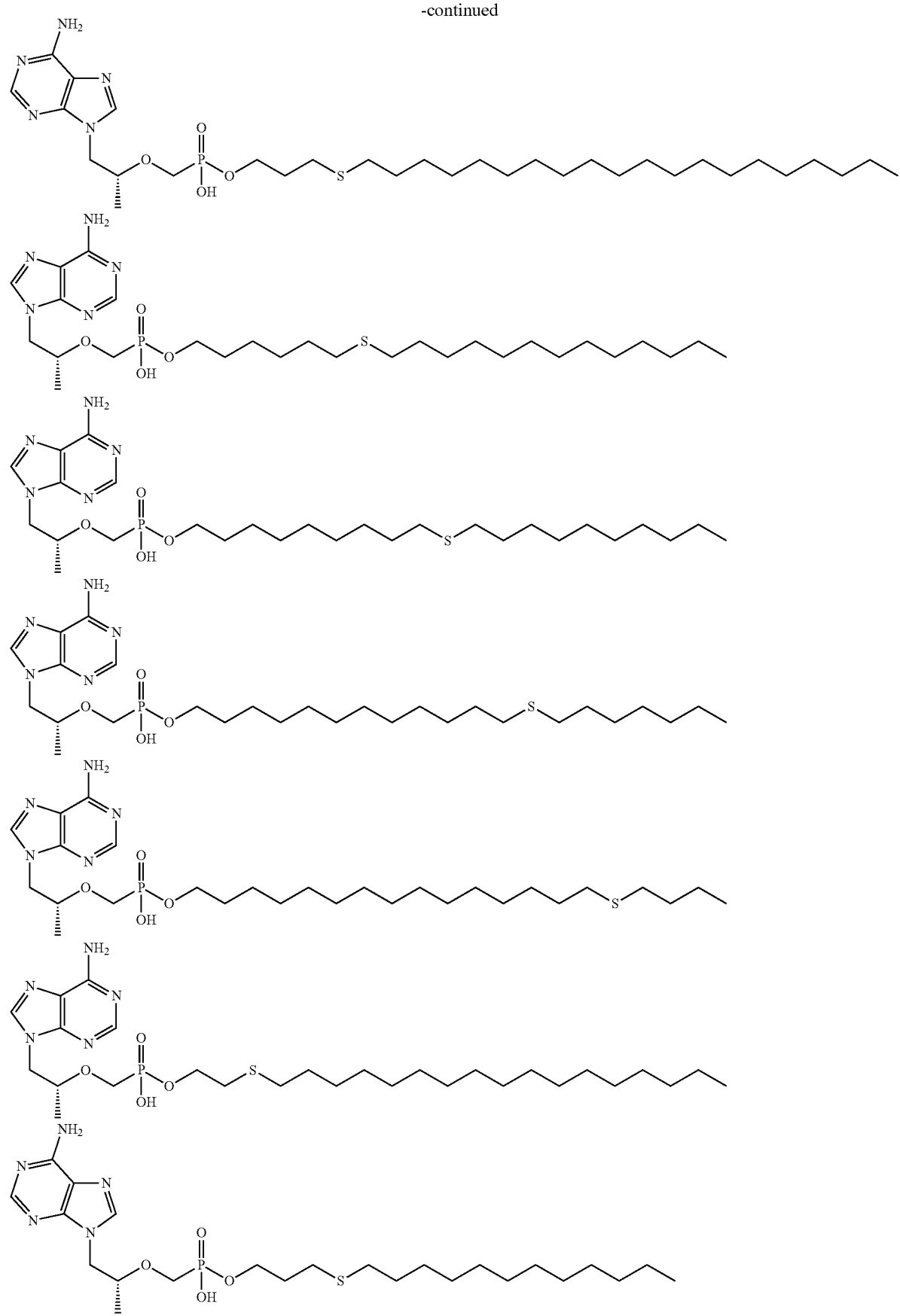

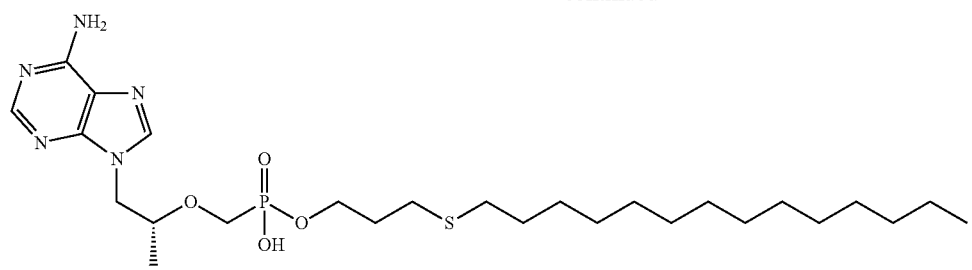
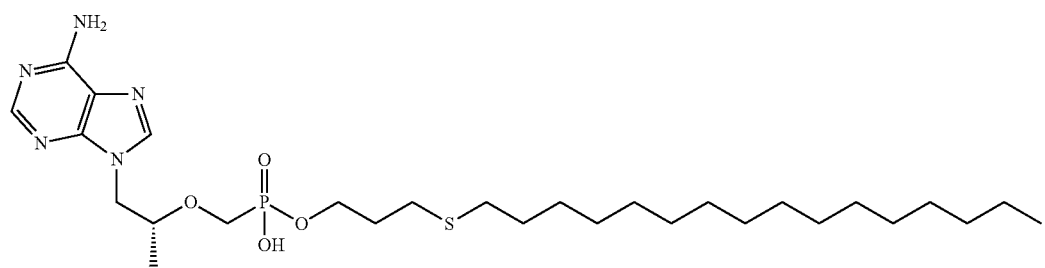
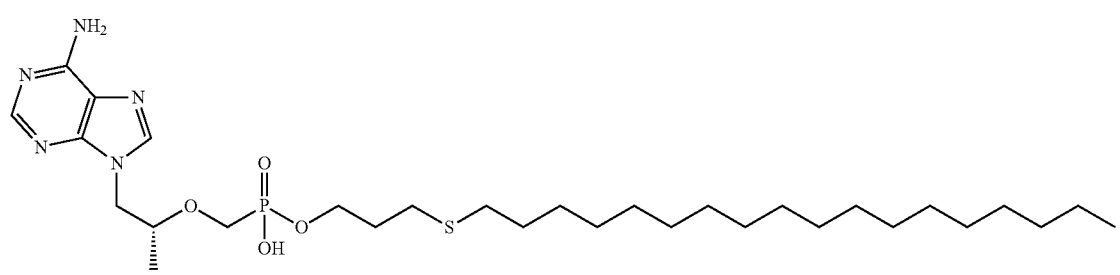
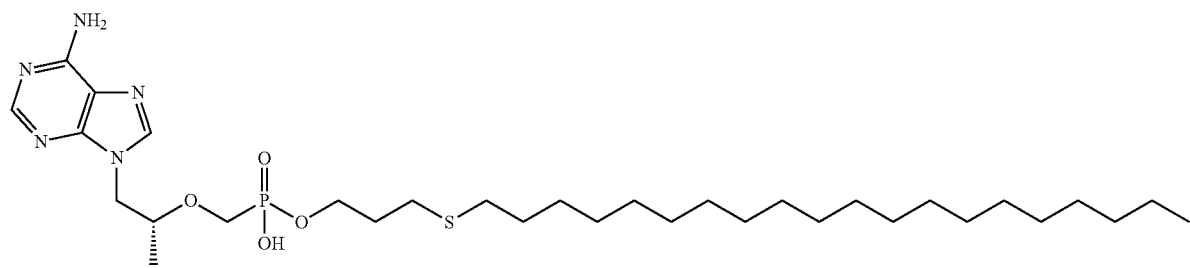
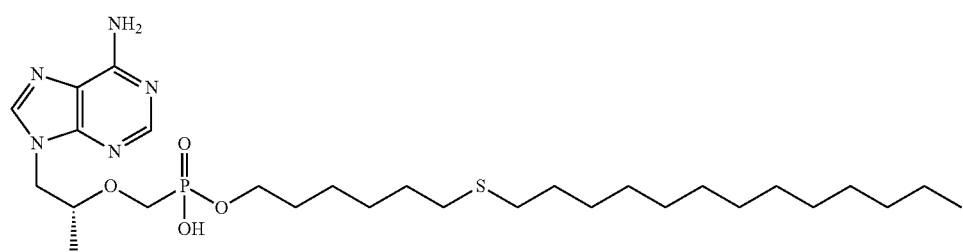
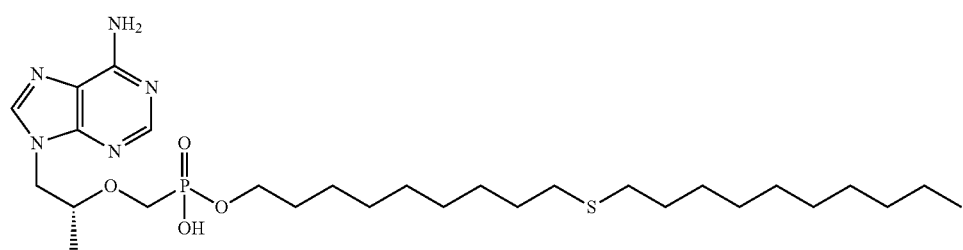

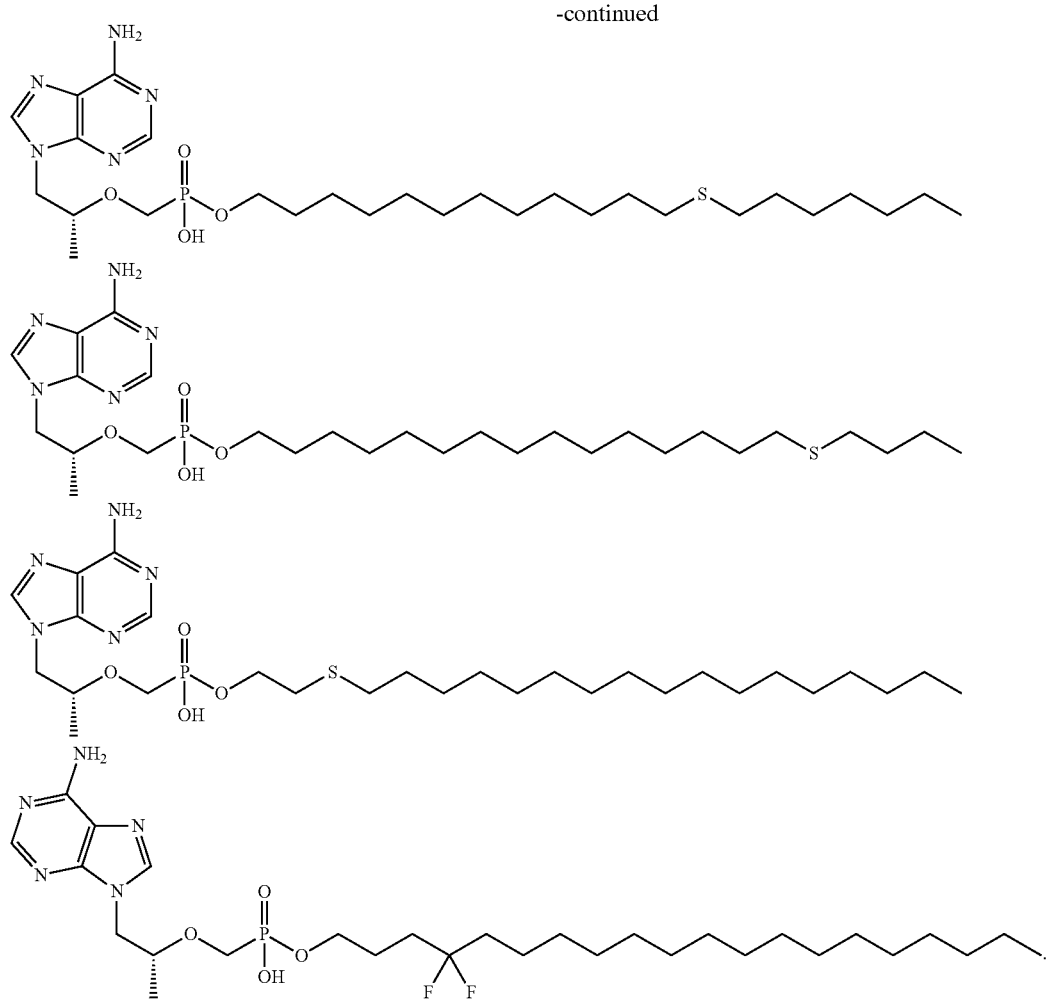

2. L—O—Y—Z

In some embodiments, both W and X are absent, i.e., L-O—Y—Z.

In some embodiments, the compounds have the following features:

L is

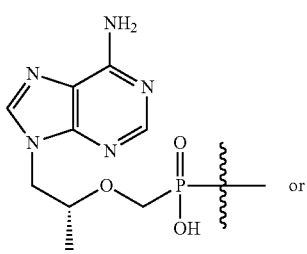 or

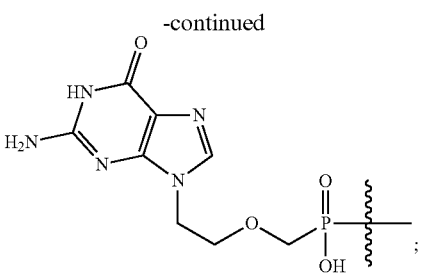;

Y is a saturated, linear $C_8$-$C_{20}$ alkyl chain (i.e., linear $C_8$-$C_{20}$ alkylene); and Z is selected from substituted methyl or ethyl, optionally substituted unsaturated $C_2$-$C_3$ alkyl, optionally substituted carbocyclyl, optionally substituted heterocyclyl, optionally substituted aryl, optionally substituted heteroaryl, Si-substituted silyl, S-substituted thiol, O-substituted hydroxyl, ester, and —$SF_5$.

In some embodiments, the compounds have the following features:
L is
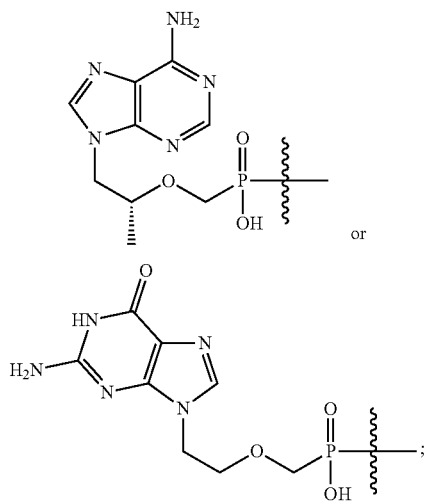
or
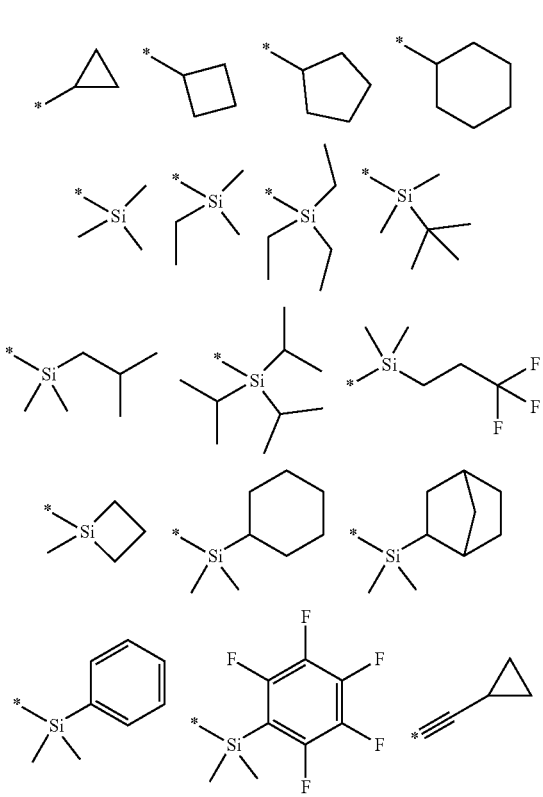
Y is a saturated, linear $C_8$-$C_{20}$ alkyl chain (i.e., linear $C_8$-$C_{20}$ alkylene); and
Z is selected from —$CD_3$, —$CF_3$, —$CD_2CD_3$, —$CF_2CF_3$, —S-Ph, —O-Ph, —C≡CH, —C≡CCD$_3$, —$CH_2FC$≡C, —$CHF_2C$≡C, —C≡CSi($CH_3$)$_3$, —C≡CC($CH_3$)$_3$, —C≡CCF$_3$, —C≡CSF$_5$, —Si($CH_3$)$_3$, —C($CH_3$)$_3$, —C(O)OCH$_3$, —SF$_5$, as well as the following:
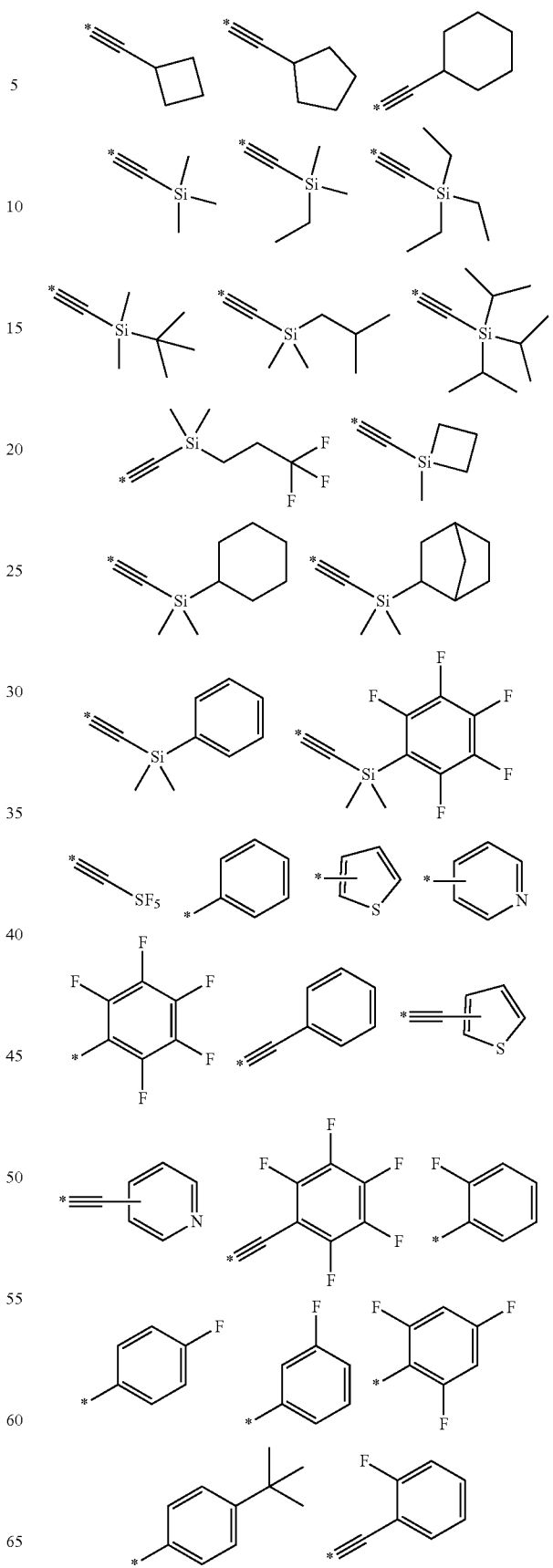

177
-continued
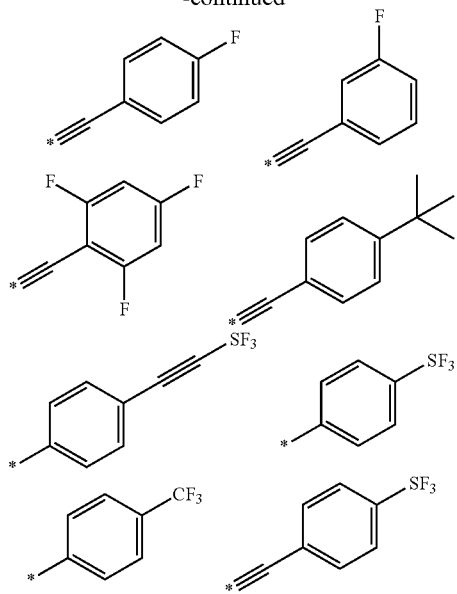
178
-continued
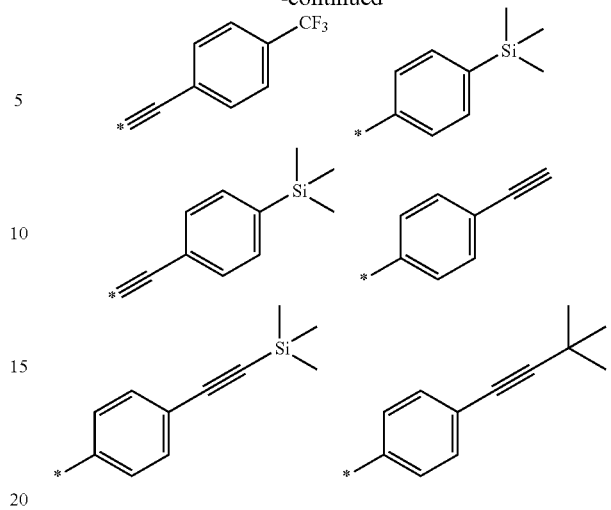
wherein * indicates the point of attachment to Y.
Exemplary compounds include, but are not limited to, the following compounds and pharmaceutically acceptable salts (such as ammonium salts) thereof:
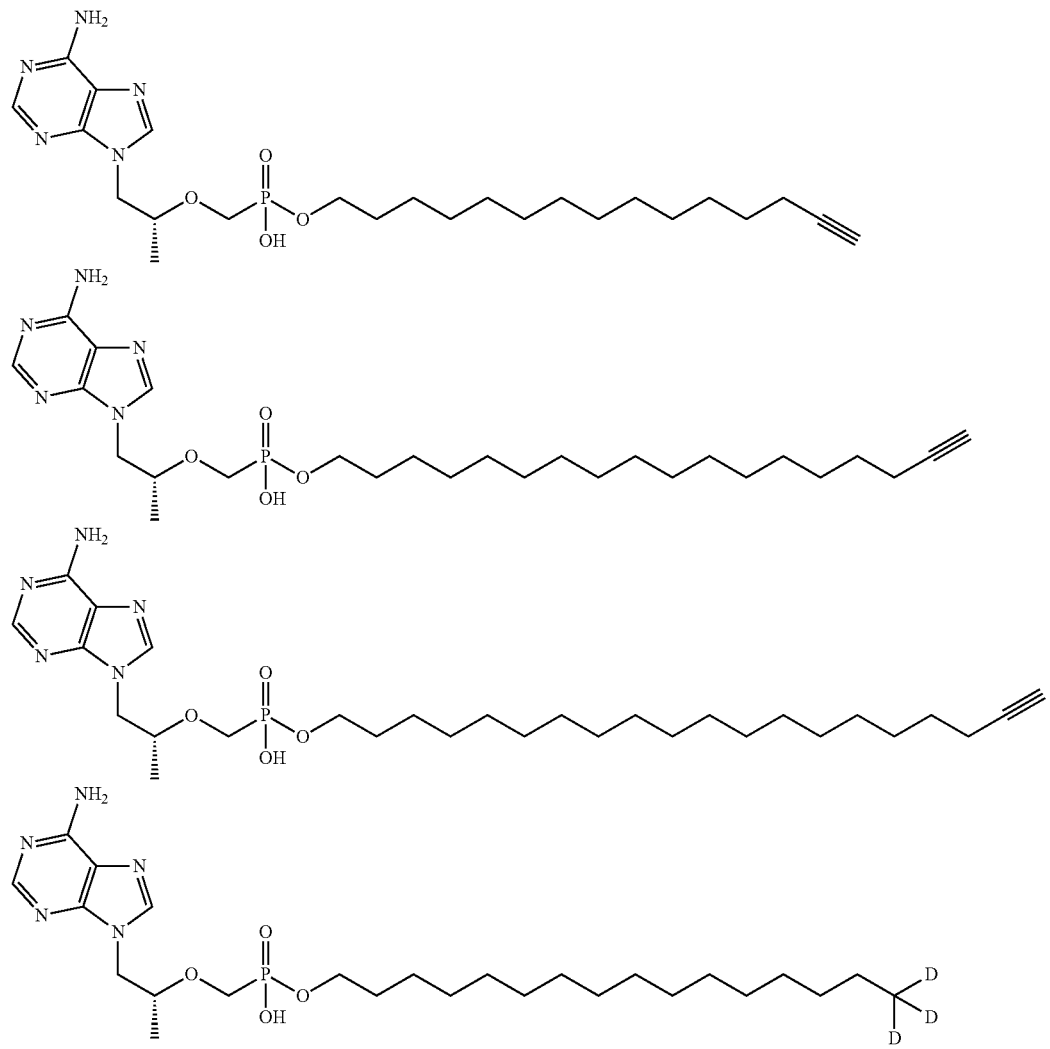

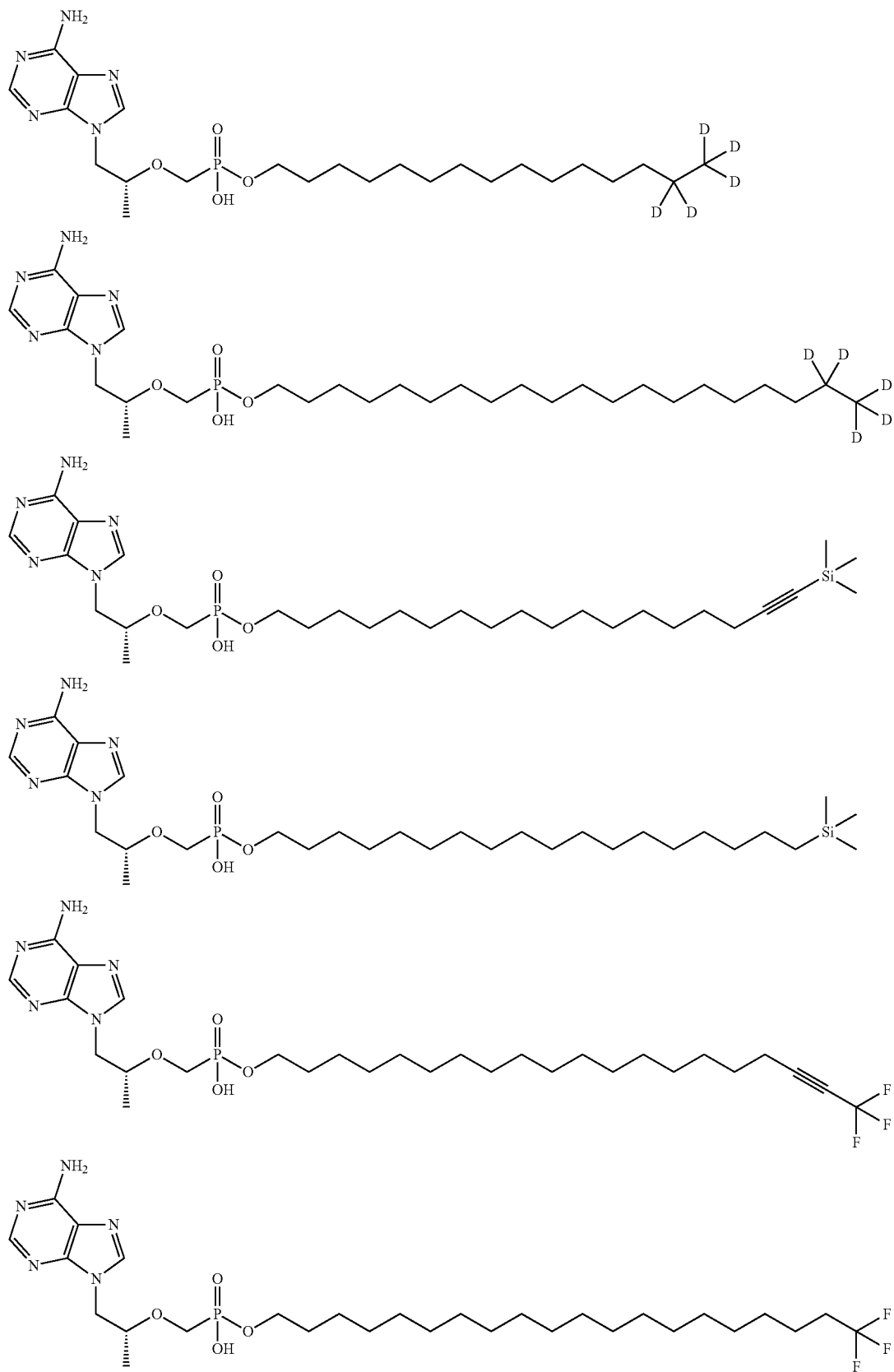

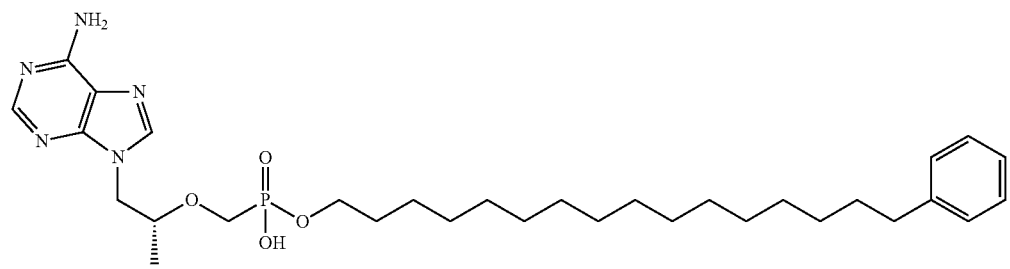
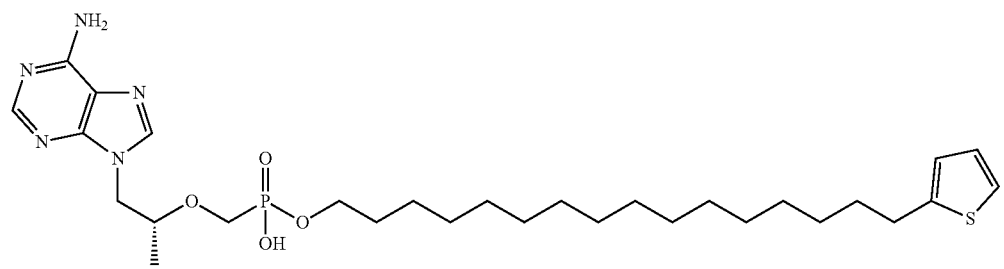
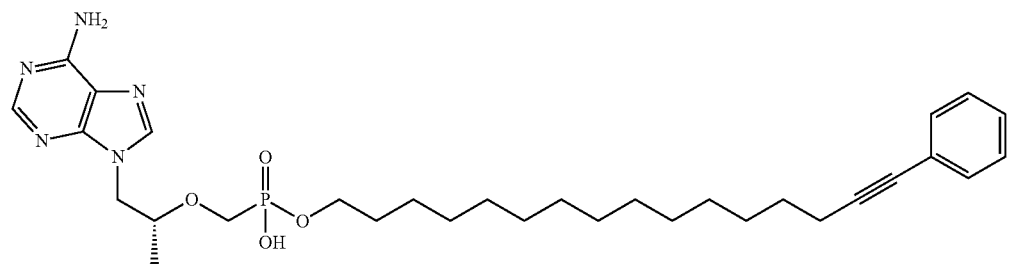
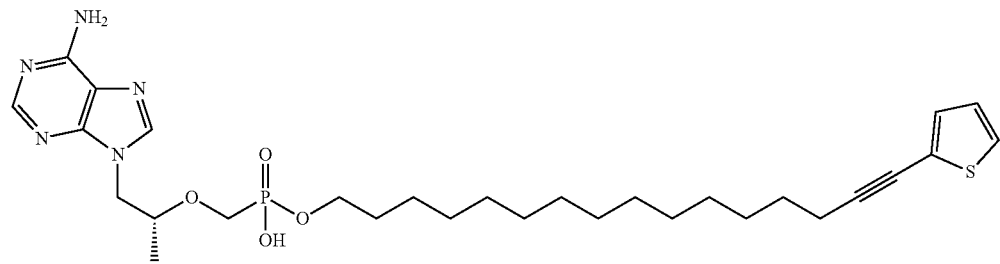
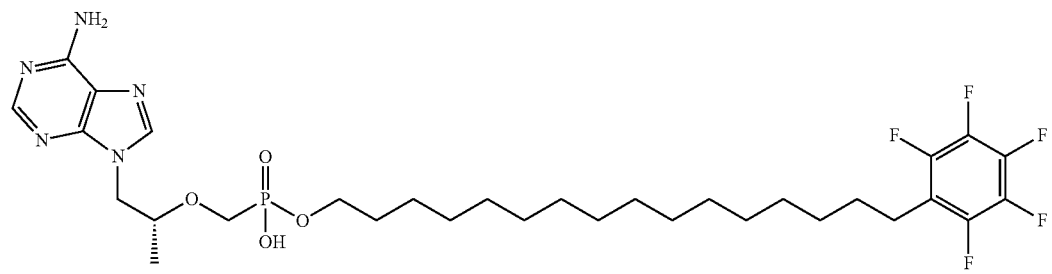
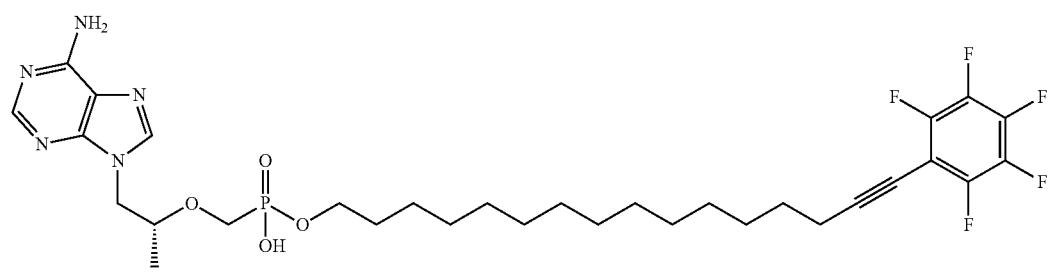

-continued
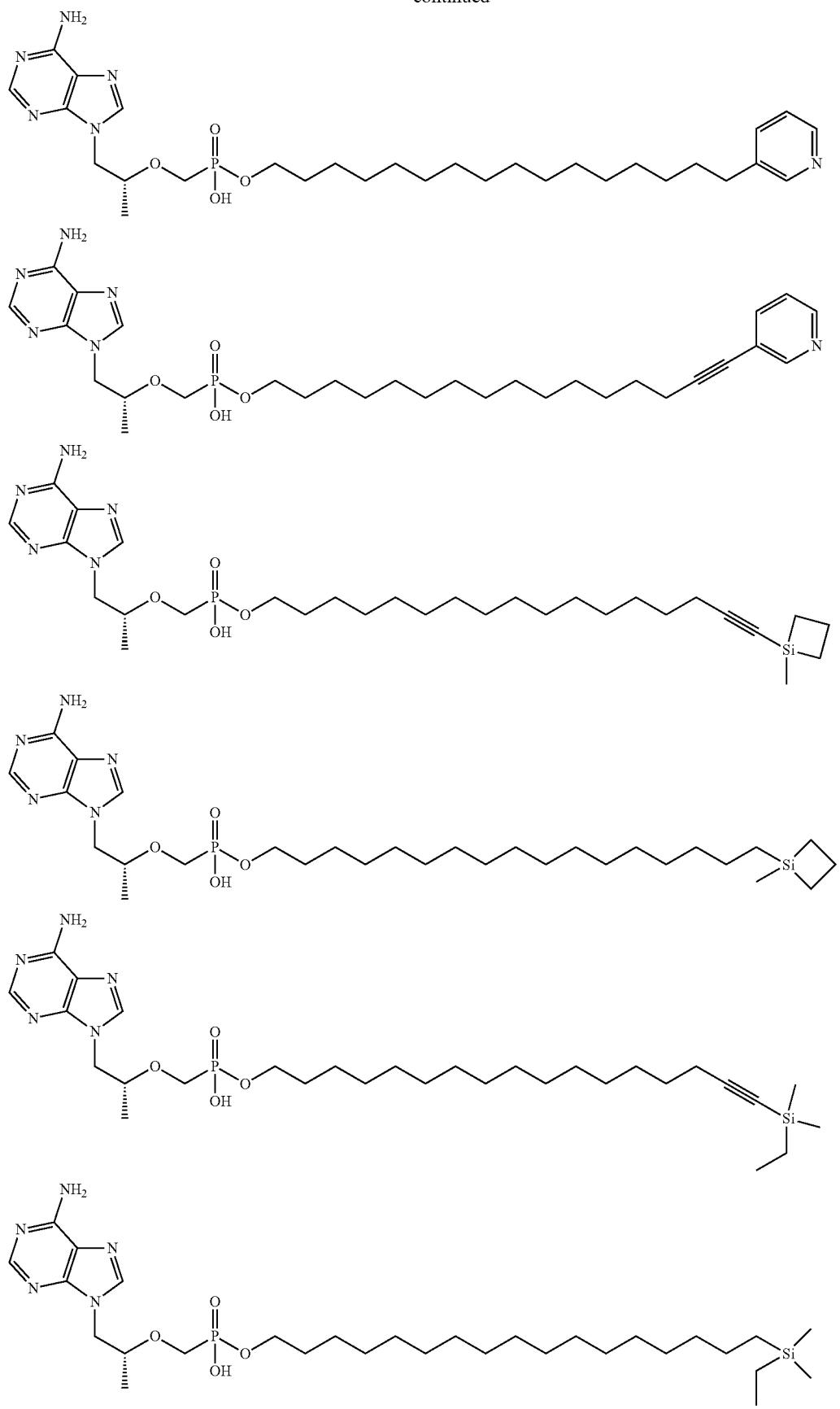

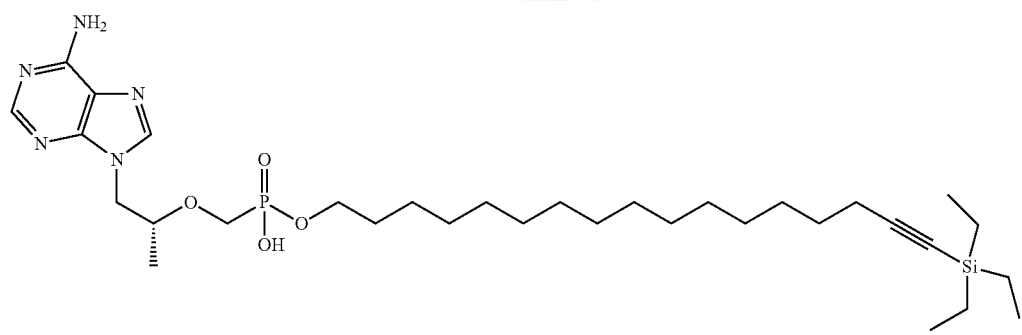
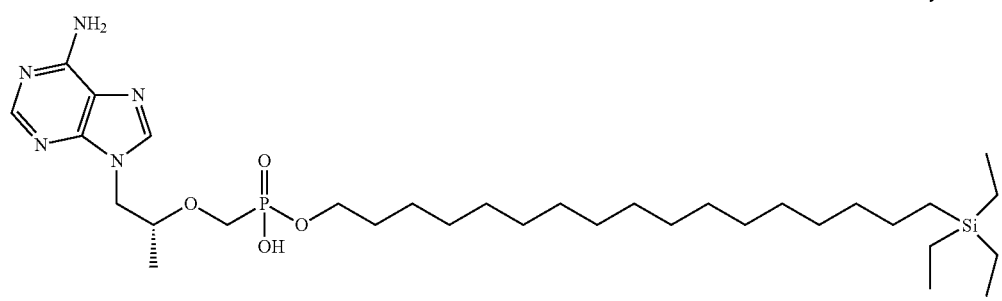
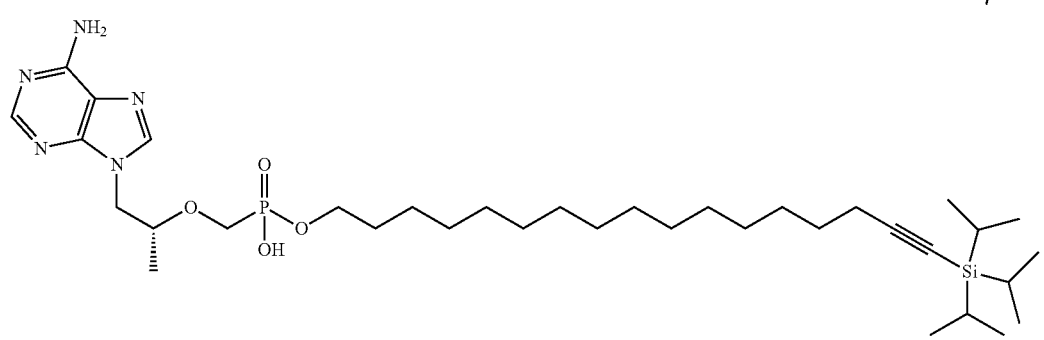
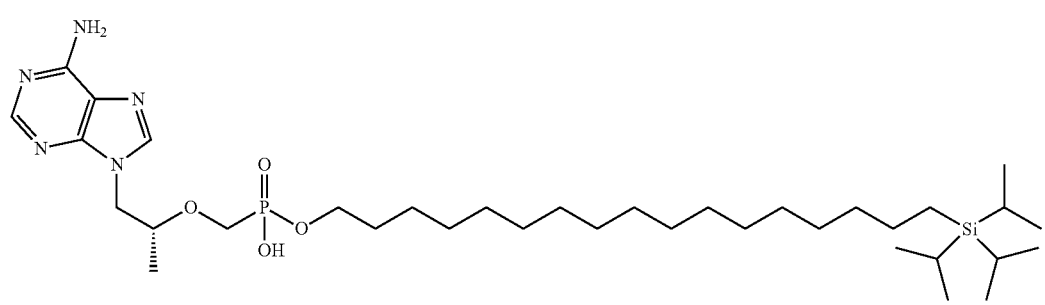
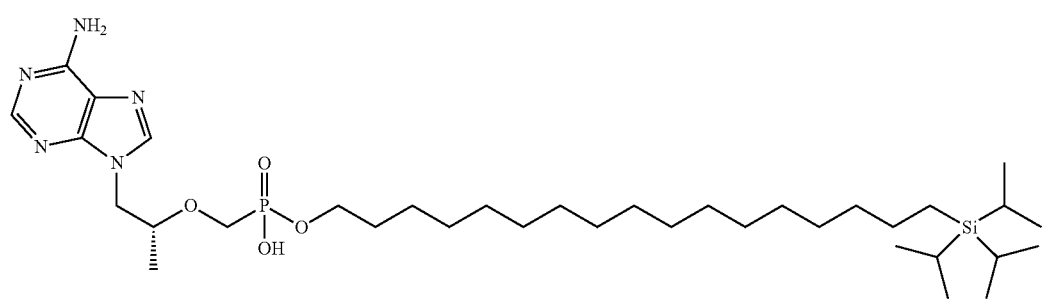

-continued
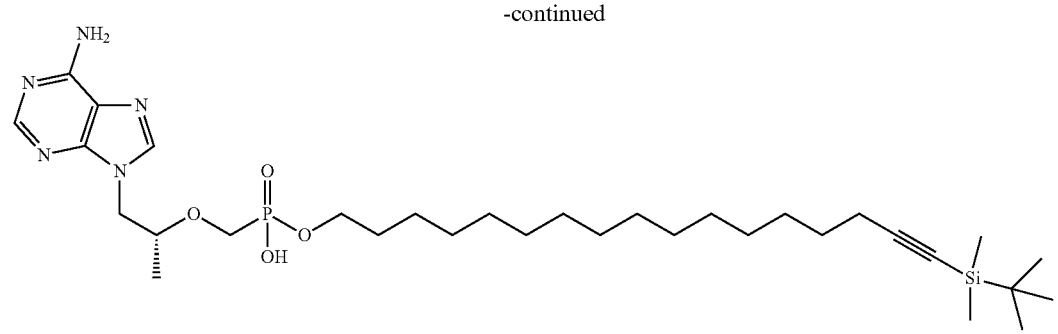
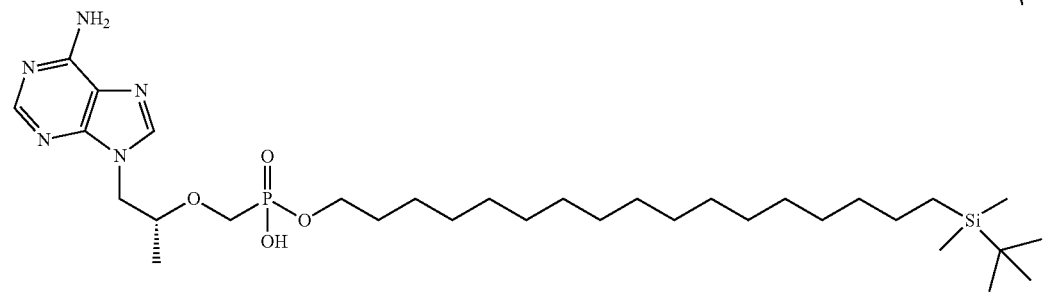
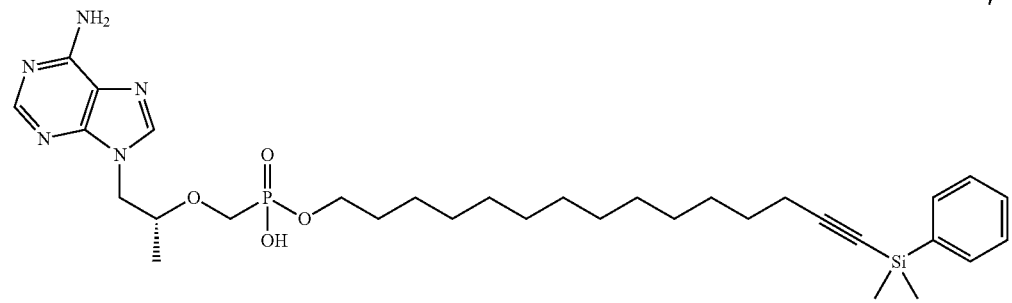
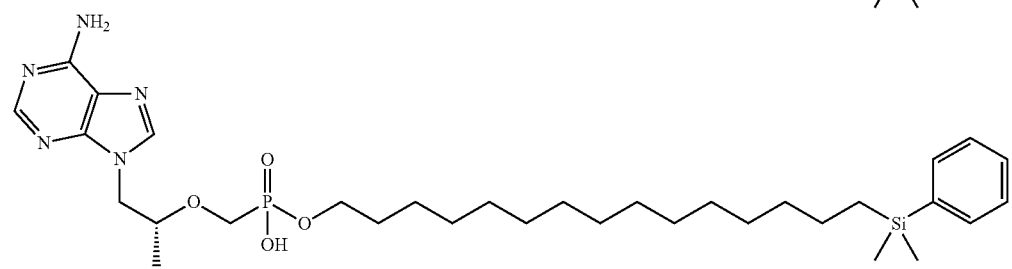
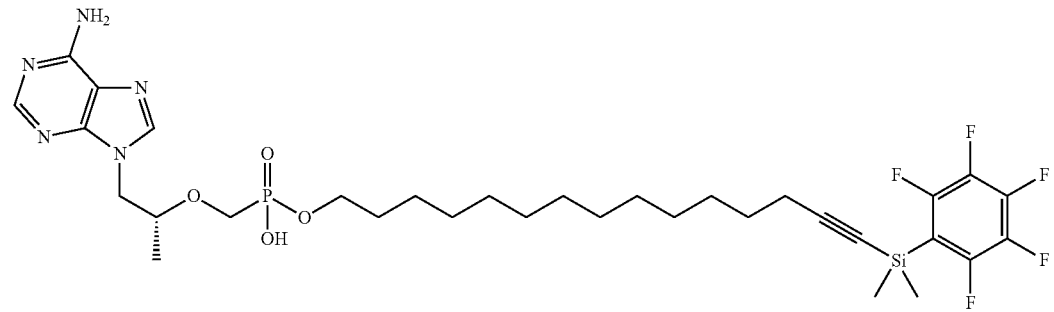
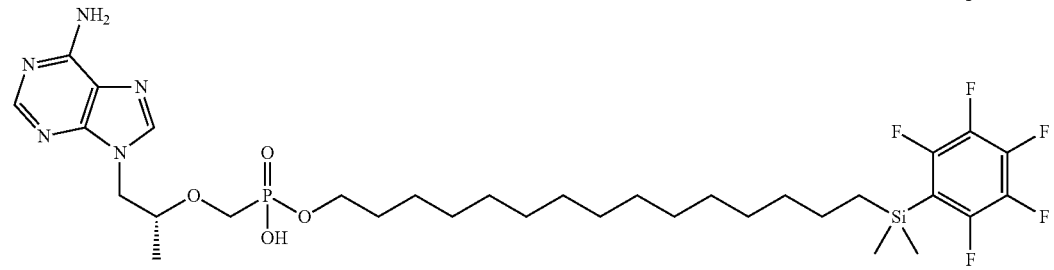

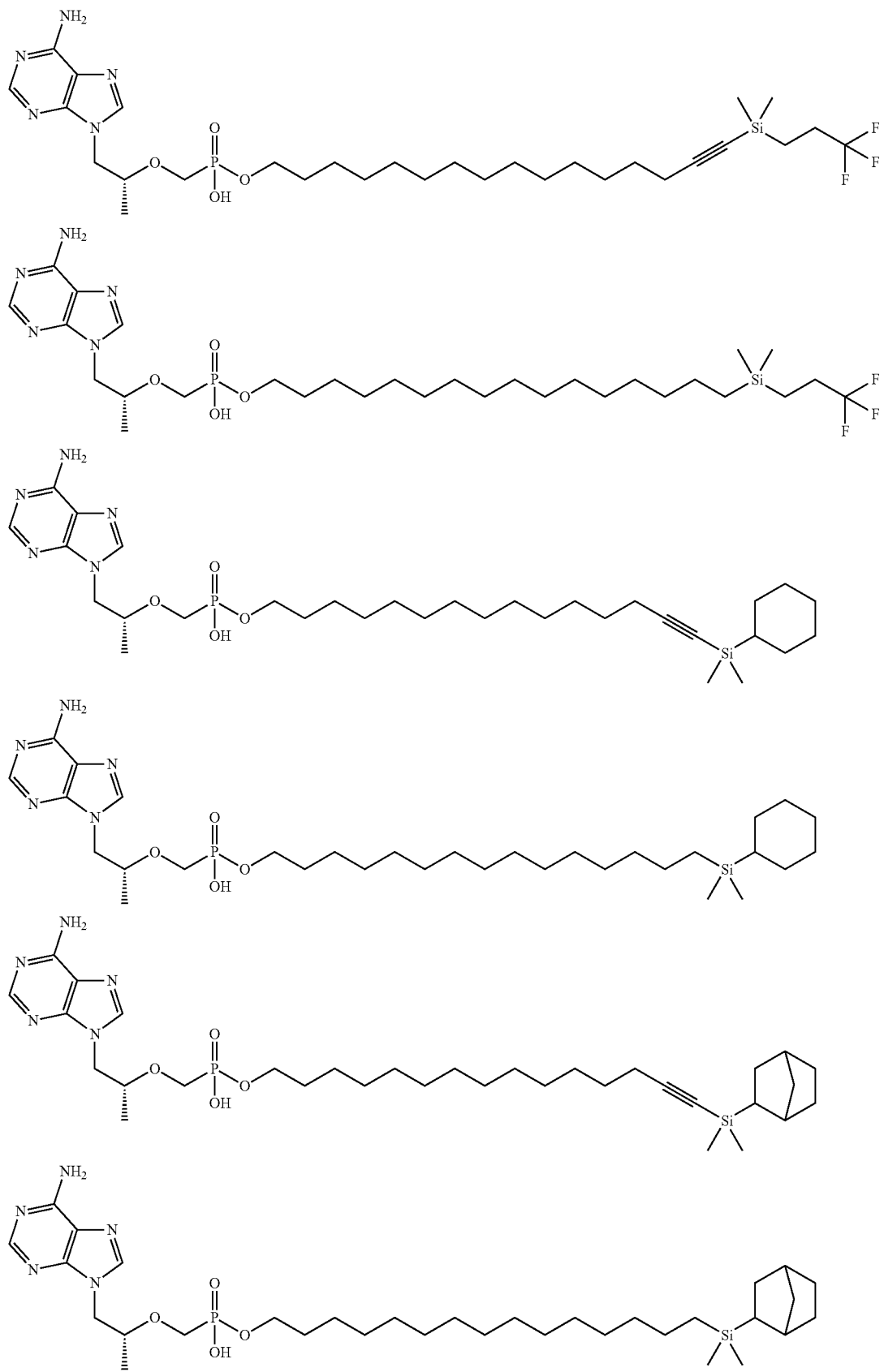

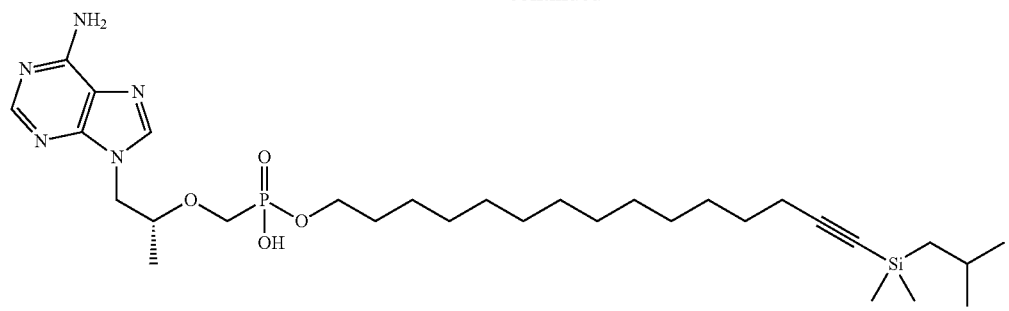
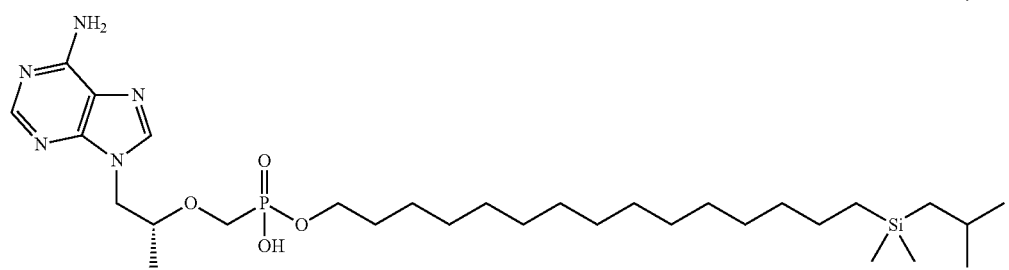
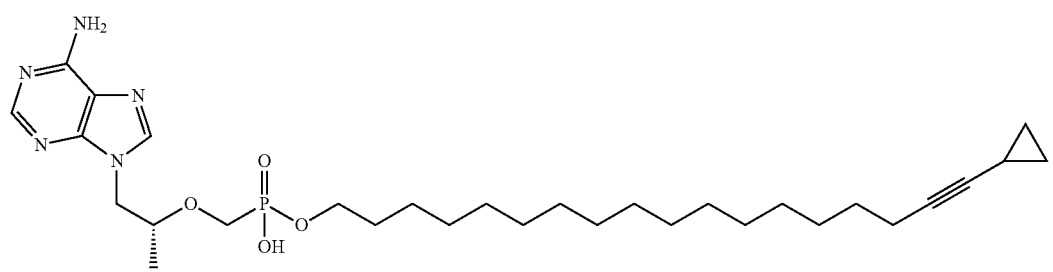
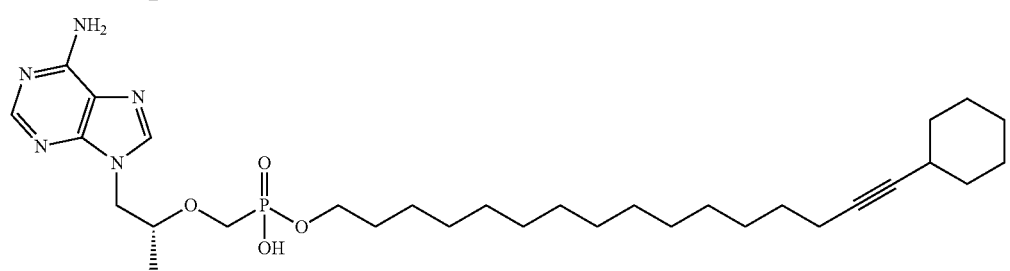
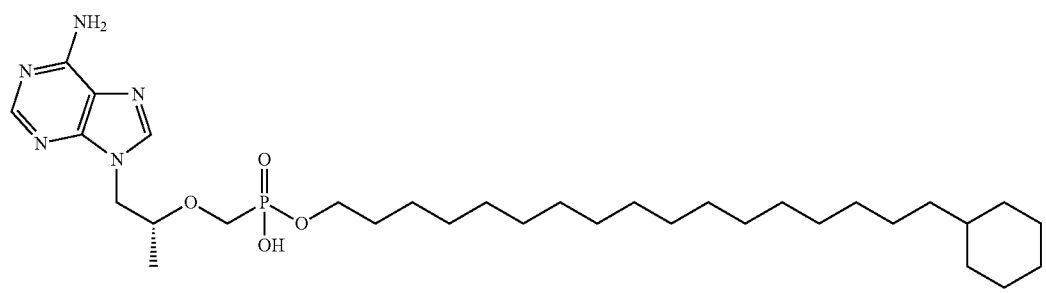
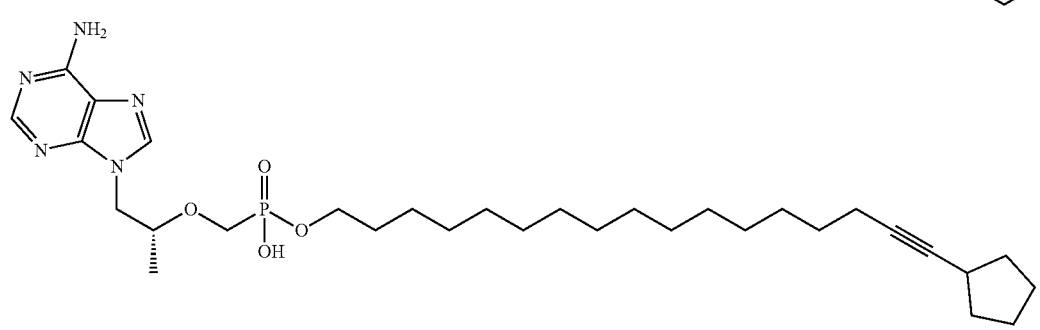

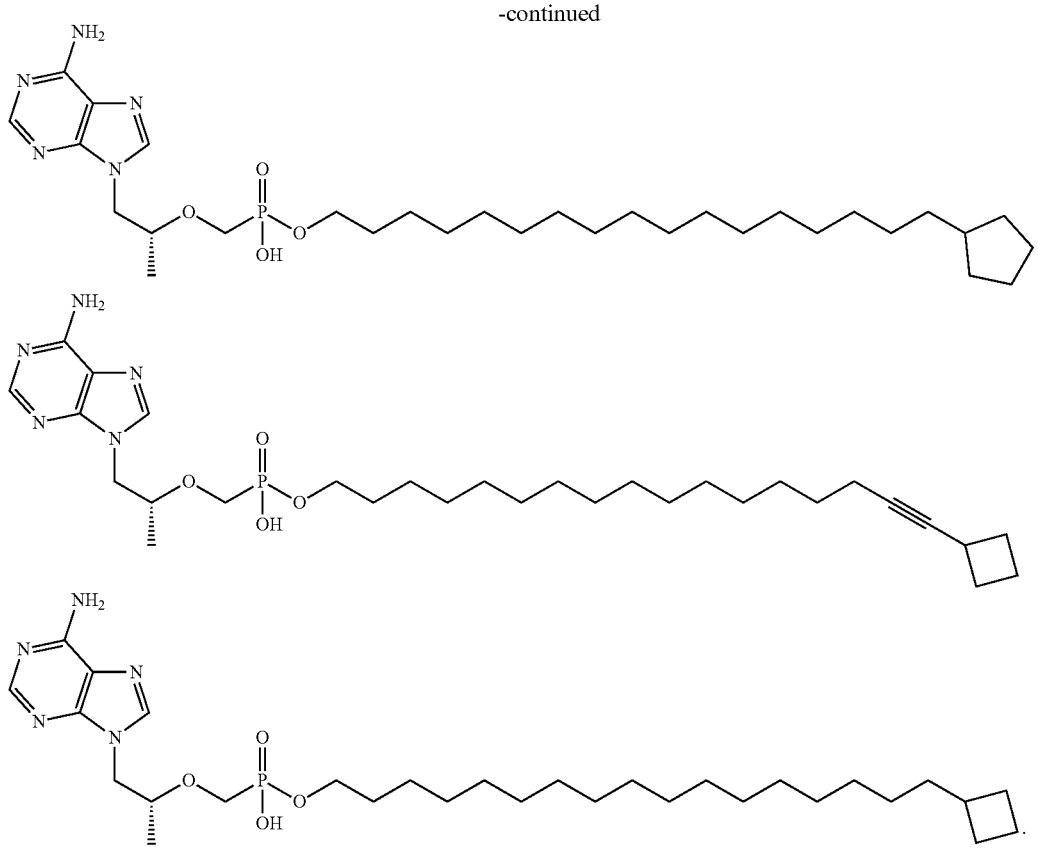

III. Additional Compounds

In accordance with an embodiment of the present disclosure there is provided a compound as shown in the formula below or salt thereof,

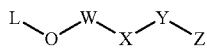

wherein
L is an acyclic nucleoside phosphonate or a linking group coupled to a nucleoside or nucleobase;
W is a saturated $C_1$ to $C_9$ alkyl chain or is a direct bond between its adjacent atoms;
X is selected from a substituted methylene or ethylene group or a heteroatom or is a direct bond between its adjacent atoms;
Y is a saturated $C_9$ to $C_{20}$ alkyl chain; and
Z is selected from an optionally substituted methyl or ethyl group, an optionally substituted unsaturated $C_2$ to $C_3$ alkyl or an optionally substituted heteroatom or is absent; and
the optional substituents may be selected from alkyl, deuterium, halogen, nitro, cyano, hydroxy, trifluoromethoxy, trifluoromethyl, trimethylsilyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, benzyl, benzoyl, carbocyclyl, aryl, and heterocyclyl.

Further features provide for
L to be an acyclic nucleoside phosphonate, such as tenofovir, cidofovir, adefovir, (9-[2-(phosphonomethoxy)ethyl] guanine), 9-(3-hydroxy-2-phosphonylmethoxypropyl)adenine or 9-(2-phosphonylmethoxyethyl)-2,6-diaminopurine;
W to be a saturated $C_2$, $C_3$ or $C_9$ alkyl chain;
X to be selected from the group comprising $CF_2$, O, S;
Y to be a $C_{13}$ to $C_{19}$ alkyl chain; and
Z to be selected from the group comprising

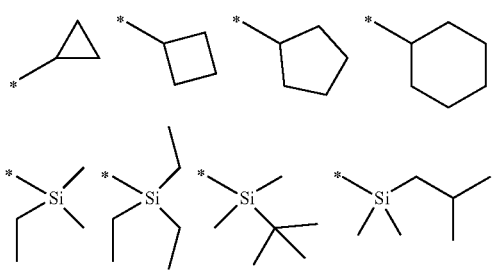

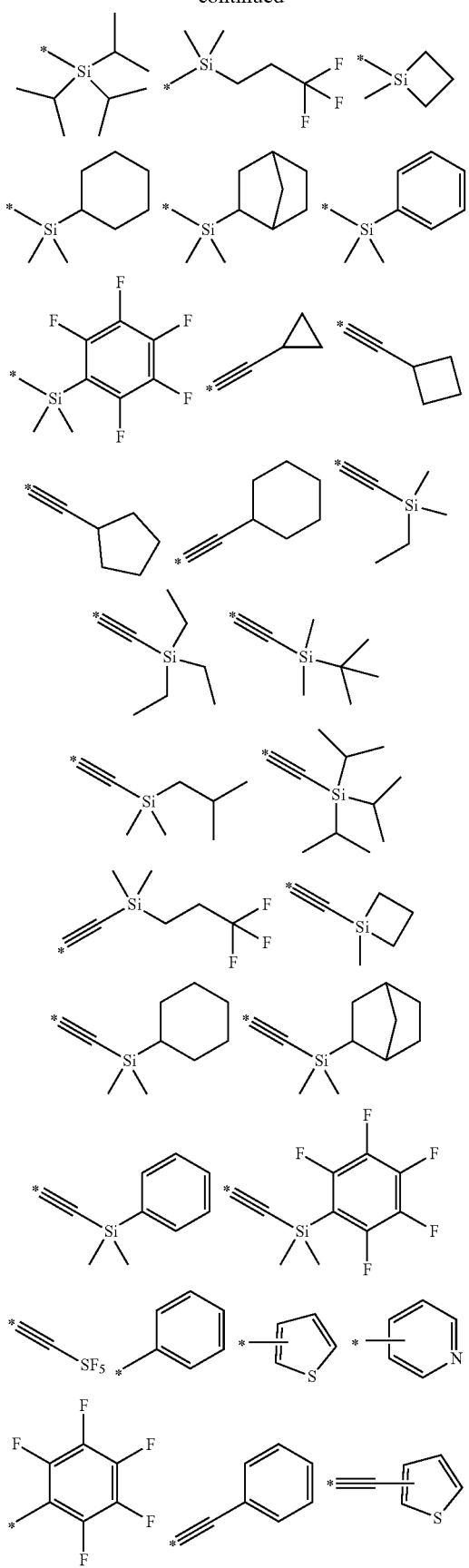

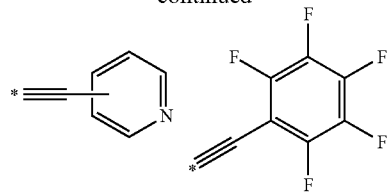

CD$_3$, CF$_3$, CD$_2$CD$_3$, SPh, C≡CH, C≡CCD$_3$, CF$_2$HC≡C, Si(CH$_3$)$_3$, C≡CSi(CH$_3$)$_3$, C≡CCF$_3$, C(O)OCH$_3$, C≡CSF$_5$ and SF$_5$, wherein * indicates the point of attachment to Y.

In accordance with another embodiment of the present disclosure there is provided a compound of the following formula or salt thereof,

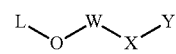

wherein
L is an acyclic nucleoside phosphonate or a linking group coupled to a nucleoside or nucleobase;
W is a C$_1$ to C$_9$ alkyl chain or is a direct bond between its adjacent atoms;
X is selected from a substituted methylene or ethylene group and a heteroatom or is a direct bond between its adjacent atoms;
Y is a C$_9$ to C$_{20}$ alkyl chain; and
the optional substituents may be selected from deuterium, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, benzyl, benzoyl, carbocyclyl, aryl, and heterocyclyl.

In accordance with yet another embodiment of the present disclosure there is provided a compound of the following formula or salt thereof,

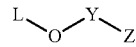

wherein
L is an acyclic nucleoside phosphonate or a linking group coupled to a nucleoside or nucleobase;
Y is a C$_9$ to C$_{20}$ alkyl chain; and
Z is selected from a substituted methyl or ethyl group, an optionally substituted, unsaturated C$_2$ to C$_3$ alkyl and an optionally substituted heteroatom or is absent; and
the optional substituents may be selected from deuterium, halogen, nitro, cyano, trifluoromethoxy, trifluoroethyl, amino, carbamoyl, mercapto, sulfamoyl, methyl, ethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylsulfinyl, ethylsulfinyl, mesyl, ethylsulfonyl, N-methylsulfamoyl, N-ethylsulfamoyl, N,N-dimethylsulfamoyl, N,N-diethylsulfamoyl, N-methyl-N-ethylsulfamoyl, benzyl, benzoyl, carbocyclyl, aryl, and heterocyclyl.

In certain embodiments, the disclosure contemplates derivatives of compounds disclosed herein such as those containing one or more, the same or different, substituents.

IV. Pharmaceutical Formulations

There are provided pharmaceutical formulations containing a compound disclosed herein. Generally, the pharmaceutical formulations also contain a pharmaceutically acceptable carrier. The pharmaceutical formulations can be in the form of tablet, capsule, pill, gel, granule, aerosol, solution (such as aqueous solution, e.g., saline or phosphate buffer saline), suspension, a nanoparticle formulation, emulsion, etc.

In some embodiments, the pharmaceutical formulations are oral formulations. In some embodiments, the pharmaceutical formulations are topical formulations.

Pharmaceutical formulations disclosed herein may be in the form of pharmaceutically acceptable salts, as generally described herein. When the compounds of the disclosure contain an acidic group as well as a basic group, the compounds of the disclosure may also form internal salts, and such compounds are within the scope of the disclosure. When a compound contains a hydrogen-donating heteroatom (e.g., NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the ammonium, aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference. In some embodiments, the pharmaceutically acceptable salts of the compounds are ammonium salts.

Pharmaceutical formulations for use in the present disclosure typically comprise an effective amount of a compound disclosed herein and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active agents, when necessary under aseptic conditions. Reference is again made to standard handbooks, such as the latest edition of Remington's Pharmaceutical Sciences.

Generally, for pharmaceutical use, the compounds may be formulated as a pharmaceutical preparation containing at least one compound disclosed herein and at least one pharmaceutically acceptable carrier, diluent or adjuvant, and optionally one or more further pharmaceutically active agents.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of at least one compound of the disclosure, e.g., about 10, 25, 50, 100, 200, 300 or 400 mg per unit dosage.

Depending upon the manner of introduction, the compounds described herein may be formulated in a variety of ways. Formulations containing one or more compounds can be prepared in various pharmaceutical forms, such as granules, tablets, capsules, suppositories, powders, controlled release formulations, solutions (such as aqueous solutions, e.g., saline, buffered saline, etc.), suspensions, emulsions, creams, gels, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

In certain embodiments, the pharmaceutical formulations comprise a compound disclosed herein and a propellant. In certain embodiments, an aerosolizing propellant is compressed air, ethanol, nitrogen, carbon dioxide, nitrous oxide, hydrofluoroalkanes (HFAs), 1,1,1,2-tetrafluoroethane, 1,1,1,2,3,3,3-heptafluoropropane or combinations thereof.

In certain embodiments, the disclosure contemplates a pressurized or unpressurized container comprising a compound herein. In certain embodiments, the container is a manual pump spray, inhaler, meter-dosed inhaler, dry powder inhaler, nebulizer, vibrating mesh nebulizer, jet nebulizer, or ultrasonic wave nebulizer.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include excipients, plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the compound to carrier and/or other substances may vary from about 0.5 to about 100 wt % (weight percent). For oral use, the pharmaceutical formulation will generally contain from about 5 to about 100% by weight of the active material. For other uses, the pharmaceutical formulation will generally have from about 0.5 to about 50 wt. % of the active material.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, MD, 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The formulation can provide pulsatile delivery of the one or more compounds. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosing profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., compound, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

The pharmaceutical formulations may also contain one or more further pharmaceutically active agents, such as described herein.

V. Methods of Using

In certain embodiments, the disclosure relates to methods of treating or preventing a viral infection or viral-associated cancer comprising administering an effective amount of a compound disclosed herein or a pharmaceutical formulation thereof to a subject in need thereof. In some embodiments, the subject is at risk of, exhibiting symptoms of, suffering from, or diagnosed with a viral infection or viral-associated cancer. In some embodiments, the compound or pharmaceutical formulation thereof is administered orally. For example, the compound or pharmaceutical formulation thereof can be administered orally to treat HIV infections. In some embodiments, the compound or pharmaceutical formulation thereof is administered topically. For example, the compound or pharmaceutical formulation thereof can be administered topically to treat HPV infections or HPV-associated cancers.

In some embodiments, the disclosed compounds and pharmaceutical formulations thereof are used to treat viral infections such as those caused by human immunodeficiency virus (HIV), hepatitis viruses, herpes viruses, flaviviruses, pox viruses, paramyxoviruses, influenzas, corona viruses, smallpox viruses, human papillomavirus (HPV), or filoviruses. In some embodiments, the disclosed compounds and pharmaceutical formulations thereof are used to treat HIV infections. In some embodiments, the disclosed compounds and pharmaceutical formulations thereof are used to treat hepatitis virus (such as HBV) infections. In some embodiments, the disclosed compounds and pharmaceutical formulations thereof are used to treat HPV infections. In some embodiments, the disclosed compounds and pharmaceutical formulations thereof are used to treat smallpox virus infections.

In some embodiments, the subject is at risk of, exhibiting symptoms of, or diagnosed with influenza A virus including subtype H1N1, influenza B virus, influenza C virus, rotavirus A, rotavirus B, rotavirus C, rotavirus D, rotavirus E, smallpox virus, SARS coronavirus, SARS-CoV-2, respiratory syncytial virus (RSV), human adenovirus types (HAdV-1 to 55), HPV Types 16, 18, 31, 33, 35, 39, 45, 51, 52, 56, 58, 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, Kaposi's sarcoma-associated herpesvirus (human herpes virus 8 or HHV-8), hepatitis A (HAV), hepatitis B (HBV), hepatitis C (HCV), hepatitis D (HDV), hepatitis E (HEV), HIV, human T-lymphotropic virus Type I (HTLV-1), Friend spleen focus-forming virus (SFFV), or xenotropic MuLV-related virus (XMRV).

In certain embodiments, the viral infection is an alphavirus, flavivirus, coronaviruses, orthomyxoviridae, paramyxoviridae, Powassan virus or filoviridae. In certain embodiments, the viral infection is selected from MERS coronavirus, Eastern equine encephalitis virus, Western equine encephalitis virus, Venezuelan equine encephalitis virus, Ross River virus, Powassan virus and Chikungunya virus.

In some embodiments, the disclosed compounds and pharmaceutical formulations thereof are used to treat viral-associated cancers such as HPV-associated cancers, HIV-associated cancers, EBV-associated cancers, HBV-associated cancers, HHV-8-associated cancers, HCV-associated cancers, and HTLV-1-related cancer. In some embodiments, the viral-associated cancers are HPV-associated cancers, including HPV-associated cervical cancers, vulvar cancers, vaginal cancers, penile cancers, anal cancers, mouth and throat cancers, and head and neck cancers. In some embodiments, the HPV-associated cancer is HPV-associated cervical cancer.

In some embodiments, methods disclosed herein are contemplated to be administered in combination with other the antiviral agent(s) such as abacavir, acyclovir, acyclovir, adefovir, amantadine, amprenavir, ampligen, arbidol, atazanavir, atripla, boceprevir, cidofovir, combivir, COMPLERA® (a combination of emtricitabine, rilpivirine, and tenofovir disoproxil fumarate), darunavir, delavirdine, didanosine, docosanol, dolutegravir, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, stavudine, STRIBILD® (a combination of elvitegravir, cobicistat, emtricitabine, and tenofovir disoproxil), tenofovir, tenofovir disoproxil, tenofovir alafenamide fumarate, tipranavir, trifluridine, trizivir, tromantadine, TRUVADA® (a combination of emtricitabine and tenofovir disoproxil fumarate), valaciclovir, valganciclovir, vicriviroc, vidarabine, viramidine, zalcitabine, zanamivir, or zidovudine, and combinations thereof.

In certain embodiments, the disclosure contemplates the treatment or prevention of a viral infection using the compounds disclosed herein and pharmaceutical formulations thereof, wherein viral infection is HIV, hepatitis B virus, HPV, or smallpox virus.

The compounds and pharmaceutical formulations thereof can be administered by a variety of routes including the oral, topical, ocular, rectal, transdermal, subcutaneous, intravenous, intramuscular or intranasal routes, depending mainly on the specific preparation used. In certain embodiments, the compounds and pharmaceutical formulations thereof are administered by inhalation through the lungs. In some embodiments, the compounds and pharmaceutical formulations thereof are administered orally. In some embodiments, the compounds and pharmaceutical formulations thereof are administered topically.

The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated.

The compound described herein can be administered adjunctively with other pharmaceutically active agents. These compounds include but are not limited to analgesics, anti-inflammatory drugs, antipyretics, antidepressants, anti-epileptics, antihistamines, antimigraine drugs, antimuscarinics, anxiolytics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. "Adjunctive administration", as used herein, means the compound can be administered in the same dosage form or in separate dosage forms with one or more other active agents.

Specific examples of the pharmaceutically active agents that can be adjunctively administered with the compounds include, but are not limited to, aceclofenac, acetaminophen, atomoxetine, almotriptan, alprazolam, amantadine, amcinonide, aminocyclopropane, amitriptyline, amlodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketanserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalycylate, methysergid(e), metoclopramide, mianserin, mifepristone, milnacipran, minaprine, mirtazapine, moclobemide, modafinil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprozin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propranolol, propizepine, propoxyphene, protriptyline, quazepam, quinupramine, reboxetine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenazine, thiazides, thioridazine, thiothixene, tiapride, tiazipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

The additional pharmaceutically active agent(s) can be formulated for immediate release, controlled release, or combinations thereof, either together with or separate from the compounds disclosed herein.

EXAMPLES

The present disclosure will now be described in more detail with reference to the following non-limiting examples. It should be noted that the particular assays used in the examples section are designed to provide an indication of activity.

General Chemical Synthesis and Characterization

Automated flash column chromatography was performed using a Teledyne ISCO CombiFlash Companion system with silica gel-packed columns (SiliCycle Inc. or RediSep® Rf). Analytical thin-layer chromatography (TLC, commercially available from Sigma-Aldrich) was carried out on aluminum-supported silica gel plates (thickness: 200 μm) or glass-supported (thickness: 240 μm) silica gel plates with fluorescent indicator (F-254). Visualization of compounds on TLC plates was accomplished with UV light (254 nm) and/or with phosphomolybdic acid (PMA) or ceric ammonium molybdate. In some cases, retention factors ($R_f$) were determined on glass-supported silica gel plates (thickness: 240 μm) with PMA stain, and calculated as an average of three runs. NMR spectra ($^1$H, $^{13}$C, $^{19}$F, and $^{31}$P) were obtained using either a Varian INOVA 600 MHz spectrometer, a Varian INOVA 500 MHz spectrometer, a Varian INOVA 400 MHz spectrometer, a Varian VNMR 400 MHz spectrometer, a Bruker AVIIIHD 600 MHz spectrometer or a Mercury 300 MHz spectrometer. NMR samples were prepared in deuterated chloroform ($CDCl_3$) or deuterated methanol ($CD_3OD$) using the residual solvent peak ($CDCl_3$: $^1H=7.26$ ppm, $^{13}C=77.16$ ppm; $CD_3OD$: $^1H=3.31$ ppm, $^{13}C=49.0$ ppm) as an internal reference. Alternatively, trifluoroacetic acid ($^{19}F=-76.55$ ppm) was used as an external reference for $^{19}F$ NMR, whereas the residual chloroform peak in $^1H$ NMR was used as an absolute reference for $^{31}P$ NMR. In some cases, phosphoric acid ($^{31}P=40.48$ ppm) as used as an external reference for $^{31}P$ NMR. MestReNova software was used to process all NMR spectra. NMR data are reported to include chemical shifts (δ) reported in ppm, multiplicities indicated as s (singlet), d (doublet), t (triplet), q (quartet), m (multiplet), br (broad), or app (apparent), coupling constants (J) reported in Hz, and integration normalized to 1 atom (H, C, F, or P). High resolution mass spectrometry (HRMS) was performed by the Emory University Mass Spectrometry Center, directed by Dr. Fred Strobel. Liquid chromatography-mass spectrometry (LC-MS) was performed on an Agilent 1200 HPLC equipped with a 6120 Quadrupole mass spectrometer (ESI-API) eluting with mixtures of HPLC grade MeOH and $H_2O$ or MeCN and $H_2O$ (all spiked with 0.1% formic acid) through an analytical, reverse-phase, Agilent C18 XDB eclipse column (50 mm×4.6 mm, 3.5 μM). LC-MS samples were prepared in a solution of 75:25 MeOH/$H_2O$ (spiked with 0.1% formic acid). Final compound purity was assessed using $^1H$ NMR and LC-MS. Melting points of intermediates and final compounds were taken on a RD-MP digital melting point determination apparatus.

Figure 1B:
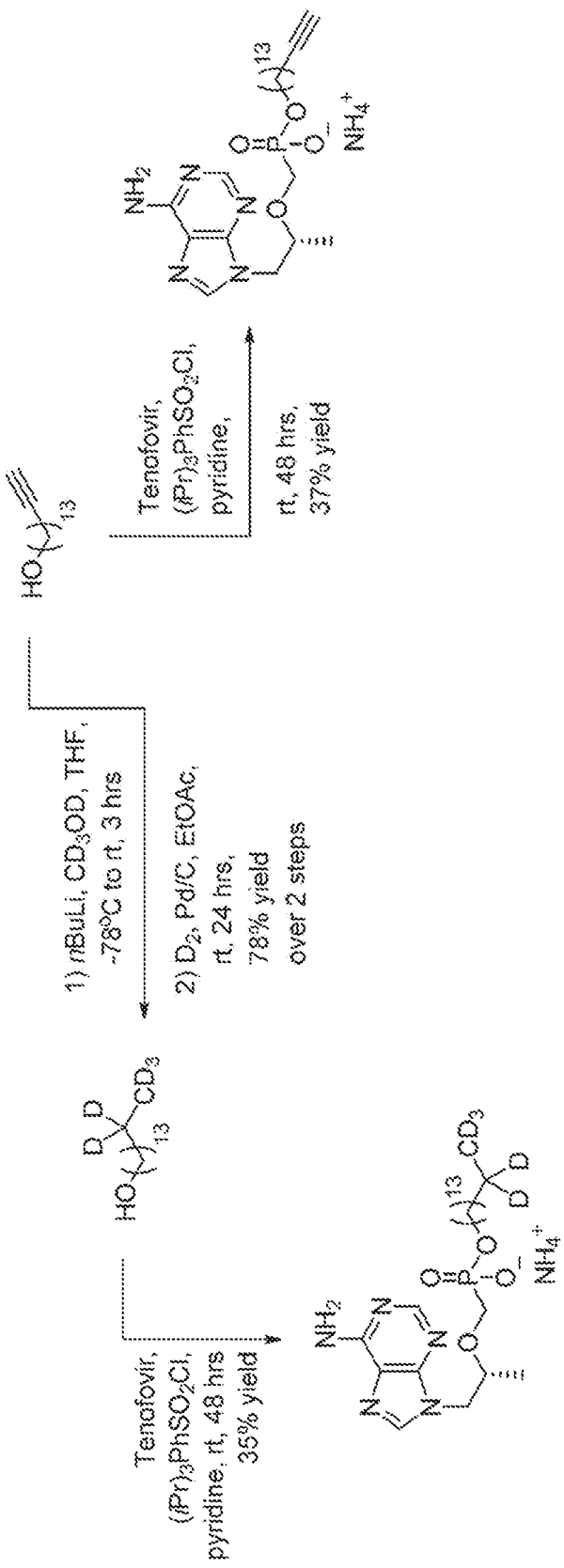
FIG. 1B illustrates the synthetic procedures involved in Examples 1-2.
Figure 2:
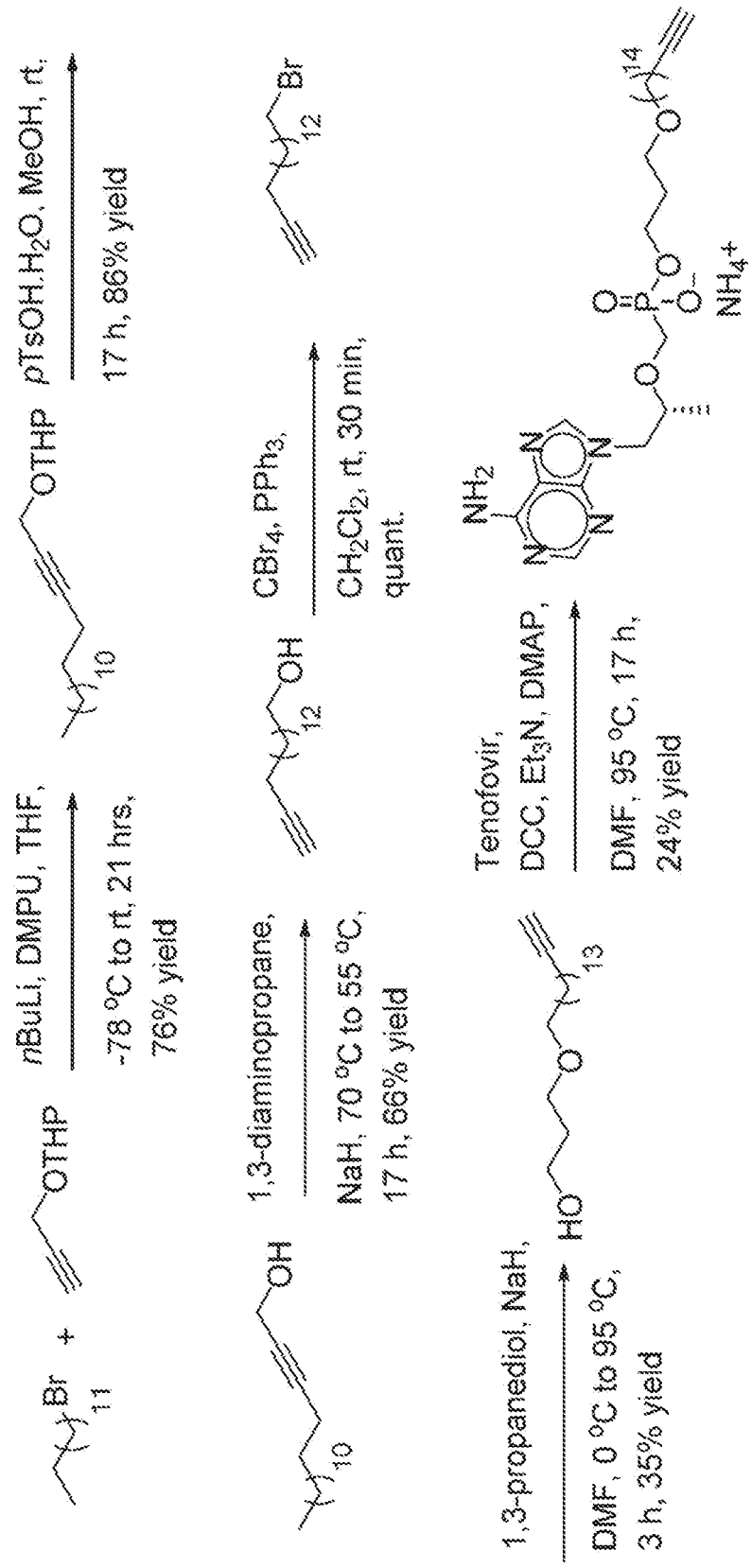
FIG. 2 illustrates the synthetic procedures involved in Example 5.
Figure 3:
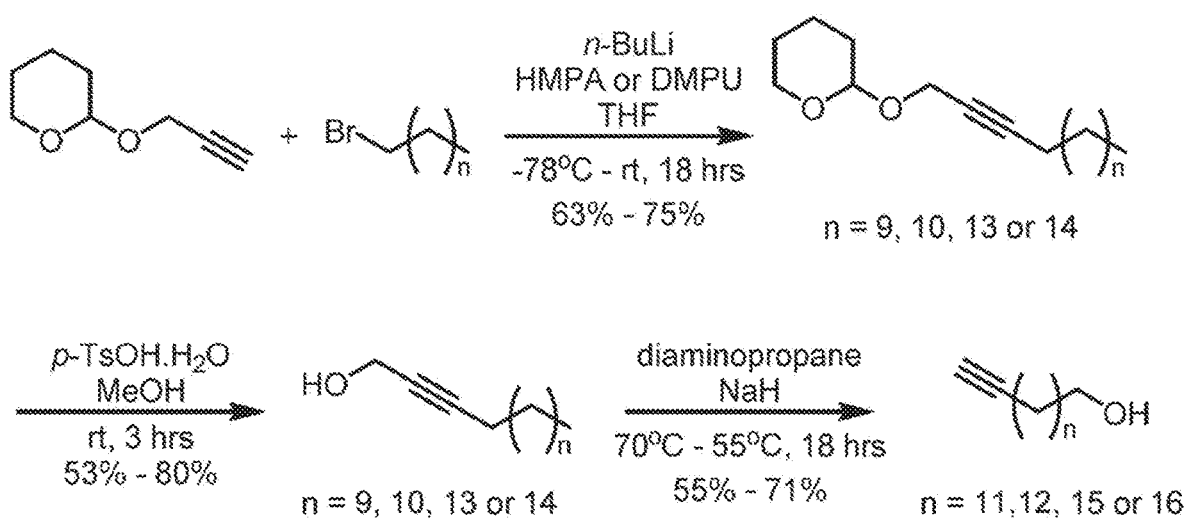
FIG. 3 illustrates the synthetic procedures for making hydroxyl-substituted alkynes with different carbon chain lengths.
Figure 4A:
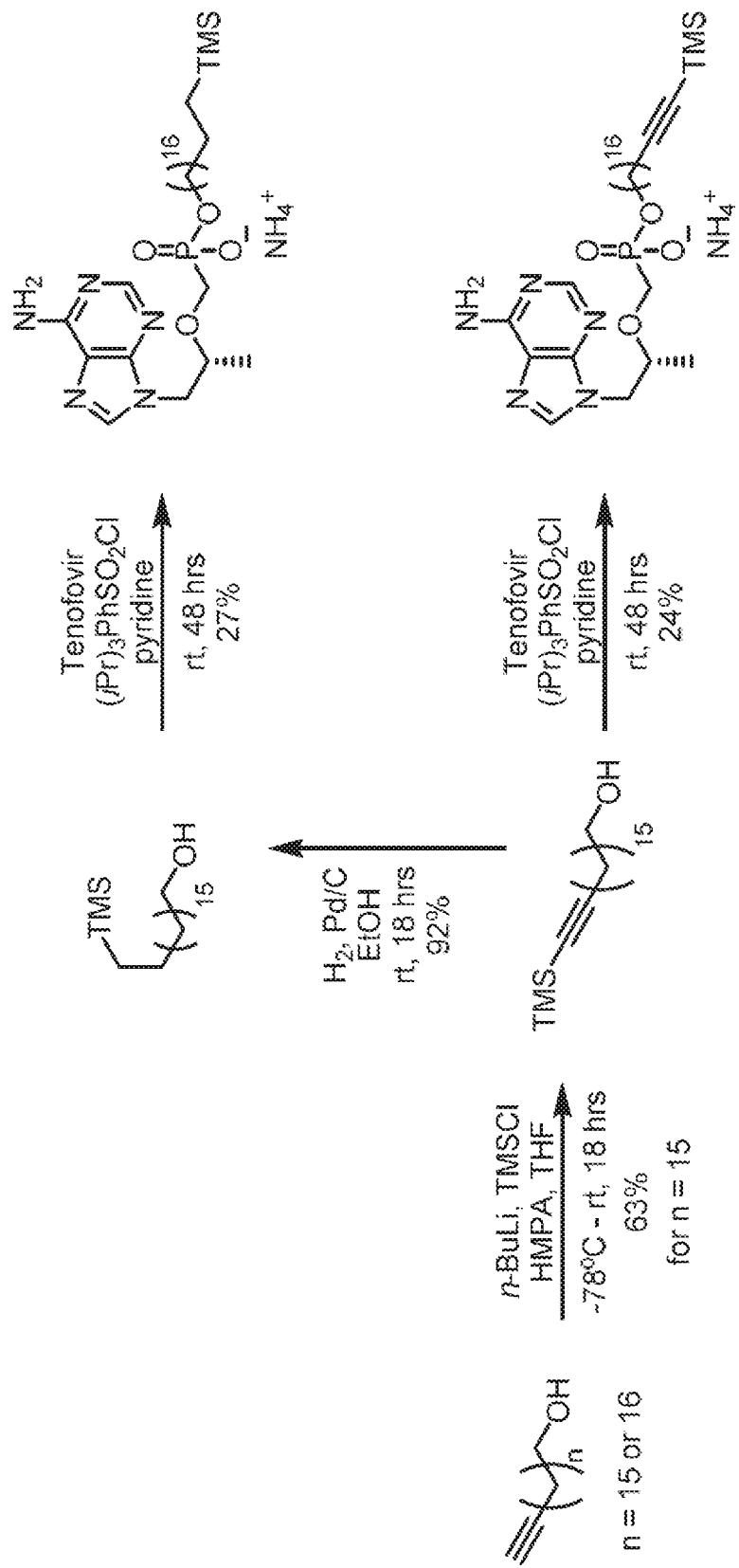
FIG. 4A illustrates the synthetic procedures involved in Examples 25-26.
Figure 4B:
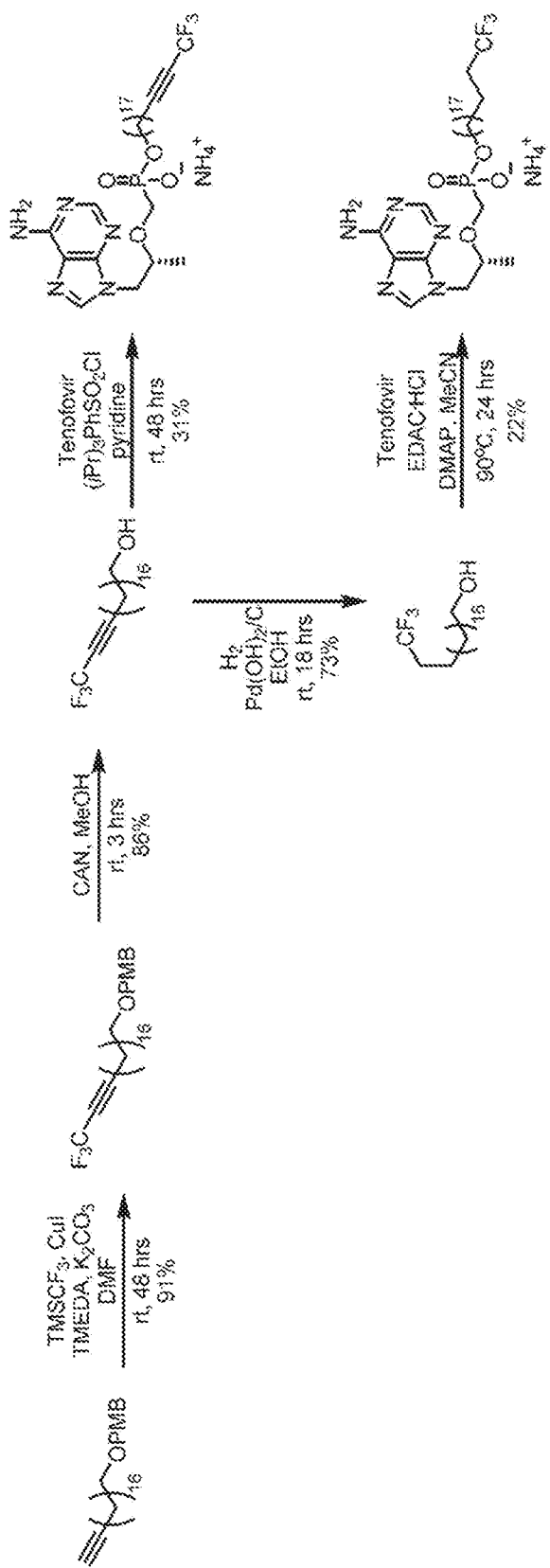
FIG. 4B illustrates the synthetic procedures involved in Examples 27-28.
Figure 5:
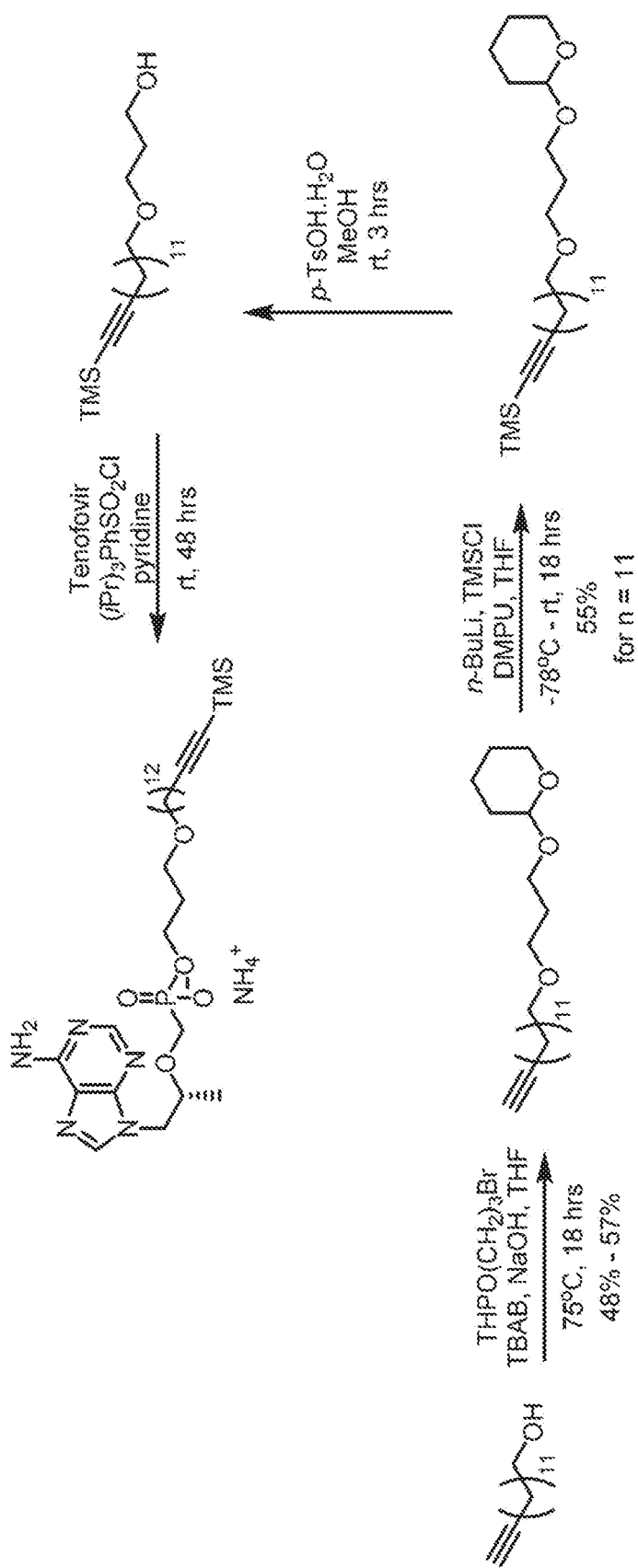
FIG. 5 illustrates the synthetic procedures involved in Example 29.
Figure 6:
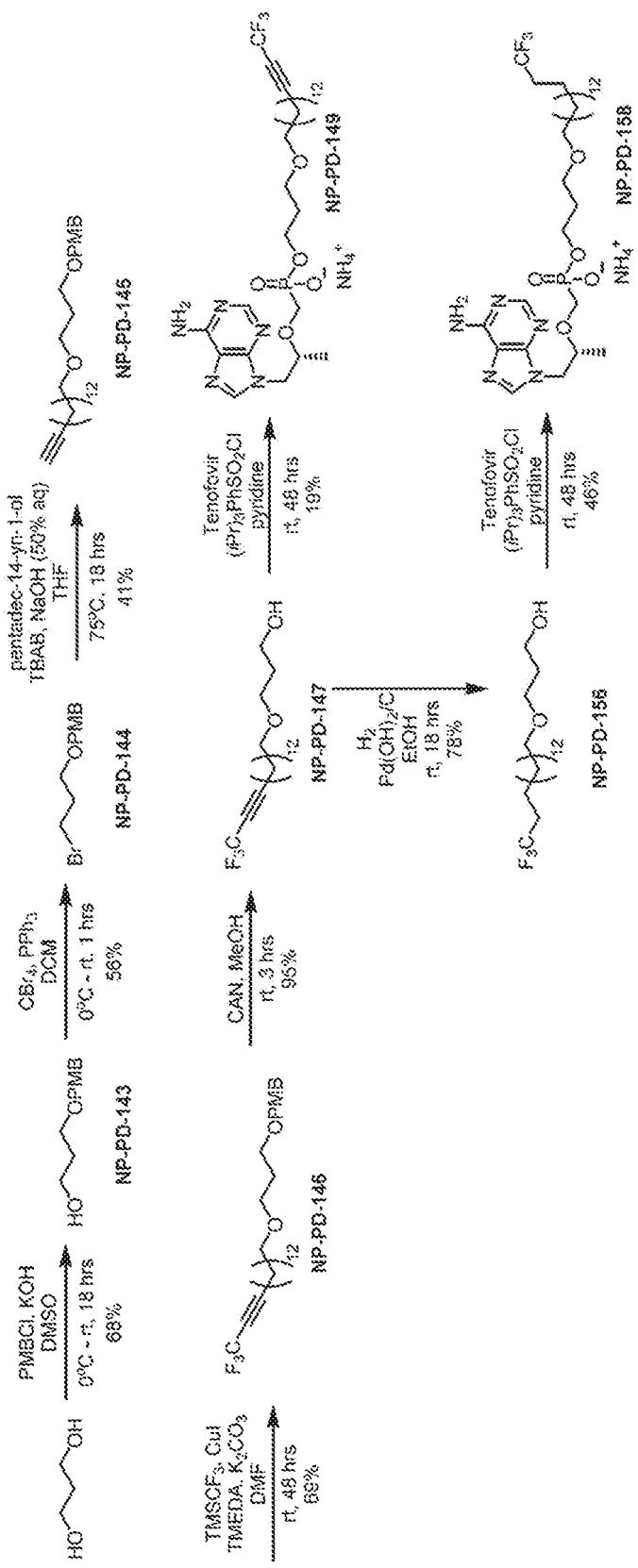
FIG. 6 illustrates the synthetic procedures involved in Examples 30 and 31.
Figure 7:
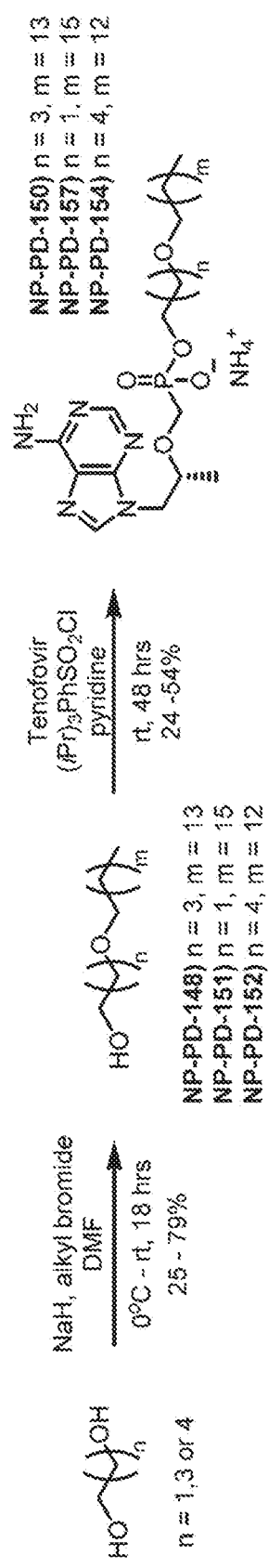
FIG. 7 illustrates the synthetic procedures involved in Examples 32-34.
Figure 8:
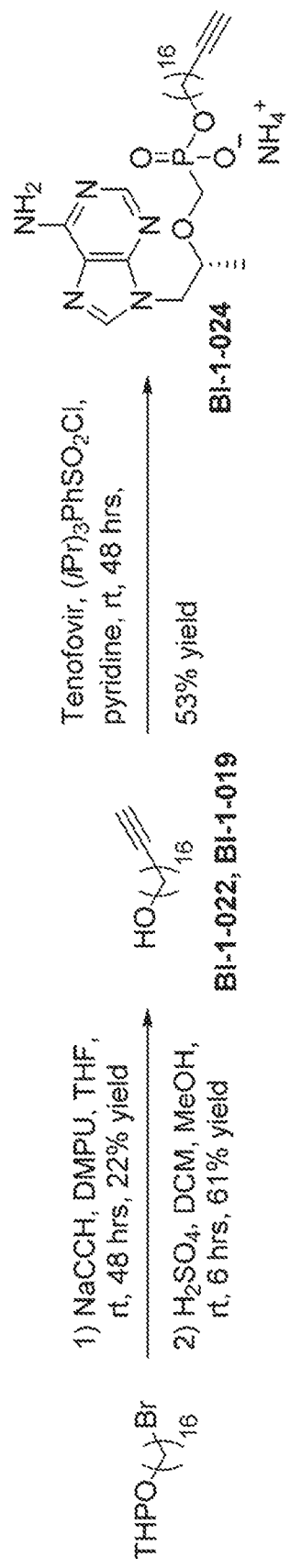
FIG. 8 illustrates the synthetic procedures involved in Example 35.
Figure 9:
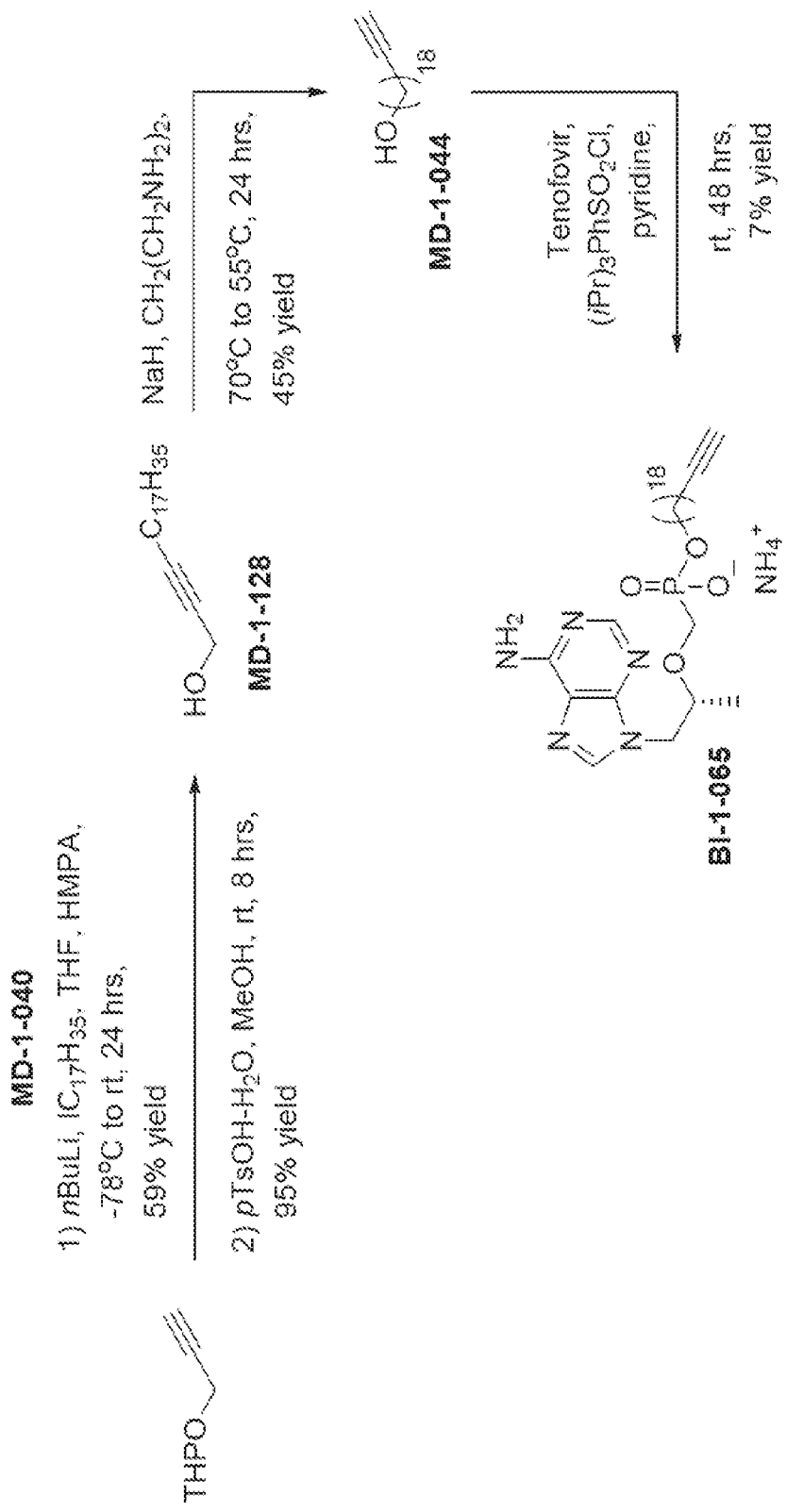
FIG. 9 illustrates the synthetic procedures involved in Example 36.
Figure 10:
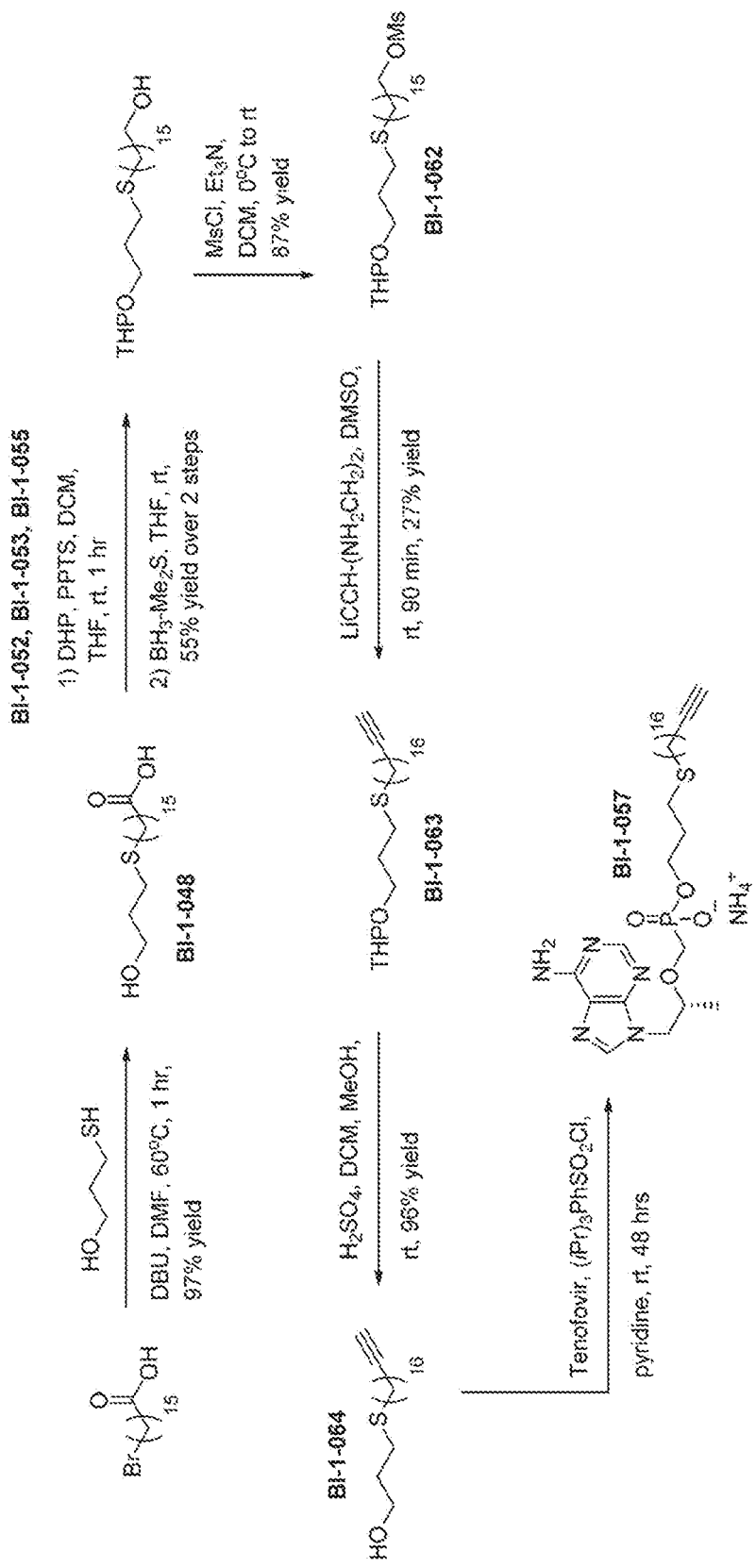
FIG. 10 illustrates the synthetic procedures involved in Example 37.
Figure 11:
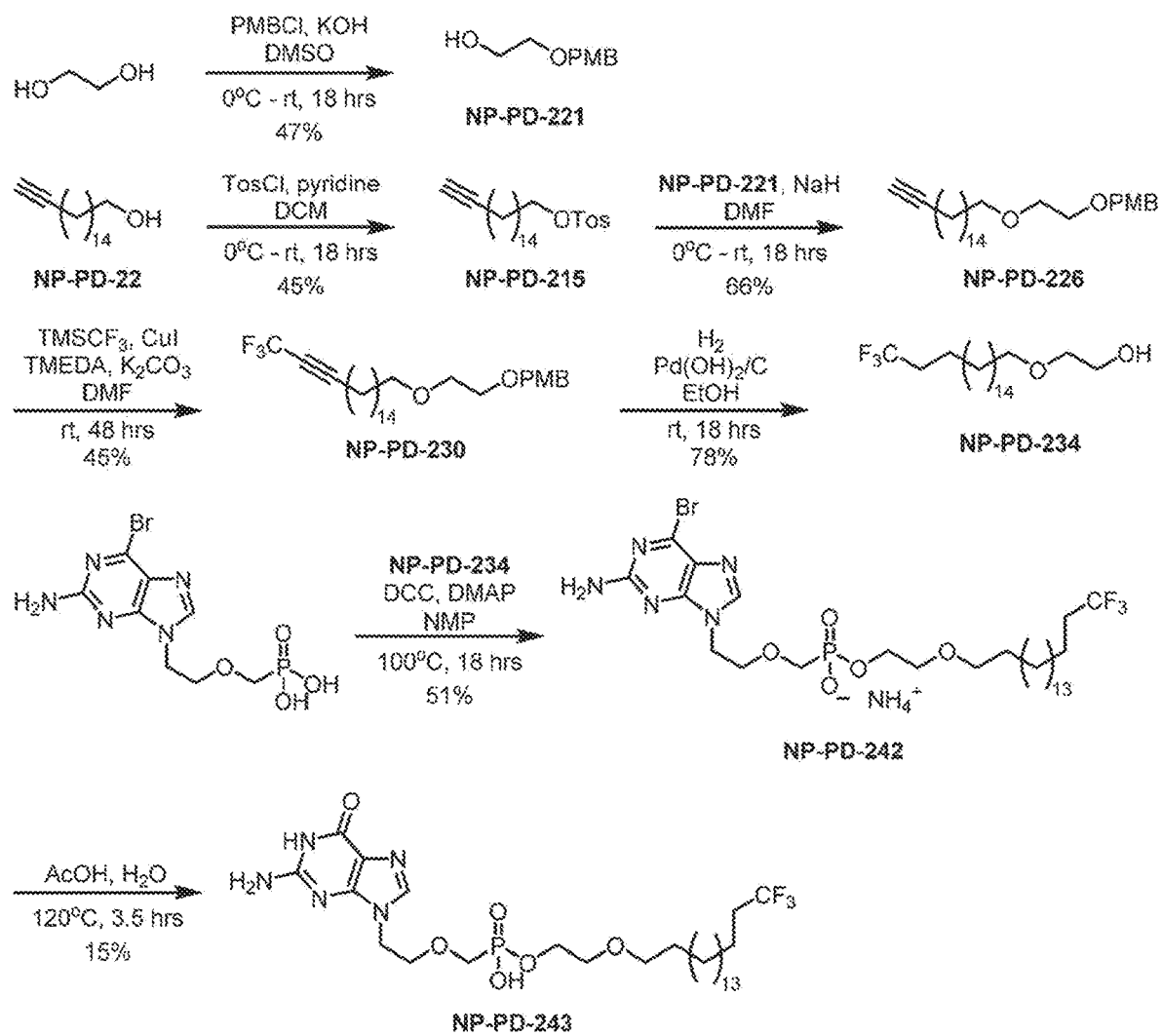
FIG. 11 illustrates the synthetic procedures involved in Example 39.
Figure 12:
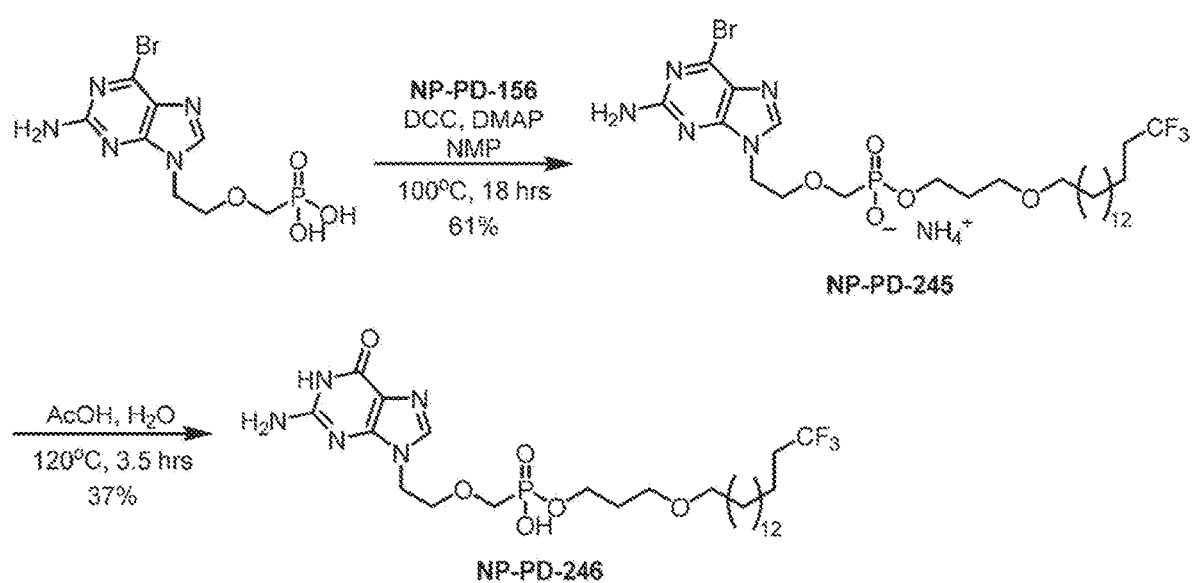
FIG. 12 illustrates the synthetic procedures involved in Example 40.

Synthetic procedures for selected examples are described in FIGS. 1-12.

Example 1. Synthesis of Ammonium pentadec-14-yn-1-yl (R)-(((1-(6-amino-9H-purin-9-yl)propan-2-yl)oxy)methyl)phosphonate A. Synthesis of (pentadec-2-yn-1-yloxy)tetrahydro-2H-pyran (EJM-8-003)

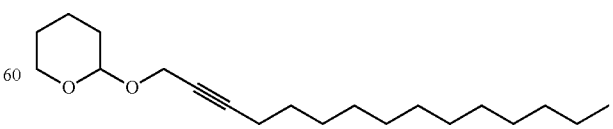

Dodecan-1-ol (10.0 g, 53.7 mmol, 1.00 eq) was added to a 1 L flask with a stir bar. Diluted with DCM (268 mL), and the resulting solution was stirred vigorously at room temperature. After addition of imidazole (4.75 g, 69.8 mmol, 1.30 eq), triphenylphosphine (18.3 g, 69.8 mmol, 1.30 eq), and iodine (17.7 g, 69.8 mmol, 1.30 eq) in succession, the resulting reaction mixture was stirred vigorously at room temperature under argon (Ar). Reaction progress was monitored by TLC. After 1.5 hrs, TLC indicated conversion of starting material to one major spot. The reaction mixture was quenched with 150 mL saturated aqueous sodium thiosulfate. The resulting organic layer was diluted with 200 mL hexanes, the small amount of precipitate was filtered, and the mother liquor was evaporated under reduced pressure to yield white solid. After addition of 400 mL hexanes, the resulting slurry was stirred vigorously overnight under Ar. In the next morning, the slurry was filtered, and the mother liquor was evaporated under reduced pressure to yield a yellow oil. The crude material was purified via silica plug eluting with 100% hexanes to yield a clear oil with a small amount of yellow solid remaining. This crude material was taken up in 100% pentane, filtered, and the mother liquor was evaporated under reduced pressure to yield a clear oil, which corresponded to the product 1-iodododecane (15.7 g, 53.0 mmol, 99% yield).

2-(2-Propynyloxy)tetrahydro-2H-pyran (4.77 g, 34.0 mmol, 1.00 eq) was added to a 250 mL oven-dried flame-dried flask equipped with a stir bar, diluted with 40 mL THF and hexamethylphosphoramide (20.7 mL, 119 mmol, 3.50 eq), cooled to −78° C., and stirred vigorously under Ar. After addition of n-butyllithium (2.5 M in hexane, 15.0 mL, 34.0 mmol, 1.00 eq) dropwise via syringe pump at a rate of 17 mL/hr, the resulting reaction mixture was stirred vigorously at −78° C. under Ar for 10 min, before warming to −30° C. and stirring for an additional 45 min. After addition of a solution of 1-iodododecane (10.1 g, 34.0 mmol, 1.00 eq) in 14 mL THF dropwise via syringe pump at a rate of 17 mL/hr, the resulting reaction mixture was allowed to slowly warm to room temperature and was stirred vigorously under Ar overnight. In the next morning, TLC indicated complete conversion of alkyl iodide and alkyne starting materials to one spot (stained with PMA). The reaction was quenched dropwise with saturated ammonium chloride, and the resulting aqueous layer was extracted 3 times with EtOAc. Combined organic layers were dried over anhydrous sodium sulfate, filtered, and evaporated under reduced pressure to yield 22.6 g of a yellow oil, which was purified via column chromatography eluting with 1:12 EtOAc to hexanes to yield a slightly yellow oil (8.40 g, 27.2 mmol, 80% yield).

B. Synthesis of pentadec-2-yn-1-ol (EJM-8-004)

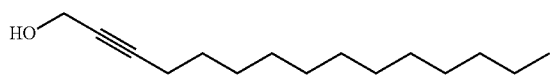 [SMILES: CCCCCCCCCCCCC#CCO]

A solution of (pentadec-2-yn-1-yloxy)tetrahydro-2H-pyran (8.40 g, 27.2 mmol, 1.00 eq) in methanol (136 mL) was added to a 500 mL flask with a stir bar. After addition of p-toluenesulfonic acid monohydrate (0.520 g, 2.72 mmol, 0.10 eq), the resulting reaction mixture was stirred vigorously at room temperature under Ar. Reaction progress was monitored by TLC. After 6.5 hrs, TLC indicated almost complete conversion of starting material to one major spot (stained with PMA). Solvent was evaporated under reduced pressure to yield a brown oil, which was purified via column chromatography, eluting with 1:6 EtOAc to hexanes to yield a white solid (3.96 g, 17.7 mmol, 65% yield).

C. Synthesis of pentadec-14-yn-1-ol (EJM-8-005)

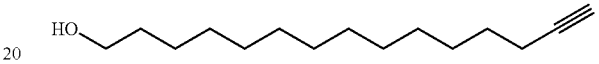

Sodium hydride (60% in mineral oil, 0.620 g, 15.6 mmol, 7.00 eq) was added to an oven-dried, flame-dried, 50 mL flask equipped with a stir bar and a reflux condenser. The dispersion was washed twice with 10 mL hexanes, before diluting with 8 mL 1,3-diaminopropane, warming to 70° C., and stirring vigorously under Ar. Over the course of 1 hr, the solution became brown, and was subsequently cooled to room temperature while stirring vigorously under Ar. After addition of a solution of pentadec-2-yn-1-ol (0.500 g, 2.23 mmol, 1.00 eq) in 1.3 mL 1,3-diaminopropane in a dropwise fashion, the resulting mixture was stirred vigorously at room temperature for 10 min, before warming to 55° C. and stirring overnight under Ar. In the next morning, the reaction mixture was cooled to 0° C., and quenched dropwise with cold water. The aqueous layer was slowly acidified with 1 M aqueous hydrochloric acid until pH=2. The resulting aqueous layer was extracted 3 times with hexanes, and combined organic layers were dried over anhydrous sodium sulfate, filtered, and evaporated under reduced pressure to yield 400 mg of a brown solid. The crude material was dissolved in 1:4 EtOAc to hexanes and filtered in an attempt to remove insoluble material. However, the particles were fine enough to pass through the filter paper. The mother liquor was evaporated under reduced pressure and purified via column chromatography eluting with 1:4 EtOAc to hexanes to yield a white crystalline solid (0.320 g, 1.43 mmol, 64% yield).

D. Synthesis of Ammonium pentadec-14-yn-1-yl (R)-(((1-(6-amino-9H-purin-9-yl)propan-2-yl)oxy) methyl)phosphonate (EJM-8-006)

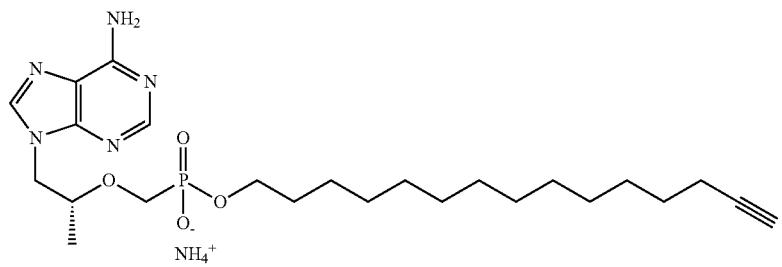

Tenofovir (100 mg, 0.350 mmol, 1.00 eq) was added to a 25 mL flame-dried flask with a stir bar, diluted with pyridine (2.90 mL), and stirred vigorously at room temperature under Ar. After addition of pentadec-14-yn-1-ol (117 mg, 0.520 mmol, 1.50 eq) and 2,4,6-triisopropylbenzenesulfonyl chloride (316 mg, 1.04 mmol, 3.00 eq), the resulting yellow reaction mixture was stirred vigorously overnight at room temperature under Ar. After 2 days, TLC indicated significant product formation. The reaction mixture was quenched with saturated aqueous ammonium chloride, and the resulting mixture was evaporated under reduced pressure. The resulting white solid was diluted with 50 mL of 4:1 DCM to MeOH, and the resulting slurry was stirred vigorously at room temperature under Ar overnight. In the next morning, the contents were filtered, and the resulting mother liquor was evaporated under reduced pressure to yield a white solid, which was purified via column chromatography eluting with 80:20:3 DCM/MeOH/NH$_4$OH to yield a waxy white solid (0.064 g, 0.130 mmol, 37% yield). $^1$H NMR (600 MHz, CD$_3$OD) δ 8.33 (s, 1H), 8.21 (s, 1H), 4.38 (dd, J=14.4 Hz, J=3.0 Hz, 1H), 4.23 (dd, J=14.4 Hz, J=6.6 Hz, 1H), 3.90 (sextet, J=3.4 Hz, 1H), 3.70-3.78 (m, 3H), 3.46 (dd, J=12.6 Hz, J=10.2 Hz, 1H), 2.14-2.18 (m, 3H), 1.45-1.52 (m, 4H), 1.40 (p, J=7.5 Hz, 2H), 1.22-1.28 (m, 16H), 1.16 (d, J=6.6 Hz, 3H). $^{13}$C NMR (150 MHz, CD$_3$OD) δ 155.1, 150.8, 150.1, 144.3, 123.1, 119.0, 85.0, 76.3 (d, J=12.2 Hz), 68.8, 65.7 (d, J=5.9 Hz), 64.9 d (J=159.9 Hz), 31.7 (d, J=6.2 Hz), 30.3, 30.3, 30.3, 30.3, 30.2, 30.1, 29.8, 29.4, 29.2, 26.5, 18.8, 16.7. $^{31}$P NMR (122 MHz, CD$_3$OD) δ 15.6. HRMS (APCI) m/z calculated for C$_{24}$H$_{41}$O$_4$N$_5$P [M+H]$^+$: 494.28907, found 494.28924. LC-MS (ESI) 50-95% MeOH in H$_2$O (0.1% HCO$_2$H), 6 min, rt=5.430, m/z=494.0 [M+H]$^+$, 491.9 [M−H]$^−$.

Example 2. Synthesis of Ammonium pentadecyl-14, 14,15,15,15-d$_5$ (R)-(((1-(6-amino-9H-purin-9-yl)propan-2-yl)oxy)methyl)phosphonate A. Synthesis of 14,14,15,15,15-pentadeuteriopentadecan-1-ol (EJM-8-033)

Pentadec-14-yn-1-ol (465 mg, 2.07 mmol, 1.00 eq) was added to an oven-dried flask with a stir bar, diluted with THF (20.7 mL), cooled to −78° C., and stirred vigorously under Ar. n-Butyllithium (2.5 M in hexane, 2.49 mL, 6.22 mmol, 3.00 eq) dropwise via syringe pump at a rate of 4 mL/hr, and the resulting mixture was stirred vigorously under Ar at −78° C. for 30 min. After this time, the cold bath was removed for 10 min, and then the reaction was quenched slowly with trideuterio(deuteriooxy)methane (0.470 mL, 10.4 mmol, 5.00 eq). The resulting mixture was stirred vigorously under Ar while slowly warming to room temperature over 2 hrs. After this time, the reaction mixture was partitioned between D$_2$O and EtOAc. The resulting aqueous layer was extracted with EtOAc twice, and combined organic layers were dried over anhydrous sodium sulfate, filtered, and evaporated under reduced pressure to yield 450 mg of a white solid, which corresponded to the product 15-deuteriopentadec-14-yn-1-ol. The crude material was carried forward without further purification.

15-Deuteriopentadec-14-yn-1-ol (295 mg, 1.31 mmol, 1.00 eq) was added to an oven-dried 100 mL flask with a stir bar. After dilution with EtOAc (26.2 mL) and addition of 10% palladium on carbon (20.9 mg, 0.020 mmol, 0.15 eq), the resulting heterogeneous mixture was stirred vigorously at room temperature under Ar. The solvent was degassed under house vacuum for 5 min, followed by Ar purge. These two steps were repeated twice more. Finally, the solvent was degassed for one final cycle, this time purging with a balloon of deuterium gas. The resulting reaction mixture was stirred vigorously at room temperature under deuterium gas overnight. In the morning, deuterium gas was removed from the flask using house vacuum and was replaced with Ar 3 times. The heterogeneous mixture was filtered over a plug of celite, which was subsequently washed with EtOAc. Solvent was evaporated under reduced pressure to yield a white solid. The crude material was purified via column chromatography (CombiFlash, 24 g column, 35 mL/min) eluting with the following gradient to yield a white solid (365 mg, 1.56 mmol, 78% yield over 2 steps): 0-3 min, 0% EtOAc in hexanes; 3-20 min, 0-25% EtOAc in hexanes; 20-25 min, 25% EtOAc in hexanes; 25-30 min, 25-50% EtOAc in hexanes.

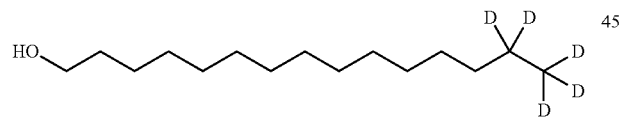

B. Synthesis of Ammonium pentadecyl-14,14,15, 15,15-d$_5$ (R)-(((1-(6-amino-9H-purin-9-yl)propan-2-yl)oxy)methyl)phosphonate (EJM-8-030)

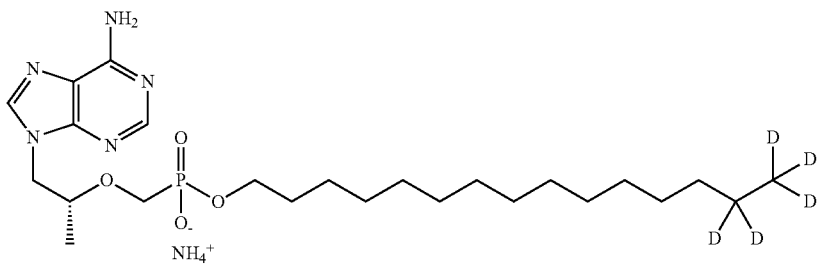

Tenofovir (200 mg, 0.700 mmol, 1.00 eq) was added to a 25 mL flame-dried flask with a stir bar, diluted with pyridine (5.80 mL), and stirred vigorously at room temperature under Ar. After addition of 14,14,15,15,15-pentadeuteriopentadecan-1-ol (228 mg, 0.970 mmol, 1.40 eq) and 2,4,6-triisopropylbenzenesulfonyl chloride (633 mg, 2.09 mmol, 3.00 eq), the resulting yellow reaction mixture was stirred vigorously overnight at room temperature under Ar. After 2 days, TLC indicated significant product formation. The reaction mixture was quenched with saturated aqueous ammonium chloride, and the resulting mixture was evaporated under reduced pressure. The resulting white solid was diluted with 50 mL of 4:1 DCM to MeOH, and the resulting slurry was stirred vigorously at room temperature under Ar overnight. In the next morning, the contents were filtered, and the resulting mother liquor was evaporated under reduced pressure to yield a white solid, which was further purified via column chromatography (CombiFlash, 24 g column, 35 mL/min) eluting with 80:20:3 DCM/MeOH/ NH$_4$OH to yield 143 mg of a white powder. $^1$H NMR and LC-MS analysis indicated 8% (iPr)$_3$PhSO$_3$H contamination. The material was purified via column chromatography (CombiFlash, 12 g column, 30 mL/min) eluting with the following gradient to yield a white solid (121 mg, 0.241 mmol, 35% yield): 0-3 min, 25% 80:20:3 DCM/MeOH/ NH$_4$OH in DCM; 3-20 min, 25-100% 80:20:3 DCM/MeOH/ NH$_4$OH in DCM; 20-30 min: 100% 80:20:3 DCM/MeOH/ NH$_4$OH. $^1$H NMR (600 MHz, CD$_3$OD) δ 8.32 (s, 1H), 8.20 (s, 1H), 4.37 (dd, J=3.6 Hz, J=14.4 Hz, 1H), 4.22 (dd, J=6.6 Hz, J=14.4 Hz, 1H), 3.87-3.91 (m, 1H), 3.69-3.79 (m, 3H), 3.46 (dd, J=10.2 Hz, J=12.6 Hz, 1H), 1.47-1.52 (m, 2H), 1.24-1.27 (m, 22H), 1.16 (d, J=6.0 Hz, 3H). $^{13}$C NMR (150 MHz, CD$_3$OD) δ 155.0, 150.9, 150.0, 144.0, 118.8, 76.2 (d, J=12.5 Hz), 65.5 (d, J=5.9 Hz), 64.7 (d, J=159.2 Hz), 48.7, 32.2-32.1 (m, 2C), 31.5 (d, J=6.2 Hz), 30.2 (3C), 30.1, 30.1, 29.9, 29.8-29.6 (m), 29.8, 26.3, 22.6-21.8 (m), 16.7, 13.6-13.0 (m). $^{31}$P NMR (122 MHz, CD$_3$OD) δ 15.5. HRMS (APCI) m/z calculated for C$_{24}$H$_{39}$D$_5$O$_4$N$_5$P [M-H]$^-$: 501.33720, found 501.33753. LC-MS (ESI) 75-95% MeOH in H$_2$O (0.1% HCO$_2$H), 5 min, rt=4.385, m/z=503.4 [M+H]$^+$, 525.3 [M+Na]$^+$, 499.6 [M-H]$^-$; 50-95% MeOH in H$_2$O (0.1% HCO$_2$H), 8 min, rt=4.723, m/z=503.3 [M+H]$^+$, 525.3 [M+Na]$^+$, 499.6 (M-H)$^-$.

Example 3. Synthesis of Ammonium hexadecyl-16,16,16-d$_3$ (R)-(((1-(6-amino-9H-purin-9-yl)propan-2-yl)oxy)methyl)phosphonate A. Synthesis of ((pentadec-14-yn-1-yloxy)methyl) benzene (NP-1-009)

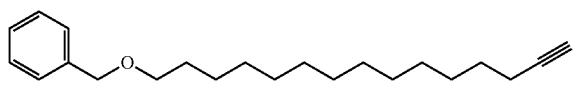 [SMILES: C#CCCCCCCCCCCCCCOCc1ccccc1]

Sodium hydride (60% in mineral oil, 196 mg, 4.90 mmol, 2.20 eq) was added to pentadec-14-yn-1-ol (500 mg, 2.23 mmol, 1.00 eq) in 10 mL THF and 0.5 mL DMF at 0° C. After 30 minutes, benzyl bromide (0.300 mL, 2.50 mmol, 1.12 eq) was added in a dropwise fashion, and the reaction was heated to 65° C. overnight. The following morning, the reaction was cooled to room temperature and subsequently quenched with saturated aqueous ammonium chloride. The resulting aqueous phase was extracted three times with EtOAc, and combined organic phases were dried over anhydrous magnesium sulfate, filtered, and concentrated under vacuum. The crude material was purified via column chromatography to yield a white solid (384 mg, 1.21 mmol, 55% yield).

B. Synthesis of (((hexadec-14-yn-1-yl-16,16,16-d$_3$) oxy)methyl)benzene (EJM-8-028)

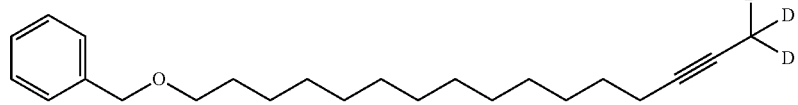

A solution of ((pentadec-14-yn-1-yloxy)methyl)benzene (192 mg, 0.610 mmol, 1.00 eq) in THF (6.10 mL) was added to an oven-dried 3-neck flask with a stir bar, and the resulting solution was cooled to -78° C. and stirred vigorously under Ar. After addition of n-butyllithium (2.5 M in hexane, 0.320 mL, 0.670 mmol, 1.10 eq) in a dropwise fashion via syringe pump at a rate of 1 mL/hr, the resulting mixture was stirred at -78° C. for 1 hr. After this time, the cold bath was removed for 10 min, and then replaced for another 10 min. Then, trideuterio(iodo)methane (0.110 mL, 1.83 mmol, 3.00 eq) was added in a dropwise fashion, and the resulting reaction mixture was stirred vigorously at -78° C. under Ar for 30 min before slowly warming to room temperature. After 20 min at room temperature, the reaction was quenched with saturated aqueous ammonium chloride, and the resulting aqueous layer was extracted 3 times with diethyl ether. Combined organic layers were dried over anhydrous sodium sulfate, filtered, and evaporated under reduced pressure to yield a yellow oil, which was further purified via column chromatography (CombiFlash, 24 g, 35 mL/min) eluting with the following gradient to yield a clear oil (174 mg, 0.525 mmol, 86% yield): 0-3 min, 0% EtOAc in hexanes; 3-13 min, 0-5% EtOAc in hexanes; 13-23 min, 5% EtOAc in hexanes; 23-30 min, 5-10% EtOAc in hexanes.

C. Synthesis of hexadecan-16,16,16-d$_3$-1-ol (EJM-8-034)

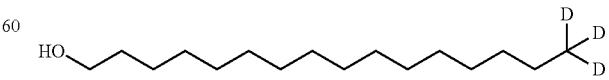

A solution of (((hexadec-14-yn-1-yl-16,16,16-d$_3$)oxy) methyl)benzene (174 mg, 0.520 mmol, 1.00 eq) in EtOAc (10.5 mL) was added to an oven-dried flask with a stir bar. After addition of 10% palladium on carbon (55.9 mg, 0.050 mmol, 0.100 eq), the resulting heterogeneous mixture was stirred vigorously at room temperature under Ar. The solvent was degassed under house vacuum for 5 min, followed by Ar purge. These two steps were repeated twice more. Finally, the solvent was degassed for one final cycle, this time purged with a balloon of hydrogen gas. The resulting reaction mixture was stirred vigorously at room temperature under hydrogen overnight. In the morning, hydrogen gas was removed from the flask using house vacuum and was replaced with Ar 3 times. The reaction mixture was then filtered over celite, which was subsequently washed thoroughly with EtOAc. Solvent was evaporated under reduced pressure to yield 173 mg of a clear oil. The crude material of 16,16,16-trideuteriohexadecoxymethylbenzene was taken forward without further purification.

16,16,16-Trideuteriohexadecoxymethylbenzene (173 mg, 0.520 mmol) was added to a 100 mL flask with a stir bar, diluted with EtOH (10.3 mL) and a small volume of EtOAc for full solubility, and the resulting solution was stirred vigorously at room temperature under Ar. After addition of 20% palladium hydroxide on carbon (72.4 mg, 0.103 mmol, 0.200 eq), the resulting heterogeneous mixture was stirred vigorously at room temperature under Ar. The solvent was degassed under house vacuum for 5 min, followed by Ar purge. These two steps were repeated twice more. Finally, the solvent was degassed for one final cycle, this time purging with a balloon of hydrogen gas. The resulting reaction mixture was stirred vigorously at room temperature under hydrogen gas overnight. In the next morning, TLC indicated complete conversion of starting material to one major product. The reaction mixture was filtered over a plug of celite, which was subsequently washed with EtOAc. The resulting solution was evaporated under reduced pressure to yield 150 mg of a white solid. The crude material was purified via column chromatography (CombiFlash, 12 g column, 25 mL/min) eluting with the following gradient to yield a white solid (122 mg, 0.497 mmol, 96% yield over 2 steps): 0-3 min, 0% EtOAc in hexanes; 3-20 min, 0-25% EtOAc in hexanes; 20-30 min, 25% EtOAc in hexanes.

D. Synthesis of Ammonium hexadecyl-16,16,16-d$_3$ (R)-(((1-(6-amino-9H-purin-9-yl)propan-2-yl)oxy)methyl)phosphonate (EJM-8-036)

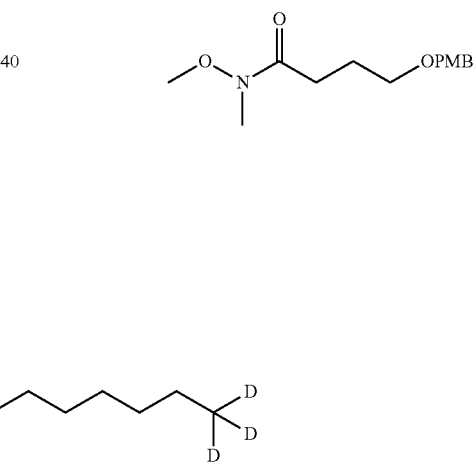

Tenofovir (100 mg, 0.350 mmol, 1.00 eq) was added to a 25 mL flame-dried flask with a stir bar and diluted with pyridine (3.48 mL). The resulting slurry was stirred vigorously at room temperature under Ar. After addition of hexadecan-16,16,16-d$_3$-1-ol (120 mg, 0.490 mmol, 1.40 eq) and 2,4,6-triisopropylbenzenesulfonyl chloride (316 mg, 1.04 mmol, 3.00 eq), the resulting yellow reaction mixture was stirred vigorously overnight at room temperature under Ar. After 2 days, TLC indicated significant product formation. The reaction mixture was quenched with saturated aqueous ammonium chloride, and the resulting mixture was evaporated under reduced pressure. The resulting white solid was diluted with 60 mL of 5:1 DCM to MeOH, and the resulting slurry was stirred vigorously at room temperature under Ar for 1 hr. After this time, the contents were filtered, the filtrate was washed thoroughly with 5:1 DCM to MeOH, and the resulting mother liquor was evaporated under reduced pressure to yield a white solid. The crude material was further purified via column chromatography (CombiFlash, 12 g column, 30 mL/min) eluting with the following gradient to yield a white solid (98.0 mg, 0.190 mmol, 55% yield): 0-3 min, 25% 80:20:3 DCM/MeOH/NH$_4$OH in DCM; 3-20 min, 25-100% 80:20:3 DCM/MeOH/NH$_4$OH in DCM; 20-30 min, 100% 80:20:3 DCM/MeOH/NH$_4$OH. $^1$H NMR (600 MHz, CD$_3$OD) δ 8.32 (s, 1H), 8.20 (s, 1H), 4.38 (dd, J=3.3 Hz, J=14.7 Hz, 1H), 4.22 (dd, J=6.6 Hz, J=14.4 Hz, 1H), 3.87-3.90 (m, 1H), 3.70-3.78 (m, 3H), 3.46 (dd, J=10.2 Hz, J=12.6 Hz, 1H), 1.47-1.52 (m, 2H), 1.23-1.27 (m, 26H), 1.16 (d, J=6.6 Hz, 3H). $^{13}$C NMR (150 MHz, CD$_3$OD) δ 155.0, 150.9, 150.0, 144.0, 129.2, 76.2 (d, J=12.5 Hz), 65.5 (d, J=5.7 Hz), 64.7 (d, J=159.2 Hz), 48.7, 32.5-32.3 (m, 3C), 31.5 (d, J=6.0 Hz), 30.2 (3C), 30.2, 30.2, 29.9, 29.9-29.8 (m), 26.3, 23.2-22.5 (m), 16.7, 14.3, 14.1-13.4 (m). $^{31}$P NMR (122 MHz, CD$_3$OD) δ 15.6. HRMS (APCI) m/z calculated for C$_{25}$H$_{41}$D$_3$O$_4$N$_5$P [M–H]$^-$: 513.34029, found 513.33931. LC-MS (ESI) 50-95% MeOH in H$_2$O (0.1% HCO$_2$H), 8 min, rt=4.613, m/z=515.3 [M+H]$^+$, 537.3 [M+Na]$^+$.

Example 4. Synthesis of Ammonium 4,4-difluoroicosyl (R)-(((1-(6-amino-9H-purin-9-yl)propan-2-yl)oxy)methyl)phosphonate A. Synthesis of N-methoxy-4-((4-methoxybenzyl)oxy)-N-methylbutanamide (EJM-8-038)

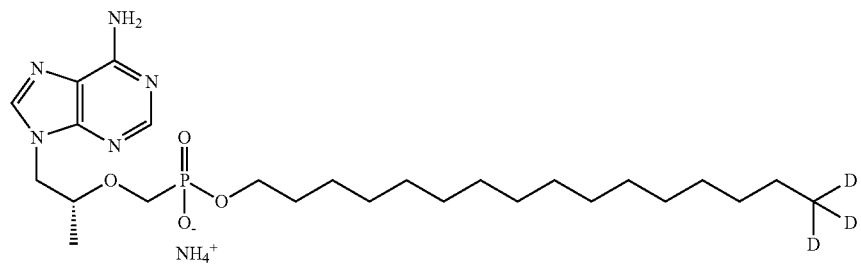

Weinreb's Salt (2.49 g, 25.6 mmol, 1.10 eq) was added to an oven-dried 500 mL flask with a stir bar. Diluted with DCM (155 mL), cooled to 0° C., and stirred vigorously under Ar. After addition of chloro(dimethyl)alumane (25.6 mL, 25.6 mmol, 1.10 eq) in a dropwise fashion via syringe pump at a rate of 10 mL/hr, and the resulting mixture was stirred vigorously at 0° C. under Ar for 1 hr. After addition of γ-butyrolactone (1.79 mL, 23.2 mmol, 1.00 eq) in a dropwise fashion via syringe pump at a rate of 4 mL/hr, the resulting reaction mixture was allowed to slowly warm to room temperature and to stir vigorously under Ar overnight. After 22 hrs, the reaction was quenched with the dropwise addition of water. The resulting aqueous layer was extracted 3 times with DCM, and combined organic layers were washed once with brine, dried over anhydrous sodium sulfate, filtered, and evaporated under reduced pressure to yield 2.49 g of a yellow oil. A solution of the crude material (2.49 g, 17.3 mmol, 1.00 eq) in 35 mL DCM was added to an oven-dried 100 mL flask with a stir bar, cooled to 0° C., and stirred vigorously under Ar. After addition of a solution of (4-methoxyphenyl)methyl 2,2,2-trichloroethanimidate (3.62 mL, 17.4 mmol, 1.10 eq) in 15 mL DCM in a dropwise fashion via syringe pump at a rate of 19 mL/hr, the resulting mixture was stirred vigorously at 0° C. under Ar for 10 min. After addition of (1R)-(−)-10-camphorsulfonic acid (200 mg, 0.860 mmol, 0.05 eq), the resulting reaction mixture was allowed to slowly warm to room temperature overnight while stirring vigorously under Ar. After 17 hrs, the reaction was quenched with saturated aqueous sodium bicarbonate. The resulting aqueous layer was extracted 4 times with DCM, and combined organic layers were dried over anhydrous sodium sulfate, filtered, and evaporated under reduced pressure to yield 7.10 g of a mixture of yellow oil and white solid. Purified via column chromatography (CombiFlash, 120 g column, 85 mL/min) eluting with a gradient mobile phase (0-3 min, 33% EtOAc in hexanes; 3-20 min, 33-75% EtOAc in hexanes; 20-25 min, 75% EtOAc in hexanes; 25-30 min, 75-100% EtOAc in hexanes) to yield a clear oil (2.10 g, 7.86 mmol, 46% yield).

B. Synthesis of 1-((4-methoxybenzyl)oxy)icos-5-yn-4-one (EJM-8-056)

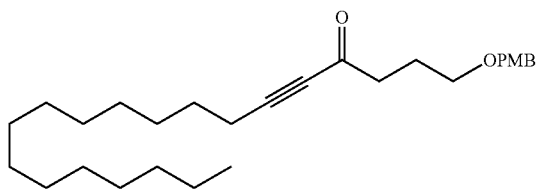

Hexadec-1-yne (0.253 mL, 0.900 mmol, 1.20 eq) was added to a 50 mL 3-neck oven-dried flask with a stir bar, diluted with 5 mL THF, cooled to −78° C., and stirred vigorously under Ar for 15 min. The solution was cloudy at this temperature, but stirring was vigorous. After addition of freshly titrated n-butyllithium (2.0 M in hexane, 0.486 mL, 0.970 mmol, 1.30 eq) dropwise, the resulting mixture was stirred at −78° C. for 15 min. After this time, the mixture was warmed to 0° C. and stirred vigorously under Ar for 15 min. N-Methoxy-4-((4-methoxybenzyl)oxy)-N-methylbutanamide (200 mg, 0.750 mmol, 1.00 eq) was added to a 50 mL oven-dried flask with a stir bar. Diluted with 2.5 mL THF, cooled to −78° C., and stirred vigorously under Ar for 15 min. The solution of lithiated alkyne was then transferred via cannula, and the resulting mixture was stirred vigorously at −78° C. under Ar for 30 min. After this time, TLC indicated only starting materials. Accordingly, the reaction mixture was warmed to room temperature and stirred for 30 min. After this time, TLC indicated generation of a new product. The reaction mixture was stirred for an additional 90 min, after which time TLC indicated further conversion of starting material to the new product, albeit with 2 impurities increasing in concentration over time. Accordingly, the reaction mixture was quenched with saturated aqueous ammonium chloride. The resulting aqueous layer was extracted 3 times with diethyl ether, and combined organic layers were dried over anhydrous sodium sulfate, filtered, and evaporated under reduced pressure to yield 455 mg of a slightly yellow oil, which was further purified via column chromatography (CombiFlash, 25 g column, 25 mL/min) eluting with a gradient mobile phase (0-3 min, 0% EtOAc in hexanes; 3-10 min, 0-33% EtOAc in hexanes; 10-13 min, 33% EtOAc in hexanes; 13-20 min, 33-100% EtOAc in hexanes; 20-25 min, 100% EtOAc in hexanes) to yield 49 mg of the starting amide and a clear oil (195 mg, 0.455 mmol, 61% yield).

C. Synthesis of 1-(((4,4-difluoroicos-5-yn-1-yl)oxy)methyl)-4-methoxy-benzene (EJM-8-057)

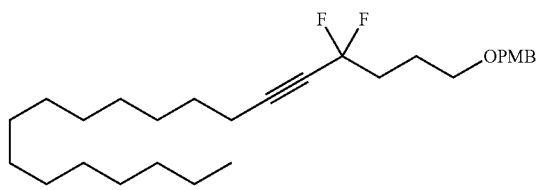

1-((4-Methoxybenzyl)oxy)icos-5-yn-4-one (970 mg, 2.26 mmol, 1.00 eq) was dissolved in DCE (2.26 mL) and added to a microwave vial with a stir bar. The resulting solution was stirred vigorously for 5 min under Ar. After addition of diethylaminosulfur trifluoride (0.900 mL, 6.79 mmol, 3.00 eq) in a dropwise fashion, followed by a single drop of EtOH, the resulting reaction tube was sealed, warmed to 60° C., and stirred vigorously for 2.5 hrs. After this time, the reaction mixture was quenched dropwise with saturated aqueous sodium bicarbonate. The resulting aqueous layer was extracted twice with DCM, and combined organic layers were dried over anhydrous sodium sulfate, filtered, and evaporated under reduced pressure to yield a brown oil. TLC indicated some conversion to product but lots of remaining starting material. Accordingly, the crude mixture was resubjected to the reaction conditions using only 1 mL DCE and stirring at 60° C. for 4 hrs. After this time, the reaction mixture was quenched dropwise with saturated aqueous sodium bicarbonate. The resulting aqueous layer was extracted twice with DCM, and combined organic layers were dried over anhydrous sodium sulfate, filtered, and evaporated under reduced pressure to yield a brown oil. TLC indicated more conversion to product and some remaining starting material. The product was purified via column chromatography (CombiFlash, 30 g column, 35 mL/min) eluting with a gradient mobile phase (0-2 min, 0% EtOAc in hexanes; 2-15 min, 0-10% EtOAc in hexanes; 15-20 min, 10% EtOAc in hexanes; 20-25 min, 10-100% EtOAc in hexanes; 25-30 min, 100% EtOAc) to yield 148 mg of the starting material and a yellow oil (340 mg, 0.755 mmol, 33% yield).

D. Synthesis of 4,4-difluoroicosan-1-ol (EJM-8-058)

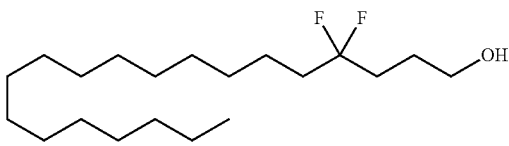 [SMILES: CCCCCCCCCCCCCCCCC(F)(F)CCCO]

1-(((4,4-Difluoroicos-5-yn-1-yl)oxy)methyl)-4-methoxybenzene (390 mg, 0.870 mmol, 1.00 eq) was added to a 50 mL flask with a stir bar. After dilution with ethyl acetate (4.5 mL) and ethanol (4.5 mL), the resulting solution was stirred vigorously at room temperature under Ar. After addition of palladium hydroxide on carbon (20% wt., 60.8 mg, 0.090 mmol, 0.100 eq), the resulting mixture was stirred vigorously under Ar. The mixture was then degassed under house vacuum for 5 min, followed by Ar flush. This vacuum flush cycle was repeated twice more before evacuating one last time for 5 min, followed by H₂ flush. The resulting reaction mixture was stirred vigorously at room temperature under H₂ balloon overnight. In the morning, the reaction mixture was filtered over a plug of celite, which was subsequently washed thoroughly with EtOAc. Solvent was evaporated under reduced pressure to yield an off-white solid. TLC indicated only about 50% conversion of the starting material to a new lower Rf spot. Accordingly, the crude material was resubjected to the reaction conditions with higher loading of palladium hydroxide on carbon (20% wt., 121 mg, 0.180 mmol, 0.200 eq), and the resulting reaction mixture was stirred vigorously overnight under hydrogen. In the next morning, the reaction mixture was filtered over a plug of celite, which was subsequently washed thoroughly with EtOAc. Solvent was evaporated under reduced pressure to yield a white solid. TLC indicated almost complete conversion of the starting material to a single lower $R_f$ spot (staining with PMA). The crude material was purified using column chromatography (CombiFlash, 10 g column, 35 mL/min), eluting with a gradient mobile phase (0-10 min, 0% MeOH in DCM; 10-20 min, 0-20% MeOH in DCM) to yield a white solid (203 mg, 0.607 mmol, 70% yield).

E. Objective to Synthesize Ammonium 4,4-difluoroicosyl (R)-(((1-(6-amino-9H-purin-9-yl)propan-2-yl)oxy)methyl)phosphonate (EJM-8-060)

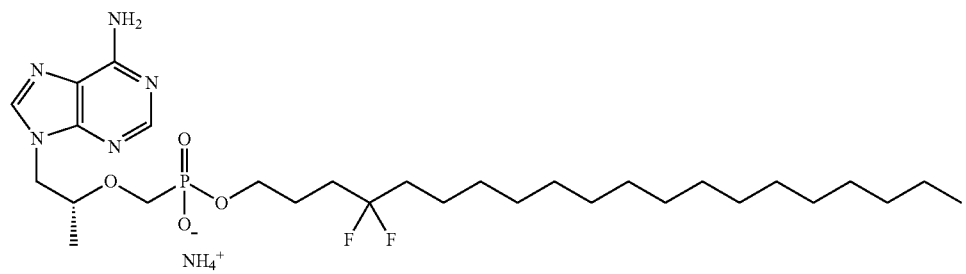 [SMILES: CCCCCCCCCCCCCCCCC(F)(F)CCCOP(=O)([O-])CO[C@H](C)Cn1cnc2c(N)ncnc21 ; [NH4+]]

4,4-difluoroicosyl (R)-(((1-(6-amino-9H-purin-9-yl)propan-2-yl)oxy)methyl)phosphonate can be synthesized by coupling tenofovir with 4,4-difluoroicosan-1-ol using methods described in Examples 1-3. An exemplary synthetic workflow is described below. Tenofovir (125 mg, 0.440 mmol, 1.00 eq) will be added to a 25 mL flame-dried flask with a stir bar. After dilution with pyridine (4.35 mL), the resulting slurry will be stirred vigorously at room temperature under Ar. After addition of 4,4-difluoroicosan-1-ol (204 mg, 0.610 mmol, 1.40 eq) and 2,4,6-triisopropylbenzenesulfonyl chloride (395 mg, 1.31 mmol, 3.00 eq), the resulting reaction mixture will be stirred vigorously overnight at room temperature under Ar. When TLC indicates significant product formation, the reaction mixture will be quenched with saturated aqueous ammonium chloride, and the resulting mixture will be evaporated under reduced pressure. The resulting solid will be diluted with 200 mL of 3:1 DCM to MeOH, and the resulting slurry will be stirred vigorously at room temperature under Ar overnight. In the next morning, the contents will be filtered, the filtrate will be washed thoroughly with 3:1 DCM to MeOH, and the resulting mother liquor will be evaporated under reduced pressure to yield the product as a solid.

Example 5. Synthesis of Ammonium 3-(hexadec-15-yn-1-yloxy)propyl (R)-(((1-(6-amino-9H-purin-9-yl)propan-2-yl)oxy)methyl)phosphonate

A. Synthesis of 2-(hexadec-2-yn-1-yloxy)tetrahydro-2H-pyran (MD-5-67)

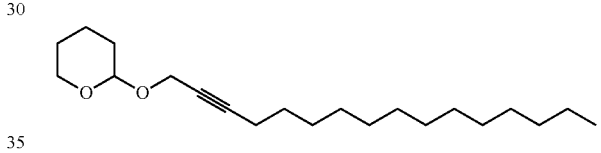

In a 250 mL three neck round bottom flask, to a mixture of 2-(2-propynyloxy)tetrahydro-2H-pyran (2.0 mL, 14.2 mmol, 1.0 eq) and 1,3-dimethyl-3,4,5,6-tetrahydro-2(1H)-pyrimidinone (5.1 mL, 42.8 mmol, 3.0 eq) was added anhydrous THF (40 mL) and cooled to −78° C. After 30 min, n-butyllithium (2.5 M in hexanes, 7.4 mL, 18.5 mmol, 1.3 eq) was added dropwise via a syringe pump at a rate of 20 mL/hr. The mixture was stirred for 1 h and then added 1-bromotridecane (4.7 mL, 18.5 mmol, 1.3 eq) dropwise over 10 min. The reaction was allowed to warm to room temperature and stirred overnight. After 21 h, TLC analysis indicated complete conversion to product ($R_f$=0.43, 7.5% EtOAc/hexanes, PMA stain). The reaction mixture was quenched by the addition of saturated ammonium chloride and extracted three times with EtOAc. The combined organic layers were dried over anhydrous Na₂SO₄, filtered and concentrated under reduced pressure to give a crude oil.

Purification by silica gel chromatography eluting with 0-5% EtOAc/hexanes yielded product as an oil (3.5 g, 10.8 mmol, 76%).

B. Synthesis of hexadec-2-yn-1-ol (MD-5-68)

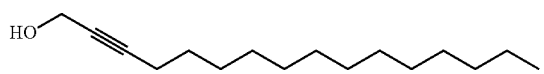 [SMILES: CCCCCCCCCCCCCC#CCO]

To a cloudy solution of 2-(hexadec-2-yn-1-yloxy)tetrahydro-2H-pyran (2.5 g, 7.7 mmol, 1.0 eq) in methanol (20 mL) was added p-toluenesulfonic acid (133.4 mg, 0.78 mmol, 0.1 eq). The resulting homogeneous solution was stirred at room temperature overnight. After 16 h, TLC (7.5% EtOAc/hexanes, PMA stain) indicated full conversion to product. The reaction mixture was concentrated under reduced pressure, redissolved in hexanes and adsorbed onto silica gel and purified by silica gel flash chromatography eluting with 0-10% EtOAc/hexanes to afford product as a white solid (1.6 g, 6.7 mmol, 86%).

C. Synthesis of hexadec-15-yn-1-ol (MD-5-69)

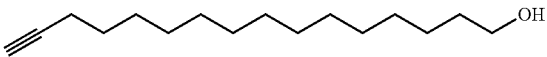 [SMILES: C#CCCCCCCCCCCCCCCO]

In a three neck round bottom flask, a solution of sodium hydride (60% dispersion in mineral oil, 2.1 g, 53.3 mmol, 8.0 eq) in 1,3-diaminopropane (27.8 mL, 333.4 mmol, 50 eq) was heated at 70° C. for 1 h. After allowing the reaction mixture to cool to room temperature, hexadec-2-yn-1-ol (1.5 g, 6.6 mmol, 1.0 eq) was added as a solid in portions and the suspension was heated at 55° C. overnight. After 17 h, the reaction mixture was allowed to cool to room temperature, quenched with water and acidified with 3 N aqueous HCl until pH=2. The mixture was then extracted with hexanes (×3), dried over Na$_2$SO$_4$, filtered and concentrated under reduced pressure to obtain a brown oil. The residue was purified by silica gel chromatography eluting with 0-5% EtOAc/hexanes to afford the product as a white solid (1.0 g, 4.38 mmol, 65% yield).

D. Synthesis of 16-bromohexadec-1-yne (MD-5-70)

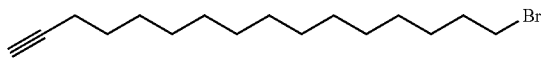 [SMILES: C#CCCCCCCCCCCCCCCBr]

To a solution of hexadec-15-yn-1-ol (500.0 mg, 2.1 mmol) in anhydrous DCM (3 mL) was added carbon tetrabromide (1043.2 mg, 3.1 mmol, 1.5 eq) and triphenylphosphene (825.1 mg, 3.1 mmol, 1.5 eq). The resulting pale yellow solution was stirred at room temperature for 30 min, TLC analysis (7.5% EtOAc/hexanes, PMA stain) indicated complete conversion. The reaction mixture was concentrated under reduced pressure followed by addition of hexanes resulted in precipitation of solids. The solids were removed by filtration and rinsed with hexanes. The filtrate was concentrated under reduced pressure to give a semi-solid which upon drying under high vacuum resulted into a white solid.

E. Synthesis of 3-(hexadec-15-yn-1-yloxy)propan-1-ol (MD-5-71)

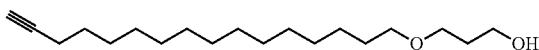 [SMILES: C#CCCCCCCCCCCCCCCOCCCO]

To a solution of 1,3-dihydroxypropane (0.5 mL, 7.0 mmol, 4.5 eq) in anhydrous DMF (3 mL) at 0° C. was added sodium hydride (60% dispersion in mineral oil, 0.09 g, 2.3 mmol, 1.5 eq) in batches and stirred at room temperature for 30 min. To this 16-bromohexadec-1-yne (0.5 g, 1.5 mmol, 1.0 eq) was added followed by iodopotassium (0.2 g, 1.5 mmol, 1.0 eq) and heated at 95° C. for 3 h. The reaction mixture was then cooled to 0° C. and quenched with slow addition of ice cold water (15 mL) and extracted with EtOAc (30 mL). The organic layer was collected and re washed with brine (2×15 mL). The organic layer was dried over Na$_2$SO$_4$, filtered and concentrated and purified by silica gel chromatography eluting with 0-30% EtOAc/hexanes to obtain product as a white solid (0.16 g, 0.5 mmol, 35% yield).

F. Synthesis of Ammonium 3-(hexadec-15-yn-1-yloxy)propyl (R)-(((1-(6-amino-9H-purin-9-yl)propan-2-yl)oxy)methyl)phosphonate (MD-5-72)

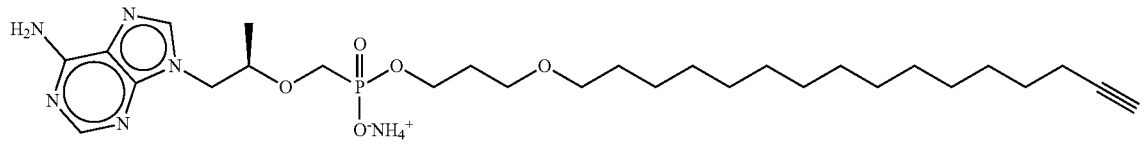

Prior to use, commercially available tenofovir was dried under vacuum oven at 55° C. overnight. A 100 mL three neck flask equipped with a condenser was charged with 3-(hexadec-15-yn-1-yloxy)propan-1-ol (155.0 mg, 0.522 mmol, 1.0 eq), tenofovir (150.15 mg, 0.522 mmol, 1.0 eq), and suspended in anhydrous DMF (2 mL) and added triethylamine (0.15 mL, 1.045 mmol, 2.0 eq) dropwise. To the resulting homogeneous solution, N,N'-dicyclohexylcarbodiimide (215.73 mg, 1.045 mmol, 2.0 eq) and 4-dimethylaminopyridine (6.3 mg, 0.052 mmol, 0.1 eq) were added and stirred at room temperature for 10 min and then heated at 95° C. overnight. After 17 h, TLC analysis indicated product (30% MeOH/CH$_2$Cl$_2$ spiked with 10% NH$_4$OH). The mixture was allowed to cool to room temperature and directly loaded on silica gel chromatography for purification eluting with 0-30% MeOH (spiked with 10% NH$_4$OH)/DCM to obtain product as a white solid. The solid was resubjected to second purification on reverse-phase C18 chromatography (CombiFlash) eluting with 5-100% MeOH/H$_2$O to obtain product in 70-90% gradient. Product fractions were pooled and concentrated and co-concentrated with methanol spiked with 10% NH$_4$OH (×3) and vacuum dried to obtain product as a white solid (73.0 mg, 0.125 mmol, 24% yield). Melting point (MP) 135° C.-160.9° C. $^1$H NMR (399 MHz, CD$_3$OD) δ 8.31 (s, 1H), 8.20 (s, 1H), 4.37 (dd, J=14.4, 3.1 Hz, 1H), 4.22 (dd, J=14.4, 6.7 Hz, 1H), 3.92-3.81 (m, 3H), 3.71 (dd, J=12.7, 9.4 Hz, 1H), 3.50-3.45 (m, 1H), 3.42 (t, J=6.4 Hz, 2H), 3.33 (t, J=6.6 Hz, 2H), 2.16-2.10 (m, 3H), 1.77 (p, J=5.5 Hz, 2H), 1.51-1.44 (m, 4H), 1.42-1.33 (m, 2H), 1.33-1.24 (m, 18H), 1.16 (d, J=6.2 Hz, 3H). $^{13}$C NMR (151 MHz, CD$_3$OD) δ 156.2, 152.3, 150.5, 144.1, 119.2, 85.0, 76.6 (d, J=12.9 Hz), 71.8, 69.0, 68.2, 65.1 (d, J=159.9 Hz), 62.8 (d, J=5.5 Hz), 48.9, 32.1 (d, J=6.1 Hz), 30.5, 30.4, 30.4, 30.4, 30.3, 29.9, 29.5, 29.4, 27.0, 18.9, 16.7. $^{31}$P NMR (162 MHz, CD$_3$OD) δ 15.45. HRMS (APCI) m/z calculated for C$_{28}$H$_{49}$N$_5$O$_5$P [M+H]$^+$: 566.34658, found 566.34623. LC-MS (ESI) 85-95% MeOH/H$_2$O (0.1% HCO$_2$H), 5 min, 1.00 mL/min, rt=2.56 min, m/z=566.4 [M+H]$^+$; LC-MS (ESI) 80-95% MeOH/H$_2$O (0.1% HCO$_2$H), 5 min, rt=3.38 min, m/z=566.4 [M+H]$^+$.

Example 6. Synthesis of Ammonium Octadecyl (R)-(((1-(6-amino-9H-purin-9-yl)propan-2-yl)oxy)methyl)phosphonate (MD-1-105)

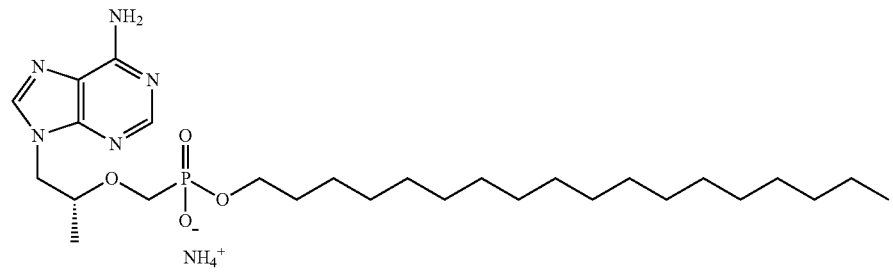 [SMILES: CCCCCCCCCCCCCCCCCCOP(=O)([O-])CO[C@H](C)Cn1cnc2c(N)ncnc21 ; [NH4+]]

To a stirring suspension of dry tenofovir (200 mg, 0.696 mmol, 1.00 eq), DCC (287 mg, 1.39 mmol, 2.00 eq), and 1-octadecanol (188 mg, 0.696 mmol, 1.00 eq) in anhydrous DMF (2.3 mL) under inert atmosphere was added triethylamine (194 μL, 1.39 mmol, 2.00 eq) and DMAP (8.51 mg, 0.0696 mmol, 10 mol %). The reaction mixture was stirred at room temperature for 10 min, then heated to 105° C. overnight. After confirming the formation of product by LC-MS, the reaction mixture was quenched with water, stirred for 20 min at room temperature, and immediately purified by normal phase column chromatography (0-70% DCM:DCM/MeOH/NH$_4$OH (80:20:3)). The product fractions were collected, concentrated under reduced pressure, and purified by reverse phase column chromatography (0-85% H$_2$O:MeOH). The product fractions were collected once again, concentrated under reduced pressure, stirred with 7 N ammonia in methanol (10 mL) for 10 min at room temperature, and dried under vacuum, yielding MD-1-105 as a white solid (132 mg, 35% yield). MP=154-184° C. (Decomp. started at 171° C.). $^1$H NMR (600 MHz, CD$_3$OD) δ 8.33 (s, 1H), 8.21 (s, 1H), 4.39 (dd, J=14.4, 3.1 Hz, 1H), 4.24 (dd, J=14.5, 6.7 Hz, 1H), 3.91 (pd, J=6.3, 2.9 Hz, 1H), 3.81-3.68 (m, 3H), 3.48 (dd, J=12.8, 10.0 Hz, 1H), 1.56-1.44 (m, 2H), 1.35-1.21 (m, 30H), 1.16 (d, J=6.3 Hz, 3H), 0.90 (t, J=7.0 Hz, 3H). $^{13}$C NMR (126 MHz, CD$_3$OD) δ 157.2, 153.5, 150.9, 144.2, 119.6, 76.9 (d, J=12.8 Hz), 65.9 (d, J=5.9 Hz), 65.6 (d, J=160.3 Hz), 33.1, 32.1 (d, J=6.3 Hz), 30.8, 30.7, 30.7, 30.7, 30.5, 26.9, 23.7, 16.8, 14.4. $^{31}$P NMR (243 MHz, CD$_3$OD) δ 15.4. HRMS (APCI) m/z calculated for C$_{27}$H$_{51}$N$_5$O$_4$P$^+$ [M+H]$^+$: 540.36732, found 540.36763. HPLC 95% MeOH in H$_2$O, 10 min, m/z=540.4 (M+H), t=2.440 min; 75-95% MeOH in H$_2$O, 10 min, m/z=540.4 (M+H), t=8.845 min.

Example 7. Synthesis of Ammonium Pentadecyl (R)-(((1-(6-amino-9H-purin-9-yl)propan-2-yl)oxy)methyl)phosphonate (MD-1-106)

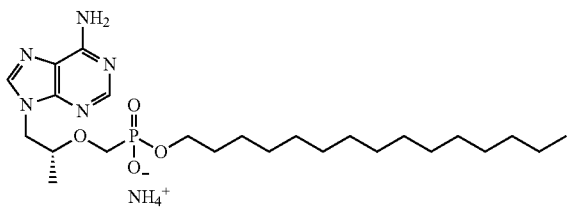 [SMILES: CCCCCCCCCCCCCCCOP(=O)([O-])CO[C@H](C)Cn1cnc2c(N)ncnc21 ; [NH4+]]

MD-1-106 was synthesized by following general procedure for MD-1-105, using 1-pentadecanol (159 mg, 0.696 mmol, 1.00 eq). Purification yielded MD-1-106 as a white powder (124 mg, 36% yield). MP=162-190° C. (Decomp. started at 179° C.). $^1$H NMR (600 MHz, CD$_3$OD) δ 8.33 (s, 1H), 8.21 (s, 1H), 4.39 (dd, J=14.5, 3.1 Hz, 1H), 4.24 (dd, J=14.4, 6.7 Hz, 1H), 3.90 (pd, J=6.3, 3.1 Hz, 1H), 3.80-3.68 (m, 3H), 3.47 (dd, J=12.8, 10.0 Hz, 1H), 1.55-1.44 (m, 2H), 1.35-1.21 (m, 24H), 1.16 (d, J=6.3 Hz, 3H), 0.90 (t, J=7.0 Hz, 3H). $^{13}$C NMR (126 MHz, CD$_3$OD) δ 157.1, 153.3, 150.9, 144.3, 119.5, 76.9 (d, J=12.9 Hz), 65.9 (d, J=5.8 Hz), 65.5 (d, J=159.7 Hz), 33.1, 32.1 (d, J=6.3 Hz), 30.8, 30.8, 30.7, 30.7, 30.5, 26.9, 23.7, 16.8, 14.4. $^{31}$P NMR (243 MHz, CD$_3$OD) δ 15.3. HRMS (APCI) m/z calculated for C$_{24}$H$_{45}$N$_5$O$_4$P$^+$ [M+H]$^+$: 498.32037, found 498.32072. HPLC 95% MeOH in H$_2$O, 10 min, m/z=498.2 (M+H), t=1.714 min; 75-95% MeOH in H$_2$O, 10 min, m/z=498.2 (M+H), t=5.635 min.

Example 8. Synthesis of Ammonium 3-(hexadecylthio)propyl (R)-(((1-(6-amino-9H-purin-9-yl)propan-2-yl)oxy)methyl) phosphonate A. Synthesis of 3-(dexadecylthio)propan-1-ol (MD-1-121)

To an Ar degassed solution of 3-mercaptopropanol (1.13 mL, 13.1 mmol, 2.00 eq) in DMF (33 mL) was added 1,8-diazabicyclo(5.4.0)undec-7-ene (1.96 mL, 13.1 mmol, 2.00 eq), and the solution was stirred for 20 min at room temperature. 1-Bromohexadecane (2.00 mL, 6.55 mmol, 1.00 eq) was added dropwise, and the reaction mixture was heated to 60° C. for 1.5 hr. After confirming complete conversion by TLC, the reaction mixture was diluted with EtOAc (10×DMF volume). The organic layer was washed with sat. aq. $NH_4Cl$ (4×), dried with $Na_2SO_4$, and concentrated, producing an off-white solid. The solid was purified by column chromatography (0-40% EtOAc in hexanes), yielding MD-1-121 as a fluffy white solid (1.85 g, 89% yield).

B. Synthesis of Ammonium 3-(hexadecylthio)propyl (R)-(((1-(6-amino-9H-purin-9-yl)propan-2-yl)oxy)methyl) phosphonate (MD-1-123)

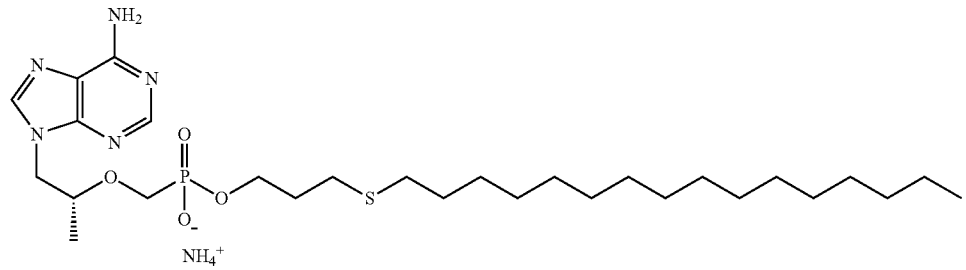 [SMILES: CCCCCCCCCCCCCCCCSCCCOP(=O)([O-])CO[C@H](C)Cn1cnc2c(N)ncnc21 ; [NH4+]]

MD-1-123 was synthesized by following general procedure for MD-1-105, using 3-(hexadecylthio)propan-1-ol (220 mg, 0.696 mmol, 1.00 eq). Purification yielded MD-1-123 as a white solid (136 mg, 33% yield). MP=160-184° C. (Decomp. started at 177° C.). $^1$H NMR (400 MHz, $CD_3OD$) δ 8.33 (s, 1H), 8.21 (s, 1H), 4.39 (dd, J=14.4, 3.1 Hz, 1H), 4.24 (dd, J=14.4, 6.7 Hz, 1H), 3.95-3.78 (m, 3H), 3.72 (dd, J=12.7, 9.5 Hz, 1H), 3.47 (dd, J=12.7, 10.1 Hz, 1H), 2.50 (t, J=7.3 Hz, 2H), 2.46-2.41 (m, 2H), 1.82-1.69 (m, 2H), 1.56-1.47 (m, 2H), 1.39-1.21 (m, 26H), 1.17 (d, J=6.2 Hz, 3H), 0.90 (t, J=6.9 Hz, 3H). $^{13}$C NMR (126 MHz, $CD_3OD$) δ 157.1, 153.3, 150.9, 144.3, 119.6, 76.9 (d, J=12.9 Hz), 65.5 (d, J=160.0 Hz), 64.6 (d, J=5.8 Hz), 33.1, 32.8, 32.2 (d, J=6.4 Hz), 30.8, 30.8, 30.8, 30.7, 30.7, 30.5, 30.4, 29.9, 29.2, 23.7, 16.8, 14.4. $^{31}$P NMR (162 MHz, $CD_3OD$) δ 15.4. HRMS (NSI) m/z calculated for $C_{28}H_{53}N_5O_4PS^+$ [M+H]$^+$: 586.35504, found 586.35506. HPLC 95% MeOH in $H_2O$, 10 min, m/z=586.2 (M+H), t=2.315 min; 75-95% MeOH in $H_2O$, 10 min, m/z=586.3 (M+H), t=8.697 min.

Example 9. Synthesis of Ammonium 9-(decylthio)nonyl (R)-(((1-(6-amino-9H-purin-9-yl)propan-2-yl)oxy)methyl)phosphonate

A. Synthesis of 9-(decylthio)nonan-1-ol (MD-1-120)

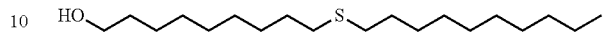

To an Ar degassed solution of 1-decanethiol (3.70 mL, 17.9 mmol, 2 eq) in DMF (34 mL) was added 1,8-diazabicyclo(5.4.0)undec-7-ene (2.68 mL, 17.9 mmol, 2 eq), and the solution was stirred for 20 min at room temperature. 9-Bromo-1-nonanol (2.00 g, 8.96 mmol, 1.00 eq) in DMF (10 mL) was then added dropwise, and the reaction mixture was heated to 60° C. for 1.5 hr. After confirming complete conversion by TLC, the reaction mixture was diluted with EtOAc (10×DMF volume). The organic layer was washed with sat. aq. $NH_4Cl$ (4×), dried with $Na_2SO_4$, and concentrated, producing an off-white solid. The crude material was washed with cold hexanes (3×), yielding MD-1-120 as a shiny white solid (2.15 g, 76% yield).

B. Synthesis of Ammonium 9-(decylthio)nonyl (R)-(((1-(6-amino-9H-purin-9-yl)propan-2-yl)oxy)methyl)phosphonate (MD-1-122)

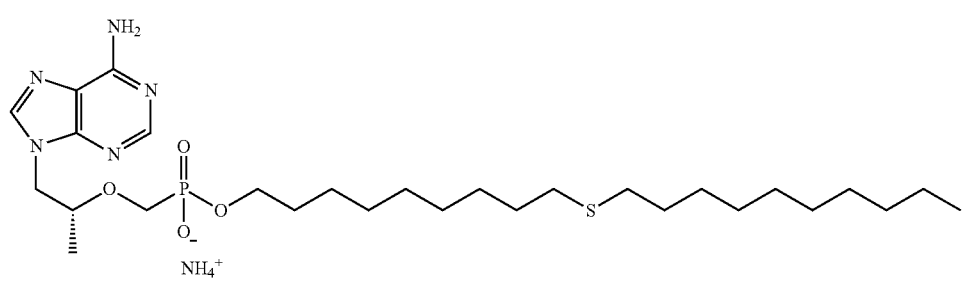 [SMILES: CCCCCCCCCCSCCCCCCCCCOP(=O)([O-])CO[C@H](C)Cn1cnc2c(N)ncnc21 ; [NH4+]]

MD-1-122 was synthesized by following general procedure for MD-1-105, using 9-(decylthio)nonan-1-ol (220 mg, 0.696 mmol, 1.00 eq). Purification yielded MD-1-122 as a white solid (122 mg, 30% yield). MP=160-190° C. (Decomp. started at 176° C.). $^1$H NMR (600 MHz, $CD_3OD$) δ 8.33 (s, 1H), 8.21 (s, 1H), 4.39 (dd, J=14.5, 3.1 Hz, 1H), 4.24 (dd, J=14.5, 6.7 Hz, 1H), 3.91 (pd, J=6.2, 3.0 Hz, 1H), 3.80-3.68 (m, 3H), 3.47 (dd, J=12.8, 10.0 Hz, 1H), 2.48 (t, J=7.3 Hz, 2H), 2.48 (t, J=7.3 Hz, 2H), 1.60-1.46 (m, 6H), 1.42-1.22 (m, 24H), 1.16 (d, J=6.2 Hz, 3H), 0.90 (t, J=7.0 Hz, 3H). $^{13}$C NMR (126 MHz, CD$_3$OD) δ 156.7, 152.8, 150.9, 144.5, 119.5, 76.9 (d, J=12.8 Hz), 65.9 (d, J=5.9 Hz), 65.5 (d, J=159.7 Hz), 33.1, 32.9, 32.1 (d, J=6.3 Hz), 30.8, 30.8, 30.7, 30.6, 30.4, 30.4, 30.3, 30.3, 29.9, 29.9, 26.9, 23.7, 16.8, 14.4. $^{31}$P NMR (243 MHz, CD$_3$OD) δ 15.3. HRMS (APCI) m/z calculated for C$_{28}$H$_{51}$N$_5$O$_4$PS$^-$ [M−H]$^-$: 584.34049. Found 584.34077. HPLC 95% MeOH in H$_2$O, 10 min, m/z=586.3 (M+H), t=1.459 min; 75-95% MeOH in H$_2$O, 10 min, m/z=586.3 (M+H), t=7.541 min.

Example 10. Synthesis of Ammonium 3-((16-methoxy-16-oxohexadecyl)thio)propyl (R)-(((1-(6-amino-9H-purin-9-yl)propan-2-yl)oxy)methyl)phosphonate A. Synthesis of Methyl 16-((3-hydroxypropyl)thio)hexadecanoate (MD-1-28)

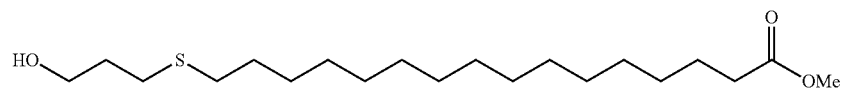 [SMILES: COC(=O)CCCCCCCCCCCCCCCSCCCO]

To an Ar degassed solution of 3-mercaptopropanol (2.35 mL, 27.2 mmol, 2.00 eq) in DMF (68 mL) was added 1,8-diazabicyclo(5.4.0)undec-7-ene (4.07 mL, 27.2 mmol, 2.00 eq), and the solution was stirred for 20 min at room temperature. 16-Bromohexadecanoate (4.75 g, 13.6 mmol, 2.00 eq) in DMF (10 mL) was then added dropwise, and the reaction mixture was heated to 60° C. for 1.5 hr. After confirming complete conversion by TLC, the reaction mixture was diluted with EtOAc (5×DMF volume). The organic layer was washed with water (4×) and brine, dried with MgSO$_4$, and concentrated, producing an off-white solid. The solid was purified by column chromatography (0-40% EtOAc in hexanes), yielding MD-1-28 as a white solid (4.29 g, 88% yield).

B. Synthesis of Ammonium 3-((16-methoxy-16-oxohexadecyl)thio)propyl (R)-(((1-(6-amino-9H-purin-9-yl)propan-2-yl)oxy)methyl)phosphonate (MD-1-124)

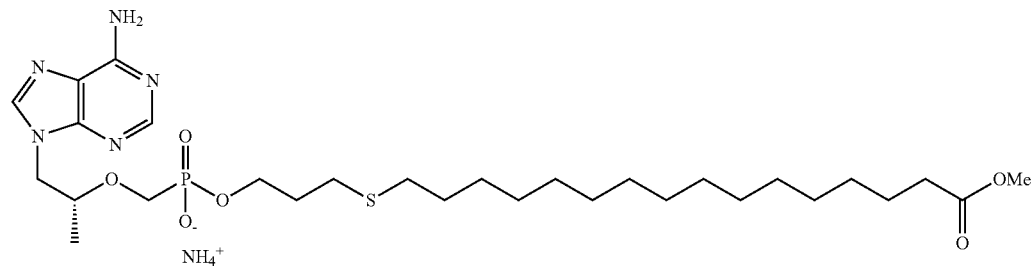

MD-1-124 was synthesized by following general procedure for MD-1-105, using methyl 16-((3-hydroxypropyl)thio)hexadecanoate (251 mg, 0.696 mmol, 1.00 eq). Purification yielded MD-1-124 as white solid (139 mg, 32% yield). MP=146-169° C. (Decomp. started at 163° C.). $^1$H NMR (600 MHz, CD$_3$OD) δ 8.32 (s, 1H), 8.20 (s, 1H), 4.38 (dd, J=14.4, 3.2 Hz, 1H), 4.24 (dd, J=14.4, 6.7 Hz, 1H), 3.93-3.80 (m, 3H), 3.72 (dd, J=12.8, 9.5 Hz, 1H), 3.65 (s, 3H), 3.47 (dd, J=12.8, 10.0 Hz, 1H), 2.51 (t, J=7.3 Hz, 2H), 2.44 (t, J=7.3 Hz, 2H), 2.31 (t, J=7.4 Hz, 2H), 1.82-1.70 (m, 2H), 1.60 (p, J=7.2 Hz, 2H), 1.52 (p, J=7.3 Hz, 2H), 1.37-1.25 (m, 22H), 1.16 (d, J=6.2 Hz, 3H). $^{13}$C NMR (151 MHz, CD$_3$OD) δ 176.1, 157.0, 153.2, 150.9, 144.3, 119.6, 76.9 (d, J=12.8 Hz), 65.5 (d, J=159.9 Hz), 64.6 (d, J=5.7 Hz), 52.0, 34.8, 32.8, 32.2 (d, J=6.3 Hz), 30.8, 30.7, 30.7, 30.7, 30.7, 30.6, 30.4, 30.2, 29.9, 29.2, 26.0, 16.8. $^{31}$P NMR (243 MHz, CD$_3$OD) δ 15.3. HRMS (APCI) m/z calculated for C$_{29}$H$_{51}$N$_5$O$_6$PS$^-$ [M−H]$^-$: 628.33031. Found 628.33149. HPLC 85-95% MeOH in H$_2$O, 10 min, m/z=630.3 (M+H), t=1.757 min; 75-95% MeOH in H$_2$O, 10 min, m/z=630.3 (M+H), t=4.839 min.

Example 11. Synthesis of Ammonium 3-((11-(phenylthio)undecyl)thio)propyl (R)-(((1-(6-amino-9H-purin-9-yl)propan-2-yl)oxy)methyl)phosphonate A. Synthesis of 11-(phenylthio)undecan-1-ol (MD-1-116)

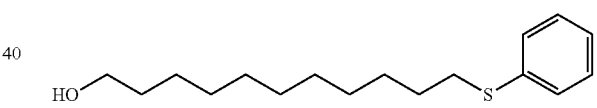

To an Ar degassed solution of thiophenol (1.62 mL, 15.9 mmol, 2.00 eq) in DMF (30 mL) was added 1,8-diazabicyclo (5.4.0)undec-7-ene (2.38 mL, 15.9 mmol, 2.00 eq), and the solution was stirred for 20 min at room temperature. 11-Bromo-1-undecanol (2.00 g, 7.96 mmol, 1.00 eq) in DMF (10 mL) was added dropwise, and the reaction mixture was heated to 60° C. for 1.5 hr. After confirming complete conversion by TLC, the reaction mixture was diluted with EtOAc (10×DMF volume). The organic layer was washed with sat. aq. NH$_4$Cl (4×) and brine, dried with Na$_2$SO$_4$, and concentrated, producing a pale yellow solid. The crude product was washed with cold hexanes (3×) to the yield MD-1-116 as a white solid (1.95 g, 87% yield).

B. Synthesis of 3-((11-(phenylthio)undecyl)thio) propan-1-ol (MD-1-118)

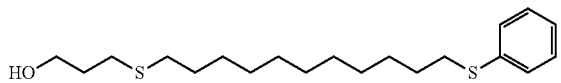 [SMILES: OCCCSCCCCCCCCCCCSc1ccccc1]

To a solution of 11-(phenylthio)undecan-1-ol (1.00 g, 3.57 mmol 1.00 eq) and triethylamine (745 µL, 5.35 mmol, 1.50 eq) in DCM (9 mL) at 0° C. under inert atmosphere was added methanesulfonyl chloride (414 µL, 5.35 mmol, 1.50 eq) dropwise. The reaction mixture was stirred at 0° C. for 15 min, then allowed to warm to room temperature for 30 min. Upon confirming complete conversion by TLC, the reaction mixture was diluted with DCM. The organic layer was washed with sat. aq. NH$_4$Cl (2×), sat. aq. NaHCO$_3$, and brine, dried with Na$_2$SO$_4$, and concentrated to yield 11-(phenylthio)undecyl methanesulfonate (1.27 g, >95% yield) as a yellow oil which was taken on immediately without further purification.

To a Ar degassed solution of 3-mercaptopropanol (612 µL, 7.08 mmol, 2.00 eq) in DMF (12 mL) was added 1,8-diazabicyclo(5.4.0)undec-7-ene (1.06 mL, 7.08 mmol, 2.00 eq), and the solution was stirred for 20 min at room temperature. 11-(Phenylthio)undecyl methanesulfonate in DMF (5 mL) was added dropwise, and the reaction mixture was heated to 60° C. for 1.5 hr. After confirming complete conversion by TLC, the reaction mixture was diluted with EtOAc (10×DMF volume), and the combined organics were washed with sat. aq. NH$_4$Cl (4×) and brine, dried with Na$_2$SO$_4$, and concentrated, producing a pale yellow solid. The solid was purified by column chromatography (0-40% EtOAc in hexanes), and the product fractions were collected, concentrated, and washed with cold hexanes (3×) to yield MD-1-118 as a white solid (858 mg, 68% yield over two steps).

C. Synthesis of Ammonium 3-((11-(phenylthio) undecyl)thio)propyl (R)-(((1-(6-amino-9H-purin-9-yl)propan-2-yl)oxy)methyl)phosphonate (MD-1-119)

MD-1-119 was synthesized by following general procedure for MD-1-105, using 3-((11-(phenylthio)undecyl)thio) propan-1-ol (247 mg, 0.696 mmol, 1.00 eq). Purification yielded MD-1-119 as white solid (111 mg, 25% yield). MP=146-173° C. (Decomp. started at 167° C.). $^1$H NMR (400 MHz, CD$_3$OD) δ 8.33 (s, 1H), 8.21 (s, 1H), 7.33-7.23 (m, 4H), 7.17-7.12 (m, 1H), 4.38 (dd, J=14.4, 3.1 Hz, 1H), 4.23 (dd, J=14.4, 6.7 Hz, 1H), 3.94-3.79 (m, 3H), 3.72 (dd, J=12.7, 9.4 Hz, 1H), 3.47 (dd, J=12.8, 10.1 Hz, 1H), 2.95-2.88 (m, 2H), 2.50 (t, J=7.3 Hz, 2H), 2.46-2.41 (m, 2H), 1.82-1.69 (m, 2H), 1.65-1.56 (m, 2H), 1.51 (p, J=7.1 Hz, 2H), 1.46-1.22 (m, 14H), 1.16 (d, J=6.2 Hz, 3H). $^{13}$C NMR (126 MHz, CD$_3$OD) δ 156.7, 152.8, 150.9, 144.4, 138.3, 130.1, 129.9, 126.7, 119.6, 76.9 (d, J=12.9 Hz), 65.4 (d, J=159.6 Hz), 64.6 (d, J=5.8 Hz), 34.3, 32.8, 32.2 (d, J=6.2 Hz), 30.8, 30.6, 30.6, 30.6, 30.3, 30.3, 30.2, 29.9, 29.7, 29.2, 16.8. $^{31}$P NMR (162 MHz, CD$_3$OD) δ 15.4. HRMS (APCI) m/z calculated for C$_{29}$H$_{45}$N$_5$O$_4$PS$_2^-$ [M−H]$^-$: 622.26561. Found 622.26573. HPLC 85-95% MeOH in H$_2$O, 10 min, m/z=624.2 (M+H), t=1.866 min; 75-95% MeOH in H$_2$O, 10 min, m/z=624.2 (M+H), t=5.534 min.

Example 12. Synthesis of Ammonium 3-(hexadec-15-yn-1-ylthio)propyl (R)-(((1-(6-amino-9H-purin-9-yl)propan-2-yl)oxy) methyl) phosphonate A. Synthesis of trimethyl(16-((tetrahydro-2H-pyran-2-yl)oxy)hexadec-1-yn-1-yl)silane (MD-1-154)

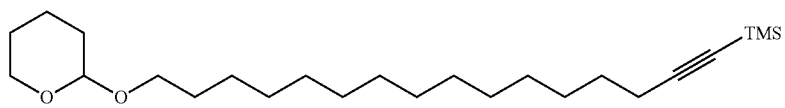

To a solution of trimethylsilylacetylene (6.88 mL, 49.7 mmol, 3.00 eq) in THF (28 mL) at −78° C. under inert atmosphere was added n-BuLi (2.5 M in hexanes, 19.9 mL, 49.7 mmol, 3.00 eq) dropwise. The reaction mixture was stirred at −78° C. for 15 min, then warmed to −40° C. for 1 hr. HMPA (8.64 mL, 49.7 mmol, 3.00 eq) and 2-(14-bromododecoxy)tetrahydropyran (6.25 g, 16.6 mmol, 1.00 eq) in THF were added dropwise at −40° C. The reaction mixture was stirred at −40° C. for 1 hr, then warmed to 0° C. for 5 hr. After confirming complete conversion by TLC, the reaction mixture was quenched with sat. aq. NH$_4$Cl, and the aqueous layer was extracted with EtOAc (3×). The collected organics were washed with sat. aq. NH$_4$Cl and brine, dried with Na$_2$SO$_4$, and concentrated to produce a golden brown oil. The residue was purified by column chromatography (0-1% EtOAc in hexanes) to yield MD-1-154 as a colorless oil (5.72 g, 88% yield).

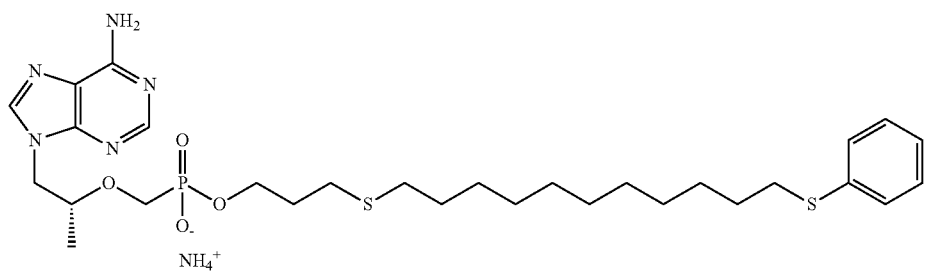

B. Synthesis of 16-(trimethylsilyl)hexadec-15-yn-1-ol (MD-1-158)

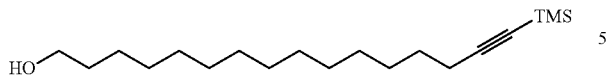

To a solution of MD-1-154 (5.72 g, 14.5 mmol) in MeOH (48 mL) under inert atmosphere was added p-toluenesulfonic acid monohydrate (276 mg, 1.45 mmol, 10 mol %), and the reaction mixture was stirred at room temperature overnight. Upon confirming complete conversion by TLC, the reaction mixture was concentrated under reduced pressure and purified by column chromatography (0-10% EtOAc in hexanes), yielding MD-1-158 as a white crystalline solid (3.09 g, 69% yield).

C. Synthesis of 3-((16-(trimethylsilyl)hexadec-15-yn-1-yl)thio)propan-1-ol (MD-1-162)

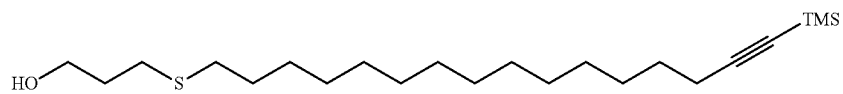 [SMILES: C[Si](C)(C)C#CCCCCCCCCCCCCCCSCCCO]

To a solution of MD-1-158 (2.53 g, 8.14 mmol, 1.00 eq) and triethylamine (1.70 mL, 12.2 mmol, 1.50 eq) in anhydrous DCM (20 mL) at 0° C. under inert atmosphere was added methanesulfonyl chloride (945 µL, 12.2 mmol, 1.50 eq) dropwise. The reaction mixture was stirred at 0° C. for 15 min, then allowed to warm to room temperature for 30 min. After confirming complete conversion by TLC, the reaction mixture was diluted with DCM. The organic layer was washed with sat. aq. NH$_4$Cl (2×), sat. aq. NaHCO$_3$, and brine, dried with Na$_2$SO$_4$, and concentrated to yield 16-(trimethylsilyl)hexadec-15-yn-1-yl methanesulfonate (3.07 g, >95% yield) as a yellow oil which was taken on immediately without further purification.

To an Ar degassed solution of 3-mercaptopropanol (1.36 mL, 15.8 mmol, 2.00 eq) in anhydrous DMF (30 mL) was added 1,8-diazabicyclo(5.4.0)undec-7-ene (2.36 mL, 15.8 mmol, 2.00 eq), and the solution was stirred for 20 min at room temperature. 16-(Trimethylsilyl)hexadec-15-yn-1-yl methanesulfonate (3.07 g, 7.89 mmol, 1.00 eq) in DMF (10 mL) was added dropwise, and the reaction mixture was heated to 60° C. for 2.5 hr. After confirming complete conversion by TLC, the reaction mixture was diluted with EtOAc (10×DMF volume). The organic layer was washed with sat. aq. NH$_4$Cl (4×), dried with Na$_2$SO$_4$, and concentrated, producing a yellow oil. The residue was purified by column chromatography (0-10% EtOAc in hexanes), yielding MD-1-162 as a colorless oil (2.67 g, 88% yield).

D. Synthesis of 3-(hexadec-15-yn-1-ylthio)propan-1-ol (MD-1-165)

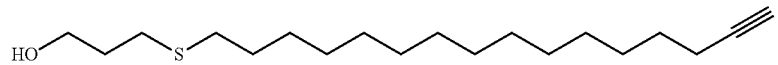 [SMILES: C#CCCCCCCCCCCCCCCSCCCO]

To a solution of MD-1-162 (2.21 g, 5.75 mmol, 1.00 eq) in anhydrous THF (38 mL) was added tetrabutylammonium fluoride (1 M in THF, 11.5 mL, 11.5 mmol, 2.00 eq), and the reaction mixture was stirred at room temperature for 45 min. After confirming complete conversion by TLC, the reaction mixture was diluted with EtOAc. The organic layer was washed with sat. aq. NH$_4$Cl (2×), dried with Na$_2$SO$_4$, and concentrated, producing a colorless oil. The residue was purified by column chromatography (0-20% EtOAc in hexanes), yielding MD-1-165 as a white powder (1.56 g, 87% yield).

E. Synthesis of Ammonium 3-(hexadec-15-yn-1-ylthio)propyl (R)-(((1-(6-amino-9H-purin-9-yl)propan-2-yl)oxy) methyl) phosphonate (MD-1-182)

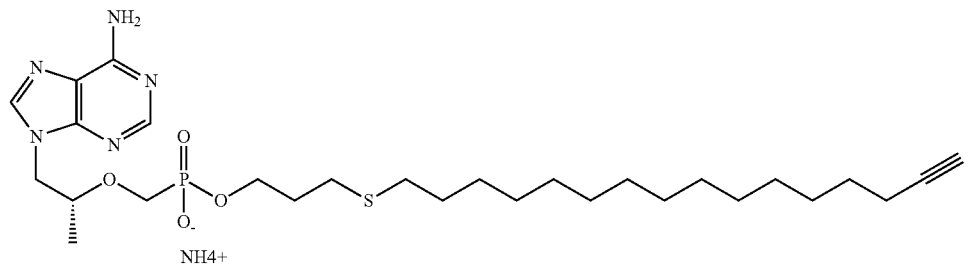

To a stirring suspension of dry tenofovir (200 mg, 0.696 mmol, 1.00 eq), DCC (287 mg, 1.39 mmol, 2.00 eq), and 3-(hexadec-15-yn-1-ylthio)propan-1-ol (218 mg, 0.696 mmol, 1.00 eq) in anhydrous NMP (2.3 mL) under inert atmosphere was added triethylamine (194 μL, 1.39 mmol, 2.00 eq) and DMAP (8.51 mg, 0.0696 mmol, 10 mol %). The reaction mixture was stirred at room temperature for 10 min, then heated to 100° C. overnight. After confirming the formation of product by LC-MS, the reaction mixture was quenched with water, stirred for 20 min at room temperature, and immediately purified by normal phase column chromatography (0-80% DCM:DCM/MeOH/NH$_4$OH (80:20:3)). The product fractions were collected and concentrated under reduced pressure to give a pale orange solid. The solid was taken up in a solution of NH$_4$OH in methanol (1:1) and purified by reverse phase column chromatography (0-85% H$_2$O:MeOH). The product fractions were collected and concentrated under reduced pressure, yielding the MD-1-182 as a white solid (206 mg, 51% yield). $^1$H NMR (600 MHz, CD$_3$OD) δ 8.33 (s, 1H), 8.22 (s, 1H), 4.39 (dd, J=14.4, 3.2 Hz, 1H), 4.24 (dd, J=14.5, 6.7 Hz, 1H), 3.95-3.81 (m, 3H), 3.73 (dd, J=12.8, 9.4 Hz, 1H), 3.49 (dd, J=12.8, 10.0 Hz, 1H), 2.51 (t, J=7.3 Hz, 2H), 2.47-2.42 (m, 2H), 2.18-2.13 (m, 3H), 1.82-1.71 (m, 2H), 1.55-1.46 (m, 4H), 1.43-1.25 (m, 20H), 1.17 (d, J=6.3 Hz, 3H). $^{13}$C NMR (151 MHz, CD$_3$OD) δ 157.1, 153.3, 150.9, 144.3, 119.6, 85.1, 76.9 (d, J=13.1 Hz), 69.3, 65.5 (d, J=160.0 Hz), 64.6 (d, J=5.7 Hz), 32.8, 32.2 (d, J=6.3 Hz), 30.8, 30.7, 30.7, 30.7, 30.7, 30.4, 30.2, 29.9, 29.8, 29.7, 29.2, 19.0, 16.8. $^{31}$P NMR (243 MHz, CD$_3$OD) δ 15.4. HRMS (NSI) m/z calculated for C$_{28}$H$_{49}$N$_5$O$_4$PS$^+$ [M+H]$^+$: 582.3237, found 582.3232. HPLC 85-95% MeOH in H$_2$O, 10 min, m/z=582.2 (M+H), t=2.057 min; 45-95% MeOH in H$_2$O, 10 min, m/z=582.3 (M+H), t=6.502 min.

Example 13. Synthesis of Ammonium 3-((12-phenyldodec-11-yn-1-yl)thio)propyl (R)-(((1-(6-amino-9H-purin-9-yl)propan-2-yl) oxy)methyl)phosphonate A. Synthesis of 2-((12-phenyldodec-11-yn-1-yl)oxy) tetrahydro-2H-pyran (MD-1-168)

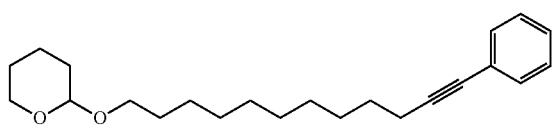 [SMILES: C(#Cc1ccccc1)CCCCCCCCCCOC1CCCCO1]

To a solution of phenylacetylene (5.40 mL, 49.2 mmol, 3.00 eq) in THF (27 mL) at −78° C. under inert atmosphere was added n-BuLi (2.5 M in hexanes, 19.7 mL, 49.2 mmol, 3.00 eq) dropwise. The reaction mixture was stirred at −78° C. for 15 min, then warmed to −40° C. for 1 hr. HMPA (8.56 mL, 49.2 mmol, 3.00 eq) and 2-(10-bromodecoxy)tetrahydropyran (5.27 g, 16.4 mmol, 1.00 eq) in THF were added dropwise at −40° C. The reaction mixture was stirred at −40° C. for 1 hr, then warmed to 0° C. for 5 hr. After confirming conversion by TLC, the reaction mixture was quenched with sat. aq. NH$_4$Cl, and the aqueous layer was extracted with EtOAc (3×). The collected organics were washed with sat. aq. NH$_4$Cl and brine, dried with Na$_2$SO$_4$, and concentrated to produce a golden brown oil. The residue was purified by column chromatography (0-1% EtOAc in hexanes) to yield MD-1-168 as a pale yellow oil (4.96 g, 88% yield).

B. Synthesis of 12-phenyldodec-11-yn-1-ol (MD-1-170)

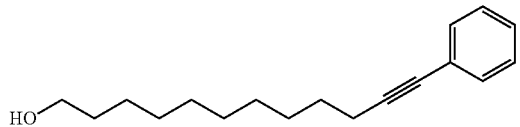 [SMILES: OCCCCCCCCCCC#Cc1ccccc1]

To a solution of MD-1-168 (4.96 g, 14.5 mmol, 1 eq) in MeOH (48 mL) under inert atmosphere was added p-toluenesulfonic acid monohydrate (276 mg, 1.45 mmol, 10 mol %), and the reaction mixture was stirred at room temperature overnight. Upon confirming complete conversion by TLC, the reaction mixture was concentrated under reduced pressure and purified by column chromatography (0-10% EtOAc in hexanes), yielding MD-1-170 as a colorless oil (3.03 g, 81% yield).

C. Synthesis of 3-((12-phenyldodec-11-yn-1-yl)thio) propan-1-ol (MD-1-174)

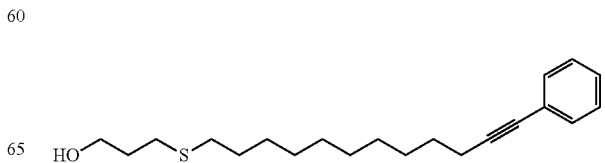

To a solution of MD-1-170 (2.61 g, 10.1 mmol, 1.00 eq) and triethylamine (2.11 mL, 15.1 mmol, 1.50 eq) in anhydrous DCM (25 mL) at 0° C. under inert atmosphere was added methanesulfonyl chloride (1.17 mL, 15.1 mmol, 1.50 eq) dropwise. The reaction mixture was stirred at 0° C. for 15 min, then allowed to warm to room temperature for 30 min. After confirming complete conversion by TLC, the reaction mixture was diluted with DCM. The organic layer was washed with sat. aq. NaHCO$_3$ (2×) and brine, dried with Na$_2$SO$_4$, and concentrated to yield 12-phenyldodec-11-yn-1-yl methanesulfonate (3.29 g, >95% yield) as a yellow oil which was taken on immediately without further purification.

To an Ar degassed solution of 3-mercaptopropanol (1.69 mL, 19.5 mmol, 2.00 eq) in anhydrous DMF (40 mL) was added 1,8-diazabicyclo(5.4.0)undec-7-ene (2.92 mL, 19.5 mmol, 2.00 eq), and the solution was stirred for 20 min at room temperature. 12-Phenyldodec-11-yn-1-yl methanesulfonate (3.29 g, 9.76 mmol, 1.00 eq) in DMF (10 mL) was added dropwise, and the reaction mixture was heated to 60° C. for 2 hr. After confirming complete conversion by TLC, the reaction mixture was diluted with EtOAc (10×DMF volume). The organic layer was washed with water (4×) and sat. aq. NH$_4$Cl, dried with Na$_2$SO$_4$, and concentrated, producing a pale yellow oil. The residue was purified by column chromatography (0-10% EtOAc in hexanes), yielding MD-1-174 as a white crystalline solid (3.09 g, 95% yield).

D. Synthesis of Ammonium 3-((12-phenyldodec-11-yn-1-yl)thio)propyl (R)-(((1-(6-amino-9H-purin-9-yl)propan-2-yl) oxy)methyl)phosphonate (MD-1-183)

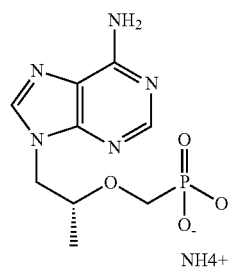

MD-1-183 was synthesized by following general procedure for MD-1-182, using 3-((12-phenyldodec-11-yn-1-yl)thio)propan-1-ol (232 mg, 0.696 mmol, 1.00 eq). Purification yields MD-1-183 as a waxy white solid (235 mg, 56% yield). $^1$H NMR (600 MHz, CD$_3$OD) δ 8.32 (s, 1H), 8.21 (s, 1H), 7.34-7.31 (m, 2H), 7.29-7.23 (m, 3H), 4.38 (dd, J=14.4, 3.2 Hz, 1H), 4.23 (dd, J=14.5, 6.7 Hz, 1H), 3.93-3.80 (m, 3H), 3.72 (dd, J=12.8, 9.4 Hz, 1H), 3.48 (dd, J=12.7, 10.0 Hz, 1H), 2.50 (t, J=7.3 Hz, 2H), 2.46-2.42 (m, 2H), 2.39 (t, J=7.0 Hz, 2H), 1.82-1.69 (m, 2H), 1.62-1.55 (m, 2H), 1.54-1.43 (m, 4H), 1.38-1.25 (m, 10H), 1.16 (d, J=6.2 Hz, 3H). $^{13}$C NMR (151 MHz, CD$_3$OD) δ 156.7, 152.8, 150.9, 144.4, 132.4, 129.3, 128.5, 125.6, 119.6, 90.9, 81.6, 76.9 (d, J=13.0 Hz), 65.4 (d, J=159.9 Hz), 64.6 (d, J=5.7 Hz), 32.8, 32.2 (d, J=6.4 Hz), 30.8, 30.6, 30.6, 30.3, 30.2, 29.9, 29.9, 29.9, 29.2, 20.0, 16.8. $^{31}$P NMR (243 MHz, CD$_3$OD) δ 15.4. HRMS (NSI) m/z calculated for C$_{30}$H$_{45}$N$_5$O$_4$PS$^+$ [M+H]$^+$: 602.2924, found 602.2918. HPLC 85-95% MeOH in H$_2$O, 10 min, m/z=602.2 (M+H), t=2.022 min; 60-95% MeOH in H$_2$O, 10 min, m/z=602.2 (M+H), t=8.347 min.

Example 14. Synthesis of Ammonium 3-((12-phenyldodecyl)thio)propyl (R)-(((1-(6-amino-9H-purin-9-yl)propan-2-yl)oxy) methyl)phosphonate A. Synthesis of 12-phenyldodecan-1-ol (MD-1-175)

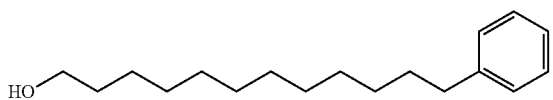 [SMILES: OCCCCCCCCCCCCc1ccccc1]

To a solution of MD-1-170 (2.65 g, 10.2 mmol, 1.00 eq) in anhydrous MeOH (102 mL) under inert atmosphere was added palladium on carbon (10 wt %, 1.09 g, 10 mol %). After purging the system under house vacuum, the reaction mixture was subjected to a balloon of hydrogen gas and stirred for 20 hr. Upon confirming complete conversion by TLC, the reaction mixture was filtered through a pad of celite and concentrated to produce a white solid. The solid was purified by column chromatography (0-10% EtOAc in hexanes) to yield MD-1-175 as a white powder (2.18 g, 81% yield).

B. Synthesis of 3-((12-phenyldodecyl)thio)propan-1-ol (MD-1-181)

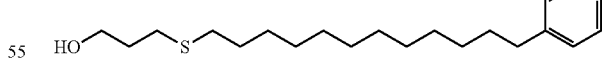

To a solution of MD-1-175 (2.09 g, 7.95 mmol, 1.00 eq) and triethylamine (1.66 mL, 11.9 mmol, 1.50 eq) in anhydrous DCM (20 mL) at 0° C. under inert atmosphere was added methanesulfonyl chloride (924 μL, 11.9 mmol, 1.50 eq) dropwise. The reaction mixture was stirred at 0° C. for 15 min, then allowed to warm to room temperature for 30 min. After confirming complete conversion by TLC, the reaction mixture was diluted with DCM. The organic layer was washed with sat. aq. NaHCO$_3$ (2×) and brine, dried with Na$_2$SO$_4$, and concentrated to yield 12-phenyldodecyl methanesulfonate (2.69 g, >95% yield) as a yellow oil which was taken on immediately without further purification.

To an Ar degassed solution of 3-mercaptopropanol (1.36 mL, 15.8 mmol, 2.00 eq) in anhydrous DMF (30 mL) was added 1,8-diazabicyclo(5.4.0)undec-7-ene (2.36 mL, 15.8 mmol, 2.00 eq), and the solution was stirred for 20 min at room temperature. 12-Phenyldodecyl methanesulfonate (2.69 g, 7.89 mmol, 1.00 eq) in DMF (10 mL) was added dropwise, and the reaction mixture was heated to 60° C. for 2.5 hr. After confirming complete conversion by TLC, the reaction mixture was diluted with EtOAc (10×DMF volume). The organic layer was washed with water (4×) and sat. aq. $NH_4Cl$, dried with $Na_2SO_4$, and concentrated, producing a pale yellow oil. The residue was purified by column chromatography (0-10% EtOAc in hexanes), yielding MD-1-181 as a white powder (2.37 g, 89% yield).

C. Synthesis of Ammonium 3-((12-phenyldodecyl)thio)propyl (R)-(((1-(6-amino-9H-purin-9-yl)propan-2-yl)oxy) methyl)phosphonate (MD-1-184)

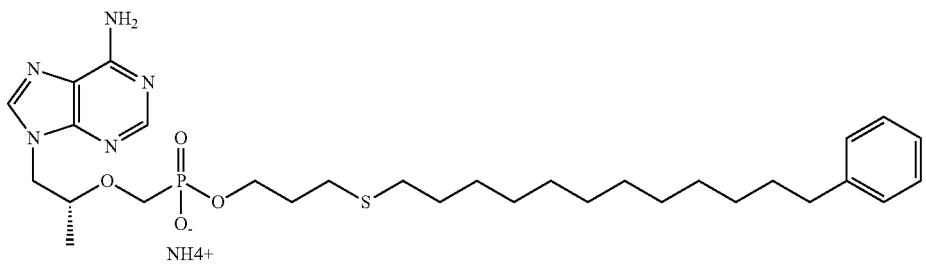

MD-1-184 was synthesized by following general procedure for MD-1-182, using 3-((12-phenyldodecyl)thio)propan-1-ol (234 mg, 0.696 mmol, 1.00 eq). Purification yielded MD-1-184 as a white solid (263 mg, 62% yield). $^1$H NMR (600 MHz, $CD_3OD$) δ 8.32 (s, 1H), 8.21 (s, 1H), 7.25-7.21 (m, 2H), 7.17-7.10 (m, 3H), 4.38 (dd, J=14.4, 3.2 Hz, 1H), 4.23 (dd, J=14.4, 6.7 Hz, 1H), 3.94-3.81 (m, 3H), 3.72 (dd, J=12.8, 9.4 Hz, 1H), 3.48 (dd, J=12.8, 10.0 Hz, 1H), 2.61-2.56 (m, 2H), 2.51 (t, J=7.3 Hz, 2H), 2.46-2.42 (m, 2H), 1.83-1.70 (m, 2H), 1.64-1.56 (m, 2H), 1.51 (p, J=7.3 Hz, 2H), 1.37-1.24 (m, 16H), 1.16 (d, J=6.2 Hz, 3H). $^{13}$C NMR (151 MHz, $CD_3OD$) δ 155.3, 151.3, 149.5, 143.1, 142.6, 128.0, 127.8, 125.2, 118.2, 75.5 (d, J=12.8 Hz), 64.0 (d, J=159.9 Hz), 63.2 (d, J=5.6 Hz), 35.5, 31.4, 31.4, 30.8 (d, J=6.7 Hz), 29.4, 29.3, 29.2, 29.0, 28.9, 28.5, 27.8, 15.4. $^{31}$P NMR (243 MHz, $CD_3OD$) δ 15.4. HRMS (NSI) m/z calculated for $C_{30}H_{49}N_5O_4PS^+$ [M+H]$^+$: 606.3237, found 606.3230. HPLC 85-95% MeOH in $H_2O$, 10 min, m/z=606.2 (M+H), t=3.206 min; 75-95% MeOH in $H_2O$, 10 min, m/z=606.2 (M+H), t=6.863 min.

Example 15. Synthesis of Ammonium 3-(octadecylthio)propyl (R)-(((1-(6-amino-9H-purin-9-yl)propan-2-yl)oxy)methyl) phosphonate A. Synthesis of 3-(octadecylthio)propan-1-ol (MD-1-177)

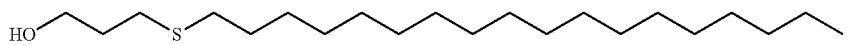 [SMILES: CCCCCCCCCCCCCCCCCCSCCCO]

To an Ar degassed solution of 3-mercaptopropanol (1.30 mL, 15.0 mmol, 2.00 eq) in anhydrous DMF (27 mL) was added 1,8-diazabicyclo(5.4.0)undec-7-ene (2.24 mL, 15.0 mmol, 2.00 eq), and the solution was stirred for 20 min at room temperature. 1-Bromooctadecane (2.5 g, 7.50 mmol, 1.00 eq) in DMF (15 mL) was added dropwise, and the reaction mixture was heated to 60° C. for 3 hr. After confirming complete conversion by TLC, the reaction mixture was diluted with EtOAc (10×DMF volume). The organic layer was washed with water (4×) and sat. aq. $NH_4Cl$, dried with $Na_2SO_4$, and concentrated, producing an off-white solid. The solid was purified by column chromatography (0-15% EtOAc in hexanes), yielding MD-1-177 as a white powder (2.34 g, 90% yield).

B. Synthesis of Ammonium 3-(octadecylthio)propyl (R)-(((1-(6-amino-9H-purin-9-yl)propan-2-yl)oxy)methyl) phosphonate (MD-1-185)

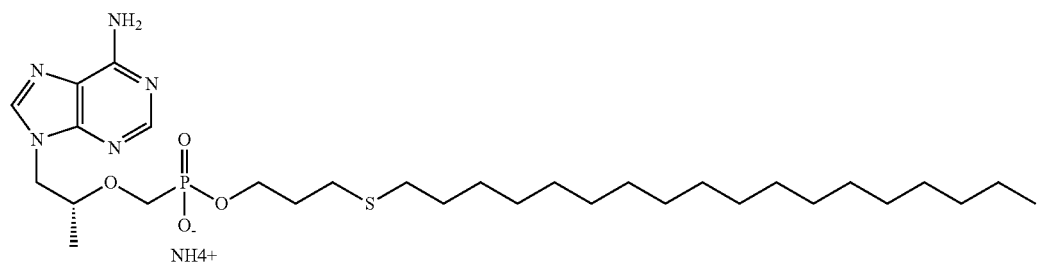

MD-1-185 was synthesized by following general procedure for MD-1-182, using 3-(octadecylthio)propan-1-ol (240 mg, 0.696 mmol, 1.00 eq). Purification yielded MD-1-185 as a white solid (269 mg, 61% yield). $^1$H NMR (600 MHz, $CD_3OD$) δ 8.33 (s, 1H), 8.21 (s, 1H), 4.39 (dd, J=14.4, 3.2 Hz, 1H), 4.24 (dd, J=14.4, 6.7 Hz, 1H), 3.94-3.81 (m, 3H), 3.72 (dd, J=12.8, 9.5 Hz, 1H), 3.48 (dd, J=12.8, 10.0 Hz, 1H), 2.51 (t, J=7.3 Hz, 2H), 2.47-2.42 (m, 2H), 1.82-1.71 (m, 2H), 1.56-1.48 (m, 2H), 1.38-1.24 (m, 30H), 1.16 (d, J=6.3 Hz, 3H), 0.89 (t, J=7.3 Hz, 3H). $^{13}$C NMR (151 MHz, $CD_3OD$) δ 157.2, 153.5, 150.9, 144.2, 119.6, 76.9 (d, J=13.0 Hz), 65.5 (d, J=160.0 Hz), 64.6 (d, J=5.6 Hz), 33.1, 32.8, 32.3 (d, J=6.3 Hz), 30.8, 30.8, 30.8, 30.7, 30.7, 30.5, 30.4, 29.9, 29.2, 23.7, 16.8, 14.4. $^{31}$P NMR (243 MHz, $CD_3OD$) δ 15.4. HRMS (NSI) m/z calculated for $C_{30}H_{57}N_5O_4PS^+$ [M+H]$^+$: 614.3863, found 614.3862. HPLC 95% MeOH in $H_2O$, 10 min, m/z=614.3 (M+H), t=2.054 min; 85-95% MeOH in $H_2O$, 10 min, m/z=614.3 (M+H), t=6.976 min.

Example 16. Synthesis of Ammonium 3-(icosylthio)propyl (R)-(((1-(6-amino-9H-purin-9-yl)propan-2-yl)oxy)methyl)phosphonate A. Synthesis of 3-(icosylthio)propan-1-ol (MD-1-179)

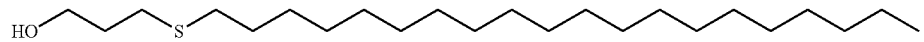 [SMILES: CCCCCCCCCCCCCCCCCCCCSCCCO]

To an Ar degassed solution of 3-mercaptopropanol (1.19 mL, 13.8 mmol, 2.00 eq) in anhydrous DMF (25 mL) was added 1,8-diazabicyclo(5.4.0)undec-7-ene (2.07 mL, 13.8 mmol, 2.00 eq), and the solution was stirred for 20 min at room temperature. 1-Bromoicosane (2.5 g, 7.89 mmol, 1.00 eq) in DMF (10 mL) was added dropwise, and the reaction mixture was heated to 65° C. for 4 hr. After confirming complete conversion by TLC, the reaction mixture was diluted with EtOAc (10×DMF volume). The organic layer was washed with sat. aq. NH$_4$Cl (4×), dried with Na$_2$SO$_4$, and concentrated, producing an off-white solid. The solid was purified by column chromatography (0-10% EtOAc in hexanes), yielding MD-1-179 as a white powder (2.12 g, 82% yield).

B. Synthesis of Ammonium 3-(icosylthio)propyl (R)-(((1-(6-amino-9H-purin-9-yl)propan-2-yl)oxy)methyl)phosphonate (MD-1-186)

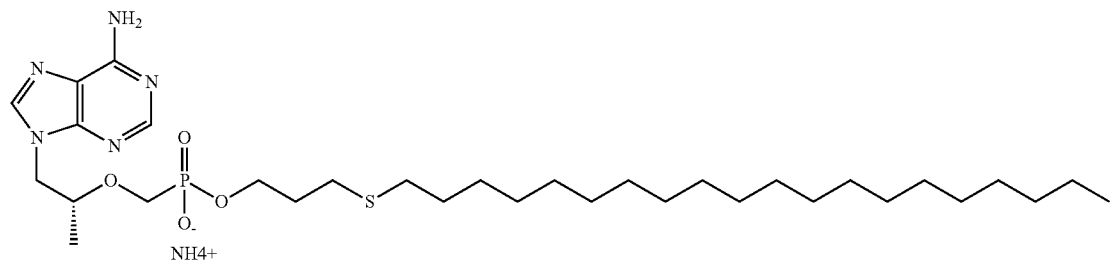

MD-1-186 was synthesized by following general procedure for MD-1-182, using 3-(icosylthio)propan-1-ol (260 mg, 0.696 mmol, 1.00 eq). Purification yielded MD-1-186 as a white solid (274 mg, 60% yield). $^1$H NMR (600 MHz, CD$_3$OD) δ 8.32 (s, 1H), 8.20 (s, 1H), 4.38 (dd, J=14.4, 3.2 Hz, 1H), 4.23 (dd, J=14.5, 6.7 Hz, 1H), 3.93-3.80 (m, 3H), 3.71 (dd, J=12.7, 9.4 Hz, 1H), 3.47 (dd, J=12.7, 10.0 Hz, 1H), 2.51 (t, J=7.3 Hz, 2H), 2.46-2.42 (m, 2H), 1.82-1.70 (m, 2H), 1.52 (tt, J=7.6, 6.4 Hz, 2H), 1.39-1.24 (m, 34H), 1.16 (d, J=6.3 Hz, 3H), 0.90 (t, J=7.0 Hz, 3H). $^{13}$C NMR (151 MHz, CD$_3$OD) δ 157.2, 153.5, 151.0, 144.2, 119.6, 76.9 (d, J=13.0 Hz), 65.5 (d, J=159.9 Hz), 64.6 (d, J=5.7 Hz), 33.1, 32.8, 32.3 (d, J=6.4 Hz), 30.8, 30.8, 30.7, 30.7, 30.5, 30.4, 29.9, 29.2, 23.7, 16.8, 14.4. $^{31}$P NMR (243 MHz, CD$_3$OD) δ 15.3. HRMS (NSI) m/z calculated for C$_{32}$H$_{61}$N$_5$O$_4$PS$^+$ [M+H]$^+$: 642.4176, found 642.4177. HPLC 95% MeOH in H$_2$O, 10 min, m/z=642.4 (M+H), t=3.178 min; 85-95% MeOH in H$_2$O, 15 min, m/z=642.4 (M+H), t=11.720 min.

Example 17. Synthesis of Ammonium 3-((14-(trimethylsilyl)tetradec-13-yn-1-yl)thio)propyl (R)-(((1-(6-amino-9H-purin-9-yl)propan-2-yl)oxy)methyl)phosphonate A. Synthesis of trimethyl(14-((tetrahydro-2H-pyran-2-yl)oxy)tetradec-1-yn-1-yl)silane (MD-1-155)

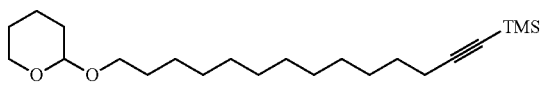 [SMILES: C[Si](C)(C)C#CCCCCCCCCCCCCOC1CCCCO1]

To a solution of trimethylsilylacetylene (7.08 mL, 51.1 mmol, 3.00 eq) in THF (28 mL) at −78° C. under inert atmosphere was added n-BuLi (2.5 M in hexanes, 20.5 mL, 51.1 mmol, 3.00 eq) dropwise. The reaction mixture was stirred at −78° C. for 15 min, then warmed to −40° C. for 1 hr. HMPA (8.90 mL, 51.1 mmol, 3.00 eq) and 2-(12-bromododecoxy)tetrahydropyran (5.96 g, 17.0 mmol, 1.00 eq) in THF were added dropwise at −40° C. The reaction mixture was stirred at −40° C. for 1 hr, then warmed to 0° C. for 5 h. After confirming complete conversion by TLC, the reaction mixture was quenched with sat. aq. NH$_4$Cl, and the aqueous layer was extracted with EtOAc (3×). The collected organics were washed with sat. aq. NH$_4$Cl and brine, dried with Na$_2$SO$_4$, and concentrated to produce a golden brown oil. The residue was purified by column chromatography (0-1% EtOAc in hexanes) to yield MD-1-155 as a colorless oil (5.49 g, 88% yield).

B. Synthesis of 14-(trimethylsilyl)tetradec-13-yn-1-ol (MD-1-157)

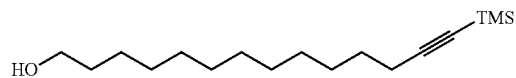 [SMILES: C[Si](C)(C)C#CCCCCCCCCCCCCO]

To a solution of MD-1-155 (5.49 g, 15.0 mmol, 1 eq) in MeOH (50 mL) under inert atmosphere was added p-toluenesulfonic acid monohydrate (285 mg, 1.50 mmol, 10 mol %), and the reaction mixture was stirred at room temperature overnight. Upon confirming complete conversion by TLC, the reaction mixture was concentrated under reduced pressure and purified by column chromatography (0-10% EtOAc in hexanes), yielding MD-1-157 as a colorless oil (3.03 g, 72% yield).

C. Synthesis of 3-((14-(trimethylsilyl)tetradec-13-yn-1-yl)thio)propan-1-ol (MD-1-160)

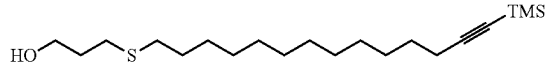 [SMILES: C[Si](C)(C)C#CCCCCCCCCCCCCSCCCO]

To a solution of MD-1-157 (2.06 g, 7.29 mmol, 1.00 eq) and triethylamine (1.52 mL, 10.9 mmol, 1.50 eq) in anhydrous DCM (18 mL) at 0° C. under inert atmosphere was added methanesulfonyl chloride (846 μL, 10.9 mmol, 1.50 eq) dropwise. The reaction mixture was stirred at 0° C. for 15 min, then allowed to warm to room temperature for 30 min. After confirming complete conversion by TLC, the reaction mixture was diluted with DCM. The organic layer was washed with sat. aq. $NH_4Cl$ (2×), sat. aq. $NaHCO_3$, and brine, dried with $Na_2SO_4$, and concentrated to yield 14-(trimethylsilyl)tetradec-13-yn-1-yl methanesulfonate (2.60 g, >95% yield) as a yellow oil which was taken on immediately without further purification.

To an Ar degassed solution of 3-mercaptopropanol (1.24 mL, 14.4 mmol, 2.00 eq) in anhydrous DMF (26 mL) was added 1,8-diazabicyclo(5.4.0)undec-7-ene (2.15 mL, 14.4 mmol, 2.00 eq), and the solution was stirred for 20 min at room temperature. 14-(Trimethylsilyl)tetradec-13-yn-1-yl methanesulfonate (2.60 g, 7.20 mmol, 1.00 eq) in DMF (10 mL) was added dropwise, and the reaction mixture was heated to 60° C. for 2.5 hr. After confirming complete conversion by TLC, the reaction mixture was diluted with EtOAc (10×DMF volume). The organic layer was washed with sat. aq. $NH_4Cl$ (4×), dried with $Na_2SO_4$, and concentrated, producing a yellow oil. The residue was purified by column chromatography (0-10% EtOAc in hexanes), yielding MD-1-160 as a colorless oil (2.22 g, 86% yield).

D. Synthesis of Ammonium 3-((14-(trimethylsilyl) tetradec-13-yn-1-yl)thio)propyl (R)-(((1-(6-amino-9H-purin-9-yl)propan-2-yl)oxy)methyl)phosphonate (MD-1-187)

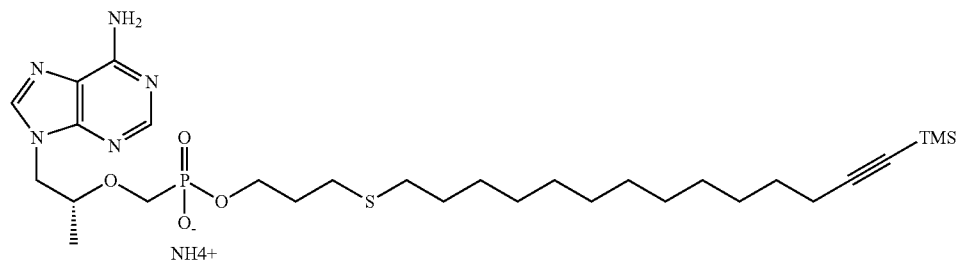

To a stirring suspension of dry tenofovir (200 mg, 0.696 mmol, 1.00 eq), DCC (287 mg, 1.39 mmol, 2.00 eq), and 3-((14-(trimethylsilyl)tetradec-13-yn-1-yl)thio)propan-1-ol (248 mg, 0.696 mmol, 1.00 eq) in anhydrous NMP (2.3 mL) under inert atmosphere was added triethylamine (194 µL, 1.39 mmol, 2.00 eq) and DMAP (8.51 mg, 0.0696 mmol, 10 mol %). The reaction mixture was stirred at room temperature for 10 min, then heated to 100° C. overnight. After confirming the formation of product by LC-MS, the reaction mixture was quenched with water, stirred for 20 min at room temperature, and immediately purified by normal phase column chromatography (0-80% DCM:MeOH). The product fractions were collected and concentrated under reduced pressure to give a pale orange solid. The solid was taken up in a solution of 80% MeOH in water and diammonium phosphate (460 mg, 3.48 mmol, 5.00 eq) was added. The mixture was stirred for 20 min and immediately purified by reverse phase column chromatography (0-85% $H_2O$:MeOH). The product fractions were collected and concentrated under reduced pressure, yielding the MD-1-187 as a white solid (226 mg, 52% yield). $^1$H NMR (600 MHz, $CD_3OD$) δ 8.34 (s, 1H), 8.22 (s, 1H), 4.39 (dd, J=14.4, 3.1 Hz, 1H), 4.24 (dd, J=14.5, 6.8 Hz, 1H), 3.94-3.80 (m, 3H), 3.73 (dd, J=12.8, 9.4 Hz, 1H), 3.48 (dd, J=12.7, 10.0 Hz, 1H), 2.50 (t, J=7.3 Hz, 2H), 2.46-2.42 (m, 2H), 2.20 (t, J=7.0 Hz, 2H), 1.81-1.70 (m, 2H), 1.54-1.45 (m, 4H), 1.42-1.24 (m, 16H), 1.17 (d, J=6.2 Hz, 3H), 0.11 (s, 9H). $^{13}$C NMR (151 MHz, $CD_3OD$) δ 156.5, 152.4, 150.8, 144.6, 119.5, 108.7, 84.8, 76.9 (d, J=12.8 Hz), 65.4 (d, J=160.3 Hz), 64.6 (d, J=5.8 Hz), 32.8, 32.2 (d, J=6.4 Hz), 30.8, 30.7, 30.7, 30.7, 30.6, 30.4, 30.1, 29.9, 29.8, 29.7, 29.18, 20.4, 16.8, 0.3. $^{31}$P NMR (243 MHz, $CD_3OD$) δ 15.5. HRMS (APCI) m/z calculated for $C_{29}H_{51}N_5O_4PSSi^-$ [M–H]$^-$: 624.3174, found 624.3178. HPLC 95% MeOH in $H_2O$, 10 min, m/z=626.3 (M+H), t=2.716 min; 75-95% MeOH in $H_2O$, 10 min, m/z=626.3 (M+H), t=7.843 min.

Example 18. Synthesis of Ammonium 3-(dodecylthio)propyl (R)-(((1-(6-amino-9H-purin-9-yl)propan-2-yl)oxy)methyl) phosphonate A. Synthesis of 3-(dodecylthio)propan-1-ol (MD-1-192)

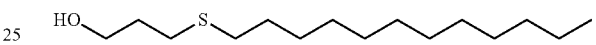

To an Ar degassed solution of 3-mercaptopropanol (1.46 mL, 16.9 mmol, 2.00 eq) in anhydrous DMF (42 mL) was added 1,8-diazabicyclo(5.4.0)undec-7-ene (2.52 mL, 16.9 mmol, 2.00 eq), and the solution was stirred for 20 min at room temperature. 1-Iodododecane (2.08 mL, 8.44 mmol, 1.00 eq) was added dropwise, and the reaction mixture was heated to 65° C. for 3 hr. After confirming complete conversion by TLC, the reaction mixture was diluted with EtOAc (10×DMF volume). The organic layer was washed with water (2×) and sat. aq. $NH_4Cl$ (2×), dried with $Na_2SO_4$, and concentrated, producing an off-white solid. The solid was purified by column chromatography (0-15% EtOAc in hexanes), yielding MD-1-192 as a white powder (1.92 g, 87% yield).

B. Synthesis of Ammonium 3-(dodecylthio)propyl (R)-(((1-(6-amino-9H-purin-9-yl)propan-2-yl)oxy)methyl) phosphonate (MD-1-217)

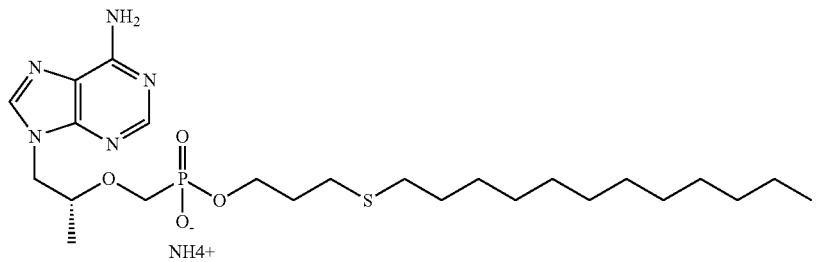

MD-1-217 was synthesized by following general procedure for MD-1-182, using 3-(dodecylthio)propan-1-ol (181 mg, 0.696 mmol, 1.00 eq). Purification yielded MD-1-217 as a white solid (232 mg, 61% yield). $^1$H NMR (600 MHz, CD$_3$OD) δ 8.33 (s, 1H), 8.21 (s, 1H), 4.39 (dd, J=14.4, 3.2 Hz, 1H), 4.24 (dd, J=14.4, 6.8 Hz, 1H), 3.95-3.81 (m, 3H), 3.72 (dd, J=12.8, 9.4 Hz, 1H), 3.48 (dd, J=12.8, 10.0 Hz, 1H), 2.51 (t, J=7.3 Hz, 2H), 2.44 (t, J=7.3 Hz, 2H), 1.82-1.71 (m, 2H), 1.52 (p, J=7.2 Hz, 2H), 1.38-1.23 (m, 18H), 1.17 (d, J=6.2 Hz, 3H), 0.90 (t, J=7.0 Hz, 3H). $^{13}$C NMR (151 MHz, CD$_3$OD) δ 156.6, 152.5, 150.8, 144.5, 119.6, 76.9 (d, J=12.9 Hz), 65.4 (d, J=160.0 Hz), 64.6 (d, J=5.6 Hz), 33.1, 32.8, 32.2 (d, J=6.2 Hz), 30.8, 30.8, 30.7, 30.7, 30.5, 30.4, 29.9, 29.2, 23.7, 16.8, 14.4. $^{31}$P NMR (243 MHz, CD$_3$OD) δ 15.4. HRMS (NSI) m/z calculated for C$_{24}$H$_{45}$N$_5$O$_4$PS$^+$ [M+H]$^+$: 530.2924, found 530.2916.

Example 19. Synthesis of Ammonium 3-(tetradecylthio)propyl (R)-(((1-(6-amino-9H-purin-9-yl)propan-2-yl)oxy)methyl) phosphonate A. Synthesis of 3-(Tetradecylthio)propan-1-ol (MD-1-193)

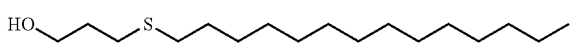 [SMILES: CCCCCCCCCCCCCCSCCCO]

To an Ar degassed solution of 3-mercaptopropanol (1.56 mL, 18.0 mmol, 2.00 eq) in anhydrous DMF (45 mL) was added 1,8-diazabicyclo(5.4.0)undec-7-ene (2.70 mL, 18.0 mmol, 2.00 eq), and the solution was stirred for 20 min at room temperature. 1-Bromotetradecane (2.68 mL, 9.02 mmol, 1.00 eq) was added dropwise, and the reaction mixture was heated to 65° C. for 3 hr. After confirming complete conversion by TLC, the reaction mixture was diluted with EtOAc (10×DMF volume). The organic layer was washed with water (2×) and sat. aq. NH$_4$Cl (2×), dried with Na$_2$SO$_4$, and concentrated, producing an off-white solid. The solid was purified by column chromatography (0-15% EtOAc in hexanes), yielding MD-1-193 as a white powder (2.57 g, >95% yield).

B. Synthesis of Ammonium 3-(tetradecylthio)propyl (R)-(((1-(6-amino-9H-purin-9-yl)propan-2-yl)oxy)methyl) phosphonate (MD-1-218)

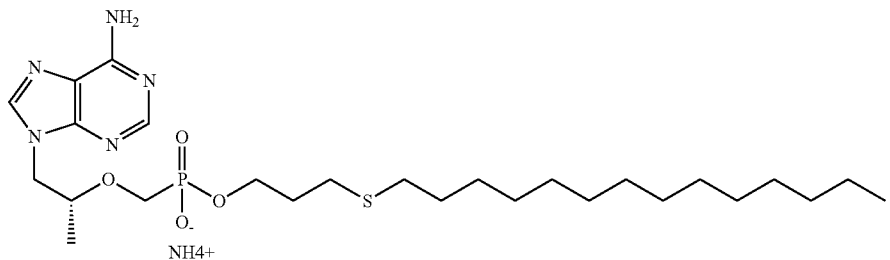

MD-1-218 was synthesized by following general procedure for MD-1-182, using 3-tetradecylsulfanylpropan-1-ol (201 mg, 0.696 mmol, 1.00 eq). Purification yielded MD-1-218 as a white solid (216 mg, 54% yield). $^1$H NMR (600 MHz, CD$_3$OD) δ 8.33 (s, 1H), 8.21 (s, 1H), 4.39 (dd, J=14.4, 3.1 Hz, 1H), 4.24 (dd, J=14.4, 6.8 Hz, 1H), 3.94-3.81 (m, 3H), 3.73 (dd, J=12.8, 9.4 Hz, 1H), 3.49 (dd, J=12.8, 10.0 Hz, 1H), 2.51 (t, J=7.2 Hz, 2H), 2.44 (t, J=7.3 Hz, 2H), 1.82-1.71 (m, 2H), 1.52 (p, J=7.2 Hz, 2H), 1.39-1.23 (m, 22H), 1.17 (d, J=6.2 Hz, 3H), 0.90 (t, J=7.0 Hz, 3H). $^{13}$C NMR (151 MHz, CD$_3$OD) δ 156.5, 152.4, 150.8, 144.5, 119.6, 76.9 (d, J=12.9 Hz), 65.4 (d, J=160.1 Hz), 64.6 (d, J=5.6 Hz), 33.1, 32.8, 32.2 (d, J=6.2 Hz), 30.8, 30.8, 30.8, 30.7, 30.7, 30.5, 30.4, 29.9, 29.2, 23.7, 16.8, 14.4. $^{31}$P NMR (243 MHz, CD$_3$OD) δ 15.5. HRMS (NSI) m/z calculated for C$_{26}$H$_{49}$N$_5$O$_4$PS$^+$ [M+H]$^+$: 558.3237, found 558.3231.

Example 20. Synthesis of Ammonium 6-(tridecylthio)hexyl (R)-(((1-(6-amino-9H-purin-9-yl)propan-2-yl)oxy)methyl) phosphonate A. Synthesis of 6-(tridecylthio)hexan-1-ol (MD-1-194)

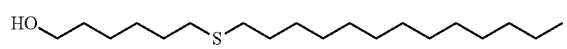 [SMILES: CCCCCCCCCCCCCSCCCCCCO]

To an Ar degassed solution of 6-mercaptohexanol (2.08 mL, 15.2 mmol, 2.00 eq) in anhydrous DMF (45 mL) was added 1,8-diazabicyclo(5.4.0)undec-7-ene (2.27 mL, 15.2 mmol, 2.00 eq), and the solution was stirred for 20 min at room temperature. 1-Bromotridecane (1.94 mL, 7.60 mmol, 1.00 eq) was added dropwise, and the reaction mixture was heated to 65° C. for 3 hr. After confirming complete conversion by TLC, the reaction mixture was diluted with EtOAc (10×DMF volume). The organic layer was washed with water (2×) and sat. aq. $NH_4Cl$ (2×), dried with $Na_2SO_4$, and concentrated, producing an off-white solid. The solid was purified by column chromatography (0-15% EtOAc in hexanes), yielding MD-1-194 as a white solid (2.19 g, 91% yield).

B. Synthesis of Ammonium 6-(tridecylthio)hexyl (R)-(((1-(6-amino-9H-purin-9-yl)propan-2-yl)oxy)methyl) phosphonate (MD-1-219)

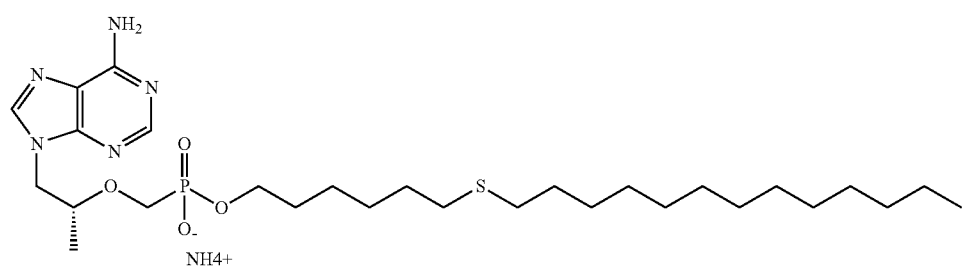 [SMILES: CCCCCCCCCCCCCSCCCCCCOP(=O)(O)CO[C@H](C)Cn1cnc2c(N)ncnc21 ; [NH4+]]

MD-1-219 was synthesized by following general procedure for MD-1-182, using 6-(tridecylthio)hexan-1-ol (220 mg, 0.696 mmol, 1.00 eq). Purification yielded MD-1-219 as a white solid (258 mg, 62% yield). $^1$H NMR (600 MHz, $CD_3OD$) δ 8.31 (s, 1H), 8.20 (s, 1H), 4.38 (dd, J=14.4, 3.1 Hz, 1H), 4.23 (dd, J=14.4, 6.8 Hz, 1H), 3.90 (pd, J=6.3, 3.1 Hz, 1H), 3.79-3.68 (m, 3H), 3.46 (dd, J=12.7, 10.1 Hz, 1H), 2.49-2.44 (m, 4H), 1.58-1.46 (m, 6H), 1.40-1.24 (m, 24H), 1.17 (d, J=6.2 Hz, 3H), 0.90 (t, J=7.0 Hz, 3H). $^{13}$C NMR (151 MHz, $CD_3OD$) δ 157.1, 153.3, 150.9, 144.3, 119.6, 76.9 (d, J=12.8 Hz), 65.8 (d, J=6.0 Hz), 65.5 (d, J=159.8 Hz), 33.1, 32.9, 32.8, 32.0 (d, J=6.2 Hz), 30.8, 30.8, 30.8, 30.7, 30.7, 30.5, 30.3, 29.9, 29.6, 26.5, 23.7, 16.8, 14.4. $^{31}$P NMR (243 MHz, $CD_3OD$) δ 15.4. HRMS (APCI) m/z calculated for $C_{28}H_{51}N_5O_4PS^-$ [M−H]$^-$: 584.3405, found 584.3408.

Example 21. Synthesis of Ammonium 12-(heptylthio)dodecyl (R)-(((1-(6-amino-9H-purin-9-yl)propan-2-yl)oxy)methyl) phosphonate (MD-1-220)

A. Synthesis of 12-(heptylthio)dodecan-1-ol (MD-1-195)

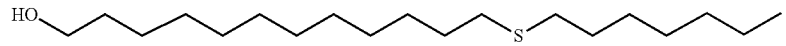 [SMILES: CCCCCCCSCCCCCCCCCCCCO]

To an Ar degassed solution of 1-heptanethiol (2.66 mL, 17.0 mmol, 2.00 eq) in anhydrous DMF (32 mL) was added 1,8-diazabicyclo(5.4.0)undec-7-ene (2.54 mL, 17.0 mmol, 2.00 eq), and the solution was stirred for 20 min at room temperature. 12-Bromo-1-dodecanol (2.25 g, 8.48 mmol, 1.00 eq) in DMF (10 mL) was added dropwise, and the reaction mixture was heated to 65° C. for 3 hr. After confirming complete conversion by TLC, the reaction mixture was diluted with EtOAc (10×DMF volume). The organic layer was washed with water (2×) and sat. aq. NH$_4$Cl (2×), dried with Na$_2$SO$_4$, and concentrated, producing an off-white solid. The solid was purified by column chromatography (0-10% EtOAc in hexanes), yielding MD-1-195 as a white powder (2.36 g, 88% yield).

B. Synthesis of Ammonium 12-(heptylthio)dodecyl (R)-(((1-(6-amino-9H-purin-9-yl)propan-2-yl)oxy)methyl) phosphonate (MD-1-220)

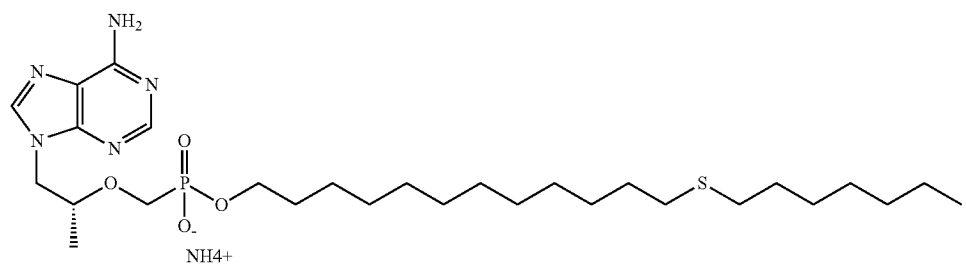 [SMILES: CCCCCCCSCCCCCCCCCCCCOP(=O)(O)CO[C@H](C)Cn1cnc2c(N)ncnc21 ; [NH4+]]

To a stirring suspension of dry tenofovir (200 mg, 0.696 mmol, 1.00 eq), DCC (287 mg, 1.39 mmol, 2.00 eq), and 12-(heptylthio)dodecan-1-ol (220 mg, 0.696 mmol, 1.00 eq) in anhydrous NMP (2.3 mL) under inert atmosphere was added TEA (194 μL, 1.39 mmol, 2.00 eq) and DMAP (8.51 mg, 0.0696 mmol, 10 mol %). The reaction mixture was stirred at room temperature for 10 min, then heated to 100° C. overnight. After confirming the formation of product by LC-MS, the reaction mixture was quenched with water, stirred for 20 min at room temperature, and immediately purified by normal phase column chromatography (0-80% DCM:DCM/MeOH/NH$_4$OH (80:20:3)). The product fractions were collected and concentrated under reduced pressure to give a light orange solid. The solid was taken up in a solution of DCM:7N NH$_3$ in MeOH (1:1, 10 mL) and stirred at room temperature overnight. The mixture was concentrated under reduced pressure and purified by reverse phase column chromatography (0-90% H$_2$O:MeOH). The product fractions were collected and concentrated under reduced pressure, yielding the MD-1-220 as a white solid (291 mg, 69% yield). $^1$H NMR (600 MHz, CD$_3$OD) δ 8.31 (s, 1H), 8.20 (s, 1H), 4.37 (dd, J=14.4, 3.1 Hz, 1H), 4.23 (dd, J=14.4, 6.7 Hz, 1H), 3.89 (pd, J=6.3, 3.1 Hz, 1H), 3.79-3.67 (m, 3H), 3.46 (dd, J=12.7, 10.0 Hz, 1H), 2.51-2.47 (m, 2H), 2.52-2.46 (m, 2H), 1.60-1.51 (m, 4H), 1.53-1.44 (m, 2H), 1.42-1.35 (m, 4H), 1.35-1.21 (m, 20H), 1.16 (d, J=6.2 Hz, 3H), 0.90 (t, J=7.0 Hz, 3H). $^{13}$C NMR (151 MHz, CD$_3$OD) δ 157.2, 153.5, 150.9, 144.2, 119.6, 76.9 (d, J=12.7 Hz), 65.9 (d, J=5.8 Hz), 65.6 (d, J=159.8 Hz), 33.0, 32.9, 32.1 (d, J=6.4 Hz), 30.8, 30.8, 30.7, 30.7, 30.7, 30.5, 30.3, 30.0, 29.9, 29.9, 26.9, 23.7, 16.8, 14.4. $^{31}$P NMR (243 MHz, CD$_3$OD) δ 15.2. HRMS (NSI) m/z calculated for C$_{28}$H$_{53}$N$_5$O$_4$PS$^+$ [M+H]$^+$: 586.3550, found 586.3542.

Example 22. Synthesis of Ammonium 15-(butyl-thio)pentadecyl (R)-(((1-(6-amino-9H-purin-9-yl) propan-2-yl)oxy)methyl) phosphonate A. Synthesis of 15-(butylthio)pentadecan-1-ol (MD-1-198)

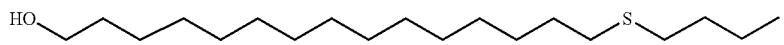 [SMILES: CCCCSCCCCCCCCCCCCCCCO]

To an Ar degassed solution of 1-butanethiol (1.74 mL, 16.3 mmol, 2.00 eq) in anhydrous DMF (31 mL) was added 1,8-diazabicyclo(5.4.0)undec-7-ene (2.43 mL, 16.3 mmol, 2.00 eq), and the solution was stirred for 20 min at room temperature. 15-Bromo-1-pentadecanol (2.5 g, 8.14 mmol, 1.00 eq) in DMF (10 mL) was added dropwise, and the reaction mixture was heated to 65° C. for 3 hr. After confirming complete conversion by TLC, the reaction mixture was diluted with EtOAc (10×DMF volume). The organic layer was washed with water (2×) and sat. aq. $NH_4Cl$ (2×), dried with $Na_2SO_4$, and concentrated, producing an off-white solid. The solid was purified by column chromatography (0-10% EtOAc in hexanes), yielding MD-1-198 as a white powder (2.31 g, 90% yield).

B. Synthesis of Ammonium 15-(butylthio)penta-decyl (R)-(((1-(6-amino-9H-purin-9-yl)propan-2-yl) oxy)methyl) phosphonate (MD-1-221)

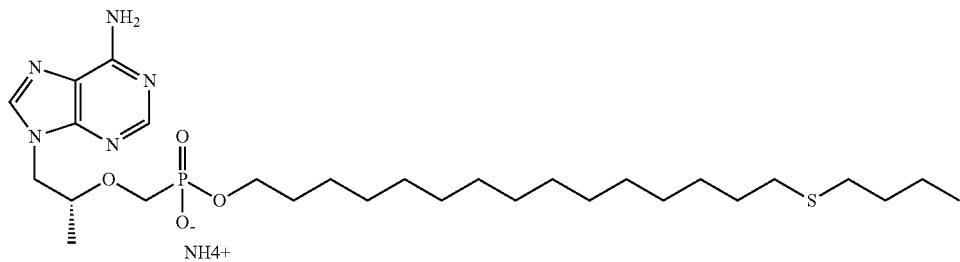 [SMILES: CCCCSCCCCCCCCCCCCCCCOP(=O)(O)CO[C@H](C)Cn1cnc2c(N)ncnc21 ; [NH4+]]

MD-1-221 was synthesized by following general procedure for MD-1-220, using 15-(butylthio)pentadecan-1-ol (220 mg, 0.696 mmol, 1.00 eq). Purification yielded MD-1-221 as a white solid (211 mg, 50% yield). $^1$H NMR (600 MHz, $CD_3OD$) δ 8.31 (s, 1H), 8.20 (s, 1H), 4.37 (dd, J=14.4, 3.1 Hz, 1H), 4.23 (dd, J=14.4, 6.7 Hz, 1H), 3.89 (pd, J=6.3, 3.0 Hz, 1H), 3.79-3.67 (m, 3H), 3.46 (dd, J=12.7, 10.0 Hz, 1H), 2.50 (t, J=7.2 Hz, 2H), 2.49 (t, J=7.3 Hz, 2H), 1.59-1.52 (m, 4H), 1.53-1.44 (m, 2H), 1.45-1.36 (m, 4H), 1.33-1.21 (m, 20H), 1.16 (d, J=6.2 Hz, 3H), 0.92 (t, J=7.4 Hz, 3H). $^{13}$C NMR (151 MHz, $CD_3OD$) δ 157.2, 153.5, 150.9, 144.2, 119.6, 76.9 (d, J=12.8 Hz), 65.9 (d, J=5.8 Hz), 65.6 (d, J=160.1 Hz), 33.0, 32.9, 32.6, 32.1 (d, J=6.3 Hz), 30.8, 30.8, 30.8, 30.7, 30.7, 30.7, 30.5, 30.3, 29.9, 26.9, 23.0, 16.8, 14.0. $^{31}$P NMR (243 MHz, $CD_3OD$) δ 15.2. HRMS (NSI) m/z calculated for $C_{28}H_{53}N_5O_4PS^+$ [M+H]$^+$: 586.3550, found 586.3546.

Example 23. Synthesis of Ammonium 2-(heptadecylthio)ethyl (R)-(((1-(6-amino-9H-purin-9-yl)propan-2-yl)oxy)methyl) phosphonate A. Synthesis of (heptadecylthio)ethan-1-ol (MD-1-212)

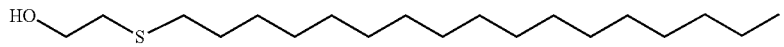 [SMILES: CCCCCCCCCCCCCCCCCSCCO]

To an Ar degassed solution of 1-bromoheptadecane (2.50 g, 7.82 mmol, 1.00 eq) in DMF (39 mL) was added cesium carbonate (5.10 g, 15.7 mmol, 2.00 eq). 2-Mercaptoethanol (1.10 mL, 15.7 mmol, 2.00 eq) was added dropwise to the suspension, and the reaction mixture was stirred at room temperature overnight. After confirming complete conversion by TLC, the reaction mixture was diluted with EtOAc (500 mL). The organic layer was washed with $H_2O$ (2×) and sat. aq. $NH_4Cl$ (2×), dried with $Na_2SO_4$, and concentrated to yield an off-white solid. The solid was purified by column chromatography (0-10% EtOAc in hexanes), yielding MD-1-212 as a white powder (2.29 g, 92% yield).

B. Synthesis of Ammonium 2-(heptadecylthio)ethyl (R)-(((1-(6-amino-9H-purin-9-yl)propan-2-yl)oxy) methyl) phosphonate (MD-1-222)

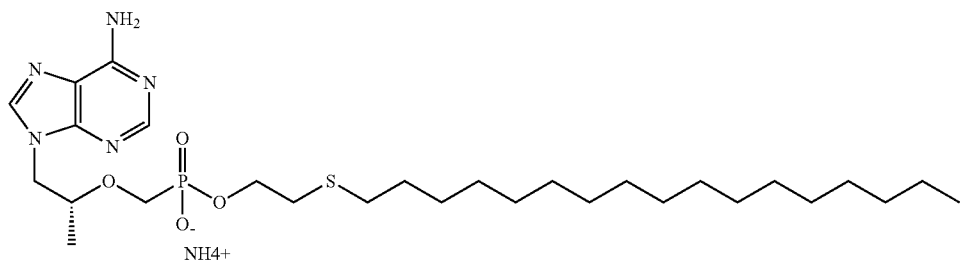 [SMILES: CCCCCCCCCCCCCCCCCSCCOP(=O)(O)CO[C@H](C)Cn1cnc2c(N)ncnc21 ; [NH4+]]

MD-1-222 was synthesized by following general procedure for MD-1-220, using (heptadecylthio)ethan-1-ol (220 mg, 0.696 mmol, 1.00 eq), Purification yielded MD-1-222 as a white solid (231 mg, 55% yield). $^1H$ NMR (600 MHz, $CD_3OD$) δ 8.32 (s, 1H), 8.20 (s, 1H), 4.38 (dd, J=14.5, 3.2 Hz, 1H), 4.23 (dd, J=14.4, 6.7 Hz, 1H), 3.94-3.84 (m, 3H), 3.72 (dd, J=12.8, 9.4 Hz, 1H), 3.49 (dd, J=12.8, 10.1 Hz, 1H), 2.62 (hept, J=7.0 Hz, 2H), 2.48 (t, J=7.3 Hz, 2H), 1.50 (p, J=7.2 Hz, 2H), 1.36-1.23 (m, 28H), 1.16 (d, J=6.2 Hz, 3H), 0.90 (t, J=7.0 Hz, 3H). $^{13}C$ NMR (151 MHz, $CD_3OD$) δ 157.2, 153.5, 151.0, 144.2, 119.6, 77.0 (d, J=12.9 Hz), 65.6 (d, J=160.3 Hz), 65.5 (d, J=5.9 Hz), 33.5 (d, J=6.3 Hz), 33.2, 33.1, 31.0, 30.8, 30.8, 30.8, 30.7, 30.7, 30.5, 30.4, 29.9, 23.7, 16.8, 14.4. $^{31}P$ NMR (243 MHz, $CD_3OD$) δ 15.2. HRMS (NSI) m/z calculated for $C_{28}H_{53}N_5O_4PS^+$ $[M+H]^+$: 586.3550, found 586.3541.

Example 24. Synthesis of Ammonium 3-((11-phenoxyundecyl)thio)propyl (R)-(((1-(6-amino-9H-purin-9-yl)propan-2-yl)oxy) methyl)phosphonate A. Synthesis of ((11-bromoundecyl)oxy)benzene (MD-1-211)

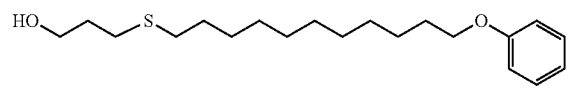 [SMILES: OCCCSCCCCCCCCCCCOc1ccccc1]

To a solution of 11-bromo-1-undecanol (3.00 g, 11.9 mmol, 1.00 eq), phenol (1.12 g, 11.9 mmol, 1.00 eq), and triphenylphosphine (3.13 g, 11.9 mmol, 1.00 eq) in THF (24 mL) at 0° C. under inert atmosphere was added DIAD (2.59 mL, 13.1 mmol, 1.10 eq) dropwise. The reaction mixture was allowed to warm to room temperature and stirred overnight. After confirming complete conversion by TLC, the reaction mixture was concentrated and immediately purified by column chromatography (0-1% EtOAc in hexanes) to yield MD-1-211 as a colorless oil (2.75 g, 70% yield).

B. Synthesis of 3-((11-phenoxyundecyl)thio)propan-1-ol (MD-1-213)

To an Ar degassed solution of ((11-bromoundecyl)oxy)benzene (2.75 g, 8.40 mmol, 1.00 eq) in DMF (21 mL) was added cesium carbonate (5.47 g, 16.8 mmol, 2.00 eq).

3-Mercaptopropanol (1.45 mL, 16.8 mmol, 2.00 eq) was added dropwise to the suspension, and the reaction mixture was stirred at room temperature overnight. After confirming complete conversion by TLC, the reaction mixture was diluted with EtOAc (500 mL). The organic layer was washed with H₂O (2×) and sat. aq. NH₄Cl (2×), dried with Na₂SO₄, and concentrated to yield an off-white solid. The solid was purified by column chromatography (0-15% EtOAc in hexanes), yielding MD-1-213 as a white powder (2.54 g, 89% yield).

C. Synthesis of Ammonium 3-((11-phenoxyundecyl)thio)propyl (R)-(((1-(6-amino-9H-purin-9-yl)propan-2-yl)oxy) methyl)phosphonate (MD-1-223)

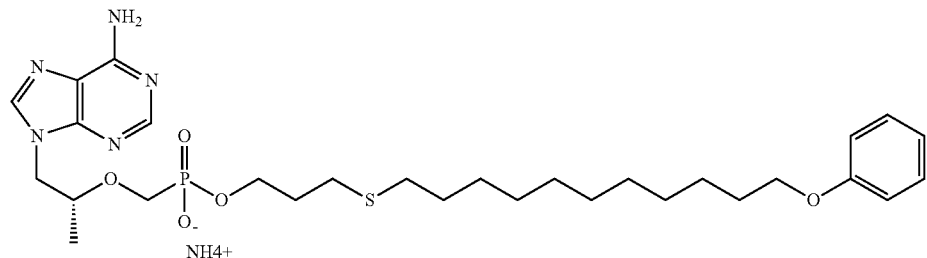 [SMILES: C[C@H](Cn1cnc2c(N)ncnc21)OCP(=O)(O)OCCCSCCCCCCCCCCCOc1ccccc1 ; [NH4+]]

MD-1-223 was synthesized by following general procedure for MD-1-220, using 3-((11-phenoxyundecyl)thio)propan-1-ol (236 mg, 0.696 mmol, 1.00 eq). Purification yielded MD-1-223 as a white solid (309 mg, 71% yield). $^1$H NMR (600 MHz, CD₃OD) δ 8.31 (s, 1H), 8.20 (s, 1H), 7.26-7.21 (m, 2H), 6.90-6.85 (m, 3H), 4.37 (dd, J=14.4, 3.2 Hz, 1H), 4.23 (dd, J=14.4, 6.7 Hz, 1H), 3.95 (t, J=6.4 Hz, 2H), 3.92-3.80 (m, 3H), 3.71 (dd, J=12.8, 9.4 Hz, 1H), 3.47 (dd, J=12.7, 10.0 Hz, 1H), 2.50 (t, J=7.3 Hz, 2H), 2.44 (t, J=7.3 Hz, 2H), 1.81-1.70 (m, 4H), 1.54-1.44 (m, 4H), 1.39-1.26 (m, 12H), 1.16 (d, J=6.2 Hz, 3H). $^{13}$C NMR (151 MHz, CD₃OD) δ 160.6, 157.2, 153.4, 150.9, 144.2, 130.4, 121.5, 119.6, 115.5, 76.9 (d, J=13.0 Hz), 68.9, 65.5 (d, J=159.9 Hz), 64.6 (d, J=5.7 Hz), 32.8, 32.2 (d, J=6.3 Hz), 30.8, 30.7, 30.7, 30.6, 30.5, 30.4, 30.4, 29.9, 29.2, 27.2, 16.8. $^{31}$P NMR (243 MHz, CD₃OD) δ 15.3. HRMS (NSI) m/z calculated for C₂₉H₄₇N₅O₅PS⁺ [M+H]⁺: 608.3030, found 608.3022.

Example 25. Synthesis of Ammonium [(1R)-2-(6-aminopurin-9-yl)-1-methyl-ethoxy]methyl-(18-trimethylsilyloctadec-17-ynoxy)phosphinate A. Synthesis of 2-octadec-2-ynoxytetrahydropyran (NP-PD-023)

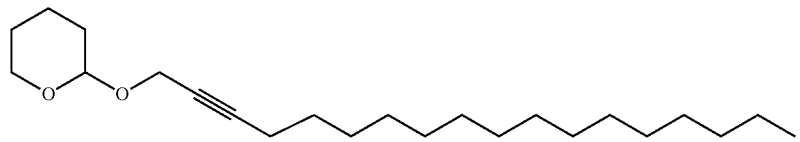 [SMILES: CCCCCCCCCCCCCCCC#CCOC1CCCCO1]

To a 250 mL oven-dried flask equipped with a stir bar was added 2-(2-propynyloxy)tetrahydro-2H-pyran (5.02 mL, 35.7 mmol, 1.00 eq), hexamethylphosphoramide (21.7 mL, 125 mmol, 3.50 eq) and THF (100 mL). The reaction mixture was cooled to −78° C. and stirred vigorously under Ar. n-Butyllithium (2.00 M in THF, 23.2 mL, 46.4 mmol, 1.30 eq) was added dropwise over a period of 15 minutes by way of an oven-dried pressure equalizing dropping funnel and the reaction was vigorously stirred at −78° C. for approximately 1 hour. Subsequently, 1-bromopentadecane (13.4 mL, 46.4 mmol, 1.30 eq) was added slowly dropwise over 10 minutes by way of a pressure equalizing dropping funnel after which the resulting reaction mixture was allowed to warm to room temperature overnight while stirring vigorously under Ar. The following day TLC indicated that all of the starting alkyne had been consumed. The reaction mixture was quenched with a saturated solution of ammonium chloride and then extracted three times into EtOAc. The organic phases were then combined, washed with brine, dried over anhydrous magnesium sulfate and concentrated in vacuo. Subsequent purification of the resulting crude material by column chromatography (2%-10% EtOAc/hexane) afforded a clear oil (7.86 g, 22.4 mmol, 63% yield).

B. Synthesis of octadec-2-yn-1-ol (NP-PD-026)

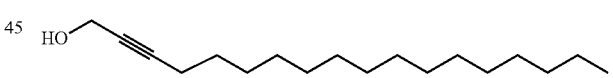

A solution of 2-octadec-2-ynoxytetrahydropyran (7.86 g, 22.4 mmol, 1.00 eq) in methanol (100 mL) was added to a 100 mL flask equipped with a stir bar. To this solution was added p-toluenesulfonic acid monohydrate (427 mg, 2.24 mmol, 0.10 eq) and the reaction mixture was stirred vigorously for 3 hours at room temperature. TLC had confirmed full consumption of the starting material. The reaction mixture was subsequently concentrated in vacuo and the resulting crude material was purified by column chromatography (2%-10% EtOAc/hexane) to afford a white solid (3.18 g, 11.9 mmol, 53%).

C. Synthesis of octadec-17-yn-1-ol (NP-PD-028)

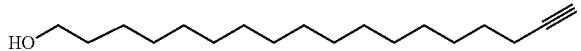 [SMILES: C#CCCCCCCCCCCCCCCCCO]

Sodium hydride (60% in mineral oil, 3.82 g, 95.5 mmol, 8.00 eq) was added to a 250 mL oven-dried flask equipped with a stir bar under an atmosphere Ar. Following dilution with 1,3-diaminopropane (40.0 mL), the flask was placed in an oil bath preheated to 70° C. After stirring for 1 hour at this temperature the reaction mixture was cooled to 55° C. Subsequently, octadec-2-yn-1-ol (3.18 g, 11.9 mmol, 1.00 eq) was dissolved in 1,3-diaminopropane (10.0 mL) and added slowly dropwise to the reaction mixture at this temperature. The reaction mixture was then left stirring vigorously overnight. The following morning the reaction was cooled to 0° C., quenched with water and acidified with a 1 N aqueous HCl solution to a pH of 2. The resulting aqueous phase was then extracted three times with hexane. The combined organic phases were then dried over magnesium sulfate and concentrated in vacuo. The resulting crude material was then purified by column chromatography (5%-20% EtOAc/hexane) to afford a white solid (1.91 g, 7.17 mmol, 60%).

D. Synthesis of 18-trimethylsilyloctadec-17-yn-1-ol (NP-PD-049)

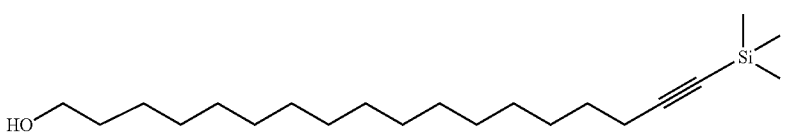 [SMILES: C[Si](C)(C)C#CCCCCCCCCCCCCCCCCO]

To a 25 mL oven-dried flask equipped with a stirrer bar was added octadec-17-yn-1-ol (200 mg, 0.751 mmol, 1.00 eq), hexamethylphosphoramide (0.392 mL, 2.25 mmol, 3.00 eq) and THF (3.00 mL) under an atmosphere of Ar. The flask was subsequently cooled to 0° C. before the slow dropwise addition of n-BuLi (2.30 M in THF, 0.979 mL, 2.25 mmol, 3.00 eq). The reaction was then warmed to room temperature and left to stir vigorously for 2 hours after which trimethylsilyl chloride (0.476 mL, 3.75 mmol, 5.00 eq) was added to the reaction mixture dropwise. After an additional 2 hours at room temperature, the reaction was quenched with saturated ammonium chloride and extracted three times into EtOAc. The organic phases were combined, washed with brine, dried over magnesium sulfate and concentrated in vacuo. The resulting crude product was purified by column chromatography (100% hexane-10% EtOAc/hexane) to yield a white solid (160 mg, 0.473 mmol, 63%).

E. Synthesis of Ammonium [(1R)-2-(6-aminopurin-9-yl)-1-methyl-ethoxy]methyl-(18-trimethylsilyloctadec-17-ynoxy)phosphinate (NP-PD-042)

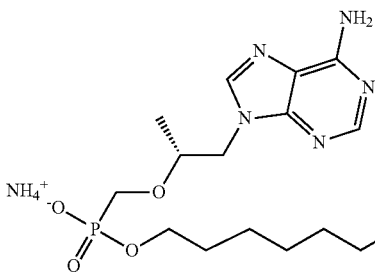

Tenofovir (100 mg, 0.348 mmol, 1.00 eq) and pyridine (2.00 mL) were added to a 25 mL oven-dried flask equipped with a stir bar under an atmosphere of Ar. This was followed by the addition of 18-trimethylsilyloctadec-17-yn-1-ol (177 mg, 0.522 mmol, 1.50 eq) and 2,4,6-triisopropylbenzenesulfonyl chloride (316 mg, 1.05 mmol, 3.00 eq). The reaction was left to stir vigorously at room temperature for 48 hours under Ar. The reaction was concentrated in vacuo, taken up in a saturated solution of ammonium chloride and concentrated once again in vacuo. The resulting salt was then vigorously stirred up in a 4:1 solution of DCM and MeOH for approximately 1 hour. The reaction was filtered and the resulting filtrate was collected, concentrated in vacuo and purified by column chromatography (100% DCM-100% 80:20:3 DCM:MeOH:NH$_4$OH) to yield a white solid (51.0 mg, 0.0816 mmol, 24%). $^1$H NMR (500 MHz, CD$_3$OD) δ 8.31 (s, 1H), 8.20 (s, 1H), 4.38 (dd, J=14.4, 2.8 Hz, 1H), 4.23 (dd, J=14.4, 6.8 Hz, 1H), 3.93-3.86 (m, 1H), 3.76-3.68 (m, 3H), 3.46 (dd, J=12.5, 10.3 Hz, 1H), 2.20 (t, J=6.9 Hz, 2H), 1.52-1.44 (m, 4H), 1.43-1.37 (m, 2H), 1.34-1.20 (m, 22H), 1.17 (d, J=6.2 Hz, 3H), 0.11 (s, 9H). $^{13}$C NMR (126 MHz, CD$_3$OD) δ 157.0, 153.2, 150.9, 144.2, 119.5, 108.7, 84.8, 76.9 (d, J$_{CP}$=13.1 Hz), 65.9 (d, J$_{CP}$=6.2 Hz), 65.5 (d, J$_{CP}$=160.2 Hz), 32.1 (d, J$_{CP}$=6.4 Hz), 30.8 (2C), 30.7 (2C), 30.5, 30.1, 29.7 (2C), 26.9, 20.4, 16.8, 0.3. $^{31}$P NMR (121 MHz, CD$_3$OD) δ 15.27. HRMS (ESI) m/z calc. for C$_{30}$H$_{55}$N$_5$O$_4$PSi [M+H]$^+$, 608.37554 found, 608.37562. LCMS (ESI) 95% ISO MeOH in H$_2$O (0.1% HCO$_2$H), 9 min, rt=3.838, m/z=608.4 [M+H]$^+$, 606.3 [M−H]$^-$; 85-95% MeOH in H$_2$O (0.1% HCO$_2$H), 10 min, rt=6.163, m/z=608.4 [M+H]$^+$, 606.4 [M−H]$^-$.

Example 26. Synthesis of Ammonium [(1R)-2-(6-aminopurin-9-yl)-1-methyl-ethoxy]methyl-(18-trimethylsilyloctadecoxy)phosphinate

A. Synthesis of 18-trimethylsilyloctadecan-1-ol (NP-PD-050)

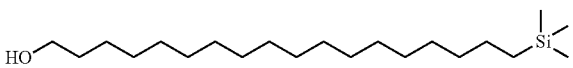 [SMILES: C[Si](C)(C)CCCCCCCCCCCCCCCCCCO]

18-Trimethylsilyloctadec-17-yn-1-ol (297 mg, 0.877 mmol, 1.00 eq) and EtOH (6.00 mL) were added to a 25 mL oven-dried flask equipped with a stir bar and fitted with a sealed hydrogen balloon. The solution was subsequently degassed under house vacuum for approximately 10 minutes and then the reaction flask was purged with Ar. This cycle was repeated twice more before the addition of a catalytic amount of palladium on carbon (10% wt, 93.3 mg, 0.0877 mmol, 0.10 eq). Once more the reaction flask was placed under vacuum before a final purge with hydrogen from the fitted hydrogen balloon. The reaction was subsequently left to stir vigorously under an atmosphere of hydrogen at room temperature for 18 hours. After this time, the heterogeneous reaction mixture was filtered over a bed of celite and the filtrate was collected and concentrated in vacuo. The resulting crude product was purified by column chromatography (5%-20% EtOAc/hexane) to yield a white solid (276 mg, 0.805 mmol, 92%).

B. Synthesis of Ammonium [(1R)-2-(6-aminopurin-9-yl)-1-methyl-ethoxy]methyl-(18-trimethylsilyloctadecoxy)phosphinate (NP-PD-051)

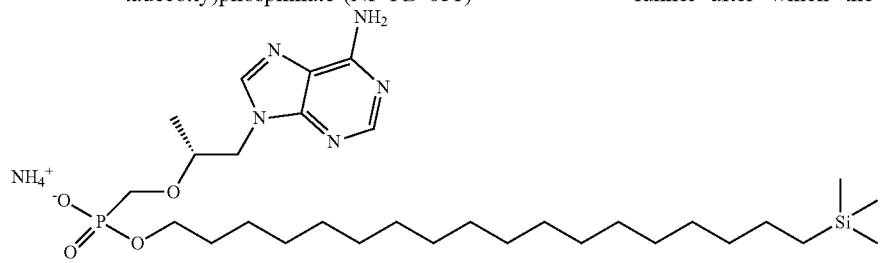

Tenofovir (150 mg, 0.522 mmol, 1.00 eq) and pyridine (2.00 mL) were added to a 25 mL oven-dried flask equipped with a stir bar under an atmosphere of Ar. This was followed by the addition of 18-trimethylsilyloctadecan-1-ol (268 mg, 0.783 mmol, 1.50 eq) and 2,4,6-triisopropylbenzenesulfonyl chloride (475 mg, 1.57 mmol, 3.00 eq). The reaction was left to stir vigorously at room temperature for 48 hours under Ar. The reaction was concentrated in vacuo, taken up in a saturated solution of ammonium chloride and concentrated once again in vacuo. The resulting salt was then vigorously stirred up in a 4:1 solution of DCM and MeOH for approximately 1 hour. The reaction was filtered and the resulting filtrate was collected, concentrated in vacuo and purified by column chromatography (100% DCM-100% 80:20:3 DCM:MeOH:NH$_4$OH) to yield a white solid (87.0 mg, 0.142 mmol, 27%). $^1$H NMR (500 MHz, CD$_3$OD) δ 8.31 (s, 1H), 8.21 (s, 1H), 4.38 (dd, J=14.4, 2.8 Hz, 1H), 4.23 (dd, J=14.4, 6.9 Hz, 1H), 3.93-3.86 (m, 1H), 3.77-3.69 (m, 3H), 3.47 (dd, J=12.6, 10.2 Hz, 1H), 1.51-1.45 (m, 2H), 1.31-1.23 (m, 30H), 1.17 (d, J=6.2 Hz, 3H), 0.51-0.47 (m, 2H), −0.03 (s, 9H). $^{13}$C NMR (126 MHz, CD$_3$OD) δ 156.7, 152.8, 150.8, 144.3, 119.5, 77.0 (d, J$_{CP}$=13.2 Hz), 65.9 (d, J$_{CP}$=6.3 Hz), 65.5 (d, J$_{CP}$=159.6 Hz), 34.7, 32.1 (d, J$_{CP}$=6.3 Hz), 30.8 (2C), 30.7, 30.5 (2C), 26.9, 25.1, 17.6, 16.9, −1.4. $^{31}$P NMR (121 MHz, CD$_3$OD) δ 15.27. HRMS (APCI) m/z calc. for C$_{30}$H$_{59}$N$_5$O$_4$PSi [M+H]$^+$, 612.40684 found, 612.40676.

LCMS (ESI) 95% ISO MeOH in H$_2$O (0.1% HCO$_2$H), 7 min, rt=5.087, m/z=612.5 [M+H]$^+$, 610.4 [M−H]$^−$.

Example 27. Synthesis of Ammonium [(1R)-2-(6-aminopurin-9-yl)-1-methyl-ethoxy]methyl-(20,20,20-trifluoroicos-18-ynoxy)phosphinate A. Synthesis of 2-nonadec-2-ynoxytetrahydropyran (NP-PD-092)

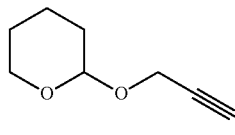

To a 250 mL oven-dried flask equipped with a stir bar was added 2-(2-propynyloxy)tetrahydro-2H-pyran (2.01 mL, 14.3 mmol, 1.00 eq), hexamethylphosphoramide (8.69 mL, 49.9 mmol, 3.50 eq) and THF (50.0 mL). The reaction mixture was cooled to −78° C. and stirred vigorously under Ar. n-Butyllithium (2.00 M in THF, 9.27 mL, 18.6 mmol, 1.30 eq) was added dropwise over a period of 15 minutes by way of an oven-dried pressure equalizing dropping funnel and the reaction was vigorously stirred at −78° C. for approximately 1 hour. Subsequently, hexadecylbromide (5.67 mL, 18.6 mmol, 1.30 eq) was added slowly dropwise over 10 minutes by way of a pressure equalizing dropping funnel after which the resulting reaction mixture was allowed to warm to room temperature overnight while stirring vigorously under Ar. The following day TLC indicated that all of the starting alkyne had been consumed. The reaction mixture was quenched with a saturated solution of ammonium chloride and then extracted three times into EtOAc. The organic phases were then combined, washed with brine, dried over anhydrous magnesium sulfate and concentrated in vacuo. Subsequent purification of the resulting crude material by column chromatography (2%-10% EtOAc/hexane) afforded a clear oil (3.89 g, 10.7 mmol, 75%).

B. Synthesis of nonadec-2-yn-1-ol (NP-PD-094)

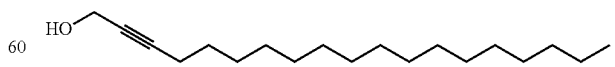

A solution of 2-nonadec-2-ynoxytetrahydropyran (3.88 g, 10.6 mmol, 1.00 eq) in methanol (40.0 mL) was added to a 100 mL flask equipped with a stir bar. To this solution was added p-toluenesulfonic acid monohydrate (183 mg, 1.06 mmol, 0.10 eq) and the reaction mixture was stirred vigorously for 3 hours at room temperature. TLC had confirmed full consumption of the starting material. The reaction mixture was subsequently concentrated in vacuo and the resulting crude material was purified by column chromatography (2%-10% EtOAc/hexane) to afford a white solid (2.24 g, 7.99 mmol, 75%).

C. Synthesis of nonadec-18-yn-1-ol (NP-PD-095)

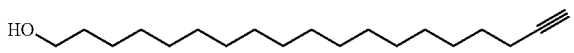 [SMILES: C#CCCCCCCCCCCCCCCCCCO]

Sodium hydride (60% in mineral oil, 2.56 g, 63.9 mmol, 8.00 eq) was added to a 250 mL oven-dried flask equipped with a stir bar under an atmosphere Ar. Following dilution with 1,3-diaminopropane (20.0 mL), the flask was placed in an oil bath preheated to 70° C. After stirring for 1 hour at this temperature the reaction mixture was cooled to 55° C. Subsequently, nonadec-2-yn-1-ol (2.24 g, 7.99 mmol, 1.00 eq) was dissolved in 1,3-diaminopropane (13.0 mL) and added slowly dropwise to the reaction mixture at this temperature. The reaction mixture was then left stirring vigorously overnight. The following morning the reaction was cooled to 0° C., quenched with water and acidified with a 1 N aqueous HCl solution to a pH of 2. The resulting aqueous phase was then extracted three times with hexane. The combined organic phases were then dried over magnesium sulfate and concentrated in vacuo. The resulting crude material was then purified by column chromatography (5%-20% EtOAc/hexane) to afford a white solid (1.24 g, 4.42 mmol, 55%).

D. Synthesis of 1-methoxy-4-(nonadec-18-ynoxymethyl)benzene (NP-PD-096)

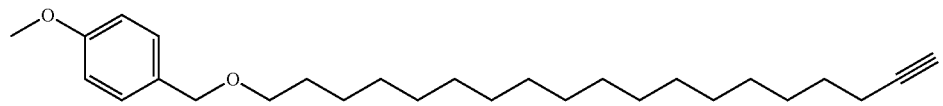 [SMILES: C#CCCCCCCCCCCCCCCCCCOCc1ccc(OC)cc1]

In a 100 mL oven-dried flask equipped with a stir bar, sodium hydride (60% in mineral oil, 481 mg, 12.0 mmol, 2.50 eq) was added to a solution of nonadec-18-yn-1-ol (1.35 g, 4.81 mmol, 1.00 eq) in DMF (20.0 mL) at 0° C. under an atmosphere of Ar. The reaction mixture was warmed to room temperature and after approximately 40 minutes, p-methoxybenzyl chloride (0.980 mL, 7.22 mmol, 1.50 eq) was added dropwise to the reaction mixture at room temperature. The reaction was heated to 50° C. and stirred vigorously under Ar overnight. The following day the reaction mixture was cooled to room temperature, quenched with a saturated solution of ammonium chloride and extracted three times into EtOAc. The organic phases were combined, washed with brine, dried over magnesium sulfate and concentrated in vacuo. The resulting crude material was then purified by column chromatography (5%-20% EtOAc/hexane) to yield a white solid (1.45 g, 3.62 mmol, 75%).

D. Synthesis of 1-methoxy-4-(20,20,20-trifluoro-icos-18-ynoxymethyl)benzene (NP-PD-098)

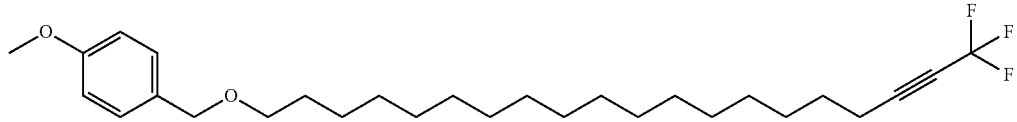 [SMILES: COc1ccc(COCCCCCCCCCCCCCCCCCC#CC(F)(F)F)cc1]

A 50 mL oven-dried flask equipped with a stir bar was charged with copper (I) iodide (610 mg, 3.20 mmol, 1.50 eq), K$_2$CO$_3$ (885 mg, 6.40 mmol, 3.00 eq) and N,N,N,N-tetramethylethylenediamine (0.483 mL, 3.20 mmol, 1.50 eq) in DMF (10.0 mL) under an atmosphere of air (balloon). The resulting blue mixture was stirred vigorously at room temperature for 15 minutes. (Trifluoromethyl)trimethylsilane (0.630 mL, 4.27 mmol, 2.00 eq) was added to the reaction mixture and the reaction was stirred for an additional 5 minutes before cooling to 0° C. To the reaction mixture was added (in one portion) a solution of 1-methoxy-4-(nonadec-18-ynoxymethyl)benzene (855 mg, 2.13 mmol, 1.00 eq) and (trifluoromethyl)trimethylsilane (0.630 mL, 4.27 mmol, 2.00 eq) in DMF (10.0 mL). The reaction was left to warm to room temperature and stirred vigorously for 48 hours. For the workup, the reaction was quenched with H$_2$O and extracted three times with DCM. The organic phases were combined, dried over MgSO$_4$, filtered and concentrated in vacuo. The crude material was subsequently purified by column chromatography (5%-20% EtOAc/hexane) to yield a white solid (906 mg, 1.93 mmol, 91%).

E. Synthesis of 20,20,20-trifluoroicos-18-yn-1-ol (NP-PD-101)

Tenofovir (100 mg, 0.348 mmol, 1.00 eq) and pyridine (2.00 mL) were added to a 25 mL oven-dried flask equipped with a stir bar under an atmosphere of Ar. This was followed by the addition of 20,20,20-trifluoroicos-18-yn-1-ol (182 mg, 0.522 mmol, 1.50 eq) and 2,4,6-triisopropylbenzenesulfonyl chloride (316 mg, 1.05 mmol, 3.00 eq). The reaction was left to stir vigorously at room temperature for 48 hours under Ar. The reaction was concentrated in vacuo, taken up in a saturated solution of ammonium chloride and concentrated once again in vacuo. The resulting salt was then vigorously stirred up in a 4:1 solution of DCM and MeOH for approximately 1 hour. The reaction was filtered and the resulting filtrate was collected, concentrated in vacuo and purified first by silica gel column chromatography (100% DCM-100% 80:20:3 DCM:MeOH:NH$_4$OH) and then by RP C18 column chromatography (10% MeOH/H$_2$O-100% MeOH) to yield a white solid (69.0 mg, 0.109 mmol, 31%). $^1$H NMR (500 MHz, CD$_3$OD) δ 8.32 (s, 1H), 8.21 (s, 1H), 4.38 (dd, J=14.4, 3.1 Hz, 1H), 4.23 (dd, J=14.4, 6.9 Hz,

HO~~~~~~~~~~~~~~~~~≡─CF$_3$

1H), 3.90 (pd, J=6.3, 3.0 Hz, 1H), 3.78-3.67 (m, 3H), 3.47 (dd, J=12.7, 10.0 Hz, 1H), 2.38 (dt, J=7.3, 3.6 Hz, 1H), 1.62-1.20 (m, 31H), 1.17 (d, J=6.2 Hz, 3H). $^{13}$C NMR (151 MHz, CD$_3$OD) δ 156.9, 153.0, 150.9, 144.3, 119.5, 115.6 (q, J$_{CF}$=254.9 Hz), 94.5, 91.5 (q, J$_{CF}$=6.2 Hz), 77.0 (d, J$_{CP}$=12.8 Hz), 68.7 (q, J$_{CF}$=51.9 Hz), 65.9 (d, J$_{CP}$=5.8 Hz), 65.5 (d, J$_{CP}$=159.9 Hz), 32.1 (d, J$_{CP}$=6.3 Hz), 30.8, 30.7 (2C), 30.6 (2C), 30.5 (2C), 30.1, 30.0, 29.8 (2C), 29.7, 28.3, 26.9, 21.3, 18.6, 16.8. $^{19}$F NMR (376 MHz, CD$_3$OD) δ −51.45 (t, J=4.0 Hz, 3F). $^{31}$P NMR (121 MHz, CD$_3$OD) δ 15.27. HRMS (APCI) m/z calc. for C$_{29}$H$_{46}$O$_4$N$_5$F$_3$P [M−H]$^-$, 616.32450 found, 616.32505. LCMS (ESI) 95% ISO MeOH in H$_2$O (0.1% HCO$_2$H), 9 min, rt=1.260, m/z=618.4 [M+H]$^+$, 616.2 [M−H]$^-$; 85-95% MeOH in H$_2$O (0.1% HCO$_2$H), 10 min, rt=2.946, m/z=618.4 [M+H]$^+$, 616.3 [M−H]$^-$.

In a 25 mL flask charged equipped with a stir bar, 1-methoxy-4-(20,20,20-trifluoroicos-18-ynoxymethyl)benzene (900 mg, 1.92 mmol, 1.00 eq) was dissolved in a mixture of MeOH (9.00 mL) and H$_2$O (0.900 mL). The reaction was cooled to 0° C. and ceric ammonium nitrate, CAN (3.16 g, 5.76 mmol, 3.00 eq) was added portion-wise. The reaction mixture was then warmed to room temperature and stirred vigorously for 3 hours or until TLC confirmed the consumption of the starting material. Subsequent quenching with H$_2$O was followed by three extractions with DCM. The organic phase was dried over magnesium sulfate and concentrated in vacuo. The resulting crude material was purified by column chromatography (100% hexane-20% EtOAc/hexane) to yield a white solid (574 mg, 1.65 mmol, 86%).

F. Synthesis of Ammonium [(1R)-2-(6-aminopurin-9-yl)-1-methyl-ethoxy]methyl-(20,20,20-trifluoro-icos-18-ynoxy)phosphinate (NP-PD-102)

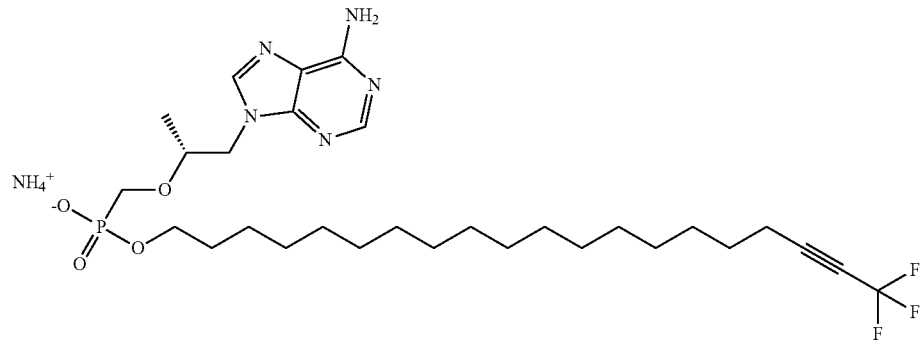

Example 28. Synthesis of Ammonium [(1R)-2-(6-aminopurin-9-yl)-1-methyl-ethoxy]methyl-(20,20,20-trifluoroicosoxy)phosphinate A. Synthesis of 20,20,20-trifluoroicosan-1-ol (NP-PD-106)

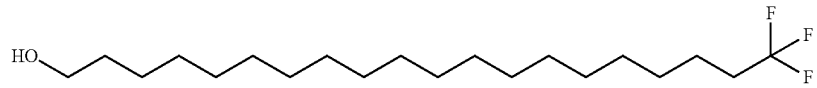 [SMILES: OCCCCCCCCCCCCCCCCCCCC(F)(F)F]

20,20,20-Trifluoroicos-18-yn-1-ol (230 mg, 0.660 mmol, 1.00 eq) and EtOH (5.00 mL) were added to a 25 mL oven-dried flask equipped with a stir bar and fitted with a sealed hydrogen balloon. The solution was subsequently degassed under house vacuum for approximately 10 minutes and then the reaction flask was purged with Ar. This cycle was repeated twice more before the addition of a catalytic amount of palladium hydroxide on carbon (20% wt, 46.3 mg, 0.0660 mmol, 0.100 eq). Once more the reaction flask was placed under vacuum before a final purge with hydrogen from the fitted hydrogen balloon. The reaction was subsequently left to stir vigorously under an atmosphere of hydrogen at room temperature for 18 hours. After this time, the heterogeneous reaction mixture was filtered over a bed of celite and the filtrate was collected and concentrated in vacuo. The resulting crude product was purified by column chromatography (5%-20% EtOAc/hexane) to yield a white solid (170 mg, 0.482 mmol, 73%).

B. Synthesis of ammonium [(1R)-2-(6-aminopurin-9-yl)-1-methyl-ethoxy]methyl-(20,20,20-trifluoroicosoxy)phosphinate (NP-PD-105)

column chromatography (100% DCM-80:30:3 DCM:MeOH:NH$_4$OH) and then a second purification by RPC18 column chromatography (10% MeOH/H$_2$O-100% MeOH) to yield a white solid (39.0 mg, 0.0611 mmol, 22%). $^1$H NMR (500 MHz, CD$_3$OD) δ 8.33 (s, 1H), 8.21 (s, 1H), 4.39 (dd, J=14.4, 3.1 Hz, 1H), 4.23 (dd, J=14.4, 6.8 Hz, 1H), 3.95-3.87 (m, 1H), 3.79-3.69 (m, 3H), 3.48 (dd, J=12.8, 10.0 Hz, 1H), 2.19-2.04 (m, 2H), 1.58-1.44 (m, 4H), 1.42-1.21 (m, 30H), 1.17 (d, J=6.2 Hz, 3H). $^{13}$C NMR (151 MHz, CD$_3$OD) δ 157.0, 153.2, 150.9, 144.3, 128.9 (q, J$_{CF}$=275.4 Hz), 119.6, 76.9 (d, J$_{CP}$=12.9 Hz), 65.9 (d, J$_{CP}$=5.9 Hz), 65.5 (d, J$_{CP}$=159.8 Hz), 34.4 (q, J$_{CF}$=28.2 Hz), 32.1 (d, J$_{CP}$=6.3 Hz), 30.8 (2C), 30.7 (2C), 30.5 (2C), 30.3, 29.8, 26.9, 23.0 (q, J$_{CF}$=3.0 Hz), 16.8. $^{19}$F NMR (376 MHz, CD$_3$OD) δ −68.71 (t, J=11.2 Hz, 3F). $^{31}$P NMR (121 MHz, CD$_3$OD) δ 15.28. HRMS (APCI) m/z calc. for C$_{29}$H$_{50}$O$_4$N$_5$F$_3$P [M−H]$^-$, 620.35580 found, 620.35498. LCMS (ESI) 95% ISO MeOH in H$_2$O (0.1% HCO$_2$H), 9 min, rt=1.367, m/z=622.4 [M+H]$^+$, 620.3 [M−H]$^-$; 85-95% MeOH in H$_2$O (0.1% HCO$_2$H), 10 min, rt=4.007, m/z=622.4 [M+H]$^+$, 620.4 [M−H]$^-$.

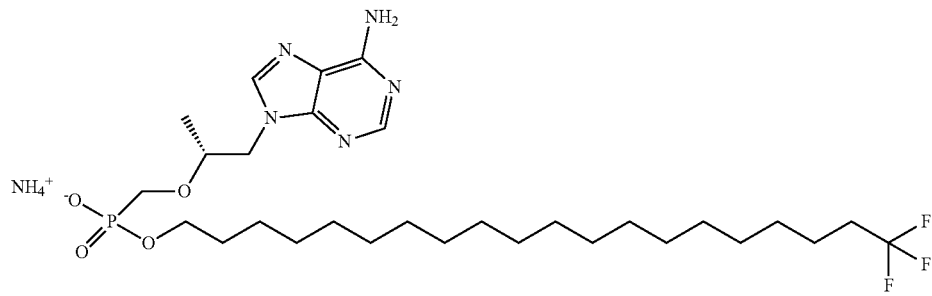

In an oven-dried 25 mL flask equipped with a stir bar, triethylamine (0.0992 mL, 557 mmol, 2.00 eq) was added to tenofovir (80.0 mg, 0.279 mmol, 1.00 eq), 20,20,20-trifluoroicosan-1-ol (147 mg, 0.418 mL, 1.50 eq), 1-(3-dimethylaminopropyl)-3-ethylcarbodiimide hydrochloride (107 mg, 0.418 mmol, 2.00 eq) and 4-dimethylaminopyridine (3.40 mg, 0.0279 mmol, 0.100 eq) in MeCN (2.00 mL) at room temperature and under an atmosphere of Ar. The reaction mixture was then heated to 90° C. and stirred vigorously at this temperature overnight. The following day the reaction was concentrated in vacuo and the resulting crude material was taken up in a 1:1 mixture of DCM (4.00 mL) and a 7 M solution of NH$_4$ in MeOH (4.00 mL) and stirred vigorously for approximately 2 hours. Subsequent concentration in vacuo was followed by purification by Example 29. Synthesis of Ammonium 3-((14-trimethylsilyl)tetradec-13-yn-1-yl)propyl(R)-(((1-(6-amino-9H-purin-9-yl)propan-2-yl)oxy)methyl)phosphonate A. Synthesis of 2-tetradec-2-ynoxytetrahydropyran (NP-PD-121)

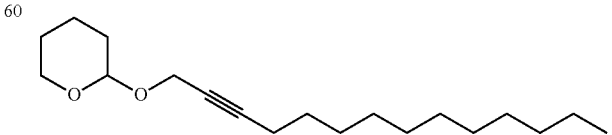

To a 250 mL oven-dried flask equipped with a stir bar was added 2-(2-propynyloxy)tetrahydro-2H-pyran (5.02 mL, 35.7 mmol, 1.00 eq), 1,3-dimethyl-3,4,5,6-tetrahydro-2 (1H)-pyrimidinone (12.9 mL, 107 mmol, 3.00 eq) and THF (100 mL). The reaction mixture was cooled to −78° C. and stirred vigorously under Ar. n-Butyllithium (2.30 M in THF, 20.2 mL, 46.4 mmol, 1.30 eq) was added dropwise over a period of 15 minutes by way of an oven-dried pressure equalizing dropping funnel and the reaction was vigorously stirred at −78° C. for approximately 1 hour. Subsequently, 1-bromoundecane (10.4 mL, 46.4 mmol, 1.30 eq) was added slowly dropwise over 10 minutes by way of a pressure equalizing dropping funnel after which the resulting reaction mixture was allowed to warm to room temperature overnight while stirring vigorously under Ar. The following day TLC indicated that all of the starting alkyne had been consumed. The reaction mixture was quenched with a saturated solution of ammonium chloride and then extracted three times into EtOAc. The organic phases were then combined, washed with brine, dried over anhydrous magnesium sulfate and concentrated in vacuo. Subsequent purification of the resulting crude material by column chromatography (2%-10% EtOAc/hexane) afforded a clear oil (6.64 g, 22.5 mmol, 63%).

B. Synthesis of tetradec-2-yn-1-ol (NP-PD-122)

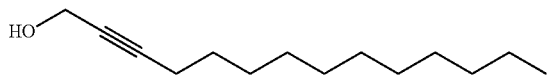

A solution of 2-tetradec-2-ynoxytetrahydropyran (6.64 g, 22.6 mmol, 1.00 eq) in methanol (100 mL) was added to a 100 mL flask equipped with a stir bar. To this solution was added p-toluenesulfonic acid monohydrate (428 mg, 2.26 mmol, 0.10 eq) and the reaction mixture was stirred vigorously for 3 hours at room temperature. TLC had confirmed full consumption of the starting material. The reaction mixture was subsequently concentrated in vacuo and the resulting crude material was purified by column chromatography (2%-10% EtOAc/hexane) to afford a white solid (3.77 g, 17.9 mmol, 80%).

C. Synthesis of tetradec-13-yn-1-ol (NP-PD-123)

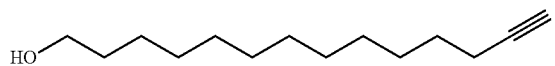

Sodium hydride (60% in mineral oil, 5.73 g, 143 mmol, 8.00 eq) was added to a 250 mL oven-dried flask equipped with a stir bar under an atmosphere Ar. Following dilution with 1,3-diaminopropane (40.0 mL), the flask was placed in an oil bath preheated to 70° C. After stirring for 1 hour at this temperature the reaction mixture was cooled to 55° C. Subsequently, tetradec-2-yn-1-ol (3.77 g, 17.9 mmol, 1.00 eq) dissolved in 1,3-diaminopropane (10.0 mL) and added slowly dropwise to the reaction mixture at this temperature. The reaction mixture was then left stirring vigorously overnight. The following morning the reaction was cooled to 0° C., quenched with water and acidified with a 1 N aqueous HCl solution to a pH of 2. The resulting aqueous phase was then extracted three times with hexane. The combined organic phases were then dried over magnesium sulfate and concentrated in vacuo. The resulting crude material was then purified by column chromatography (5%-20% EtOAc/hexane) to afford a white solid (2.50 g, 11.9 mmol, 66%).

D. Synthesis of 2-(3-tetradec-13-ynoxypropoxy)tetrahydropyran (NP-PD-124)

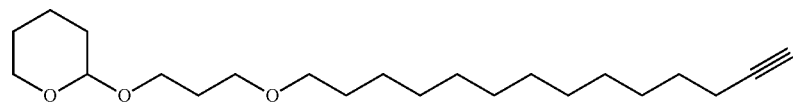 [SMILES: C#CCCCCCCCCCCCCOCCCOC1CCCCO1]

Tetradec-13-yn-1-ol (600 mg, 2.85 mmol, 1.00 eq) was added to a 25 mL flask equipped with a stir bar and fitted with a reflux condenser. Tetradec-13-yn-1-ol was then diluted with THF (3.00 mL) and a saturated aqueous NaOH solution (3.00 mL). tetrabutylammonium bromide (184 mg, 0.571 mmol, 0.200 eq) and 2-(3-bromopropoxy)tetrahydropyran (0.532 mL, 3.14 mmol, 1.10 eq) was added to the reaction mixture which was subsequently heated to reflux (75° C.), and stirred vigorously overnight. The following day, the reaction mixture was cooled to room temperature and then partitioned between DCM and water. The resulting aqueous layer was extracted 3 times with DCM, and the resulting organic phases were combined, washed with brine, dried over anhydrous magnesium sulfate and concentrated in vacuo. The resulting crude material was purified by column chromatography (100% hexane-10% EtOAc/hexane) to yield a clear oil (486 mg, 1.38 mmol, 48%).

E. Synthesis of trimethyl-[14-(3-tetrahydropyran-2-yloxypropoxy)tetradec-1-ynyl]silane (NP-PD-127)

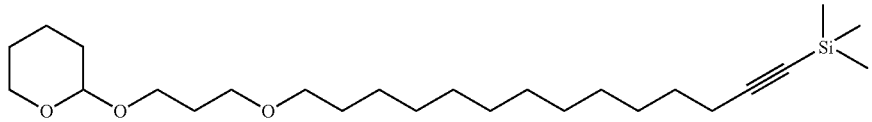 [SMILES: C[Si](C)(C)C#CCCCCCCCCCCCCOCCCOC1CCCCO1]

To a 25 mL oven-dried flask equipped with a stirrer bar was added 2-(3-tetradec-13-ynoxypropoxy)tetrahydropyran (801 mg, 2.27 mmol, 1.00 eq), 1,3-dimethyl-3,4,5,6-tetrahydro-2(1H)-pyrimidinone (0.824 mL, 6.82 mmol, 3.00 eq) and THF (10.0 mL) under an atmosphere of Ar. The flask was subsequently cooled to −78° C. before the slow dropwise addition of n-BuLi (2.00 M in THF, 2.84 mL, 5.68 mmol, 2.50 eq). After 2 hours at −78° C., the reaction was warmed to 0° C. and left to stir vigorously for 1 hours. The reaction was then re-cooled to −78° C. and trimethylsilyl chloride (0.307 mL, 5.68 mmol, 2.50 eq) was added to the reaction mixture dropwise. The reaction was then allowed to warm to room temperature overnight. The following morning the reaction was quenched with a saturated ammonium chloride solution and extracted three times into EtOAc. The organic phases were combined, washed with brine, dried over magnesium sulfate and concentrated in vacuo. The resulting crude product was purified by column chromatography (100% hexane-10% EtOAc/hexane) to yield a clear oil (528 mg, 1.24 mmol, 55%).

F. Synthesis of 3-(14-trimethylsilyltetradec-13-ynoxy)propan-1-ol (NP-PD-128)

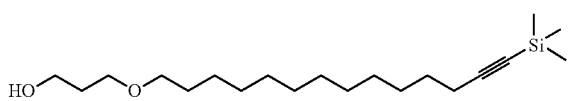 [SMILES: C[Si](C)(C)C#CCCCCCCCCCCCCOCCCO]

A solution of trimethyl-[14-(3-tetrahydropyran-2-yloxypropoxy)tetradec-1-ynyl]silane (520 mg, 1.22 mmol, 1.00 eq) in methanol (5.00 mL) was added to a 100 mL flask equipped with a stir bar. To this solution was added p-toluenesulfonic acid monohydrate (23.3 mg, 0.122 mmol, 0.100 eq) and the reaction mixture was stirred vigorously for 3 hours at room temperature. TLC had confirmed full consumption of the starting material. The reaction mixture was subsequently concentrated in vacuo and the resulting crude material was purified by column chromatography (2%-10% EtOAc/hexane) to afford a clear oil (310 mg, 0.910 mmol, 74%).

G. Synthesis of Ammonium 3-((14-trimethylsilyl)tetradec-13-yn-1-yl)propyl(R)-(((1-(6-amino-9H-purin-9-yl)propan-2-yl)oxy)methyl)phosphonate (NP-PD-130)

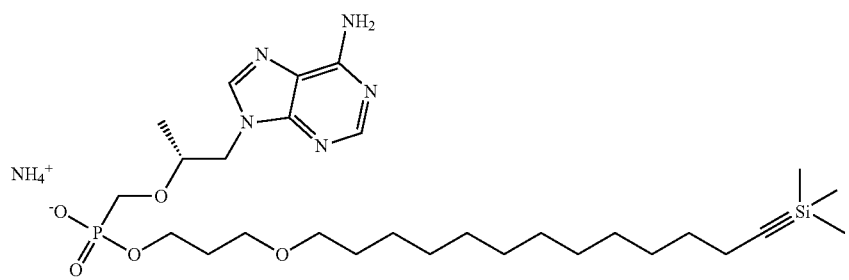

Tenofovir (170 mg, 0.592 mmol, 1.00 eq) and pyridine (2.00 mL) were added to a 25 mL oven-dried flask equipped with a stir bar under an atmosphere of Ar. This was followed by the addition of 3-(14-trimethylsilyltetradec-13-ynoxy)propan-1-ol (302 mg, 0.888 mmol, 1.50 eq) and 2,4,6-triisopropylbenzenesulfonyl chloride (538 mg, 1.78 mmol, 3.00 eq). The reaction was left to stir vigorously at room temperature for 48 hours under Ar. The reaction was concentrated in vacuo, taken up in a saturated solution of ammonium chloride and concentrated once again in vacuo. The resulting salt was then vigorously stirred up in a 4:1 solution of DCM and MeOH for approximately 1 hour. The reaction was filtered and the resulting filtrate was collected, concentrated in vacuo and purified first by silica gel column chromatography (100% DCM-100% 80:20:3 DCM:MeOH:NH$_4$OH) and then by RP C18 column chromatography (10% MeOH/H$_2$O-100% MeOH) to yield a white solid (145 mg, 0.231 mmol, 39%). $^1$H NMR (500 MHz, CD$_3$OD) δ 8.31 (s, 1H), 8.21 (s, 1H), 4.38 (dd, J=14.4, 3.2 Hz, 1H), 4.23 (dd, J=14.4, 6.8 Hz, 1H), 3.94-3.82 (m, 3H), 3.72 (dd, J=12.8, 9.5 Hz, 1H), 3.52-3.39 (m, 3H), 3.33 (t, J=6.6 Hz, 2H), 2.19 (t, J=7.0 Hz, 2H), 1.80-1.73 (m, 2H), 1.54-1.44 (m, 4H), 1.43-1.34 (m, 2H), 1.32-1.25 (m, 14H), 1.17 (d, J=6.2 Hz, 3H), 0.10 (s, 9H). $^{13}$C NMR (126 MHz, CD$_3$OD) δ 156.8, 152.9, 150.9, 144.3, 119.5, 108.7, 84.8, 76.9 (d, J$_{CP}$=12.7 Hz), 72.0, 68.4, 65.4 (d, J$_{CP}$=160.4 Hz), 63.1 (d, J$_{CP}$=5.6 Hz), 49.1, 32.4 (d, J$_{CP}$=6.1 Hz), 30.8, 30.72 (2C), 30.6 (2C), 30.1, 29.7 (2C), 27.3, 20.4, 16.9. $^{31}$P NMR (121 MHz, CD$_3$OD) δ 15.45 HRMS (APCI) m/z calc. for C$_{29}$H$_{51}$O$_5$N$_5$PSi [M−H], 608.34026 found, 608.34068. LCMS (ESI) 95% ISO MeOH in H$_2$O (0.1% HCO$_2$H), 7 min, rt=2.025, m/z=610.4 [M+H]$^+$, 608.3 M−H]$^−$; 85-95% MeOH in H$_2$O (0.1% HCO$_2$H), 10 min, rt=3.023, m/z=610.4 [M+H]$^+$, 608.2 [M−H]$^−$.

Example 30. Synthesis of Ammonium [(1R)-2-(6-aminopurin-9-yl)-1-methyl-ethoxy]methyl-[3-(16,16,16-trifluorohexadec-14-ynoxy)propoxy]phosphinate

A. Synthesis of 3-[(4-methoxyphenyl)methoxy]propan-1-ol (NP-PD-143)

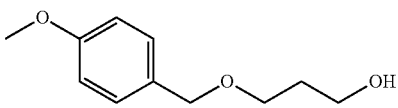

A solution of 1,3-dihydroxypropane (4.58 mL, 63.9 mmol) in DMSO (50 mL) was cooled to 0° C. At this temperature, potassium hydroxide (3.58 g, 63.9 mmol) was added portion-wise and the mixture was stirred at room temperature until most of the KOH pellets had dissolved before being treated with 4-methoxybenzyl chloride (PMBCl) (4.33 mL, 31.9 mmol) at room temperature. The reaction was stirred for 18 h. When TLC indicated complete consumption of PMBCl, the mixture was cooled to 0° C. again, diluted with DCM and carefully quenched by the addition of 1 N HCl. Afterwards it was warmed to room temperature again, the phases were separated and the aqueous layer was extracted three times with DCM. The combined organic extracts were dried over MgSO₄ and then concentrated down under reduced pressure. The residue was purified by flash column chromatography on silica gel (10-50% EtOAc/hexane) to afford 3-[(4-methoxyphenyl)methoxy]propan-1-ol (4.26 g, 21.7 mmol, 68% yield) as a clear oil.

B. Synthesis of 1-(3-bromopropoxymethyl)-4-methoxy-benzene (NP-PD-144)

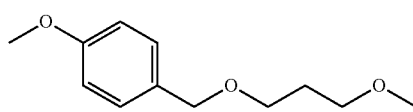

Triphenylphosphine (8.54 g, 32.6 mmol) was added to a solution of 3-[(4-methoxyphenyl)methoxy]propan-1-ol (4.26 g, 21.7 mmol) and carbon tetrabromide (8.64 g, 26.1 mmol) in DCM (100 mL) at 0° C. The reaction mixture was stirred for 1 h, then the solvent was removed in vacuo and the residue was purified by column chromatography on silica gel (5-40% EtOAc/hexane) to give the 1-(3-bromopropoxymethyl)-4-methoxy-benzene (3.13 g, 12.1 mmol, 56% yield) as a clear oil.

C. Synthesis of 1-methoxy-4-(3-pentadec-14-ynoxypropoxymethyl)benzene (NP-PD-145)

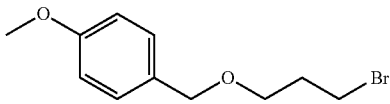

NP-PD-144 (3.25 g, 14.5 mmol, 1.20 eq) was added to a 250 mL flask equipped with a stir bar and fitted with a reflux condenser. Pentadec-14-yn-ol was then diluted with THF (20 mL) and a saturated aqueous NaOH solution (20 mL). Tetrabutylammonium bromide (779 mg, 2.42 mmol, 0.200 eq) and 1-(3-bromopropoxymethyl)-4-methoxy-benzene (3.13 g, 12.1 mmol, 1.00 eq) was added to the reaction mixture which was subsequently heated to reflux (75° C.), and stirred vigorously overnight. The following day, the reaction mixture was cooled to room temperature and then partitioned between DCM and water. The resulting aqueous layer was extracted 3 times with DCM, and the resulting organic phases were combined, washed with brine, dried over anhydrous magnesium sulfate and concentrated in vacuo. The resulting crude material was purified by column chromatography (100% hexane-10% EtOAc/hexane) to yield a clear oil (2.01 g, 4.99 mmol, 41%).

D. Synthesis of 1-methoxy-4-[3-(16,16,16-trifluorohexadec-14-ynoxy)propoxymethyl]benzene (NP-PD-146)

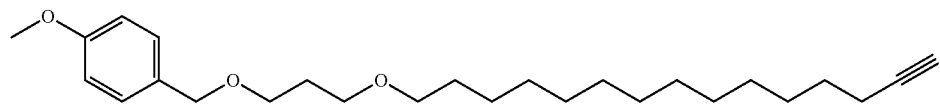 [SMILES: C#CCCCCCCCCCCCCCOCCCOCc1ccc(OC)cc1]

A 100 mL oven-dried flask equipped with a stir bar was charged with copper (I) iodide (1.35 g, 7.08 mmol, 1.50 eq), K₂CO₃ (1.96 g, 14.2 mmol, 3.00 eq) and N,N,N',N'-tetramethylethylenediamine (1.06 mL, 7.08 mmol, 1.50 eq) in DMF (10 mL) under an atmosphere of air (balloon). The resulting blue mixture was stirred vigorously at room temperature for 15 minutes. (Trifluoromethyl)trimethylsilane (1.40 mL, 9.44 mmol, 2.00 eq) was added to the reaction mixture and the reaction was stirred for an additional 5 minutes before cooling to 0° C. To the reaction mixture was added (in one portion) a solution of NP-PD-145 (1.90 g, 4.72 mmol, 1.00 eq) and (trifluoromethyl)trimethylsilane (1.40 mL, 9.44 mmol, 2.00 eq) in DMF (10 mL). The reaction was left to warm to room temperature and stirred vigorously for 48 hours. For the workup, the reaction was quenched with H₂O and extracted three times with DCM. The organic phases were combined, dried over MgSO₄, filtered and concentrated in vacuo. The crude material was subsequently purified by column chromatography (5%-20% EtOAc/hexane) to yield a clear oil (1.53 g, 3.25 mmol, 69%).

E. Synthesis of 3-(16,16,16-trifluorohexadec-14-ynoxy)propan-1-ol (NP-PD-147)

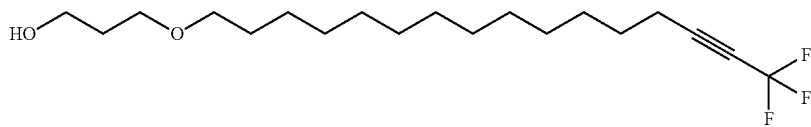 [SMILES: OCCCOCCCCCCCCCCCCCC#CC(F)(F)F]

In a 25 mL flask charged equipped with a stir bar, NP-PD-146 (1.53 g, 3.25 mmol) was dissolved in a mixture of methanol (10 mL) and water (1 mL). The reaction was cooled to 0° C. and ceric ammonium nitrate (5.35 g, 9.75 mmol) was added portion-wise. The reaction mixture was then warmed to room temperature and stirred vigorously for 3 hours or until TLC confirmed the consumption of the starting material. Subsequent quenching with H2O was followed by three extractions with DCM. The organic phase was dried over magnesium sulfate and concentrated in vacuo. The resulting crude material was purified by column chromatography (100% hexane-20% EtOAc/hexane) to yield 3-(16,16,16-trifluorohexadec-14-ynoxy)propan-1-ol (1.08 g, 3.08 mmol, 95% yield) as a white solid.

F. Synthesis of Ammonium [(1R)-2-(6-aminopurin-9-yl)-1-methyl-ethoxy]methyl-[3-(16,16,16-trifluorohexadec-14-ynoxy)propoxy]phosphinate (NP-PD-149)

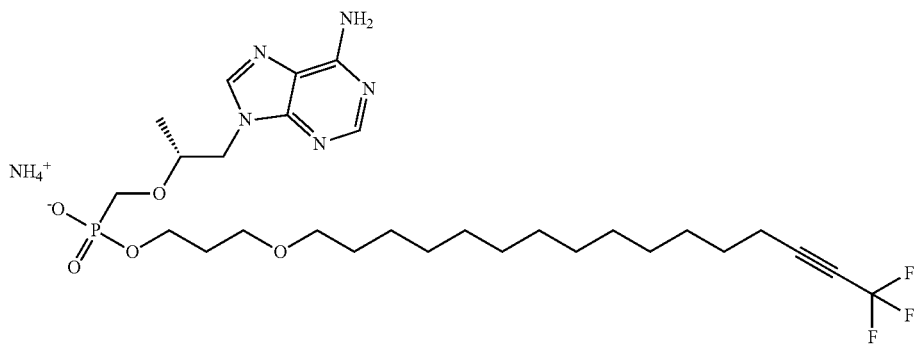

Tenofovir (250 mg, 0.870 mmol, 1.00 eq) and pyridine (3.00 mL) were added to a 25 mL oven-dried flask equipped with a stir bar under an atmosphere of Ar. This was followed by the addition of 3-(16,16,16-trifluorohexadec-14-ynoxy)propan-1-ol (458 mg, 1.31 mmol, 1.50 eq) and 2,4,6-triisopropylbenzenesulfonyl chloride (791 mg, 2.61 mmol, 3.00 eq). The reaction was left to stir vigorously at room temperature for 48 hours under Ar. The reaction was concentrated in vacuo, taken up in a saturated solution of ammonium chloride and concentrated once again in vacuo. The resulting salt was then vigorously stirred up in a 4:1 solution of DCM and MeOH for approximately 1 hour. The reaction was filtered and the resulting filtrate was collected, concentrated in vacuo and purified first by silica gel column chromatography (100% DCM-100% 80:20:3 DCM:MeOH:NH$_4$OH) and then by RP C18 column chromatography (10% MeOH/H$_2$O-100% MeOH). The product fractions were collected once again, concentrated under reduced pressure, stirred with 7 N ammonia in methanol (10 mL) for 10 min at room temperature, and dried under vacuum, to yield a white solid (105 mg, 0.165 mmol, 19%). $^1$H NMR (500 MHz, CD$_3$OD) δ 8.34 (s, 1H), 8.22 (s, 1H), 4.40 (dd, J=14.4, 3.2 Hz, 1H), 4.24 (dd, J=14.4, 6.7 Hz, 1H), 3.95-3.84 (m, 3H), 3.73 (dd, J=12.8, 9.4 Hz, 1H), 3.50 (dd, J=12.8, 9.9 Hz, 1H), 3.44 (t, J=6.4 Hz, 2H), 3.35 (t, J=6.6 Hz, 2H), 2.43-2.36 (m, 2H), 1.82-1.74 (m, 2H), 1.58 (p, J=7.1 Hz, 2H), 1.54-1.46 (m, 2H), 1.46-1.38 (m, 2H), 1.33-1.25 (m, 16H), 1.16 (d, J=6.2 Hz, 3H). $^{13}$C NMR (151 MHz, CD$_3$OD) δ 156.2, 151.9, 150.8, 144.7, 119.5, 115.7 (q, J$_{CP}$=254.9 Hz), 91.6 (q, J$_{CF}$=6.2 Hz), 76.9 (d, J$_{CP}$=12.7 Hz), 72.0, 68.4, 65.3 (d, J$_{CP}$=159.9 Hz), 63.1 (d, J$_{CP}$=5.6 Hz), 32.4 (d, J$_{CP}$=6.3 Hz), 30.8, 30.7 (3C), 30.6, 30.5, 30.0, 29.8, 28.3, 27.3, 18.6, 16.8. $^{19}$F NMR (376 MHz, CD$_3$OD) δ −51.54 (t, J=3.9 Hz, 3F). $^{31}$P NMR (121 MHz, CD$_3$OD) δ 15.53. HRMS (APCI) m/z calc. for C$_{28}$H$_{44}$O$_5$N$_5$F$_3$P [M−H], 618.30376 found, 618.30418. LCMS (ESI) 95% ISO MeOH in H$_2$O (0.1% HCO$_2$H), 5 min, rt=0.704, m/z=620.4 [M+H]$^+$, 618.2 [M−H]$^-$; 25-95% MeOH in H$_2$O (0.1% HCO$_2$H), 6 min, rt=4.417, m/z=620.2 [M+H]$^+$, 618.2 [M−H]$^-$.

Example 31. Synthesis of Ammonium [(1R)-2-(6-aminopurin-9-yl)-1-methyl-ethoxy]methyl-[3-(16,16,16-trifluorohexadecoxy)propoxy]phosphinate A. Synthesis of 3-(16,16,16-trifluorohexadecoxy)propan-1-ol (NP-PD-156)

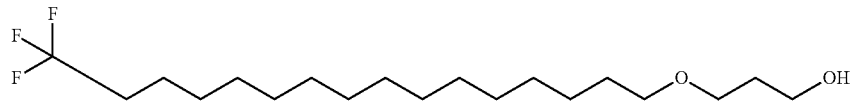 [SMILES: OCCCOCCCCCCCCCCCCCCCCC(F)(F)F]

3-(16,16,16-Trifluorohexadec-14-ynoxy)propan-1-ol (580 mg, 1.66 mmol, 1.00 eq) and EtOAc (10 mL) were added to an 50 mL oven-dried flask equipped with a stir bar and fitted with a sealed hydrogen balloon. The solution was subsequently degassed under house vacuum for approximately 10 minutes and then the reaction flask was purged with Ar. This cycle was repeated twice more before the addition of a catalytic amount of palladium hydroxide on carbon (20% wt, 116 mg, 0.166 mmol, 0.10 eq). Once more the reaction flask was placed under vacuum before a final purge with hydrogen from the fitted hydrogen balloon. The reaction was subsequently left to stir vigorously under an atmosphere of hydrogen at room temperature for 18 hours. After this time, the heterogeneous reaction mixture was filtered over a bed of celite and the filtrate was collected and concentrated in vacuo. The resulting crude product was purified by column chromatography (5%-20% EtOAc/hexane) to yield a white solid (460 mg, 1.30 mmol, 78%).

B. Synthesis of Ammonium [(1R)-2-(6-aminopurin-9-yl)-1-methyl-ethoxy]methyl-[3-(16,16,16-trifluorohexadecoxy)propoxy]phosphinate (NP-PD-158)

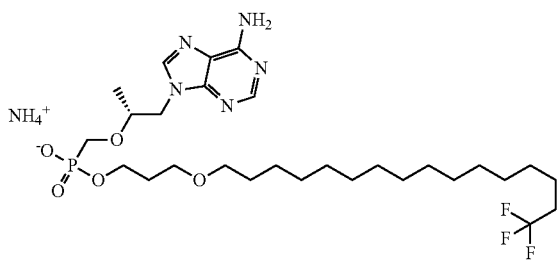

Tenofovir (200 mg, 0.696 mmol, 1.00 eq) and pyridine (3.00 mL) were added to a 25 mL oven-dried flask equipped with a stir bar under an atmosphere of Ar. This was followed by the addition of 3-(16,16,16-trifluorohexadecoxy)propan-1-ol (370 mg, 1.05 mmol, 1.50 eq) and 2,4,6-triisopropylbenzenesulfonyl chloride (633 mg, 2.09 mmol, 3.00 eq). The reaction was left to stir vigorously at room temperature for 48 hours under Ar. The reaction was concentrated in vacuo, taken up in a saturated solution of ammonium chloride and concentrated once again in vacuo. The resulting salt was then vigorously stirred up in a 4:1 solution of DCM and MeOH for approximately 1 hour. The reaction was filtered and the resulting filtrate was collected, concentrated in vacuo and purified first by silica gel column chromatography (100% DCM-100% 80:20:3 DCM:MeOH:NH$_4$OH) and then by RP C18 column chromatography (10% MeOH/H$_2$O-100% MeOH). The product fractions were collected once again, concentrated under reduced pressure, stirred with 7 N ammonia in methanol (10 mL) for 10 min at room temperature, and dried under vacuum, to yield a white solid (203 mg, 0.317 mmol, 46%). $^1$H NMR (600 MHz, CD$_3$OD) δ 8.32 (s, 1H), 8.20 (s, 1H), 4.38 (dd, J=14.4, 3.2 Hz, 1H), 4.24 (dd, J=14.4, 6.6 Hz, 1H), 3.93-3.84 (m, 3H), 3.71 (dd, J=12.8, 9.5 Hz, 1H), 3.47 (dd, J=12.8, 9.9 Hz, 1H), 3.44 (t, J=6.4 Hz, 2H), 3.34 (t, J=6.6 Hz, 2H), 2.17-2.07 (m, 2H), 1.82-1.73 (m, 2H), 1.57-1.52 (m, 2H), 1.51-1.47 (m, 2H), 1.41-1.35 (m, 2H), 1.33-1.26 (m, 20H), 1.16 (d, J=6.2 Hz, 3H). $^{13}$C NMR (151 MHz, CD$_3$OD) δ 157.0, 153.2, 150.9, 144.3, 128.9 (q, J$_{CF}$=275.5 Hz), 119.6, 76.9 (d, J$_{CF}$=13.0 Hz), 72.0, 68.5, 66.0, 64.9, 63.1 (d, J$_{CP}$=5.7 Hz), 34.4 (q, J$_{CF}$=28.1 Hz), 32.4 (d, J$_{CP}$=6.4 Hz), 30.8 (2C), 30.7 (2C), 30.6, 30.5, 30.3, 29.8, 27.3, 23.0, 22.9 (q, J$_{CF}$=2.9 Hz), 16.8. $^{19}$F NMR (376 MHz, CD$_3$OD) δ −68.76 (t, J=11.2 Hz, 3F). $^{31}$P NMR (162 MHz, CD$_3$OD) δ 15.39. HRMS (APCI) m/z calc. for C$_{28}$H$_{48}$O$_5$F$_3$N$_5$P [M−H]−, 622.33506 found, 622.33497. LCMS (ESI) 95% ISO MeOH in H$_2$O (0.1% HCO$_2$H), 7 min, rt=4.143, m/z=624.3 [M+H]$^+$, 622.3 [M−H]$^-$; 85-95% MeOH in H$_2$O (0.1% HCO$_2$H), 10 min, rt=5.133, m/z=624.3 [M+H]$^+$, 622.2 [M−H]$^-$.

Example 32. Synthesis of Ammonium 4-pentadecoxybutoxy-[[rac-(1R)-2-(6-aminopurin-9-yl)-1-methyl-ethoxy]methyl]phosphinate A. Synthesis of 4-pentadecoxybutan-1-ol (NP-PD-148)

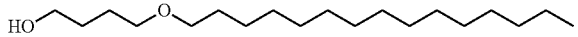 [SMILES: CCCCCCCCCCCCCCCOCCCCO]

Sodium hydride (60% suspended in mineral oil, 103 mg, 2.57 mmol) was added to butane-1,4-diol (0.23 mL, 2.6 mmol) in DMF (10 mL) at 0° C. in an oven-dried two-neck flask under an atmosphere of Ar. After vigorous stirring for 1 hour at 0° C., 1-bromopentadecane (0.50 mL, 1.7 mmol) was added dropwise. The reaction mixture was subsequently allowed to warm to room temperature and after vigorous stirring for 5 hours was slowly quenched with water. The reaction was extracted three times into DCM. The organic phases were combined, dried over MgSO$_4$ and concentrated in vacuo. The resulting crude product was then purified by column chromatography (5%-30% EtOAc/hexanes) to yield 4-pentadecoxybutan-1-ol (405 mg, 1.35 mmol, 79% yield) as a white solid.

B. Synthesis of Ammonium 4-pentadecoxybutoxy-[[rac-(1R)-2-(6-aminopurin-9-yl)-1-methyl-ethoxy]methyl]phosphinate (NP-PD-150)

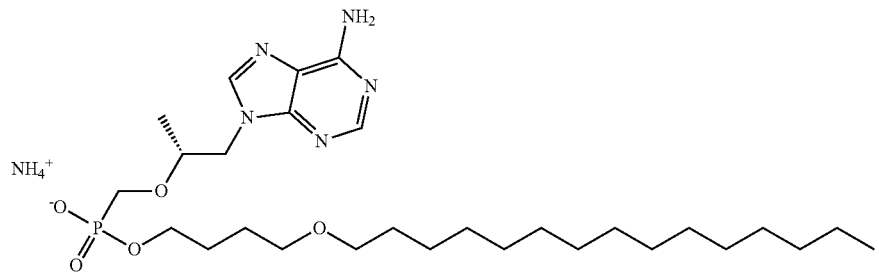

Tenofovir (250 mg, 0.870 mmol, 1.00 eq) and pyridine (3.00 mL) were added to a 25 mL oven-dried flask equipped with a stir bar under an atmosphere of Ar. This was followed by the addition of 4-pentadecoxybutan-1-ol (392 mg, 1.31 mmol, 1.50 eq) and 2,4,6-triisopropylbenzenesulfonyl chloride (791 mg, 2.61 mmol, 3.00 eq). The reaction was left to stir vigorously at room temperature for 48 hours under Ar. The reaction was concentrated in vacuo, taken up in a saturated solution of ammonium chloride and concentrated once again in vacuo. The resulting salt was then vigorously stirred up in a 4:1 solution of DCM and MeOH for approximately 1 hour. The reaction was filtered and the resulting filtrate was collected, concentrated in vacuo and purified first by silica gel column chromatography (100% DCM-100% 80:20:3 DCM:MeOH:NH$_4$OH) and then by RP C18 column chromatography (10% MeOH/H$_2$O-100% MeOH) to yield a white solid (278 mg, 0.474 mmol, 54%). $^1$H NMR (600 MHz, CD$_3$OD) δ 8.31 (s, 1H), 8.20 (s, 1H), 4.37 (dd, J=14.4, 3.2 Hz, 1H), 4.23 (dd, J=14.4, 6.7 Hz, 1H), 3.93-3.86 (m, 1H), 3.83-3.74 (m, 2H), 3.71 (dd, J=12.7, 9.5 Hz, 1H), 3.47 (dd, J=12.7, 10.0 Hz, 1H), 3.39-3.35 (m, 4H), 1.60-1.54 (m, 4H), 1.54-1.48 (m, 2H), 1.28 (s, 24H), 1.16 (d, J=6.2 Hz, 3H), 0.90 (t, J=7.0 Hz, 3H). $^{13}$C NMR (151 MHz, CD$_3$OD) δ 157.2, 153.5, 151.0, 144.3, 119.6, 76.9 (d, J$_{CP}$=13.1 Hz), 71.9, 71.5, 66.1, 65.7 (d, J$_{CP}$=5.7 Hz), 65.0, 33.1, 30.8 (5C), 30.7 (2C), 30.6, 30.5, 28.9 (d, J$_{CP}$=6.5 Hz), 27.3, 27.1, 23.7, 16.8, 14.4. $^{31}$P NMR (162 MHz, CD$_3$OD) δ 15.27. HRMS (APCI) m/z calc. for C$_{28}$H$_{51}$O$_5$N$_5$P [M–H]$^-$, 568.36333 found, 568.36270.

Example 33. Synthesis of Ammonium [rac-(1R)-2-(6-aminopurin-9-yl)-1-methyl-ethoxy]methyl-(5-tetradecoxypentoxy)phosphinate A. Synthesis of 5-tetradecoxypentan-1-ol (NP-PD-152)

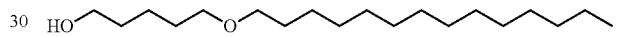

Sodium hydride (60% suspended in mineral oil, 108 mg, 2.71 mmol) was added to pentane-1,5-diol (0.28 mL, 2.7 mmol) in DMF (16 mL) at 0° C. in an oven-dried two-neck flask under an atmosphere of Ar. After vigorous stirring for 1 hour at 0° C., 1-bromotetradecane (500 g, 1.80 mmol) was added dropwise. The reaction mixture was subsequently allowed to warm to room temperature and after vigorous stirring for 5 hours was slowly quenched with water. The reaction was then extracted three times into DCM. The organic phases were combined, dried over MgSO$_4$ and concentrated in vacuo. The resulting crude product was then purified by column chromatography (5%-30% EtOAc/hexanes) to yield 5-tetradecoxypentan-1-ol (257 mg, 0.856 mmol, 47% yield) as a white solid.

B. Synthesis of Ammonium [rac-(1R)-2-(6-aminopurin-9-yl)-1-methyl-ethoxy]methyl-(5-tetradecoxypentoxy)phosphinate (NP-PD-154)

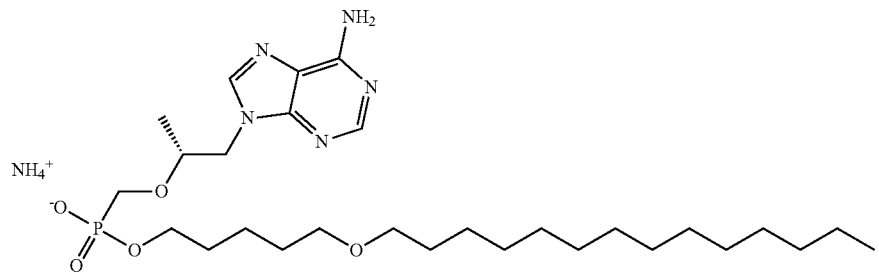

Tenofovir (120 mg, 0.418 mmol, 1.00 eq) and pyridine (2.00 mL) were added to a 25 mL oven-dried flask equipped with a stir bar under an atmosphere of Ar. This was followed by the addition of 5-tetradecoxypentan-1-ol (188 mg, 0.627 mmol, 1.50 eq) and 2,4,6-triisopropylbenzenesulfonyl chloride (380 mg, 1.25 mmol, 3.00 eq). The reaction was left to stir vigorously at room temperature for 48 hours under Ar. The reaction was concentrated in vacuo, taken up in a saturated solution of ammonium chloride and concentrated once again in vacuo. The resulting salt was then vigorously stirred up in a 4:1 solution of DCM and MeOH for approximately 1 hour. The reaction was filtered and the resulting filtrate was collected, concentrated in vacuo and purified first by silica gel column chromatography (100% DCM-100% 80:20:3 DCM:MeOH:NH$_4$OH) and then by RP C18 column chromatography (10% MeOH/H$_2$O-100% MeOH) to yield a white solid (85 mg, 0.15 mmol, 35%). $^1$H NMR (600 MHz, CD$_3$OD) δ 8.31 (s, 1H), 8.20 (s, 1H), 4.37 (dd, J=14.4, 3.2 Hz, 1H), 4.23 (dd, J=14.4, 6.8 Hz, 1H), 3.93-3.86 (m, 1H), 3.79-3.68 (m, 3H), 3.46 (dd, J=12.7, 10.1 Hz, 1H), 3.37 (q, J=6.4 Hz, 4H), 1.56-1.49 (m, 6H), 1.36-1.26 (m, 24H), 1.16 (d, J=6.2 Hz, 3H), 0.90 (t, J=7.0 Hz, 3H). $^{13}$C NMR (151 MHz, CD$_3$OD) δ 157.2, 153.5, 151.0, 144.2, 119.6, 76.9 (d, J$_{CP}$=12.8 Hz), 71.9 (d, J$_{CP}$=15.1 Hz), 66.1, 65.8 (d, J$_{CP}$=5.9 Hz), 65.0, 33.1, 31.9 (2C), 30.8 (3C), 30.7, 30.6, 30.5 (2C), 27.3, 23.7, 23.6, 16.8, 14.4. $^{31}$P NMR (162 MHz, CD$_3$OD) δ 15.27. HRMS (APCI) m/z calc. for C$_{28}$H$_{51}$O$_5$N$_5$P [M–H]$^-$, 568.36333 found, 568.36284.

Example 34. Synthesis of Ammonium 2-heptadecoxyethoxy-[[rac-(1R)-2-(6-aminopurin-9-yl)-1-methyl-ethoxy]methyl]phosphinate A. Synthesis of 2-heptadecoxyethanol (NP-PD-151)

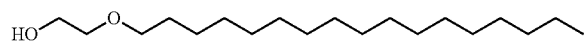 [SMILES: CCCCCCCCCCCCCCCCCOCCO]

Sodium hydride (60% suspended in mineral oil, 188 mg, 4.70 mmol) was added to ethylene glycol (0.26 mL, 4.7 mmol) in DMF (16 mL) at 0° C. in an oven-dried two-neck flask under an atmosphere of Ar. After vigorous stirring for 1 hour at 0° C., 1-bromoheptadecane (1.0 g, 3.13 mmol) was added portion-wise. The reaction mixture was subsequently allowed to warm to room temperature overnight. The following morning the reaction was slowly quenched with water. The reaction was then extracted three times into DCM. The organic phases were combined, dried over MgSO$_4$ and concentrated in vacuo. The resulting crude product was then purified by column chromatography (5%-30% EtOAc/hexanes) to yield 2-heptadecoxyethanol (237 mg, 0.789 mmol, 25% yield) as a white solid.

B. Synthesis of Ammonium 2-heptadecoxyethoxy-[[rac-(1R)-2-(6-aminopurin-9-yl)-1-methyl-ethoxy]methyl]phosphinate (NP-PD-157)

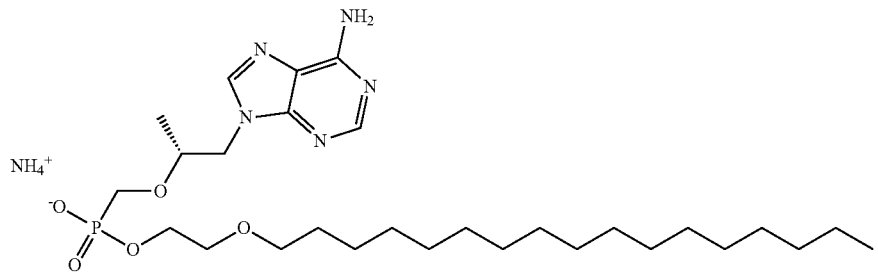

Tenofovir (120 mg, 0.418 mmol, 1.00 eq) and pyridine (2.00 mL) were added to a 25 mL oven-dried flask equipped with a stir bar under an atmosphere of Ar. This was followed by the addition of 2-heptadecoxyethanol (188 mg, 0.627 mmol, 1.50 eq) and 2,4,6-triisopropylbenzenesulfonyl chloride (380 mg, 1.25 mmol, 3.00 eq). The reaction was left to stir vigorously at room temperature for 48 hours under Ar. The reaction was concentrated in vacuo, taken up in a saturated solution of ammonium chloride and concentrated once again in vacuo. The resulting salt was then vigorously stirred up in a 4:1 solution of DCM and MeOH for approximately 1 hour. The reaction was filtered and the resulting filtrate was collected, concentrated in vacuo and purified first by silica gel column chromatography (100% DCM-100% 80:20:3 DCM:MeOH:NH$_4$OH) and then by RP C18 column chromatography (10% MeOH/H$_2$O-100% MeOH) to yield a white solid (58 mg, 0.099 mmol, 24%). $^1$H NMR (600 MHz, CD$_3$OD) δ 8.33 (s, 1H), 8.20 (s, 1H), 4.38 (dd, J=14.4, 3.2 Hz, 1H), 4.23 (dd, J=14.4, 6.6 Hz, 1H), 3.96-3.86 (m, 3H), 3.73 (dd, J=12.8, 9.4 Hz, 1H), 3.53-3.44 (m, 3H), 3.41-3.34 (m, 2H), 1.51-1.44 (m, 2H), 1.34-1.23 (m, 28H), 1.15 (d, J=6.3 Hz, 3H), 0.90 (t, J=7.0 Hz, 3H). $^{13}$C NMR (151 MHz, CD$_3$OD) δ 157.2, 153.5, 151.0, 144.3, 119.6, 76.9 (d, J$_{CP}$=12.7 Hz), 72.3, 71.7 (d, J$_{CP}$=6.8 Hz), 66.2, 65.1 (d, J$_{CP}$=5.6 Hz), 33.1, 30.8 (4C), 30.7, 30.6, 30.5, 27.2, 23.7, 16.8, 14.4. $^{31}$P NMR (162 MHz, CD$_3$OD) δ 15.52. HRMS (APCI) m/z calc. for C$_{28}$H$_{51}$O$_5$N$_5$P [M–H]$^-$, 568.36333 found, 568.36321.

Example 35. Synthesis of Ammonium octadec-17-yn-1-yl ((((R)-1-(6-amino-9H-purin-9-yl)propan-2-yl)oxy)methyl)phosphonate A. Synthesis of octadec-17-yn-1-ol (BI-1-019)

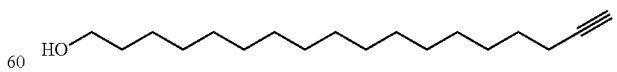

To a stirring solution of 1,3-dimethyl-3,4,5,6-tetrahydro-2(1H)-pyrimidinone (9.1 mL, 74.9 mmol, 12.2 eq) in THF (10 mL) in a flame-dried flask under inert atmosphere was added sodium acetylide (1.97 g, 14.8 mmol, 1.20 eq) at room temperature. Then, 2-(16-bromohexadecoxy)tetrahydropyran (2.50 g, 6.17 mmol, 1.00 eq) in a concentrated THF solution was slowly added to the reaction mixture over 5 minutes. The reaction was subsequently stirred at room temperature overnight. The next day, TLC (hexanes/EtOAc 4:1, stain with PMA) indicated mostly starting material. To push the reaction forward, dry potassium iodide (0.250 g, 1.51 mmol, 0.245 eq) was added and the reaction mixture was heated to 60° C. for 2 hrs. After this time, TLC indicated no further reaction progress. Accordingly, the reaction mixture was heated to 80° C. and stirred for an additional 2 hrs. After this time, TLC indicated no additional reaction progress. The reaction was therefore cooled to 0° C., additional sodium acetylide (0.296 g, 6.17 mmol, 1.00 eq) was added, and the resulting reaction mixture was allowed to slowly warm to room temperature. After 1.5 hrs, TLC indicated some reaction progress. DMPU (0.37 mL, 3.09 mmol, 0.500 eq) and additional potassium iodide were added, and the resulting reaction mixture was stirred vigorously at room temperature overnight. The next day, a small aliquot of the reaction was quenched with saturated aqueous sodium bicarbonate. The resulting aqueous layer was extracted with EtOAc, and combined organic layers were dried over anhydrous sodium sulfate, filtered, and evaporated under reduced pressure. $^1$H NMR of the crude material revealed complete consumption of starting material, formation of the desired alkyne, and formation of an alkene byproduct (via E2 elimination) in a 4:1 ratio. Accordingly, the bulk reaction mixture was quenched with water and diluted with brine, and the resulting aqueous layer was extracted 3 times with EtOAc. Combined organic layers were washed with water and brine, dried over anhydrous sodium sulfate, filtered, and evaporated under reduced pressure. The crude material was purified via silica gel column chromatography (RediSep® Gold column, hexanes/EtOAc, 0-9% EtOAc over 20 min) to yield a mixture of the desired alkyne and an alkene byproduct. The mixture of products was then dissolved in DCM (20 mL) and treated with m-CPBA (1.60 g, 9.26 mmol, 1.50 eq), and progress of the resulting reaction was monitored by TLC (hexanes/EtOAc 4:1, stain with KMnO$_4$). After 5 hrs, TLC revealed selective consumption of the alkene. Accordingly, the reaction mixture was washed with saturated sodium bicarbonate, which was back extracted with DCM. Combined organic layers were washed with brine, dried over anhydrous sodium sulfate, filtered, and evaporated under reduced pressure. The resulting residue was purified via silica gel column chromatography (RediSep® Gold column, hexanes/EtOAc 0-4%) to furnish the desired product, 2-octadec-17-ynoxytetrahydropyran (0.477 g, 1.36 mmol, 22% yield).

To a stirring solution of 2-octadec-17-ynoxytetrahydropyran (0.477 g, 1.36 mmol, 1.00 eq) in a mixture of DCM/MeOH was added 10 drops of aqueous H$_2$SO$_4$ (1.8 M). The reaction mixture was stirred at room temperature for 1 hr. After this time, TLC (hexanes/EtOAc 4:1) indicated minimal conversion of starting material. Accordingly, an additional 10 drops of aqueous H$_2$SO$_4$ (1.8 M) was added, and the reaction mixture was stirred for an additional 5 hrs at room temperature. After this time, TLC indicated that most of the starting material was consumed. Therefore, the reaction was quenched with water and diluted with DCM. The resulting organic layer was washed 3 times with brine, dried over anhydrous sodium sulfate, filtered, and evaporated under reduced pressure. The crude material was purified via silica gel column chromatography (hexanes/EtOAc 0-13% EtOAc) to yield the title compound (0.220 g, 0.826 mmol, 61% yield).

B. Synthesis of Ammonium octadec-17-yn-1-yl ((((R)-1-(6-amino-9H-purin-9-yl)propan-2-yl)oxy)methyl)phosphonate (BI-1-24)

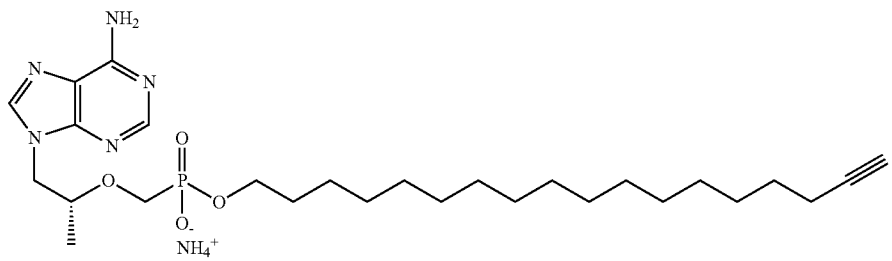

To a stirring mixture of tenofovir (0.075 g, 0.261 mmol, 1.00 eq) and octadec-17-yn-1-ol (0.084 g, 0.313 mmol, 1.20 eq) in anhydrous pyridine (3 mL) at room temperature was added 2,4,6-triisopropylbenzene-1-sulfonyl chloride (0.237 g, 0.783 mmol, 3.00 eq), and the resulting reaction mixture was stirred for 24 hrs. After this time, the mixture was treated with MeOH (0.75 mL) and water (0.25 mL) and stirred for 15 minutes before concentrating the reaction mixture under reduced pressure. The crude material was dissolved in DCM, 10 drops of trifluoroacetic acid were added, and the resulting solution was stirred at room temperature for 30 min. After this time, the solution was diluted with DCM, washed with saturated aqueous sodium bicarbonate, washed with brine 3 times, dried over anhydrous sodium sulfate, filtered, and evaporated under reduced pressure. The crude material was purified by silica gel column chromatography (DCM/80:20:3 DCM:MeOH:NH$_4$OH 0-48% gradient), furnishing the titled compound as a white powder (0.077 g, 0.139 mmol, 53% yield). $^1$H NMR (399 MHz, CDCl$_3$/CD$_3$OD) δ 8.26 (s, 1H), 8.18 (s, 1H), 4.69 (s, 2H), 4.33 (dd, J=14.3, 2.7 Hz, 1H), 4.05 (dd, J=14.4, 7.7 Hz, 1H), 3.80-3.67 (m, 4H), 3.32 (dd, J=12.7, 10.2 Hz, 1H), 2.13 (td, J=7.1, 2.7 Hz, 2H), 1.91 (t, J=2.7 Hz, 1H), 1.53-1.43 (m, 4H), 1.38-1.29 (m, 2H), 1.26-1.14 (m, 25H). $^{13}$C NMR (100 MHz, CDCl$_3$/CD$_3$OD) δ 155.0, 151.7, 149.4, 142.8, 118.2, 84.7, 75.9 (d, J=13.1 Hz), 73.7, 68.0, 65.0 (d, J=5.8 Hz), 64.1 (d, J=159.5 Hz), 30.9 (d, J=6.2 Hz), 29.58, 29.56, 29.54, 29.51, 29.4, 29.3, 29.0, 28.7, 28.4, 25.6, 18.3, 16.3. $^{31}$P NMR (162 MHz, CDCl$_3$/CD$_3$OD) δ 16.1. HRMS (ESI) m/z calculated for C$_{27}$H$_{45}$N$_5$O$_4$P [M−H]$^-$: 534.3214, found 534.3217. Elemental analysis calculated for C$_{27}$H$_{46}$N$_5$O$_4$P: C, 58.67; H, 8.94; N, 15.21; found C, 58.33; H, 8.85; N, 14.29.

Example 36. Synthesis of Ammonium icos-19-yn-1-yl (R)-(((1-(6-amino-9H-purin-9-yl)propan-2-yl)oxy)methyl)phosphonate

A. Synthesis of 2-(icos-2-yn-1-yloxy)tetrahydro-2H-pyran (MD-1-40)

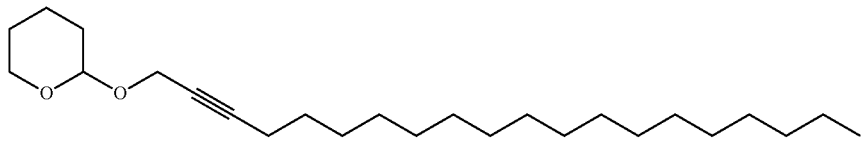 [SMILES: CCCCCCCCCCCCCCCCCC#CCOC1CCCCO1]

To a solution of 2-(2-propynyloxy)tetrahydropyran (2.10 g, 15.0 mmol, 1.00 eq) and hexamethylphosphoramide (9.12 mL, 52.4 mmol, 3.50 eq) in THF (43 mL) at −78° C. under inert atmosphere was added n-butyllithium (5.99 mL of 2.5 M in hexanes, 15.0 mmol, 1.00 eq) dropwise. After the reaction mixture was stirred for 1 hr, 1-bromoheptadecane (4.78 g, 15.0 mmol, 1.00 eq) dissolved in THF was added dropwise. The reaction mixture was allowed to warm slowly to room temperature and stirred overnight. After significant conversion was confirmed by TLC, the reaction mixture was quenched with sat. aq. NH$_4$Cl (150 mL) and stirred for 10 min. The aqueous layer was extracted with EtOAc (3×), and the combined organics were washed with water and brine, dried with Na$_2$SO$_4$, and concentrated under reduced pressure, producing a golden brown oil. The residue was purified by column chromatography (0-5% EtOAc in hexanes), yielding MD-1-40 as a pale yellow oil (3.36 g, 59% yield).

B. Synthesis of icos-2-yn-1-ol (MD-1-128)

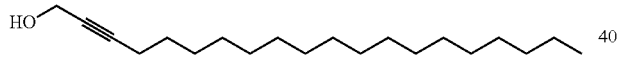

To a solution of 2-(icos-2-yn-1-yloxy)tetrahydro-2H-pyran (3.60 g, 9.52 mmol, 1.00 eq) in MeOH (32 mL) under inert atmosphere was added p-toluenesulfonic acid monohydrate (181 mg, 0.952 mmol, 10 mol %), and the reaction mixture was stirred at room temperature for 8 hr. Upon confirming complete conversion by TLC, the reaction mixture was concentrated under reduced pressure, producing an off-white solid. The solid was taken up in EtOAc, and the organic layer was washed with sat. aq. NH$_4$Cl (3×), dried with Na$_2$SO$_4$, and concentrated. The resulting residue was purified by column chromatography (0-15% EtOAc in hexanes), yielding MD-1-128 as a white solid (2.52 g, 90% yield).

C. Synthesis of icos-19-yn-1-ol (MD-1-44)

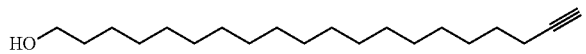 [SMILES: C#CCCCCCCCCCCCCCCCCCCO]

1,3-Diaminopropane (28.3 mL) was added to sodium hydride (60% dispersion in mineral oil, 2.17 g, 54.3 mmol, 8.00 eq) under inert atmosphere, and the reaction mixture was heated to 70° C. for 1 hr. After allowing the reaction mixture to cool to room temperature, icos-2-yn-1-ol (2.00 g, 6.79 mmol, 1.00 eq) was added as a solid in portions, and the suspension was heated to 55° C. overnight. After confirming complete conversion by TLC, the reaction mixture was quenched with water and acidified with 3 N HCl solution until reaching a pH of 2. The aqueous layer was extracted with hexanes (3×) and EtOAc (2×), dried over Na$_2$SO$_4$, and concentrated under to reduced pressure, producing a brown oil. The residue was purified by column chromatography (0-20% EtOAc in hexanes), yielding MD-1-44 as a white solid (904 mg, 45% yield).

D. Synthesis of Ammonium icos-19-yn-1-yl (R)-(((1-(6-amino-9H-purin-9-yl)propan-2-yl)oxy)methyl)phosphonate (BI-1-065)

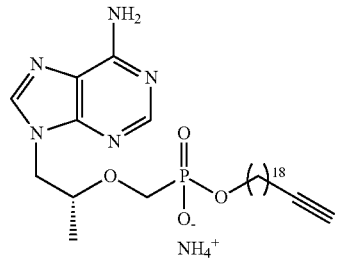

To a stirring solution of icos-19-yn-1-ol (0.492 g, 1.67 mmol, 1.20 eq) and 2,4,6-triisopropylbenzenesulfonyl chloride (1.27 g, 4.18 mmol, 3.00 eq) in anhydrous pyridine (13.9 mL) at room temperature was added tenofovir (0.400 g, 1.39 mmol, 1.00 eq), and the resulting reaction mixture was stirred for 48 hrs. After this time, solvent was evaporated under reduced pressure. The resulting crude material was dissolved in DCM, trifluoroacetic acid (1.0 mL) was added, and the resulting solution was stirred at room temperature for 30 min. The mixture was subsequently diluted with DCM, washed with saturated aqueous sodium bicarbonate, washed with saturated aqueous ammonium chloride, dried over anhydrous sodium sulfate, filtered, and evaporated under reduced pressure. The crude material was purified by silica gel column chromatography (DCM/80:20:3 DCM:MeOH:NH$_4$OH 0-48% gradient) furnished the titled compound as a white powder (0.057 g, 0.098 mmol, 7% yield). $^1$H NMR (400 MHz, Chloroform-d) δ 8.10 (s, 1H), 8.04 (s, 1H), 4.18 (dd, J=14.4, 2.9 Hz, 1H), 3.97 (dd, J=14.4, 7.0 Hz, 1H), 3.70-3.49 (m, 4H), 3.23 (dd, J=12.7, 10.2 Hz, 1H), 1.98 (td, J=7.1, 2.6 Hz, 2H), 1.80 (t, J=2.6 Hz, 1H), 1.41-1.26 (m, 4H), 1.21-1.17 (m, 2H), 1.13-1.03 (m, 26H), 1.00 (d, J=6.2 Hz, 3H). $^{13}$C NMR (100 MHz, CDCl$_3$) δ 155.03, 151.61, 149.43, 142.80, 118.17, 84.58, 75.70 (d, J=13.0 Hz), 73.44, 67.94, 64.09 (d, J=168.6 Hz), 64.87, 47.94, 30.85 (d, J=6.4 Hz), 29.54, 29.52, 29.50, 29.45, 29.35, 29.24, 28.95, 28.59, 28.35, 25.60, 18.14, 16.09. $^{31}$P NMR (162 MHz, CDCl$_3$) δ 16.55.

Example 37. Synthesis of Ammonium 3-(octadec-17-yn-1-ylthio)propyl (R)-(((1-(6-amino-9H-purin-9-yl)propan-2-yl)oxy)methyl)phosphonate A. Synthesis of 16-((3-hydroxypropyl)thio)hexadecanoic acid (BI-1-048)

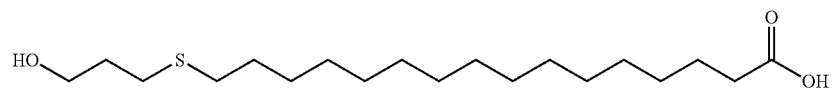 [SMILES: O=C(O)CCCCCCCCCCCCCCCSCCCO]

A stirring solution of 3-sulfanylpropan-1-ol (0.77 mL, 8.95 mmol, 2.00 eq) in DMF (59.6 mL) was flushed with nitrogen and kept under inert atmosphere before the addition of 1,8-diazabicyclo[5.4.0]undec-7-ene (1.34 mL, 8.95 mmol, 2.00 eq). The mixture was stirred for 20 min before the dropwise addition of 16-bromohexadecanoic acid (1.50 g, 4.47 mmol 1.00 eq) in a concentrated DMF solution. The resulting reaction mixture was heated to 60° C. and stirred under inert atmosphere for 1 hr, after which time TLC (hexanes/EtOAc 1:1, KMnO$_4$) indicated complete consumption of starting material. The reaction mixture was diluted with dilute aqueous hydrochloric acid and extracted with EtOAc. Combined organic layers were washed 3 times with brine, dried over anhydrous sodium sulfate, and concentrated under reduced pressure to reveal the title compound (1.50 g, 4.33 mmol, 97% yield). 1H NMR (399 MHz, CDCl$_3$) δ 3.77 (t, J=6.1 Hz, 2H), 2.63 (t, J=7.1 Hz, 2H), 2.52 (dd, J=8.0, 6.9 Hz, 2H), 2.34 (t, J=7.5 Hz, 2H), 1.85 (tt, J=7.2, 6.0 Hz, 2H), 1.67-1.53 (m, 4H), 1.40-1.17 (m, 26H).

B. Synthesis of 16-((3-((tetrahydro-2H-pyran-2-yl)oxy)propyl)thio)hexadecan-1-ol (BI-1-055)

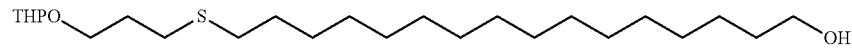

To a stirring solution of 16-((3-hydroxypropyl)thio)hexadecanoic acid (1.00 g, 2.89 mmol) in THF (15.7 mL) and DCM (39.2 mL) was added pyridinium tosylate (0.218 g, 0.870 mmol, 0.300 eq) and 3,4-dihydro-2H-pyran (0.53 mL, 5.77 mmol, 2.00 eq). The resulted reaction mixture was stirred at room temperature for 1 hr, after which time TLC (4:1 hexanes/EtOAc, KMnO$_4$) indicated complete consumption of starting material and two product spots. The reaction mixture was diluted with DCM, washed 3 times with brine, dried over anhydrous sodium sulfate, and concentrated under reduced pressure. The crude material was purified via silica gel column chromatography (hexanes/EtOAc 0-4.5% EtOAc gradient over 20 minutes) to afford a colorless oil as the desired product 16-((3-((tetrahydro-2H-pyran-2-yl)oxy)propyl)thio)hexadecanoic acid (0.688 g, 1.60 mmol, 55% yield) and the analogous THP-ester tetrahydropyran-2-yl 16-(3-tetrahydropyran-2-yloxypropylsulfanyl)hexadecanoate as a pale yellow crystalline solid (0.272 g, 0.528 mmol, 18% yield). Each of these products was then independently treated with borane-dimethyl sulfide to converge on the desired primary alcohol. A solution of tetrahydropyran-2-yl 16-(3-tetrahydropyran-2-yloxypropylsulfanyl)hexadecanoate (0.300 g, 0.580 mmol, 1.00 eq) in THF (2.92 mL) was flushed under inert atmosphere for 10 minutes before borane-dimethyl sulfide complex (0.11 mL, 1.17 mmol, 2.00 eq) was injected in dropwise fashion under inert atmosphere at room temperature. The resulting reaction mixture was stirred at room temperature for 2 hrs, after which time TLC (hexanes/EtOAc 4:1, visualize with PMA) indicated incomplete consumption of starting material. Accordingly, additional borane-dimethyl sulfide complex (0.11 mL, 1.17 mmol, 2.00 eq) was added in dropwise fashion at room temperature, and the resulting reaction mixture was stirred at room temperature overnight. The next day, TLC indicated complete conversion of starting material. Accordingly, the reaction was quenched dropwise with water, diluted with DCM, washed 3 times with brine, dried over anhydrous sodium sulfate, and concentrated under reduced pressure to afford the desire product 16-(3-tetrahydropyran-2-yloxypropylsulfanyl)hexadecan-1-ol (0.066 g, 0.158 mmol, 27% yield). A solution of 16-(3-tetrahydropyran-2-yloxypropylsulfanyl)hexadecanoic acid (0.800 g, 1.86 mmol, 1.00 eq) in THF (31.9 mL) was flushed under inert atmosphere for 10 minutes before borane-dimethyl sulfide complex (0.35 mL, 3.71 mmol, 2.00 eq) was injected dropwise under inert atmosphere. The resulting reaction mixture was stirred at room temperature. Once TLC (hexanes/EtOAc 4:1, visualize with PMA) indicated disappearance of starting material, the reaction was quenched with water in dropwise fashion, diluted with DCM, washed 3 times with brine, dried over anhydrous sodium sulfate, and concentrated under reduced pressure to afford the desire product 16-((3-((tetrahydro-2H-pyran-2-yl)oxy)propyl)thio)hexadecan-1-ol (0.715 g, 1.72 mmol, 92% yield).

C. Synthesis of 16-((3-((tetrahydro-2H-pyran-2-yl)oxy)propyl)thio)hexadecyl methanesulfonate (BI-1-062)

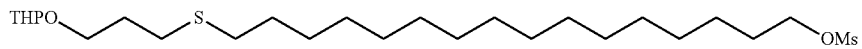

To a stirring solution of 16-((3-((tetrahydro-2H-pyran-2-yl)oxy)propyl)thio)hexadecan-1-ol (1.00 g, 2.40 mmol, 1.00 eq) and triethylamine (0.84 mL, 6.00 mmol, 2.50 eq) in DCM (14.4 mL) at 0° C. under inert atmosphere was added methanesulfonyl chloride (0.37 mL, 4.80 mmol, 2.00 eq) in dropwise fashion. The resulting milky white reaction mixture was stirred at 0° C. for 15 min before allowing it to slowly warm to room temperature. After complete conversion of starting material was confirmed by TLC, the reaction mixture was diluted with DCM, washed once with water, washed once with aqueous hydrochloric acid (1.0 N), washed once with saturated aqueous sodium bicarbonate, washed once with brine, dried over anhydrous magnesium sulfate, filtered, and concentrated under reduced pressure. The crude residue was purified via silica gel column chromatography (hexanes/EtOAc gradient, 9-50% EtOAc) to yield a white solid (1.03 g, 2.08 mmol, 87% yield).

D. Synthesis of 2-(3-(octadec-17-yn-1-ylthio)propoxy)tetrahydro-2H-pyran (BI-1-063)

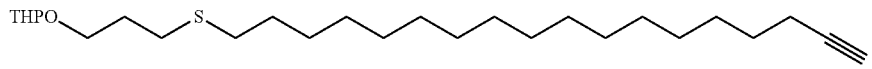

Lithium acetylide ethylenediamine complex (1.03 g, 10.1 mmol, 5.00 eq) was added to a flame-dried flask, diluted with DMSO (8 mL), and stirred vigorously at room temperature under Ar for 10 min. To the resulting orange solution was added a solution of 16-((3-((tetrahydro-2H-pyran-2-yl)oxy)propyl)thio)hexadecyl methanesulfonate (1.00 g, 2.02 mmol, 1.00 eq) in DMSO (2 mL), and the resulting reaction mixture was stirred at room temperature under Ar for 30 min. After this time, TLC indicated complete consumption of starting material. Accordingly, the reaction mixture was carefully poured over ice, and the resulting aqueous layer was extracted 3 times with diethyl ether. Combined organic layers were dried over anhydrous sodium sulfate, filtered, and concentrated under reduced pressure. The crude material was purified via silica gel column chromatography (hexanes/EtOAc 0-3.8%) to afford the desired product (0.235 g, 0.553 mmol, 27% yield).

E. Synthesis of 3-(octadec-17-yn-1-ylthio)propan-1-ol (BI-1-064)

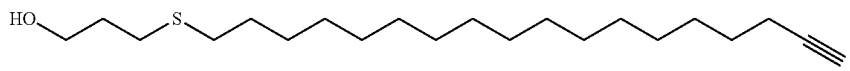 [SMILES: C#CCCCCCCCCCCCCCCCCSCCCO]

To a stirring solution of 2-(3-(octadec-17-yn-1-ylthio)propoxy)tetrahydro-2H-pyran (0.285 g, 0.670 mmol, 1.00 eq) in a mixture of DCM/MeOH was added aqueous sulfuric acid (1.8 M, 0.37 mL, 0.670 mmol, 1.00 eq). The resulting reaction mixture was stirred at room temperature while monitored reaction progress by TLC (hexanes/EtOAc 4:1). Once TLC indicated complete consumption of starting material, the reaction was diluted with DCM, washed 3 times with brine, dried over anhydrous sodium sulfate, filtered, and evaporated under reduced pressure. The crude material was purified via silica gel column chromatography (hexanes/EtOAc gradient) to yield the desired product (0.220 g, 0.646 mmol, 96% yield).

F. Synthesis of Ammonium 3-(octadec-17-yn-1-ylthio)propyl (R)-(((1-(6-amino-9H-purin-9-yl)propan-2-yl)oxy)methyl)phosphonate (BI-1-057)

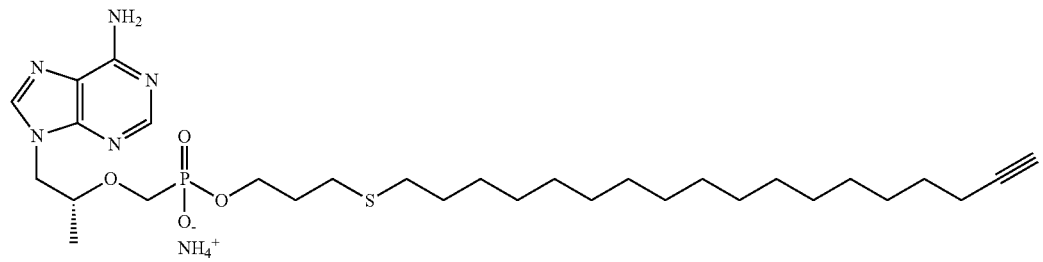

To a stirring mixture of tenofovir (0.200 g, 0.700 mmol, 1.00 eq) and 2,4,6-triisopropylbenzenesulfonyl chloride (0.211 g, 0.696 mmol, 1.00 eq) in anhydrous pyridine (3.5 mL) was added 3-(octadec-17-yn-1-ylthio)propan-1-ol (0.261 g, 0.766 mmol, 1.10 eq) at room temperature, and the resulting reaction mixture was stirred vigorously at room temperature for 48 hrs. After this time, the reaction was quenched with water, and the resulting mixture was stirred for an additional 30 min before concentrating under reduced pressure. The crude material was partitioned between saturated ammonium chloride and DCM, and the resulting aqueous layer was extracted with DCM. Combined organic layers were dried over anhydrous sodium sulfate, filtered, and concentrated under reduced pressure. The crude material was purified by silica gel column chromatography (DCM/80:20:3 DCM:MeOH:NH$_4$OH gradient) to furnish the titled compound as a white powder. $^1$H NMR (399 MHz, CDCl$_3$) δ 8.17 (s, 1H), 8.12 (s, 1H), 4.25 (dd, J=14.3, 3.0 Hz, 1H), 4.03 (dd, J=14.4, 7.1 Hz, 1H), 3.80-3.75 (m, 2H), 3.70 (td, J=6.6, 2.9 Hz, 1H), 3.62 (dd, J=12.6, 9.3 Hz, 1H), 3.34-3.21 (m, 1H), 2.43 (t, J=7.2 Hz, 2H), 2.35 (t, J=7.4 Hz, 2H), 2.05 (td, J=7.1, 2.6 Hz, 2H), 1.86 (t, J=2.7 Hz, 1H), 1.71 (p, J=6.7 Hz, 2H), 1.53-1.35 (m, 4H), 1.28-1.20 (m, 4H), 1.13 (s, 20H), 1.07 (d, J=6.3 Hz, 3H). $^{13}$C NMR (101 MHz, CDCl$_3$) δ 154.7, 151.3, 149.4, 143.0, 118.2, 84.8, 75.9 (d, J=13.2 Hz), 68.0, 64.1 (d, J=160.3 Hz), 63.5 (d, J=5.8 Hz), 48.1, 32.0, 30.7 (d, J=6.4 Hz), 29.6, 29.6, 29.6, 29.6, 29.6, 29.5, 29.5, 29.3, 29.1, 28.9, 28.7, 28.4, 28.1, 18.3, 16.3. $^{31}$P NMR (162 MHz, CDCl$_3$) δ 16.07.

Example 38. Bioanalytical Assays for Prodrugs of Tenofovir

A. Methods

1. Antiviral Assay

Prodrugs of tenofovir were evaluated for HIV activity. It was expected that intrinsic HIV activity was identical among these prodrugs since they all contain the tenofovir moiety. Assuming that plasma membrane permeability is not a limiting factor for activation of these lipophilic prodrugs, changes in EC$_{50}$ values relative to CMX157 (hexadecyloxypropyl tenofovir) (EC$_{50}$=20.0 nM) can be interpreted to represent changes in phospholipase C (PLC) cleavage kinetics. Briefly, HIV single-cycle, replication-incompetent assays (*AIDS* 2010, 24, 1651-1655) using pseudoviral particles (*J. Virol.* 2009, 83, 9094-9101) containing firefly luciferase RNA as an indicator of viral infection were conducted in HEK293 cells. As expression of luciferase protein in this system depends on HIV RT-mediated reverse transcription of luciferase RNA to cDNA, luminescence in response to luciferin treatment directly correlates with the level of viral infection, facilitating measurements of HIV RT inhibitor activity expressed as IC$_{50}$ (prodrug concentration that inhibits 50% reverse transcription). Cytotoxicity to HEK293 cells was assessed by monitoring mitochondrial activity (*Acta Pharmacol. Sin.* 2004, 25, 385-389) prior to pseudoviral assay to establish the maximum concentrations to be used when measuring antiviral activity.

2. Fluorometric CYP450 Enzyme Inhibition Assays

The CYP450 inhibition assays utilized microsomes from insect cells expressing human recombinant individual cDNA-expressed CYP isoforms 3A4 and 2D6, as well as the fluorogenic probe that produces fluorescent metabolite. Standard inhibitors were co-incubated with fluorogenic substrates and their inhibitory potential (IC$_{50}$) was determined. Assay conditions in terms of CYP450 protein concentration and time of incubation were standardized, enzyme kinetics parameters of each fluorescent probe substrate were estimated and IC$_{50}$ values of inhibitors were determined and validated on different days to check reproducibility.

Test compounds were prepared in 100% DMSO or 100% MeOH and did not exceed a final concentration of <0.2% in the final reaction. A 100 mM sodium phosphate buffer was prepared and adjusted to pH 7.4. In a separate falcon tube, a 2× enzyme/substrate (E/S) solution was prepared in phosphate buffer. The final concentration of CYP2D6 (CORNING®) and 7-amido-4-methyl coumaric acid (AMMC) was 10 nM and 4 μM, and CYP3A4 (CORNING®) and 7-benzyloxy-4-(trifluoromethyl) coumarin (BFC) was 20 nM and 40 μM, respectively. In a separate falcon tube, a 2×NADPH regenerating system (NRS) was prepared in phosphate buffer. The final concentration for each component in the assay was as follows:

CYP2D6 assay: 0.008 mM NADPH, 3.3 mM glucose 6-phosphate, 0.4 U of glucose-6-phosphate dehydrogenase per mL CYP3A4 assay: 2.45 mM NADPH, 24.7 mM glucose 6-phosphate, 1.25 U of glucose-6-phosphate dehydrogenase per mL Both enzymatic assays were conducted in a 96-well microtiter plate (Black, CORNING® COSTAR®) with a final volume of 100 µL. Preparation of the plate began with the addition of 74 µL of the E/S in the first well, and 50 µL to all subsequent wells (from 2-11). The test compounds (1 µL) were dissolved in the first well to give the first row a final volume of 75 µL. A 1:3 serial dilution of the test compound was conducted by removing 25 µL from the first well and diluting it with the second and so forth until the tenth row. Final concentrations yielded a range from 200 µM-0.01 µM. Well no. 11 contained no inhibitor, and well no. 12 contained no enzyme. Both were used as controls for background fluorescence. The plate was incubated for 30 min at 37° C. After incubation, the reaction was initiated by the addition of 50 µL of the 2×NRS to each well.

Immediately (within 1 min) the fluorescence was measured using a microplate reader (BIOTEK® Synergy Neo2). CYP2D6 was monitored at Ex/Em=410/460 nm, and CYP3A4 monitored at Ex/Em=410/538 nm in kinetic mode that scanned every 5 min for 60 mins. Data was exported and analyzed using Graph Pad Prism 7. Fluorescence readout was normalized to the fluorescence intensity of the reaction in the absence of the test substance (well no. 11, 0% inhibition) and the mixture of reaction components in the presence of "Inhibitor Cocktail" (well no. 12, 100% inhibition). The $IC_{50}$ value was derived after the data was fitted on a 10-point curve using a four-parameter logistic regression model.

3. Metabolic Stability Assay

The LC-MS/MS analysis was performed using Agilent 1260 Infinity II HPLC, coupled with an Agilent G6460 triple quadrupole mass spectrometer (Agilent Technologies, USA). All the data were acquired employing Agilent 6460 Quantitative Analysis data processing software.

Reverse-phase HPLC separation for each compound was achieved either on an Agilent Porshell 120 EC-C8 column (2.1×50 mm, 2.7 µm), or on an Agilent Zorbax XDB C18 column (2.1×50 mm, 3.5 µm) with a mobile phase composed of methanol-water-formic acid or acetonitrile-water-formic acid (0.1%) at a flow rate of 0.5 mL/min (changes for some compounds). Each method was developed in the presence of an internal standard (ISTD) $d_5$-7-ethoxy coumarin. The column temperature was maintained at 40° C. for most of the samples otherwise noted. The detection was operated in the Agilent JetStream electrospray positive ionization using multiple reaction monitoring mode (MRM).

Other MS conditions were as follows: dwell time 100 ms; gas flow 10 L/min; nebulizer pressure 45 psi; delta EMV 200 V; fragmentor voltage and collision energy for individual compounds vary.

Test compounds were dissolved in 100% DMSO or 100% MeOH to make 10 mM stock solutions. Verapamil (Sigma Aldrich) aided as a positive control and was dissolved in 100% DMSO to make 10 mM stock solutions. The 10 mM stock solution of test and control compounds were further diluted in potassium phosphate buffer (100 mM, pH 7.4) to 500 µM to ensure the organic solvent content was <0.2%. Human liver microsomes (HLMs) were purchased from Xenotech at 20 mg/mL. NADPH (Sigma Aldrich) 10 mM stocks were prepared in deionized water.

The HLM assay was prepared in a 1.5 mL Eppendorf tube with a final volume of 1100 µL for duplicate runs. Each reaction contained phosphate buffer (928.4 µL), liver microsomes (55 µL), and test compound resulting in a final concentration of 3 µM (6.6 µL of 500 µM). The reaction was initiated with 110 µL of 10 mM NADPH. Aliquots (100 µL) were removed in duplicate at 0, 15, 30, 60, 120 min (for prodrug compounds) and 0, 5, 10, 15, 30 min (verapamil, positive control compound) time intervals and quenched in cold 100 mL of 100% methanol which contained internal standard (ISTD: $d_5$-7-ethoxy coumarin 4 µM). Before centrifugation each of the aliquoted tubes were vortexed to make sure compounds were in the solution. The aliquots were centrifuged at 12,000 g for 5 min and the supernatant removed and placed in an LC-MS vial. Each time point was assessed using LC-MS and the area, based on the extracted ion, was integrated with respect to the ISTD. Positive controls were conducted at a final volume of 550 µL to give each time point in a single run. A no-NADPH negative control with test or control compound was performed in a single run (150 µL) at the longest time point. Controls were processed and analyzed like the test compounds. Each time point was run in duplicates followed by in-between blank washes to avoid the carryover and to equilibrate the column.

B. Results

The following tables detail the bioanalytical results of exemplary compounds of the present disclosure.

TABLE 1

Bioanalytical results of exemplary lipid prodrugs of tenofovir

| Compound ID | Lipid Motif | Linear Atom # | HLM $t_{1/2}$ (min) | CYP450 $IC_{50}$ (µm) 2D6 | CYP450 $IC_{50}$ (µm) 3A4 | HIV $IC_{50}$ (µm) | St. Dev (µm) | $CC_{50}$ (µm) | St. Dev (µm) | Therapeutic Index |
|---|---|---|---|---|---|---|---|---|---|---|
| TFV | — | — | >120 | >50.0 | 45.8 | 2.06 | 0.141 | >100 | — | >49 |
|  |  |  |  |  |  | 1.60 | 0.123 | 35.4 | 0.8 | 22 |
| TDF | — | — |  |  | >20 |  |  |  |  |  |
| TAF | — | — | 26 | >50.0 | 21.0 | 0.002 | 0.001 | >100 | — | >50,000 |
|  |  |  |  |  |  | 0.001 | 0.001 | >100 | — | >100,000 |
| CMX157 | $C_3H_6OC_{16}H_{33}$ | 20 | 42 | 70.8 | 53.3 | 0.018 | 0.010 | 97.6 | 2.68 | 5,422 |
| MD-1-123 | $C_3H_6SC_{16}H_{33}$ | 20 | 42 | 110 | 58.0 | 0.010 | 0.002 | 49.8 | 2.89 | 4,980 |
| MD-1-105 | $C_{18}H_{37}$ | 18 | 13 | 20.0 | 52.9 | 0.094 | 0.031 | 84.1 | 4.95 | 895 |
| MD-1-106 | $C_{15}H_{31}$ | 15 | 13 | 22.0 | 54.9 | 2.06 | 0.967 | >100 | — | >49 |
| EJM-8-030 | $C_{13}H_{26}CD_2CD_3$ | 15 | 20 | 38.3 | 52.2 | 4.64 | 2.51 | >100 | — | >22 |
| EJM-8-036 | $C_{15}H_{30}CD_3$ | 16 | 21 | 20.6 | 87.4 | 2.16 | 1.40 | 94.4 | 2.98 | 44 |

TABLE 1-continued

Bioanalytical results of exemplary lipid prodrugs of tenofovir

| Compound ID | Lipid Motif | Linear Atom # | HLM $t_{1/2}$ (min) | CYP450 $IC_{50}$ (μm) 2D6 | CYP450 $IC_{50}$ (μm) 3A4 | HIV $IC_{50}$ (μm) | St. Dev (μm) | $CC_{50}$ (μm) | St. Dev (μm) | Therapeutic Index |
|---|---|---|---|---|---|---|---|---|---|---|
| B1-1-065 | $C_{18}H_{36}CCH$ | 20 | >120 | 21.9 | >50 | 1.18 | 0.533 | 99.5 | 0.74 | 84 |
| B1-1-024 | $C_{16}H_{32}CCH$ | 18 | >120 | 2.39 | 18.7 | 2.03 | 1.05 | >100 | — | >49 |
| EJM-8-006 | $C_{13}H_{26}CCH$ | 15 | 94 | 84.9 | 54.8 | 28.6 | 7.81 | >100 | — | >3 |
| NP-PD-042 | $C_{16}H_{32}CCSi(CH_3)_3$ | 20 | >120 | 27.1 | 27.0 | 0.086 | 0.018 | 68.1 | 4.74 | 792 |
| NP-PD-051 | $C_{18}H_{36}Si(CH_3)_3$ | 20 | >120 | 16.4 | 51.4 | 0.093 | 0.008 | 26.2 | 0.43 | 282 |
| NP-PD-102 | $C_{17}H_{34}CCCF_3$ | 20 | >120 | >20 | >20 | 0.186 | 0.015 | 78.7 | 8.34 | 423 |
| NP-PD-105 | $C_{19}H_{38}CF_3$ | 20 | >120 | >20 | >20 | 0.120 | 0.003 | 72.4 | 6.22 | 603 |

TFV: tenofovir;
TDF: tenofovir disoproxil fumarate;
TAF: tenofovir alafenamide fumarate
$CC_{50}$ refers to the 50% cytotoxic concentration, i.e., the compound's concentration required for the reduction of cell viability by 50%.
Therapeutic index = $CC_{50}/IC_{50}$
Italicized results stemmed from assays conducted M the absence of human serum albumin.

TABLE 2

Bioanalytical results of lipid prodrugs of tenofovir containing oxyalkyl linkers

| Compound ID | Lipid Motif | Linear Atom # | HLM $t_{1/2}$ (min) | CYP450 $IC_{50}$ (μm) 2D6 | CYP450 $IC_{50}$ (μm) 3A4 | HIV $IC_{50}$ (μm) | St. Dev (μm) | $CC_{50}$ (μm) | St. Dev (μm) | Therapeutic Index |
|---|---|---|---|---|---|---|---|---|---|---|
| CMX157 | $C_3H_6OC_{16}H_{33}$ | 20 | 42 | 70.8 | 53.3 | 0.018 | 0.010 | 97.6 | 2.68 | 5,422 |
| MD-5-72 | $C_3H_6OC_{14}H_{28}CCH$ | 20 | >120 | >20 | >20 | 0.132 | 0.007 | >100 | — | >758 |
| NP-PD-149 | $C_3H_6OC_{13}H_{26}CCCF_3$ | 20 | >120 | >20 | 12.0 | 0.023 | 0.003 | >100 | — | >4,348 |
| NP-PD-158 | $C_3H_6OC_{15}H_{30}CF_3$ | 20 | >120 | >20 | >20 | 0.049 | 0.010 | >100 | — | >4,348 |
| NP-PD-130 | $C_3H_6OC_{12}H_{24}CCSi(CH_3)_3$ | 20 | >120 | 21.7 | >20 | 0.069 | 0.016 | >100 | — | >2,041 |
| NP-PD-157 | $C_2H_4OC_{17}H_{31}$ | 20 | 35 | | | 0.003 | 0.001 | 69.6 | 1.31 | 27,840 |
| NP-PD-150 | $C_4H_8OC_{15}H_{31}$ | 20 | 48 | | | 0.030 | 0.014 | >100 | — | >3,333 |
| NP-PD-154 | $C_5H_{10}OC_{14}H_{29}$ | 20 | 29 | | | 0.052 | 0.003 | >100 | — | >1,923 |

TABLE 3

Bioanalytical results of lipid prodrugs of tenofovir containing mercaptoalkyl linkers

| Compound ID | Lipid Motif | Linear Atom # | HLM $t_{1/2}$ (min) | CYP450 $IC_{50}$ (μm) 2D6 | CYP450 $IC_{50}$ (μm) 3A4 | HIV $IC_{50}$ (μm) | St. Dev (μm) | $CC_{50}$ (μm) | St. Dev (μm) | Therapeutic Index |
|---|---|---|---|---|---|---|---|---|---|---|
| MD-1-122 | $C_2H_5SC_{17}H_{35}$ | 20 | 66 | >20 | >20 | 0.004 | 0.003 | 28.6 | 3.70 | 7,150 |
| MD-1-123 | $C_3H_6SC_{16}H_{33}$ | 20 | 42 | 110 | 58.0 | 0.010 | 0.002 | 49.8 | 2.89 | 4,980 |
| MD-1-219 | $C_6H_{12}SC_{13}H_{27}$ | 20 | 66 | | | 0.073 | 0.011 | >100 | — | >1,370 |
| MD-1-122 | $C_9H_{18}SC_{10}H_{21}$ | 20 | 13 | | | 0.058 | 0.009 | >100 | — | >1,724 |
| MD-1-220 | $C_{12}H_{24}SC_7H_{15}$ | 20 | | | | 0338 | 0.004 | >100 | — | >296 |
| MD-1-221 | $C_{15}H_{30}SC_4H_9$ | 20 | | >20 | >20 | 0.302 | 0.062 | >100 | — | >331 |
| MD-1-186 | $C_3H_6SC_{20}H_{41}$ | 24 | >120 | | | | | | | |
| MD-1-185 | $C_3H_6SC_{18}H_{37}$ | 22 | >120 | | | | | | | |

TABLE 3-continued

Bioanalytical results of lipid prodrugs of tenofovir containing mercaptoalkyl linkers

| Compound ID | Lipid Motif | Linear Atom # | HLM $t_{1/2}$ (min) | CYP450 $IC_{50}$ (μm) 2D6 | CYP450 $IC_{50}$ (μm) 3A4 | HIV $IC_{50}$ (μm) | St. Dev (μm) | $CC_{50}$ (μm) | St. Dev (μm) | Therapeutic Index |
|---|---|---|---|---|---|---|---|---|---|---|
| MD-1-218 | $C_3H_6SC_{14}H_{29}$ | 18 | | | | 0.007 | 0.006 | >100 | — | |
| MD-1-217 | $C_3H_6SC_{12}H_{25}$ | 16 | | | | 0.583 | 0.188 | >100 | — | |
| MD-1-124 | $C_3H_6SC_{15}H_{30}CO_2CH_3$ | 20 | 36 | 19.2 | 40.8 | 1.42 | 0.675 | >100 | — | >70 |
| MD-1-182 | $C_3H_6SC_{14}H_{28}CCH$ | 20 | 96 | | | 0.028 | 0.0002 | >100 | — | >3,571 |
| BI-1-057 | $C_3H_6SC_{16}H_{32}CCH$ | 22 | >120 | 20.2 | 37.0 | 0.0079 | 0.066 | 75.0 | 0.74 | 949 |
| MD-1-183 | $C_3H_6SC_{10}H_{20}CCPh$ | 20 | 72 | >20 | | 0.008 | 0.0004 | >100 | — | >12,500 |
| MD-1-184 | $C_3H_6SC_{12}H_{24}Ph$ | 20 | 69 | >20 | | 0.008 | 0.001 | >100 | — | >12,500 |
| MD-1-187 | $C_3H_6SC_{12}H_{24}CCSi(CH_3)_3$ | 20 | >120 | >20 | >20 | 0.024 | 0.0001 | >100 | — | >4,167 |
| MD-1-119 | $C_3H_6SC_{11}H_{22}SPh$ | 20 | 12 | 36.3 | 11.0 | 0.050 | 0.008 | >100 | — | >2,000 |
| MD-1-223 | $C_3H_6SC_{11}H_{22}OPh$ | 20 | 15 | >20 | >20 | 0.009 | 0.004 | >100 | — | >11,111 |

Example 39. Synthesis of 2-(2-amino-6-oxo-1H-purin-9-yl)ethoxymethyl-[2-(18,18,18-trifluorooctadecoxy)ethoxy]phosphinic Acid A. Synthesis of 2-[(4-methoxyphenyl)methoxy]ethanol (NP-PD-221)

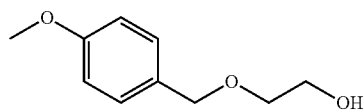

A solution of ethylene glycol (7.12 mL, 128 mmol, 2.00 eq) in DMSO (100 mL) was cooled to 0° C. At this temperature, potassium hydroxide (KOH) pellets (7.17 g, 128 mmol, 2.00 eq) were added portion-wise and the mixture was allowed to warm to room temperature and then stirred at this temperature until most of the KOH pellets had dissolved. At this point 4-methoxybenzyl chloride (PMBCl) (8.66 mL, 63.9 mmol, 1.00 eq) was added dropwise to the reaction mixture at room temperature. The reaction was stirred for 18 h. When TLC indicated complete consumption of PMBCl, the mixture was cooled to 0° C. again, diluted with 30 mL $Et_2O$ and carefully quenched by the addition of 1 N HCl. Afterwards it was warmed to room temperature again, the phases were separated and the aqueous layer was extracted with $Et_2O$. The combined organic extracts were dried over $MgSO_4$ and then concentrated down under reduced pressure. The residue was purified by flash column chromatography on silica gel (10%-40% EtOAc/hexanes) to afford NP-PD-221 as yellow oil (5.46 g, 30.0 mmol, 47% yield).

B. Synthesis of heptadec-16-ynyl 4-methylbenzenesulfonate (NP-PD-215)

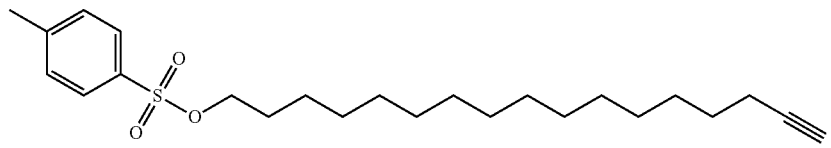 [SMILES: C#CCCCCCCCCCCCCCCCOS(=O)(=O)c1ccc(C)cc1]

To a solution of heptadec-16-yn-1-ol (3.05 g, 12.1 mmol, 1.00 eq) in DCM (50 mL) at 0° C. and under an atmosphere of argon was added pyridine (1.95 mL, 24.2 mmol, 2.00 eq) and then p-toluenesulfonyl chloride (3.46 g, 18.1 mmol, 1.5 eq) and the reaction stirred at room temperature overnight. The reaction was subsequently diluted with DCM and then quenched with water. The phases were separated and the organic layer was washed with 2M HCl, followed by a saturated $NaHCO_3$ solution, water, brine and then dried with $MgSO_4$. The solvent was concentrated in vacuo and the resulting crude material was then purified by way of silica gel flash column chromatography (100 hexanes-10% EtOAc/hexanes) to yield NP-PD-215 as a white solid (2.21 g, 5.44 mmol, 45% yield).

C. Synthesis of 1-(2-heptadec-16-ynoxyethoxymethyl)-4-methoxy-benzene (NP-PD-226)

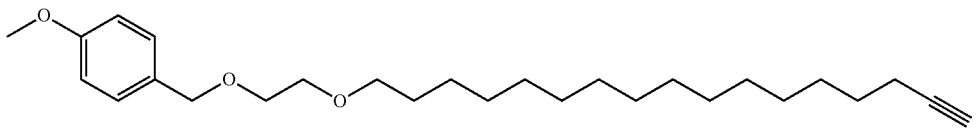 [SMILES: C#CCCCCCCCCCCCCCCCOCCOCc1ccc(OC)cc1]

To an oven-dried 100 mL 3-neck round bottomed flask charged with a stirrer bar was added 2-[(4-methoxyphenyl)methoxy]ethanol (750 mg, 4.12 mmol, 1.00 eq) at room temperature under an atmosphere of Ar. Following dilution of 2-[(4-methyoxyphenyl)methoxy]ethanol with DMF (20 mL), the resulting solution was cooled to 0° C. (ice bath). 60% Sodium hydride (198 mg, 4.94 mmol, 1.20 eq) was then added portion-wise at 0° C. After approximately 30 minutes at this temperature, heptadec-16-ynyl 4-methylbenzenesulfonate (2.01 g, 4.94 mmol, 1.20 eq) was added portion-wise and the resulting suspension was allowed to warm to room temperature and stirred vigorously at this temperature overnight. The following morning TLC indicated consumption of starting material. The reaction was subsequently cooled to room temperature, quenched with a saturated ammonium chloride solution and extracted three times into DCM. The resulting organic phases were combined, dried over MgSO$_4$ and then concentrated in vacuo. The crude material was then purified by silica gel column chromatography (20%-80% DCM/hexanes) to yield 1-(2-heptadec-16-ynoxyethoxymethyl)-4-methoxy-benzene (1.13 g, 2.71 mmol, 66% yield) as a white solid.

D. Synthesis of 1-methoxy-4-[2-(18,18,18-trifluorooctadec-16-ynoxy)ethoxymethyl]benzene (NP-PD-230)

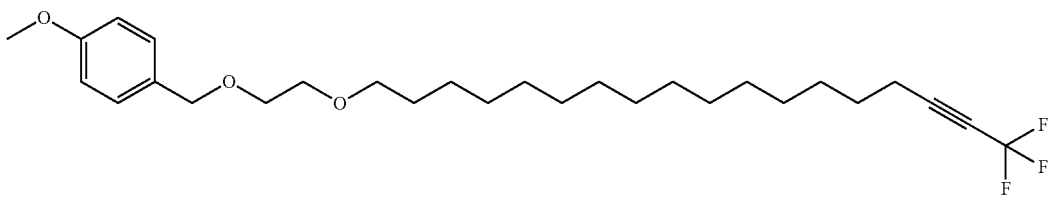 [SMILES: COc1ccc(COCCOCCCCCCCCCCCCCCCC#CC(F)(F)F)cc1]

A 100 mL oven-dried flask equipped with a stir bar was charged with copper iodide (775 mg, 4.07 mmol, 1.50 eq), potassium carbonate (1.12 g, 8.14 mmol, 3.00 eq) and N,N,N'N'-tetramethylethylenediamine (608 µL, 4.07 mmol, 1.50 eq) in DMF (10 mL) under an atmosphere of air (balloon). The resulting blue mixture was stirred vigorously at room temperature for 15 minutes. (Trifluoromethyl)trimethylsilane (0.80 mL, 5.4 mmol, 2.0 eq) was added to the reaction mixture and the reaction was stirred for an additional 5 minutes before cooling to 0° C. To the reaction mixture was added (in one portion) a solution of 1-(2-heptadec-16-ynoxyethoxymethyl)-4-methoxy-benzene (1.13 g, 2.71 mmol, 1.00 eq) and (trifluoromethyl)trimethylsilane (0.80 mL, 5.4 mmol, 2.0 eq) in DMF (10 mL). The reaction was left to warm to room temperature and stirred vigorously for 48 hours. For the workup, the reaction was quenched with H$_2$O and extracted three times with DCM. The organic phases were combined, dried over MgSO$_4$, filtered and concentrated in vacuo. The crude material was subsequently purified by column chromatography (5%-20% EtOAc/hexane) to yield NP-PD-230 (595 mg, 1.23 mmol, 45% yield) as a white solid.

E. Synthesis of 2-(18,18,18-trifluorooctadecoxy)ethanol (NP-PD-234)

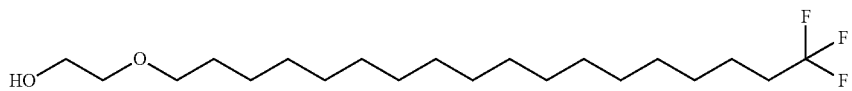 [SMILES: OCCOCCCCCCCCCCCCCCCCCC(F)(F)F]

1-Methoxy-4-[2-(18,18,18-trifluorooctadec-16-ynoxy)ethoxymethyl]benzene (595 mg, 1.23 mmol, 1.00 eq) and ethyl acetate (6.0 mL) were added to an 50 mL oven-dried flask equipped with a stir bar and fitted with a sealed hydrogen balloon. The solution was subsequently degassed under house vacuum for approximately 10 minutes and then the reaction flask was purged with Ar. This cycle was repeated twice more before the addition of a catalytic amount of palladium hydroxide on carbon (20% wt, 86 mg, 0.12 mmol, 0.10 eq). Once more the reaction flask was placed under vacuum before a final purge with hydrogen from the fitted hydrogen balloon. The reaction was subsequently left to stir vigorously under an atmosphere of hydrogen at room temperature for 18 hours. After this time, the heterogeneous reaction mixture was filtered over a bed of celite and the filtrate was collected and concentrated in vacuo. The resulting crude product was purified by column chromatography (5%-20% EtOAc/hexane) to NP-PD-234 (353 mg, 0.958 mmol, 78% yield) as a white solid.

F. Synthesis of Ammonium 2-(2-amino-6-bromo-purin-9-yl)ethoxymethyl-[2-(18,18,18-trifluorooctadecoxy)ethoxy]phosphinate (NP-PD-242)

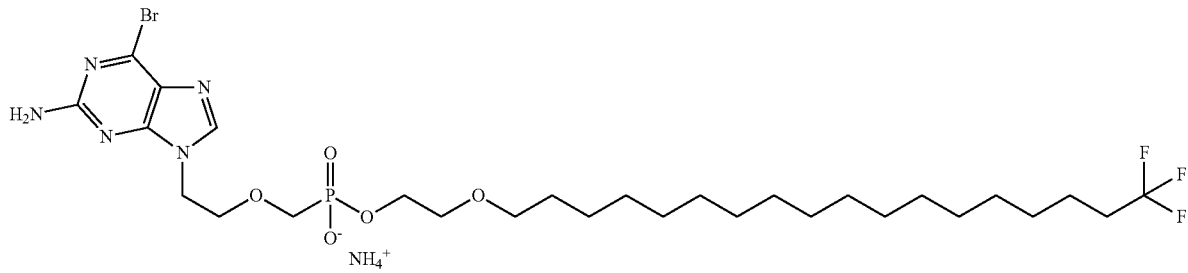 [SMILES: Nc1nc(Br)c2ncn(CCOCP(=O)([O-])OCCOCCCCCCCCCCCCCCCCCC(F)(F)F)c2n1 ; [NH4+]]

2-(2-Amino-6-bromo-purin-9-yl)ethoxymethylphosphonic acid was prepared according to literature procedures described by Holý et al. [*J. Med. Chem.* 1999. 42, 2064-2086] and Yu et al. [*J. Med. Chem.* 1992. 35, 2958-2969].

To an oven dried 25 mL Schlenk tube charged with a stirrer bar 2-(2-amino-6-bromo-purin-9-yl)ethoxymethylphosphonic acid (50 mg, 0.14 mmol, 1.0 eq), N,N'-dicyclohexylcarbodiimide (59 mg, 0.28 mmol, 2.0 eq), 2-(18,18,18-trifluorooctadecoxy)ethanol (63 mg, 0.17 mmol, 1.2 eq) and NMP (1.0 mL) were added under an atmosphere of argon. To this resulting suspension 4-dimethylaminopyridine (1.73 mg, 0.0100 mmol, 0.100 eq) was added at room temperature. Following the addition of all reagents the reaction was heated to 100° C. and left stirring vigorously at this temperature overnight. The following morning the TLC indicated product formation. The reaction mixture was cooled to room temperature before quenching with distilled water. The reaction mixture was concentrated in vacuo and the resulting crude material was purified by silica flash column chromatography (100% DCM-100% 80:20:3 DCM:MeOH:NH$_4$OH solution over 15 minutes) to yield NP-PD-242 (52 mg, 0.072 mmol, 51% yield) as a pale yellow solid. $^1$H NMR (400 MHz, CD$_3$OD) δ 8.20 (s, 1H), 4.32 (t, J=5.0 Hz, 2H), 3.96-3.83 (m, 4H), 3.65 (d, J=8.8 Hz, 2H), 3.45 (t, J=4.9 Hz, 2H), 3.36 (t, J=6.6 Hz, 2H), 2.20-2.04 (m, 2H), 1.58-1.44 (m, 4H), 1.43-1.21 (m, 27H). HRMS (ESI) m/z calc. for C$_{28}$H$_{47}$O$_5$N$_5$$^{79}$BrF$_3$P [M-H]$^-$, 700.24558 found, 700.24642.

G. Synthesis of 2-(2-amino-6-oxo-1H-purin-9-yl) ethoxymethyl-[2-(18,18,18-trifluorooctadecoxy) ethoxy]phosphinic Acid (NP-PD-243)

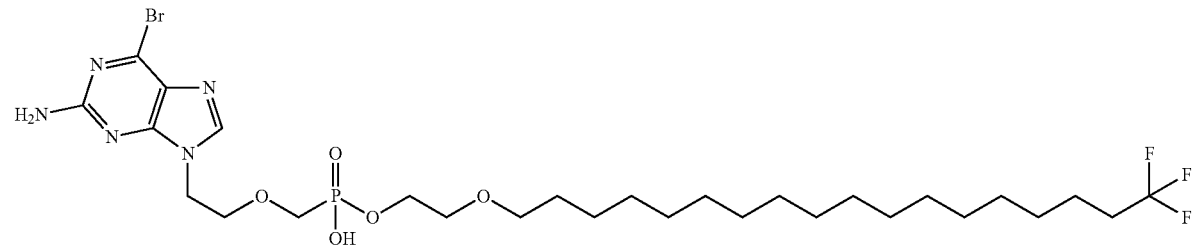 [SMILES: Nc1nc(Br)c2ncn(CCOCP(=O)(O)OCCOCCCCCCCCCCCCCCCCCC(F)(F)F)c2n1]

A 25 mL reaction flask was equipped with a magnetic stirrer and a condenser. NP-PD-242 (52 mg, 0.070 mmol), glacial acetic acid (1.6 mL), and water (0.4 mL) were added to the reaction flask. The resulting mixture was vigorously stirred and heated to reflux. The reaction was monitored by TLC, and following reaction completion (after approximately 3.5 hours), the reaction mixture was cooled to 5° C., and stirred for 18 h. The resulting precipitate was filtered, subsequently dried under vacuum and then recrystallized from hot 80:20 isopropanol/water. The precipitated solids were filtered and dried under vacuum to give NP-PD-243 (7.0 mg, 0.011 mmol, 15% yield) as off-white solid. $^1$H NMR (400 MHz, DMSO-d$_6$) δ 10.53 (s, 1H), 7.66 (s, 1H), 6.43 (s, 2H), 4.09 (t, J=5.3 Hz, 2H), 3.95-3.86 (m, 2H), 3.78 (t, J=5.3 Hz, 2H), 3.67 (d, J=8.5 Hz, 2H), 3.44 (t, J=4.8 Hz, 2H), 3.36-3.27 (m, 4H), 2.29-2.14 (m, 2H), 1.50-1.39 (m, 4H), 1.37-1.16 (m, 25H). $^{19}$F NMR (376 MHz, DMSO-d$_6$) δ -64.49 (t, J=11.7 Hz). HRMS (ESI) m/z calc. for C$_{28}$H$_{48}$O$_6$N$_5$F$_3$P [M-H]$^-$, 638.32998 found, 638.33096.

Example 40. Synthesis of 2-(2-amino-6-oxo-1H-purin-9-yl)ethoxymethyl-[3-(16,16,16-trifluorohexadecoxy)propoxy]phosphinic Acid A. Synthesis of Ammonium 2-(2-amino-6-bromo-purin-9-yl)ethoxymethyl-[3-(16,16,16-trifluorohexadecoxy)propoxy]phosphinate (NP-PD-245)

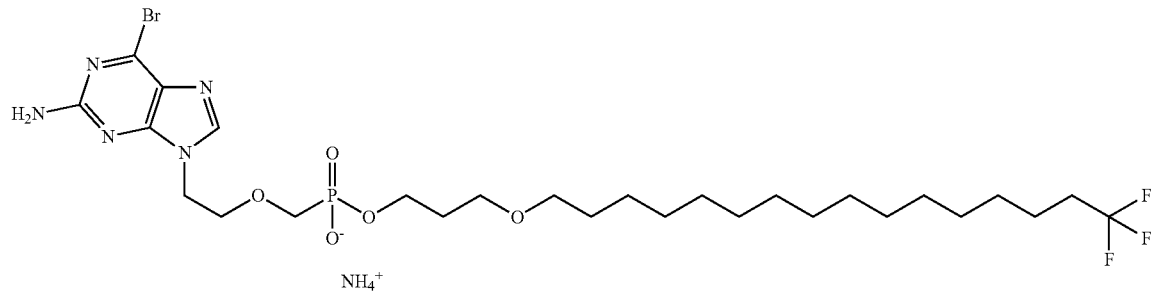 [SMILES: Nc1nc(Br)c2ncn(CCOCP(=O)([O-])OCCCOCCCCCCCCCCCCCCCC(F)(F)F)c2n1 ; [NH4+]]

2-(2-Amino-6-bromo-purin-9-yl)ethoxymethylphosphonic acid was prepared according to literature procedures described by Holý et al. [*J. Med. Chem.* 1999. 42, 2064-2086] and Yu et al. [*J. Med. Chem.* 1992. 35, 2958-2969].

To an oven dried 25 mL Schlenk tube charged with a stirrer bar 2-(2-amino-6-bromo-purin-9-yl)ethoxymethylphosphonic acid (100 mg, 0.280 mmol, 1.00 eq), —N,N'-dicyclohexylcarbodiimide (117 mg, 0.570 mmol, 2.00 eq), 3-(16,16,16-trifluorohexadecoxy)propan-1-ol (121 mg, 0.340 mmol, 1.20 eq) and NMP (2.0 mL) were added under an atmosphere of Ar. To this resulting suspension 4-dimethylaminopyridine (3.5 mg, 0.030 mmol, 0.10 eq) was added at room temperature. Following the addition of all reagents the reaction was heated to 100° C. and left stirring vigorously at this temperature overnight. The following morning the TLC indicated product formation. The reaction mixture was cooled to room temperature before quenching with distilled water. The reaction mixture was concentrated in vacuo and the resulting crude material was purified by silica flash column chromatography (100% DCM-100% 80:20:3 DCM:MeOH:NH$_4$OH solution) to yield NP-PD-245 (122 mg, 0.173 mmol, 61% yield) as a yellow solid. $^1$H NMR (600 MHz, CD$_3$OD) δ 8.19 (s, 1H), 4.35-4.30 (m, 2H), 3.91-3.83 (m, 4H), 3.63 (d, J=8.8 Hz, 2H), 3.41 (t, J=6.4 Hz, 2H), 3.33 (t, J=6.6 Hz, 2H), 2.18-2.06 (m, 2H), 1.78-1.72 (m, 2H), 1.57-1.45 (m, 4H), 1.41-1.23 (m, 22H). HRMS (ESI) m/z calc. for C$_{27}$H$_{45}$O$_5$N$_5$$^{79}$BrF$_3$P [M–H]$^-$, 686.22993 found, 686.23121.

B. Synthesis of 2-(2-amino-6-oxo-1H-purin-9-yl)ethoxymethyl-[3-(16,16,16-trifluorohexadecoxy)propoxy]phosphinic Acid (NP-PD-246)

A 25 mL reaction flask was equipped with a magnetic stirrer and a condenser. NP-PD-245 (122 mg, 0.173 mmol), glacial acetic acid (4.8 mL), and water (1.2 mL) were added to the reaction flask. The resulting mixture was vigorously stirred and heated to reflux. The reaction was monitored by TLC, and following reaction completion (after approximately 3.5 hours), the reaction mixture was cooled to 5° C., and stirred for 18 h. The resulting precipitate was filtered, subsequently dried under vacuum and then recrystallized from hot 80:20 isopropanol/water. The precipitated solids were filtered and dried under vacuum to give NP-PD-246 (40 mg, 0.064 mmol, 37% yield) as off-white solid. $^1$H NMR (600 MHz, DMSO-d$_6$) δ 10.52 (s, 1H), 7.65 (s, 1H), 6.41 (s, 2H), 4.10 (t, J=5.3 Hz, 2H), 3.89 (q, J=6.7 Hz, 2H), 3.79 (t, J=5.3 Hz, 2H), 3.68 (d, J=8.4 Hz, 2H), 3.36 (t, J=6.3 Hz, 2H), 3.30 (t, J=6.6 Hz, 2H), 2.26-2.14 (m, 2H), 1.73 (p, J=6.4 Hz, 2H), 1.50-1.41 (m, 4H), 1.34-1.29 (m, 2H), 1.28-1.21 (m, 20H). $^{13}$C NMR (151 MHz, DMSO-d$_6$) δ 156.7, 153.5, 151.1, 137.6, 127.7 (q, J$_{CF}$=276.7 Hz), 116.3, 70.2 (d, J$_{CP}$=11.4 Hz), 70.1, 66.2, 65.5, 64.4, 62.2 (d, J$_{CP}$=5.9 Hz), 42.2, 32.4 (q, J$_{CF}$=27.3 Hz), 30.5 (d, J$_{CP}$=5.8 Hz), 29.2, 29.0 (2 C), 28.9 (2 C), 28.8, 28.5, 27.9, 25.7, 21.4 (q, J$_{CF}$=3.0 Hz). HRMS (ESI) m/z calc. for C$_{27}$H$_{46}$O$_6$N$_5$F$_3$P [M–H]$^-$, 624.31433 found, 624.31451.

What is claimed is:

1. A compound having a structure of Formula I or a pharmaceutically acceptable salt thereof:

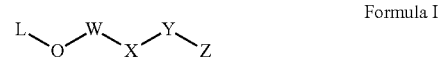

Formula I

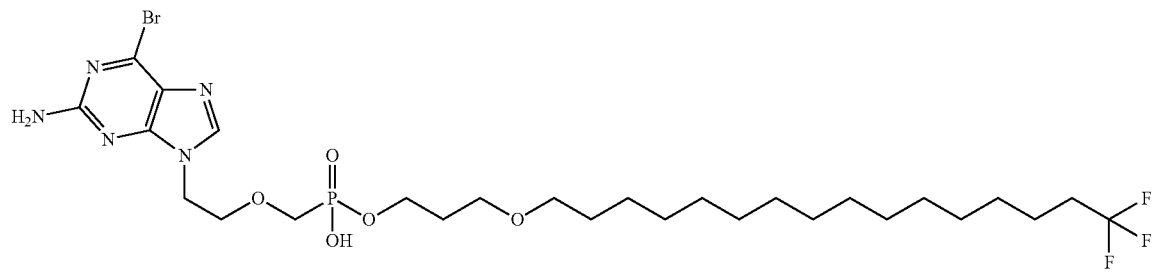

wherein:

L is an acyclic nucleoside phosphonate;

W is a saturated $C_1$-$C_9$ alkyl chain;

X is selected from the group consisting of substituted methylene or ethylene, —O—, —S—, —S(=O)—, and —S(O)$_2$—;

Y is a saturated $C_2$-$C_{20}$ alkyl chain; and

Z is selected from the group consisting of —C≡CCD$_3$, —C≡CCH$_2$F, —C≡CCHF$_2$, —C≡CCF$_3$, —C≡CC(CH$_3$)$_3$,

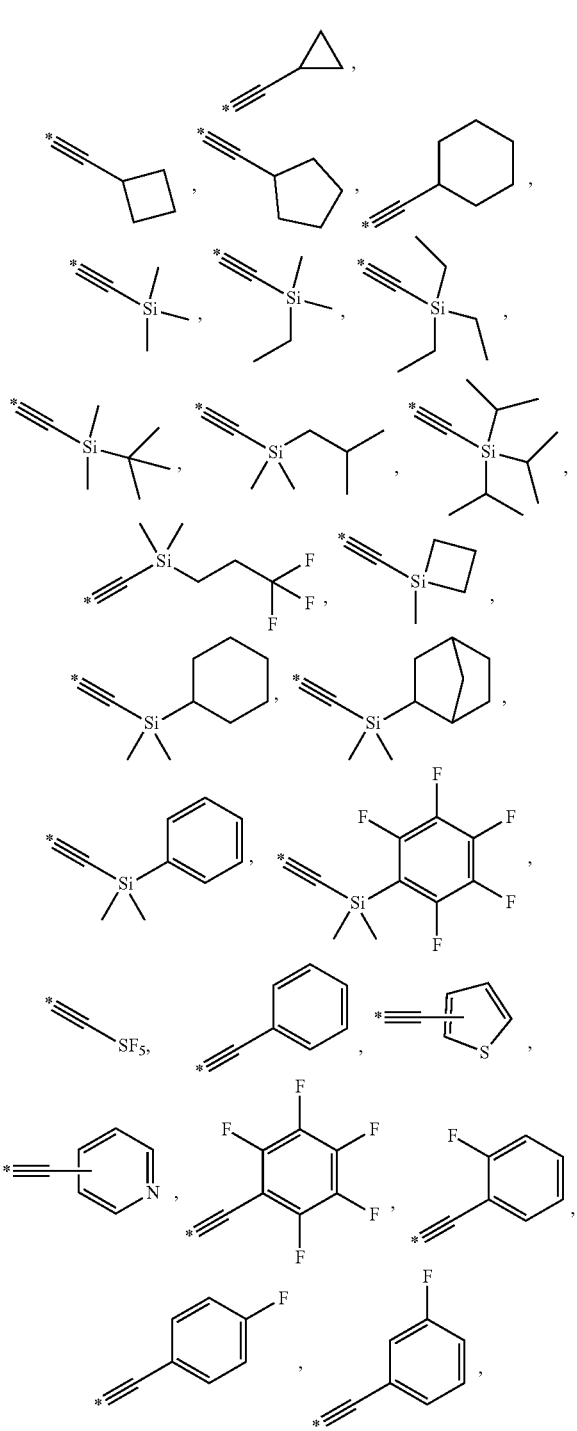

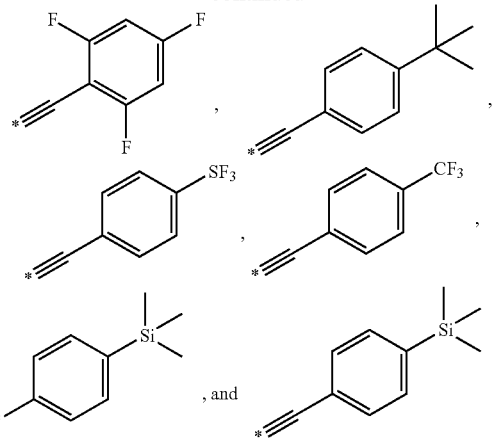

, and

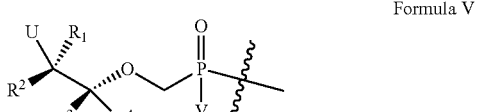

wherein * indicates the point of attachment to Y.

2. The compound of claim 1, wherein L has a structure of Formula V:

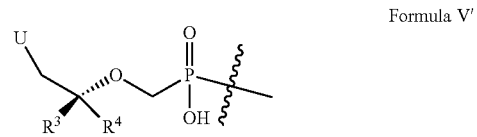

Formula V wherein:

U is a nucleobase;

V is —O—R$^Y$ or —S—R$^Z$;

R$^1$, R$^2$, R$^3$, and R$^4$ are independently selected from the group consisting of hydrogen, deuterium, halogen, azido, cyano, isocyano, nitrate, nitrosooxy, nitroso, nitro, formyl, carboxyl, optionally substituted alkyl, optionally substituted heteroalkyl, optionally substituted carbocyclyl, optionally substituted heterocyclyl, optionally substituted aryl, optionally substituted heteroaryl, azo, acyl, optionally O-substituted hydroxyl, optionally S-substituted mercapto, sulfinyl, sulfonyl, sulfonate, optionally N-substituted amino, optionally N-substituted amide, optionally N-substituted sulfamoyl, optionally Si-substituted silyl, ester, carbonate ester, optionally substituted carbamate, optionally N-substituted aminooxy, and optionally N- and/or O-substituted hydroxyamino; and R$^Y$ and R$^Z$ are independently selected from the group consisting of hydrogen, optionally substituted alkyl, optionally substituted heteroalkyl, optionally substituted carbocyclyl, optionally substituted heterocarbocyclyl, optionally substituted aryl, and optionally substituted heteroaryl.

3. The compound of claim 2, wherein L has a structure of Formula V':

Formula V' wherein U, R$^3$, and R$^4$ are the same as defined in claim 2.

4. The compound of claim 3, wherein L is selected from the group consisting of:

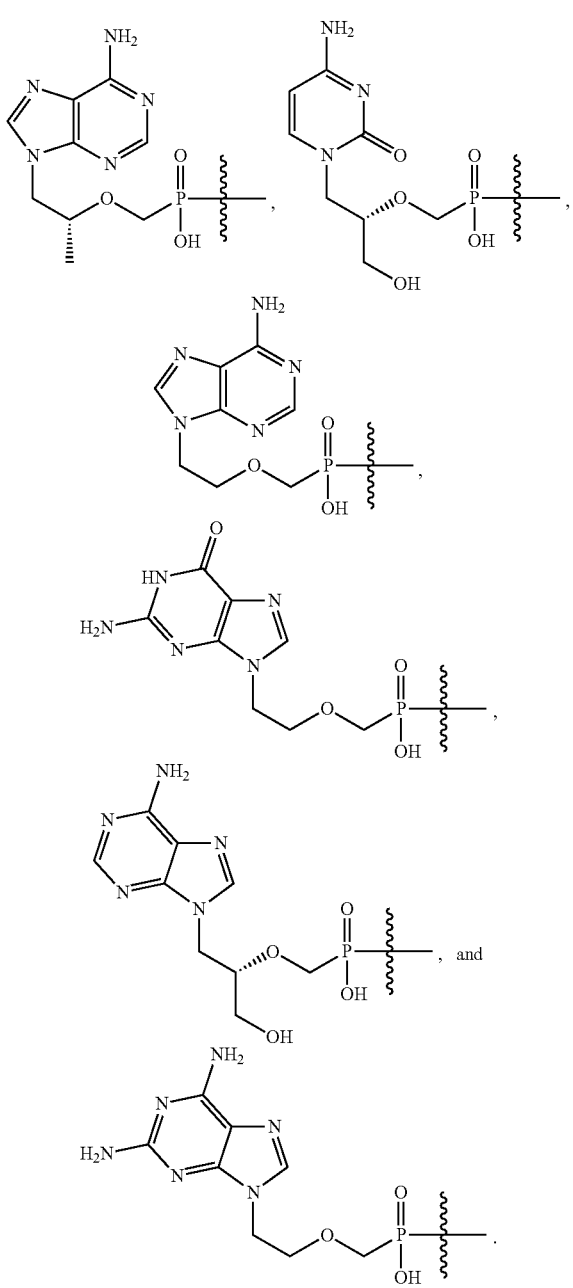

, and

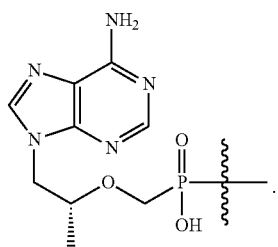 [SMILES: *P(=O)(O)CO[C@H](C)Cn1cnc2c(N)ncnc21]

5. The compound of claim 4, wherein L is

6. The compound of claim 4, wherein L is

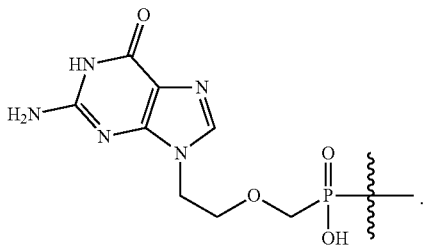 [SMILES: *P(=O)(O)COCCn1cnc2c(=O)[nH]c(N)nc21]

7. The compound of claim 1, wherein W is a linear $C_1$-$C_9$ alkylene.

8. The compound of claim 7, wherein W is $CH_2CH_2$— or $CH_2CH_2CH_2$—.

9. The compound of claim 1, wherein X is —$CF_2$—, —O—, or —S—.

10. The compound of claim 1, wherein Y is a linear $C_2$-$C_{20}$ alkylene.

11. The compound of claim 10, wherein Y is a linear $C_8$-$C_{20}$ alkylene.

12. The compound of claim 1, wherein Z is —C≡CSi$(CH_3)_3$.

13. The compound of claim 1, wherein:
L is

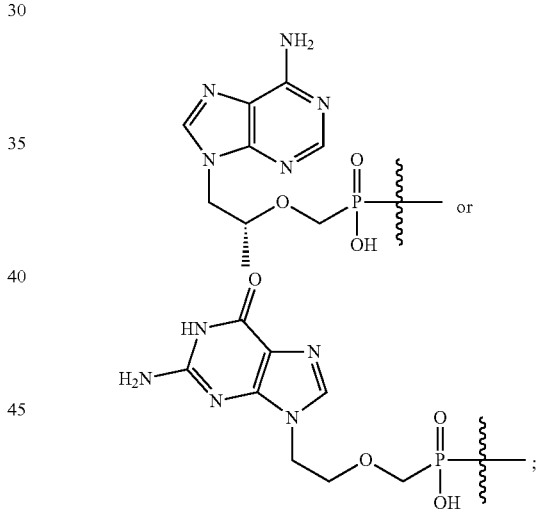

W is —$CH_2CH_2$— or —$CH_2CH_2CH_2$—;
X is —$CF_2$—, —O—, or —S—; and
Y is a linear $C_8$-$C_{20}$ alkylene.

14. The compound of claim 13, wherein the compound is selected from the group consisting of:
 4,4-difluoro-18-(trimethylsilyl)octadec-17-yn-1-yl hydrogen ((((R)-1-(6-amino-9H-purin-9-yl)propan-2-yl)oxy)methyl)phosphonate,
 4,4,20,20,20-pentafluoroicos-18-yn-1-yl hydrogen ((((R)-1-(6-amino-9H-purin-9-yl)propan-2-yl)oxy)methyl) phosphonate,
 3-((14-(trimethylsilyl)tetradec-13-yn-1-yl)thio)propyl hydrogen ((((R)-1-(6-amino-9H-purin-9-yl)propan-2-yl)oxy)methyl)phosphonate,
 3-((16, 16,16-trifluorohexadec-14-yn-1-yl)thio)propyl hydrogen ((((R)-1-(6-amino-9H-purin-9-yl)propan-2-yl)oxy)methyl)phosphonate, 3-((12-phenyldodec-11-yn-1-yl)thio)propyl hydrogen ((((R)-1-(6-amino-9H-purin-9-yl)propan-2-yl)oxy)methyl)phosphonate, 3-((12-(thiophen-2-yl)dodec-11-yn-1-yl)thio)propyl hydrogen ((((R)-1-(6-amino-9H-purin-9-yl)propan-2-yl)oxy)methyl)phosphonate, 3-((13-(thiophen-2-yl)tridec-12-yn-1-yl)thio)propyl hydrogen ((((R)-1-(6-amino-9H-purin-9-yl)propan-2-yl)oxy)methyl)phosphonate, 3-((12-(perfluorophenyl)dodec-11-yn-1-yl)thio)propyl hydrogen ((((R)-1-(6-amino-9H-purin-9-yl)propan-2-yl)oxy)methyl)phosphonate, 3-((12-(pyridin-3-yl)dodec-11-yn-1-yl)thio)propyl hydrogen ((((R)-1-(6-amino-9H-purin-9-yl)propan-2-yl)oxy)methyl)phosphonate, 3-((12-cyclohexyldodec-11-yn-1-yl)thio)propyl hydrogen ((((R)-1-(6-amino-9H-purin-9-yl)propan-2-yl)oxy)methyl)phosphonate, 3-((12-(4-fluorophenyl)dodec-11-yn-1-yl)thio)propyl hydrogen ((((R)-1-(6-amino-9H-purin-9-yl)propan-2-yl)oxy)methyl)phosphonate, 3-((12-(3-fluorophenyl)dodec-11-yn-1-yl)thio)propyl hydrogen ((((R)-1-(6-amino-9H-purin-9-yl)propan-2-yl)oxy)methyl)phosphonate, 3-((12-(2-fluorophenyl)dodec-11-yn-1-yl)thio)propyl hydrogen ((((R)-1-(6-amino-9H-purin-9-yl)propan-2-yl)oxy)methyl)phosphonate, 3-((12-(2,4,6-trifluorophenyl)dodec-11-yn-1-yl)thio)propyl hydrogen ((((R)-1-(6-amino-9H-purin-9-yl)propan-2-yl)oxy)methyl)phosphonate, 3-((13-cyclopentyltridec-12-yn-1-yl)thio)propyl hydrogen ((((R)-1-(6-amino-9H-purin-9-yl)propan-2-yl)oxy)methyl)phosphonate, 3-((14-cyclopropyltetradec-13-yn-1-yl)thio)propyl hydrogen ((((R)-1-(6-amino-9H-purin-9-yl)propan-2-yl)oxy)methyl)phosphonate, 3-((10-(4-(tert-butyl)phenyl)dec-9-yn-1-yl)thio)propyl hydrogen ((((R)-1-(6-amino-9H-purin-9-yl)propan-2-yl)oxy)methyl)phosphonate, 3-((15, 15-dimethylhexadec-13-yn-1-yl)thio)propyl hydrogen ((((R)-1-(6-amino-9H-purin-9-yl)propan-2-yl)oxy)methyl)phosphonate, 3-((13-cyclobutyltridec-12-yn-1-yl)thio)propyl hydrogen ((((R)-1-(6-amino-9H-purin-9-yl)propan-2-yl)oxy)methyl)phosphonate, 3-((13-(1-methylsiletan-1-yl)tridec-12-yn-1-yl)thio)propyl hydrogen ((((R)-1-(6-amino-9H-purin-9-yl)propan-2-yl)oxy)methyl)phosphonate, 3-((13-(ethyldimethylsilyl)tridec-12-yn-1-yl)thio)propyl hydrogen ((((R)-1-(6-amino-9H-purin-9-yl)propan-2-yl)oxy)methyl)phosphonate, 3-((13-(triethylsilyl)tridec-12-yn-1-yl)thio)propyl hydrogen ((((R)-1-(6-amino-9H-purin-9-yl)propan-2-yl)oxy)methyl)phosphonate, 3-((13-(triisopropylsilyl)tridec-12-yn-1-yl)thio)propyl hydrogen ((((R)-1-(6-amino-9H-purin-9-yl)propan-2-yl)oxy)methyl)phosphonate, 3-((13-(tert-butyldimethylsilyl)tridec-12-yn-1-yl)thio)propyl hydrogen ((((R)-1-(6-amino-9H-purin-9-yl)propan-2-yl)oxy)methyl)phosphonate, 3-((11-(dimethyl(phenyl)silyl)undec-10-yn-1-yl)thio)propyl hydrogen ((((R)-1-(6-amino-9H-purin-9-yl)propan-2-yl)oxy)methyl)phosphonate, 3-((11-(dimethyl(perfluorophenyl)silyl)undec-10-yn-1-yl)thio)propyl hydrogen ((((R)-1-(6-amino-9H-purin-9-yl)propan-2-yl)oxy)methyl)phosphonate, 3-((12-(dimethyl(3,3,3-trifluoropropyl)silyl)dodec-11-yn-1-yl)thio)propyl hydrogen ((((R)-1-(6-amino-9H-purin-9-yl)propan-2-yl)oxy)methyl)phosphonate, 3-((11-(cyclohexyldimethylsilyl)undec-10-yn-1-yl)thio)propyl hydrogen ((((R)-1-(6-amino-9H-purin-9-yl)propan-2-yl)oxy)methyl)phosphonate, 3-((11-(bicyclo[2.2.1]heptan-2-yldimethylsilyl)undec-10-yn-1-yl)thio)propyl hydrogen ((((R)-1-(6-amino-9H-purin-9-yl)propan-2-yl)oxy)methyl)phosphonate, 3-((12-(isobutyldimethylsilyl)dodec-11-yn-1-yl)thio)propyl hydrogen ((((R)-1-(6-amino-9H-purin-9-yl)propan-2-yl)oxy)methyl)phosphonate, 3-((15-(pentafluoro-$\lambda_6$-sulfanyl)pentadec-14-yn-1-yl)thio)propyl hydrogen ((((R)-1-(6-amino-9H-purin-9-yl)propan-2-yl)oxy)methyl)phosphonate, 3-((11-(4-(pentafluoro-$\lambda_6$-sulfanyl)phenyl)undec-10-yn-1-yl)thio)propyl hydrogen ((((R)-1-(6-amino-9H-purin-9-yl)propan-2-yl)oxy)methyl)phosphonate, 3-((11-(4-(trifluoromethyl)phenyl)undec-10-yn-1-yl)thio)propyl hydrogen ((((R)-1-(6-amino-9H-purin-9-yl)propan-2-yl)oxy)methyl)phosphonate, 3-((10-(4-(trimethylsilyl)phenyl)dec-9-yn-1-yl)thio)propyl hydrogen ((((R)-1-(6-amino-9H-purin-9-yl)propan-2-yl)oxy)methyl)phosphonate, 3-((15-(trimethylsilyl)pentadec-14-yn-1-yl)oxy)propyl hydrogen ((((R)-1-(6-amino-9H-purin-9-yl)propan-2-yl)oxy)methyl)phosphonate, 3-((14-(trimethylsilyl)tetradec-13-yn-1-yl)oxy)propyl hydrogen ((((R)-1-(6-amino-9H-purin-9-yl)propan-2-yl)oxy)methyl)phosphonate, 3-((16, 16, 16-trifluorohexadec-14-yn-1-yl)oxy)propyl hydrogen ((((R)-1-(6-amino-9H-purin-9-yl)propan-2-yl)oxy)methyl)phosphonate, 3-((12-phenyldodec-11-yn-1-yl)oxy)propyl hydrogen ((((R)-1-(6-amino-9H-purin-9-yl)propan-2-yl)oxy)methyl)phosphonate, 3-((12-(thiophen-2-yl)dodec-11-yn-1-yl)oxy)propyl hydrogen ((((R)-1-(6-amino-9H-purin-9-yl)propan-2-yl)oxy)methyl)phosphonate, 3-((13-(thiophen-2-yl)tridec-12-yn-1-yl)oxy)propyl hydrogen ((((R)-1-(6-amino-9H-purin-9-yl)propan-2-yl)oxy)methyl)phosphonate, 3-((12-(pyridin-3-yl)dodec-11-yn-1-yl)oxy)propyl hydrogen ((((R)-1-(6-amino-9H-purin-9-yl)propan-2-yl)oxy)methyl)phosphonate, 3-((12-(perfluorophenyl)dodec-11-yn-1-yl)oxy)propyl hydrogen ((((R)-1-(6-amino-9H-purin-9-yl)propan-2-yl)oxy)methyl)phosphonate, 3-((12-(4-fluorophenyl)dodec-11-yn-1-yl)oxy)propyl hydrogen ((((R)-1-(6-amino-9H-purin-9-yl)propan-2-yl)oxy)methyl)phosphonate, 3-((12-(3-fluorophenyl)dodec-11-yn-1-yl)oxy)propyl hydrogen ((((R)-1-(6-amino-9H-purin-9-yl)propan-2-yl)oxy)methyl)phosphonate, 3-((12-(2-fluorophenyl)dodec-11-yn-1-yl)oxy)propyl hydrogen ((((R)-1-(6-amino-9H-purin-9-yl)propan-2-yl)oxy)methyl)phosphonate, 3-((12-(2,4,6-trifluorophenyl)dodec-11-yn-1-yl)oxy)propyl hydrogen ((((R)-1-(6-amino-9H-purin-9-yl)propan-2-yl)oxy)methyl)phosphonate, 3-((10-(4-(tert-butyl)phenyl)dec-9-yn-1-yl)oxy)propyl hydrogen ((((R)-1-(6-amino-9H-purin-9-yl)propan-2-yl)oxy)methyl)phosphonate, 3-((15,15-dimethylhexadec-13-yn-1-yl)oxy)propyl hydrogen ((((R)-1-(6-amino-9H-purin-9-yl)propan-2-yl)oxy)methyl)phosphonate, 3-((14-cyclopropyltetradec-13-yn-1-yl)oxy)propyl hydrogen ((((R)-1-(6-amino-9H-purin-9-yl)propan-2-yl)oxy)methyl)phosphonate, 3-((12-cyclohexyldodec-11-yn-1-yl)oxy)propyl hydrogen ((((R)-1-(6-amino-9H-purin-9-yl)propan-2-yl)oxy)methyl)phosphonate, 3-((13-cyclopentyltridec-12-yn-1-yl)oxy)propyl hydrogen ((((R)-1-(6-amino-9H-purin-9-yl)propan-2-yl)oxy)methyl)phosphonate, 3-((13-cyclobutyltridec-12-yn-1-yl)oxy)propyl hydrogen ((((R)-1-(6-amino-9H-purin-9-yl)propan-2-yl)oxy)methyl)phosphonate, 3-((13-(1-methylsiletan-1-yl)tridec-12-yn-1-yl)oxy)propyl hydrogen ((((R)-1-(6-amino-9H-purin-9-yl)propan-2-yl)oxy)methyl)phosphonate, 3-((13-(ethyldimethylsilyl)tridec-12-yn-1-yl)oxy)propyl hydrogen ((((R)-1-(6-amino-9H-purin-9-yl)propan-2-yl)oxy)methyl)phosphonate, 3-((13-(triethylsilyl)tridec-12-yn-1-yl)oxy)propyl hydrogen ((((R)-1-(6-amino-9H-purin-9-yl)propan-2-yl)oxy)methyl)phosphonate, 3-((13-(triisopropylsilyl)tridec-12-yn-1-yl)oxy)propyl hydrogen ((((R)-1-(6-amino-9H-purin-9-yl)propan-2-yl)oxy)methyl)phosphonate, 3-((13-(tert-butyldimethylsilyl)tridec-12-yn-1-yl)oxy)propyl hydrogen ((((R)-1-(6-amino-9H-purin-9-yl)propan-2-yl)oxy)methyl)phosphonate, 3-((11-(dimethyl(phenyl)silyl)undec-10-yn-1-yl)oxy)propyl hydrogen ((((R)-1-(6-amino-9H-purin-9-yl)propan-2-yl)oxy)methyl)phosphonate, 3-((11-(dimethyl(perfluorophenyl)silyl)undec-10-yn-1-yl)oxy)propyl hydrogen ((((R)-1-(6-amino-9H-purin-9-yl)propan-2-yl)oxy)methyl)phosphonate, 3-((12-(dimethyl(3,3,3-trifluoropropyl)silyl)dodec-11-yn-1-yl)oxy)propyl hydrogen ((((R)-1-(6-amino-9H-purin-9-yl)propan-2-yl)oxy)methyl)phosphonate, 3-((11-(cyclohexyldimethylsilyl)undec-10-yn-1-yl)oxy)propyl hydrogen ((((R)-1-(6-amino-9H-purin-9-yl)propan-2-yl)oxy)methyl)phosphonate, 3-((11-(bicyclo[2.2.1]heptan-2-yldimethylsilyl)undec-10-yn-1-yl)oxy)propyl hydrogen ((((R)-1-(6-amino-9H-purin-9-yl)propan-2-yl)oxy)methyl)phosphonate, 3-((12-(isobutyldimethylsilyl)dodec-11-yn-1-yl)oxy)propyl hydrogen ((((R)-1-(6-amino-9H-purin-9-yl)propan-2-yl)oxy)methyl)phosphonate, 3-((15-(pentafluoro-$\lambda_6$-sulfanyl)pentadec-14-yn-1-yl)oxy)propyl hydrogen ((((R)-1-(6-amino-9H-purin-9-yl)propan-2-yl)oxy)methyl)phosphonate, 3-((11-(4-(pentafluoro-$\lambda_6$-sulfanyl)phenyl)undec-10-yn-1-yl)oxy)propyl hydrogen ((((R)-1-(6-amino-9H-purin-9-yl)propan-2-yl)oxy)methyl)phosphonate, 3-((11-(4-(trifluoromethyl)phenyl)undec-10-yn-1-yl)oxy)propyl hydrogen ((((R)-1-(6-amino-9H-purin-9-yl)propan-2-yl)oxy)methyl)phosphonate, 3-((10-(4-(trimethylsilyl)phenyl)dec-9-yn-1-yl)oxy)propyl hydrogen ((((R)-1-(6-amino-9H-purin-9-yl)propan-2-yl)oxy)methyl)phosphonate, 2-((15-(trimethylsilyl)pentadec-14-yn-1-yl)thio)ethyl hydrogen ((((R)-1-(6-amino-9H-purin-9-yl)propan-2-yl)oxy)methyl)phosphonate, 2-((16-(trimethylsilyl)hexadec-15-yn-1-yl)thio)ethyl hydrogen ((((R)-1-(6-amino-9H-purin-9-yl)propan-2-yl)oxy)methyl)phosphonate, 2-((17,17,17-trifluoroheptadec-15-yn-1-yl)thio)ethyl hydrogen ((((R)-1-(6-amino-9H-purin-9-yl)propan-2-yl)oxy)methyl)phosphonate, 2-((13-phenyltridec-12-yn-1-yl)thio)ethyl hydrogen ((((R)-1-(6-amino-9H-purin-9-yl)propan-2-yl)oxy)methyl)phosphonate, 2-((13-(thiophen-2-yl)tridec-12-yn-1-yl)thio)ethyl hydrogen ((((R)-1-(6-amino-9H-purin-9-yl)propan-2-yl)oxy)methyl)phosphonate, 2-((14-(thiophen-2-yl)tetradec-13-yn-1-yl)thio)ethyl hydrogen ((((R)-1-(6-amino-9H-purin-9-yl)propan-2-yl)oxy)methyl)phosphonate, 2-((13-(perfluorophenyl)tridec-12-yn-1-yl)thio)ethyl hydrogen ((((R)-1-(6-amino-9H-purin-9-yl)propan-2-yl)oxy)methyl)phosphonate, 2-((13-(pyridin-3-yl)tridec-12-yn-1-yl)thio)ethyl hydrogen ((((R)-1-(6-amino-9H-purin-9-yl)propan-2-yl)oxy)methyl)phosphonate, 2-((13-cyclohexyltridec-12-yn-1-yl)thio)ethyl hydrogen ((((R)-1-(6-amino-9H-purin-9-yl)propan-2-yl)oxy)methyl)phosphonate, 2-((13-(4-fluorophenyl)tridec-12-yn-1-yl)thio)ethyl hydrogen ((((R)-1-(6-amino-9H-purin-9-yl)propan-2-yl)oxy)methyl)phosphonate, 2-((13-(3-fluorophenyl)tridec-12-yn-1-yl)thio)ethyl hydrogen ((((R)-1-(6-amino-9H-purin-9-yl)propan-2-yl)oxy)methyl)phosphonate, 2-((13-(2-fluorophenyl)tridec-12-yn-1-yl)thio)ethyl hydrogen ((((R)-1-(6-amino-9H-purin-9-yl)propan-2-yl)oxy)methyl)phosphonate, 2-((13-(2,4,6-trifluorophenyl)tridec-12-yn-1-yl)thio)ethyl hydrogen ((((R)-1-(6-amino-9H-purin-9-yl)propan-2-yl)oxy)methyl)phosphonate, 2-((14-cyclopentyltetradec-13-yn-1-yl)thio)ethyl hydrogen ((((R)-1-(6-amino-9H-purin-9-yl)propan-2-yl)oxy)methyl)phosphonate, 2-((15-cyclopropylpentadec-14-yn-1-yl)thio)ethyl hydrogen ((((R)-1-(6-amino-9H-purin-9-yl)propan-2-yl)oxy)methyl)phosphonate, 2-((11-(4-(tert-butyl)phenyl)undec-10-yn-1-yl)thio)ethyl hydrogen ((((R)-1-(6-amino-9H-purin-9-yl)propan-2-yl)oxy)methyl)phosphonate, 2-((16,16-dimethylheptadec-14-yn-1-yl)thio)ethyl hydrogen ((((R)-1-(6-amino-9H-purin-9-yl)propan-2-yl)oxy)methyl)phosphonate, 2-((14-cyclobutyltetradec-13-yn-1-yl)thio)ethyl hydrogen ((((R)-1-(6-amino-9H-purin-9-yl)propan-2-yl)oxy)methyl)phosphonate, 2-((14-(1-methylsiletan-1-yl)tetradec-13-yn-1-yl)thio)ethyl hydrogen ((((R)-1-(6-amino-9H-purin-9-yl)propan-2-yl)oxy)methyl)phosphonate, 2-((14-(ethyldimethylsilyl)tetradec-13-yn-1-yl)thio)ethyl hydrogen ((((R)-1-(6-amino-9H-purin-9-yl)propan-2-yl)oxy)methyl)phosphonate, 2-((14-(triethylsilyl)tetradec-13-yn-1-yl)thio)ethyl hydrogen ((((R)-1-(6-amino-9H-purin-9-yl)propan-2-yl)oxy)methyl)phosphonate, 2-((14-(triisopropylsilyl)tetradec-13-yn-1-yl)thio)ethyl hydrogen ((((R)-1-(6-amino-9H-purin-9-yl)propan-2-yl)oxy)methyl)phosphonate, 2-((14-(tert-butyldimethylsilyl)tetradec-13-yn-1-yl)thio)ethyl hydrogen ((((R)-1-(6-amino-9H-purin-9-yl)propan-2-yl)oxy)methyl)phosphonate, 2-((12-(dimethyl(phenyl)silyl)dodec-11-yn-1-yl)thio)ethyl hydrogen ((((R)-1-(6-amino-9H-purin-9-yl)propan-2-yl)oxy)methyl)phosphonate, 2-((12-(dimethyl(perfluorophenyl)silyl)dodec-11-yn-1-yl)thio)ethyl hydrogen ((((R)-1-(6-amino-9H-purin-9-yl)propan-2-yl)oxy)methyl)phosphonate, 2-((13-(dimethyl(3,3,3-trifluoropropyl)silyl)tridec-12-yn-1-yl)thio)ethyl hydrogen ((((R)-1-(6-amino-9H-purin-9-yl)propan-2-yl)oxy)methyl)phosphonate, 2-((12-(cyclohexyldimethylsilyl)dodec-11-yn-1-yl)thio)ethyl hydrogen ((((R)-1-(6-amino-9H-purin-9-yl)propan-2-yl)oxy)methyl)phosphonate, 2-((12-(bicyclo[2.2.1]heptan-2-yldimethylsilyl)dodec-11-yn-1-yl)thio)ethyl ((((R)-1-(6-amino-9H-purin-9-yl)propan-2-yl)oxy)methyl)phosphonate, hydrogen 2-((13-(isobutyldimethylsilyl)tridec-12-yn-1-yl)thio)ethyl hydrogen ((((R)-1-(6-amino-9H-purin-9-yl)propan-2-yl)oxy)methyl)phosphonate, 2-((16-(pentafluoro-$\lambda_6$-sulfanyl)hexadec-15-yn-1-yl)thio)ethyl hydrogen ((((R)-1-(6-amino-9H-purin-9-yl)propan-2-yl)oxy)methyl)phosphonate, 2-((12-(4-(pentafluoro-$\lambda_6$-sulfanyl)phenyl)dodec-11-yn-1-yl)thio)ethyl hydrogen ((((R)-1-(6-amino-9H-purin-9-yl)propan-2-yl)oxy)methyl)phosphonate, 2-((12-(4-(trifluoromethyl)phenyl)dodec-11-yn-1-yl)thio)ethyl hydrogen ((((R)-1-(6-amino-9H-purin-9-yl)propan-2-yl)oxy)methyl)phosphonate, 2-((11-(4-(trimethylsilyl)phenyl)undec-10-yn-1-yl)thio)ethyl hydrogen ((((R)-1-(6-amino-9H-purin-9-yl)propan-2-yl)oxy)methyl)phosphonate, 2-((15-(trimethylsilyl)pentadec-14-yn-1-yl)oxy)ethyl hydrogen ((((R)-1-(6-amino-9H-purin-9-yl)propan-2-yl)oxy)methyl)phosphonate, 2-((16-(trimethylsilyl)hexadec-15-yn-1-yl)oxy)ethyl hydrogen ((((R)-1-(6-amino-9H-purin-9-yl)propan-2-yl)oxy)methyl)phosphonate, 2-((17,17,17-trifluoroheptadec-15-yn-1-yl)oxy)ethyl hydrogen ((((R)-1-(6-amino-9H-purin-9-yl)propan-2-yl)oxy)methyl)phosphonate, 2-((13-phenyltridec-12-yn-1-yl)oxy)ethyl hydrogen ((((R)-1-(6-amino-9H-purin-9-yl)propan-2-yl)oxy)methyl)phosphonate, 2-((13-(thiophen-2-yl)tridec-12-yn-1-yl)oxy)ethyl hydrogen ((((R)-1-(6-amino-9H-purin-9-yl)propan-2-yl)oxy)methyl)phosphonate, 2-((14-(thiophen-2-yl)tetradec-13-yn-1-yl)oxy)ethyl hydrogen ((((R)-1-(6-amino-9H-purin-9-yl)propan-2-yl)oxy)methyl)phosphonate, 2-((13-(perfluorophenyl)tridec-12-yn-1-yl)oxy)ethyl hydrogen ((((R)-1-(6-amino-9H-purin-9-yl)propan-2-yl)oxy)methyl)phosphonate, 2-((13-(pyridin-3-yl)tridec-12-yn-1-yl)oxy)ethyl hydrogen ((((R)-1-(6-amino-9H-purin-9-yl)propan-2-yl)oxy)methyl)phosphonate, 2-((13-cyclohexyltridec-12-yn-1-yl)oxy)ethyl hydrogen ((((R)-1-(6-amino-9H-purin-9-yl)propan-2-yl)oxy)methyl)phosphonate, 2-((13-(4-fluorophenyl)tridec-12-yn-1-yl)oxy)ethyl hydrogen ((((R)-1-(6-amino-9H-purin-9-yl)propan-2-yl)oxy)methyl)phosphonate, 2-((13-(3-fluorophenyl)tridec-12-yn-1-yl)oxy)ethyl hydrogen ((((R)-1-(6-amino-9H-purin-9-yl)propan-2-yl)oxy)methyl)phosphonate, 2-((13-(2-fluorophenyl)tridec-12-yn-1-yl)oxy)ethyl hydrogen ((((R)-1-(6-amino-9H-purin-9-yl)propan-2-yl)oxy)methyl)phosphonate, 2-((13-(2,4,6-trifluorophenyl)tridec-12-yn-1-yl)oxy)ethyl hydrogen ((((R)-1-(6-amino-9H-purin-9-yl)propan-2-yl)oxy)methyl)phosphonate, 2-((14-cyclopentyltetradec-13-yn-1-yl)oxy)ethyl hydrogen ((((R)-1-(6-amino-9H-purin-9-yl)propan-2-yl)oxy)methyl)phosphonate, 2-((15-cyclopropylpentadec-14-yn-1-yl)oxy)ethyl hydrogen ((((R)-1-(6-amino-9H-purin-9-yl)propan-2-yl)oxy)methyl)phosphonate, 2-((11-(4-(tert-butyl)phenyl)undec-10-yn-1-yl)oxy)ethyl hydrogen ((((R)-1-(6-amino-9H-purin-9-yl)propan-2-yl)oxy)methyl)phosphonate, 2-((16,16-dimethylheptadec-14-yn-1-yl)oxy)ethyl hydrogen ((((R)-1-(6-amino-9H-purin-9-yl)propan-2-yl)oxy)methyl)phosphonate, 2-((14-cyclobutyltetradec-13-yn-1-yl)oxy)ethyl hydrogen ((((R)-1-(6-amino-9H-purin-9-yl)propan-2-yl)oxy)methyl)phosphonate, 2-((14-(1-methylsiletan-1-yl)tetradec-13-yn-1-yl)oxy)ethyl ((((R)-1-(6-amino-9H-purin-9-yl)propan-2-yl)oxy)methyl)phosphonate, 2-((14-(ethyldimethylsilyl)tetradec-13-yn-1-yl)oxy)ethyl hydrogen ((((R)-1-(6-amino-9H-purin-9-yl)propan-2-yl)oxy)methyl)phosphonate, 2-((14-(triethylsilyl)tetradec-13-yn-1-yl)oxy)ethyl hydrogen ((((R)-1-(6-amino-9H-purin-9-yl)propan-2-yl)oxy)methyl)phosphonate, 2-((14-(triisopropylsilyl)tetradec-13-yn-1-yl)oxy)ethyl hydrogen ((((R)-1-(6-amino-9H-purin-9-yl)propan-2-yl)oxy)methyl)phosphonate, 2-((14-(tert-butyldimethylsilyl)tetradec-13-yn-1-yl)oxy)ethyl hydrogen ((((R)-1-(6-amino-9H-purin-9-yl)propan-2-yl)oxy)methyl)phosphonate, 2-((12-(dimethyl(phenyl)silyl)dodec-11-yn-1-yl)oxy)ethyl hydrogen ((((R)-1-(6-amino-9H-purin-9-yl)propan-2-yl)oxy)methyl)phosphonate, 2-((12-(dimethyl(perfluorophenyl)silyl)dodec-11-yn-1-yl)oxy)ethyl hydrogen ((((R)-1-(6-amino-9H-purin-9-yl)propan-2-yl)oxy)methyl)phosphonate, 2-((13-(dimethyl(3,3,3-trifluoropropyl)silyl)tridec-12-yn-1-yl)oxy)ethyl hydrogen ((((R)-1-(6-amino-9H-purin-9-yl)propan-2-yl)oxy)methyl)phosphonate, 2-((12-(cyclohexyldimethylsilyl)dodec-11-yn-1-yl)oxy)ethyl hydrogen ((((R)-1-(6-amino-9H-purin-9-yl)propan-2-yl)oxy)methyl)phosphonate, 2-((12-(bicyclo[2.2.1]heptan-2-yldimethylsilyl)dodec-11-yn-1-yl)oxy)ethyl hydrogen ((((R)-1-(6-amino-9H-purin-9-yl)propan-2-yl)oxy)methyl)phosphonate, 2-((13-(isobutyldimethylsilyl)tridec-12-yn-1-yl)oxy)ethyl hydrogen ((((R)-1-(6-amino-9H-purin-9-yl)propan-2-yl)oxy)methyl)phosphonate, 2-((16-(pentafluoro-$\lambda_6$-sulfanyl)hexadec-15-yn-1-yl)oxy)ethyl hydrogen ((((R)-1-(6-amino-9H-purin-9-yl)propan-2-yl)oxy)methyl)phosphonate, 2-((12-(4-(pentafluoro-$\lambda_6$-sulfanyl)phenyl)dodec-11-yn-1-yl)oxy)ethyl hydrogen ((((R)-1-(6-amino-9H-purin-9-yl)propan-2-yl)oxy)methyl)phosphonate, 2-((12-(4-(trifluoromethyl)phenyl)dodec-11-yn-1-yl)oxy)ethyl hydrogen ((((R)-1-(6-amino-9H-purin-9-yl)propan-2-yl)oxy)methyl)phosphonate, 2-((11-(4-(trimethylsilyl)phenyl)undec-10-yn-1-yl)oxy)ethyl hydrogen ((((R)-1-(6-amino-9H-purin-9-yl)propan-2-yl)oxy)methyl)phosphonate, 2-((15-(trimethylsilyl)pentadec-14-yn-1-yl)oxy)ethyl hydrogen ((2-(2-amino-6-oxo-1,6-dihydro-9H-purin-9-yl)ethoxy)methyl)phosphonate, 2-((15-(trimethylsilyl)pentadec-14-yn-1-yl)thio)ethyl hydrogen ((2-(2-amino-6-oxo-1,6-dihydro-9H-purin-9-yl)ethoxy)methyl)phosphonate, 2-((16-(trimethylsilyl)hexadec-15-yn-1-yl)oxy)ethyl hydrogen ((2-(2-amino-6-oxo-1,6-dihydro-9H-purin-9-yl)ethoxy)methyl)phosphonate, 2-((16-(trimethylsilyl)hexadec-15-yn-1-yl)thio)ethyl hydrogen ((2-(2-amino-6-oxo-1,6-dihydro-9H-purin-9-yl)ethoxy)methyl)phosphonate, 3-((14-(trimethylsilyl)tetradec-13-yn-1-yl)thio)propyl hydrogen ((2-(2-amino-6-oxo-1,6-dihydro-9H-purin-9-yl)ethoxy)methyl)phosphonate, and 3-((14-(trimethylsilyl)tetradec-13-yn-1-yl)oxy)propyl hydrogen ((2-(2-amino-6-oxo-1,6-dihydro-9H-purin-9-yl)ethoxy)methyl)phosphonate, or pharmaceutically acceptable salts thereof.

15. The compound of claim 14, wherein the compound is selected from the group consisting of:

3-((14-(trimethylsilyl)tetradec-13-yn-1-yl)thio)propyl hydrogen ((((R)-1-(6-amino-9H-purin-9-yl)propan-2-yl)oxy)methyl)phosphonate, 3-((14-(trimethylsilyl)tetradec-13-yn-1-yl)oxy)propyl hydrogen ((((R)-1-(6-amino-9H-purin-9-yl)propan-2-yl)oxy)methyl)phosphonate, 2-((15-(trimethylsilyl)pentadec-14-yn-1-yl)thio)ethyl hydrogen ((((R)-1-(6-amino-9H-purin-9-yl)propan-2-yl)oxy)methyl)phosphonate, 2-((16-(trimethylsilyl)hexadec-15-yn-1-yl)thio)ethyl hydrogen ((((R)-1-(6-amino-9H-purin-9-yl)propan-2-yl)oxy)methyl)phosphonate, 2-((15-(trimethylsilyl)pentadec-14-yn-1-yl)oxy)ethyl hydrogen ((((R)-1-(6-amino-9H-purin-9-yl)propan-2-yl)oxy)methyl)phosphonate, 2-((16-(trimethylsilyl)hexadec-15-yn-1-yl)oxy)ethyl hydrogen ((((R)-1-(6-amino-9H-purin-9-yl)propan-2-yl)oxy)methyl)phosphonate, 2-((15-(trimethylsilyl)pentadec-14-yn-1-yl)oxy)ethyl hydrogen ((2-(2-amino-6-oxo-1,6-dihydro-9H-purin-9-yl)ethoxy)methyl)phosphonate, 2-((15-(trimethylsilyl)pentadec-14-yn-1-yl)thio)ethyl hydrogen ((2-(2-amino-6-oxo-1,6-dihydro-9H-purin-9-yl)ethoxy)methyl)phosphonate, 2-((16-(trimethylsilyl)hexadec-15-yn-1-yl)oxy)ethyl hydrogen ((2-(2-amino-6-oxo-1,6-dihydro-9H-purin-9-yl)ethoxy)methyl)phosphonate, 2-((16-(trimethylsilyl)hexadec-15-yn-1-yl)thio)ethyl hydrogen ((2-(2-amino-6-oxo-1,6-dihydro-9H-purin-9-yl)ethoxy)methyl)phosphonate, 3-((14-(trimethylsilyl)tetradec-13-yn-1-yl)thio)propyl hydrogen ((2-(2-amino-6-oxo-1,6-dihydro-9H-purin-9-yl)ethoxy)methyl)phosphonate, and 3-((14-(trimethylsilyl)tetradec-13-yn-1-yl)oxy)propyl hydrogen ((2-(2-amino-6-oxo-1,6-dihydro-9H-purin-9-yl)ethoxy)methyl)phosphonate, or pharmaceutically acceptable salts thereof.

16. A pharmaceutical formulation, comprising the compound of claim 1 and a pharmaceutically acceptable carrier.

17. The pharmaceutical formulation of claim 16, wherein the pharmaceutical formulation is in the form of tablet, capsule, pill, gel, cream, granule, solution, suspension, emulsion, or nanoparticulate formulation.

18. The pharmaceutical formulation of claim 16, wherein the pharmaceutical formulation is an oral formulation.

19. A method of treating a viral infection or viral-associated cancer in a subject in need thereof, comprising administering an effective amount of the compound of claim 1 to the subject.

20. The method of claim 19, wherein the compound is administered orally.

21. The method of claim 19, wherein the viral infection is an infection caused by human immunodeficiency virus (HIV), hepatitis viruses, herpes viruses, flaviviruses, pox viruses, paramyxoviruses, influenza viruses, coronaviruses, smallpox viruses, human papillomavirus (HPV), or filoviruses.

22. The method of claim 21, wherein the viral infection is HIV infection.

23. The method of claim 19, wherein the viral-associated cancer is HPV-associated cancer.

* * * * *